US006541489B1

(12) United States Patent
Barta et al.

(10) Patent No.: US 6,541,489 B1
(45) Date of Patent: Apr. 1, 2003

(54) AROMATIC SULFONE HYDROXAMIC ACID METALLOPROTEASE INHIBITOR

(75) Inventors: Thomas E. Barta, Evanston; Daniel P. Becker, Glenview, both of IL (US); Terri L. Boehm, Ballwin; Gary A. De Crescenzo, St. Charles, both of MO (US); Clara I. Villamil, Glenview, IL (US); Joseph J. McDonald, Ballwin, MO (US); John N. Freskos, Clayton, MO (US); Daniel P. Getman, Chesterfield, MO (US)

(73) Assignee: G. D. Searle & Company, St.Louis, MO (US)

( * ) Notice: Subject to any disclaimer, the term of this patent is extended or adjusted under 35 U.S.C. 154(b) by 0 days.

(21) Appl. No.: 09/554,082

(22) PCT Filed: Nov. 12, 1998

(86) PCT No.: PCT/US98/23242

§ 371 (c)(1),
(2), (4) Date: Jul. 31, 2000

(87) PCT Pub. No.: WO99/25687

PCT Pub. Date: May 27, 1999

Related U.S. Application Data

(60) Provisional application No. 60/066,007, filed on Nov. 14, 1997.

(51) Int. Cl.[7] ..................... A61K 31/445; C07D 211/06

(52) U.S. Cl. ........................ 514/330; 546/192; 546/225

(58) Field of Search ................................ 546/192, 225; 514/330

(56) References Cited

U.S. PATENT DOCUMENTS

| | | | |
|---|---|---|---|
| 4,595,700 A | 6/1986 | Donald et al. | 514/616 |
| 5,932,595 A | 8/1999 | Bender et al. | 514/317 |

FOREIGN PATENT DOCUMENTS

| | | | | |
|---|---|---|---|---|
| EP | 266182 | * | 5/1988 | |
| EP | 0 266 182 | | 5/1988 | |
| EP | 0 606 046 | | 7/1994 | |
| EP | 0 780 386 | | 6/1997 | |
| EP | 780386 | * | 6/1997 | |
| EP | 0 930 067 | | 7/1999 | |
| JP | 4-338331 | | 11/1992 | |
| WO | 90/05719 | | 5/1990 | |
| WO | 93/20047 | | 10/1993 | |
| WO | 94/02466 | | 2/1994 | |
| WO | 94/24140 | | 10/1994 | |
| WO | 95/09841 | | 4/1995 | C07F/323/60 |
| WO | 95/12389 | | 5/1995 | |
| WO | 96/06074 | | 2/1996 | C07C/259/06 |
| WO | 96/11209 | | 4/1996 | |
| WO | 97/20624 | | 6/1997 | |
| WO | WO 97/24117 | * | 7/1997 | |
| WO | 97/24117 | | 7/1997 | |
| WO | 98/37877 | | 9/1998 | |
| WO | 98/38163 | | 9/1998 | |
| WO | 99/42436 | | 8/1999 | |

OTHER PUBLICATIONS

Gearing et al. *Nature*, 376, 555–557 (1994).
McGeehan et al., *Nature* 376, 558–561 (1994).
Mitchell et al., *J. Clin. Invest.*, 97:761–768.
Reboul et al., *J. Clin Invest.*, 97:2011–2019 (1996).
Schwartz et al., *Progr. Med. Chem.*, 29:271–334 (1992).
Rasmussen et al., *Pharmalcol. Ther.*, 75(1): 69–75 (1997).
Denis et al., *Invest. New Drugs*, 15(3): 175–185 (1997).
A Model of Angiogenesis in the Mouse Cornea; Kenyon, BM, et al., Investigative Ophthalmology & Visual Science, Jul. 1996, vol. 37, No. 8.
Knight et al., *FEBS Lett.* 296(3):263 (1992).
Luckow et al., *J. Virol.*, 67:4566–4579 (1993).
McClure et al, "Matrix metalloprotease . . . " CA 131:125454 (1999).
Dack et al. "Preparation of N–hydroxytetrahydro . . . " CA 131:44740 (1999).

* cited by examiner

*Primary Examiner*—Zinna Northington Davis
(74) *Attorney, Agent, or Firm*—Harness, Dickey & Pierce, P.L.C.

(57) ABSTRACT

A treatment process is disclosed that comprises administering an effective amount of an aromatic sulfone hydroxamic acid that exhibits excellent inhibitory activity of one or more matrix metalloprotease (MMP) enzymes, such as MMP-2, MMP-9, and MMP-13, while exhibiting substantially less inhibition at least of MMP-1 to a host having a condition associated with pathological matrix metalloprotease activity. The administered enzyme inhibitor corresponds in structure to formula (I), below, or a pharmaceutically acceptable salt thereof, wherein $R^1$ and $R^2$ are both hydrido or $R^1$ and $R^2$ together with the atoms to which they are bonded form a 5- to 8-membered ring containing one, two, or three heteroatoms in the ring that are oxygen, sulfur, or nitrogen. $R^3$ in formula (I) is an optionally substituted aryl or optionally substituted heteroaryl radical. Also disclosed are metalloprotease inhibitor compounds having those selective activities, processes for manufacture of such compounds and pharmaceutical compositions using an inhibitor.

(I)

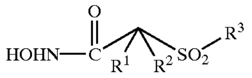

19 Claims, No Drawings

AROMATIC SULFONE HYDROXAMIC ACID METALLOPROTEASE INHIBITOR

CROSS-REFERENCE TO RELATED PATENT APPLICATION

This patent claims priority to PCT application PCT/US98/23242 (filed Nov. 12, 1998, and published as International Publication No. WO 99/25687), which, in turn, claims priority to U.S. Provisional Patent Application Serial No. 60/066,007 (filed Nov. 14, 1997). This patent also claims priority to U.S. Provisional Patent Application Serial No. 60/066,007. The entire text of each of the above patent applications is incorporated by reference into this application.

TECHNICAL FIELD

This invention is directed to proteinase (protease) inhibitors, and more particularly to the use of aromatic sulfone hydroxamic acid compounds that, inter alia, are selective inhibitors of matrix metalloproteinases in a process for treating conditions associated with pathological matrix metalloproteinase activity, the selective inhibitors themselves, compositions of proteinase inhibitors, intermediates for the syntheses of proteinase inhibitors, and processes for the preparation of proteinase inhibitors.

BACKGROUND OF THE INVENTION

Connective tissue, extracellular matrix constituents and basement membranes are required components of all mammals. These components are the biological materials that provide rigidity, differentiation, attachments and, in some cases, elasticity to biological systems including human beings and other mammals. Connective tissues components include, for example, collagen, elastin, proteoglycans, fibronectin and laminin. These biochemicals makeup, or are components of structures, such as skin, bone, teeth, tendon, cartilage, basement membrane, blood vessels, cornea and vitreous humor.

Under normal conditions, connective tissue turnover and/or repair processes are controlled and in equilibrium. The loss of this balance for whatever reason leads to a number of disease states. Inhibition of the enzymes responsible loss of equilibrium provides a control mechanism for this tissue decomposition and, therefore, a treatment for these diseases.

Degradation of connective tissue or connective tissue components is carried out by the action of proteinase enzymes released from resident tissue cells and/or invading inflammatory or tumor cells. A major class of enzymes involved in this function are the zinc metalloproteinases (metalloproteases).

The metalloprotease enzymes are divided into classes with some members having several different names in common use. Examples are: collagenase I (MMP-1, fibroblast collagenase; EC 3.4.24.3); collagenase II (MMP-8, neutrophil collagenase; EC 3.4.24.34), collagenase III (MMP-13), stromelysin 1 (MMP-3; EC 3.4.24.17), stromelysin 2 (MMP-10; EC 3.4.24.22), proteoglycanase, matrilysin (MMP-7), gelatinase A (MMP-2, 72 kDa gelatinase, basement membrane collagenase; EC 3.4.24.24), gelatinase B (MMP-9, 92 kDa gelatinase; EC 3.4.24.35), stromelysin 3 (MMP-11), metalloelastase (MMP-12, HME, human macrophage elastase) and membrane MMP (MMP-14). MMP is an abbreviation or acronym representing the term Matrix Metalloprotease with the attached numerals providing differentiation between specific members of the MMP group.

The uncontrolled breakdown of connective tissue by metalloproteases is a feature of many pathological conditions. Examples include rheumatoid arthritis, osteoarthritis, septic arthritis; corneal, epidermal or gastric ulceration; tumor metastasis, invasion or angiogenesis; periodontal disease; proteinuria; Alzheimers Disease; coronary thrombosis and bone disease. Defective injury repair processes also occur. This can produce improper wound healing leading to weak repairs, adhesions and scarring. These latter defects can lead to disfigurement and/or permanent disabilities as with post-surgical adhesions.

Metalloproteases are also involved in the biosynthesis of tumor necrosis factor (TNF), and inhibition of the production or action of TNF and related compounds is an important clinical disease treatment mechanism. TNF-$\alpha$, for example, is a cytokine that at present is thought to be produced initially as a 28 kD cell-associated molecule. It is released as an active, 17 kD form that can mediate a large number of deleterious effects in vitro and in vivo. For example, TNF can cause and/or contribute to the effects of inflammation, rheumatoid arthritis, autoimmune disease, multiple sclerosis, graft rejection, fibrotic disease, cancer, infectious diseases, malaria, mycobacterial infection, meningitis, fever, psoriasis, cardiovascular/pulmonary effects such as post-ischemic reperfusion injury, congestive heart failure, hemorrhage, coagulation, hyperoxic alveolar injury, radiation damage and acute phase responses like those seen with infections and sepsis and during shock such as septic shock and hemodynamic shock. Chronic release of active TNF can cause cachexia and anorexia. TNF can be lethal, and TNF can help control the growth of tumor cells.

TNF-$\alpha$ convertase is a metalloprotease involved in the formation of soluble TNF-$\alpha$. Inhibition of TNF-$\alpha$ convertase (TACE) inhibits production of active TNF-$\alpha$. Compounds that inhibit both MMPs activity and TNF-$\alpha$ production have been disclosed in WIPO International Publication Nos. WO 94/24140, WO 94/02466 and WO 97/20824. Compounds that inhibit MMPs such as collagenase, stromelysin and gelatinase have been shown to inhibit the release of TNF (Gearing et al. *Nature* 376, 555–557 (1994), McGeehan et al., *Nature* 376, 558–561 (1994)). There remains a need for effective MMP inhibitors. There also remains a need for effective TNF-$\alpha$ convertase inhibiting agents.

MMPs are involved in other biochemical processes in mammals as well. Included is the control of ovulation, post-partum uterine involution, possibly implantation, cleavage of APP ($\beta$-Amyloid Precursor Protein) to the amyloid plaque and inactivation of $\alpha_1$-protease inhibitor ($\alpha_1$-PI). Inhibition of these metalloproteases permits the control of fertility and the treatment or prevention of Alzheimers Disease. In addition, increasing and maintaining the levels of an endogenous or administered serine protease inhibitor drug or biochemical such as $\alpha_1$-PI supports the treatment and prevention of diseases such as emphysema, pulmonary diseases, inflammatory diseases and diseases of aging such as loss of skin or organ stretch and resiliency.

Inhibition of selected MMPs can also be desirable in other instances. Treatment of cancer and/or inhibition of metastasis and/or inhibition of angiogenesis are examples of approaches to the treatment of diseases wherein the selective inhibition of stromelysin, gelatinase A or B, or collagenase III appear to be the relatively most important enzyme or enzymes to inhibit especially when compared with collagenase I (MMP-1). A drug that does not inhibit collagenase I can have a superior therapeutic profile. Osteoarthritis, another prevalent disease wherein it is believed that cartilage degradation of inflamed joints is at least partially caused by MMP-13 released from cells such as stimulated chrondrocytes, may be best treated by administration of drugs one of whose modes of action is inhibition of MMP-13. See, for example, Mitchell et al., *J. Clin. Invest.,* 97:761–768 (1996) and Reboul et al., *J. Clin. Invest.,* 97:2011–2019 (1996).

Inhibitors of metalloproteases are known. Examples include natural biochemicals such as tissue inhibitors of metalloproteinases (TIMPs), $\alpha_2$-macroglobulin and their analogs or derivatives. These endogenous inhibitors are high molecular weight protein molecules that form inactive complexes with metalloproteases. A number of smaller peptide-like compounds that inhibit metalloproteases have been described. Mercaptoamide peptidyl derivatives have shown ACE inhibition in vitro and in vivo. Angiotensin converting enzyme (ACE) aids in the production of angiotensin II, a potent pressor substance in mammals and inhibition of this enzyme leads to the lowering of blood pressure.

Thiol group-containing amide or peptidyl amide-based metalloprotease (MMP) inhibitors are known as is shown in, for example, WO95/12389, WO96/11209 and U.S. Pat. No. 4,595,700. Hydroxamate group-containing MMP inhibitors are disclosed in a number of published patent applications such as WO 95/29892, WO 97/24117, WO 97/49679 and EP 0 780 386 that disclose carbon back-boned compounds, and WO 90/05719, WO 93/20047, WO 95/09841 and WO 96/06074 that disclose hydroxamates that have a peptidyl back-bones or peptidomimetic back-bones, as does the article by Schwartz et al., *Progr. Med. Chem.,* 29:271–334 (1992) and those of Rasmussen et al., *Pharmacol. Ther.,* 75(1J): 69–75 (1997) and Denis et al., *Invest. New Drugs,* 15(3): 175–185 (1997).

One possible problem associated with known MMP inhibitors is that such compounds often exhibit the same or similar inhibitory effects against each of the MMP enzymes. For example, the peptidomimetic hydroxamate known as batimastat is reported to exhibit $IC_{50}$ values of about 1 to about 20 nanomolar (nM) against each of MMP-1, MMP-2, MMP-3, MMP-7, and MMP-9. Marimastat, another peptidomimetic hydroxamate was reported to be another broad-spectrum MMP inhibitor with an enzyme inhibitory spectrum very similar to batimastat, except that marimastat exhibited an $IC_{50}$ value against MMP-3 of 230 nM. Rasmussen et al., *Pharmacol. Ther.,* 75(1): 69–75 (1997).

Meta analysis of data from Phase I/II studies using marimastat in patients with advanced, rapidly progressive, treatment-refractory solid tumor cancers (colorectal, pancreatic, ovarian, prostate) indicated a dose-related reduction in the rise of cancer-specific antigens used as surrogate markers for biological activity. Although marimastat exhibited some measure of efficacy via these markers, toxic side effects were noted. The most common drug-related toxicity of marimastat in those clinical trials was musculoskeletal pain and stiffness, often commencing in the small joints in the hands, spreading to the arms and shoulder. A short dosing holiday of 1–3 weeks followed by dosage reduction permits treatment to continue. Rasmussen et al., *Pharmacol. Ther.,* 75(1): 69–75 (1997). It is thought that the lack of specificity of inhibitory effect among the MMPs may be the cause of that effect.

International application WO 98/38163, published on Sep. 3, 1998 disclose a large group of hydroxamate inhibitors of MMPs and TACE. The compounds of WO 98/38163 contain one or two substituents adjacent to the hydroxamate functionality and a substituent that can be an aromatic sulfonyl group adjacent to those one or two substituents.

International application WO 98/37877, published on Sep. 3, 1998 discloses compounds that contain a 5- to 7-membered heterocyclic ring adjacent to the hydroxamate functionality and can contain an aromatic sulfonyl group adjacent to the heterocyclic ring.

Although many of the known MMP inhibitors such as batimastat, marimastat and the hydroxamates of WO 98/37877 and WO 98/38163 exhibit a broad spectrum of activity against MMPs, those compounds are not particularly selective in their inhibitory activity. This lack of selectivity may be the cause of the musculoskeletal pain and stiffness observed with their use. In addition, it can be therapeutically advantageous to utilize a medicament that is selective in its activity as compared to a generally active material so that treatment can be more closely tailored to the pathological condition presented by the host mammal. The disclosure that follows describes a process for treating a host mammal having a condition associated with pathological matrix metalloprotease activity that utilizes a compound that selectively inhibits one or more MMPs, while exhibiting less activity against at least MMP-1.

SUMMARY OF THE INVENTION

The present invention is directed to a treatment process that comprises administering a contemplated aromatic sulfone hydroxamic acid metalloprotease inhibitor in an effective amount to a host mammal having a condition associated with pathological metalloprotease activity. A contemplated molecule, inter alia, exhibits excellent inhibitory activity of one or more matrix metalloprotease (MMP) enzymes, such as MMP-2, MMP-9 and MMP-13, while exhibiting substantially less inhibition at least of MMP-1. By "substantially less" it is meant that a contemplated compound exhibits an $IC_{50}$ value ratio against one or more of MMP-2, MMP-9 or MMP-13 as compared to its $IC_{50}$ value against MMP-1, e.g., $IC_{50}$ MMP-2:$IC_{50}$ MMP-1, that is less than about 1:10, preferably less than about 1:100, and most preferably less than about 1:1000 in the in vitro inhibition assay utilized hereinafter. The invention also contemplates particular compounds that selectively inhibit the activity of one or more of MMP-2, MMP-9 and MMP-13, while exhibiting substantially less inhibition at least of MMP-1, as well as a composition containing such a MMP inhibitor as active ingredient. The invention further contemplates intermediates in the preparation of a contemplated aromatic sulfone hydroxamic acid molecule and a process for preparing an aromatic sulfone hydroxamic acid molecule.

Briefly, one embodiment of the present invention is directed to a treatment process that comprises administering a contemplated aromatic sulfone hydroxamic acid metalloprotease inhibitor that selectively inhibits matrix metalloprotease activity as above in an effective amount to a host mammal having a condition associated with pathological metalloprotease activity. The administered enzyme inhibitor corresponds in structure to formula (I), below, or a pharmaceutically acceptable salt thereof:

I

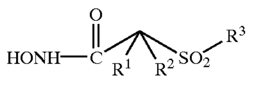

wherein $R^1$ and $R^2$ are both hydrido or $R^1$ and $R^2$ together with the atoms to which they are bonded form a 5- to 8-membered ring containing one, two or three heteroatoms in the ring that are oxygen, sulfur or nitrogen.

$R^3$ in formula I is an optionally substituted aryl or optionally substituted heteroaryl radical. When $R^3$ is a substituted aryl or heteroaryl radical, a contemplated substituent is selected from the group consisting of an aryl, heteroaryl, aralkyl, heteroaralkyl, aryloxy, arylthio, aralkoxy, heteroaralkoxy, aralkoxyalkyl, aryloxyalkyl, aralkanoylalkyl, arylcarbonylalkyl, aralkylaryl, aryloxyalkylaryl, aralkoxyaryl, arylazoaryl, arylhydrazinoaryl, alkylthioaryl, arylthioalkyl, alkylthioaralkyl, aralkylthioalkyl, an aralkylthioaryl radical, the sulfoxide or sulfone of any of the thio substituents, and a fused ring structure comprising two or more 5- or 6-membered rings selected from the group consisting of aryl, heteroaryl, carbocyclic and heterocyclic.

The substituent bonded to the aryl or heteroaryl radical of which the $R^3$ radical is comprised itself can be substituted with one or more substituents; i.e., the substituting substituent is optionally substituted. When that aryl or heteroaryl radical is substituted, and the substituting moiety (group, substituent, or radical) is itself substituted, the last-named substituent is independently selected from the group consisting of a cyano, perfluoroalkyl, trifluoromethoxy, trifluoromethylthio, haloalkyl, trifluoromethylalkyl, aralkoxycarbonyl, aryloxycarbonyl, hydroxy, halo, alkyl, alkoxy, nitro, thiol, hydroxycarbonyl, aryloxy, arylthio, aralkyl, aryl, arylcarbonylamino, heteroaryloxy, heteroarylthio, heteroaralkyl, cycloalkyl, heterocyclooxy, heterocyclothio, heterocycloamino, cycloalkyloxy, cycloalkylthio, heteroaralkoxy, heteroaralkylthio, aralkoxy, aralkylthio, aralkylamino, heterocyclo, heteroaryl, arylazo, hydroxycarbonylalkoxy, alkoxycarbonylalkoxy, alkanoyl, arylcarbonyl, aralkanoyl, alkanoyloxy, aralkanoyloxy, hydroxyalkyl, hydroxyalkoxy, alkylthio, alkoxyalkylthio, alkoxycarbonyl, aryloxyalkoxyaryl, arylthioalkylthioaryl, aryloxyalkylthioaryl, arylthioalkoxyaryl, hydroxycarbonylalkoxy, hydroxycarbonylalkylthio, alkoxycarbonylalkoxy, alkoxycarbonylalkylthio, amino, wherein the amino nitrogen is (i) unsubstituted, or (ii) substituted with one or two substituents that are independently selected from the group consisting of an alkyl, aryl, heteroaryl, aralkyl, cycloalkyl, aralkoxycarbonyl, alkoxycarbonyl, arylcarbonyl, aralkanoyl, heteroarylcarbonyl, heteroaralkanoyl and an alkanoyl group, or (iii) wherein the amino nitrogen and two substituents attached thereto form a 5- to 8-membered heterocyclo or heteroaryl ring containing zero to two additional heteroatoms that are nitrogen, oxygen or sulfur and which ring itself is (a) unsubstituted or (b) substituted with one or two groups independently selected from the group consisting of an aryl, alkyl, heteroaryl, aralkyl, heteroaralkyl, hydroxy, alkoxy, alkanoyl, cycloalkyl, heterocycloalkyl, alkoxycarbonyl, hydroxyalkyl, trifluoromethyl, benzofused heterocycloalkyl, hydroxyalkoxyalkyl, aralkoxycarbonyl, hydroxycarbonyl, aryloxycarbonyl, benzofused heterocycloalkoxy, benzofused cycloalkylcarbonyl, heterocycloalkylcarbonyl, and a cycloalkylcarbonyl group, carbonylamino wherein the carbonylamino nitrogen is (i) unsubstituted, or (ii) is the reacted amine of an amino acid, or (iii) substituted with one or two radicals selected from the group consisting of an alkyl, hydroxyalkyl, hydroxyheteroaralkyl, cycloalkyl, aralkyl, trifluoromethylalkyl, heterocycloalkyl, benzofused heterocycloalkyl, benzofused heterocycloalkyl, benzofused cycloalkyl, and an N,N-dialkylsubstituted alkylamino-alkyl group, or (iv) the carboxamido nitrogen and two substituents bonded thereto together form a 5- to 8-membered heterocyclo, heteroaryl or benzofused heterocycloalkyl ring that is itself unsubstituted or substituted with one or two radicals independently selected from the group consisting of an alkyl, alkoxycarbonyl, nitro, heterocycloalkyl, hydroxy, hydroxycarbonyl, aryl, aralkyl, heteroaralkyl and an amino group, wherein the amino nitrogen is (i) unsubstituted, or (ii) substituted with one or two substituents that are independently selected from the group consisting of alkyl, aryl, and heteroaryl, or (iii) wherein the amino nitrogen and two substituents attached thereto form a 5- to 8-membered heterocyclo or heteroaryl ring, and an aminoalkyl group wherein the aminoalkyl nitrogen is (i) unsubstituted, or (ii) substituted with one or two substituents independently selected from the group consisting of an alkyl, aryl, aralkyl, cycloalkyl, aralkoxycarbonyl, alkoxycarbonyl, and an alkanoyl group, or (iii) wherein the aminoalkyl nitrogen and two substituents attached thereto form a 5- to 8-membered heterocyclo or heteroaryl ring.

In preferred practice, $R^1$ and $R^2$ together with the atoms to which they are bonded form a 6-membered ring.

An $R^3$ radical preferably has a length that is greater than that of a pentyl group [a $-(CH_2)_4CH_3$ chain] and more preferably greater than about that of a hexyl group [a $-(CH_2)_5CH_3$ chain]. An $R^3$ radical preferably has a length that is less than that of an icosyl group [a $-(CH_2)_{19}CH_3$ chain], and more preferably a length that is less than that of a stearyl group [a $-(CH_2)_{17}CH_3$ chain). A preferred $R^3$ group contains two or more 5- or 6-membered rings. A contemplated $R^3$ group, when rotated about an axis drawn through the $SO_2$-bonded 1-position and the substituent-bonded 4-position of a 6-membered ring or the $SO_2$-bonded 1-position and substituent-bonded 3- or 4-position of a 5-membered ring, defines a three-dimensional volume whose widest dimension has the width in a direction transverse to that axis to rotation of about one furanyl ring to about two phenyl rings.

It is also preferred that a $R^3$ radical be a single-ringed aryl or heteroaryl group that is 5- or 6-membered, and is itself substituted at its own 4-position when a 6-membered ring or at its own 3- or 4-position when a 5-membered ring with an optionally substituted substituent selected from the group consisting of one other single-ringed aryl or heteroaryl group, a $C_3$–$C_{14}$ alkyl group, a N-piperidyl group, a N-piperazyl group, a phenoxy group, a thiophenoxy group, a 4-thiopyridyl group, a phenylazo group and a benzamido group. The substituent of the 5- or 6-membered aryl or heteroaryl group can itself be substituted as discussed before.

A preferred compound for use in a contemplated process has a structure that corresponds to formula II, below, or a pharmaceutically acceptable salt thereof:

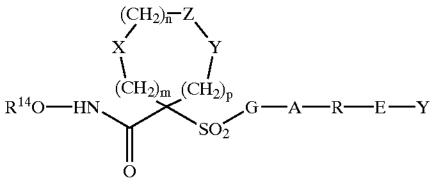

II wherein $R^{14}$ is hydrido, a pharmaceutically acceptable cation or $C(W)R^{15}$ where W is O or S and $R^{15}$ is selected from the group consisting of an $C_1$–$C_6$-alkyl, aryl, $C_1$–$C_6$-alkoxy, heteroaryl-$C_1$–$C_6$-alkyl, $C_3$–$C_8$-cycloalkyl-$C_1$–$C_6$-alkyl, aryloxy, ar-$C_1$–$C_6$-alkoxy, ar-$C_1$–$C_6$-alkyl, heteroaryl and amino $C_1$–$C_6$-alkyl group wherein the aminoalkyl nitrogen is (i) unsubstituted or (ii) substituted with one or two substituents independently selected from the group consisting of an $C_1$–$C_6$-alkyl, aryl, ar-$C_1$–$C_6$-alkyl, $C_3$–$C_8$-cycloalkyl-$C_1$–$C_6$-alkyl, ar-$C_1$–$C_6$-alkoxycarbonyl, $C_1$–$C_6$-alkoxycarbonyl, and $C_1$–$C_6$-alkanoyl radical, or (iii) wherein the amino $C_1$–$C_6$-alkyl nitrogen and two substituents attached thereto form a 5- to 8-membered heterocyclo or heteroaryl ring;

m is zero, 1 or 2;

n is zero, 1 or 2;

p is zero, 1 or 2;

the sum of m+n +p=1, 2, 3 or 4;

(a) one of X, Y and Z is selected from the group consisting of C(O), $NR^6$, O, S, S(O), $S(O)_2$ and $NS(O)_2R^7$, and the remaining two of X, Y and Z are $CR^8R^9$, and $CR^{10}R^{11}$, or (b) X and Z or Z and Y together constitute a moiety that is selected from the group consisting of $NR^6C(O)$, $NR^6S(O)$, $NR^6S(O)_2$, $NR^6S$, $NR^6O$, SS, $NR^6NR^6$ and OC(O), with the remaining one of X, Y and Z being $CR^8R^9$, or (c) n is zero and X, Y and Z together constitute a moiety selected from the group consisting of

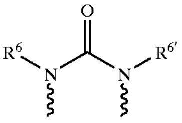 , 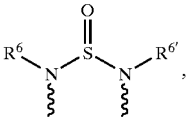 , 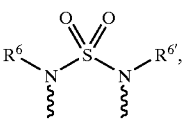

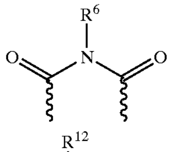 , 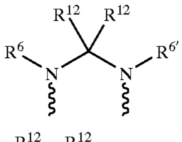 , 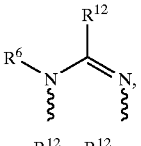

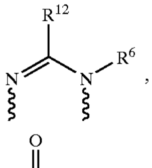 , 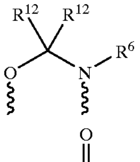 , 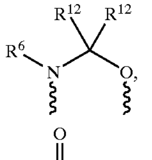

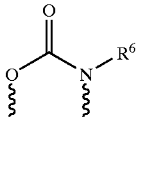 , 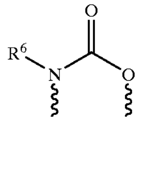 , 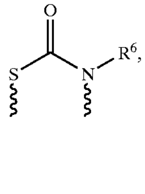

-continued

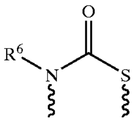 , 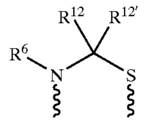 , 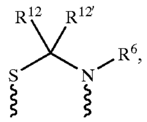

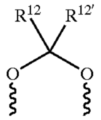 , 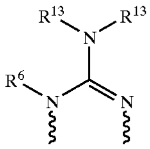 and 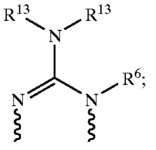

wherein wavy lines are bonds to the atoms of the depicted ring;

$R^6$ and $R^{6'}$ are independently selected from the group consisting of hydrido, $C_1$–$C_6$-alkanoyl, $C_6$-aryl -$C_1$–$C_6$-alkyl, aroyl, bis($C_1$–$C_6$-alkoxy-$C_1$–$C_6$-alkyl)-$C_1$–$C_6$-alkyl, $C_1$–$C_6$-alkyl, $C_1$–$C_6$-haloalkyl, $C_1$–$C_6$-perfluoroalkyl, $C_1$–$C_6$-trifluoromethylalkyl, $C_1$–$C_6$-perfluoroalkoxy-$C_1$–$C_6$-alkyl, $C_1$–$C_6$-alkoxy-$C_1$–$C_6$-alkyl, $C_3$–$C_6$-cycloalkyl, $C_3$–$C_8$-heterocycloalkyl, $C_3$–$C_8$-heterocycloalkylcarbonyl, $C_6$-aryl, $C_5$–$C_6$-heterocyclo, $C_5$–$C_6$-heteroaryl, $C_3$–$C_8$-cycloalkyl-$C_1$–$C_6$-alkyl, $C_6$-aryloxy-$C_1$–$C_6$-alkyl, heteroaryloxy-$C_1$–$C_6$-alkyl, heteroaryl-$C_1$–$C_6$-alkoxy-$C_1$–$C_6$-alkyl, heteroarylthio-$C_1$–$C_6$-alkyl, $C_6$-arylsulfonyl, $C_1$–$C_6$-alkylsulfonyl, $C_5$–$C_6$-heteroarylsulfonyl, carboxy-$C_1$–$C_6$-alkyl, $C_1$–$C_4$-alkoxycarbonyl-$C_1$–$C_6$-alkyl, aminocarbonyl, $C_1$–$C_6$-alkyliminocarbonyl, $C_6$-aryliminocarbonyl, $C_5$–$C_6$-heterocycloiminocarbonyl, $C_6$-arylthio-$C_1$–$C_6$-alkyl, $C_1$–$C_6$-alkylthio-$C_1$–$C_6$-alkyl, $C_6$-arylthio-$C_3$–$C_6$-alkenyl, $C_1$–$C_4$-alkylthio-$C_3$–$C_6$-alkenyl, $C_5$–$C_6$-heteroaryl-$C_1$–$C_6$-alkyl, halo-$C_1$–$C_6$-alkanoyl, hydroxy-$C_1$–$C_6$-alkanoyl, thiol-$C_1$–$C_6$-alkanoyl, $C_3$–$C_6$-alkenyl, $C_3$–$C_6$-alkynyl, $C_1$–$C_4$-alkoxy-$C_1$–$C_4$-alkyl, $C_1$–$C_5$-alkoxycarbonyl, aryloxycarbonyl, $NR^8R^9$—$C_1$–$C_5$-alkylcarbonyl, hydroxy-$C_1$–$C_5$-alkyl, an aminocarbonyl wherein the aminocarbonyl nitrogen is (i) unsubstituted or (ii) substituted with one or two radicals independently selected from the group consisting of $C_1$–$C_6$-alkyl, ar-$C_1$–$C_6$-alkyl, $C_3$–$C_8$-cycloalkyl and a $C_1$–$C_6$-alkanoyl group, hydroxyaminocarbonyl, an aminosulfonyl group wherein the aminosulfonyl nitrogen is (i) unsubstituted or (ii) substituted with one or two radicals independently selected from the group consisting of $C_1$–$C_6$-alkyl, ar-$C_1$–$C_6$-alkyl, $C_3$–$C_8$-cycloalkyl and a $C_1$–$C_6$-alkanoyl group, an amino-$C_1$–$C_6$-alkylsulfonyl group wherein the amino-$C_1$–$C_6$-alkylsulfonyl nitrogen is (i) unsubstituted or (ii) substituted with one or two radicals independently selected from the group consisting of $C_1$–$C_6$-alkyl, ar-$C_1$–$C_6$-alkyl, $C_3$–$C_8$-cycloalkyl and a $C_1$–$C_6$-alkanoyl group and an amino-$C_1$–$C_6$-alkyl group wherein the aminoalkyl nitrogen is (i) unsubstituted or (ii) substituted with one or two radicals independently selected from the group consisting of $C_1$–$C_6$-alkyl, ar-$C_1$–$C_6$-alkyl, $C_3$–$C_8$-cycloalkyl and a $C_1$–$C_6$-alkanoyl group;

$R^7$ is selected from the group consisting of a arylalkyl, aryl, heteroaryl, heterocyclo, $C_1C_6$-alkyl, $C_3$–$C_6$- alkynyl, $C_3$–$C_6$-alkenyl, $C_1$–$C_6$-carboxyalkyl and a $C_1$–$C_6$-hydroxyalkyl group;

$R^8$ and $R^9$ and $R^{10}$ and $R^{11}$are independently selected from the group consisting of a hydrido, hydroxy, $C_1$–$C_6$-alkyl, aryl, ar-$C_1$–$C_6$-alkyl, heteroaryl, heteroar-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aralkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylar-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, the sulfoxide or sulfone of any said thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl and an amino-$C_1$–$C_6$-alkyl group wherein the aminoalkyl nitrogen is (i) unsubstituted or (ii) substituted with one or two radicals independently selected from the group consisting of $C_1$–$C_6$-alkyl, ar-$C_1$–$C_6$-alkyl, cycloalkyl and $C_1$–$C_6$-alkanoyl, or wherein $R^8$ and $R^9$ or $R^{10}$ and $R^{11}$and the carbon to which they are bonded form a carbonyl group, or wherein $R^8$ and $R^9$ or $R^{10}$ and $R^{11}$, or $R^8$ and $R^{10}$ together with the atoms to which they are bonded form a 5- to 8-membered carbocyclic ring, or a 5- to 8-membered heterocyclic ring containing one or two heteroatoms that are nitrogen, oxygen, or sulfur, with the proviso that only one of $R^8$ and $R^9$ or $R^{10}$ and $R^{11}$is hydroxy;

$R^{12}$ and $R^{12'}$ are independently selected from the group consisting of a hydrido, $C_1$–$C_6$-alkyl, aryl, ar-$C_1$–$C_6$-alkyl, heteroaryl, heteroaralkyl, $C_2$–$C_6$-alkynyl, $C_2$–$C_6$-alkenyl, thiol-$C_1$–$C_6$-alkyl, cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aryloxy-$C_1$–$C_6$-alkyl, amino-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylar-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, $C_1$–$C_6$-alkylthio-$C_1$–$C_6$-alkyl, arylthio-$C_1$–$C_6$-alkyl, heteroarylthio-$C_1$–$C_6$-alkyl, the sulfoxide or sulfone of any said thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl and an amino-$C_1$–$C_6$-alkyl group wherein the aminoalkyl nitrogen is (i) unsubstituted or (ii) substituted with one or two radicals independently selected from the group consisting of $C_1$–$C_6$-alkyl, ar-$C_1$–$C_6$-alkyl, cycloalkyl and $C_1$–$C_6$-alkanoyl;

$R^{13}$ is selected from the group consisting of a hydrido, benzyl, phenyl, $C_1$–$C_6$-alkyl, $C_2$–$C_6$-alkynyl, $C_2$–$C_6$-alkenyl and a $C_1$–$C_6$-hydroxyalkyl group; and G—A—R—E—Y is a substituent that preferably has a length greater than that of a pentyl group, and more preferably has a length greater than that of a hexyl group. The substituent G—A—R—E—Y preferably has a length that is less than that of an icosyl group, and is more preferably less than that of a stearyl group. In this substituent:

G is an aryl or heteroaryl group;

A is selected from the group consisting of (1) —O—;

(2) —S—;

(3) —$NR^{17}$—;

(4) —CO—N($R^{17}$) or —N($R^{17}$)—CO—, wherein $R^{17}$ is hydrogen, $C_1$–$C_4$-alkyl, or phenyl;

(5) —CO—O— or —O—CO—;

(6) —O—CO—O—;

(7) —HC═CH—;

(8) —NH—CO—NH—;

(9) —C≡C—;

(10) —NH—CO—O— or —O—CO—NH—;

(11) —N═N—;

(12) —NH—NH—; and

(13) —CS—N($R^{18}$)— or —N($R^{18}$)—CS—, wherein $R^{18}$ is hydrogen $C_1$–$C_4$-alkyl, or phenyl; or

(14) A is absent and G is bonded directly to R;

R is a moiety selected from the group consisting of alkyl, alkoxyalkyl, aryl, heteroaryl, cycloalkyl, heterocycloalkyl, aralkyl, heteroaralkyl, heterocycloalkylalkyl, cycloalkylalkyl, cycloalkoxyalkyl, heterocycloalkoxyalkyl, aryloxyalkyl, heteroaryloxyalkyl, arylthioalkyl, heteroarylthioalkyl, cycloalkylthioalkyl, and a heterocycloalkylthioalkyl group wherein the aryl or heteroaryl or cycloalkyl or heterocycloalkyl substituent is (i) unsubstituted or (ii) substituted with one or two radicals selected from the group consisting of a halo, alkyl, perfluoroalkyl, perfluoroalkoxy, perfluoroalkylthio, trifluoromethylalkyl, amino, alkoxycarbonylalkyl, alkoxy, $C_1$–$C_2$-alkylene-dioxy, hydroxycarbonylalkyl, hydroxycarbonylalkylamino, nitro, hydroxy, hydroxyalkyl, alkanoylamino, and a alkoxycarbonyl group, and R is other than alkyl or alkoxyalkyl when A is —O— or —S—;

E is selected from the group consisting of (1) —CO($R^{19}$)— or —($R^{19}$)CO—, wherein $R^{19}$ is a heterocycloalkyl, or a cycloalkyl group;

(2) —CONH— or —HNCO—; and (3) —CO—;

(4) —$SO_2$—$R^{19}$— or —$R^{19}$—$SO_2$—;

(5) —$SO_2$—;

(6) —NH—$SO_2$— or —$SO_2$—NH—; or (7) E is absent and R is bonded directly to Y; and Y is absent or is selected from the group consisting of a hydrido, alkyl, alkoxy, haloalkyl, aryl, aralkyl, cycloalkyl, heteroaryl, hydroxy, aryloxy, aralkoxy, heteroaryloxy, heteroaralkyl, perfluoroalkoxy, perfluoroalkylthio, trifluoromethylalkyl, alkenyl, heterocycloalkyl, cycloalkyl, trifluoromethyl, alkoxycarbonyl, and a aminoalkyl group, wherein the aryl or heteroaryl or heterocycloalkyl group is (i) unsubstituted or (ii) substituted with one or two radicals independently selected from the group consisting of an alkanoyl, halo, nitro, aralkyl, aryl, alkoxy, and an amino group wherein the amino nitrogen is (i) unsubstituted or (ii) substituted with one or two groups independently selected from hydrido, alkyl, and an aralkyl group.

A particularly preferred compound for use in a contemplated process corresponds in structure to formula III, below, or a pharmaceutically acceptable salt thereof:

III

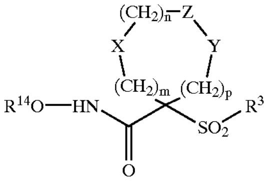

wherein m, n, p, X, Z, Y and $R^{14}$ are as defined above for formula II, and the $R^3$ radical that is defined below is a sub-set of the previously discussed G—A—R—E—Y substituents.

Thus, $R^3$ is a radical that is comprised of a single-ringed aryl or heteroaryl group that is 5- or 6-membered, and is itself substituted at its own 4-position when a 6-membered ring and at its own 3- or 4-position when a 5-membered ring with a substituent selected from the group consisting of a thiophenoxy, 4-chlorophenoxy, 3-chlorophenoxy, 4-methoxyphenoxy, 3-benzodioxol-5-yloxy, 3,4-dimethylphenoxy, 4-fluorophenoxy, 4-fluorothiophenoxy, phenoxy, 4-trifluoromethoxy-phenoxy, 4-trifluoromethylphenoxy, 4-(trifluoromethylthio)-phenoxy, 4-(trifluoromethylthio)-thiophenoxy, 4-chloro-3flourophenoxy, _4-isopropoxyphenoxy, 4-isopropylphenoxy, (2-methyl-1,3-benzothiazol-5-yl) oxy, 4-(1H-imidazol-1-yl)phenoxy, 4-chloro-3-methylphenoxy, 3-methylphenoxy, 4-ethoxyphenoxy, 3,4-difluorophenoxy, 4-chloro-3-methylphenoxy, 4-fluoro-3-chlorophenoxy, 4-(1H-1,2,4-triazol-1-yl)phenoxy, 3,5-difluorophenoxy, 3,4-dichlorophenoxy, 4-cyclopentylphenoxy, 4-bromo-3-methylphenoxy, 4-bromophenoxy, 4-methylthiophenoxy, 4-phenylphenoxy, 4-benzylphenoxy, 6-quinolinyloxy, 4-amino-3-methylphenoxy, 3-methoxyphenoxy, 5,6,7,8-tetrahydro-2-naphthalenyloxy, 3-hydroxymethylphenoxy, N-piperidyl, N-piperazinyl and a 4-benzyloxyphenoxy group.

A more particularly preferred compound for use in a contemplated process has a structure that corresponds to formula IV, below, or a pharmaceutically acceptable salt thereof:

IV

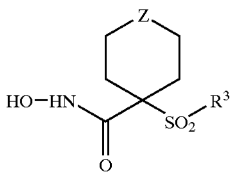

wherein $R^3$ is as defined above for formula I, more preferably as defined for formula II (wherein this $R^3$ group is the G—A—R—E—Y substituent), and more preferably still as defined for formula III, and Z is selected group the group consisting of O, S, $NR^6$, SO, $SO_2$, and $NSO_2R^7$, wherein $R^6$ is selected from the group consisting of hydrido, $C_1$–$C_5$-alkyl, $C_1$–$C_5$-alkanoyl, benzyl, benzoyl, $C_3$–$C_5$-alkynyl, $C_3$–$C_5$-alkenyl, $C_1$–$C_3$-alkoxy-$C_1$–$C_4$-alkyl, $C_3$–$C_6$-cycloalkyl, heteroaryl-$C_1$–$C_6$-alkyl, $C_1$–$C_5$-hydroxyalkyl, $C_1$–$C_5$-carboxyalkyl, $C_1$–$C_5$-alkoxy $C_1$–$C_5$-alkylcarbonyl, and $NR^8R^9$—$C_1$–$C_5$-alkylcarbonyl or $NR^8R^9$—$C_1$–$C_5$-alkyl wherein $R^8$ and $R^9$ are independently hydrido, $C_1$–$C_5$-alkyl, $C_1$-$C_5$-alkoxycarbonyl or aryl-$C_1$–$C_5$-alkoxycarbonyl, or $NR^8R^9$ together form a heterocyclic ring containing 5- to 8-atoms in the ring; and $R^7$ is selected from the group consisting of an arylalkyl, aryl, heteroaryl, heterocyclo, $C_1$–$C_6$-alkyl, $C_3$–$C_6$-alkynyl, $C_3$–$C_6$-alkenyl, $C_1$–$C_6$-carboxyalkyl and a $C_1$–$C_6$-hydroxyalkyl group.

A still more preferred group of compounds for use in a contemplated process correspond in structure to formula V, below, or a pharmaceutically acceptable salt thereof:

V

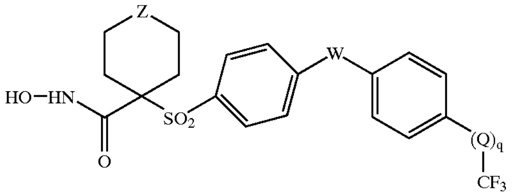

wherein

Z is as previously defined in formula IV;

W and Q are independently oxygen (O), $NR^6$ or sulfur (S), and $R^6$ is as defined in formula IV; and q is zero or one such that when q is zero, the trifluoromethyl group is bonded directly to the depicted phenyl ring.

The use of a compound of formulas I–V, or a pharmaceutically acceptable salt of one of those compounds is contemplated in a before-described process. In addition, the compounds of formulas II, III, IV and V, and their pharmaceutically acceptable salts are contemplated compounds of this invention.

The present invention also contemplates a precursor or intermediate compound that is useful in preparing a compound of formulas I–V. Such an intermediate compound corresponds in structure to formula VI, below:

VI

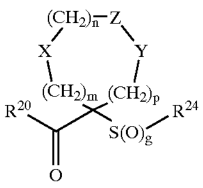

wherein m, n, p, X, Z and Y are as defined above for formula II, g is zero, 1 or 2 and $R^{24}$ is $R^3$ as defined in formulas I, III or IV, is the substituent G—A—R—E—Y of formula II (formula VIA) or is $R^{3'}$, an aryl or heteroaryl group that is substituted with a coupling substituent reactive for coupling with another moiety (formula VIB), such as a nucleophilically displaceable leaving group, D.

VIA

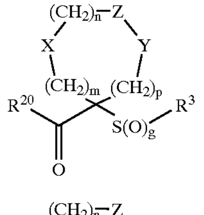

VIB

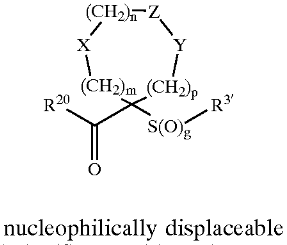

Exemplary nucleophilically displaceable leaving groups, D, include a halo (fluoro, chloro, bromo, or idodo) nitro, azido, phenylsulfoxido, aryloxy, $C_1$–$C_6$-alkoxy, a $C_1$–$C_6$-alkylsulfonate or arylsulfonate group and a trisubstituted ammonium group in which the three substituents are independently aryl, ar-$C_1$–$C_6$-alkyl or $C_1$–$C_6$-alkyl.

$R^{20}$ is (a) —Q—$R^{21}$, where $R^{21}$ is selected from the group consisting of a hydrido, $C_1$–$C_6$-alkyl, aryl, ar-$C_1$–$C_6$-alkyl group and a pharmaceutically acceptable cation, or (b) —NH—O—$R^{22}$ wherein $R^{22}$ is a selectively removable protecting group such as a 2-tetrahydropyranyl, $C_1$–$C_6$-acyl, aroyl, benzyl, p-methoxybenzyloxycarbonyl (MOZ), benzyloxycarbonyl, $C_1$–$C_6$-alkoxycarbonyl, $C_1$–$C_6$-alkoxy-$CH_2$—, $C_1$–$C_6$-alkoxy-$C_1$–$C_6$-alkoxy-$CH_2$—, trisubstituted silyl group or o-nitrophenyl group, peptide synthesis resin and the like. Trisubstituted silyl group is substituted with $C_1$–$C_6$-alkyl, aryl, or ar-$C_1$–$C_6$-alkyl.

A particularly preferred precursor intermediate to an intermediate compound of formula VI is an intermediate compound of formula VII

VII

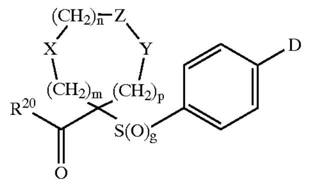

wherein m, n, p, g, X, Z, Y, D and $R^{20}$ are as defined above for formula VI.

Among the several benefits and advantages of the present invention are the provision of compounds and compositions effective as inhibitors of matrix metalloproteinase activity, the provision of such compounds and compositions that are effective for the inhibition of metalloproteinases implicated in diseases and disorders involving uncontrolled breakdown of connective tissue.

More particularly, a benefit of this invention is the provision of a compound and composition effective for selectively inhibiting certain metalloproteinases, such as one or more of MMP-2, MMP-9 and MMP-13, associated with pathological conditions such as, for example, rheumatoid arthritis, osteoarthritis, septic arthritis, corneal, epidermal or gastric ulceration, tumor metastasis, invasion or angiogenesis, periodontal disease, proteinuria, Alzheimer's Disease, coronary thrombosis and bone disease.

An advantage of the invention is the provision of compounds, compositions and methods effective for treating such pathological conditions by selective inhibition of a metalloproteinase such as MMP-2, MMP-9 or MMP-13 associated with such conditions with minimal side effects resulting from inhibition of other metalloproteinases, such as MMP-1, whose activity is necessary or desirable for normal body function.

Yet another advantage of the invention is the provision of a process for preparing such compounds.

Another benefit is the provision of a method for treating a pathological condition associated with abnormal matrix metalloproteinase activity.

A further advantage of the invention is the provision of a process for preparing such compositions.

Still further benefits and advantages of the invention will be apparent to the skilled worker from the disclosure that follows.

DETAILED DESCRIPTION OF THE INVENTION

In accordance with the present invention, it has been discovered that certain aromatic sulfone hydroxamic acids (hydroxamates) are effective for inhibition of matrix metalloproteinases ("MMPs") believed to be associated with uncontrolled or otherwise pathological breakdown of connective tissue. In particular, it has been found that these certain aromatic sulfone hydroxamates are effective for inhibition of one or more enzymes such as MMP-2, MMP-9 and MMP-13, which can be particularly destructive to tissue if present or generated in abnormal quantities or concentrations, and thus exhibit a pathological activity. Included in that pathological activity is the assistance of tumors and tumor cells in the process of penetrating basement membrane, and developing a new or improved blood supply; i.e., angiogenesis.

Moreover, it has been discovered that these aromatic sulfone hydroxamates are selective in the inhibition of one or more of MMP-2, MMP-9 and MMP-13 without excessive inhibition of other collagenases essential to normal bodily function such as tissue turnover and repair. More particularly, it has been found that a contemplated aromatic sulfone hydroxamate of the invention, or a pharmaceutically acceptable salt thereof, is particularly active in inhibiting of one or more of MMP-2, MMP-9 and MMP-13 in an in vitro assay that is predictive of in vivo activity. In addition, while being selective for one or more of MMP-2, MMP-9 and MMP-13, a contemplated aromatic sulfone hydroxamate, or its salt, has a limited or minimal in vitro inhibitory effect on MMP-1.

There is thus a substantial difference in the activity of a compound used in a contemplated process toward one or more of MMP-2, MMP-9 and MMP-13 and MMP-1. This substantial difference is assayed using the in vitro inhibition assay discussed in the examples. A substantial difference in activity corresponds to a compound exhibiting an $IC_{50}$ value against one or more of MMP-2, MMP-9 and MMP-13 that is about 0.1 times that of the compound against MMP-1, and more preferably 0.01 times that against MMP-1 and most preferably 0.001 times that against MMP-1, or more. Indeed, some compounds exhibit selectivity differences measured by $IC_{50}$ values that exceed the bounds of the assay at the number 100,000-fold. These selectivities are illustrated in the Inhibition Tables hereinafter.

Put differently, a contemplated compound can inhibit the activity of MMP-2 compared to MMP-9 or MMP-13 and MMP-1. Similarly, a contemplated compound can inhibit the activity of MMP-13 and MMP-2, while exhibiting less inhibition against MMP-1 and MMP-9. In addition, a contemplated compound can inhibit the activity of a MMP enzyme, while having less of an effect on tumor necrosis factor release.

The advantages of the selectivity of a contemplated compound can be appreciated, without wishing to be bound by theory, by considering the therapeutic uses the compounds. For example, inhibition of MMP-1 is suggested to be undesirable due to its role as a housekeeping enzyme, helping to maintain normal connective tissue turnover and repair. Inhibition of MMP-1 can lead to toxicities or side effects such as such as joint or connective tissue deterioration and pain. On the other hand, MMP-13 has been suggested to be intimately involved in the destruction of joint components in diseases such as osteoarthritis. Thus, potent and selective inhibition of MMP-13 compared with inhibition MMP-1 is highly desirable because a MMP-13 inhibitor can have a positive effect on disease progression in a patient in addition to having an anti-inflammatory effect.

Inhibition of MMP-2 and MMP-9 can be desirable for inhibition of tumor growth, metastasis, invasion and/or angiogenesis. A profile of selective inhibition of MMP-2 and MMP-9 relative to MMP-1 can provide a therapeutic advantage.

Yet another advantage of a contemplated compound is the selectivity with respect to tumor necrosis factor release and/or tumor necrosis factor receptor release that provides the physician with another factor to help select the best drug for a particular patient. While not wishing to be bound by theory, it is believed that there are several factors to this type of selectivity to be considered.

The first is that presence of tumor necrosis factor can be desirable for the control of cancer in the organism, so long as TNF is not present in a toxic excess. Thus, uncontrolled inhibition of release of TNF can be counterproductive and actually can be considered an adverse side effect even in cancer patients. In addition, selectivity with respect to inhibition of the release of the tumor necrosis factor receptor can also be desirable. The presence of that receptor can be desirable for maintaining a controlled tumor necrosis level in the mammal by binding excess TNF.

A contemplated selective MMP inhibitor compound useful in a contemplated process can be administered to by various routes and provide adequate therapeutic blood levels of enzymatically active inhibitor. A compound can be administered, for example, by the oral (IG, PO) or intravenous (IV) routes. Oral administration is advantageous if the patient is ambulatory, not hospitalized, physically able and sufficiently responsible to take drug at the required intervals. This is true even if the person is being treated with more than one drug for one or more diseases. On the other hand, IV drug administration is an advantage in a hospital setting wherein the dose and thus the blood levels can well controlled. A contemplated inhibitor can also be formulated for IM administration if desired. This route of administration can be desirable for the administration of prodrugs or regular drug delivery to patients that are either physically weak or have a poor compliance record or require constant drug blood levels.

Thus, in one embodiment, the present invention is directed to a treatment process that comprises administering a contemplated aromatic sulfone hydroxamic acid metalloprotease inhibitor, or a pharmaceutically acceptable salt thereof, in an effective amount to a host mammal having a condition associated with pathological matrix metalloprotease activity. A contemplated aromatic sulfone hydroxamate inhibitor compound useful in such a process inhibits the activity of one or more of MMP-2, MMP-9 and MMP-13, and exhibits substantially less inhibitory activity against at least MMP-1 in the in vitro assay noted above and discussed in detail hereinbelow. An aromatic sulfone hydroxamate inhibitor compound for use in a contemplated process corresponds in structure to formula I, below:

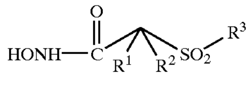

I wherein

In one embodiment, $R^1$ and $R^2$ are both hydrido. In another embodiment, $R^1$ and $R^2$ together with the atoms to which they are bonded form a 5- to 8-membered ring containing one, two or three heteroatoms in the ring that are oxygen, sulfur or nitrogen.

It is preferred that $R^1$ and $R^2$ together with the atoms to which they are bonded form a five- to eight-membered ring that contains one or two heteroatoms in the ring, although $R^1$ and $R^2$ together with the atoms to which they are bonded form a 5- to 8-membered ring containing one, two or three heteroatoms. The heterocyclic ring can itself also be substituted with up to six $C_1$–$C_6$-alkyl groups or groups that comprise a another 5- to 8-membered carbocyclic or heterocyclic ring, an amino group, or contain one or two oxo (carbonyl) groups.

$R^3$ in formula I is an optionally substituted aryl or optionally substituted heteroaryl radical. That R3 radical is selected from the group consisting of an aryl, heteroaryl, aralkyl, heteroaralkyl, aralkoxy, heteroaralkoxy, aralkoxyalkyl, aryloxyalkyl, aralkanoylalkyl, arylcarbonylalkyl, aralkylaryl, aryloxyalkylaryl, aralkoxyaryl, arylazoaryl, arylhydrazinoaryl, alkylthioaryl, arylthioalkyl, alkylthioaralkyl, aralkylthioalkyl, an aralkylthioaryl radical, the sulfoxide or sulfone of any of the thio substituents, and a fused ring structure comprising two or more 5- or 6-membered rings selected from the group consisting of aryl, heteroaryl, carbocyclic and heterocyclic.

The substituent of which $R^3$ is comprised itself is unsubstituted or substituted with one or more substituents independently selected from the group consisting of a cyano, perfluoroalkyl, trifluoromethylalkyl, hydroxy, halo, alkyl, alkoxy, nitro, thiol, hydroxycarbonyl, aryloxy, arylthio, aralkyl, aryl, heteroaryloxy, heteroarylthio, heteroaralkyl, cycloalkyl, heterocyclooxy, heterocyclothio, heterocycloamino, cycloalkyloxy, cycloalkylthio, heteroaralkoxy, heteroaralkylthio, aralkoxy, aralkylthio, aralkylamino, heterocyclo, heteroaryl, arylazo, hydroxycarbonylalkoxy, alkoxycarbonylalkoxy, alkanoyl, arylcarbonyl, aralkanoyl, alkanoyloxy, aralkanoyloxy, hydroxyalkyl, hydroxyalkoxy, alkylthio, alkoxyalkylthio, alkoxycarbonyl, aryloxyalkoxyaryl, arylthioalkylthioaryl, aryloxyalkylthioaryl, arylthioalkoxyaryl, hydroxycarbonylalkoxy, hydroxycarbonylalkylthio, alkoxycarbonylalkoxy, alkoxycarbonylalkylthio, amino, wherein the amino nitrogen is (i) unsubstituted, or (ii) substituted with one or two substituents that are independently selected from the group consisting of an alkyl, aryl, heteroaryl, aralkyl, cycloalkyl, aralkoxycarbonyl, alkoxycarbonyl, arylcarbonyl, aralkanoyl, heteroarylcarbonyl, heteroaralkanoyl and an alkanoyl group, or (iii) wherein the amino nitrogen and two substituents attached thereto form a 5- to 8-membered heterocyclo or heteroaryl ring containing zero to two additional heteroatoms that are nitrogen, oxygen or sulfur and which ring itself is (a) unsubstituted or (b) substituted with one or two groups independently selected from the group consisting of an aryl, alkyl, heteroaryl, aralkyl, heteroaralkyl, hydroxy, alkoxy, alkanoyl, cycloalkyl, heterocycloalkyl, alkoxycarbonyl, hydroxyalkyl, trifluoromethyl, benzofused heterocycloalkyl, hydroxyalkoxyalkyl, aralkoxycarbonyl, hydroxycarbonyl, aryloxycarbonyl, benzofused heterocycloalkoxy, benzofused cycloalkylcarbonyl, heterocycloalkylcarbonyl, and a cycloalkylcarbonyl group, carbonylamino wherein the carboxamido nitrogen is (i) unsubstituted, or (ii) is the reacted amine of an amino acid, or (iii) substituted with one or two radicals selected from the group consisting of an alkyl, hydroxyalkyl, hydroxyheteroaralkyl, cycloalkyl, aralkyl, trifluoromethylalkyl, heterocycloalkyl, benzofused heterocycloalkyl, benzofused heterocycloalkyl, benzofused cycloalkyl, and an N,N-dialkylsubstituted alkylamino-alkyl group, or (iv) the carboxamido nitrogen and two substituents bonded thereto together form a 5- to 8-membered heterocyclo, heteroaryl or benzofused heterocycloalkyl ring that is itself unsubstituted or substituted with one or two radicals independently selected from the group consisting of an alkyl, alkoxycarbonyl, nitro, heterocycloalkyl, hydroxy, hydroxycarbonyl, aryl, aralkyl, heteroaralkyl and an amino group, wherein the amino nitrogen is (i) unsubstituted, or (ii) substituted with one or two substituents that are independently selected from the group consisting of alkyl, aryl, and heteroaryl, or (iii) wherein the amino nitrogen and two substituents attached thereto form a 5- to 8-membered heterocyclo or heteroaryl ring, and an aminoalkyl group wherein the aminoalkyl nitrogen is (i) unsubstituted, or (ii) substituted with one or two substituents independently selected from the group consisting of an alkyl, aryl, aralkyl, cycloalkyl, aralkoxycarbonyl, alkoxycarbonyl, and an alkanoyl group, or (iii) wherein the aminoalkyl nitrogen and two substituents attached thereto form a 5- to 8-membered heterocyclo or heteroaryl ring. A compound of formula I can also be used in the form of a pharmaceutically acceptable salt. The $R^3$ radical has a length that is greater than that of a pentyl group [a $—(CH_2)_4CH_3$ chain], and is more preferably greater than about the length of a hexyl group [a $—(CH_2)_5CH_3$ chain]. A $R^3$ group has a length that is less than that of an icosyl group [eicosyl; a $—(CH_2)_{19}CH_3$ chain), and more preferably, a length that is less than that of a stearyl group [a $—(CH_2)_{17}CH_3$ chain). When rotated about an axis drawn through the $SO_2$-bonded 1-position and the substituent-bonded 4-position of a 6-membered ring or the $SO_2$-bonded 1-position and substituent-bonded 3- or 4-position of a 5-membered ring, a contemplated $R^3$ radical defines a three-dimensional volume whose widest dimension has the width of about one furanyl ring to about two phenyl rings in a direction transverse to that axis to rotation.

Where the $SO_2$-linked $R^3$ radical is 4-phenoxyphenyl for purposes of illustration, a contemplated compound can be viewed as a phenoxyphenylsulfone derivative of the desired 5- to 8-membered ring N-hydroxycarboxamide. Exemplary compounds can therefore be named:

N-hydroxy-1-methyl-[4-(phenoxyphenylsulfonyl)]-4-piperidinecarboxamide,
N-hydroxy-[4-(phenoxyphenylsulfonyl)]tetrahydro-2H-pyran-4-carboxamide,
N-hydroxy-1-methyl-[2,6-dioxo-4-(phenoxyphenylsulfonyl)]-4-piperidinecarboxamide,
N-hydroxy-2,2-dimethyl-[5-(phenoxyphenylsulfonyl) ]-1,3-dioxane-5-carboxamide,
N-hydroxy-1,2-dimethyl-6-oxo-[4-(phenoxyphenylsulfonyl)]-4-piperidinecarboxamide,
N-hydroxy-2,2,6,6,tetramethyl-[4-(phenoxyphenylsulfonyl)]-4-piperidinecarboxamide,
N-hydroxy-1,3-dimethyl-[5-(phenoxyphenylsulfonyl)]-hexahydro-5-pyrimidinecarboxamide,
2-amino-N-hydroxy-[5-(phenoxyphenylsulfonyl)]-1, 4, 5, 6-tetrahydro-5-pyrimidinecarboxamide,
N-hydroxy-1,1-dioxo-[4-(phenoxyphenylsulfonyl)]-1(λ6), 2,6-thiadizinane-4-carboxamide,
N-hydroxy-2-oxo-[5-(phenoxyphenylsulfonyl)]-hexahydro-5-pyrimidinecarboxamide,
N-hydroxy-[2-(phenoxyphenylsulfonyl)]tetrahydro-2-furancarboxamide,
N-hydroxy-1-methyl-[2-(phenoxyphenylsulfonyl)]-2-pyrrolidinecarboxamide,
N-hydroxy-2-methyl-[4-(phenoxyphenylsulfonyl)]-4-piperidinecarboxamide,
N-hydroxy-[3-(phenoxyphenylsulfonyl)]-8-azabicyclo [3.2.1]octane-3-carboxamide,
N-hydroxy-1,1-dioxo-[4-(phenoxyphenylsulfonyl)]-hexahydro-1(lambda6)-thiopyran-4-carboxamide,
N-hydroxy-[3-(phenoxyphenylsulfonyl)]tetrahydro-3-furancarboxamide,
N-hydroxy-[3-(phenoxyphenylsulfonyl)]-3-pyrrolidinecarboxamide,
N-hydroxy-4-[[4-(phenylthio)phenyl]sulfonyl]-1-(2-propynyl)-4-piperidinecarboxamide, monohydrochloride,
N-hydroxy-4-[[4-(phenylthio)phenyl]sulfonyl]-1-(2-propynyl)-4-piperidinecarboxamide, monomethanesulfonate,
tetrahydro-N-hydroxy-4-[[4-[4-[(trifluoromethyl]phenoxy] phenyl]-sulfonyl]-2H-pyran-4-carboxamide,
N-hydroxy-1-(4-pyridinylmethyl)-4-[[4-[4-(triflouromethyl)phenoxy]phenyl]-sulfonyl]-4-piperidinecarboxamide,hydrochloride,
N-hydroxy-1-(3-pyridinylmethyl)-4-[[4-[4-trifluoromethyl) phenoxy]phenyl]-sulfonyl]-4-piperidinecarboxamide, dihydrochloride,
N-hydroxy-1-(2-pyridinylmethyl)-4-[[4-[4-(trifluoromethyl)phenoxy]phenyl]-sulfonyl]-4-piperidinecarboxamide, dihydrochloride,
hydroxy-1-(3-pyridinylmethyl)-4-[[4-[4-(trifluoromethoxy) phenoxy]phenyl]-sulfonyl]-4-piperidinecarboxamide, dihydrochloride,
N-hydroxy-1-(2-methoxyethyl)-4-[[4-[4-(trifluoromethoxy) phenoxy]phenyl]sulfonyl}-4-piperidinecarboxamide, monohydrochloride,
N-hydroxy-1-(2-methoxyethyl)-4-[[4-[4-(trifluoromethyl) phenoxy]phenyl]sulfonyl}-4-piperidinecarboxamide, monohydrochloride,
N-hydroxy-1-(2-methoxyethyl)-4-[[4-[4-[(trifluoromethyl) thio]phenoxy]phenyl]sulfonyl]-4-piperidinecarboxamide, monohydrochloride,
1-cyclopropyl-N-hydroxy-4-[[4-[4-(trifluoromethyl) phenoxy]phenyl]sulfonyl]-4-piperidine-carboxamide, monohydrochloride, and the like.

Several exemplary $R^1$ and $R^2$ groups that together form a contemplated heterocyclic ring are shown in the Tables that follow hereinafter, as well as in the descriptions of those 5- to 8-membered rings and the specific Examples, as are several contemplated aromatic sulfone hydroxamic acid compounds.

In more preferred practice, $R^1$ and $R^2$ of formula I together with the atom to which they are bonded form a 5- to 8-membered ring that contains one, two or three heteroatoms. Most preferably, that ring is a 6-membered ring that contains one heteroatom located at the 4-position relative to the position at which the $SO_2$ group is bonded. Other preferred compounds for use in a contemplated process correspond in structure to one or more of formulas II, III, IV or V, which are discussed hereinafter.

In one embodiment, a preferred compound used in a contemplated process has a structure that corresponds to formula II, below:

II

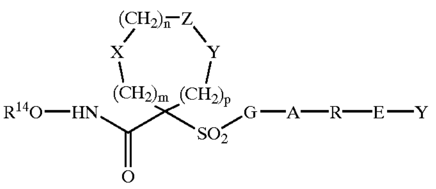

wherein $R^{14}$ is hydrido, a pharmaceutically acceptable cation or $C(W)R^{15}$ where W is O or S and $R^{15}$ is selected from the group consisting of an $C_1$–$C_6$-alkyl, aryl, $C_1$–$C_6$-alkoxy, heteroaryl-$C_1$–$C_6$-alkyl, $C_3$–$C_8$-cycloalkyl-$C_1$–$C_6$-alkyl, aryloxy, ar-$C_1$–$C_6$-alkoxy, ar-$C_1$–$C_6$-alkyl, heteroaryl and amino $C_1$–$C_6$-alkyl group wherein the aminoalkyl nitrogen is (i) unsubstituted or (ii) substituted with one or two substituents independently selected from the group consisting of an $C_1$–$C_6$-alkyl, aryl, ar-$C_1$–$C_6$-alkyl, $C_3$–$C_8$-cycloalkyl-$C_1$–$C_6$-alkyl, ar-$C_1$–$C_6$-alkoxycarbonyl, $C_1$–$C_6$-alkoxycarbonyl, and $C_1$–$C_6$-alkanoyl radical, or (iii) wherein the amino $C_1$–$C_6$-alkyl nitrogen and two substituents attached thereto form a 5- to 8-membered heterocyclo or heteroaryl ring;

m is zero, 1 or 2;

n is zero, 1 or 2;

p is zero, 1 or 2;

the sum of m+n+p=1, 2, 3 or 4;

(a) one of X, Y and Z is selected from the group consisting of C(O), $NR^6$, O, S, S(O), $S(O)_2$ and $NS(O)_2R^7$, and the remaining two of X, Y and Z are $CR^8R^9$, and $CR^{10}R^{11}$, or (b) X and Z or Z and Y together constitute a moiety that is selected from the group consisting of $NR^6C(O)$, $NR^6S(O)$, $NR^6S(O)_2$, $NR^6S$, $NR^6O$, SS, $NR^6NR^6$ and OC(O), with the remaining one of X, Y and Z being $CR^8R^9$, or (c) n is zero and X, Y and Z together constitute a moiety selected from the group consisting of

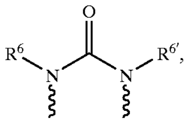, 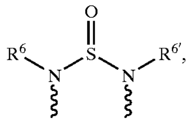, 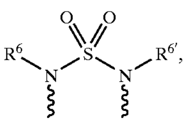,

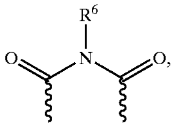, 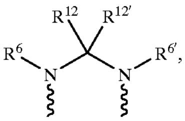, 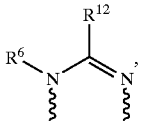,

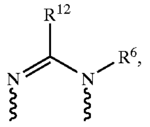, 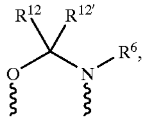, 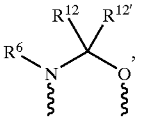,

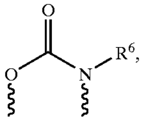, 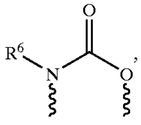, 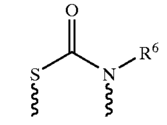

-continued

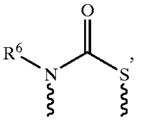, 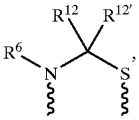, 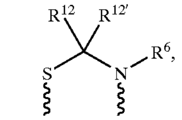,

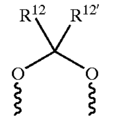 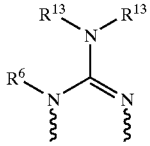 and 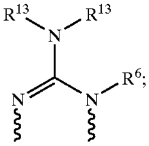;

wherein wavy lines are bonds to the atoms of the depicted ring;

$R^6$ and $R^{6'}$ are independently selected from the group consisting of hydrido, $C_1$–$C_6$-alkanoyl, $C_6$-aryl-$C_1$–$C_6$-alkyl, aroyl, bis($C_1$–$C_6$-alkoxy-$C_1$–$C_6$-alkyl)-$C_1$–$C_6$-alkyl, $C_1$–$C_6$-alkyl, $C_1$–$C_6$-haloalkyl, $C_1$–$C_6$-perfluoroalkoxy, $C_1$–$C_6$-trifluoromethylalkyl, $C_1$–$C_6$-perfluoroalkoxy-$C_1$–$C_6$-alkyl, $C_1$–$C_6$-alkoxy-$C_1$–$C_6$-alkyl, $C_3$–$C_6$-cycloalkyl, $C_3$–$C_8$-heterocycloalkyl, $C_3$–$C_8$-heterocycloalkylcarbonyl, $C_6$-aryl, $C_5$–$C_6$-heterocyclo, $C_5$–$C_6$-heteroaryl, $C_3$–$C_8$-cycloalkyl-$C_1$–$C_6$-alkyl, $C_6$-aryloxy-$C_1$–$C_6$-alkyl, heteroaryloxy-$C_1$–$C_6$-alkyl, heteroaryl-$C_1$–$C_6$-alkoxy-$C_1$–$C_6$-alkyl, heteroarylthio-$C_1$–$C_6$-alkyl, $C_6$-arylsulfonyl, $C_1$–$C_6$-alkylsulfonyl, $C_5$–$C_6$-heteroarylsulfonyl, carboxy-$C_1$–$C_6$-alkyl, $C_1$–$C_4$-alkoxycarbonyl-$C_1$–$C_6$-alkyl, aminocarbonyl, $C_1$–$C_6$-alkyliminocarbonyl, $C_6$-aryliminocarbonyl, $C_5$–$C_6$-heterocycloiminocarbonyl, $C_6$-arylthio-$C_1$–$C_6$-alkyl, $C_1$–$C_6$-alkylthio-$C_1$–$C_6$-alkyl, $C_6$-arylthio-$C_3$–$C_6$-alkenyl, $C_1$–$C_4$-alkylthio-$C_3$–$C_6$-alkenyl, $C_5$–$C_6$-heteroaryl-$C_1$–$C_6$-alkyl, halo-$C_1$–$C_6$-alkanoyl, hydroxy-$C_1$–$C_6$-alkanoyl, thiol-$C_1$–$C_6$-alkanoyl, $C_3$–$C_6$-alkenyl, $C_3$–$C_6$-alkynyl, $C_1$–$C_4$-alkoxy-$C_1$–$C_4$-alkyl, $C_1$–$C_5$-alkoxycarbonyl, aryloxycarbonyl, $NR^8R^9$—$C_1$–$C_5$-alkylcarbonyl, hydroxy-$C_1$–$C_5$-alkyl, an aminocarbonyl wherein the aminocarbonyl nitrogen is (i) unsubstituted or (ii) substituted with one or two radicals independently selected from the group consisting of $C_1$–$C_6$-alkyl, ar-$C_1$–$C_6$-alkyl, $C_3$–$C_8$-cycloalkyl and a $C_1$–$C_6$-alkanoyl group, hydroxyaminocarbonyl, an aminosulfonyl group wherein the aminosulfonyl nitrogen is (i) unsubstituted or (ii) substituted with one or two radicals independently selected from the group consisting of $C_1$–$C_6$-alkyl, ar-$C_1$–$C_6$-alkyl, $C_3$–$C_8$-cycloalkyl and a $C_1$–$C_6$-alkanoyl group, an amino-$C_1$–$C_6$-alkylsulfonyl group wherein the amino-$C_1$–$C_6$-alkylsulfonyl nitrogen is (i) unsubstituted or (ii) substituted with one or two radicals independently selected from the group consisting of $C_1$–$C_6$-alkyl, ar-$C_1$–$C_6$-alkyl, $C_3$–$C_8$-cycloalkyl and a $C_1$–$C_6$-alkanoyl group and an amino-$C_1$–$C_6$-alkyl group wherein the aminoalkyl nitrogen is (i) unsubstituted or (ii) substituted with one or two radicals independently selected from the group consisting of $C_1$–$C_6$-alkyl, ar-$C_1$–$C_6$-alkyl, $C_3$–$C_8$-cycloalkyl and a $C_1$–$C_6$-alkanoyl group;

$R^7$ is selected from the group consisting of a benzyl, phenyl, $C_1$–$C_6$-alkyl, $C_3$–$C_6$-alkynyl, $C_3$–$C_6$-alkenyl and a $C_1$–$C_6$-hydroxyalkyl group;

$R^8$ and $R^9$ and $R^{10}$ and $R^{11}$ are independently selected from the group consisting of a hydrido, hydroxy, $C_1$–$C_6$-alkyl, aryl, ar-$C_1$–$C_6$-alkyl, heteroaryl, heteroar-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aralkoxy-$C_1$–$C_6$-alkyl, $C_1$–$C_6$-alkoxy-$C_1$–$C_6$-alkoxy-$C_1$–$C_6$-alkyl, hydroxy-$C_1$-$C_6$-alkyl, hydroxycarbonyl-$C_1$–$C_6$-alkyl, hydroxycarbonylar-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, the sulfoxide or sulfone of any said thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl and an amino-$C_1$–$C_6$-alkyl group wherein the aminoalkyl nitrogen is (i) unsubstituted or (ii) substituted with one or two radicals independently selected from the group consisting of $C_1$–$C_6$-alkyl, ar-$C_1$–$C_6$-alkyl, cycloalkyl and $C_1$–$C_6$-alkanoyl, or wherein $R^8$ and $R^9$ or $R^{10}$ and $R^{11}$ and the carbon to which they are bonded form a carbonyl group, or wherein $R^8$ and $R^9$ or $R^{10}$ and $R^{11}$, or $R^8$ and $R^{10}$ together with the atoms to which they are bonded form a 5- to 8-membered carbocyclic ring, or a 5- to 8-membered heterocyclic ring containing one or two heteroatoms that are nitrogen, oxygen, or sulfur, with the proviso that only one of $R^8$ and $R^9$ or $R^{10}$ and $R^{11}$ is hydroxy;

$R^{12}$ and $R^{12'}$are independently selected from the group consisting of a hydrido, $C_1$–$C_6$-alkyl, aryl, ar-$C_1$–$C_6$-alkyl, heteroaryl, heteroaralkyl, $C_2$–$C_6$-alkynyl, $C_2$–$C_6$-alkenyl, thiol-$C_1$–$C_6$-alkyl, cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aryloxy-$C_1$–$C_6$-alkyl, amino-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylar-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, $C_1$–$C_6$-alkylthio-$C_1$–$C_6$-alkyl, arylthio-$C_1$–$C_6$-alkyl, heteroarylthio-$C_1$–$C_6$-alkyl, the sulfoxide or sulfone of any said thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl and an amino-$C_1$–$C_6$-alkyl group wherein the aminoalkyl nitrogen is (i) unsubstituted or (ii) substituted with one or two radicals independently selected from the group consisting of $C_1$–$C_6$-alkyl, ar-$C_1$–$C_6$-alkyl, cycloalkyl and $C_1$–$C_6$-alkanoyl;

$R^{13}$ is selected from the group consisting of a hydrido, benzyl, phenyl, $C_1$–$C_6$-alkyl, $C_2$–$C_6$-alkynyl, $C_2$–$C_6$-alkenyl and a $C_1$–$C_6$-hydroxyalkyl group; and G—A—R—E—Y is a substituent that preferably has a length greater than that of a pentyl group, and more preferably has a length greater than that of a hexyl group. The substituent G—A—R—E—Y preferably has a length that is less than that of an icosyl group, and is more preferably less than that of a stearyl group. In this substituent:

G is an aryl or heteroaryl group;

A is selected from the group consisting of (1) —O—;

(2) —S—;

(3) —$NR^{17}$—;

(4) —CO—$N(R^{17})$ or —$N(R^{17})$—CO—, wherein $R^{17}$ is hydrogen, $C_1$–$C_4$-alkyl, or phenyl;

(5) —CO—O— or —O—CO—;

(6) —O—CO—O—;

(7) —HC=CH—;

(8) —NH—CO—NH—;

(9) —C≡C—;

(10) —NH—CO—O— or —O—CO—NH—;

(11) —N=N—;

(12) —NH—NH—; and

(13) —CS—$N(R^{18})$— or —$N(R^{18})$—CS—, wherein $R^{18}$ is hydrogen $C_1$–$C_4$-alkyl, or phenyl; or

(14) A is absent and G is bonded directly to R;

R is a moiety selected from the group consisting of alkyl, alkoxyalkyl, aryl, heteroaryl, cycloalkyl, heterocycloalkyl, aralkyl, heteroaralkyl, heterocycloalkylalkyl, cycloalkylalkyl, cycloalkoxyalkyl, heterocycloalkoxyalkyl, aryloxyalkyl, heteroaryloxyalkyl, arylthioalkyl, heteroarylthioalkyl, cycloalkylthioalkyl, and a heterocycloalkylthioalkyl group wherein the aryl or heteroaryl or cycloalkyl or heterocycloalkyl substituent is (i) unsubstituted or (ii) substituted with one or two radicals selected from the group consisting of a halo, alkyl, perfluoroalkyl, perfluoroalkoxy, perfluoroalkylthio, trifluoromethylalkyl, amino, alkoxycarbonylalkyl, alkoxy, $C_1$–$C_2$-alkylene-dioxy, hydroxycarbonylalkyl, hydroxycarbonylalkylamino, nitro, hydroxy, hydroxyalkyl, alkanoylamino, and a alkoxycarbonyl group, and R is other than alkyl or alkoxyalkyl when A is —O— or —S—;

E is selected from the group consisting of (1) —$CO(R^{19})$— or —$(R^{19})CO$—, wherein $R^{19}$ is a heterocycloalkyl, or a cycloalkyl group;

(2) —CONH— or —HNCO—; and (3) —CO—;

(4) —$SO_2$—$R^{19}$— or —$R^{19}$—$SO_2$—;

(5) —$SO_2$—;

(6) —NH—$SO_2$— or —$SO_2$—NH—; or (7) E is absent and R is bonded directly to Y; and Y is absent or is selected from the group consisting of a hydrido, alkyl, alkoxy, haloalkyl, aryl, aralkyl, cycloalkyl, heteroaryl, hydroxy, aryloxy, aralkoxy, heteroaryloxy, heteroaralkyl, perfluoroalkoxy, perfluoroalkylthio, trifluoromethylalkyl, alkenyl, heterocycloalkyl, cycloalkyl, trifluoromethyl, alkoxycarbonyl, and a aminoalkyl group, wherein the aryl or heteroaryl or heterocycloalkyl group is (i) unsubstituted or (ii) substituted with one or two radicals independently selected from the group consisting of an alkanoyl, halo, nitro, aralkyl, aryl, alkoxy, and an amino group wherein the amino nitrogen is (i) unsubstituted or (ii) substituted with one or two groups independently selected from hydrido, alkyl, and an aralkyl group.

The substituent —G—A—R—E—Y preferably contains two to four carbocyclic or heterocyclic rings, including the aryl or heteroaryl group, G. More preferably, each of those rings is 6-membered. Additional separate preferences for a compound of formula II include: (a) that A is —O— or —S—, (b) R is an aryl, heteroaryl, cycloalkyl or heterocycloalkyl group, (c) E is absent, and (d) Y is selected from the group consisting of hydrido, an alkyl, alkoxy, perfluoroalkoxy and a perfluoroalkylthio group.

A more preferred compound for use in a contemplated process has a structure that corresponds to formula III, below:

III

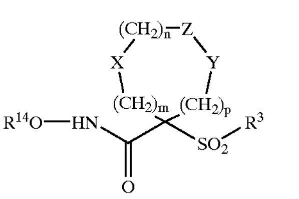

wherein $R^3$ is a single-ringed aryl or heteroaryl group that is 5- or 6-membered, and is itself substituted at its own 4-position when a 6-membered ring and at its own 3- or 4-position when a 5-membered ring with a substituent selected from the group consisting of a thiophenoxy, 4-chlorophenoxy, 3-chlorophenoxy, 4-methoxyphenoxy, 3-benzodioxol-5-yloxy, 3,4-dimethylphenoxy, 4-fluoro-phenoxy, 4-fluorothiophenoxy, phenoxy, 4-trifluoromethoxyphenoxy, 4-trifluoromethylphenoxy, 4-(trifluoromethylthio)phenoxy, 4-(trifluoromethylthio)thiophenoxy, 4-chloro-3-fluorophenoxy, 4-isopropoxyphenoxy, 4-isopropylphenoxy, (2-methyl-1,3-benzothiazol-5-yl)oxy, 4-(1H-imidazol-1-yl)phenoxy, 4-chloro-3-methylphenoxy, 3-methylphenoxy, 4-ethoxyphenoxy, 3,4-difluorophenoxy, 4-chloro-3-methylphenoxy, 4-fluoro-3-chlorophenoxy, 4-(1H-1,2,4-triazol-1-yl)phenoxy, 3,5-difluorophenoxy, 3,4-dichlorophenoxy, 4-cyclopentylphenoxy, 4-bromo-3-methylphenoxy, 4-bromophenoxy, 4-methylthiophenoxy, 4-phenylphenoxy, 4-benzylphenoxy, 6-quinolinyloxy, 4-amino-3-methylphenoxy, 3-methoxyphenoxy, 5,6,7,8-tetrahydro-2-naphthalenyloxy, 3-hydroxymethylphenoxy, and a 4-benzyloxyphenoxy group;

$R^{14}$ is hydrido, a pharmaceutically acceptable cation or $C(W)R^{15}$ where W is O or S and $R^{15}$ is selected from the group consisting of an $C_1$–$C_6$-alkyl, aryl, $C_1$–$C_6$-alkoxy, heteroaryl-$C_1$–$C_6$-alkyl, $C_3$–$C_8$-cycloalkyl-$C_1$–$C_6$-alkyl, aryloxy, ar-$C_1$–$C_6$-alkoxy, ar-$C_1$–$C_6$-alkyl, heteroaryl and amino $C_1$–$C_6$-alkyl group wherein the aminoalkyl nitrogen is (i) unsubstituted or (ii) substituted with one or two substituents independently selected from the group consisting of an $C_1$–$C_6$-alkyl, aryl, ar-$C_1$–$C_6$-alkyl, $C_3$–$C_8$-cycloalkyl-$C_1$–$C_6$-alkyl, ar-$C_1$–$C_6$-alkoxycarbonyl, $C_1$–$C_6$-alkoxycarbonyl, and a $C_1$–$C_6$-alkanoyl radical, or (iii) wherein the amino $C_1$–$C_6$-alkyl nitrogen and two substituents attached thereto form a 5- to 8-membered heterocyclo or heteroaryl ring;

m is zero, 1 or 2;

n is zero, 1 or 2;

p is zero, 1 or 2;

the sum of m+n+p=1, 2, 3 or 4;

(a) one of X, Y and Z is selected from the group consisting of C(O), $NR^6$, O, S, S(O), $S(O)_2$ and $NS(O)_2R^7$, and the remaining two of X, Y and Z are $CR^8R^9$, and $CR^{10}R^{11}$, or (b) x and Z or Z and Y together constitute a moiety that is selected from the group consisting of $NR^6C(O)$, $NR^6S(O)$, $NR^6S(O)_2$, $NR^6S$, $NR^6S$, SS, $NR^6NR^6$ and OC(O), with the remaining one of X, Y and Z being $CR^8R^9$, or (c) n is zero and X, Y and Z together constitute a moiety selected from the group consisting of

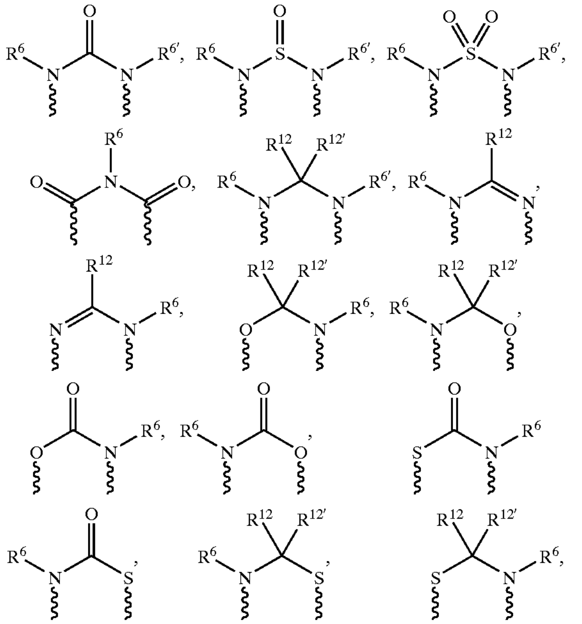

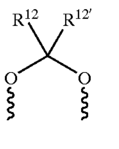

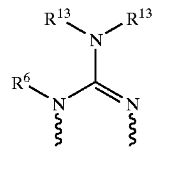

and

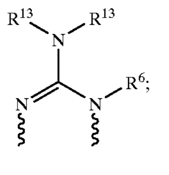

wherein wavy lines are bonds to the atoms of the depicted ring;

$R^6$ and $R^{6'}$ are independently selected from the group consisting of hydrido, $C_1$–$C^6$-alkanoyl, $C_6$-aryl-$C_1$–$C_6$-alkyl, aroyl, bis($C_1$–$C_6$-alkoxy-$C_1$–$C_6$-alkyl)-$C_1$–$C_6$-alkyl$C_1$–$C_6$-alkyl, $C_1$–$C_6$-haloalkyl, $C_1$–$C_6$-perfluoroalkyl, $C_1$–$C_6$-trifluoromethylalkyl, $C_1$–$C_6$-perfluoroalkoxy-$C_1$–$C_6$-alkyl, $C_1$–$C_6$-alkoxy-$C_1$–$C_6$-alkyl, $C_3$–$C_6$-cycloalkyl, $C_3$–$C_8$-heterocycloalkyl, $C_3$–$C_8$-heterocycloalkylcarbonyl, $C_6$-aryl, $C_5$–$C_6$-heterocyclo, $C_5$–$C_6$-heteroaryl, $C_3$–$C_8$-cycloalkyl-$C_1$–$C_6$-alkyl, $C_6$-aryloxy-$C_1$–$C_6$-alkyl, heteroaryloxy-$C_1$–$C_6$-alkyl, heteroaryl-$C_1$–$C_6$-alkoxy-$C_1$–$C_6$-alkyl, heteroarylthio-$C_1$–$C_6$-alkyl, $C_6$-aryisulfonyl, $C_1$–$C_6$-alkylsulfonyl, $C_5$–$C_6$-heteroarylsulfonyl, carboxy-$C_1$–$C_6$-alkyl, $C_1$–$C_4$-alkoxycarbonyl-$C_1$–$C_6$-alkyl, aminocarbonyl, $C_1$–$C_6$-alkyliminocarbonyl, $C_6$-aryliminocarbonyl, $C_5$–$C_6$-heterocycloiminocarbonyl, $C_6$-arylthio-$C_1$–$C_6$-alkyl, $C_1$–$C_6$-alkylthio-$C_1$–$C_6$-alkyl, $C_6$-arylthio-$C_3$–$C_6$-alkenyl, $C_1$–$C_4$-alkylthio-$C_3$–$C_6$-alkenyl, $C_5$–$C_6$-heteroaryl-$C_1$–$C_6$-alkyl, halo-$C_1$–$C_6$-alkanoyl, hydroxy-$C_1$–$C_6$-alkanoyl, thiol-$C_1$–$C_6$-alkanoyl, $C_3$–$C_6$-alkenyl, $C_3$–$C_6$-alkynyl, $C_1$–$C_4$-alkoxy-$C_1$–$C_4$-alkyl, $C_1$–$C_5$-alkoxycarbonyl, aryloxycarbonyl, $NR^8R^9$—$C_1$–$C_5$-alkylcarbonyl, hydroxy-$C_1$–$C_5$-alkyl, an aminocarbonyl wherein the aminocarbonyl nitrogen is (i) unsubstituted or (ii) substituted with one or two radicals independently selected from the group consisting of $C_1$–$C_6$-alkyl, ar-$C_1$–$C_6$-alkyl, $C_3$–$C_8$-cycloalkyl and a $C_1$–$C_6$-alkanoyl group, hydroxyaminocarbonyl, an aminosulfonyl group wherein the aminosulfonyl nitrogen is (i) unsubstituted or (ii) substituted with one or two radicals independently selected from the group consisting of $C_1$–$C_6$-alkyl, ar-$C_1$–$C_6$-alkyl, $C_3$–$C_8$-cycloalkyl and a $C_1$–$C_6$-alkanoyl group, an amino-$C_1$–$C_6$-alkylsulfonyl group wherein the amino-$C_1$–$C_6$-alkylsulfonyl nitrogen is (i) unsubstituted or (ii) substituted with one or two radicals independently selected from the group consisting of $C_1$–$C_6$-alkyl, ar-$C_1$–$C_6$-alkyl, $C_3$–$C_8$-cycloalkyl and a $C_1$–$C_6$-alkanoyl group and an amino-$C_1$–$C_6$-alkyl group wherein the aminoalkyl nitrogen is (i) unsubstituted or (ii) substituted with one or two radicals independently selected from the group consisting of $C_1$–$C_6$-alkyl, ar-$C_1$–$C_6$-alkyl, $C_3$–$C_8$-cycloalkyl and a $C_1$–$C_6$-alkanoyl group;

$R^7$ is selected from the group consisting of a benzyl, phenyl, $C_1$–$C_6$-alkyl, $C_3$–$C_6$-alkynyl, $C_3$–$C_6$-alkenyl and a $C_1$–$C_6$-hydroxyalkyl group;

$R^8$ and $R^9$ and $R^{10}$ and $R^{11}$ are independently selected from the group consisting of a hydrido, hydroxy, $C_1$–$C_6$-alkyl, aryl, ar-$C_1$–$C_6$-alkyl, heteroaryl, heteroar-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aralkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylar-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, the sulfoxide or sulfone of any said thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl and an amino-$C_1$–$C_6$-alkyl group wherein the aminoalkyl nitrogen is (i) unsubstituted or (ii) substituted with one or two radicals independently selected from the group consisting of $C_1$–$C_6$-alkyl, ar-$C_1$–$C_6$-alkyl, cycloalkyl and $C_1$–$C_6$-alkanoyl, or wherein $R^8$ and $R^9$ or $R^{10}$ and $R^{11}$ and the carbon to which they are bonded form a carbonyl group, or wherein $R^8$ and $R^9$ or $R^{10}$ and $R^{11}$, or $R^8$ and $R^{10}$ together with the atoms to which they are bonded form a 5- to 8-membered carbocyclic ring, or a 5- to 8-membered heterocyclic ring containing one or two heteroatoms that are nitrogen, oxygen, or sulfur, with the proviso that only one of $R^8$ and $R^9$ or $R^{10}$ and $R^{11}$ is hydroxy;

$R^{12}$ and $R^{12'}$ are independently selected from the group consisting of a hydrido, $C_1$–$C_6$-alkyl, aryl, ar-$C_1$–$C_6$-alkyl, heteroaryl, heteroaralkyl, $C_2$–$C_6$-alkynyl, $C_2$–$C_6$-alkenyl, thiol-$C_1$–$C_6$-alkyl, cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aryloxy-$C_l$–$C_6$-alkyl, amino-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylar-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, $C_1$–$C_6$-alkylthio-$C_1$–$C_6$-alkyl, arylthio-$C_1$–$C_6$-alkyl, heteroarylthio-$C_1$–$C_6$-alkyl, the sulfoxide or sulfone of any said thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl and an amino-$C_1$–$C_6$-alkyl group wherein the aminoalkyl nitrogen is (i) unsubstituted or (ii) substituted with one or two radicals independently selected from the group consisting of $C_1$–$C_6$-alkyl, ar-$C_1$–$C_6$-alkyl, cycloalkyl and $C_1$–$C_6$-alkanoyl; and $R^{13}$ is selected from the group consisting of a hydrido, benzyl, phenyl, $C_1$–$C_6$-alkyl, $C_2$–$C_6$-alkynyl, $C_2$–$C_6$-alkenyl and a $C_1$–$C_6$-hydroxyalkyl group. Again, the use of a compound of formula III as a pharmaceutically acceptable salt is also contemplated.

Preferences related to a compound of formula III that also apply to a compound of formula II include the following, which are independently preferred: (a) the sum of m+n+p=1 or 2, and more preferably 2; (b) Z is O, S or $NR^6$; (c) $R^6$ is selected from the group consisting of $C_3$–$C_6$-cycloalkyl, $C_1$–$C_6$-alkyl, $C_3$–$C_6$-alkenyl, $C_3$–$C_6$-alkynyl, $C_1$–$C_6$-alkoxy-$C_1$–$C_6$-alkyl, amino-$C_1$–$C_6$-alkyl, aminosulfonyl, heteroaryl-$C_1$–$C_6$-alkyl, aryloxycarbonyl, and $C_1$–$C_6$-alkoxycarbonyl; and (d) m=n= zero, p=1, and Y is $NR^6$. Another preference for a compound of both of formulas II and III is that $R^{14}$ be hydrido, or that W of the $C(W)R^{15}$ pro-drug form be O and $R^{15}$ be a $C_1$–$C_6$-alkyl, aryl, $C_1$–$C_6$-alkoxy, heteroaryl-$C_1$–$C_6$-alkyl, $C_3$–$C_8$-cycloalkyl-$C_1$–$C_6$-alkyl, or aryloxy group.

A still more preferred compound for use in a contemplated process corresponds in structure to formula IV, below:

IV

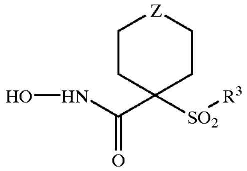

Here, $R^3$ is as defined above as to formulas I, III and more preferably as defined as to formula II (wherein the $R^3$ radical is the substituent G—A—R—E—Y). Most preferably, $R^3$ is as defined in formula III.

Z is selected group the group consisting of O, S, $NR^6$, SO, $SO_2$, and $NSO_2R^7$, wherein $R^6$ is selected from the group consisting of hydrido, $C_1$–$C_5$-alkyl, $C_1$–$C_5$-alkanoyl, benzyl, benzoyl, $C_3$–$C_5$-alkynyl, $C_3$–$C_5$-alkenyl, $C_1$–$C_3$-alkoxy-$C_1$–$C_4$-alkyl, $C_3$–$C_6$-cycloalkyl, heteroaryl-$C_1$–$C_6$-alkyl, $C_1$–$C_5$-hydroxyalkyl, $C_1$–$C_5$-carboxyalkyl, $C_1$–$C_5$-alkoxy $C_1$–$C_5$-alkylcarbonyl, and $NR^8R^9$—$C_1$–$C_5$-alkylcarbonyl or $NR^8R^9$—$C_1$–$C_5$-alkyl wherein $R^8$ and $R^9$ are independently hydrido, $C_l$–$C_5$-alkyl, $C_1$–$C_5$-alkoxycarbonyl or aryl-$C_1$–$C_5$-alkoxycarbonyl, or $NR^8R^9$ together form a heterocyclic ring containing 5- to 8-atoms in the ring; and $R^7$ is selected from the group consisting of an arylalkyl, aryl, heteroaryl, heterocyclo, $C_1$–$C_6$-alkyl, $C_3$–$C_6$-alkynyl, $C_3$–$C_6$-alkenyl, $C_1$–$C_6$-carboxyalkyl and a $C_1$–$C_6$-hydroxyalkyl group. Most preferably, Z is O or $NR^6$. Here too, the use of a compound of formula IV as a pharmaceutically acceptable salt is contemplated.

A still more preferred group of contemplated compounds for use in a contemplated process correspond in structure to formula V, below;

V

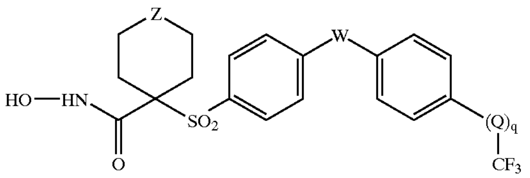

wherein

Z is as previously defined for formula IV;

W and Q are independently oxygen (O), $NR^6$ or sulfur (S), and $R^6$ is as defined in formula IV; and q is zero or one such that when q is zero, Q is absent and the trifluoromethyl group is bonded directly to the depicted phenyl ring. Here again, the use of a compound of formula IV as a pharmaceutically acceptable salt is contemplated.

Particularly preferred compounds within the group defined by formula V have the structural formulas shown below:

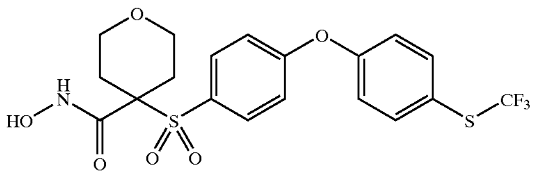

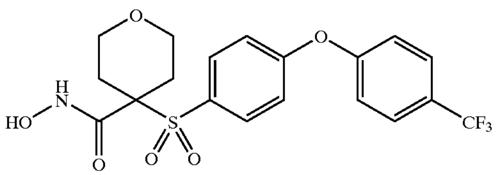

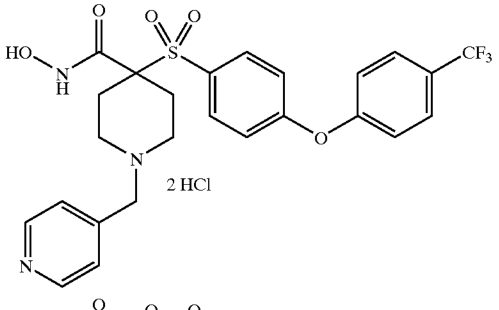

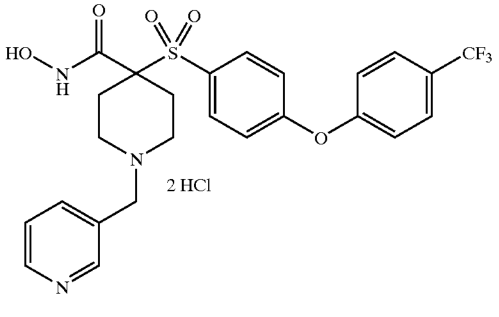

-continued

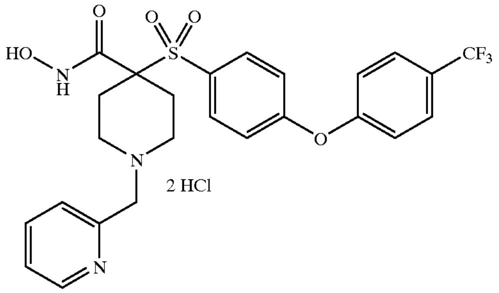

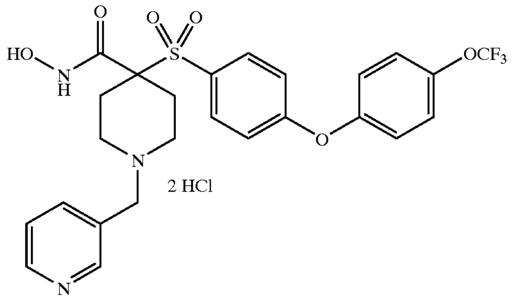

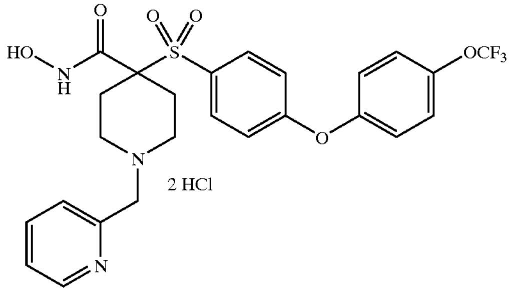

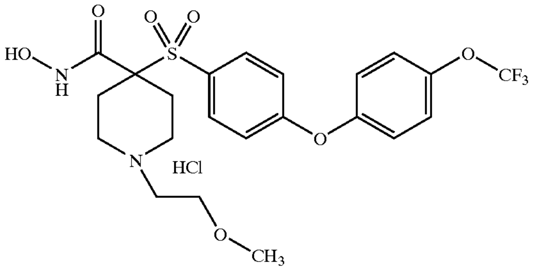

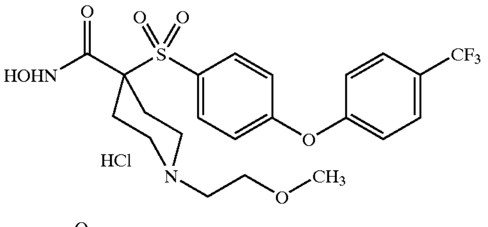

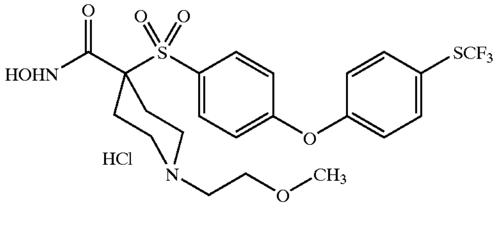

-continued

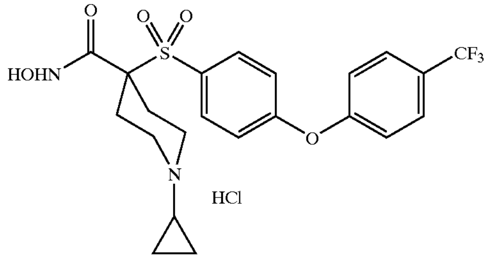

Also particularly preferred are the following compounds:

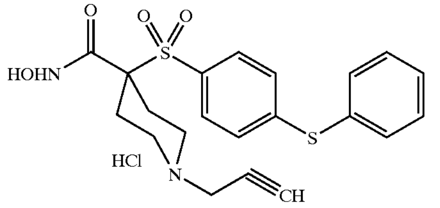

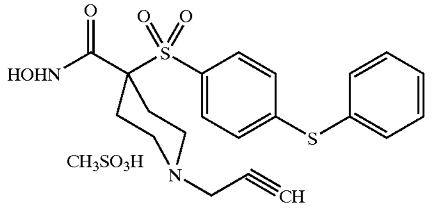

Several particularly preferred compounds whose structures correspond to formulas I through V are illustrated in the Tables and examples provided hereinafter.

As was noted before, the compounds of formulas II, III, IV and V, and their pharmaceutically acceptable salts are themselves contemplated compounds of the invention.

In preferred practice, an $SO_2$-linked $R^3$ radical is an aryl or heteroaryl group that is a 5- or 6-membered single-ring that is itself substituted with one other single-ringed aryl or heteroaryl group or, with an alkyl or alkoxy group having a chain length of 3 to about 16 carbon atoms (and more preferably a length of up to about 14 carbon atoms), a phenoxy group, a thiophenoxy [$C_6H_5$—S—] group, a phenylazo [$C_6H_5$—$N_2$—] group, a N-piperidyl [$C_5H_{10}N$—] group, a N-piperazyl [$NC_4H_9N$—] group or a benzamido [—$NHC(O)C_6H_5$] group. The $SO_2$-linked single-ringed aryl or heteroaryl $R^3$ group here is substituted at its own 4-position when a 6-membered ring and at its own 3- or 4-position when a 5-membered ring.

The $SO_2$-linked aryl or heteroaryl group of a $R^3$ radical is preferably itself substituted at the 4-position when a 6-membered ring or the 3- or 4-position when a 5-membered ring. A particularly preferred substituent is a single-ringed aryl or heteroaryl, phenoxy, thiophenoxy, phenylazo, N -piperidyl, N-piperazyl or benzamido group that is unsubstituted or can itself be substituted.

The 4- and 3-positions of rings discussed here are numbered from the sites of substituent bonding as compared to formalized ring numbering positions used in heteroaryl nomenclature, as is discussed further hereinbelow. Here, single atoms such as halogen moieties (fluoro, chloro, bromo, or iodo) or substituents that contain one to a chain length of about five atoms other than hydrogen such as phenyl, $C_1$–$C_4$ alkyl, trifluoromethyl, trifluoromethoxy, trifluorothiomethyl or carboxyethyl groups are preferred, although longer substituents can be accommodated up to a total length of an icosyl group.

Exemplary particularly preferred substituted $SO_2$-linked $R^3$ radicals include 4-(phenyl)phenyl [biphenyl], 4-(4'-methoxyphenyl)-phenyl, 4-(phenoxy)phenyl, 4-(thiophenyl) phenyl [4-(phenylthio)phenyl], 4-(azophenyl)phenyl, 4-[(4'-trifluoromethylthio)phenoxy]phenyl, 4-[(4'-trifluoromethylthio)thiophenyl]phenyl, 4-[(4'-trifluoromethyl)phenoxy]phenyl, 4-[(4'-trifluoromethyl) thiophenyl]phenyl, 4-[(4'-trifluoromethoxy)phenoxy] phenyl, 4-[(4'-trifluoromethoxy)thiophenyl]phenyl, 4-[(4'-phenyl)N-piperidyl]phenyl, 4-[(4'-acetyl)N-piperazyl] phenyl and 4-(benzamido)phenyl.

Inasmuch as a contemplated $SO_2$-linked aryl or heteroaryl radical of an $R^3$ group is itself preferably substituted with a 6-membered ring, two nomenclature systems are used together herein for ease in understanding substituent positions. The first system uses position numbers for the ring directly bonded to the $SO_2$-group, whereas the second system uses ortho, meta or para for the position of one or more substituents of a 6-membered ring bonded to a $SO_2$-linked aryl or heteroaryl radical. Although ortho, meta and para positional nomenclature is normally not used with aliphatic ring systems, it is believed more readily understood for describing the present compounds when used in conjunction with the numerical system for the first ring bonded to the $SO_2$-group. When a $R^3$ radical is other than a 6-membered ring, substituent positions are numbered from the position of linkage to the aromatic or heteroaromatic ring. Formal chemical nomenclature is used in naming particular compounds.

Thus, the 1-position of an above-discussed $SO_2$-linked aryl or heteroaryl group is the position at which the $SO_2$-group is bonded to the ring. The 4- and 3-positions of rings discussed here are numbered from the sites of substituent bonding from the $SO_2$-linkage as compared to formalized ring numbering positions used in heteroaryl nomenclature.

When examined along its longest chain of atoms, an $R^3$ radical including its own substituent has a total length that is greater than a saturated chain of five carbon atoms (a pentyl group), and preferably has a length greater than that of a saturated chain of six carbon atoms (a hexyl group); i.e., a length of about a heptyl chain or longer. An $R^3$ radical also has a length that is less than that of a saturated chain of about 20 carbon atoms [an icosyl group (icosyl was formerly spelled eicosyl)] and more preferably about 18 carbon atoms (a stearyl group). Most preferably, the length of $R^3$ is about that of an 8 to about 12 carbon atom chain, even though many more atoms may be present in ring structures or substituents. This length requirement is discussed further below.

Looked at more generally, and aside from specific moieties from which it is constructed, an $R^3$ radical (group or moiety) has a length that is greater than that of a pentyl group. Such an $R^3$ radical also has a length that is less than that of an icosyl (didecyl) group. That is to say that $R^3$ is a radical having a minimal length longer that a saturated five carbon chain, and preferably greater than a hexyl group, but is shorter than the length of a saturated twenty carbon atom chain, and preferably shorter than an eighteen carbon chain. Most preferably, $R^3$ has a length greater than that of an octyl group and less than that of a lauryl group.

More specifically, an $R^3$ group has a minimal length of a hexyl group only when that substituent is comprised of two rings that can be fused or simply covalently linked together by exocyclic bonding. When $R^3$ does not contain two linked or fused rings, e.g., where a $R^3$ radical includes an alkyl or second, third or fourth ring substituent, $R^3$ has a length that is greater than that of a hexyl group. Exemplary of such two ring $R^3$ groups are a 2-naphthyl group or a 2-quinolinyl group (each with a six carbon chain length)and 8-purinyl (with a five carbon atom chain length). Without wishing to be bound by theory, it is believed that the presence of multiple rings in $R^3$ enhances selectivity of the enzyme activity inhibitor profile.

The radical chain lengths are measured along the longest linear atom chain in the radical, following the skeletal atoms around a ring where necessary. Each atom in the chain, e.g. carbon, oxygen, sulfur or nitrogen, is presumed to be carbon for ease in calculation.

Such lengths can be readily determined by using published bond angles, bond lengths and atomic radii, as needed, to draw and measure a desired, usually staggered, chain, or by building models using commercially available kits whose bond angles, lengths and atomic radii are in accord with accepted, published values. Radical (substituent) lengths can also be determined somewhat less exactly by assuming that all atoms have bond lengths saturated carbon, that unsaturated bonds have the same lengths as saturated bonds and that bond angles for unsaturated bonds are the same as those for saturated bonds, although the above-mentioned modes of measurement are preferred. For example, a phenyl or pyridyl group has a length of a four carbon chain, as does a propoxy group, whereas a biphenyl group has a length of about an eight carbon chain using such a measurement mode.

In addition, a $R^3$ group when rotated about an axis drawn through the $SO_2$-bonded 1-position and the 4-position of a 6-membered ring or the $SO_2$-bonded position and substituent-bonded 3- or 4-position of a 5-membered ring defines a three-dimensional volume whose widest dimension has the width of about one furanyl ring to about two phenyl rings in a direction transverse to that axis to rotation.

Thus, a 2-naphthyl substituent or an 8-purinyl substituent is an appropriately sized $R^3$ group when examined using the above rotational width criterion as well as the before-discussed criterion. On the other hand, a 1-naphthyl group or a 7- or 9-purinyl group is too wide upon rotation and is excluded from being an $R^3$ group.

As a consequence of these length and width requirements, $R^3$ radicals such as 4-(phenyl)phenyl [biphenyl], 4-(4'-methoxyphenyl)-phenyl, 4-(phenoxy)phenyl, 4-(thiophenyl) phenyl [4-(phenylthio)phenyl], 4-(azophenyl)phenyl, 4-[(4'-trifluoromethylthio)phenoxy]phenyl, 4-[(4'-trifluoromethylthio)thiophenyl]phenyl, 4-[(4'-trifluoromethyl)phenoxy]phenyl, 4-[(4'-trifluoromethyl) thiophenyl]phenyl, 4-[(4'-trifluoromethoxy)phenoxy] phenyl, 4-[(4'-trifluoromethoxy)thiophenyl]phenyl, 4-[(4'-phenyl)N -piperidyl]phenyl, 4-[(4'-acetyl)N-piperazyl] phenyl and 4-(benzamido)phenyl are particularly preferred $R^3$ radicals. Those substituents can themselves also be substituted in the second ring from the $SO_2$ group at the meta- or para-position or both with a single atom or a substituent containing a longest chain length that is preferably of up to five atoms, excluding hydrogen.

Without wishing to be bound by theory, the length of a $R^3$ radical substituent bonded to the $SO_2$ group is believed to play a role in the overall activity of a contemplated inhibitor compound against MMP enzymes generally. The length of the $R^3$ radical group also appears to play a role in the selective activity of an inhibitor compound against particular MMP enzymes.

In particularly preferred practice, $R^3$ is a $PhR^{23}$ group, wherein Ph is phenyl. The phenyl ring (Ph) of a $PhR^{23}$ group is substituted at its para-position (4-position) by an $R^{23}$ group that can be another single-ringed aryl or heteroaryl group, a piperidyl group, a piperazinyl group, a phenoxy group, a thiophenoxy [$C_6H_5$—S—] group, a phenylazo [$C_6H_5$—$N_2$—] group or a benzamido [-NHC(O)$C_6H_5$) group.

In one embodiment of a particularly preferred aromatic sulfone hydroxamate inhibitor compound, an $R^{23}$ substituent is phenoxy and is itself substituted at its own para-position with a moiety that is selected from the group consisting of a halogen, a $C_1$–$C_4$ alkoxy group, a $C_1$–$C_4$ alkyl group, a dimethylamino group, a carboxyl $C_1$–$C_3$ alkylene group, a $C_1$–$C_4$ alkoxy carbonyl $C_1$–$C_3$ alkylene group, a trifluoromethylthio group, a trifluoromethoxy group, a trifluoromethyl group and a carboxamido $C_1$–$C_3$ alkylene group, or is substituted at the meta- and para-positions by a methylenedioxy group. It is to be understood that any $R^{23}$ substituent can be substituted with a moiety from the above list. Such substitution at the para-position is preferred.

The present invention also contemplates an intermediate compound that is useful in preparing a compound of formulas I–V. Such an intermediate compound corresponds in structure to formula VI, below:

VI

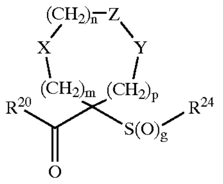

wherein g is zero, 1 or 2;

$R^{20}$ is (a) —O—$R^{21}$, where $R^{21}$ is selected from the group consisting of a hydrido, $C_1$–$C_6$-alkyl, aryl, ar-$C_1$–$C_6$-alkyl group and a pharmaceutically acceptable cation, or (b) —NH—O—$R^{22}$ wherein $R^{22}$ is a selectively removable protecting group such as a 2-tetrahydropyranyl, $C_1$–$C_6$-acyl, aroyl, benzyl, p-methoxybenzyl (MOZ) carbonyl-$C_1$–$C_6$-alkoxy, trisubstituted silyl group or o-nitrophenyl group, peptide systhesis resin and the like, wherein trisubstituted silyl group is substituted with $C_1$–$C_6$-alkyl, aryl, or ar-$C_1$–$C_6$-alkyl;

m is zero, 1 or 2;

n is zero, 1 or 2;

p is zero, 1 or 2;

the sum of m+n+p=1, 2, 3 or 4;

(a) one of X, Y and Z is selected from the group consisting of C(O), $NR^6$, O, S, S(O), $S(O)_2$ and $NS(O)_2R^7$, and the remaining two of X, Y and Z are $CR^8R^9$, and $CR^{10}R^{11}$, or (b) X and Z or Z and Y together constitute a moiety that is selected from the group consisting of $NR^6C(O)$, $NR^6S(O)$, $NR^6S(O)_2$, $NR^6S$, $NR^6O$, SS, $NR^6NR^6$ and OC(O), with the remaining one of X, Y and Z being $CR^8R^9$, or (c) n is zero and X, Y and Z together constitute a moiety selected from the group consisting of

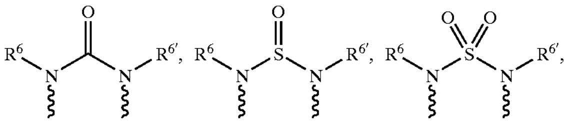

-continued

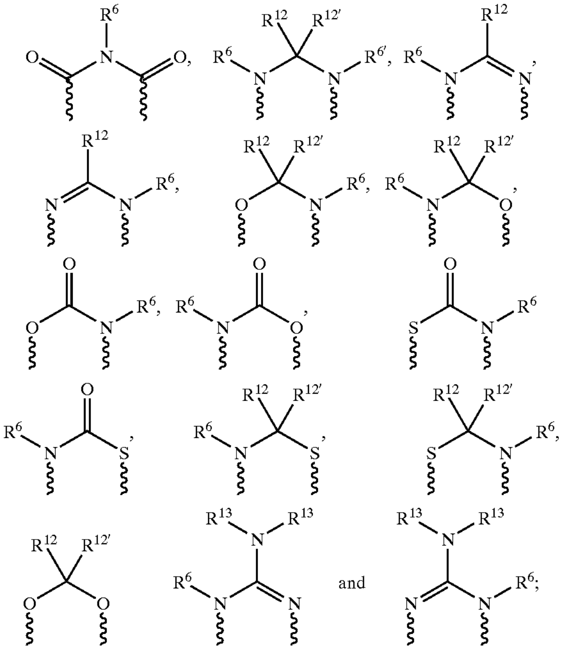

wherein wavy lines are bonds to the atoms of the depicted ring;

$R^6$ and $R^{6'}$ are independently selected from the group consisting of hydrido, $C_1$–$C_6$-alkanoyl, $C_6$-aryl-$C_1$–$C_6$-alkyl, aroyl, bis($C_1$–$C_6$-alkoxy-$C_1$–$C_6$-alkyl)-$C_1$–$C_6$-alkyl, $C_1$–$C_6$-alkyl, $C_1$–$C_6$-haloalkyl, $C_1$–$C_6$-perfluoroalkyl, $C_1$–$C_6$-trifluoromethylalkyl, $C_1$–$C_6$-perfluoroalkoxy-$C_1$–$C_6$-alkyl, $C_1$–$C_6$-alkoxy-$C_1$–$C_6$-alkyl, $C_3$–$C_6$-cycloalkyl, $C_3$–$C_8$-heterocycloalkyl, $C_3$–$C_8$-heterocycloalkylcarbonyl, $C_6$-aryl, $C_5$–$C_6$-heterocyclo, $C_5$–$C_6$-heteroaryl, $C_3$–$C_8$-cycloalkyl-$C_1$–$C_6$-alkyl, $C_6$-aryloxy-$C_1$–$C_6$-alkyl, heteroaryloxy-$C_1$–$C_6$-alkyl, heteroaryl-$C_1$–$C_6$-alkoxy-$C_1$–$C_6$-alkyl, heteroarylthio-$C_1$–$C_6$-alkyl, $C_6$-arylsulfonyl, $C_1$–$C_6$-alkylsulfonyl, $C_5$–$C_6$-heteroarylsulfonyl, carboxy-$C_1$–$C_6$-alkyl, $C_1$–$C_4$-alkoxycarbonyl-$C_1$–$C_6$-alkyl, aminocarbonyl, $C_1$–$C_6$-alkyliminocarbonyl, $C_6$-aryliminocarbonyl, $C_5$–$C_6$-heterocycloiminocarbonyl, $C_6$-arylthio-$C_1$–$C_6$-alkyl, $C_1$–$C_6$-alkylthio-$C_1$–$C_6$-alkyl, $C_6$-arylthio-$C_3$–$C_6$-alkenyl, $C_1$–$C_4$-alkylthio-$C_3$–$C_6$-alkenyl, $C_5$–$C_6$-heteroaryl-$C_1$–$C_6$-alkyl, halo-$C_1$–$C_6$-alkanoyl, hydroxy-$C_1$–$C_6$-alkanoyl, thiol-$C_1$–$C_6$-alkanoyl, $C_3$–$C_6$-alkenyl, $C_3$–$C_6$-alkynyl, $C_1$–$C_4$-alkoxy-$C_1$–$C_4$-alkyl, $C_1$–$C_5$-alkoxycarbonyl, aryloxycarbonyl, $NR^8R^9$—$C_1$—$C_5$-alkylcarbonyl, hydroxy-$C_1$–$C_5$-alkyl, an aminocarbonyl wherein the aminocarbonyl nitrogen is (i) unsubstituted or (ii) substituted with one or two radicals independently selected from the group consisting of $C_1$–$C_6$-alkyl, ar-$C_1$–$C_6$-alkyl, $C_3$–$C_8$-cycloalkyl and a $C_1$–$C_6$-alkanoyl group, hydroxyaminocarbonyl, an aminosulfonyl group wherein the aminosulfonyl nitrogen is (i) unsubstituted or (ii) substituted with one or two radicals independently selected from the group consisting of $C_1$–$C_6$-alkyl, ar-$C_1$–$C_6$-alkyl, $C_3$–$C_8$-cycloalkyl and a $C_1$–$C_6$-alkanoyl group, an amino-$C_1$–$C_6$-alkylsulfonyl group wherein the amino-$C_1$–$C_6$-alkylsulfonyl nitrogen is (i) unsubstituted or (ii) substituted with one or two radicals independently selected from the group consisting of $C_1$–$C_6$-alkyl, ar-$C_1$–$C_6$-alkyl, $C_3$–$C_8$ -cycloalkyl and a $C_1$–$C_6$-alkanoyl group and an amino-$C_1$–$C_6$-alkyl group wherein the aminoalkyl nitrogen is (i) unsubstituted or (ii) substituted with one or two radicals independently selected from the group consisting of $C_1$–$C_6$-alkyl, ar-$C_1$–$C_6$-alkyl, $C_3$–$C_8$-cycloalkyl and a $C_1$–$C_6$-alkanoyl group;

$R^7$ is selected from the group consisting of a benzyl, phenyl, $C_1$–$C_6$-alkyl, $C_3$–$C_6$-alkynyl, $C_3$–$C_6$-alkenyl and a $C_1$–$C_6$-hydroxyalkyl group;

$R^8$ and $R^9$ and $R^{10}$and $R^{11}$ are independently selected from the group consisting of a hydrido, hydroxy, $C_1$–$C_6$-alkyl, aryl, ar-$C_1$–$C_6$-alkyl, heteroaryl, heteroar-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aralkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylar-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, the sulfoxide or sulfone of any said thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl and an amino-$C_1$–$C_6$-alkyl group wherein the aminoalkyl nitrogen is (i) unsubstituted or (ii) substituted with one or two radicals independently selected from the group consisting of $C_1$–$C_6$-alkyl, ar-$C_1$–$C_6$-alkyl, cycloalkyl and $C_1$–$C_6$-alkanoyl, or wherein $R^8$ and $R^9$ or $R^{10}$ and $R^{11}$ and the carbon to which they are bonded form a carbonyl group, or wherein $R^8$ and $R^9$ or $R^{10}$ and $R^{11}$, or $R^8$ and $R^{10}$ together with the atoms to which they are bonded form a 5- to 8-membered carbocyclic ring, or a 5- to 8-membered heterocyclic ring containing one or two heteroatoms that are nitrogen, oxygen, or sulfur, with the proviso that only one of $R^8$ and $R^9$ or $R^{10}$ and $R^{11}$is hydroxy;

$R^{12}$ and $R^{12'}$are independently selected from the group consisting of a hydrido, $C_1$–$C_6$-alkyl, aryl, ar-$C_1$–$C_6$-alkyl, heteroaryl, heteroaralkyl, $C_2$–$C_6$-alkynyl, $C_2$–$C_6$-alkenyl, thiol-$C_1$–$C_6$-alkyl, cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aryloxy-$C_1$–$C_6$-alkyl, amino-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylar-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, $C_1$–$C_6$-alkylthio-$C_1$–$C_6$ -alkyl, arylthio-$C_1$–$C_6$-alkyl, heteroarylthio-$C_1$–$C_6$-alkyl, the sulfoxide or sulfone of any said thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl and an amino-$C_1$–$C_6$-alkyl group wherein the aminoalkyl nitrogen is (i) unsubstituted or (ii) substituted with one or two radicals independently selected from the group consisting of $C_1$–$C_6$-alkyl, ar-$C_1$–$C_6$-alkyl, cycloalkyl and $C_1$–$C_6$-alkanoyl;

$R^{13}$ is selected from the group consisting of a hydrido, benzyl, phenyl, $C_1$–$C_6$-alkyl, $C_2$–$C_6$-alkynyl, $C_2$–$C_6$-alkenyl and a $C_1$–$C_6$-hydroxyalkyl group; and $R^{24}$ is $R^3$ as defined in formulas I, III, IV or is the substituent G—A—R—E—Y of formula II (formula VIA). Alternatively, $R^{24}$ is $R^{3'}$, an aryl or heteroaryl group that is substituted with a coupling substituent reactive for coupling with another moiety (formula VIB), such as a nucleophilically displaceable leaving group, D.

VIA

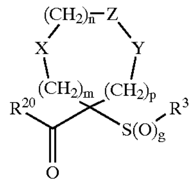

VIB

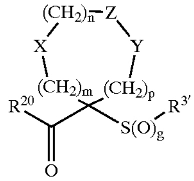

Exemplary nucleophilically displaceable leaving groups, D, include a halo (fluoro, chloro, bromo, or idodo) nitro, azido, phenylsulfoxido, aryloxy, $C_1$–$C_6$-alkoxy, a $C_1$–$C_6$-alkylsulfonate or arylsulfonate group and a trisubstituted ammonium group in which the three substituents are independently aryl, ar-$C_1$–$C_6$-alkyl or $C_1$–$C_6$-alkyl. Additional coupling substituents include, without limitation, a hydroxyl group and an amino group that can be coupled with carbonyl-containing moieties to form esters, urethanes, carbonates, amides and ureas. Similarly, a carboxyl coupling substituent can be used to form an ester, thioester or amide. Thus, a coupling substituent is useful in converting a coupling substituent-containing aryl or heteroaryl group into a substituent such as a G—A—R—E—Y substituent discussed hereinabove by the formation of a covalent bond.

A compound of formula VI can be coupled with another moiety at the $R^{3'}$ coupling substituent to form a compound whose newly formed $R^3$ group is that of formulas I, III, IV or —G—A—R—E—Y. Exemplary of such couplings are the nucleophilic displacement to form ethers and thioethers, as well as the formation of ester, amide, urea, carbonate, urethane and the like linkages.

A particularly preferred precursor intermediate to an intermediate compound of formula VI is an intermediate compound of formula VII, below

VII

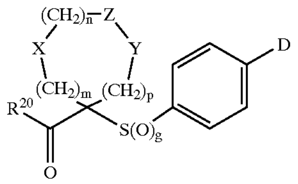

wherein m, n, p, g, X, Z, Y, D and $R^{20}$ are as defined above for formula VI.

$R^{20}$ is preferably —NH—O—$R^{22}$, wherein $R^{22}$ is a selectively removable protecting group such as a 2-tetrahydropyranyl, $C_1$–$C_6$-acyl, aroyl, benzyl, p-methoxybenzyl (MOZ) carbonyl-$C_1$–$C_6$-alkoxy, o-nitrohenyl group, a peptide syntheisi resin such as a so-called Merrifield's Peptide Resin commercially available from Sigma Chemical Co., and the like, with 2-tetrahydropyranyl being particularly preferred. An —NH—O—$R^{22}$ group ($R^{20}$) in formulas VI and VII is therefore seen to be a reaction product of a hydroxyl amine whose oxygen is bonded to a selectively removable protecting group and a carboxyl group.

In regard to a compound of each of formulas VI and VII, the subscript letter "g" is used to show the oxidation state of the sulfur atom. Where g is zero, the sulfur is unoxidized, and the compound depicted is typically the sulfide reaction product of a sulfur-containing synthon as is illustrated in the examples hereinafter. Where g is 1, the sulfur is oxidized to a sulfoxide, whereas when g is 2, the sulfur is oxidized to a sulfone as is also illustrated hereinafter. A compound of formulas VI or VII wherein g is zero or 1 are themselves typically intermediates in the formation of a similar compound wherein g is 2 and the intermediate is a preferred sulfone.

A preferred intermediate therefore corresponds in structure to formula VIIA, below

VIIA

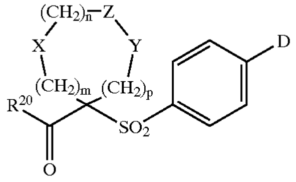

In the written descriptions of molecules and groups, molecular descriptors can be combined to produce words or phrases that describe structural groups or are combined to describe structural groups. Such descriptors are used in this document. Common illustrative examples include such terms as aralkyl (or arylalkyl), heteroaralkyl, heterocycloalkyl, cycloalkylalkyl, aralkoxyalkoxycarbonyl and the like. A specific example of a compound encompassed with the latter descriptor aralkoxyalkoxycarbonyl is $C_6H_5$—$CH_2$—$CH_2$—O—$CH_2$—O—(C=O)—to wherein $C_6H_5$— is phenyl. It is also to be noted that a structural group can have more than one descriptive word or phrase in the art, for example, heteroaryloxyalkylcarbonyl can also be termed heteroaryloxyalkanoyl. Such combinations are used herein in the description of the processes, compounds and compositions of this invention and further examples are described below. The following list is not intended to be exhaustive or drawn out but provide illustrative examples of words or phrases (terms) that are used herein.

As utilized herein, the term "alkyl", alone or in combination, means a straight-chain or branched-chain alkyl radical containing 1 to about 12 carbon atoms, preferably 1 to about 10 carbon atoms, and more preferably 1 to about 6 carbon atoms. Examples of such radicals include methyl, ethyl, n-propyl, isopropyl, n-butyl, isobutyl, sec-butyl, tert-butyl, pentyl, iso-amyl, hexyl, octyl and the like.

The term "alkenyl", alone or in combination, means a straight-chain or branched-chain hydrocarbon radical having one or more double bonds and containing 2 to about 12 carbon atoms preferably 2 to about 10 carbon atoms, and more preferably, 2 to about 6 carbon atoms. Examples of suitable alkenyl radicals include ethenyl (vinyl), 2-propenyl, 3-propenyl, 1,4-pentadienyl, 1,4-butadienyl, 1-butenyl, 2-butenyl, 3-butenyl, decenyl and the like.

The term "alkynyl", alone or in combination, means a straight-chain hydrocarbon radical having one or more triple bonds and containing 2 to about 12 carbon atoms, preferably 2 to about 10 carbon atoms, and more preferably, 2 to out 6 carbon atoms. Examples of alkynyl radicals include ethynyl, 2-propynyl, 3-propynyl, decynyl, 1-butynyl, 2-butynyl, 3-butynyl, and the like.

The term "carbonyl" or "oxo", alone or in combination, means a —C(=O)— group wherein the remaining two bonds (valences) can be independently substituted. The term carbonyl is also intended to encompass a hydrated carbonyl group —$C(OH)_2$—.

The term "thiol" or "sulfhydryl", alone or n combination, means a —SH group. The term "thio" or "thia", alone or in combination, means a thiaether group; i.e., an ether group wherein the ether oxygen is replaced by a sulfur atom.

The term "amino", alone or in combination, means an amine or —$NH_2$ group whereas the term mono-substituted amino, alone or in combination, means a substituted amine —N(H)(substituent) group wherein one hydrogen atom is replaced with a substituent, and disubstituted amine means a —$N(substituent)_2$ wherein two hydrogen atoms of the amino group are replaced with independently selected substituent groups.

Amines, amino groups and amides are compounds that can be designated as primary (I°), secondary (II°) or tertiary (III°) or unsubstituted, mono-substituted or N,N-disubstituted depending on the degree of substitution of the amino nitrogen. Quaternary amine (ammonium)(IV°) means a nitrogen with four substituents (—N+$(substituent)_4$] that is positively charged and accompanied by a counter ion, whereas N-oxide means one substituent is oxygen and the group is represented as [—N+$(substituent)_3$—$O^-$]; i.e., the charges are internally compensated.

The term "cyano", alone or in combination, means a —C-triple bond-N (—C≡N) group. The term "azido", alone or in combination, means a —N-triple bond-N (—N≡N) group. The term "hydroxyl", alone or in combination, means a —OH group. The term "nitro", alone or in combination, means a —$NO_2$ group. The term "azo", alone or in combination, means a —N=N—group wherein the bonds at the terminal positions can be independently substituted.

The term "hydrazino", alone or in combination, means a —NH—NH—group wherein the depicted remaining two bonds (valences) can be independently substituted. The hydrogen atoms of the hydrazino group can be replaced, independently, with substituents and the nitrogen atoms can form acid addition salts or be quaternized.

The term "sulfonyl", alone or in combination, means a —$SO_2$— group wherein the depicted remaining two bonds (valences) can be independently substituted. The term "sulfoxido", alone or in combination, means a —SO— group wherein the remaining two bonds (valences) can be independently substituted.

The term "sulfone", alone or in combination, means a —$SO_2$— group wherein the depicted remaining two bonds (valences) can be independently substituted. The term "sulfenamide", alone or in combination, means a —SON= group wherein the remaining three depicted bonds (valences) can be independently substituted. The term "sulfide", alone or in combination, means a —S— group wherein the remaining two bonds (valences) can be independently substituted.

The term "alkoxy", alone or in combination, means an alkyl ether radical wherein the term alkyl is as defined above. Examples of suitable alkyl ether radicals include methoxy, ethoxy, n-propoxy, isopropoxy, n-butoxy, isobutoxy, sec-butoxy, tert-butoxy and the like.

The term "cycloalkyl", alone or in combination, means a cyclic alkyl radical that contains 3 to about 8 carbon atoms. The term "cycloalkylalkyl" means an alkyl radical as defined above that is substituted by a cycloalkyl radical containing 3 to about 8, preferably 3 to about 6, carbon atoms. Examples of such cycloalkyl radicals include cyclopropyl, cyclobutyl, cyclopentyl, cyclohexyl and the like.

A heterocyclic (heterocyclo) or heterocyclo portion of a heterocyclocarbonyl, heterocyclooxy-carbonyl, heterocycloalkoxycarbonyl, or heterocycloalkyl group or the like is a saturated or partially unsaturated monocyclic, bicyclic or tricyclic heterocycle that contains one or more hetero atoms selected from nitrogen, oxygen and sulphur. Such a moiety can be optionally substituted on one or more ring carbon atoms by halogen, alkyl, alkoxy, oxo, and the like, and/or on a secondary nitrogen atom (i.e.,—NH—) of the ring by alkyl, aralkoxycarbonyl, alkanoyl, aryl or arylalkyl or on a tertiary nitrogen atom (i.e., =N—) by oxido and that is attached via a carbon atom. The tertiary nitrogen atom with three substituents can also attached to form a N-oxide [=N(O)—] group.

The term "aryl", alone or in combination, means a 5- or 6-membered carbocyclic aromatic ring-containing moiety or a fused ring system containing two or three rings that have all carbon atoms in the ring; i.e., a carbocyclic aryl radical. Exemplary carbocyclic aryl radicals include phenyl, indenyl and naphthyl radicals.

The term "heteroaryl", alone or in combination means a 5- or 6-membered aromatic ring-containing moiety or a fused ring system (radical) containing two or three rings that have carbon atoms and also one or more heteroatoms in the ring(s) such as sulfur, oxygen and nitrogen. Examples of such heterocyclic or heteroaryl groups are pyrrolidinyl, piperidyl, piperazinyl, morpholinyl, thiamorpholinyl, pyrrolyl, imidazolyl (e.g., imidazol-4-yl, 1-benzyloxycarbonylimidazol-4-yl, and the like), pyrazolyl, pyridyl, pyrazinyl, pyrimidinyl, furyl, tetrahydrofuryl, thienyl, triazolyl, oxazolyl, oxadiazoyl, thiazolyl, thiadiazoyl, indolyl (e.g., 2-indolyl, and the like), quinolinyl, (e.g., 2-quinolinyl, 3-quinolinyl, 1-oxido-2-quinolinyl, and the like), isoquinolinyl (e.g., 1-isoquinolinyl, 3-isoquinolinyl, and the like), tetrahydroquinolinyl (e.g., 1,2,3,4-tetrahydro-2-quinolyl, and the like), 1,2,3,4-tetrahydroisoquinolinyl (e.g., 1,2,3,4-tetrahydro-1-oxo-isoquinolinyl, and the like), quinoxalinyl, β-carbolinyl, 2-benzofurancarbonyl, benzothiophenyl, 1-, 2-, 4- or 5-benzimidazolyl, and the like radicals.

When an aryl or heteroaryl radical is a substituting moiety (group, substituent, or radical), it can itself substituted, the last-named substituent is independently selected from the group consisting of a cyano, perfluoroalkyl, trifluoromethoxy, trifluoromethylthio, haloalkyl, trifluoromethylalkyl, aralkoxycarbonyl, aryloxycarbonyl, hydroxy, halo, alkyl, alkoxy, nitro, thiol, hydroxycarbonyl, aryloxy, arylthio, aralkyl, aryl, arylcarbonylamino, heteroaryloxy, heteroarylthio, heteroaralkyl, cycloalkyl, heterocyclooxy, heterocyclothio, heterocycloamino, cycloalkyloxy, cycloalkylthio, heteroaralkoxy, heteroaralkylthio, aralkoxy, aralkylthio, aralkylamino, heterocyclo, heteroaryl, arylazo, hydroxycarbonylalkoxy, alkoxycarbonylalkoxy, alkanoyl, arylcarbonyl, aralkanoyl, alkanoyloxy, aralkanoyloxy, hydroxyalkyl, hydroxyalkoxy, alkylthio, alkoxyalkylthio, alkoxycarbonyl, aryloxyalkoxyaryl, arylthioalkylthioaryl, aryloxyalkylthioaryl, arylthioalkoxyaryl, hydroxycarbonylalkoxy, hydroxycarbonylalkylthio, alkoxycarbonylalkoxy, alkoxycarbonylalkylthio, amino, wherein the amino nitrogen is (i) unsubstituted, or (ii) substituted with one or two substituents that are independently selected from the group consisting of an alkyl, aryl, heteroaryl, aralkyl, cycloalkyl, aralkoxycarbonyl, alkoxycarbonyl, arylcarbonyl, aralkanoyl, heteroarylcarbonyl, heteroaralkanoyl and an alkanoyl group, or (iii) wherein the amino nitrogen and two substituents attached thereto form a 5- to 8-membered heterocyclo or heteroaryl ring containing zero to two additional heteroatoms that are nitrogen, oxygen or sulfur and which ring itself is (a) unsubstituted or (b) substituted with one or two groups independently selected from the group consisting of an aryl, alkyl, heteroaryl, aralkyl, heteroaralkyl, hydroxy, alkoxy, alkanoyl, cycloalkyl, heterocycloalkyl, alkoxycarbonyl, hydroxyalkyl, trifluoromethyl, benzofused heterocycloalkyl, hydroxyalkoxyalkyl, aralkoxycarbonyl, hydroxycarbonyl, aryloxycarbonyl, benzofused heterocycloalkoxy, benzofused cycloalkylcarbonyl, heterocycloalkycarbonyl, and a cycloalkylcarbonyl group, carbonylamino wherein the carbonylamino nitrogen is (i) unsubstituted, or (ii) is the reacted amine of an amino acid, or (iii) substituted with one or two radicals selected from the group consisting of an alkyl, hydroxyalkyl, hydroxyheteroaralkyl, cycloalkyl, aralkyl, trifluoromethylalkyl, heterocycloalkyl, benzofused heterocycloalkyl, benzofused heterocycloalkyl, benzofused cycloalkyl, and an N,N-dialkylsubstituted alkylamino-alkyl group, or (iv) the carboxamido nitrogen and two substituents bonded thereto together form a 5- to 8-membered heterocyclo, heteroaryl or benzofused heterocycloalkyl ring that is itself unsubstituted or substituted with one or two radicals independently selected from the group consisting of an alkyl, alkoxycarbonyl, nitro, heterocycloalkyl, hydroxy, hydroxycarbonyl, aryl, aralkyl, heteroaralkyl and an amino group, wherein the amino nitrogen is (i) unsubstituted, or (ii) substituted with one or two substituents that are independently selected from the group consisting of alkyl, aryl, and heteroaryl, or (iii) wherein the amino nitrogen and two substituents attached thereto form a 5- to 8-membered heterocyclo or heteroaryl ring, and an aminoalkyl group wherein the aminoalkyl nitrogen is (i) unsubstituted, or (ii) substituted with one or two substituents independently selected from the group consisting of an alkyl, aryl, aralkyl, cycloalkyl, aralkoxycarbonyl, alkoxycarbonyl, and an alkanoyl group, or (iii) wherein the aminoalkyl nitrogen and two substituents attached thereto form a 5- to 8-membered heterocyclo or heteroaryl ring.

The term "aralkyl", alone or in combination, means an alkyl radical as defined above in which one hydrogen atom is replaced by an aryl radical as defined above, such as benzyl, 2-phenylethyl and the like.

The term "aralkoxycarbonyl", alone or in combination, means a radical of the formula aralkyl-O—C(O)— in which the term "aralkyl" has the significance given above. An example of an aralkoxycarbonyl radical is benzyloxycarbonyl.

The term "aryloxy" means a radical of the formula aryl-O— in which the term aryl has the significance given above. The phenoxy radical is an exemplary aryloxy radical.

The terms "heteroaralkyl" and "heteroaryloxy" mean radicals structurally similar to aralkyl and aryloxy that are formed from heteroaryl radicals. Exemplary radicals include 4-picolinyl and 2-pyrimidinoxy, respectively.

The terms "alkanoyl" or "alkylcarbonyl", alone or in combination, means an acyl radical derived from an alkanecarboxylic acid, examples of which include formyl, acetyl, propionyl, butyryl, valeryl, 4-methylvaleryl, and the like.

The term "cycloalkylcarbonyl" means an acyl group derived from a monocyclic or bridged cycloalkanecarboxylic acid such as cyclopropanecarbonyl, cyclohexanecarbonyl, adamantanecarbonyl, and the like, or from a benz-fused monocyclic cycloalkanecarboxylic acid that is optionally substituted by, for example, alkanoylamino, such as 1,2,3,4-tetrahydro-2-naphthoyl, 2-acetamido-1,2,3,4-tetrahyaro-2-naphthoyl.

The terms "aralkanoyl" or "aralkylcarbonyl" mean an acyl radical derived from an aryl-substituted alkanecarboxylic acid such as phenylacetyl, 3-phenylpropionyl (hydrocinnamoyl), 4-phenylbutyryl, (2-naphthyl)acetyl, 4-chlorohydrocinnamoyl, 4-aminohydrocinnamoyl, 4-methoxyhydrocinnamoyl and the like.

The terms "aroyl" or "arylcarbonyl" means an acyl radical derived from an aromatic carboxylic acid. Examples of such radicals include aromatic carboxylic acids, an optionally substituted benzoic or naphthoic acid such as benzoyl, 4-chlorobenzoyl, 4-carboxybenzoyl, 4-(benzyloxycarbonyl)benzoyl, 1-naphthoyl, 2-naphthoyl, 6-carboxy-2 naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like.

The term "cycloalkylalkoxycarbonyl" means an acyl group of the formula cycloalkylalkyl-O—CO— wherein cycloalkylalkyl has the significance given above. The term "aryloxyalkanoyl" means an acyl radical of the formula aryl-O-alkanoyl wherein aryl and alkanoyl have the significance given above. The term "heterocyclooxycarbonyl" means an acyl group having the formula heterocyclo-O—CO— wherein heterocyclo is as defined above.

The term "heterocycloalkanoyl" is an acyl radical of the formula heterocyclo-substituted alkane carboxylic acid wherein heterocyclo has the significance given above. The term "heterocycloalkoxycarbonyl" means an acyl radical of the formula heterocyclo-substituted alkane-O—CO— wherein heterocyclo has the significance given above. The term "heteroaryloxycarbonyl" means an acyl radical represented by the formula heteroaryl-O—CO— wherein heteroaryl has the significance given above.

The term "aminocarbonyl" (carboxamide) alone or in combination, means an amino-substituted carbonyl (carbamoyl) group derived from an amine reacted with a carboxylic acid wherein the amino (amido nitrogen) group is unsubstituted (—$NH_2$) or a substituted primary or secondary amino group containing one or two substituents selected from the group consisting of hydrogen, alkyl, aryl, aralkyl, cycloalkyl, cycloalkylalkyl radicals and the like, as recited. A hydroxamate is a N-hydroxycarboxamide.

The term "aminoalkanoyl" means an acyl group derived from an amino-substituted alkanecarboxylic acid wherein the amino group can be a primary or secondary amino group containing substituents independently selected from hydrogen, alkyl, aryl, aralkyl, cycloalkyl, cycloalkylalkyl radicals and the like.

The term "halogen" means fluoride, chloride, bromide or iodide. The term "haloalkyl" means an alkyl radical having the significance as defined above wherein one or more hydrogens are replaced with a halogen. Examples of such haloalkyl radicals include chloromethyl, 1-bromoethyl, fluoromethyl, difluoromethyl, trifluoromethyl, 1,1,1-trifluoroethyl and the like.

The term "perfluoroalkyl" means an alkyl group wherein each hydrogen has been replaced by a fluorine atom.

Examples of such perfluoroalkyl groups, in addition to trifluoromethyl above, are perfluorobutyl, perfluoroisopropyl, perfluorododecyl and perfluorodecyl.

The term "perfluoroalkoxy" alone or in combination, means a perfluoroalkyl ether radical wherein the term perfluoroalkyl is as defined above. Examples of such perfluoroalkoxy groups, in addition to trifluoromethoxy ($F_3C$—O—), are perfluorobutoxy, perfluoroisopropoxy, perfluorododecoxy and perfluorodecoxy.

The term "perfluoroalkylthio" alone or in combination, means a perfluoroalkyl thioether radical wherein the term perfluoroalkyl is as defined above. Examples of such perfluoroalkylthio groups, in addition to trifluoromethylthio ($F_3C$—S—), are perfluorobutylthio, perfluoroisopropylthio, perfluorododecylthio and perfluorodecylthio.

The term "aromatic ring" in combinations such as substituted-aromatic ring sulfone or substituted-aromatic ring sulfoxide means aryl or heteroaryl as defined before.

The term "pharmaceutically acceptable" is used adjectivally herein to mean that the modified noun is appropriate for use in a pharmaceutical product. Pharmaceutically acceptable cations include metallic ions and organic ions. More preferred metallic ions include, but are not limited to appropriate alkali metal (Group Ia) salts, alkaline earth metal (Group IIa) salts and other physiological acceptable metal ions. Exemplary ions include aluminum, calcium, lithium, magnesium, potassium, sodium and zinc in their usual valences. Preferred organic ions include protonated tertiary amines and quaternary ammonium cations, including in part, trimethylamine, diethylamine, N,N'-dibenzylethylenediamine, chloroprocaine, choline, diethanolamine, ethylenediamine, meglumine (N-methylglucamine) and procaine. Exemplary pharmaceutically acceptable acids include without limitation hydrochloric acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid oxalacetic acid, fumaric acid, propionic acid, aspartic acid, glutamic acid, benzoic acid, and the like.

"M" utilized in the reaction schemes that follow represents a leaving group such as halogen, phosphate ester or sulfate ester.

Preparation of Useful Compounds

Schemes A through C and Schemes 1 through 19 hereinbelow illustrate chemical processes and transformations that can be useful for the preparation of compounds useful in this invention; i.e., compounds of formulas I, II, III, IV and V and similar cyclic inhibitors. In addition, the preparation of compounds of formula VI and formula VII is illustrated. Compounds of formula VI and formula VII can be used as intermediates in the preparation of the compounds of formulas I, II, III, IV and V or pro-drugs or MMP inhibitors.

In Schemes A through C, the symbol J independently represents $R^{20}$ or other synthetically useful groups such as amides, acid chlorides, mixed anhydrides and the like. The n is 0, 1 or 2 and is preferred to be 1 or 2 in Scheme C. The n of these schemes corresponds to g in formulas VI and VII., and is zero, 1 or 2. The symbol m is 1 or 2. The symbol r is independently 1, 2 or 3. The symbol P represents a protecting group that can also be a member of the group $R^6$. In Scheme A, for simplicity and clarity of illustration positional isomers are illustrated with a bond through the ring in standard fashion. Later Schemes typically only show one positional isomer but positional isomers are represented by these structures and reactions in a manner consistent with Formula I, II, III, IV, V, VI, VII above. Similarly, the symbol B represents O, S. SO, $SO_2$ and $NR^6$. The symbols C and C' independently are electrophilic groups or groups capable of participating in a condensation reaction. Here to it should be noted that the six-membered ring is shown for illustrative purposes but the procedures and/or reagents are applicable to and represent combinations the permit the preparation of 5- to 8-membered rings.

The structures in Schemes 1 through 19 are also shown with compounds that represent the other compounds of this invention. The aromatic ring in Scheme C is aryl and heteroaryl. The moieties of —A—R—E—Y are as defined before. Reactions illustrated involving a spiroheterocyclic nitrogen atom may not be applicable to those compounds with sulfur or oxygen.

Scheme A

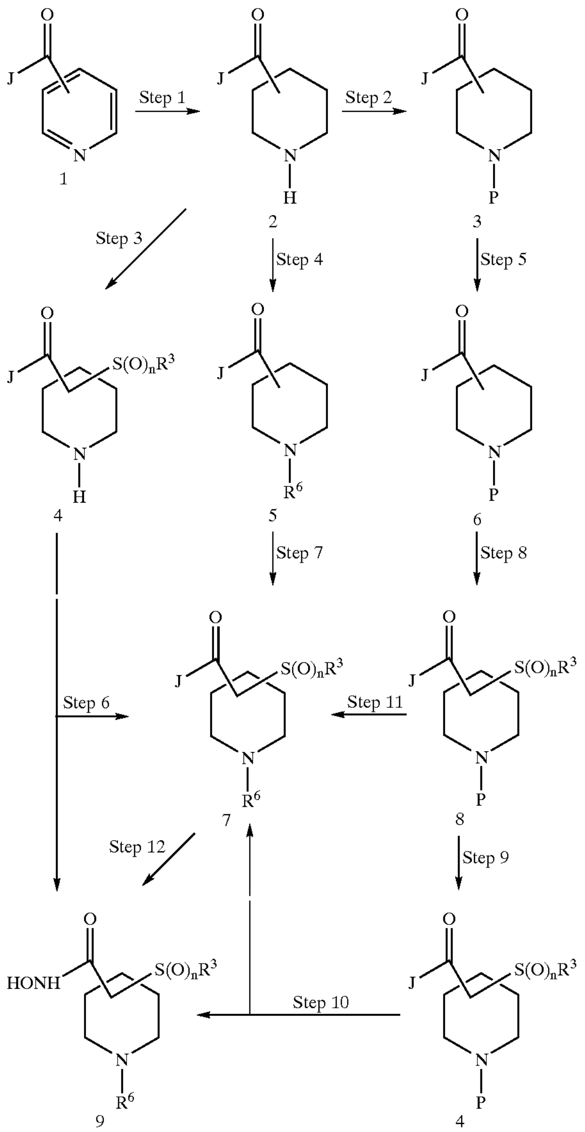

Scheme A shows in step 1 the reduction of a heteraryl compound to a carboxyl derivative. Generally, the first product is a hydrogen-containing amine heterocycle when the starting material is aromatic or an $R^6$-containing heterocycle when a partially unsaturated heterocycle is the starting material.

Compound 2 can be treated in several ways depending on the needs of the chemist. In Step 2, the nitrogen can be protected by preparing, for example, a carbobenzoxy (Z) or tert-butoxycarbonyl derivative. Such acylations can be carried out by methods well known in the art, especially the art of amino acid and peptide synthesis. The process of acylation with activated carboxyl group- or activated sulfonyl group-containing reagents to prepare contemplated compounds is carried out in the same manner. Examples of such acylating groups are carbonyl azides, halides, anhydrides, mixed anhydrides, carbodiimide derivatives or other less traditional activated ester groups such as the hydroxybenzotriazole derivative. These acylations can be run in the presence of base including mild bases such as triethylamine or N-ethylmorpholine if desired. The preparation of some activated ester reagents and their use to prepare other compounds useful in this invention is discussed below. It should be recalled that the groups constituting P and serving as a selectively removable protecting group can also be included as part of the group $R^6$.

Step 4 of Scheme A shows the alkylation or acylation of Compound 2 to produce compound 5. The process of acylation and alkylation are as discussed herein. In Step 5, the group J can be changed if desired. An example of such a change is exchange of an ester for a THP-protected hydroxamate conversion of a THP-protected hydroxamate inot a hydroxamate or conversion of an acid into a protected hydroxamate or the like.

Steps 3, 7 and 8 show the preparation of sulfur-containing derivatives of the contemplated compounds or intermediates to those compounds. The starting material for the above steps (e.g., compounds 2, 5 and 6) can be treated with a base to deprotonate the carbon alpha to the carbonyl function. This anion can be reacted with a sulfur electrophile to produce a sulfone, sulfoxide or sulfide. Such electrophiles can be of the form of, for example, $R^{24}S—SR^{24}$, $R^{24}SO_2C_1$, $R^{24}SC_1$, $R^{24}SOC_1$, $R^{24}S(O)—SR_{24}$ and the like where $R^{24}$ is as defined before or is an aryl or heteroaryl sulfur-containing material containing a coupling substituent, $R^{3'}$, that can be used to prepare one of the $R^{24}$-containing groups. Preparation of the anion requires a base and a strong base may be required such as one of the metal amides, hydrides or alkyls discussed herein. The solvents are nonprotic, and dipolar aprotic solvents are preferred along with an inert atmosphere. Subsequent schemes usually utilize $R^3$ for the $R^{24}$ group for ease of illustration.

It should be noted that these processes produce sulfides (thio ethers), sulfoxides or sulfones depending on starting material. In addition, the sulfides can be oxidized to sulfoxides or sulfones, and the sulfoxides can be oxidized to their corresponding sulfone derivatives. The choice of position in the synthetic sequence to change the oxidation state of sulfur as well as the decision to change oxidation state is under the control of the chemist skilled in the art. Methods of oxidizing sulfur are discussed hereinbelow.

Scheme A, Steps 6, 9, 10 and 12 independently illustrate the interconversion of groups within J. Examples of such interconversions include exchange of an ester for hydroxamic acid or hydroxamic acid derivative, conversion of a carboxylic acid into an activated carbonyl derivative or into a hydroxamic acid or hydroxamic acid derivative (pro-drug or protected derivative), or removal of a protecting group from a hydroxamate derivative. The preparation of activated carbonyl compounds their reaction with nucleophiles such as hydroxamic acid, protected hydroxamates or hydroxamic acid pro-drugs is discussed below as is the conversion of protected hydroxamic acid derivatives into hydroxamic acids. The preparation of, for example, hydroxybenzotriazole/carbodiimide, derived products is discussed herein. The preparation or hydrolysis of esters, amides, amide derivatives, acid chlorides, acid anhydrides, mixed anhydrides and the like are synthetic methods very well known in the art, andare not discussed in detail herein. Step 6 illustrates the conversion of compound 4 into compound 9, without first being converted into compound 7.

Scheme B

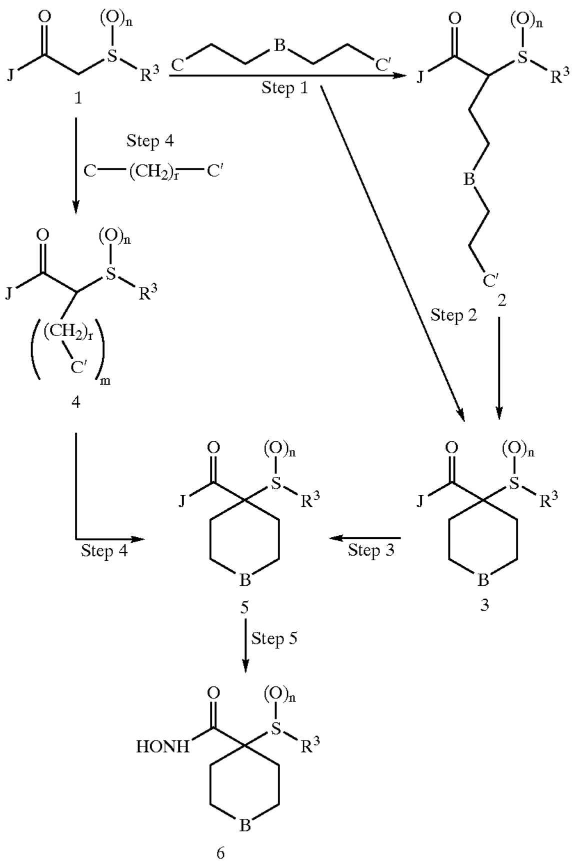

Scheme B illustrates an alternate method of preparing contemplated compounds. The reagent shown above the arrow in Step 1 is a reagent with two active groups in addition to the heteroatoms (B) noted before. Here again, the particular reagent illustrated was selected to permit a clear illustration of the reaction, but it is also intended to represent reagents that permit the preparation of the heteroatom position, and 5-, 7- and 8-membered ring size compounds. These reagents are readily selected by those skilled in the art.

C and C' in this Step 1 reagent are independently an electophile or a group convertible into an electrophile. Such groups include halides, sulfonic acid esters, epoxides, thioepoxides, hydroxyl groups, and the like. This reagent is reacted with a nucleophilic anion of a sulfur containing carbonyl compound such as compound 1. The anion is formed by deprotonation of compound 1 and examples of bases suitable for such a deprotonation are discussed below. Treatment with the above electrophilic reagent is carried out under alkylating conditions well known in the art and discussed herein. The product of this reaction can be either Compound 2 or Compound 3; i.e., the reaction can be carried out as a pot or two step process as required.

Step 3 illustrates the interconversion of J groups if desired as discussed above for Scheme A. Step 4 uses reagent where C, for example, represents a nucleophile as discussed above and C' represents an electrophile or a nucleophile such as hydroxyl, thiol or $R^6$-amino. It is noted that C' can be, independently, a nucleophile or an electrophile when m is 2; i.e., the C' groups are not required to be the same when m is 2. When m is 2, treatment with a second mole of base provides the skilled chemist an alternative preparation of Compound 5. When C' is hydroxyl, thiol, or $R^6$-amino and m is 2, the person skilled in the art can condense Compound 4 with, for example, an aldehyde or ketone, under reductive conditions or with subsequent reduction to form a contemplated compound. As above, the compound where m is 2 can be made in one step (one pot process) or two steps, thus permitting the chemist the choice of having the reagent(s) be the same (one pot) or different (two step).

Scheme B also illustrates the interconversions of the groups within J, the oxidation state of the sulfur and groups on nitrogen; i.e., $R^6$ groups, to provide the contemplated compounds. These methods and processes are discussed above for the reactions of Scheme A.

The $R^6$ function can be changed and/or further modified in compounds or at steps in the Schemes as desired or required by the person skilled in the art to prepare the contemplated compounds. Interconversion of dual purpose functional groups such as short or long term protecting groups into other $R^6$ groups has been mentioned. Many other routine and/or useful conversions, including the preparation of synthetic intermediates, are very well known in the art. A few non-limiting examples of such conversions or reactions include: reductions; nucleophilic displacement/substitution reactions; exchange or preparation of carboxylic or sulfonic acids, amides, esters, acid halides, mixed anhydrides and the like; electrophilic displacement/substitution reactions; oxidations; ring/chain conversions, ring opening reactions, condensation reactions including those involving sulfonyl or carbonyl groups and/or carbon-hydrogen bonds influenced by either or both of those groups. The selection of preparative methods or conversion methods of the contemplated compounds and the order of the reaction(s) is made by the skilled person. It is expected that should a particular sequence or method prove to be undesirable that an alternative will be selected and used. Included is the choice of Scheme C

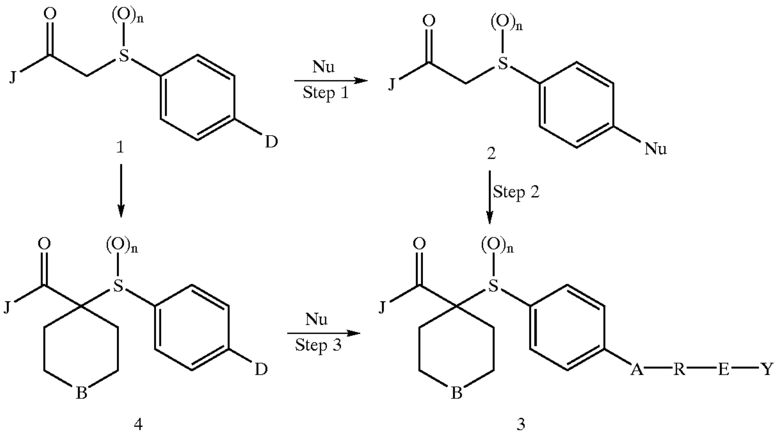

Scheme C illustrates the nucleophilic displacement of a group D as defined herein. This reaction is carried out in a similar manner to the displacement reactions discussed herein. The choice of oxidation state of the sulfur is made by the person skilled in the art, but sulfoxide or sulfone groups are preferred, and the sulfone is most preferred. The displacement can be carried out either before or after the methylene next to the carbonyl group is reacted to form a spiro heterocyclic group.

Steps 1, 2 and 3 also illustrate that although the nucleophilic displacement can be carried out with one nucleophile (Nu), the product of this reaction can be modified by methods well known in the art and as shown herein to provide the group —A—R—E—Y as defined hereinbefore.

A non-limiting illustration of such a process is provided when D is fluoride. The fluoride leaving group can be directly displaced with the anion of 4-trifluoromethylphenol, 4-trifluoromethoxyphenol, 4-trifluoromethylthiophenol and the like to provide a contemplated compound. This is a one pot process from Compound 4. Other compounds included in —A—R—E—Y can be prepared by displacing the fluoride leaving group with ammonia to provide an amine, which can then be acylated by methods discussed wherein with, for example, 4-trifluoromethylbenzoyl chloride, to form another contemplated product compound.

preparing/adding the groups in a single step using a convergent inhibitor strategy or preparing the final $R^6$ group following a stepwise strategy.

Thus, in general, the choices of starting material and reaction conditions can vary as is well known to those skilled in the art. Usually, no single set of conditions is limiting because variations can be applied as required. Conditions are also selected as desired to suit a specific purpose such as small scale preparations or large scale preparations. In either case, the use of less safe or less environmentally sound materials or reagents is usually be minimized. Examples of such materials are diazomethane, diethyl ether, heavy metal salts, dimethyl sulfide, chloroform, benzene and the like.

These reactions can be carried out under a dry inert atmosphere such a nitrogen or argon if desired. Selected reactions known to those skilled in the art, can be carried out under a dry atmosphere such as dry air whereas other synthetic steps, for example, aqueous acid or base ester or amide hydrolysis, can be carried out under laboratory air. In addition, some processes of these syntheses can be carried out in a pressure apparatus at pressures above, equal to or below atmospheric pressure. The use of such an apparatus aids in the control of gaseous reagents such as hydrogen, ammonia, trimethylamine, methylamine, oxygen and the like, and can also help prevent the leakage of air or humidity into a reaction in progress. This discussion is not intended to be exhaustive as it is readily noted that additional or alternative methods, conditions, reactions or systems can be identified and used by a chemist of ordinary skill.

The illustrated reactions are usually carried out at a temperature of between −25° C. to solvent reflux under an inert atmosphere such as nitrogen or argon. The solvent or solvent mixture can vary widely depending upon reagents and other conditions and can include polar or dipolar aprotic solvents as listed or mixtures of these solvents. Reactions can be carried out at lower temperatures such as dry ice/acetone or liquid nitrogen temperature if desired to carry out such reactions as metalations or anion formations using strong bases.

In some cases, amines such as triethylamine, pyridine or other non-reactive bases can serve as reagents and/or solvents and/or co-solvents. In some instances, in these reactions and other reactions in these Schemes, protecting groups can be used to maintain or retain groups in other parts of a molecule(s) at locations that is(are) not desired reactive centers. Examples of such groups that the skilled person can maintain or retain include, amines, other hydroxyls, thiols, acids and the like. Such protecting groups can include acyl groups, arylalkyl groups, carbamoyl groups, ethers, alkoxyalkyl ethers, cycloalkyloxy ethers, arylalkyl groups, silyl groups including trisubstituted silyl groups, ester groups and the like. Examples of such protecting groups include acetyl, trifluoroacetyl, tetrahydropyran (THP), benzyl, tert-butoxy carbonyl (BOC or TBOC), benzyloxycarbonyl (Z or CBZ), tert-butyldimethylsilyl (TBDMS) or methoxyethoxymethylene (MEM) groups. The preparation of such protected compounds as well as their removal is well known in the art. The protecting groups can also be used as substituents in the contemplated compounds whose utility is as a drug rather than as a synthetic intermediate.

Many reactions or processes involve bases that can act as reactants, reagents, deprotonating agents, acid scavengers, salt forming reagents, solvents, co-solvents and the like. Bases that can be used include, for example, metal hydroxides such as sodium, potassium, lithium, cesium or magnesium hydroxide, oxides such as those of sodium, potassium, lithium, calcium or magnesium, metal carbonates such as those of sodium, potassium, lithium, cesium, calcium or magnesium, metal bicarbonates such as sodium bicarbonate or potassium bicarbonate, primary (I°), secondary (II°) or tertiary (III°) organic amines such as alkyl amines, arylalkyl amines, alkylarylalkyl amines, heterocyclic amines or heteroaryl amines, ammonium hydroxides or quaternary ammonium hydroxides. As non-limiting examples, such amines can include triethylamine, trimethylamine, diisopropylamine, methyldiisopropylamine, diazabicyclononane, tribenzylamine, dimethylbenzylamine, morpholine, N-methylmorpholine, N,N'-dimethylpiperazine, N-ethylpiperidine, 1,1,5,5-tetramethylpiperidine, dimethylaminopyridine, pyridine, quinoline, tetramethylethylenediamine, and the like. Non-limiting examples of ammonium hydroxides, usually made from amines and water, can include ammonium hydroxide, triethylammonium hydroxide, trimethylammonium hydroxide, methyldiiospropylammonium hydroxide, tribenzylammonium hydroxide, dimethylbenzylammonium hydroxide, morpholinium hydroxide, N-methylmorpholinium hydroxide, N,N'-dimethylpiperazinium hydroxide, N-ethylpiperidinium hydroxide, and the like. As non-limiting examples, quaternary ammonium hydroxides can include tetraethylammonium hydroxide, tetramethylammonium hydroxide, dimethyldiiospropyl-ammonium hydroxide, benzylmethyldiisopropylammonium hydroxide, methyldiazabicyclononylammonium hydroxide, methyltribenzylammonium hydroxide, N,N-dimethyl-morpholiniumhydroxide, N,N,N',N'-tetramethylpiperazinium hydroxide, and N-ethyl-N'-hexylpiperidinium hydroxide and the like.

Metal hydrides, amides or alcoholates such as calcium hydride, sodium hydride, potassium hydride, lithium hydride, aluminum hydride, diisobutylaluminum hydride (DIBAL) sodium methoxide, potassium tert-butoxide, calcium ethoxide, magnesium ethoxide, sodium amide, potassium diisopropyl amide and the like can also be suitable reagents. Organometallic deprotonating agents such as alkyl or aryl lithium reagents such as methyl lithium, phenyl lithium, tert-butyl lithium, lithium acetylide or butyl lithium, Grignard reagents such as methylmagnesium bromide or methymagnesium chloride, organocadmium reagents such as dimethylcadmium and the like can also serve as bases for causing salt formation or catalyzing the reaction. Quaternary ammonium hydroxides or mixed salts are also useful for aiding phase transfer couplings or serving as phase transfer reagents. Pharmaceutically acceptable bases can be reacted with acids to form contemplated pharmaceutically acceptable salts. It should also be noted that optically active bases can be used to make optically active salts which can be used for optical resolutions.

Generally, reaction media can comprise a single solvent, mixed solvents of the same or different classes or serve as a reagent in a single or mixed solvent system. The solvents can be protic, non-protic or dipolar aprotic. Non-limiting examples of protic solvents include water, methanol (MeOH), denatured or pure 95% or absolute ethanol, isopropanol and the like. Typical non-protic solvents include acetone, tetrahydrofuran (THF), dioxane, diethyl ether, tert-butylmethyl ether (TBME), aromatics such as xylene, toluene, or benzene, ethyl acetate, methyl acetate, butyl acetate, trichloroethane, methylene chloride, ethylenedichloride (EDC), hexane, heptane, isooctane, cyclohexane and the like. Dipolar aprotic solvents include compounds such as dimethylformamide (DMF), dimethylacetamide (DMAc), acetonitrile, DMSO, hexamethylphosphorus triamide (HMPA), nitromethane, tetramethylurea, N-methylpyrrolidone and the like. Non-limiting examples of reagents that can be used as solvents or as part of a mixed solvent system include organic or inorganic mono- or multi-protic acids or bases such as hydrochloric acid, phosphoric acid, sulfuric acid, acetic acid, formic acid, citric acid, succinic acid, triethylamine, morpholine, N-methylmorpholine, piperidine, pyrazine, piperazine, pyridine, potassium hydroxide, sodium hydroxide, alcohols or amines for making esters or amides or thiols for making contemplated products and the like.

The preparation of compounds contemplated herein can require the oxidation of nitrogen or sulfur to N-oxide derivatives or sulfoxides or sulfones. Reagents for this process can include, in a non-limiting example, peroxymonosulfate (OXONE®), hydrogen peroxide, meta-chloroperbenzoic acid, perbenzoic acid, peracetic acid, perlactic acid, tert-butyl peroxide, tert-butyl hypochlorite, sodium hydpochlorite, hypochlorous acid, sodium meta-periodate, periodic acid and the like with the weaker agents being most useful for the preparation of sulfones and sulfoxides. Protic, non-protic, dipolar aprotic solvents, either pure or mixed, can be chosen, for example, methanol/water.

The oxidation can be carried out at temperature of about −78° to about 50° degrees Centigrade, and normally selected from a range −10° C. to about 40° C. Sulfoxides are best prepared using one equivalent of oxidizing agent. It can be desirable in the case of more active oxidizing agents, but not required, that the reactions be carried out under an inert gas atmosphere with or without degassed solvents. It should be noted that the oxidation of sulfides to sulfones can be carried out in one step or two steps via the sulfoxide as desired by the chemist.

Reduction is a well known process in the art with a useful method being hydrogenation. In such cases (catalytic reduction), there can be a metal catalyst such as Rh, Pd, Pt, Ni or the like with or without an additional support such as carbon, barium carbonate and the like. Solvents can be protic or non-protic pure solvents or mixed solvents as required. The reductions can be carried out at atmospheric pressure to a pressure of multiple atmospheres with atmospheric pressure to about 40 pounds per square inch (psi) preferred or very high pressures in special hydrogenation equipment well known in the art.

Reductive alkylation of amines or active methylene compounds is also a useful method of preparing compounds. Such alkylations can be carried out under reductive hydrogenation conditions as presented above using, for example, aldehydes or ketones. Hydride transfer reagents such as sodium cyanoborohydride, aluminum hydride, lithium aluminumhydride, borane, sodium borohydride, di-isobutylaluminum hydride and the like are also useful as reagents for reductive alkylation. Acyl groups can be reduced in a similar manner to produce substituted amines.

Alternative methods of alkylating carbon or nitrogen are direct alkylation. Such an alkylation, as is well known in the art, can be carried by treatment of an activated carbon containing at least one hydrogen with base to form the corresponding anion, adding an electrophilic reagent and permitting the SN2 reaction to proceed. An amine to be alkylated is treated similarly except that deprotonation may not be required. Electrophiles include halogen derivatives, sulfonate esters, epoxides and the like.

Bases and solvents for alkylation reactions are those discussed above. Preferred are bases that are hindered such that competition with the electrophile is minimized. Additional preferred bases are metal hydrides, amide anions or organometallic bases such as n-butyl lithium. The solvents, solvent mixtures or solvent/reagent mixtures discussed are satisfactory but non-protic or dipolar aprotic solvents such as acetone, acetonitrile, DMF and the like are examples of preferred classes.

Acids are used in many reactions during various syntheses. For example, removal of the THP protecting group to produce the hydroxamic acid. The acid can be a mono-, di- or tri-protic organic or inorganic acid. Examples of acids include hydrochloric acid, phosphoric acid, sulfuric acid, acetic acid, formic acid, citric acid, succinic acid, hydrobromic acid, hydrofluoric acid, carbonic acid, phosphorus acid, p-toluene sulfonic acid, trifluoromethane sulfonic acid, trifluoroacetic acid, difluoroacetic acid, benzoic acid, methane sulfonic acid, benzene sulfonic acid, 2,6-dimethylbenzene sulfonic acid, trichloroacetic acid, nitrobenzoic acid, dinitrobenzoic acid, trinitrobenzoic acid, and the like. They can also be Lewis acids such as aluminum chloride, borontrifluoride, antimony pentafluoride and the like. Acids in a protic can also be used to hydrolyze esters, amides and the like as well as catalyze exchange reactions.

Conversion of a carboxylic acid protected as an ester or amide into a hydroxamic acid or hydroxamic acid derivative such as an O-arylalkylether or O-cycloalkoxyalkylether group is useful. In the case where hydroxylamine is used, treatment of an ester or amide with one or more equivalents of hydroxylamine hydrochloride at room temperature or above in a solvent or solvents, usually protic or partially protic, such as those listed above can provide a hydroxamic acid directly. This exchange process can be further catalyzed by the addition of additional acid. Alternatively, a base such as a salt of an alcohol used as a solvent, for example, sodium methoxide in methanol, can be used to form hydroxylamine from hydroxylamine hydrochloride in situ which can exchange with an ester or amide. As mentioned above, exchange can be carried out with a protected hydroxyl amine such as tetrahydropyranylhydroxyamine ($THPONH_2$), benzylhydroxylamine ($BnONH_2$), and the like in which case compounds such as shown in Schemes A, B and C that are tetrahydropyranyl (THP) or benzyl (Bn) hydroxamic acid derivatives are the products. Removal of the protecting groups when desired, for example, following further transformations in another part of the molecule or following storage, is accomplished by standard methods well known in the art such as acid hydrolysis of the THP group as discussed above or reductive removal of the benzyl group with hydrogen and a metal catalyst such as palladium, platinum, palladium on carbon or nickel.

In the case where $R^{20}$ is hydroxyl; i.e., where the intermediate is a carboxylic acid, standard coupling reactions can be used. For example, the acid can be converted into an acid chloride, mixed anhydride or activated ester such as hydroxybenzotriazole and treated with hydroxylamine or a protected hydroxylamine in the presence of a non-competitive base to the nitrogen acylated compound. This is the same product as discussed above. Couplings of this nature are well known in the art and especially the art related to peptide and amino acid chemistry.

Compounds contemplated herein can possess one or more asymmetric carbon atoms and are thus capable of existing in the form of optical isomers, enantiomers, diastereoisomers, as well as in the form of racemic or nonracemic mixtures. A compound can also exist in other isomeric forms such as ortho, meta and para isomers, cis and trans isomers, syn and anti isomers, E and Z isomers, tautomeric isomers, alpha and beta isomers, axial and equatorial isomers and isomers due to hindered rotation. An isomer can exist in equilibrium with another isomer in a mammal or a test system. Such a compound can also exist as an isomeric equilibrium system with a solvent or water, for example, as a hydrated ketone or aldehyde, as is well known in the art. All isomers are included as compounds of this invention.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, are applicable to the preparation of the corresponding compounds that are contemplated.

Scheme 1
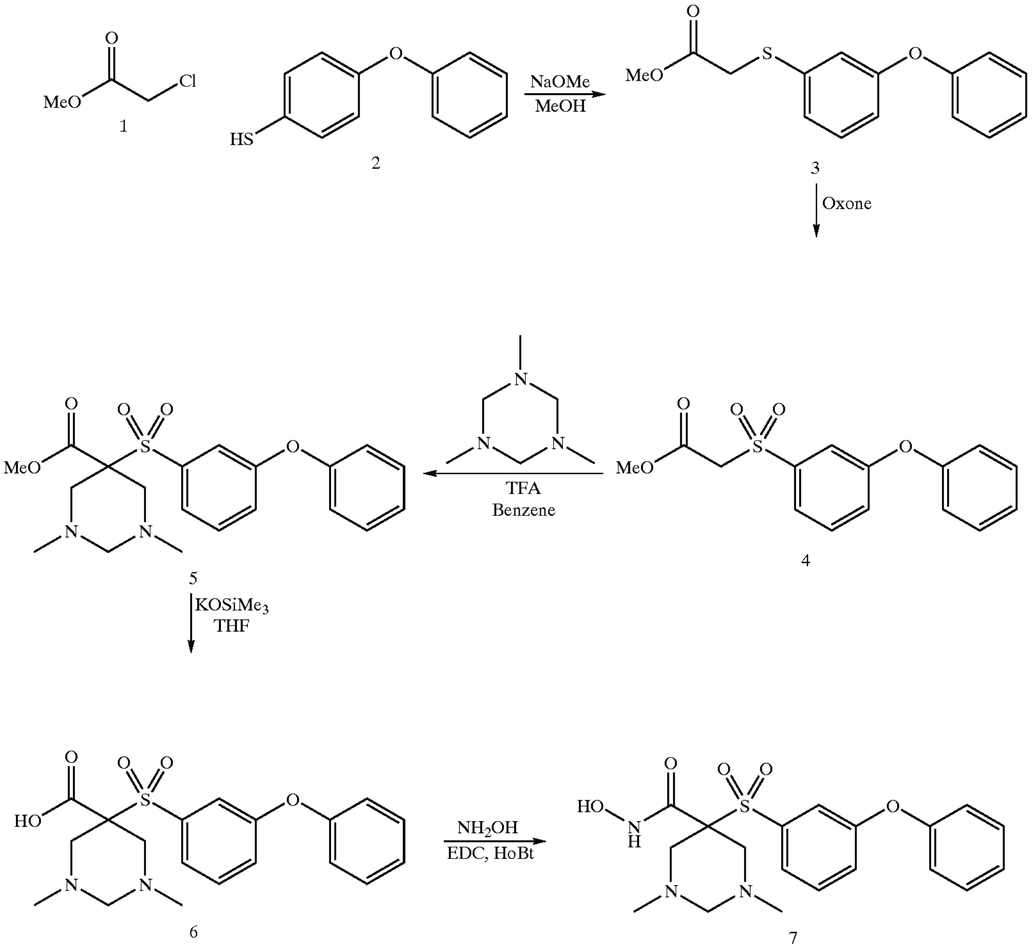
Scheme 2
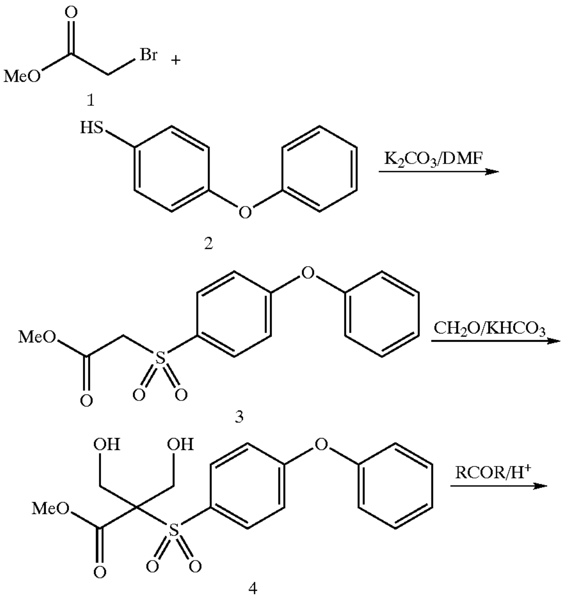
-continued
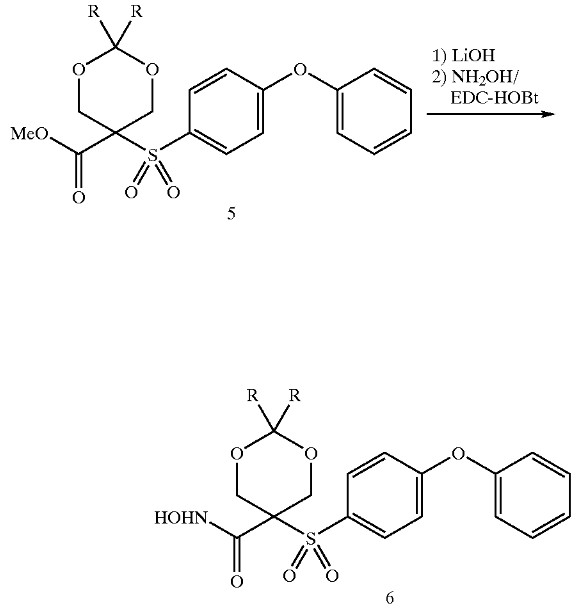

Scheme 3
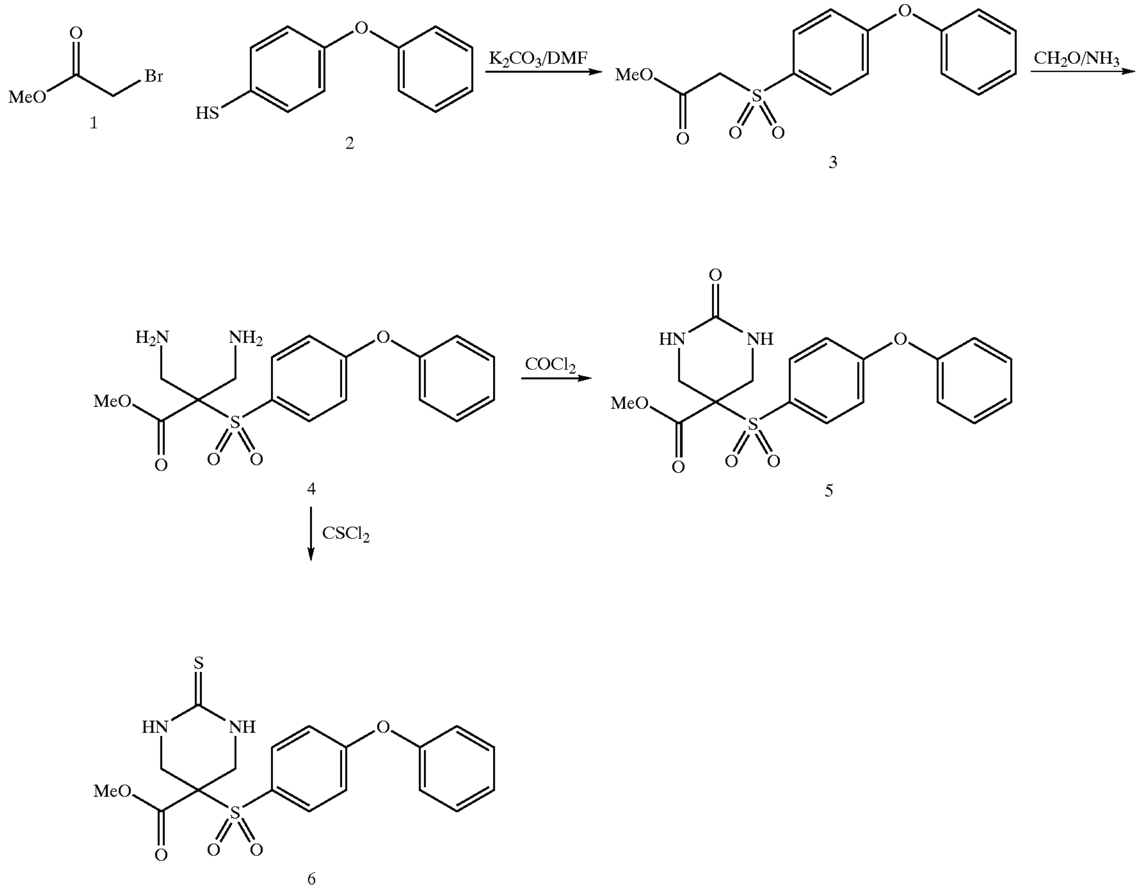
Scheme 4
-continued
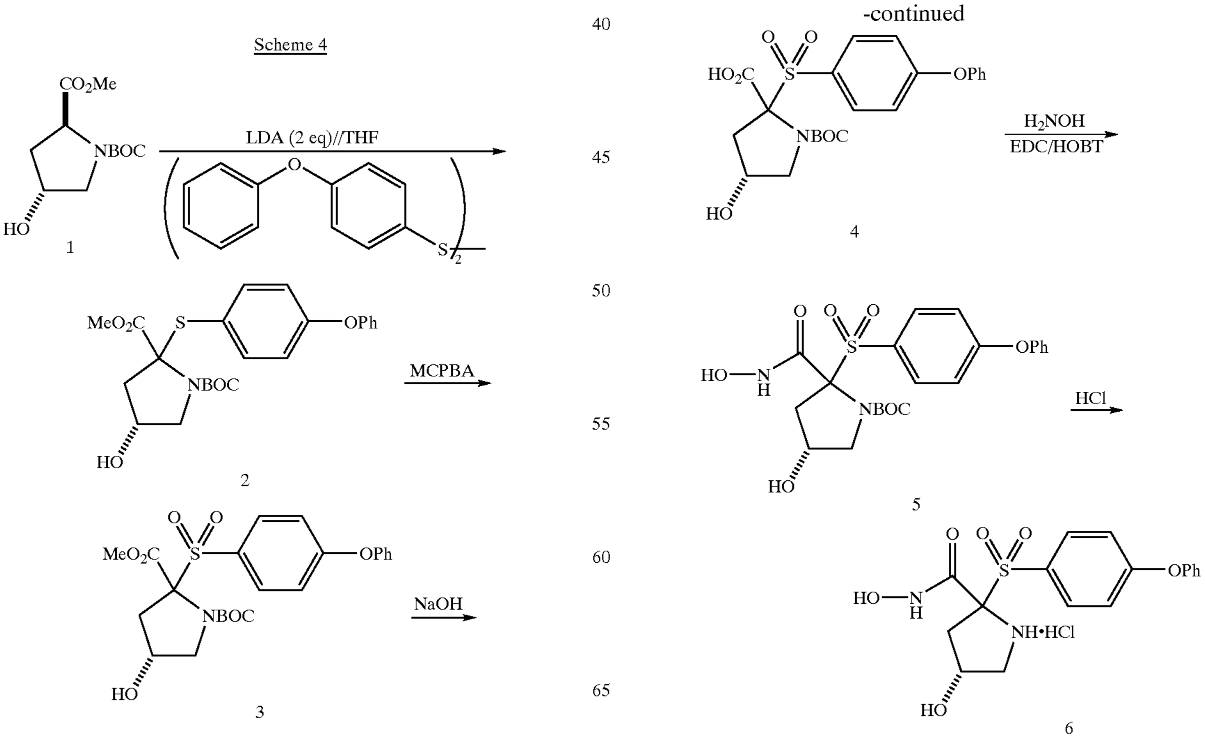

Scheme 5
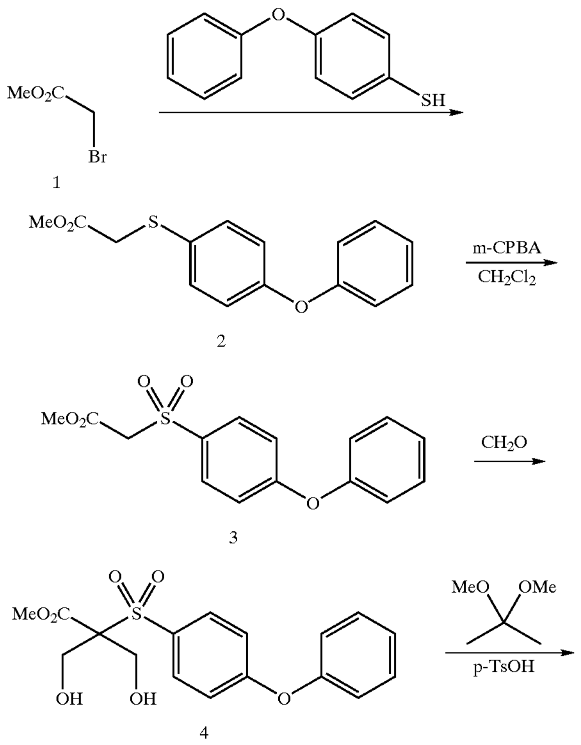
-continued
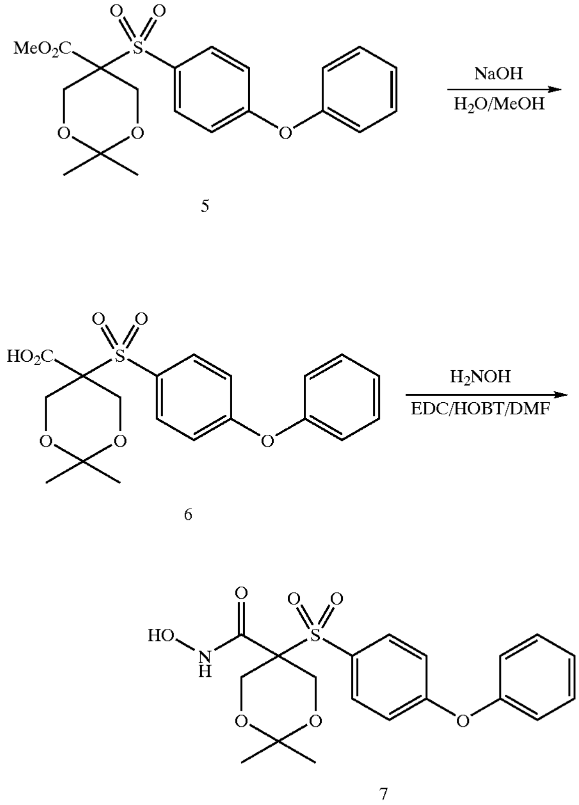
Scheme 6
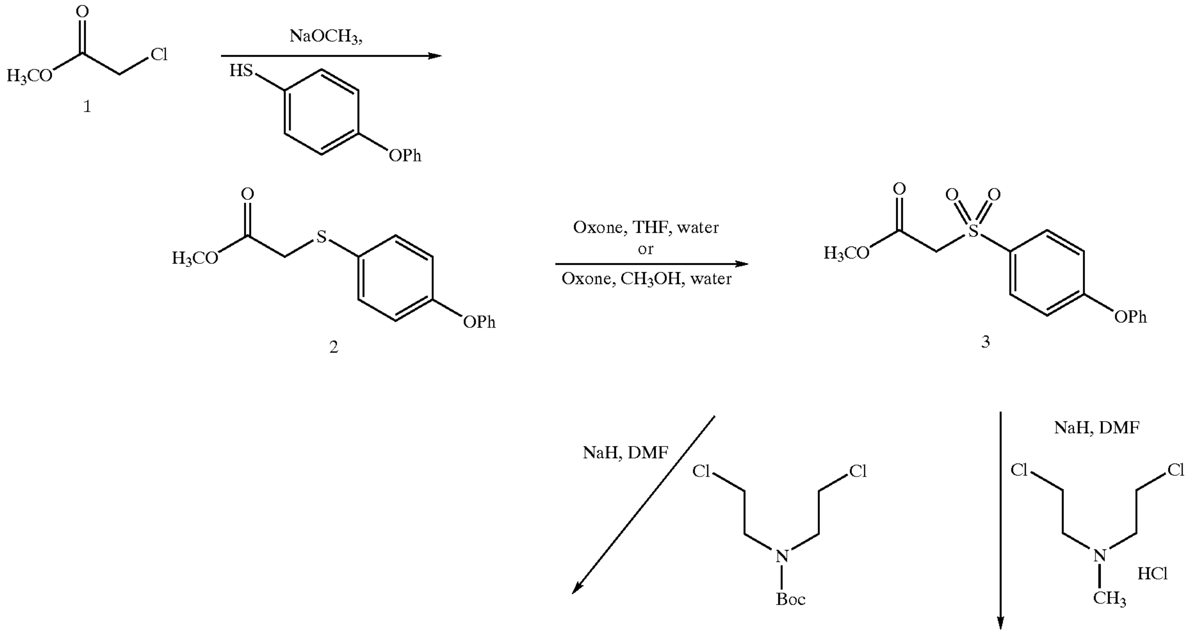

-continued
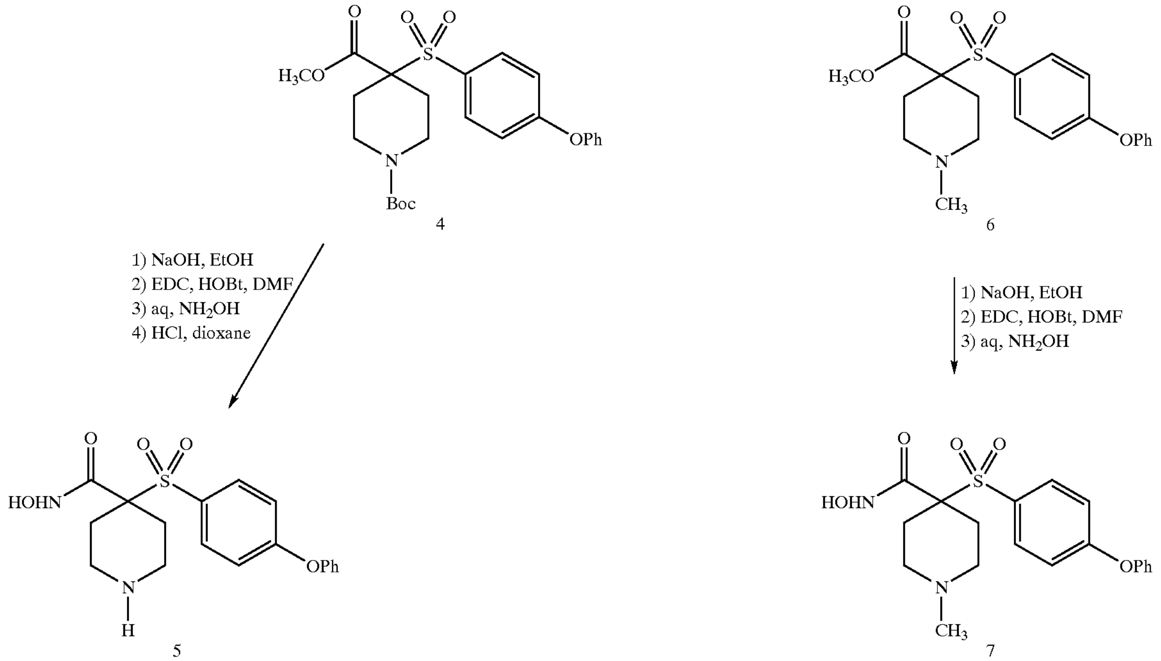
4 6 5 7
Scheme 7
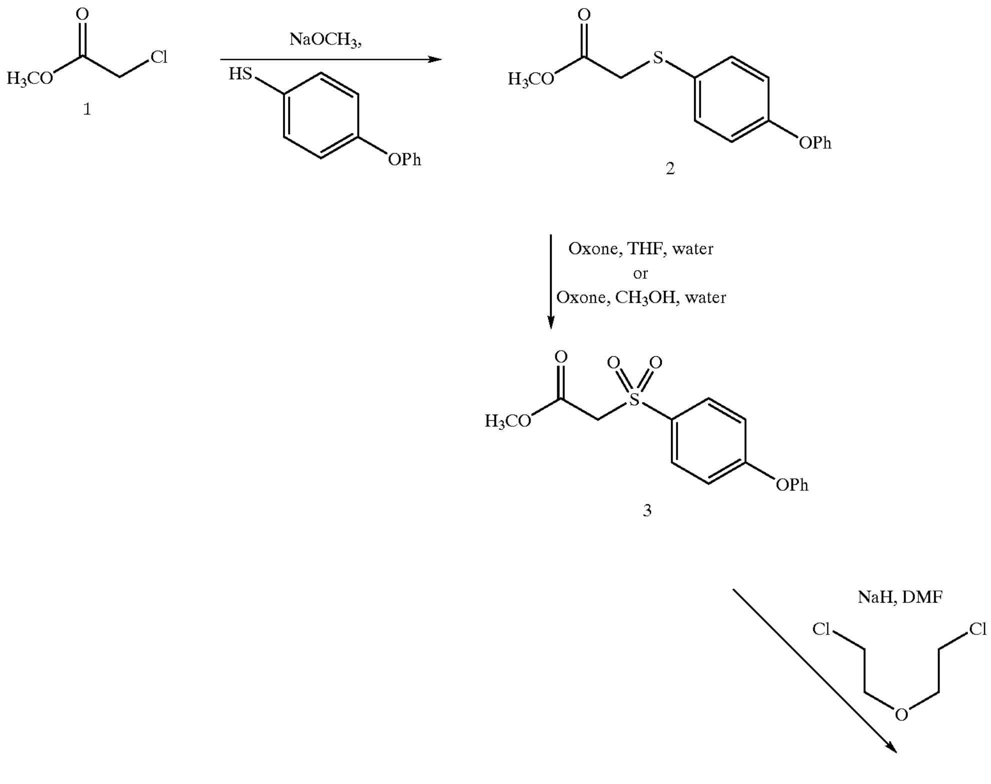
1 2 3

-continued
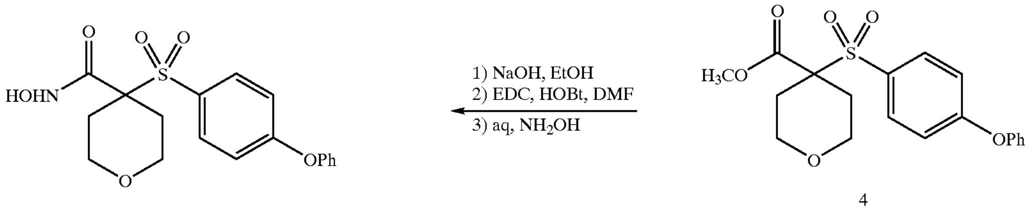
5 4
Scheme 8
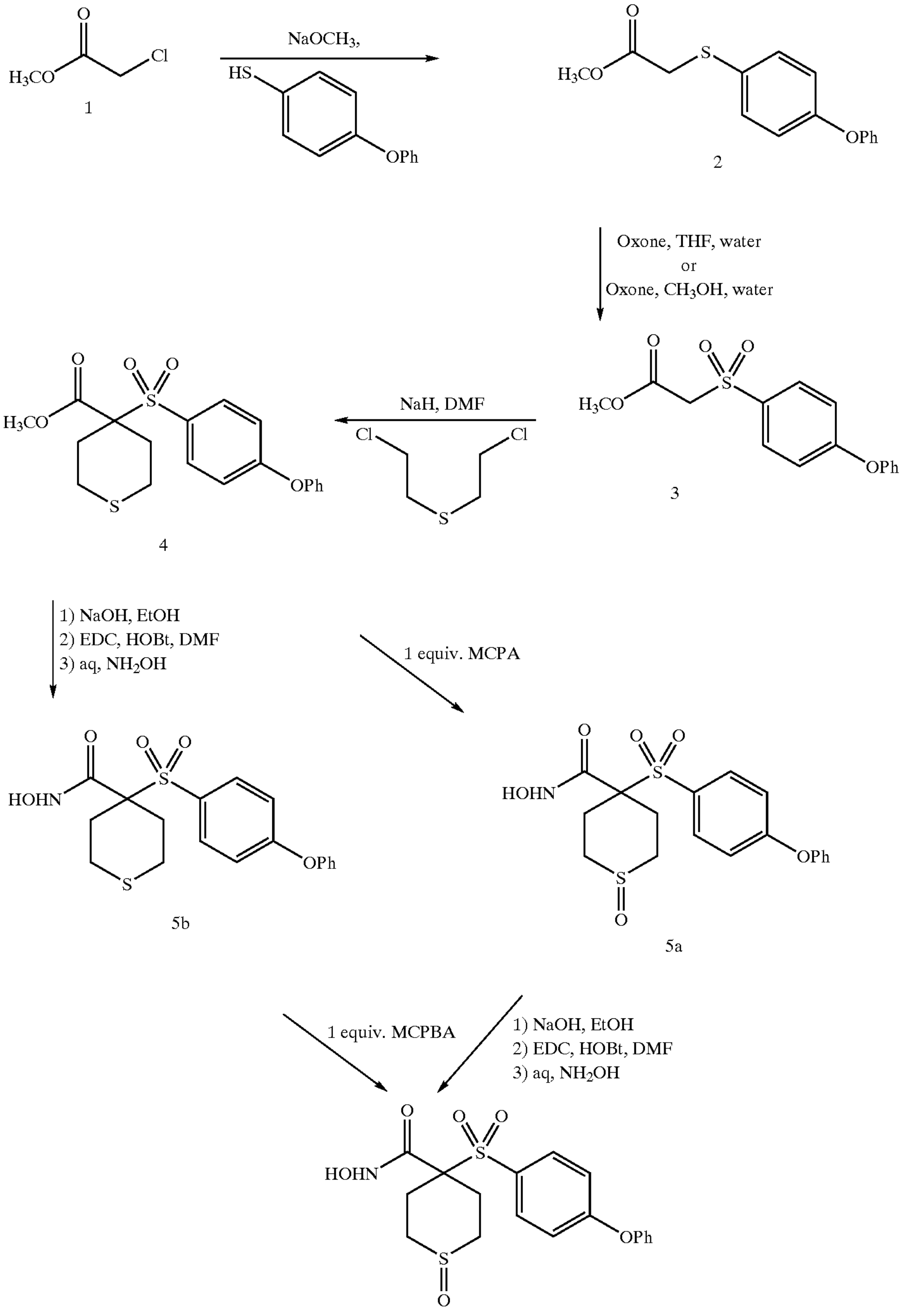
1 2 3 4 5b 5a 6

Scheme 9
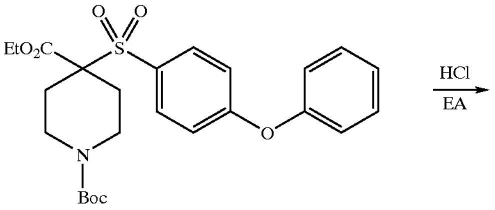
1
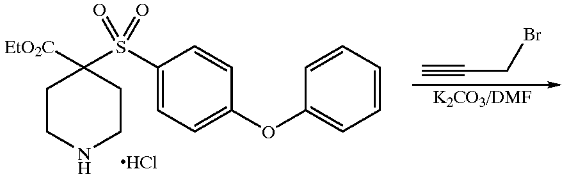
2
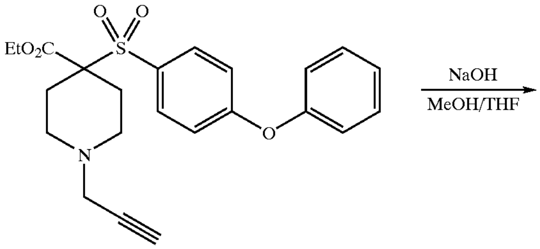
3
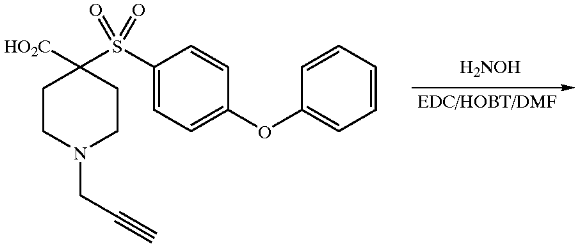
4
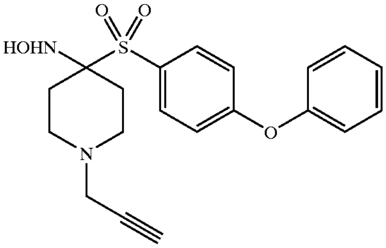
5
Scheme 10
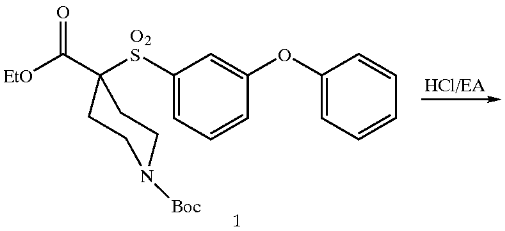
1
-continued
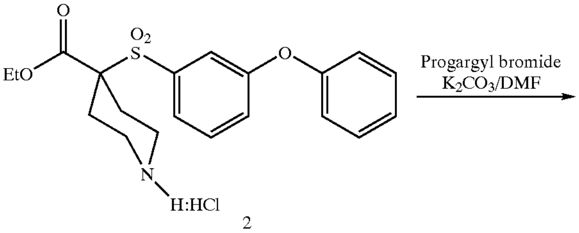
2
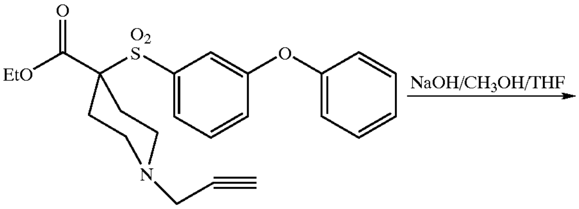
3
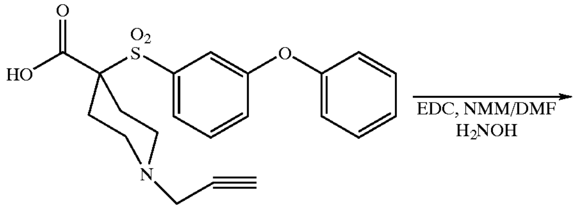
4
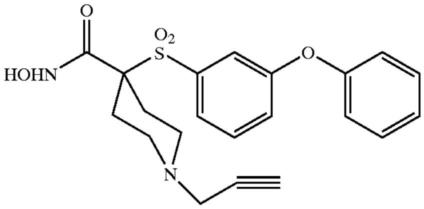
5
Scheme 11
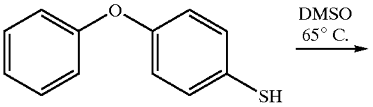
1
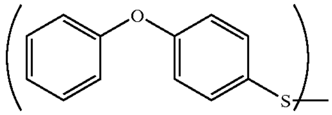
z
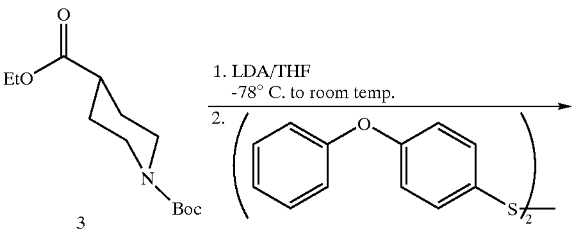
3

-continued
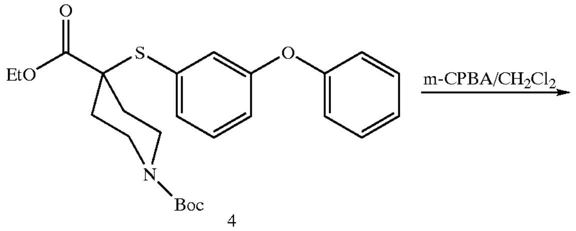
4
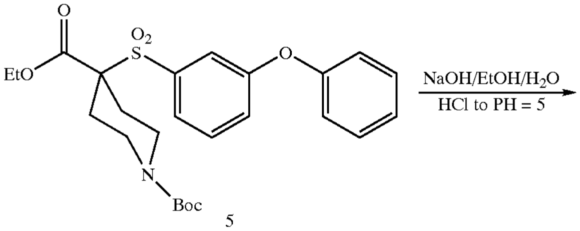
5
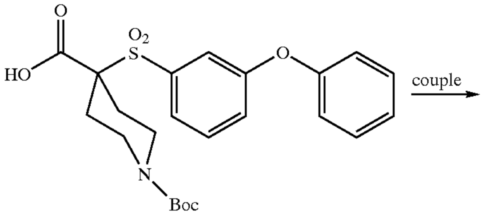
91% as the Na salt
6
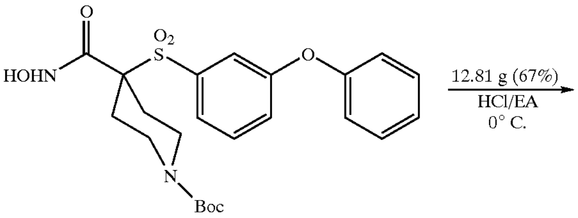
7
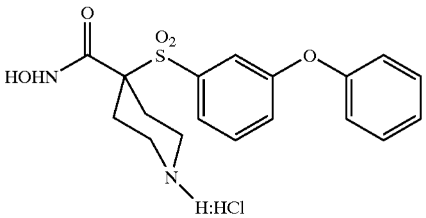
10.82 g (98%)
SC-75474
8
Scheme 12
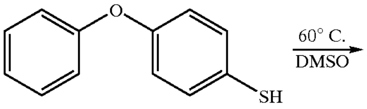
1
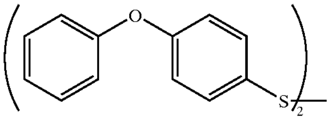
2
-continued
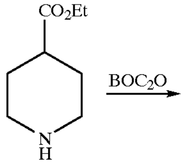
3
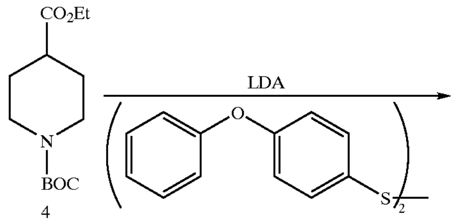
4
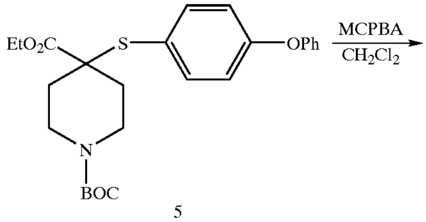
5
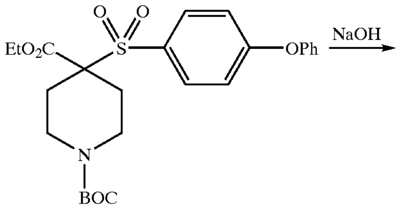
6
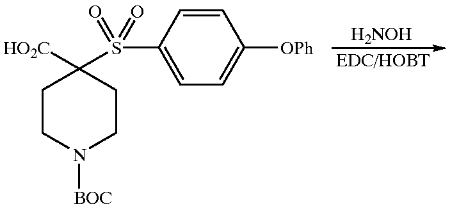
7
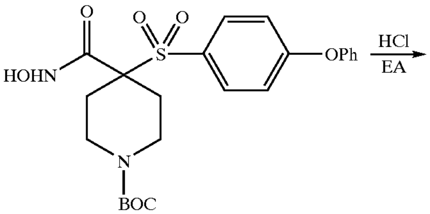
8
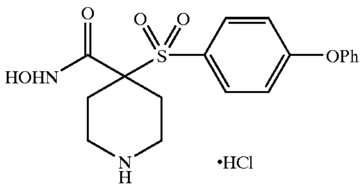
9

Scheme 13
In a similar manner, the following analogs can be made.
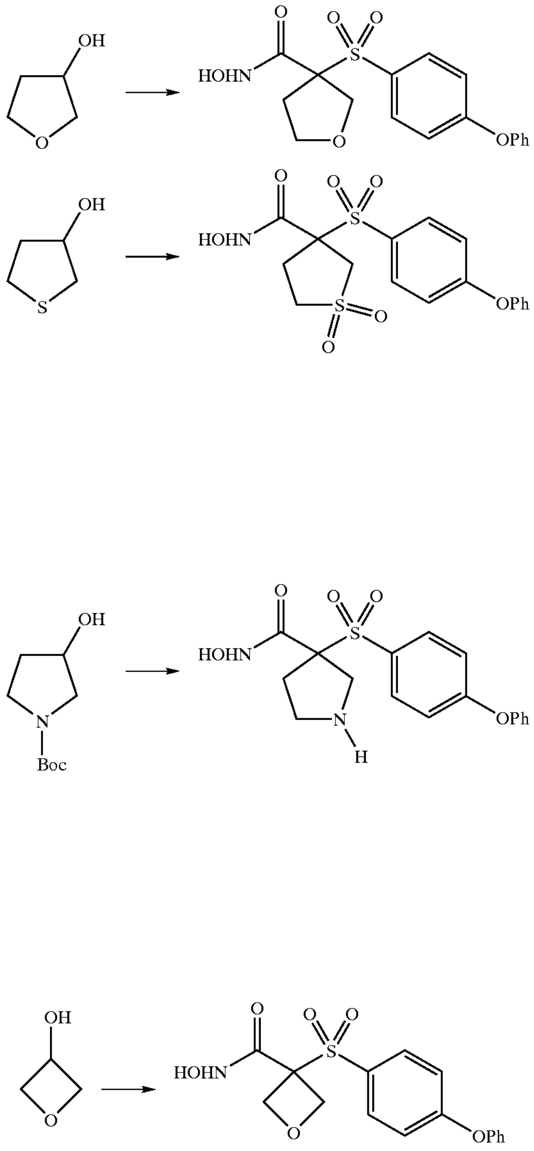
Scheme 14
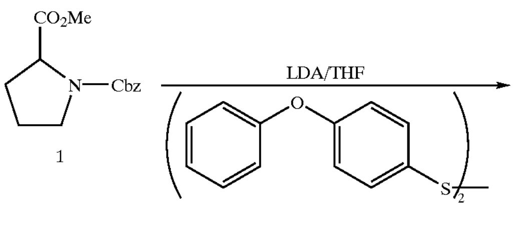
1
-continued
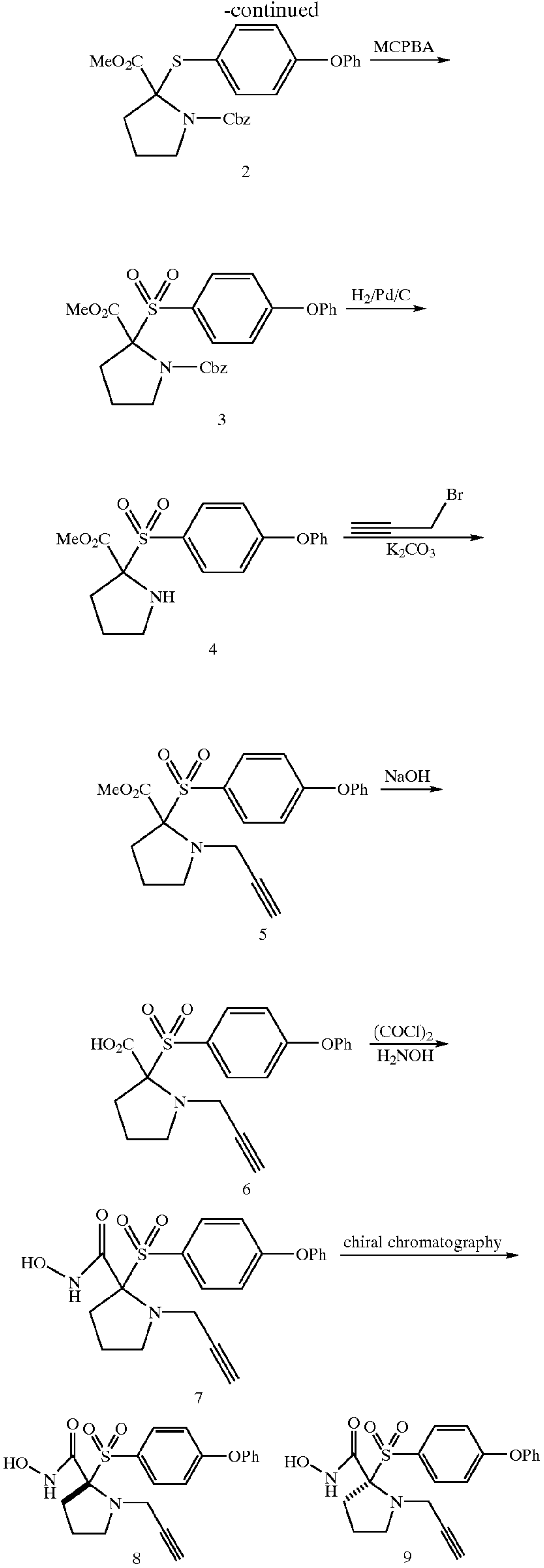
2
3
4
5
6
7
8
9

Scheme 15
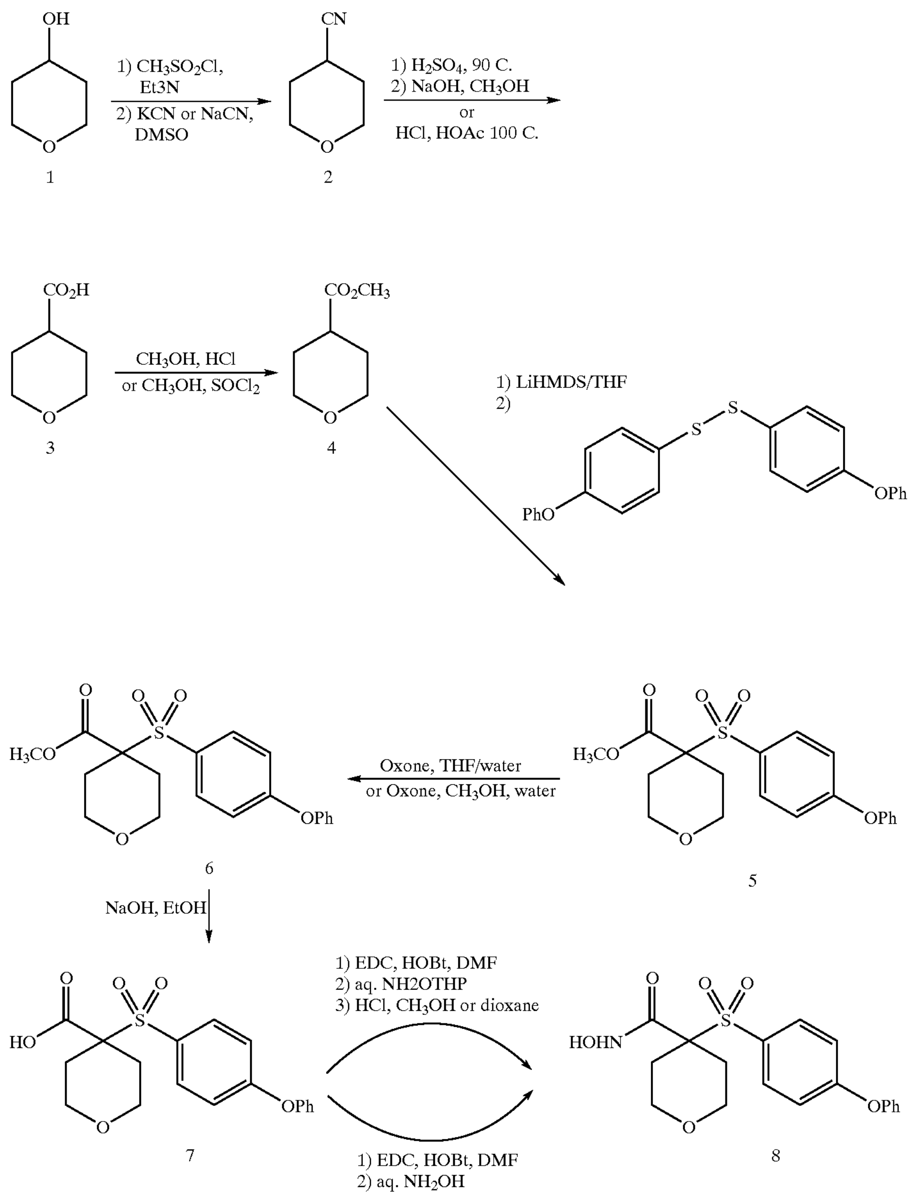
Scheme 16
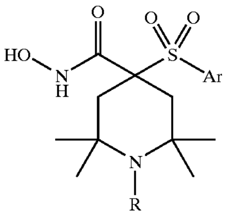
5
-continued
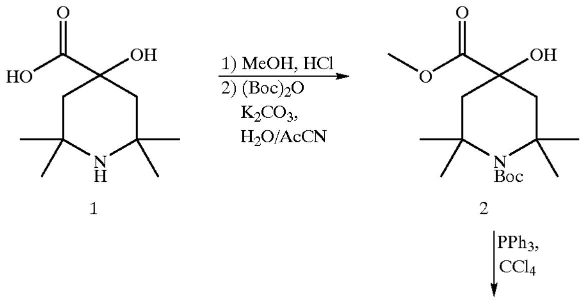

-continued
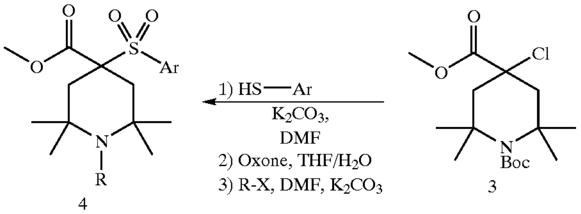
4 3
4
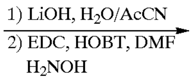
5
Scheme 17
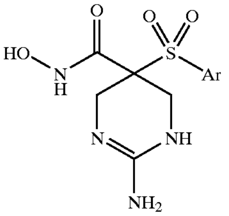
3
-continued
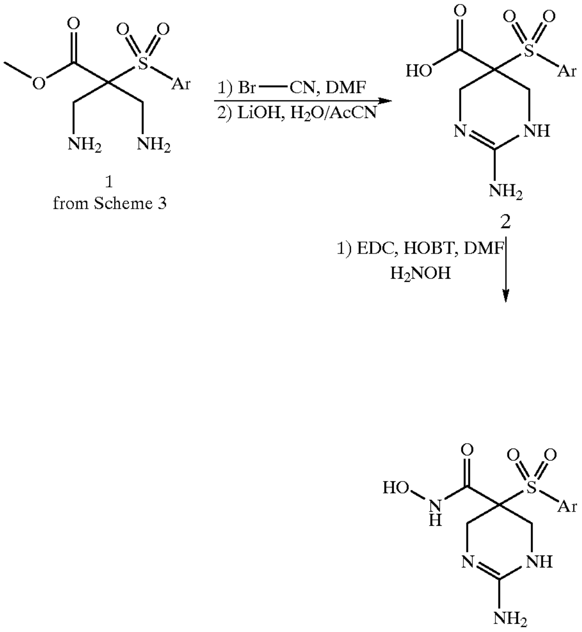
1
from Scheme 3
2
3
Scheme 18
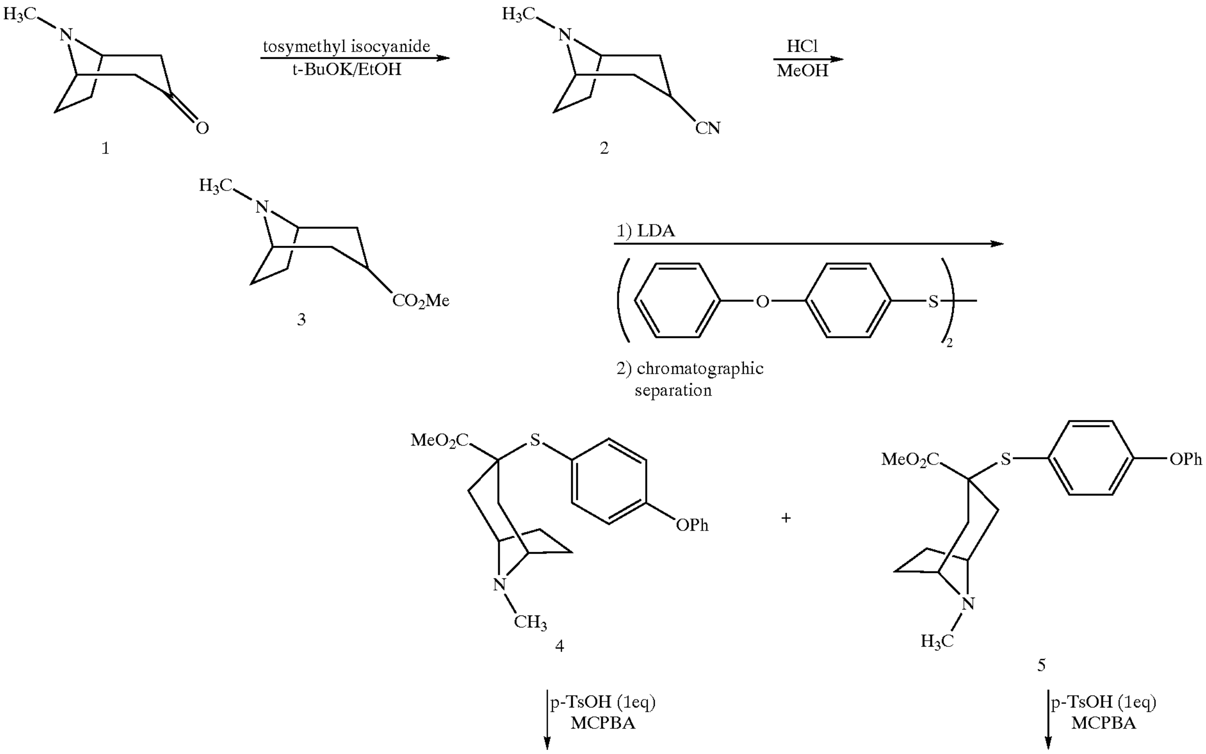
1 2 3 4 5

-continued
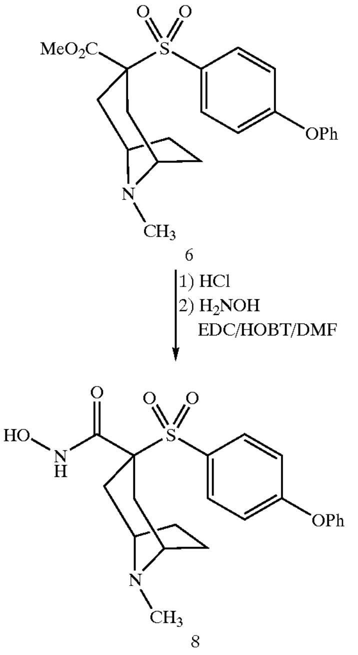
6
8
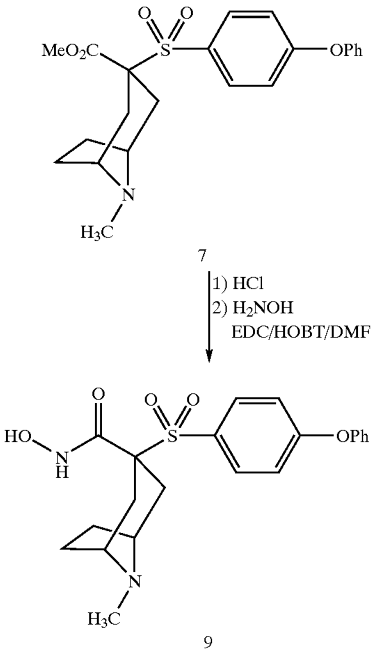
7
9
Scheme 19
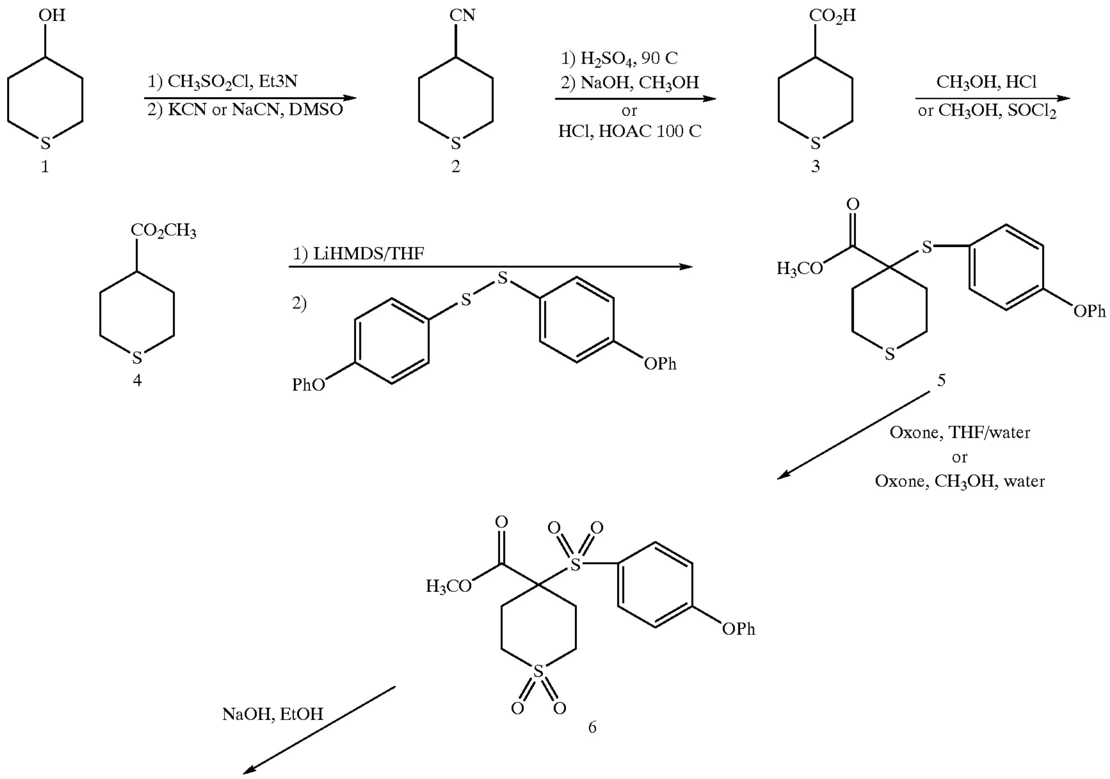
1
2
3
4
5
6

-continued

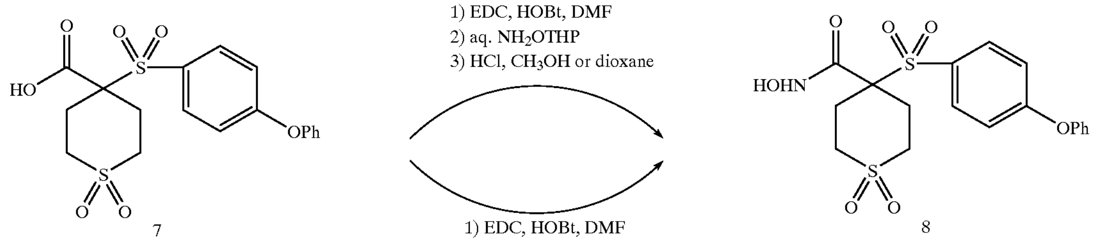

7 8

Table 1 through Table 150, below, show several contemplated aromatic sulfone hydroxamic acid inhibitor compounds or structural formulas that illustrate substituent groups. Each group of compounds is illustrated by a generic formula, or formulae, followed by a series of preferred moieties or groups that constitute various substituents that can be attached at the position clearly shown in the generic structure. The substituent symbols, e.g., R1 and R2 and R3, are as shown in each Table, and are typically not those used before. One or two bonds (wavy lines) are shown with those substituents to indicate the respective positions of attachment in the illustrated compound. This system is well known in the chemical communication arts and is widely used in scientific papers and presentations. For example in Table 2, R1 and R2 together with the atoms to which they are bonded is the variable group with the structural entities that can substitute for R1 and R2 together shown in the balance of that table.

TABLE 1

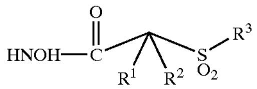

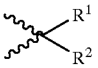

| | |
|---|---|
| 1 | 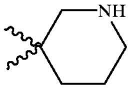 |
| 2 | 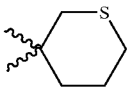 |
| 3 | 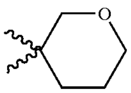 |
| 4 | 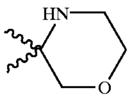 |
| 5 | 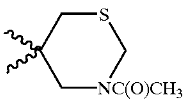 |

TABLE 1-continued

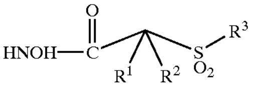

| | |
|---|---|
| 6 | 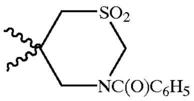 |
| 7 | 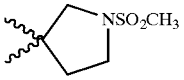 |
| 8 | 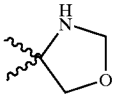 |
| 9 | 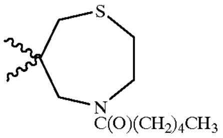 |
| 10 | 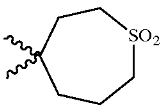 |
| 11 | 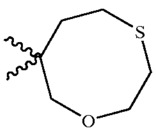 |
| 12 | 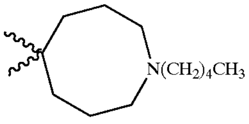 |

TABLE 2
| | | |
|---|---|---|
| | 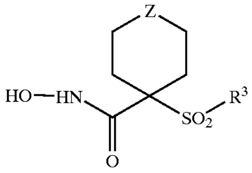 | II |
| 1 | 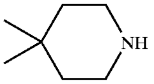 | |
| 2 | 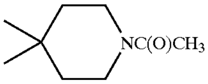 | |
| 3 | 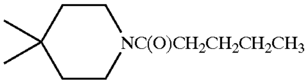 | |
| 4 | 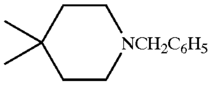 | |
| 5 | 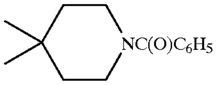 | |
| 6 | 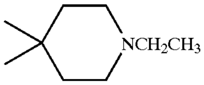 | |
| 7 | 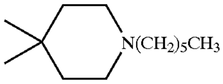 | |
| 8 | 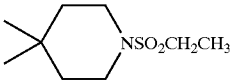 | |
| 9 | 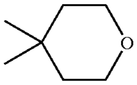 | |
| 10 | 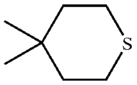 | |
| 11 | 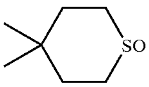 | |
| 12 | 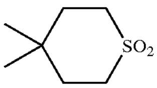 | |
TABLE 3
| | |
|---|---|
| | 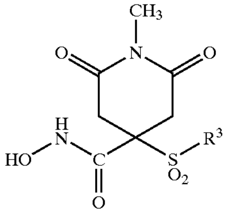 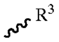 |
| 1 | 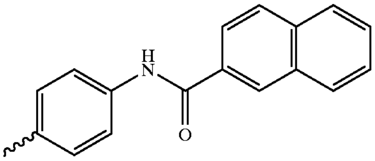 |
| 2 | 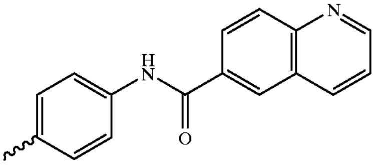 |
| 3 | 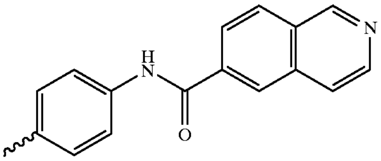 |
| 4 | 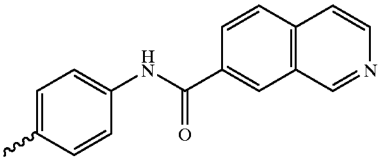 |
| 5 | 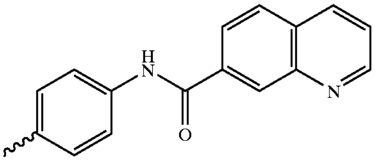 |
| 6 | 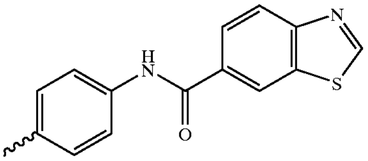 |
| 7 | 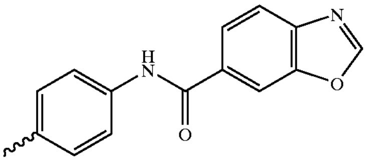 |

TABLE 3-continued
| |
|---|
| 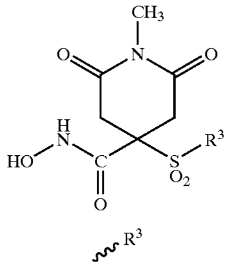 |
| | |
|---|---|
| 8 | 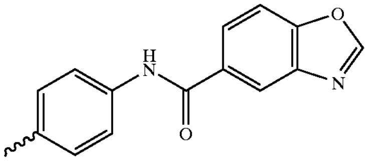 |
| 9 | 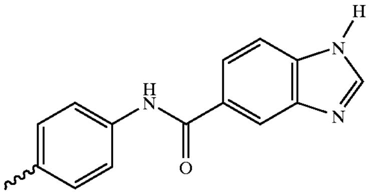 |
| 10 | 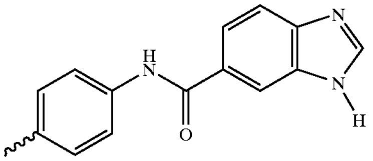 |
| 11 | 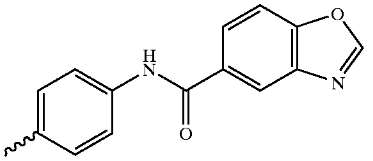 |
| 12 | 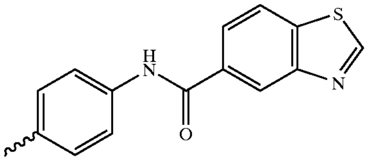 |
| 13 | 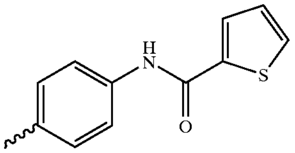 |
| 14 | 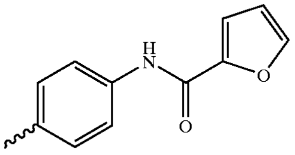 |
TABLE 3-continued
| |
|---|
| 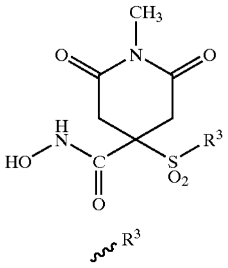 |
| | |
|---|---|
| 15 | 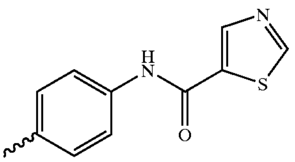 |
| 16 | 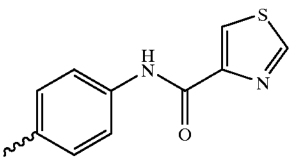 |
| 17 | 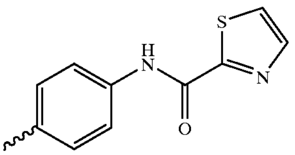 |
| 18 | 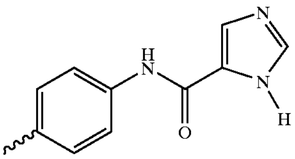 |
TABLE 4
| |
|---|
| 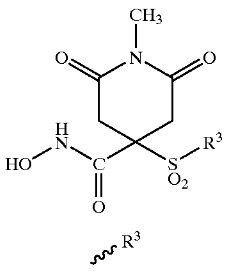 |
| | |
|---|---|
| 1 | 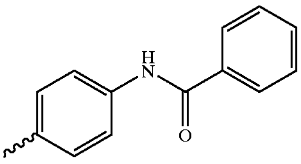 |

TABLE 4-continued
| | |
|---|---|
| | 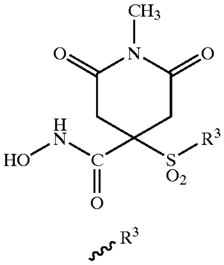 |
| 2 | 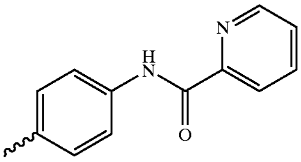 |
| 3 | 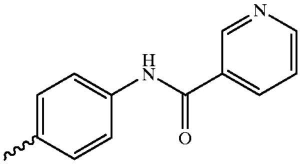 |
| 4 | 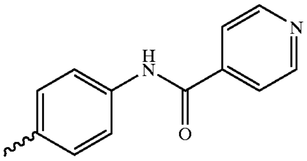 |
| 5 | 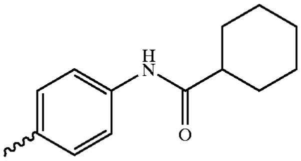 |
| 6 | 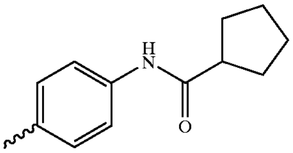 |
| 7 | 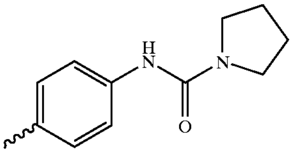 |
| 8 | 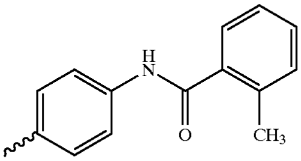 |
TABLE 4-continued
| | |
|---|---|
| | 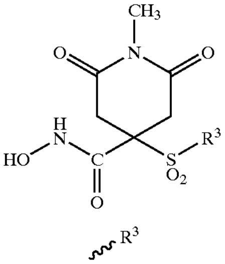 |
| 9 | 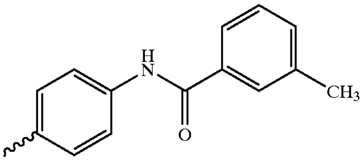 |
| 10 | 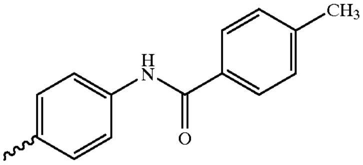 |
| 11 | 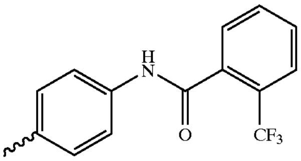 |
| 12 | 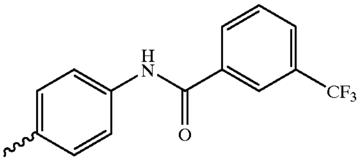 |
| 13 | 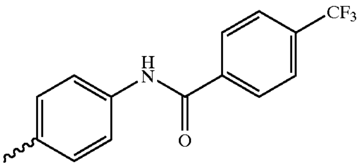 |
| 14 | 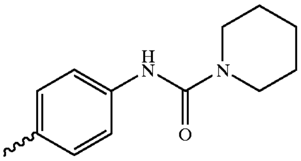 |
| 15 | 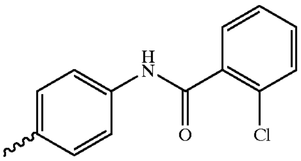 |

TABLE 4-continued
| | |
|---|---|
| | 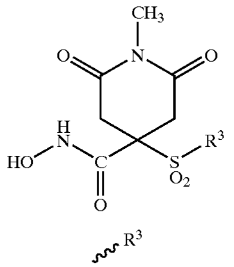 |
| 16 | 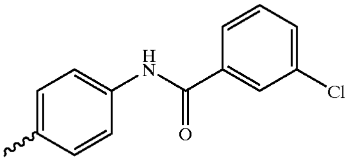 |
| 17 | 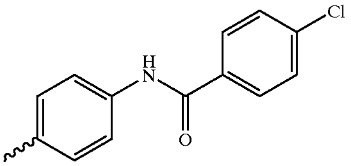 |
| 18 | 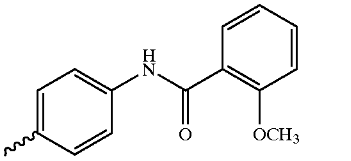 |
| 19 | 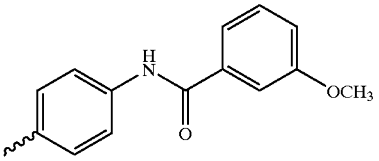 |
| 20 | 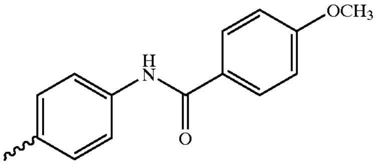 |
| 21 | 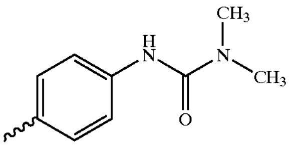 |
TABLE 5
| | |
|---|---|
| | 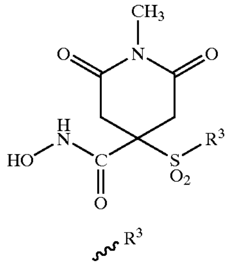 |
| 1 | 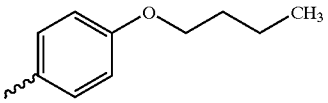 |
| 2 | 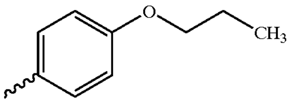 |
| 3 | 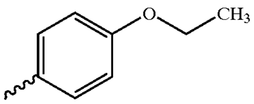 |
| 4 | 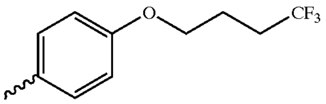 |
| 5 | 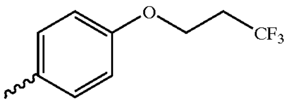 |
| 6 | 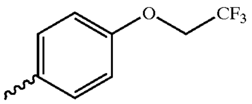 |
| 7 | 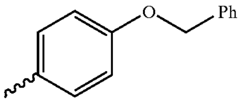 |
| 8 | 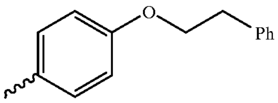 |
| 9 | 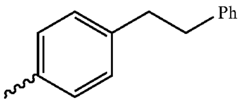 |
| 10 | 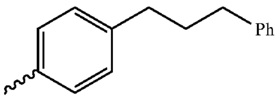 |

TABLE 5-continued
| | |
|---|---|
| | 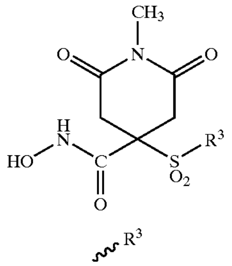 |
| 11 | 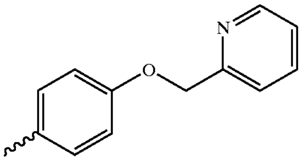 |
| 12 | 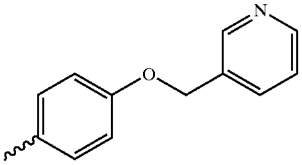 |
| 13 | 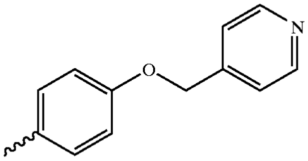 |
| 14 | 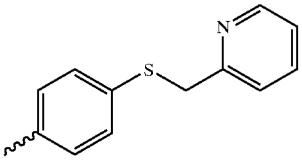 |
| 15 | 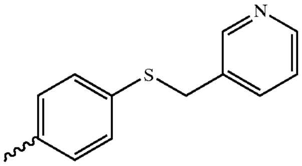 |
| 16 | 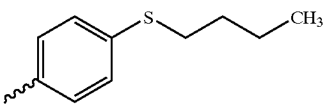 |
| 17 | 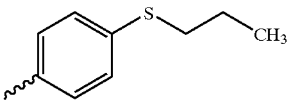 |
| 18 | 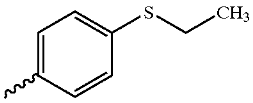 |
TABLE 5-continued
| | |
|---|---|
| | 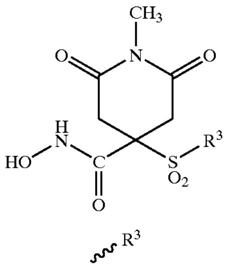 |
| 19 | 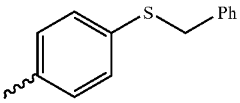 |
| 20 | 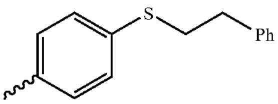 |
| 21 | 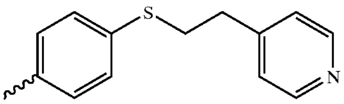 |
| 22 | 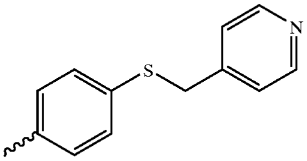 |
TABLE 6
| | |
|---|---|
| | 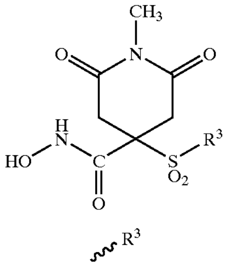 |
| 1 | 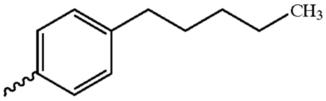 |
| 2 | 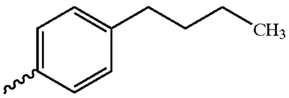 |
| 3 | 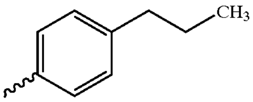 |

TABLE 6-continued
| 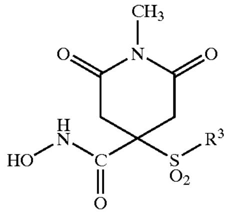 | |
|---|---|
| | 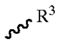 |
| 4 | 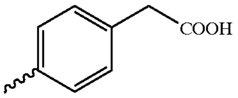 |
| 5 | 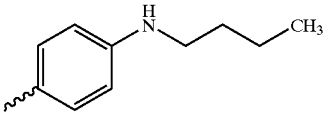 |
| 6 | 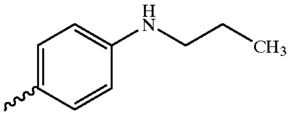 |
| 7 | 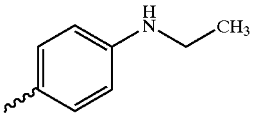 |
| 8 | 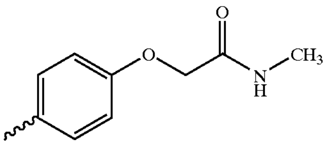 |
| 9 | 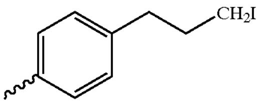 |
| 10 | 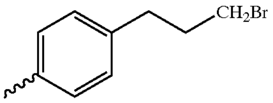 |
| 11 | 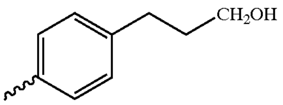 |
| 12 | 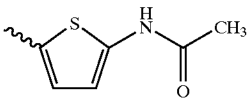 |
| 13 | 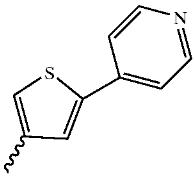 |
TABLE 6-continued
| 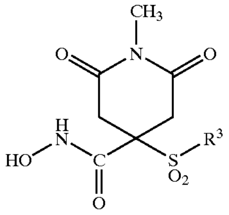 | |
|---|---|
| | 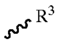 |
| 14 | 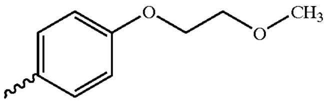 |
| 15 | 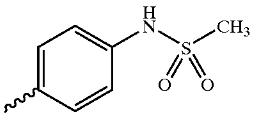 |
| 16 | 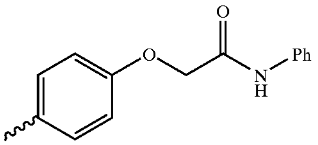 |
| 17 | 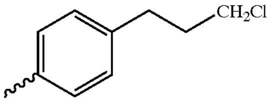 |
| 18 | 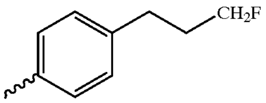 |
| 19 | 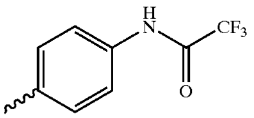 |
| 20 | 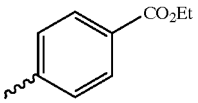 |
| 21 | 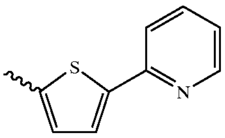 |
| 22 | 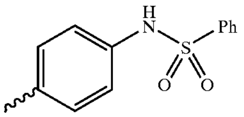 |
| 23 | 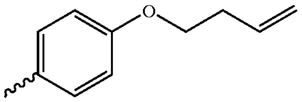 |

TABLE 6-continued
| | 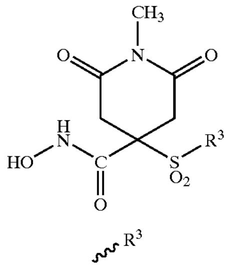 |
|---|---|
| 24 | 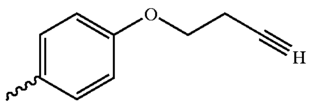 |
| 25 | 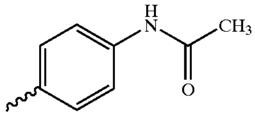 |
| 26 | 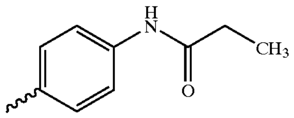 |
| 27 | 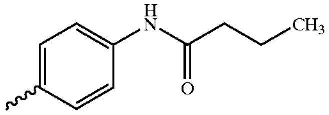 |
| 28 | 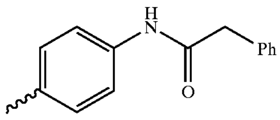 |
| 29 | 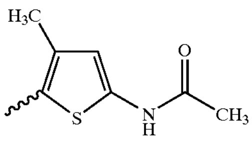 |
| 30 | 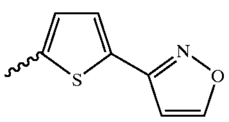 |
TABLE 7
| | 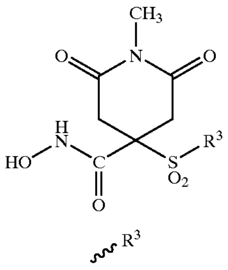 |
|---|---|
| 1 | 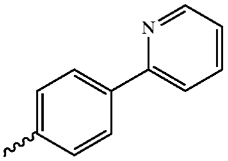 |
| 2 | 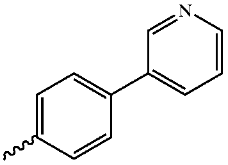 |
| 3 | 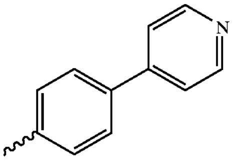 |
| 4 | 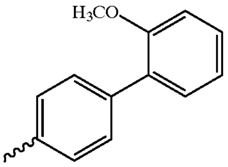 |
| 5 | 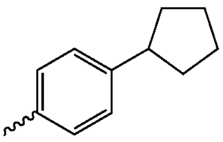 |
| 6 | 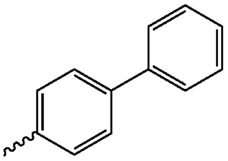 |
| 7 | 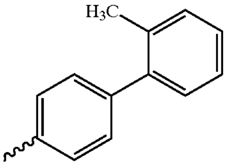 |

TABLE 7-continued
| 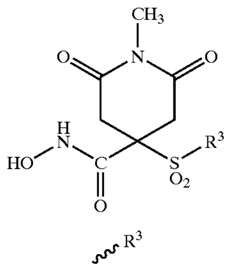 | |
|---|---|
| 8 | 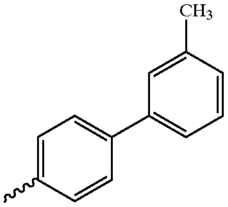 |
| 9 | 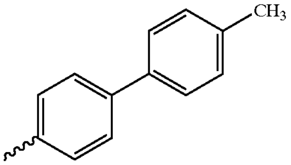 |
| 10 | 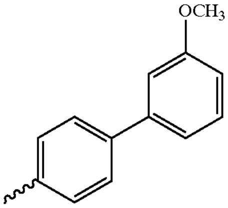 |
| 11 | 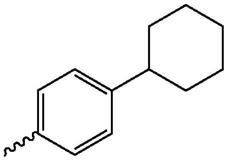 |
| 12 | 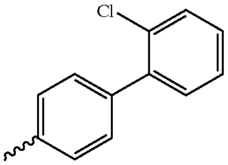 |
| 13 | 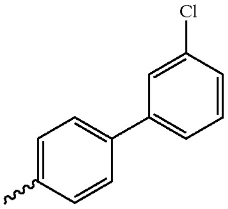 |
TABLE 7-continued
| 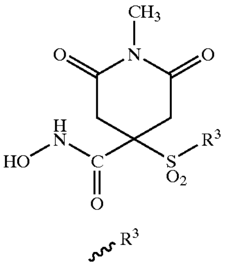 | |
|---|---|
| 14 | 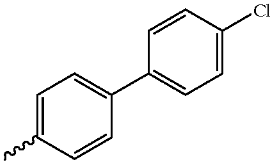 |
| 15 | 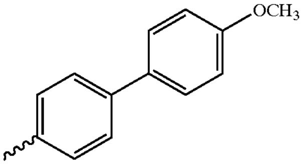 |
| 16 | 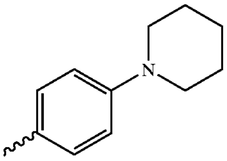 |
| 17 | 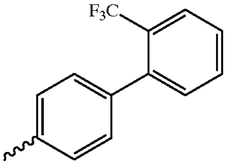 |
| 18 | 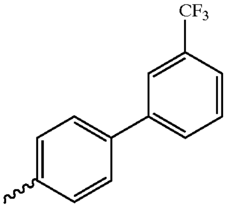 |
| 19 | 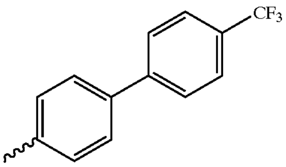 |
| 20 | 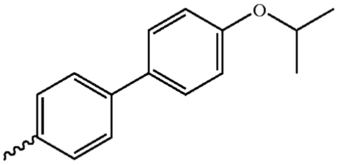 |

TABLE 7-continued
| | |
|---|---|
| | 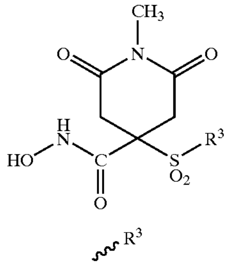 |
| 21 | 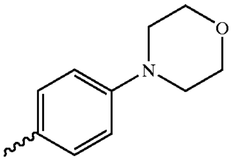 |
TABLE 8
| | |
|---|---|
| | 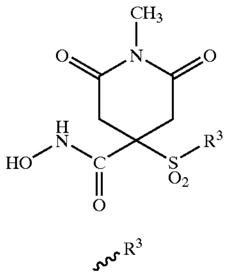 |
| 1 | 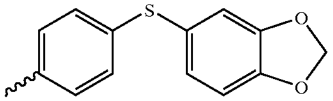 |
| 2 | 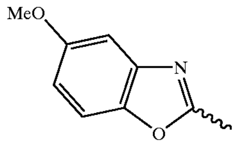 |
| 3 | 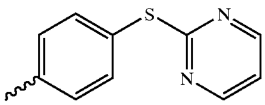 |
| 4 | 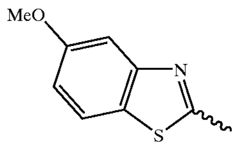 |
| 5 | 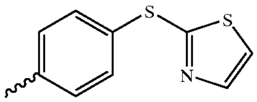 |
| 6 | 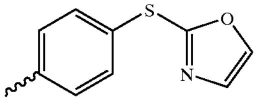 |
TABLE 8-continued
| | |
|---|---|
| | 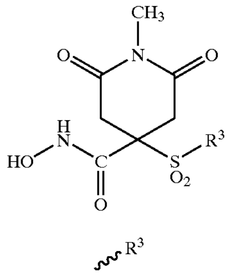 |
| 7 | 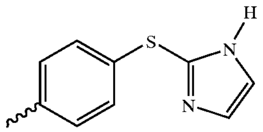 |
| 8 | 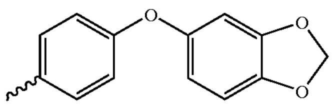 |
| 9 | 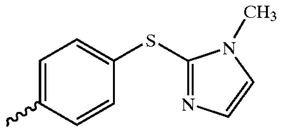 |
| 10 | 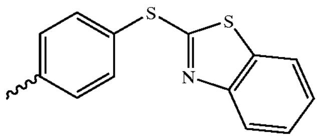 |
| 11 | 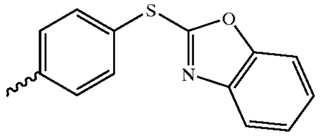 |
TABLE 9
| | |
|---|---|
| | 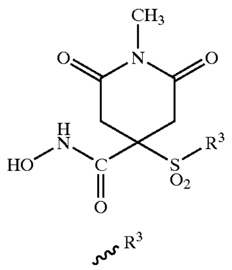 |
| 1 | 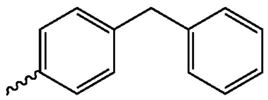 |

TABLE 9-continued
| | |
|---|---|
| | 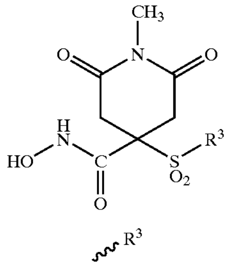 |
| 2 | 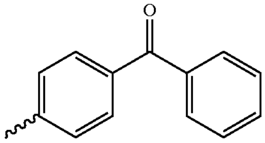 |
| 3 | 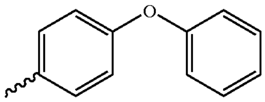 |
| 4 | 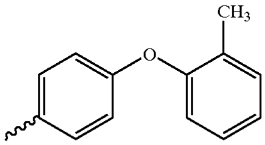 |
| 5 | 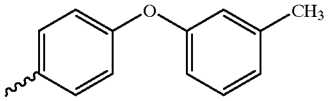 |
| 6 | 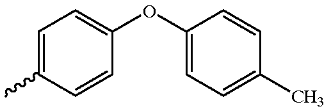 |
| 7 | 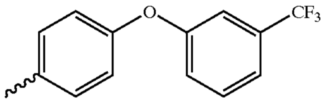 |
| 8 | 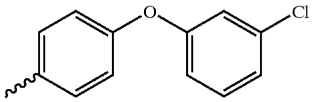 |
| 9 | 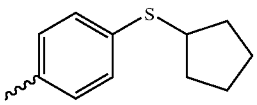 |
| 10 | 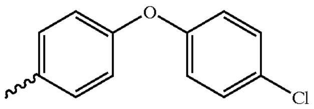 |
| 11 | 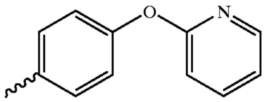 |
TABLE 9-continued
| | |
|---|---|
| | 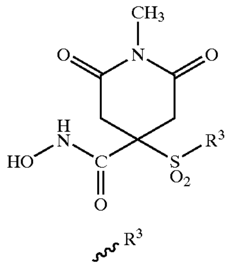 |
| 12 | 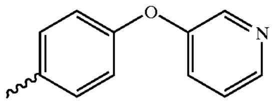 |
| 13 | 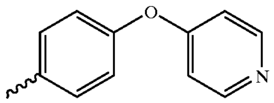 |
| 14 | 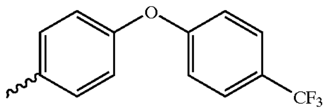 |
| 15 | 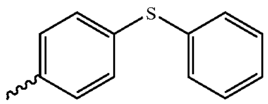 |
| 16 | 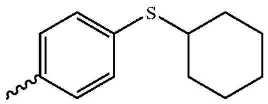 |
| 17 | 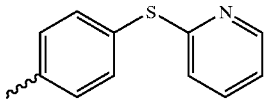 |
| 18 | 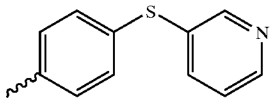 |
| 19 | 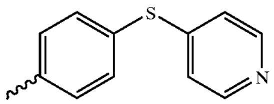 |
| 20 | 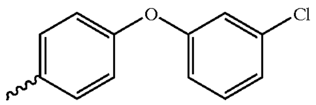 |
| 21 | 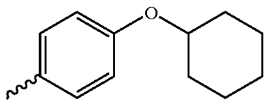 |

TABLE 10
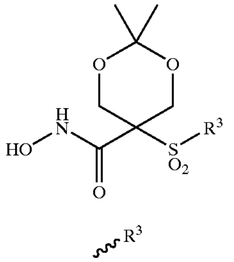
| | |
|---|---|
| 1 | 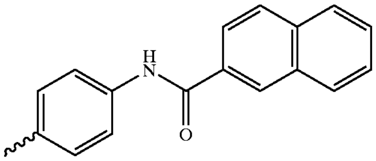 |
| 2 | 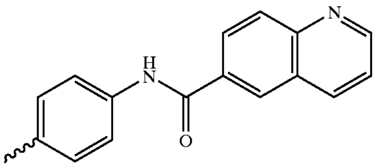 |
| 3 | 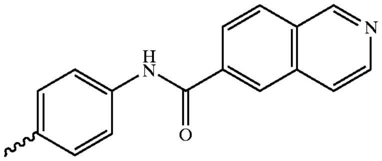 |
| 4 | 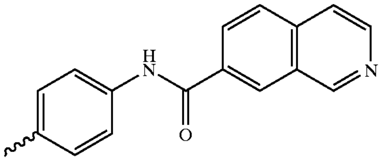 |
| 5 | 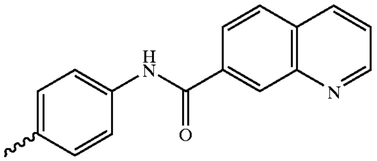 |
| 6 | 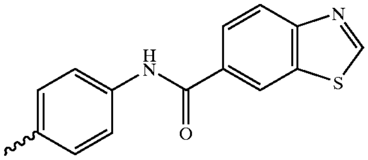 |
| 7 | 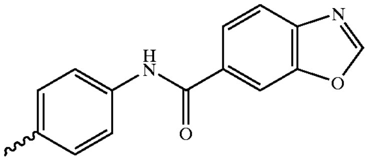 |
TABLE 10-continued
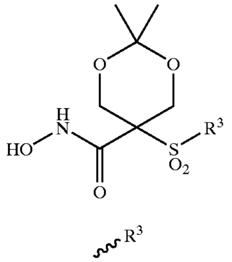
| | |
|---|---|
| 8 | 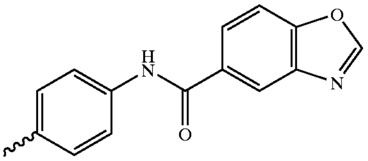 |
| 9 | 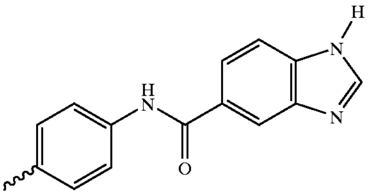 |
| 10 | 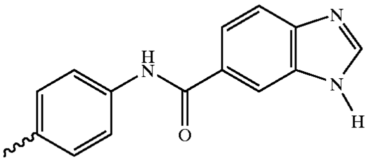 |
| 11 | 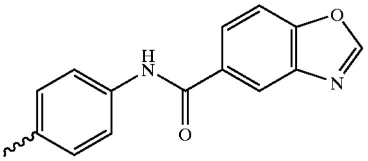 |
| 12 | 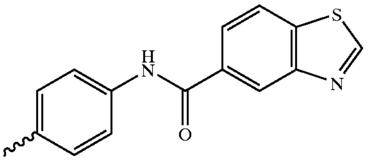 |
| 13 | 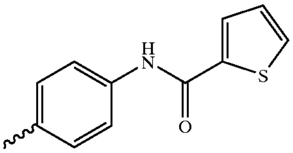 |
| 14 | 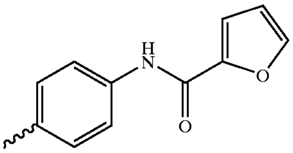 |

TABLE 10-continued
| | |
|---|---|
| | 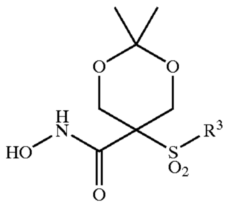 |
| | 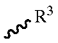 |
| 15 | 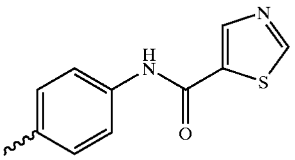 |
| 16 | 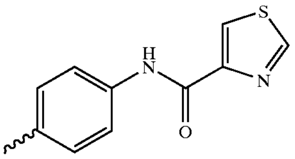 |
| 17 | 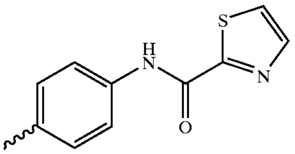 |
| 18 | 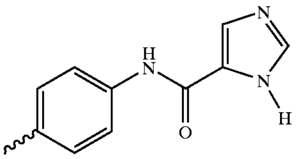 |
TABLE 11
| | |
|---|---|
| | 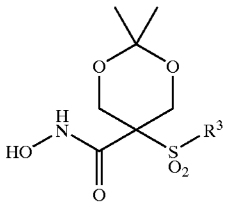 |
| | 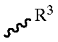 |
| 1 | 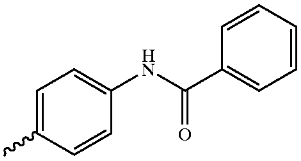 |
TABLE 11-continued
| | |
|---|---|
| | 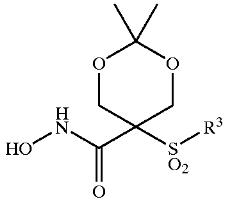 |
| | 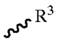 |
| 2 | 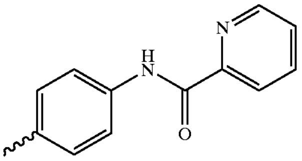 |
| 3 | 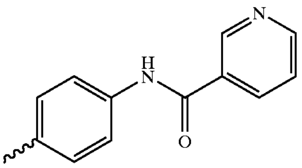 |
| 4 | 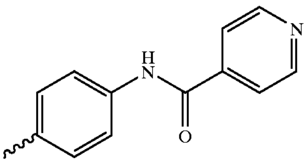 |
| 5 | 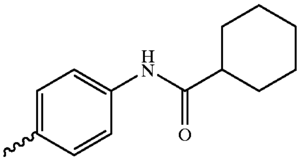 |
| 6 | 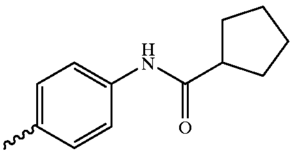 |
| 7 | 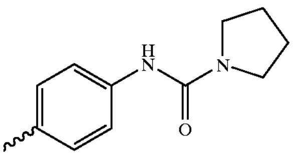 |
| 8 | 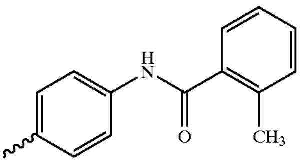 |

TABLE 11-continued
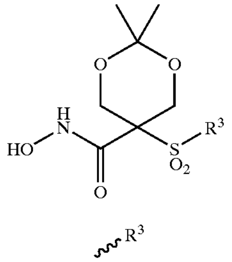
9
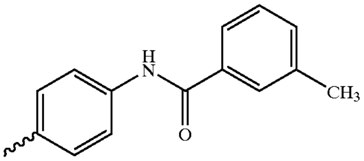
10
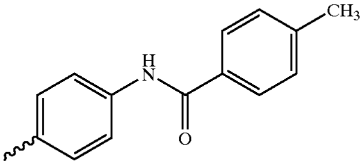
11
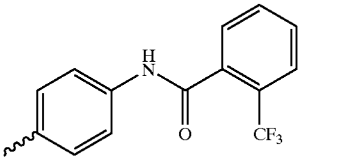
12
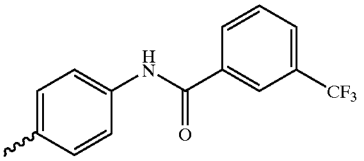
13
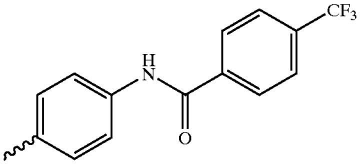
14
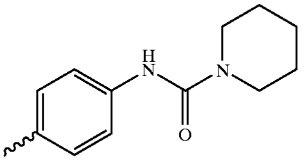
15
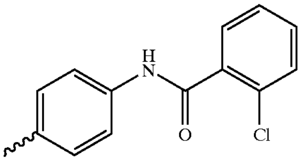
TABLE 11-continued
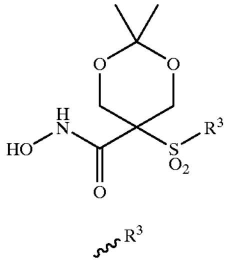
16
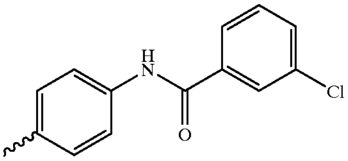
17
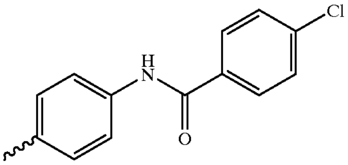
18
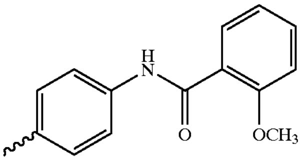
19
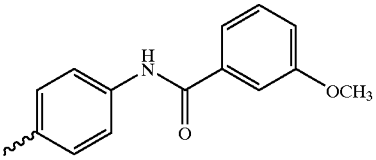
20
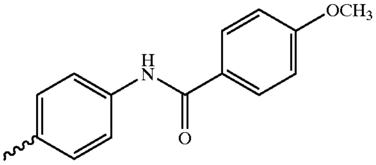
21
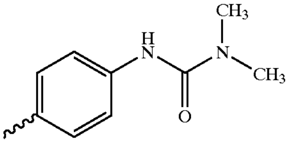

TABLE 12
| | |
|---|---|
| 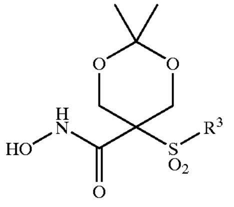 | 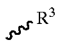 |
| 1 | 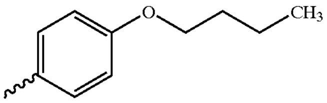 |
| 2 | 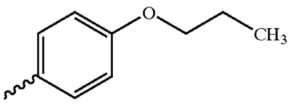 |
| 3 | 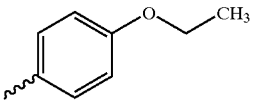 |
| 4 | 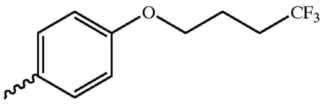 |
| 5 | 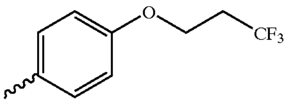 |
| 6 | 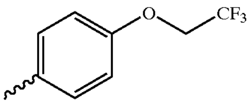 |
| 7 | 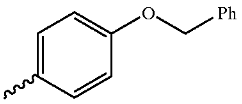 |
| 8 | 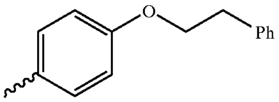 |
| 9 | 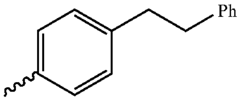 |
| 10 | 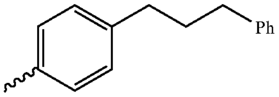 |
TABLE 12-continued
| | |
|---|---|
| 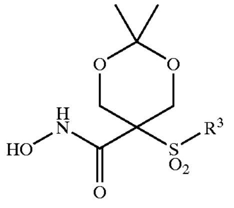 | 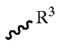 |
| 11 | 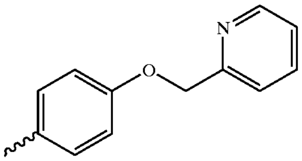 |
| 12 | 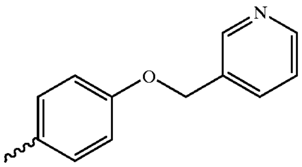 |
| 13 | 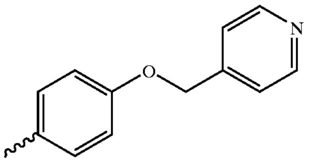 |
| 14 | 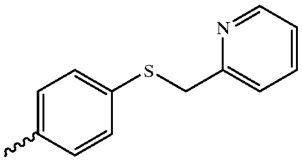 |
| 15 | 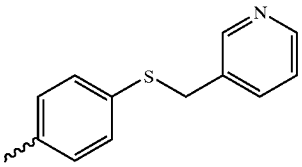 |
| 16 | 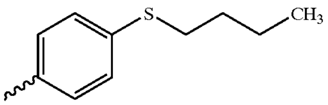 |
| 17 | 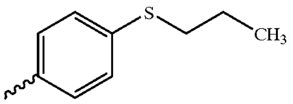 |
| 18 | 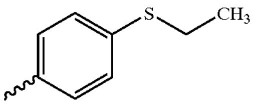 |

TABLE 12-continued
| | |
|---|---|
| | 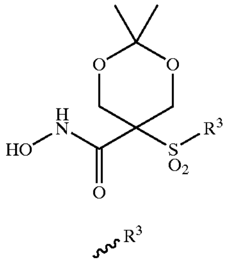 |
| 19 | 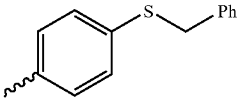 |
| 20 | 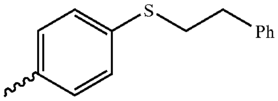 |
| 21 | 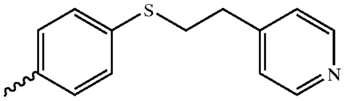 |
| 22 | 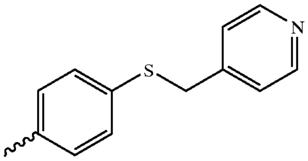 |
TABLE 13
| | |
|---|---|
| | 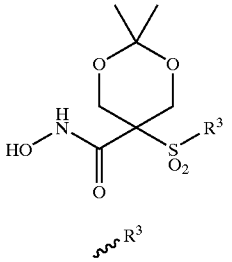 |
| 1 | 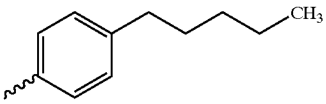 |
| 2 | 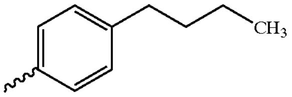 |
| 3 | 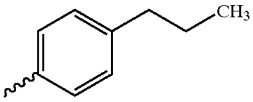 |
TABLE 13-continued
| | |
|---|---|
| | 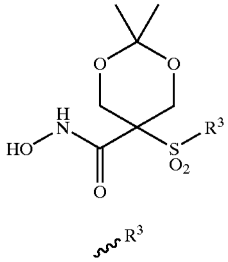 |
| 4 | 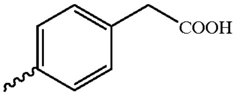 |
| 5 | 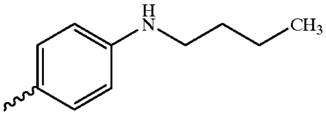 |
| 6 | 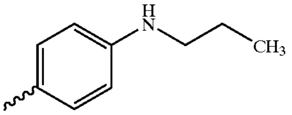 |
| 7 | 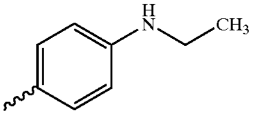 |
| 8 | 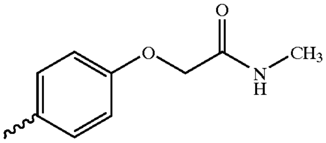 |
| 9 | 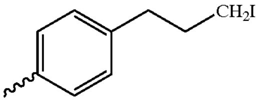 |
| 10 | 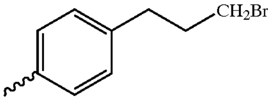 |
| 11 | 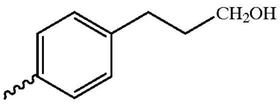 |
| 12 | 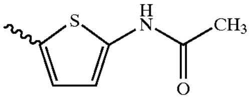 |
| 13 | 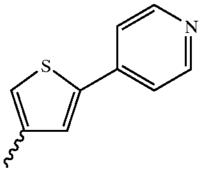 |

TABLE 13-continued
| | |
|---|---|
| | 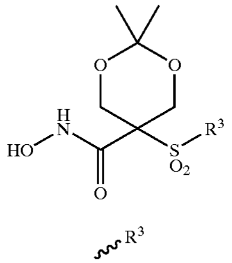 |
| 14 | 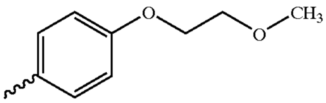 |
| 15 | 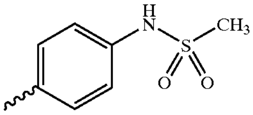 |
| 16 | 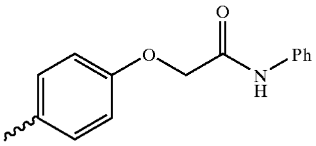 |
| 17 | 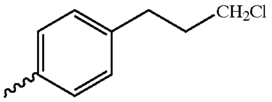 |
| 18 | 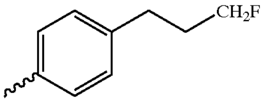 |
| 19 | 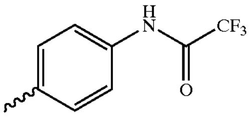 |
| 20 | 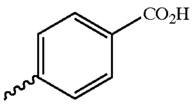 |
| 21 | 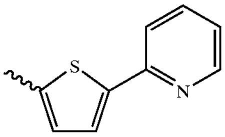 |
| 22 | 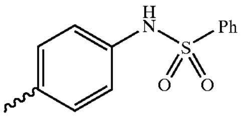 |
| 23 | 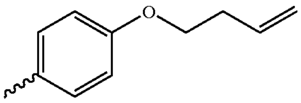 |
TABLE 13-continued
| | |
|---|---|
| | 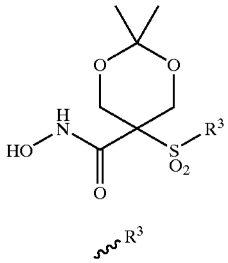 |
| 24 | 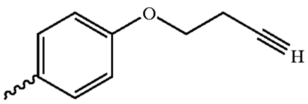 |
| 25 | 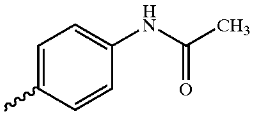 |
| 26 | 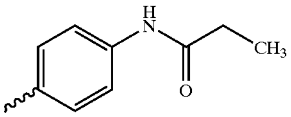 |
| 27 | 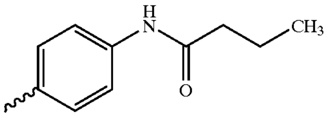 |
| 28 | 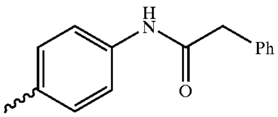 |
| 29 | 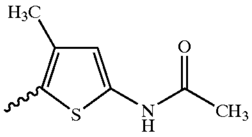 |
| 30 | 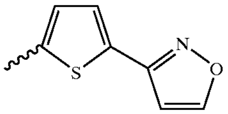 |

TABLE 14
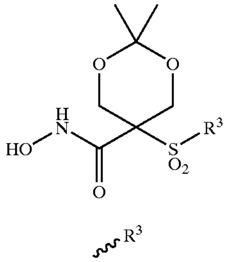
1
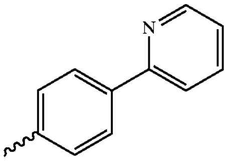
2
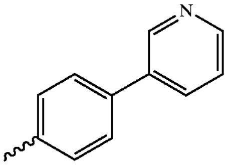
3
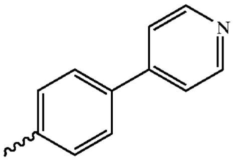
4
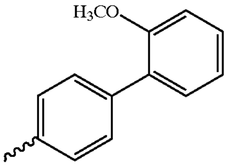
5
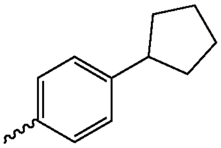
6
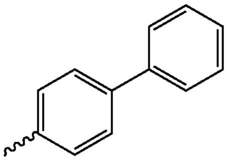
7
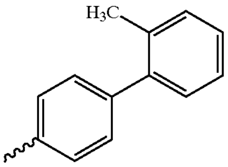
TABLE 14-continued
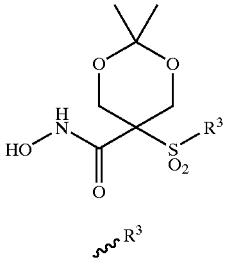
8
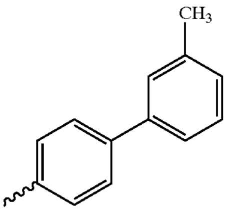
9
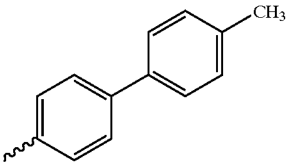
10
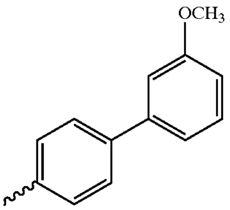
11
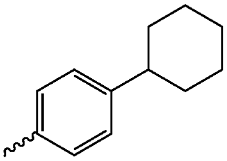
12
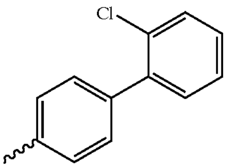
13
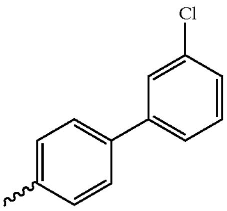

TABLE 14-continued
| 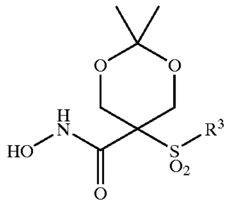 | |
|---|---|
| | 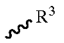 |
| 14 | 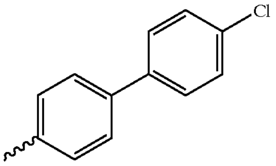 |
| 15 | 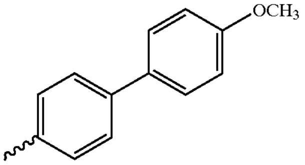 |
| 16 | 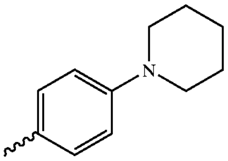 |
| 17 | 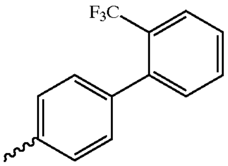 |
| 18 | 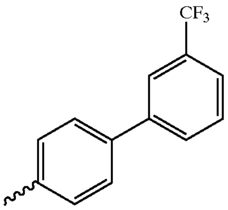 |
| 19 | 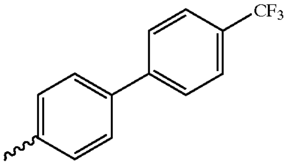 |
| 20 | 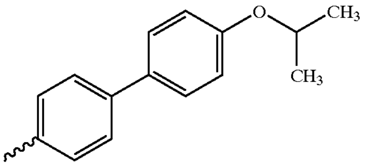 |
TABLE 14-continued
| 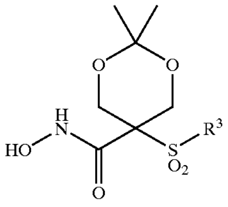 | |
|---|---|
| | 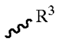 |
| 21 | 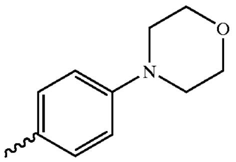 |
TABLE 15
| 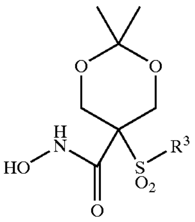 | |
|---|---|
| | 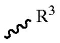 |
| 1 | 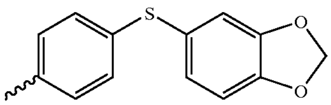 |
| 2 | 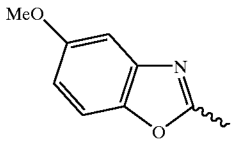 |
| 3 | 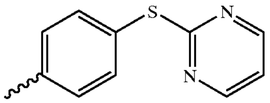 |
| 4 | 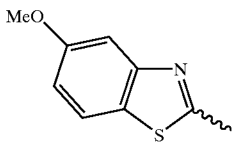 |
| 5 | 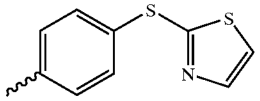 |
| 6 | 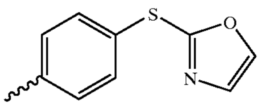 |

TABLE 15-continued
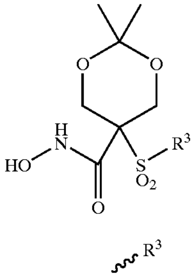
| | |
|---|---|
| 7 | 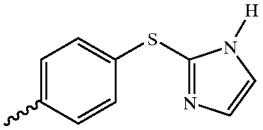 |
| 8 | 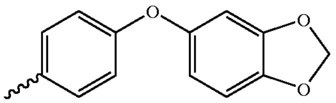 |
| 9 | 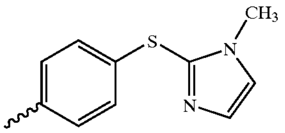 |
| 10 | 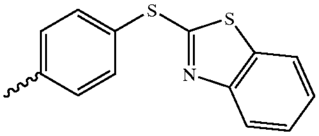 |
| 11 | 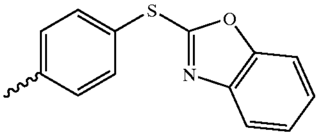 |
TABLE 16
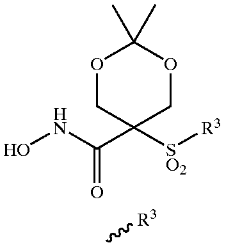
| | |
|---|---|
| 1 | 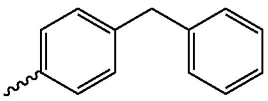 |
| 2 | 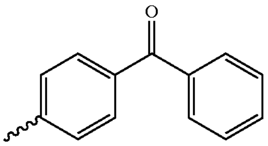 |
TABLE 16-continued
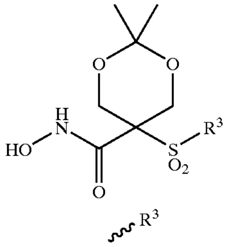
| | |
|---|---|
| 3 | 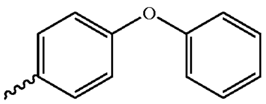 |
| 4 | 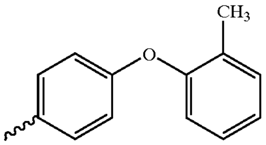 |
| 5 | 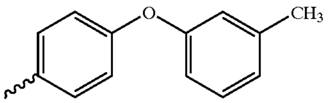 |
| 6 | 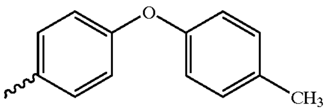 |
| 7 | 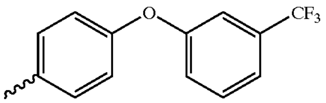 |
| 8 | 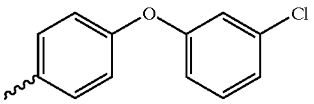 |
| 9 | 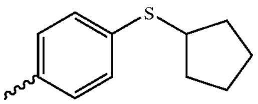 |
| 10 | 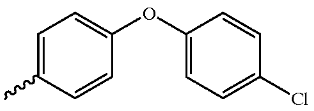 |
| 11 | 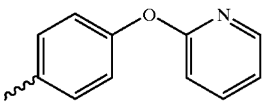 |
| 12 | 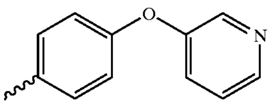 |

TABLE 16-continued
| | |
|---|---|
| 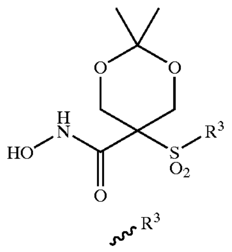 | |
| 13 | 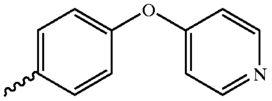 |
| 14 | 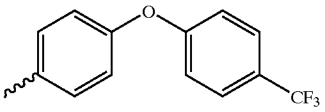 |
| 15 | 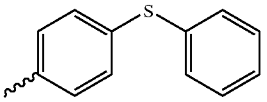 |
| 16 | 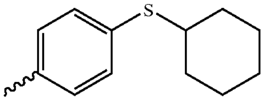 |
| 17 | 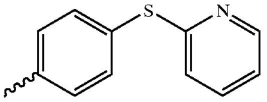 |
| 18 | 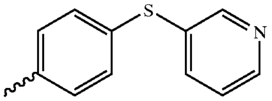 |
| 19 | 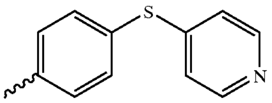 |
| 20 | 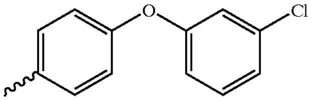 |
| 21 | 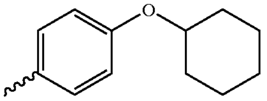 |
TABLE 17
| | |
|---|---|
| 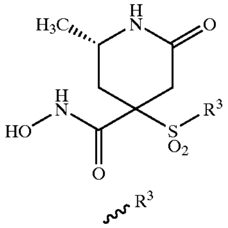 | |
| 1 | 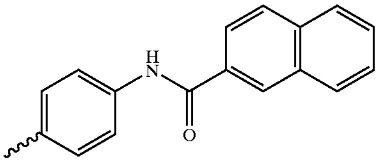 |
| 2 | 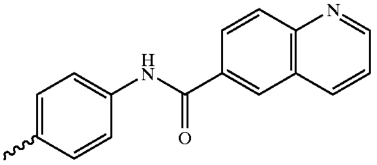 |
| 3 | 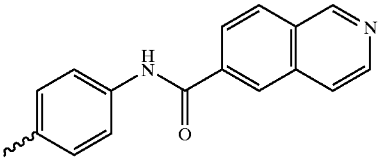 |
| 4 | 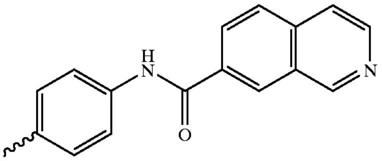 |
| 5 | 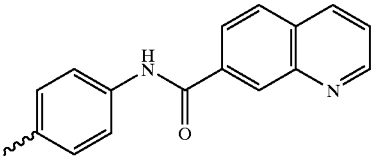 |
| 6 | 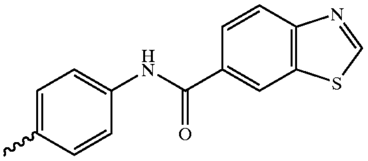 |
| 7 | 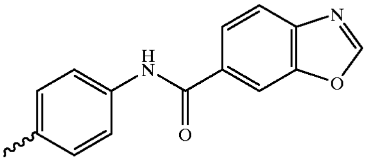 |

TABLE 17-continued
| | |
|---|---|
| | 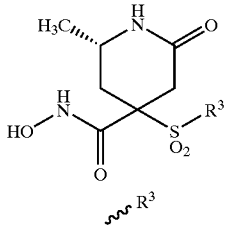 |
| 8 | 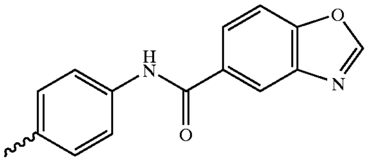 |
| 9 | 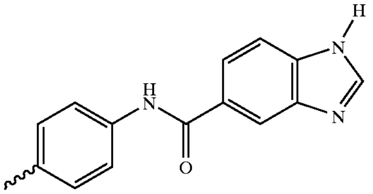 |
| 10 | 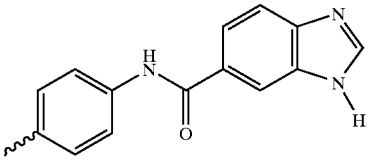 |
| 11 | 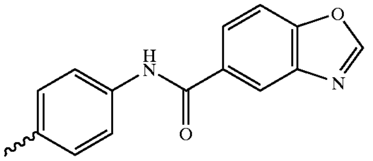 |
| 12 | 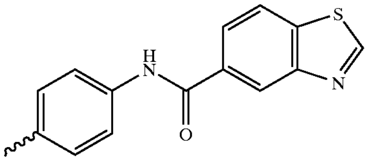 |
| 13 | 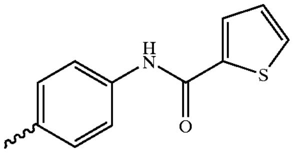 |
| 14 | 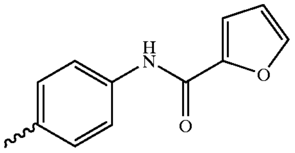 |
TABLE 17-continued
| | |
|---|---|
| | 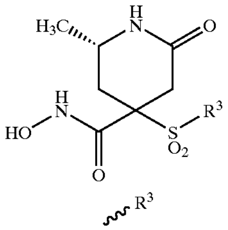 |
| 15 | 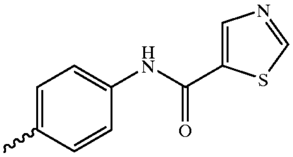 |
| 16 | 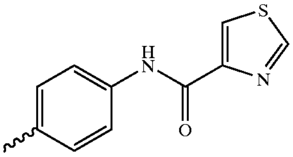 |
| 17 | 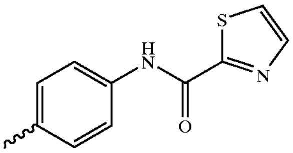 |
| 18 | 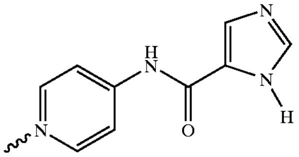 |
TABLE 18
| | |
|---|---|
| | 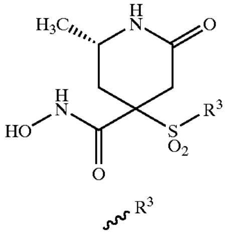 |
| 1 | 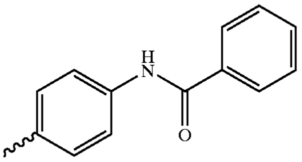 |
| 2 | 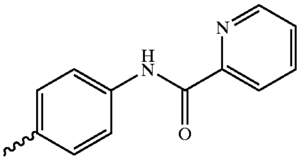 |

TABLE 18-continued
| | 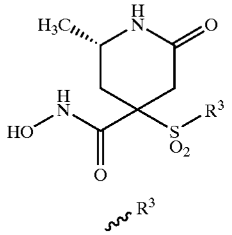 |
|---|---|
| 3 | 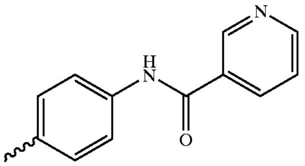 |
| 4 | 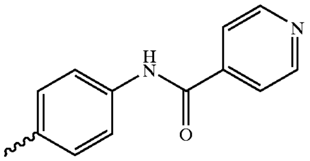 |
| 5 | 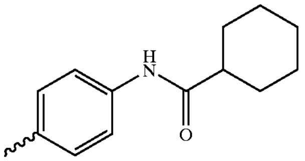 |
| 6 | 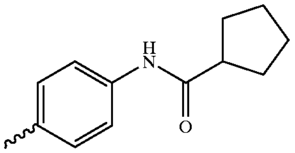 |
| 7 | 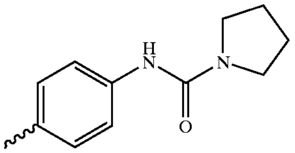 |
| 8 | 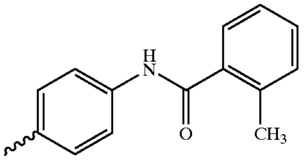 |
| 9 | 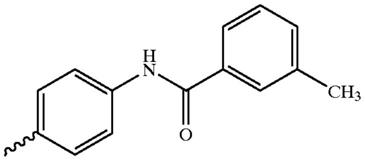 |
TABLE 18-continued
| | 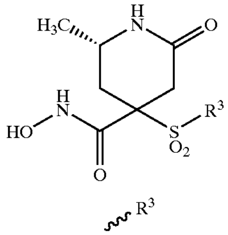 |
|---|---|
| 10 | 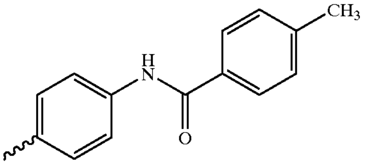 |
| 11 | 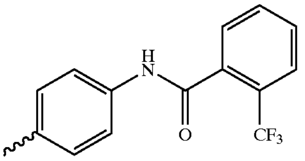 |
| 12 | 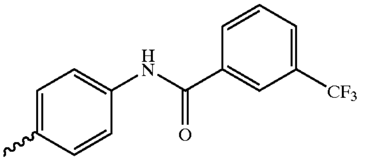 |
| 13 | 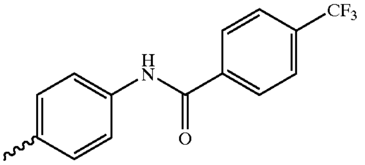 |
| 14 | 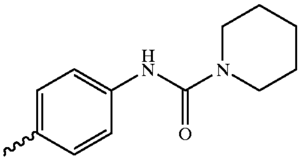 |
| 15 | 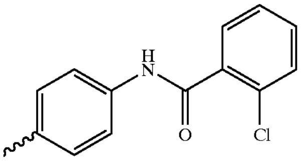 |
| 16 | 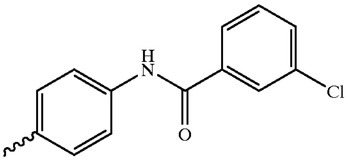 |

TABLE 18-continued
| | |
|---|---|
| 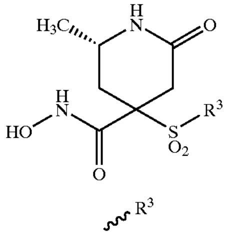 | |
| 17 | 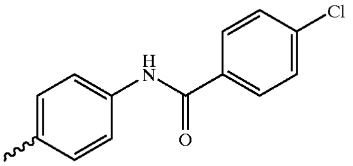 |
| 18 | 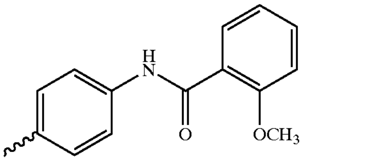 |
| 19 | 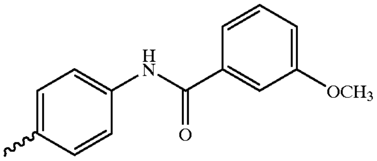 |
| 20 | 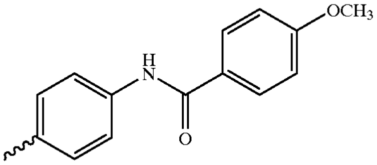 |
| 21 | 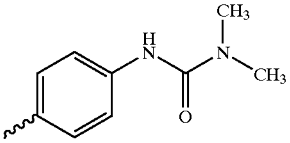 |
TABLE 19
| | |
|---|---|
| 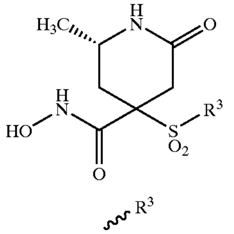 | |
| 1 | 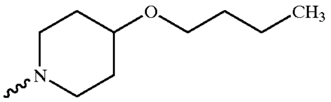 |
TABLE 19-continued
| | |
|---|---|
| 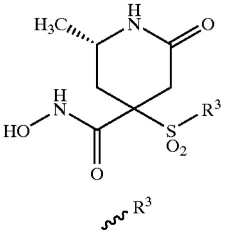 | |
| 2 | 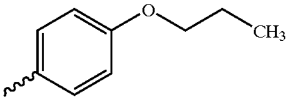 |
| 3 | 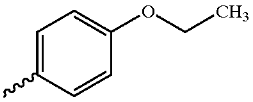 |
| 4 | 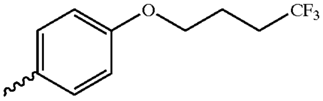 |
| 5 | 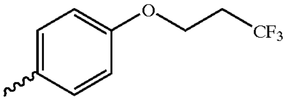 |
| 6 | 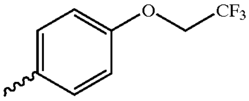 |
| 7 | 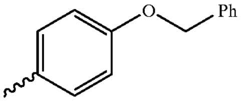 |
| 8 | 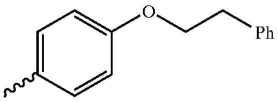 |
| 9 | 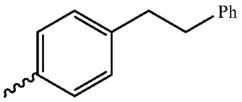 |
| 10 | 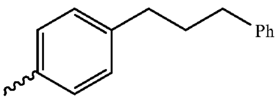 |
| 11 | 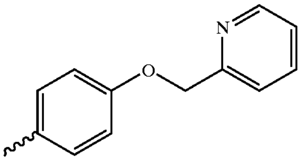 |

TABLE 19-continued
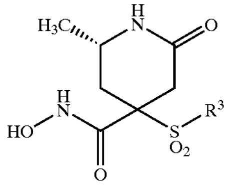
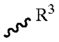
| | |
|---|---|
| 12 | 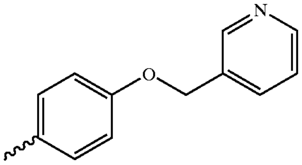 |
| 13 | 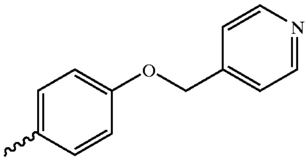 |
| 14 | 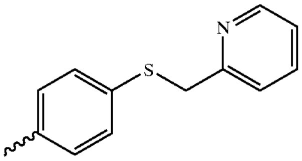 |
| 15 | 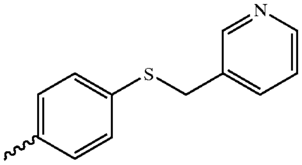 |
| 16 | 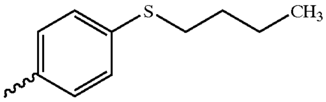 |
| 17 | 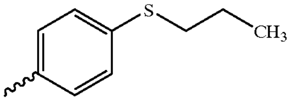 |
| 18 | 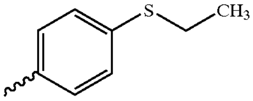 |
| 19 | 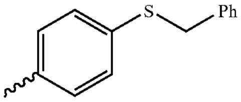 |
| 20 | 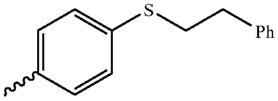 |
TABLE 19-continued
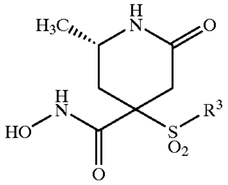
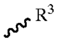
| | |
|---|---|
| 21 | 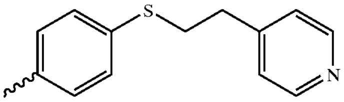 |
| 22 | 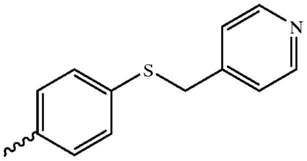 |
TABLE 20
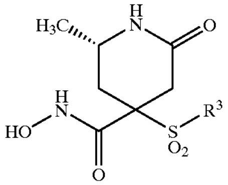
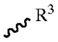
| | |
|---|---|
| 1 | 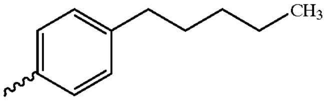 |
| 2 | 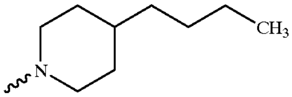 |
| 3 | 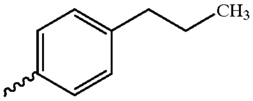 |
| 4 | 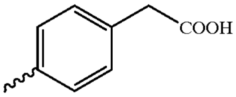 |
| 5 | 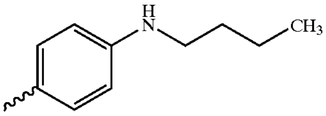 |
| 6 | 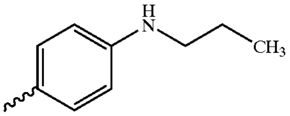 |

TABLE 20-continued
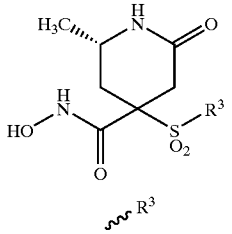
| | |
|---|---|
| 7 | 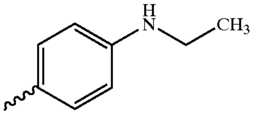 |
| 8 | 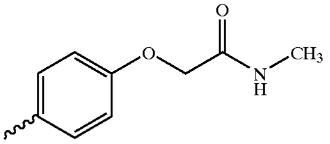 |
| 9 | 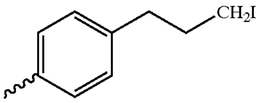 |
| 10 | 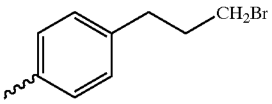 |
| 11 | 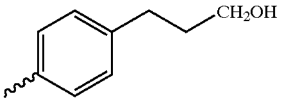 |
| 12 | 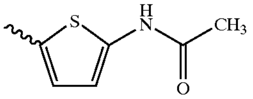 |
| 13 | 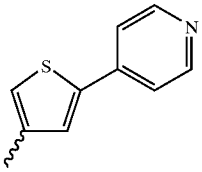 |
| 14 | 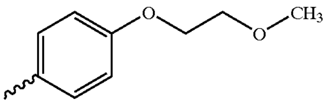 |
| 15 | 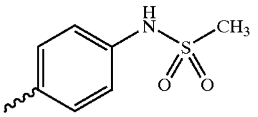 |
TABLE 20-continued
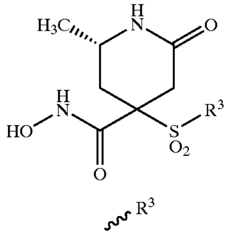
| | |
|---|---|
| 16 | 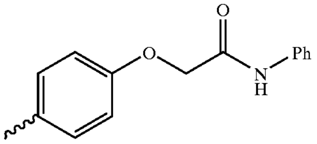 |
| 17 | 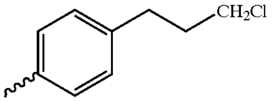 |
| 18 | 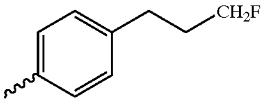 |
| 19 | 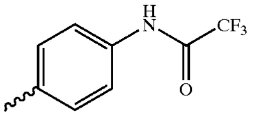 |
| 20 | 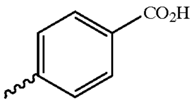 |
| 21 | 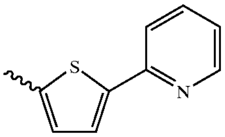 |
| 22 | 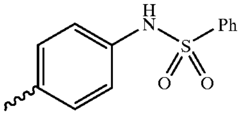 |
| 23 | 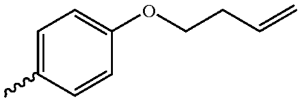 |
| 24 | 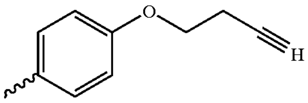 |
| 25 | 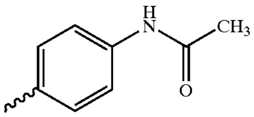 |

TABLE 20-continued
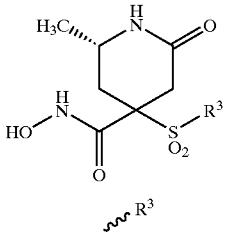
| | |
|---|---|
| 26 | 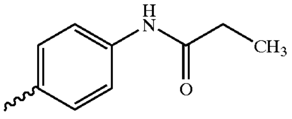 |
| 27 | 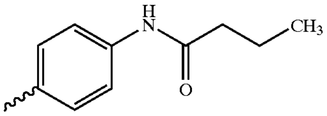 |
| 28 | 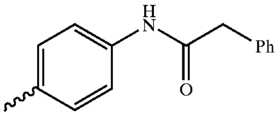 |
| 29 | 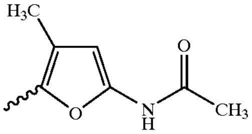 |
| 30 | 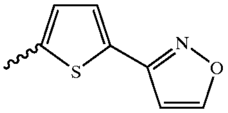 |
TABLE 21
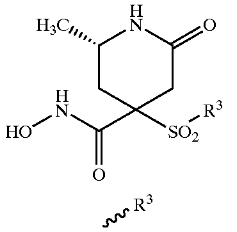
| | |
|---|---|
| 1 | 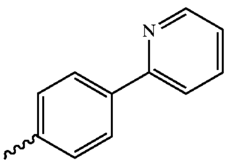 |
| 2 | 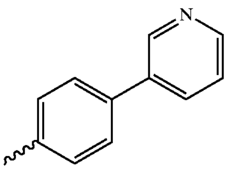 |
TABLE 21-continued
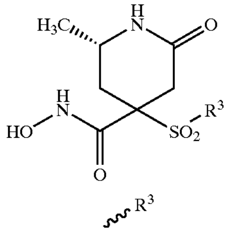
| | |
|---|---|
| 3 | 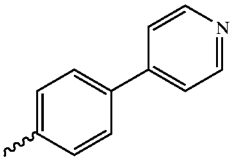 |
| 4 | 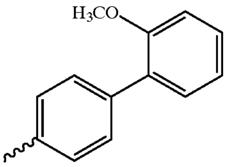 |
| 5 | 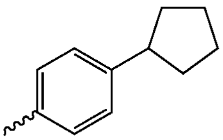 |
| 6 | 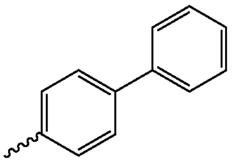 |
| 7 | 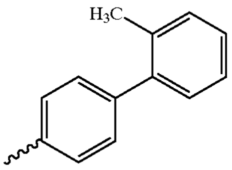 |
| 8 | 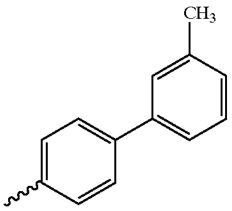 |
| 9 | 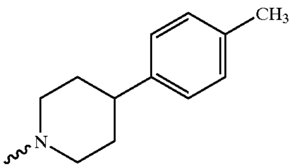 |

TABLE 21-continued
| 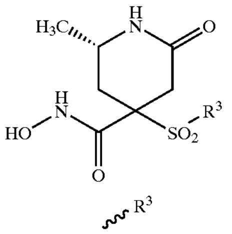 | |
|---|---|
| 10 | 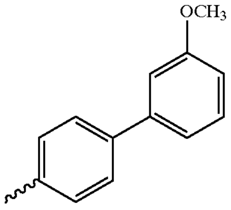 |
| 11 | 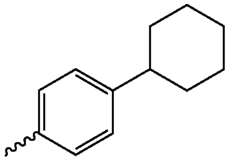 |
| 12 | 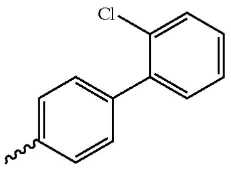 |
| 13 | 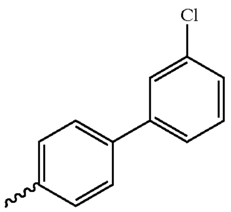 |
| 14 | 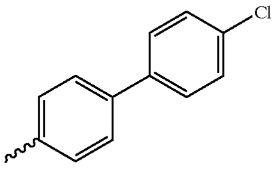 |
| 15 | 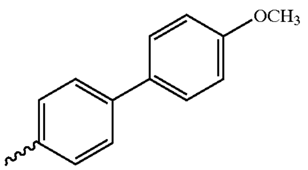 |
| 16 | 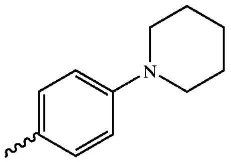 |
TABLE 21-continued
| 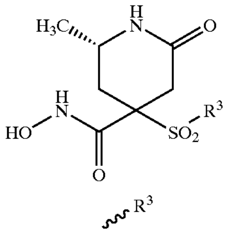 | |
|---|---|
| 17 | 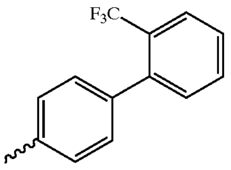 |
| 18 | 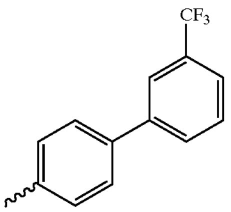 |
| 19 | 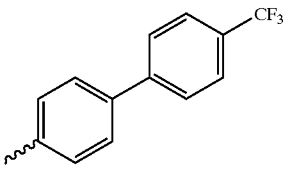 |
| 20 | 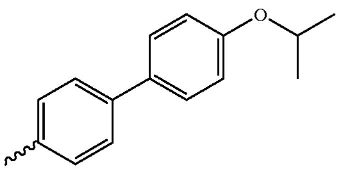 |
| 21 | 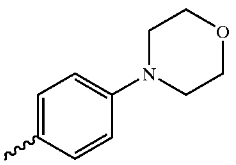 |

TABLE 22
| | |
|---|---|
| | 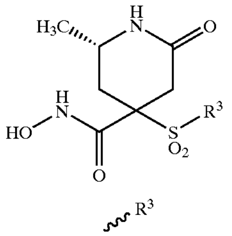 |
| 1 | 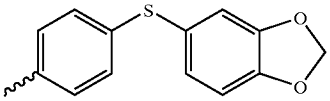 |
| 2 | 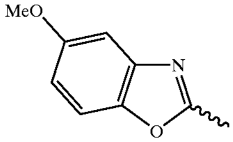 |
| 3 | 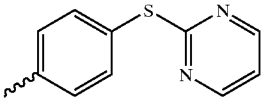 |
| 4 | 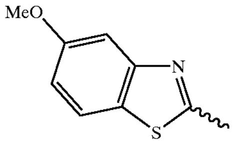 |
| 5 | 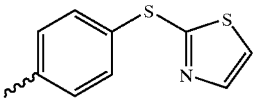 |
| 6 | 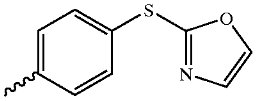 |
| 7 | 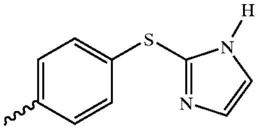 |
| 8 | 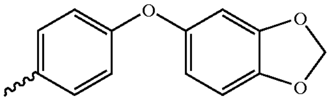 |
| 9 | 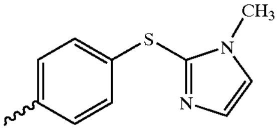 |
| 10 | 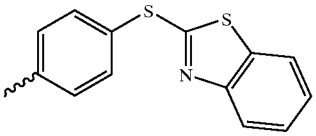 |
TABLE 22-continued
| | |
|---|---|
| | 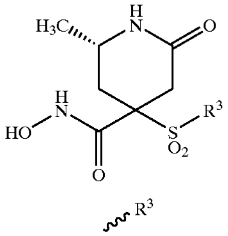 |
| 11 | 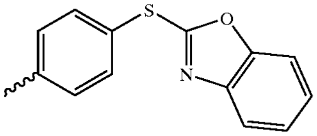 |
TABLE 23
| | |
|---|---|
| | 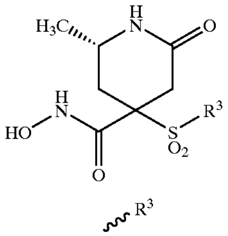 |
| 1 | 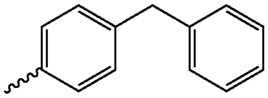 |
| 2 | 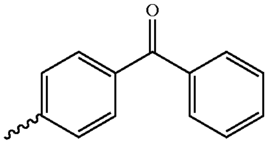 |
| 3 | 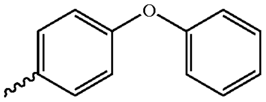 |
| 4 | 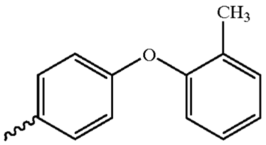 |
| 5 | 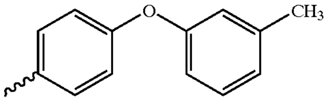 |
| 6 | 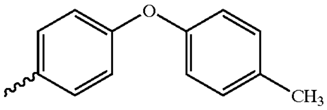 |

TABLE 23-continued
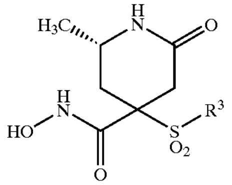
| | |
|---|---|
| 7 | 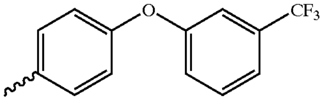 |
| 8 | 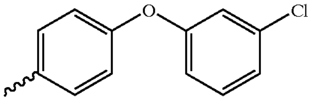 |
| 9 | 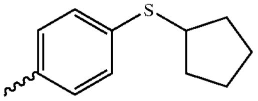 |
| 10 | 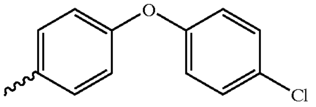 |
| 11 | 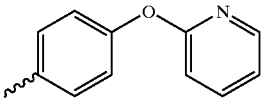 |
| 12 | 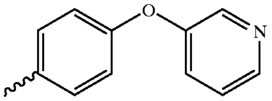 |
| 13 | 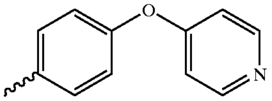 |
| 14 | 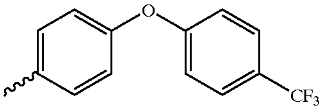 |
| 15 | 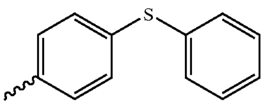 |
| 16 | 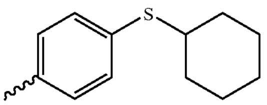 |
| 17 | 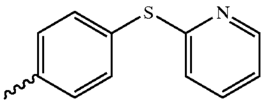 |
TABLE 23-continued
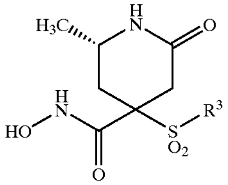
| | |
|---|---|
| 18 | 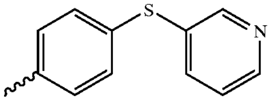 |
| 19 | 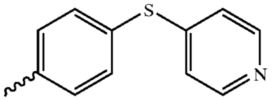 |
| 20 | 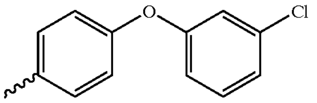 |
| 21 | 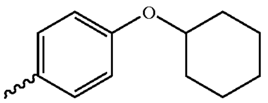 |
TABLE 24
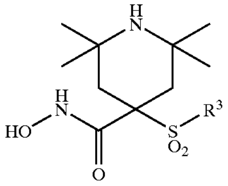
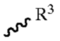
| | |
|---|---|
| 1 | 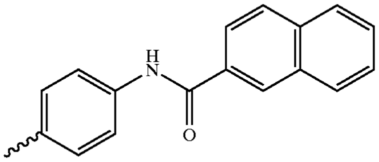 |
| 2 | 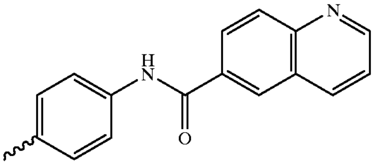 |
| 3 | 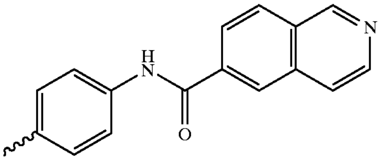 |

TABLE 24-continued
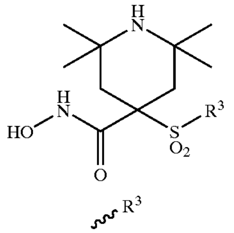
| | |
|---|---|
| 4 | 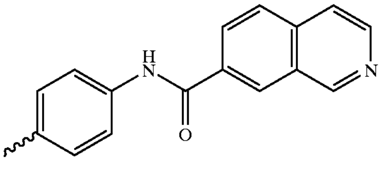 |
| 5 | 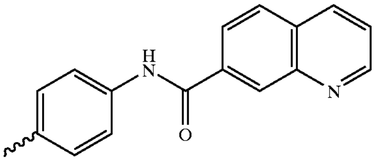 |
| 6 | 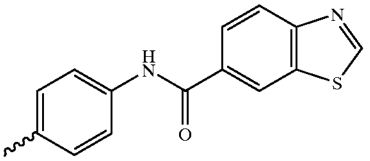 |
| 7 | 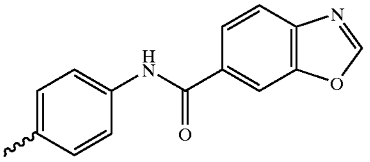 |
| 8 | 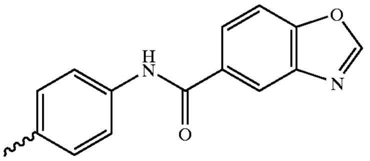 |
| 9 | 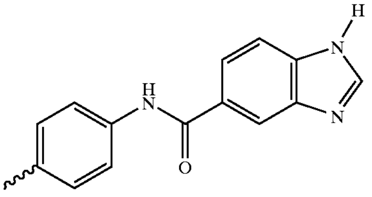 |
| 10 | 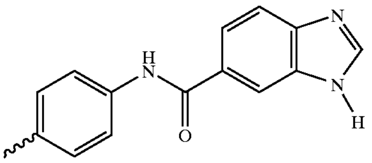 |
TABLE 24-continued
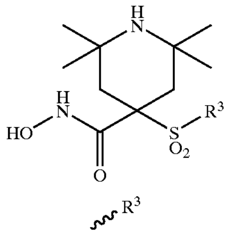
| | |
|---|---|
| 11 | 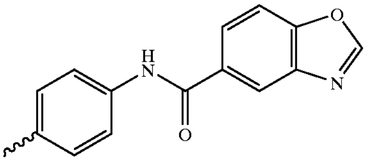 |
| 12 | 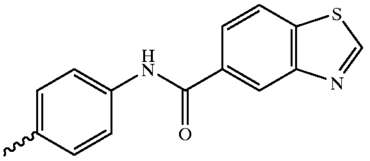 |
| 13 | 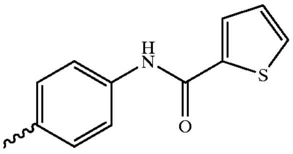 |
| 14 | 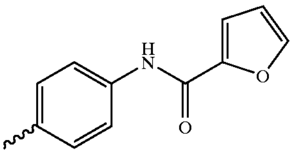 |
| 15 | 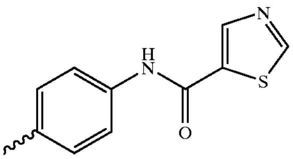 |
| 16 | 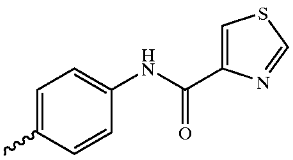 |
| 17 | 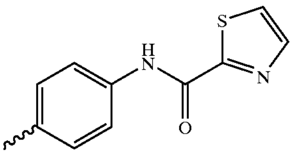 |

TABLE 24-continued
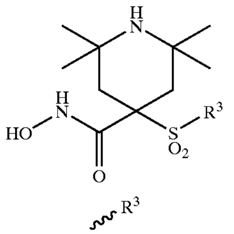
| | |
|---|---|
| 18 | 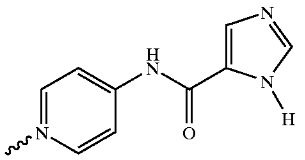 |
TABLE 25
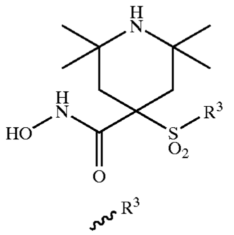
| | |
|---|---|
| 1 | 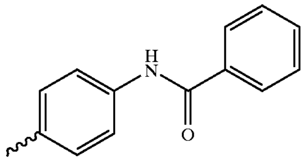 |
| 2 | 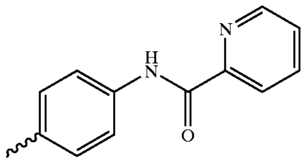 |
| 3 | 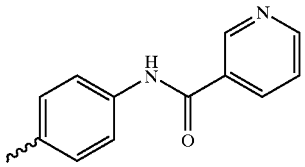 |
| 4 | 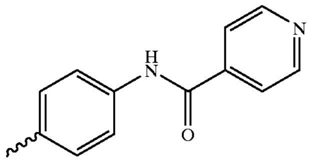 |
TABLE 25-continued
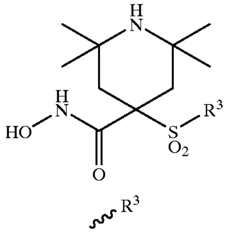
| | |
|---|---|
| 5 | 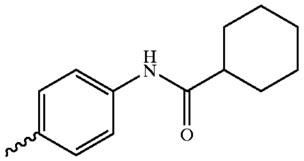 |
| 6 | 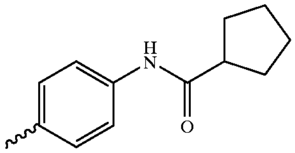 |
| 7 | 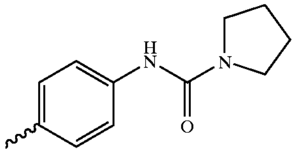 |
| 8 | 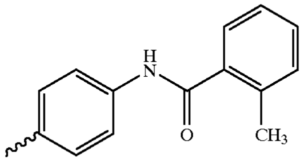 |
| 9 | 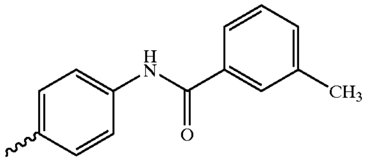 |
| 10 | 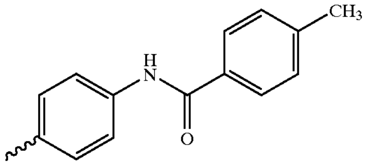 |
| 11 | 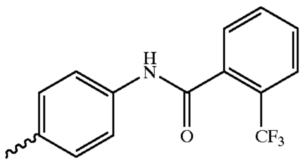 |

TABLE 25-continued
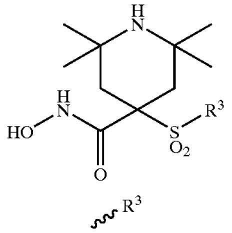
| | |
|---|---|
| 12 | 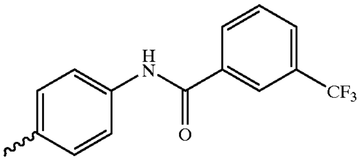 |
| 13 | 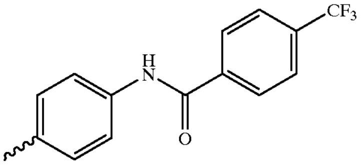 |
| 14 | 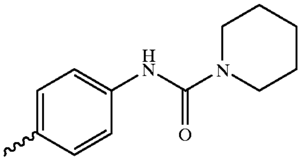 |
| 15 | 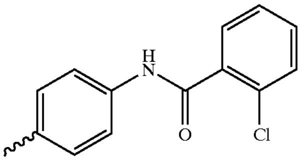 |
| 16 | 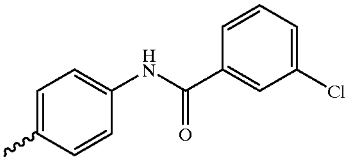 |
| 17 | 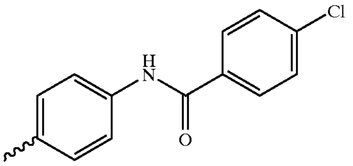 |
| 18 | 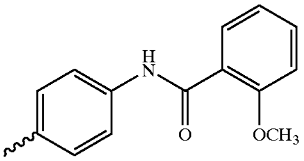 |
TABLE 25-continued
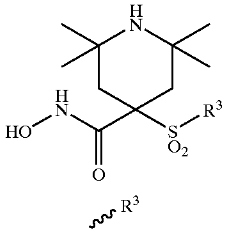
| | |
|---|---|
| 19 | 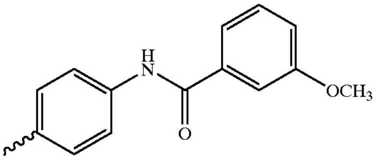 |
| 20 | 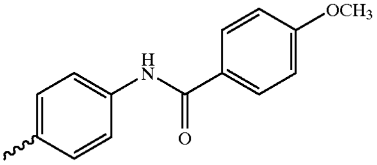 |
| 21 | 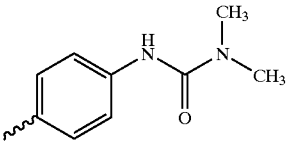 |
TABLE 26
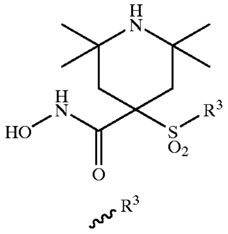
| | |
|---|---|
| 1 | 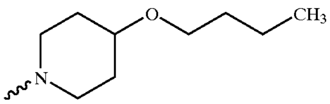 |
| 2 | 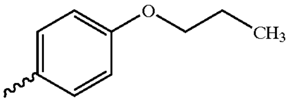 |
| 3 | 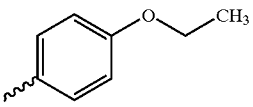 |
| 4 | 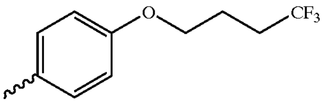 |

TABLE 26-continued
| | 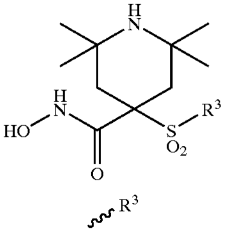 |
|---|---|
| 5 | 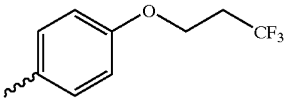 |
| 6 | 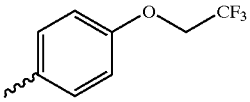 |
| 7 | 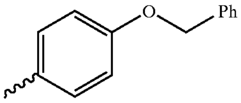 |
| 8 | 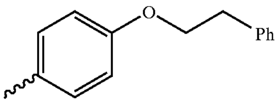 |
| 9 | 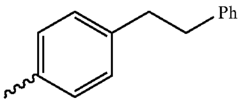 |
| 10 | 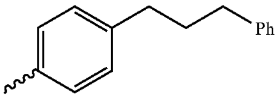 |
| 11 | 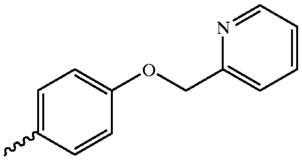 |
| 12 | 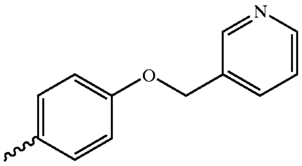 |
| 13 | 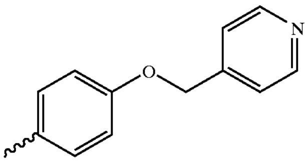 |
TABLE 26-continued
| | 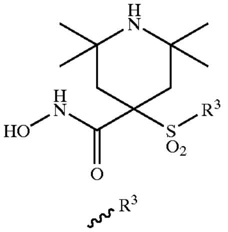 |
|---|---|
| 14 | 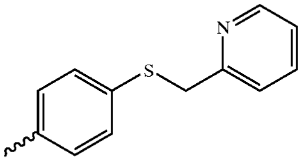 |
| 15 | 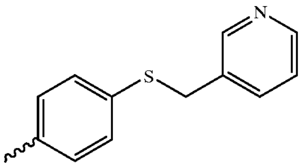 |
| 16 | 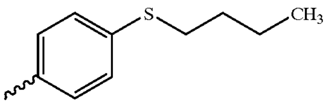 |
| 17 | 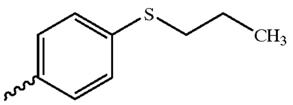 |
| 18 | 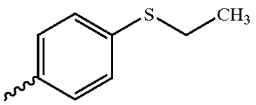 |
| 19 | 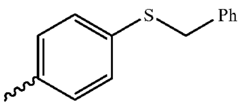 |
| 20 | 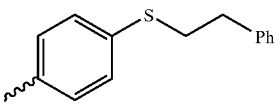 |
| 21 | 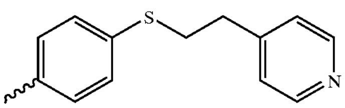 |
| 22 | 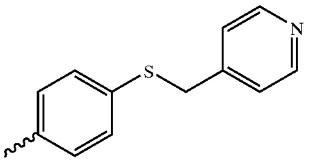 |

TABLE 27
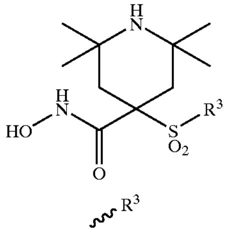
| | |
|---|---|
| 1 | 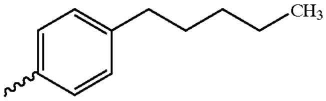 |
| 2 | 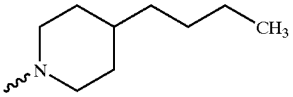 |
| 3 | 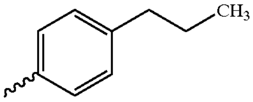 |
| 4 | 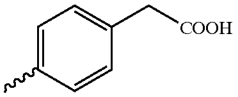 |
| 5 | 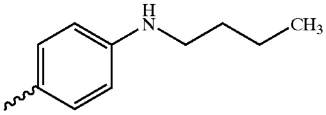 |
| 6 | 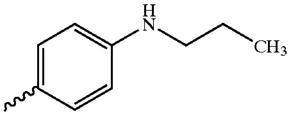 |
| 7 | 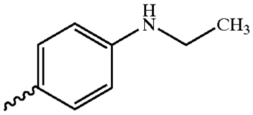 |
| 8 | 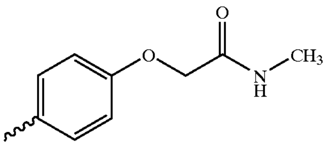 |
| 9 | 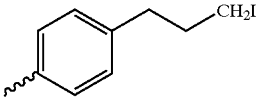 |
| 10 | 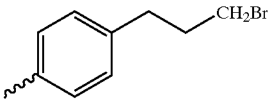 |
| 11 | 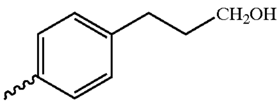 |
TABLE 27-continued
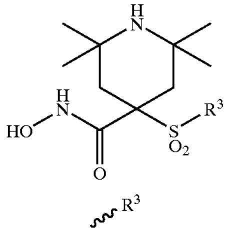
| | |
|---|---|
| 12 | 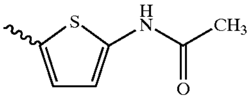 |
| 13 | 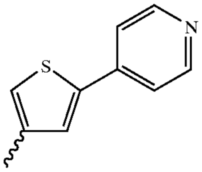 |
| 14 | 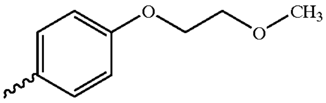 |
| 15 | 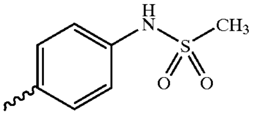 |
| 16 | 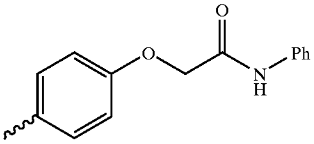 |
| 17 | 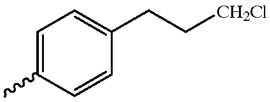 |
| 18 | 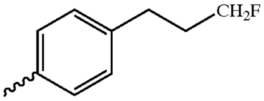 |
| 19 | 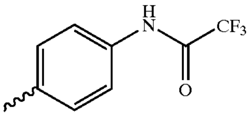 |
| 20 | 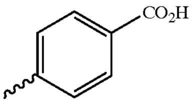 |
| 21 | 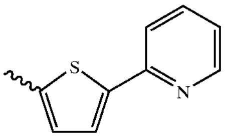 |

TABLE 27-continued
| 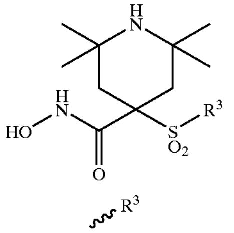 | |
|---|---|
| 22 | 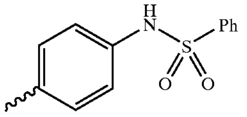 |
| 23 | 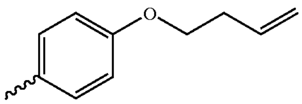 |
| 24 | 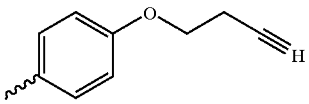 |
| 25 | 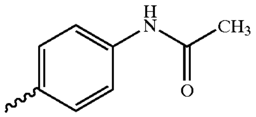 |
| 26 | 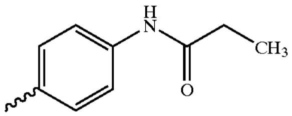 |
| 27 | 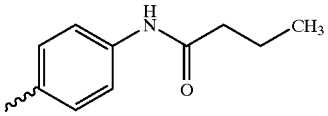 |
| 28 | 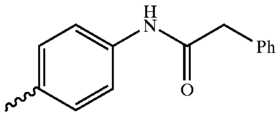 |
| 29 | 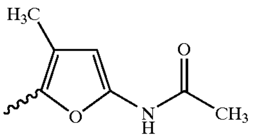 |
| 30 | 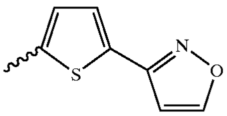 |
TABLE 28
| 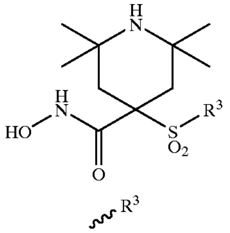 | |
|---|---|
| 1 | 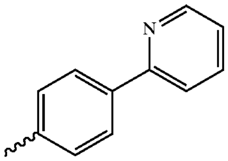 |
| 2 | 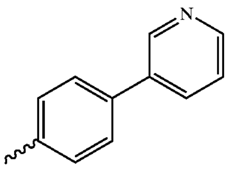 |
| 3 | 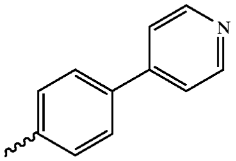 |
| 4 | 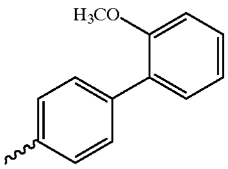 |
| 5 | 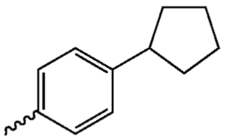 |
| 6 | 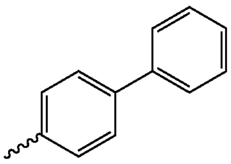 |
| 7 | 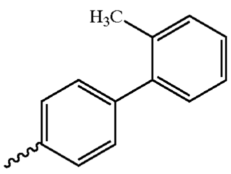 |

TABLE 28-continued
| 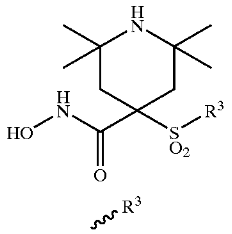 | |
|---|---|
| 8 | 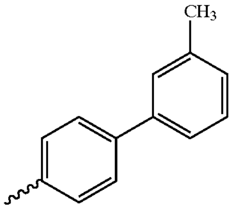 |
| 9 | 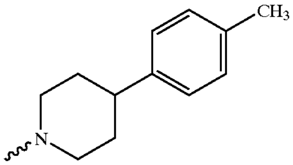 |
| 10 | 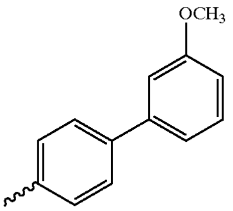 |
| 11 | 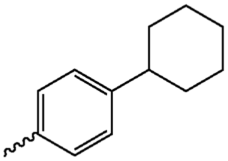 |
| 12 | 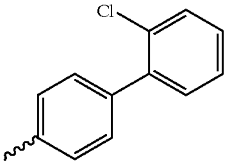 |
| 13 | 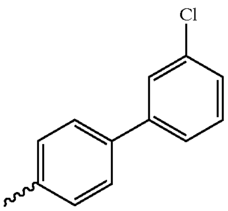 |
| 14 | 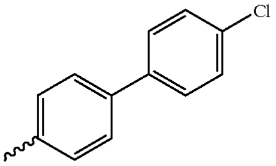 |
TABLE 28-continued
| 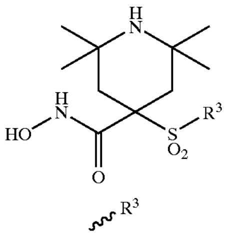 | |
|---|---|
| 15 | 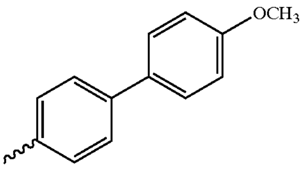 |
| 16 | 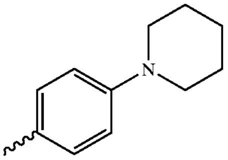 |
| 17 | 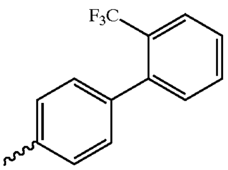 |
| 18 | 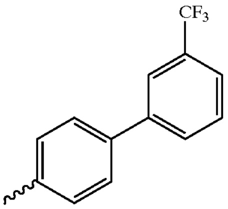 |
| 19 | 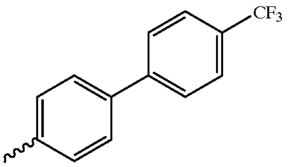 |
| 20 | 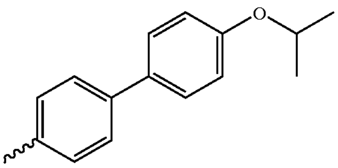 |
| 21 | 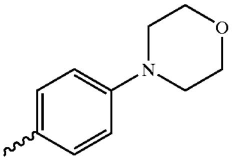 |

TABLE 29
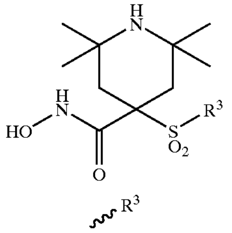
| | |
|---|---|
| 1 | 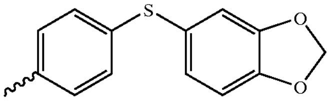 |
| 2 | 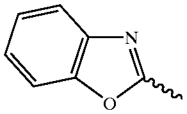 |
| 3 | 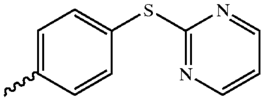 |
| 4 | 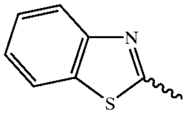 |
| 5 | 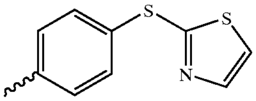 |
| 6 | 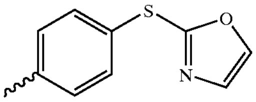 |
| 7 | 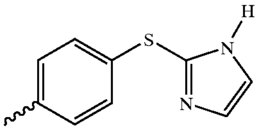 |
| 8 | 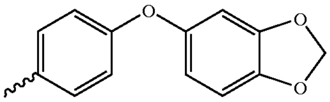 |
| 9 | 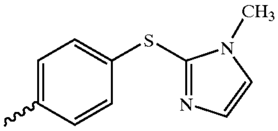 |
| 10 | 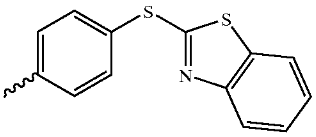 |
TABLE 29-continued
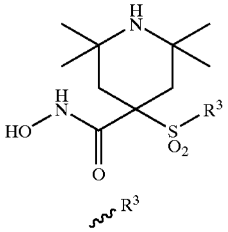
| | |
|---|---|
| 11 | 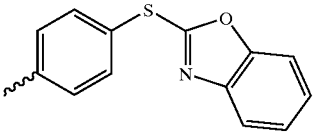 |
TABLE 30
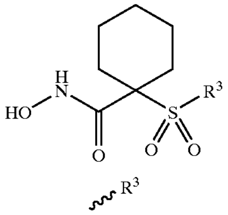
| | |
|---|---|
| 1 | 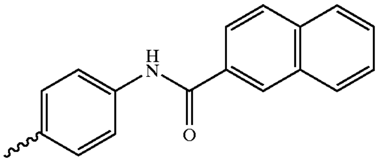 |
| 2 | 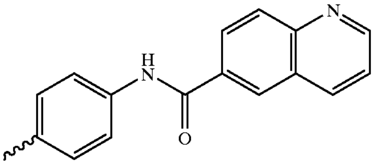 |
| 3 | 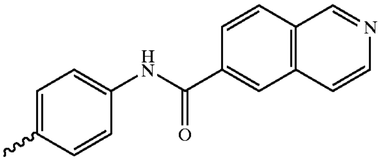 |
| 4 | 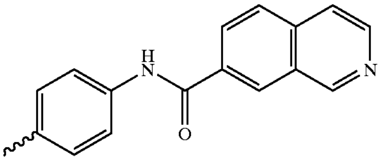 |
| 5 | 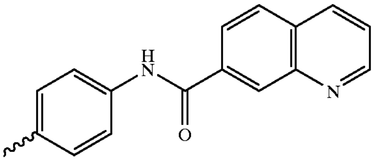 |

TABLE 30-continued
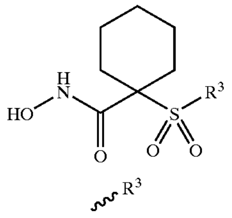
| | |
|---|---|
| 6 | 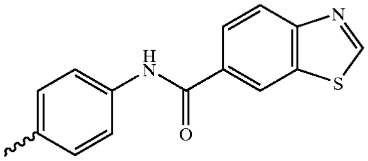 |
| 7 | 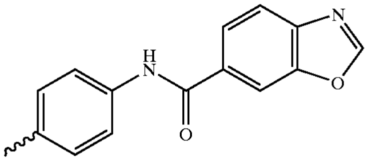 |
| 8 | 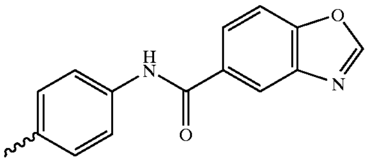 |
| 9 | 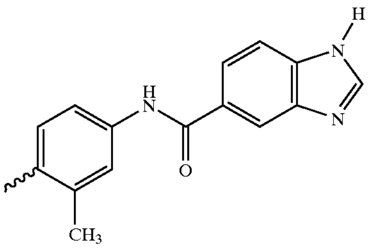 |
| 10 | 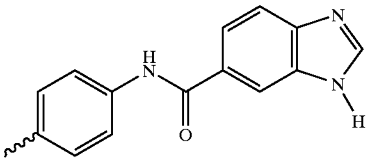 |
| 11 | 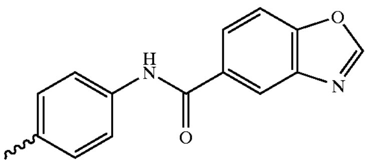 |
| 12 | 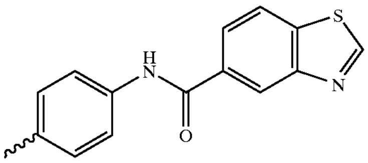 |
TABLE 30-continued
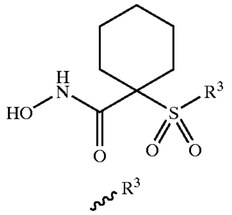
| | |
|---|---|
| 13 | 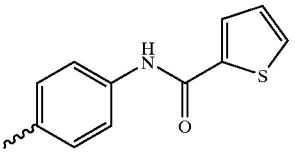 |
| 14 | 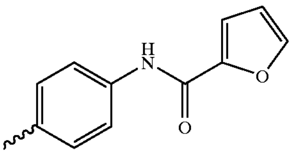 |
| 15 | 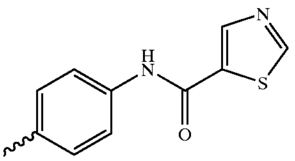 |
| 16 | 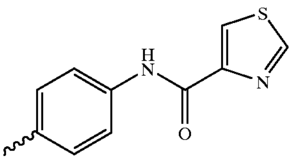 |
| 17 | 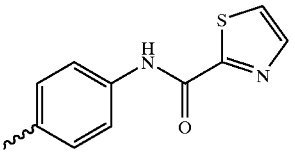 |
| 18 | 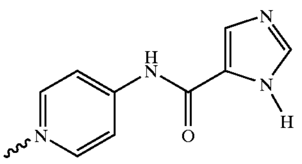 |

TABLE 31
| 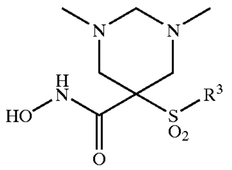 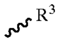 | |
|---|---|
| 1 | 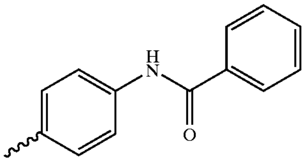 |
| 2 | 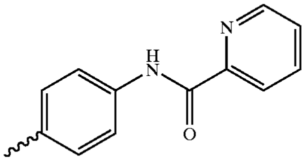 |
| 3 | 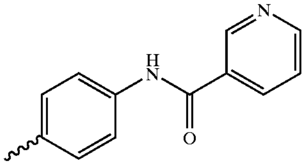 |
| 4 | 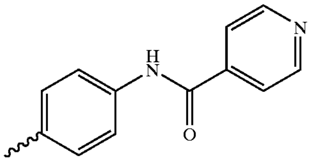 |
| 5 | 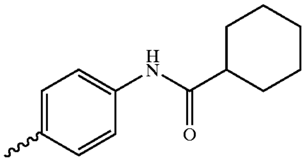 |
| 6 | 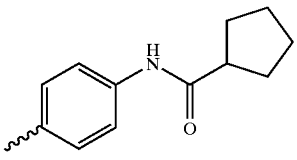 |
| 7 | 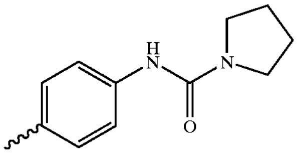 |
TABLE 31-continued
| 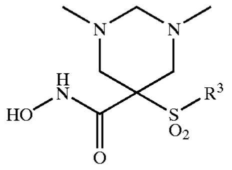 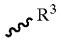 | |
|---|---|
| 8 | 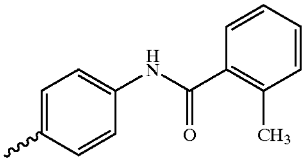 |
| 9 | 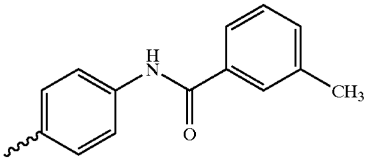 |
| 10 | 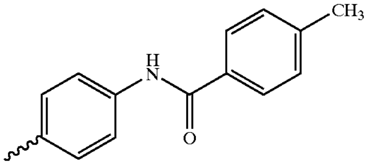 |
| 11 | 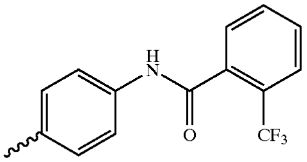 |
| 12 | 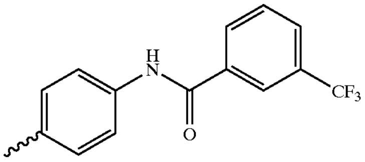 |
| 13 | 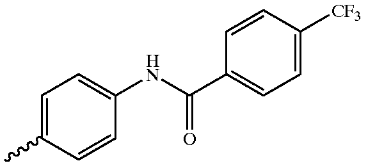 |
| 14 | 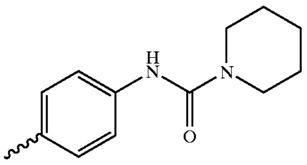 |

TABLE 31-continued
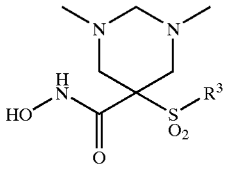
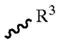
| | |
|---|---|
| 15 | 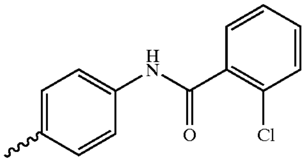 |
| 16 | 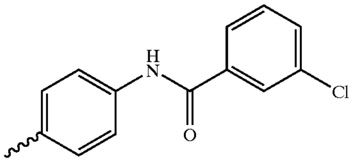 |
| 17 | 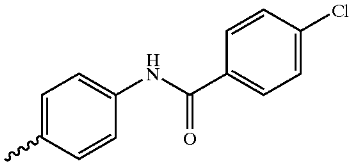 |
| 18 | 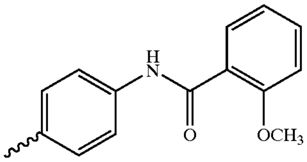 |
| 19 | 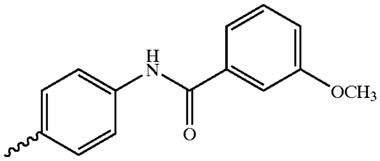 |
| 20 | 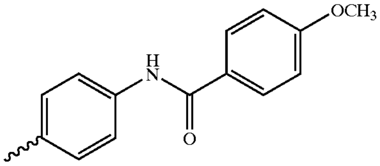 |
| 21 | 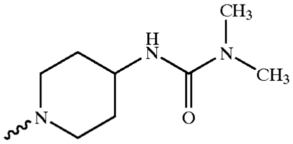 |
TABLE 32
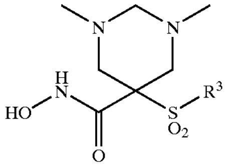
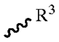
| | |
|---|---|
| 1 | 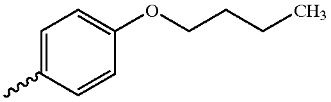 |
| 2 | 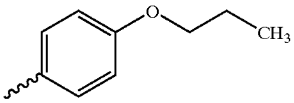 |
| 3 | 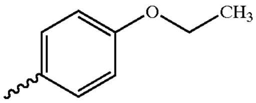 |
| 4 | 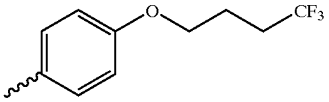 |
| 5 | 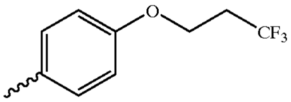 |
| 6 | 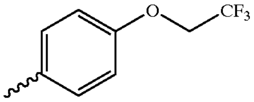 |
| 7 | 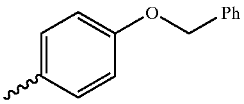 |
| 8 | 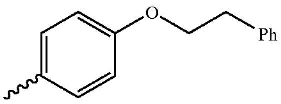 |
| 9 | 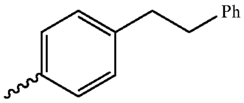 |
| 10 | 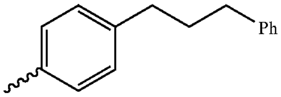 |
| 11 | 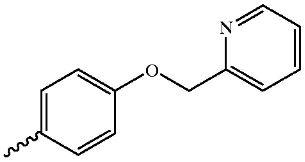 |

TABLE 32-continued
| 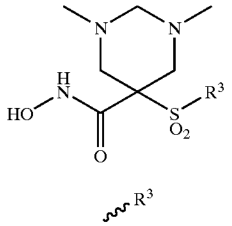 | |
| --- | --- |
| 12 | 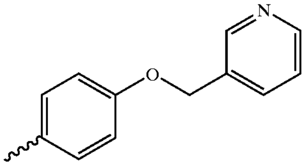 |
| 13 | 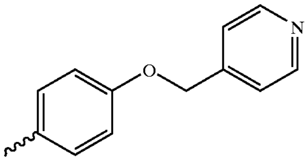 |
| 14 | 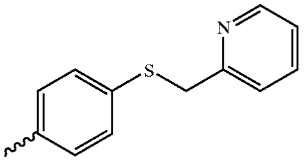 |
| 15 | 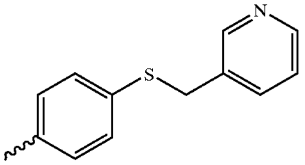 |
| 16 | 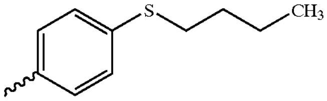 |
| 17 | 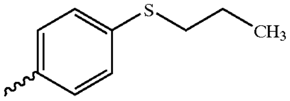 |
| 18 | 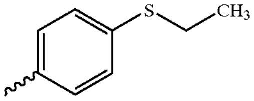 |
| 19 | 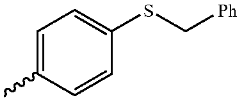 |
| 20 | 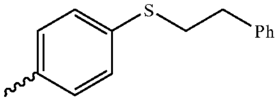 |
TABLE 32-continued
| 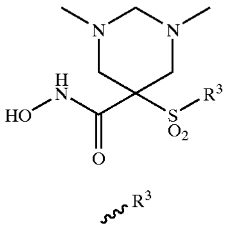 | |
| --- | --- |
| 21 | 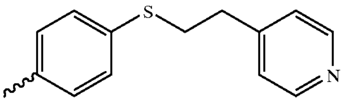 |
| 22 | 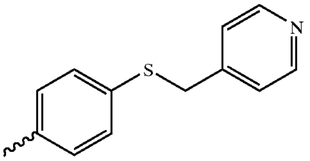 |
TABLE 33
| 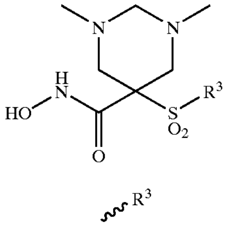 | |
| --- | --- |
| 1 | 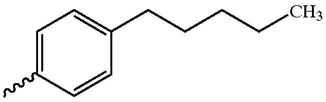 |
| 2 | 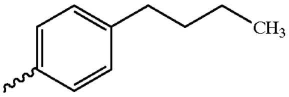 |
| 3 | 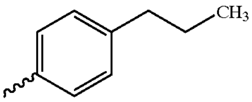 |
| 4 | 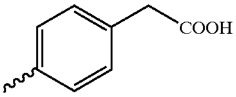 |
| 5 | 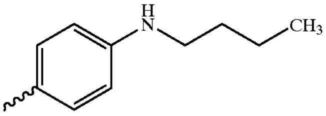 |
| 6 | 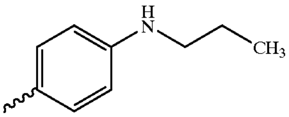 |

TABLE 33-continued
| | |
|---|---|
| | 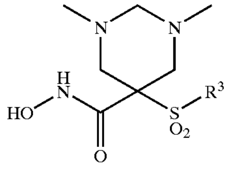 |
| | 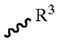 |
| 7 | 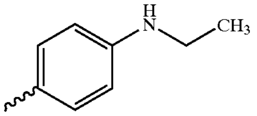 |
| 8 | 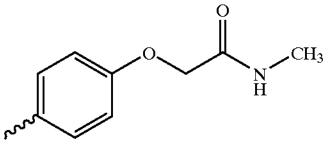 |
| 9 | 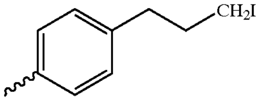 |
| 10 | 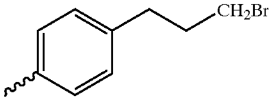 |
| 11 | 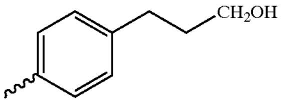 |
| 12 | 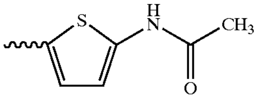 |
| 13 | 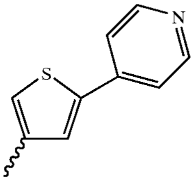 |
| 14 | 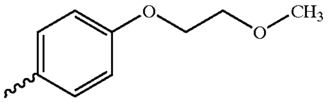 |
| 15 | 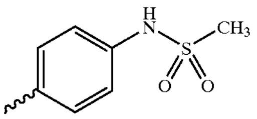 |
| 16 | 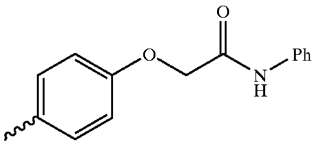 |
TABLE 33-continued
| | |
|---|---|
| | 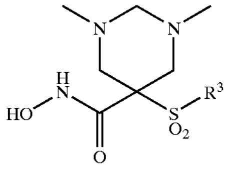 |
| | 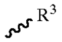 |
| 17 | 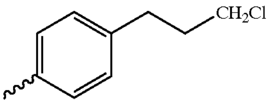 |
| 18 | 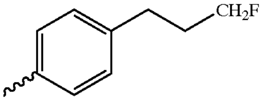 |
| 19 | 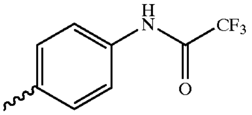 |
| 20 | 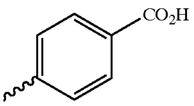 |
| 21 | 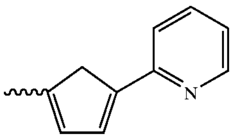 |
| 22 | 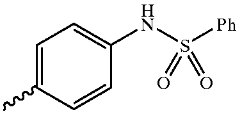 |
| 23 | 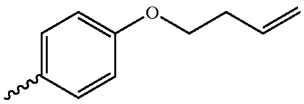 |
| 24 | 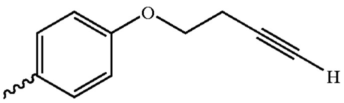 |
| 25 | 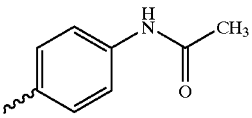 |
| 26 | 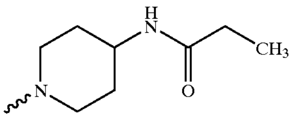 |

TABLE 33-continued
| | |
|---|---|
| | 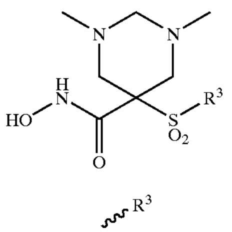 |
| 27 | 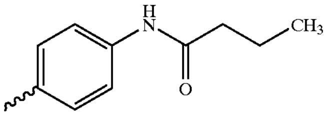 |
| 28 | 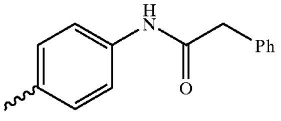 |
| 29 | 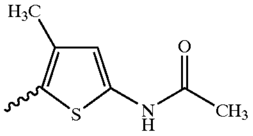 |
| 30 | 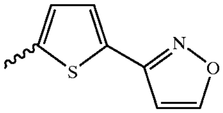 |
TABLE 34
| | |
|---|---|
| | 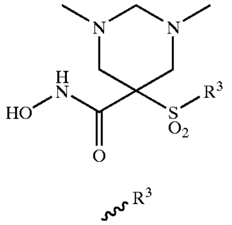 |
| 1 | 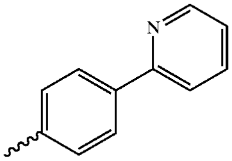 |
| 2 | 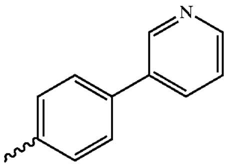 |
TABLE 34-continued
| | |
|---|---|
| | 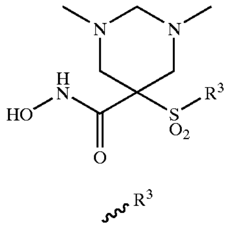 |
| 3 | 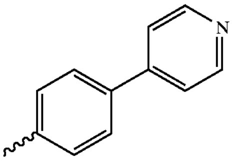 |
| 4 | 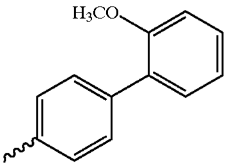 |
| 5 | 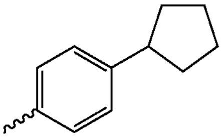 |
| 6 | 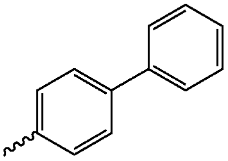 |
| 7 | 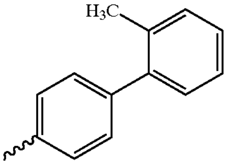 |
| 8 | 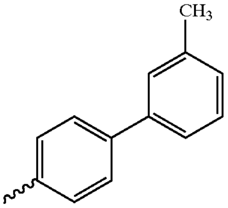 |
| 9 | 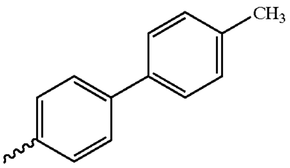 |

TABLE 34-continued
| 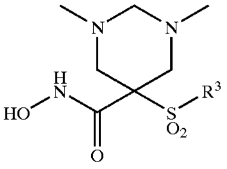 |
| --- |
| 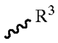 |
| 10 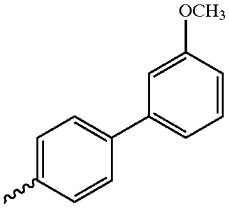 |
| 11 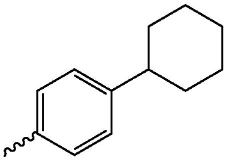 |
| 12 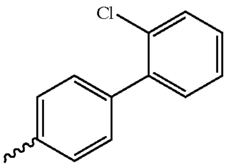 |
| 13 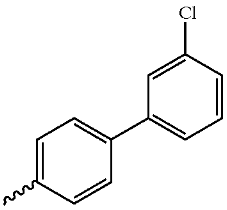 |
| 14 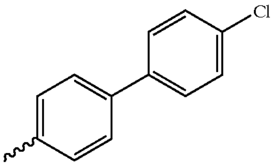 |
| 15 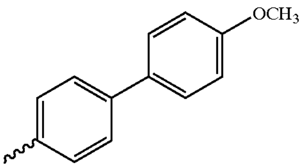 |
| 16 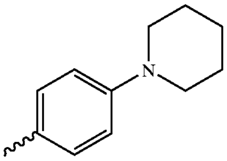 |
TABLE 34-continued
| 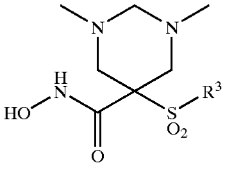 |
| --- |
| 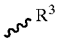 |
| 17 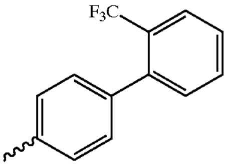 |
| 18 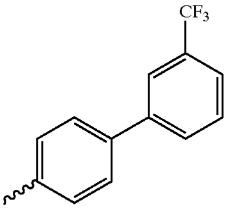 |
| 19 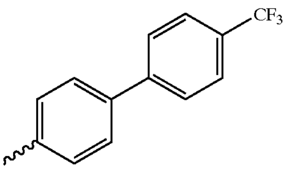 |
| 20 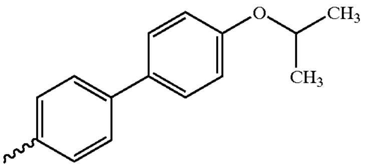 |
| 21 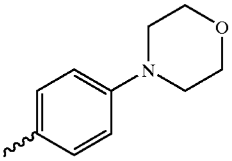 |
TABLE 35
| 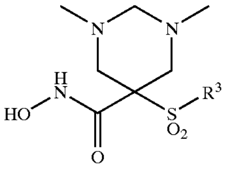 |
| --- |
| 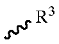 |
| 1 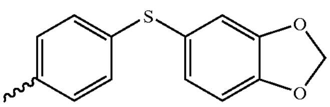 |

TABLE 35-continued
| | |
|---|---|
| 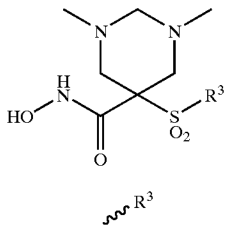 | |
| 2 | 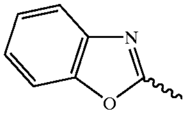 |
| 3 | 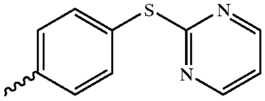 |
| 4 | 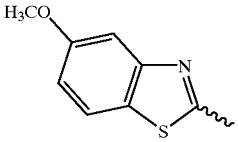 |
| 5 | 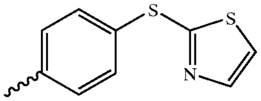 |
| 6 | 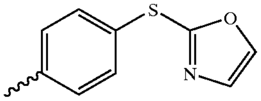 |
| 7 | 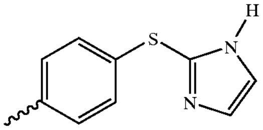 |
| 8 | 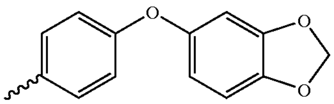 |
| 9 | 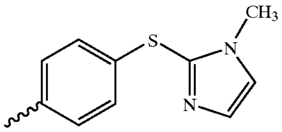 |
| 10 | 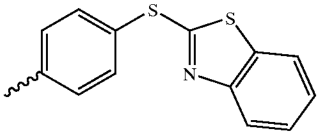 |
TABLE 35-continued
| | |
|---|---|
| 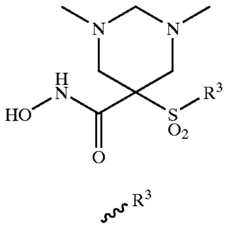 | |
| 11 | 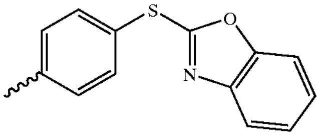 |
TABLE 36
| | |
|---|---|
| 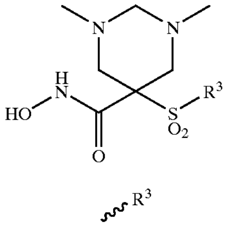 | |
| 2 | 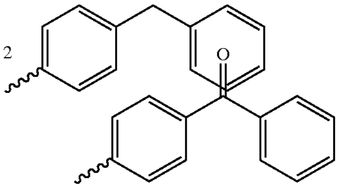 |
| 3 | 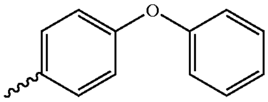 |
| 4 | 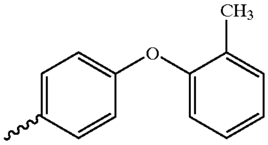 |
| 5 | 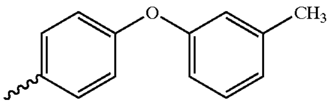 |
| 6 | 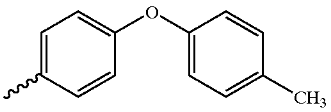 |
| 7 | 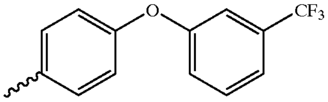 |

TABLE 36-continued
| | |
|---|---|
| | 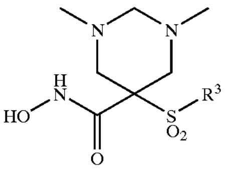 |
| | 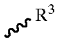 |
| 8 | 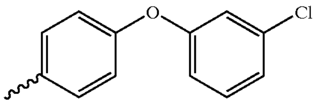 |
| 9 | 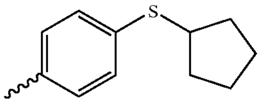 |
| 10 | 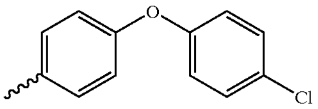 |
| 11 | 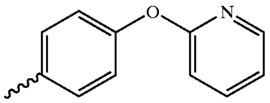 |
| 12 | 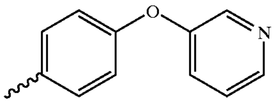 |
| 13 | 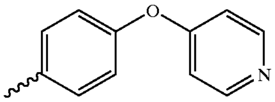 |
| 14 | 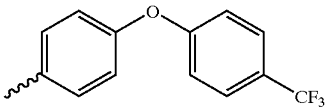 |
| 15 | 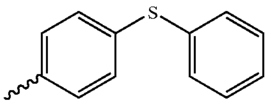 |
| 16 | 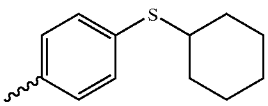 |
| 17 | 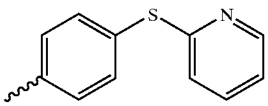 |
| 18 | 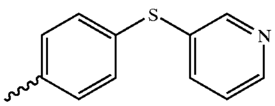 |
TABLE 36-continued
| | |
|---|---|
| | 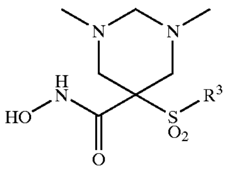 |
| | 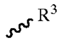 |
| 19 | 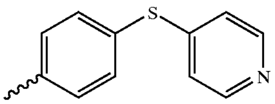 |
| 20 | 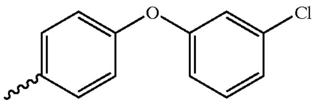 |
| 21 | 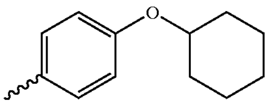 |
TABLE 37
| | |
|---|---|
| | 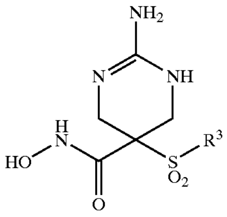 |
| | 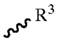 |
| 1 | 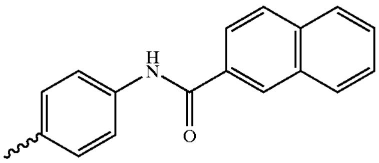 |
| 2 | 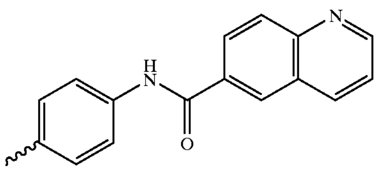 |
| 3 | 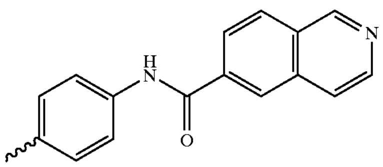 |

TABLE 37-continued
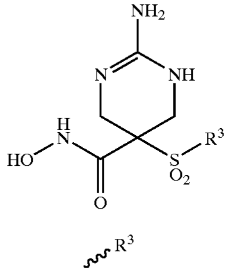
| | |
|---|---|
| 4 | 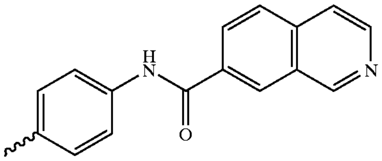 |
| 5 | 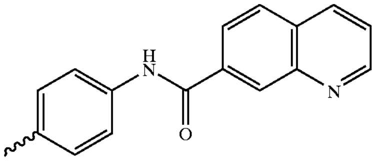 |
| 6 | 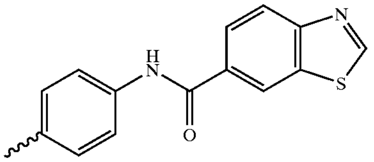 |
| 7 | 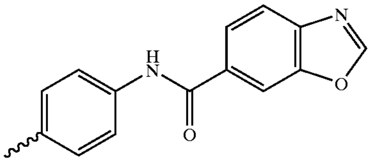 |
| 8 | 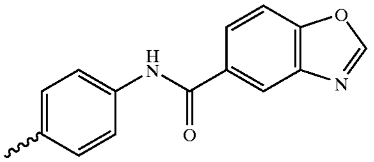 |
| 9 | 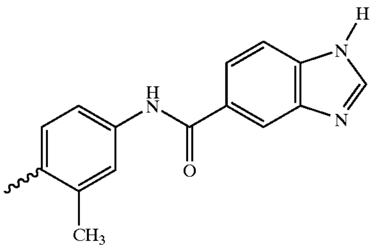 |
| 10 | 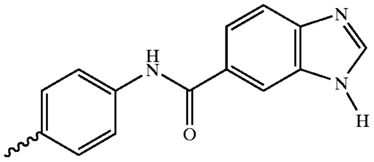 |
TABLE 37-continued
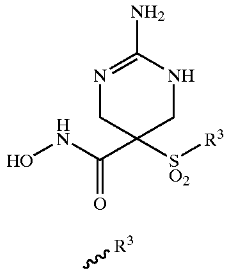
| | |
|---|---|
| 11 | 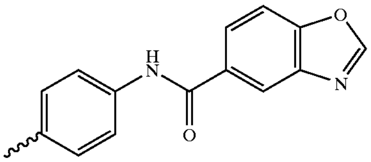 |
| 12 | 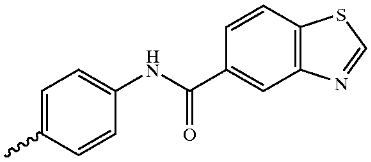 |
| 13 | 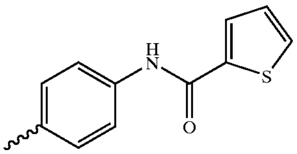 |
| 14 | 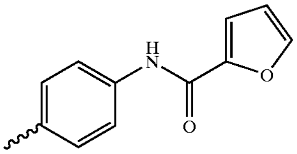 |
| 15 | 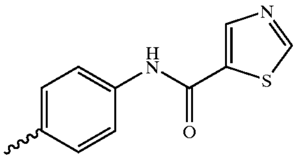 |
| 16 | 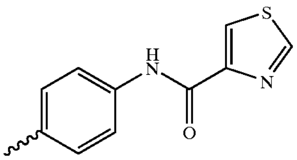 |
| 17 | 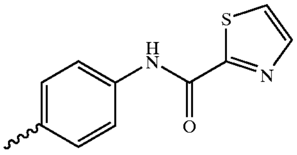 |

TABLE 37-continued
| | |
|---|---|
| | 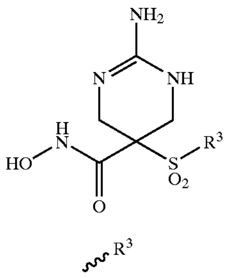 |
| 18 | 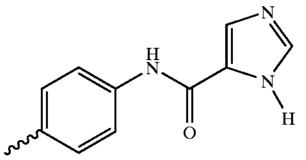 |
TABLE 38
| | |
|---|---|
| | 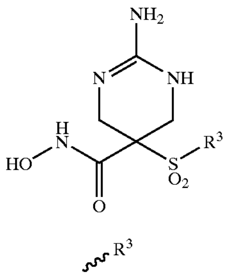 |
| 1 | 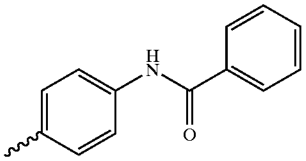 |
| 2 | 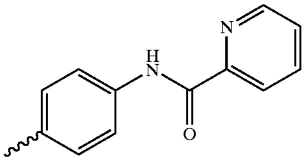 |
| 3 | 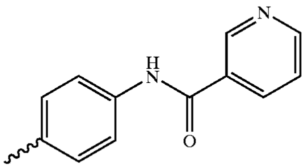 |
| 4 | 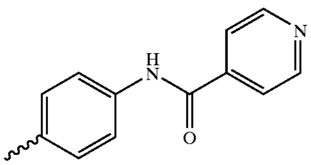 |
TABLE 38-continued
| | |
|---|---|
| | 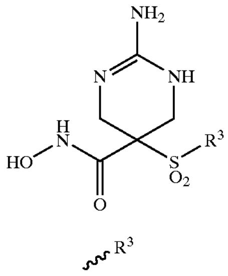 |
| 5 | 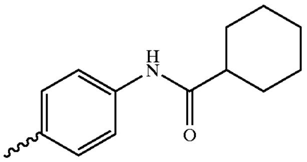 |
| 6 | 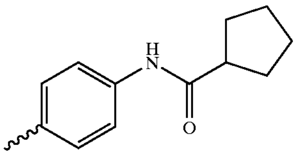 |
| 7 | 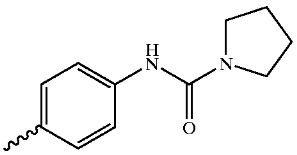 |
| 8 | 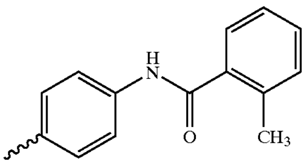 |
| 9 | 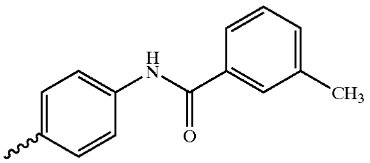 |
| 10 | 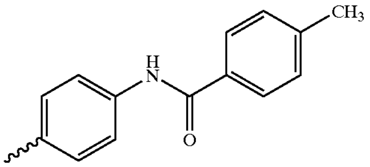 |
| 11 | 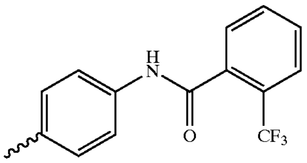 |

TABLE 38-continued
| 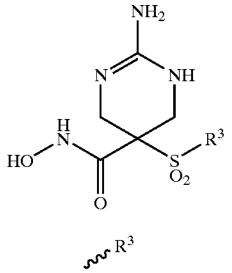 | |
|---|---|
| 12 | 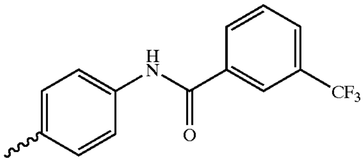 |
| 13 | 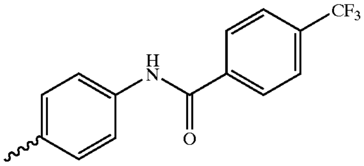 |
| 14 | 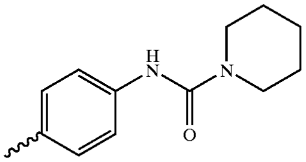 |
| 15 | 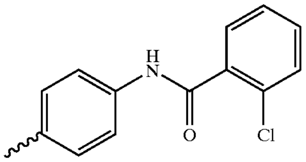 |
| 16 | 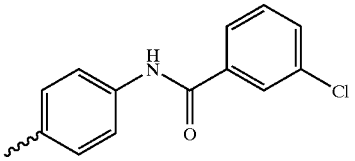 |
| 17 | 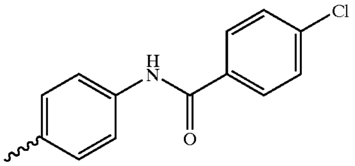 |
| 18 | 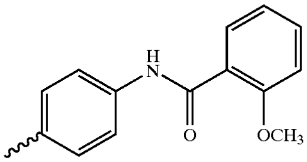 |
TABLE 38-continued
| 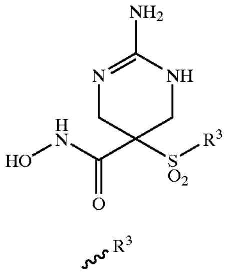 | |
|---|---|
| 19 | 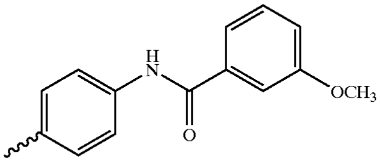 |
| 20 | 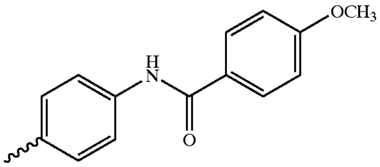 |
| 21 | 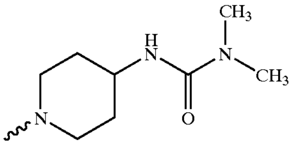 |
TABLE 39
| 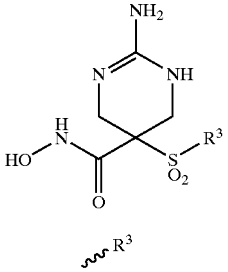 | |
|---|---|
| 1 | 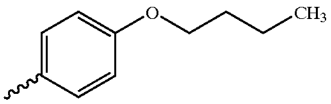 |
| 2 | 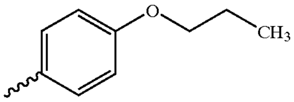 |
| 3 | 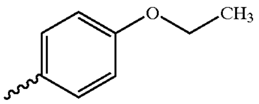 |

TABLE 39-continued
| | 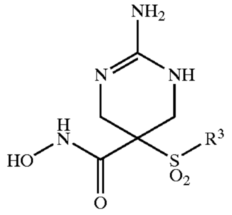 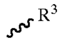 |
|---|---|
| 4 | 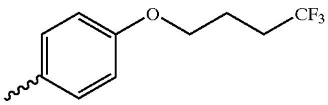 |
| 5 | 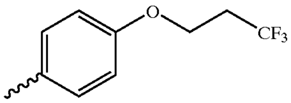 |
| 6 | 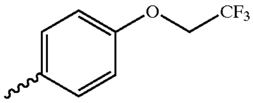 |
| 7 | 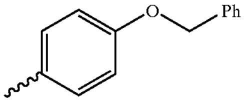 |
| 8 | 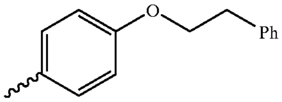 |
| 9 | 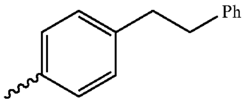 |
| 10 | 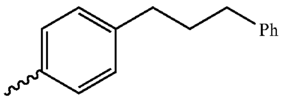 |
| 11 | 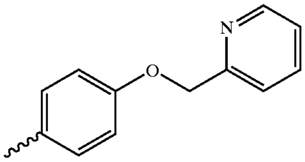 |
| 12 | 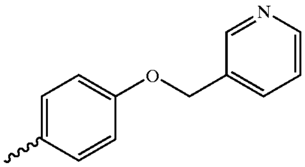 |
| | 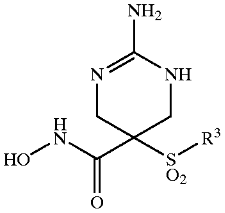 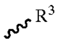 |
| 13 | 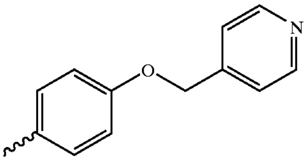 |
| 14 | 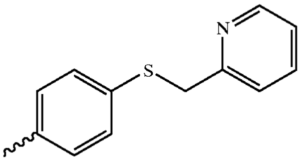 |
| 15 | 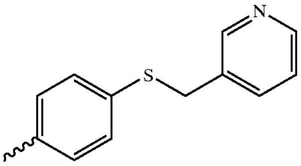 |
| 16 | 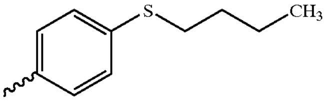 |
| 17 | 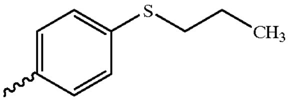 |
| 18 | 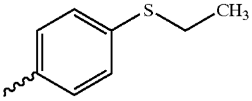 |
| 19 | 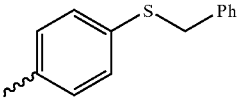 |
| 20 | 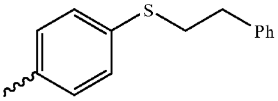 |
| 21 | 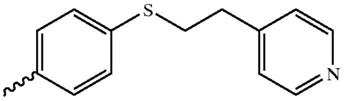 |

TABLE 39-continued
| | 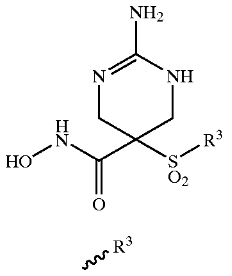 |
|---|---|
| 22 | 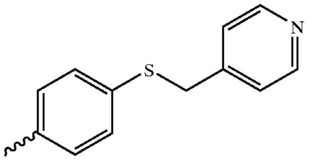 |
TABLE 40
| | 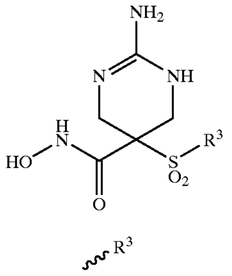 |
|---|---|
| 1 | 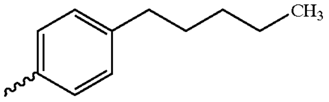 |
| 2 | 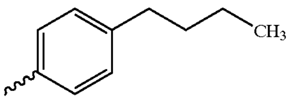 |
| 3 | 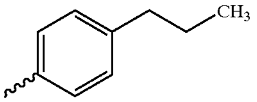 |
| 4 | 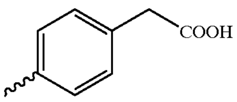 |
| 5 | 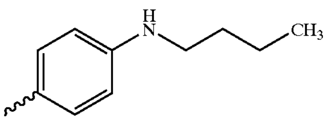 |
| 6 | 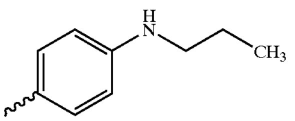 |
TABLE 40-continued
| | 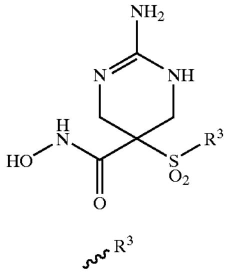 |
|---|---|
| 7 | 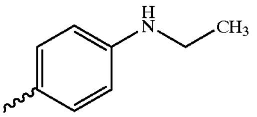 |
| 8 | 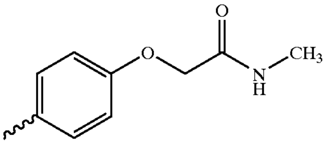 |
| 9 | 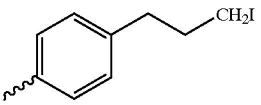 |
| 10 | 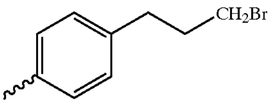 |
| 11 | 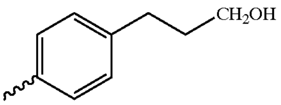 |
| 12 | 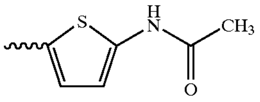 |
| 13 | 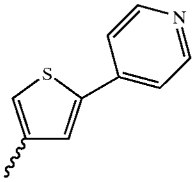 |
| 14 | 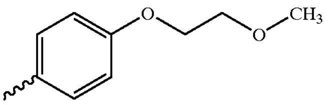 |
| 15 | 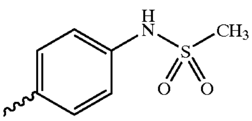 |

TABLE 40-continued
| | 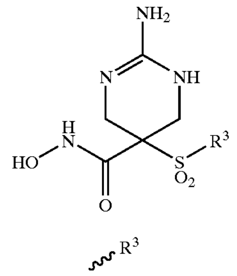 |
|---|---|
| 16 | 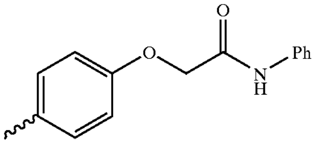 |
| 17 | 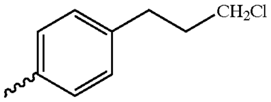 |
| 18 | 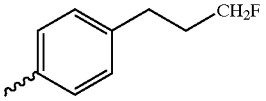 |
| 19 | 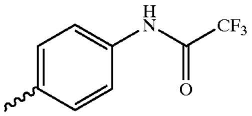 |
| 20 | 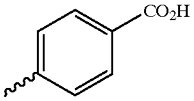 |
| 21 | 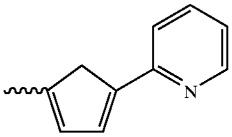 |
| 22 | 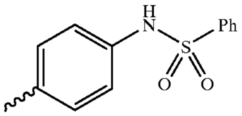 |
| 23 | 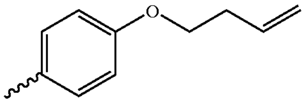 |
| 24 | 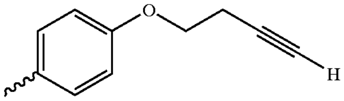 |
| 25 | 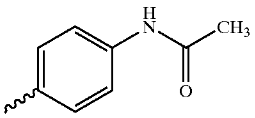 |
TABLE 40-continued
| | 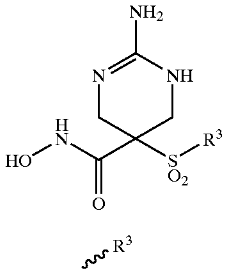 |
|---|---|
| 26 | 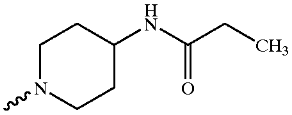 |
| 27 | 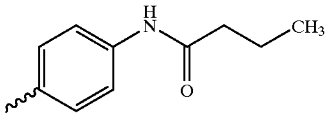 |
| 28 | 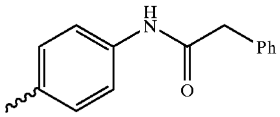 |
| 29 | 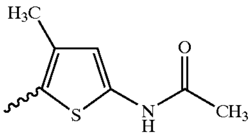 |
| 30 | 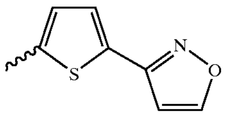 |
TABLE 41
| | 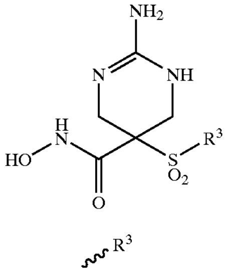 |
|---|---|
| 1 | 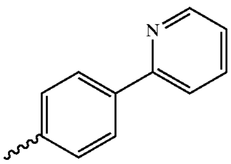 |

TABLE 41-continued
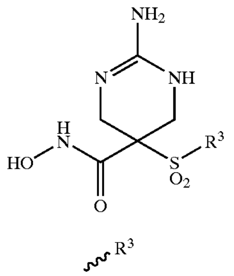
| | |
|---|---|
| 2 | 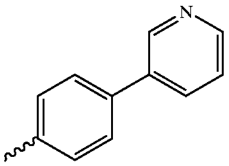 |
| 3 | 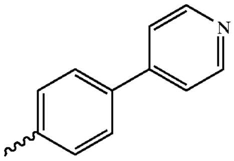 |
| 4 | 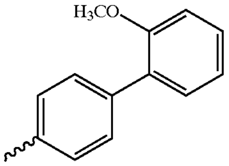 |
| 5 | 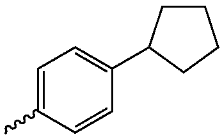 |
| 6 | 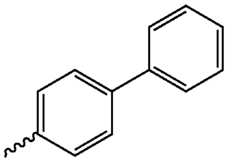 |
| 7 | 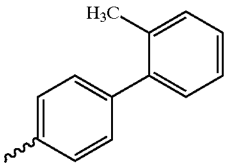 |
| 8 | 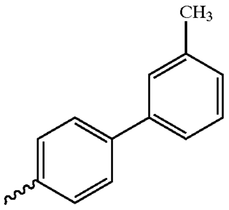 |
TABLE 41-continued
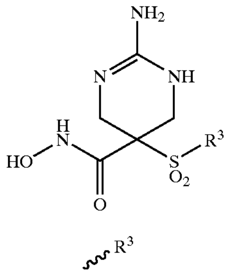
| | |
|---|---|
| 9 | 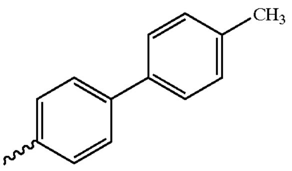 |
| 10 | 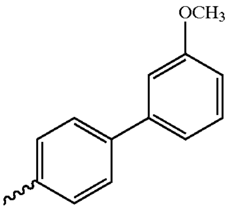 |
| 11 | 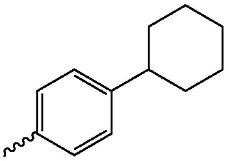 |
| 12 | 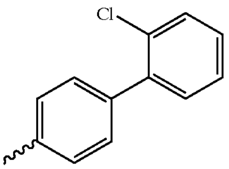 |
| 13 | 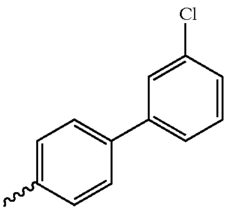 |
| 14 | 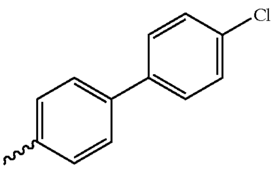 |
| 15 | 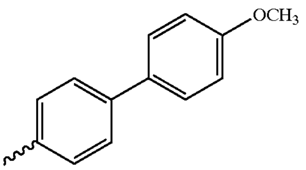 |

TABLE 41-continued
| | |
|---|---|
| | 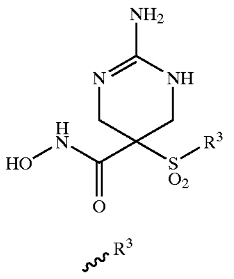 |
| 16 | 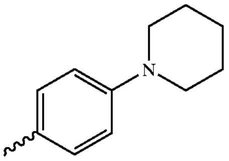 |
| 17 | 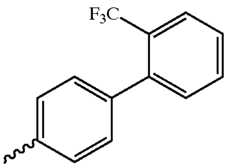 |
| 18 | 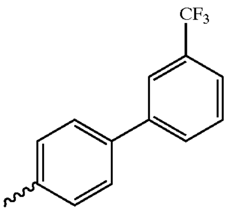 |
| 19 | 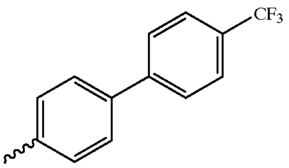 |
| 20 | 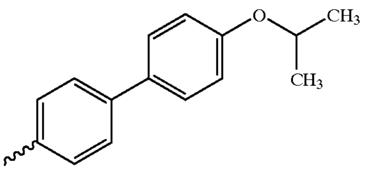 |
| 21 | 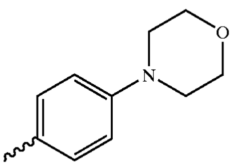 |
TABLE 42
| | |
|---|---|
| | 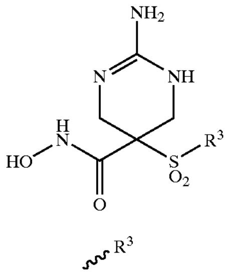 |
| 1 | 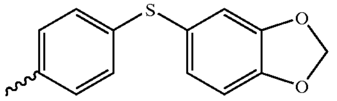 |
| 2 | 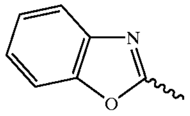 |
| 3 | 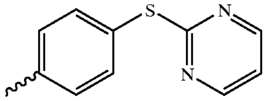 |
| 4 | 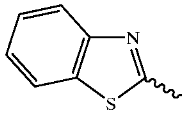 |
| 5 | 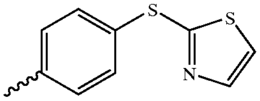 |
| 6 | 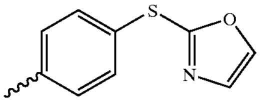 |
| 7 | 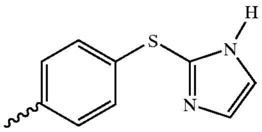 |
| 8 | 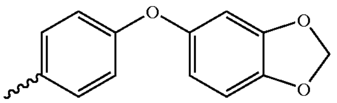 |
| 9 | 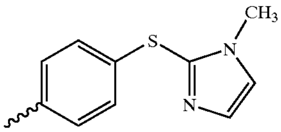 |
| 10 | 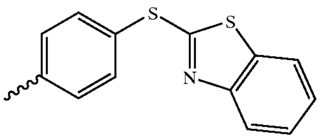 |

TABLE 42-continued
| | |
|---|---|
| | 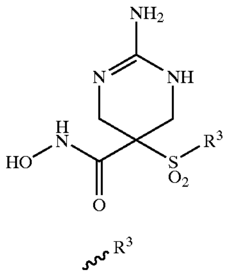 |
| 11 | 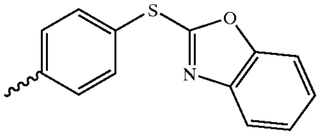 |
TABLE 43
| | |
|---|---|
| | 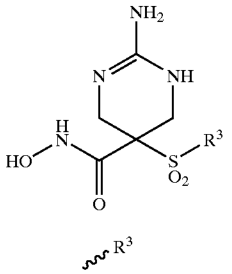 |
| 1 | 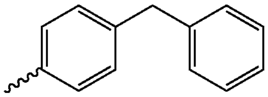 |
| 2 | 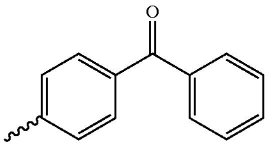 |
| 3 | 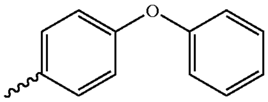 |
| 4 | 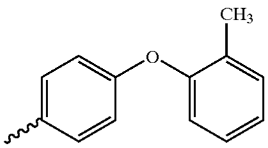 |
| 5 | 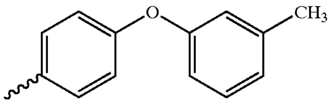 |
| 6 | 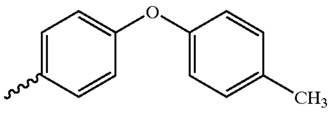 |
TABLE 43-continued
| | |
|---|---|
| | 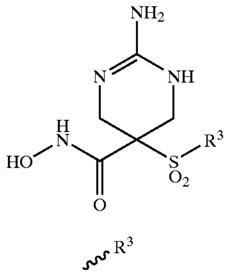 |
| 7 | 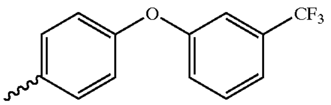 |
| 8 | 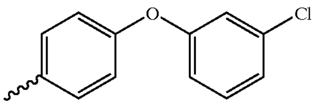 |
| 9 | 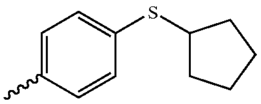 |
| 10 | 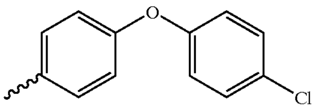 |
| 11 | 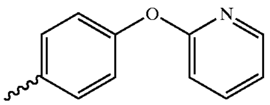 |
| 12 | 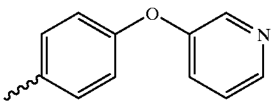 |
| 13 | 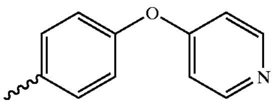 |
| 14 | 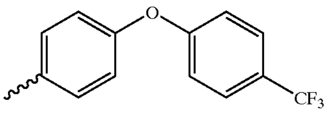 |
| 15 | 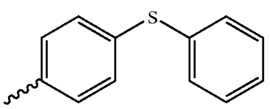 |
| 16 | 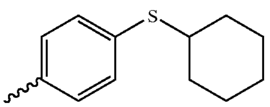 |
| 17 | 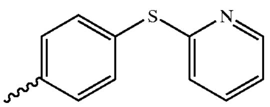 |

TABLE 43-continued
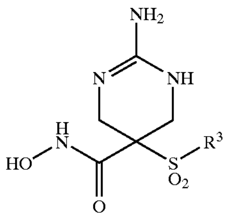
| | |
|---|---|
| 18 | 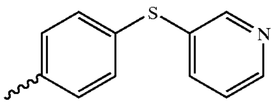 |
| 19 | 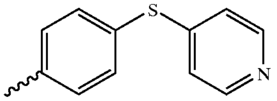 |
| 20 | 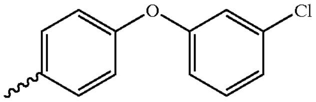 |
| 21 | 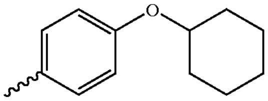 |
TABLE 44
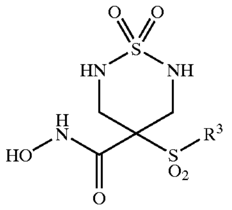
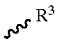
| | |
|---|---|
| 1 | 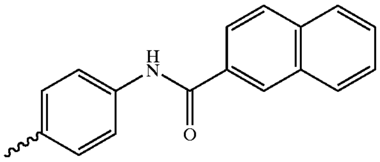 |
| 2 | 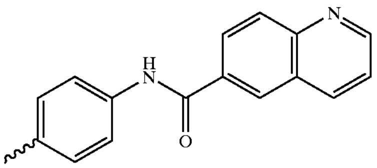 |
TABLE 44-continued
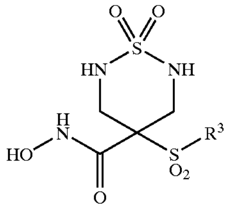
| | |
|---|---|
| 3 | 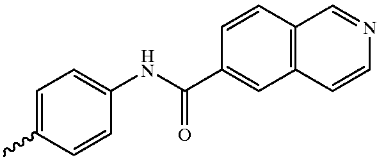 |
| 4 | 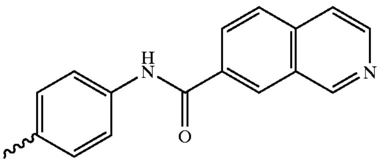 |
| 5 | 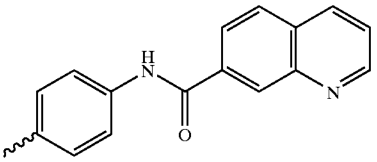 |
| 6 | 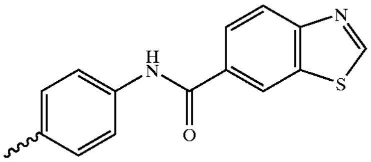 |
| 7 | 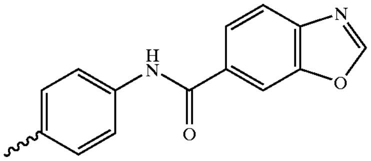 |
| 8 | 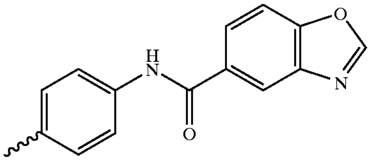 |
| 9 | 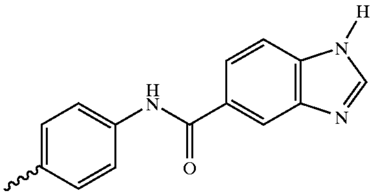 |

TABLE 44-continued
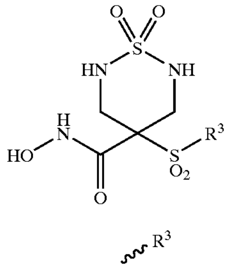
| | |
|---|---|
| 10 | 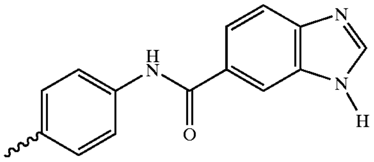 |
| 11 | 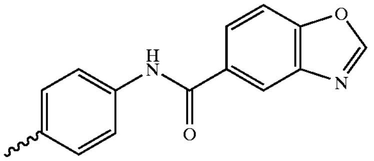 |
| 12 | 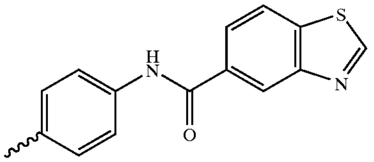 |
| 13 | 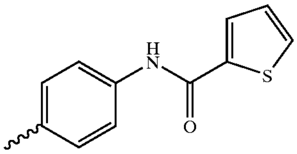 |
| 14 | 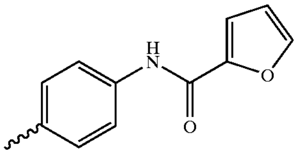 |
| 15 | 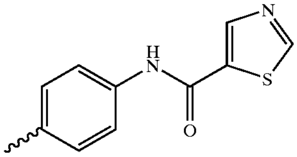 |
| 16 | 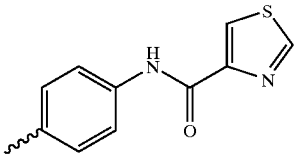 |
TABLE 44-continued
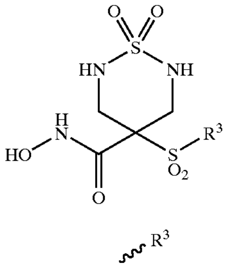
| | |
|---|---|
| 17 | 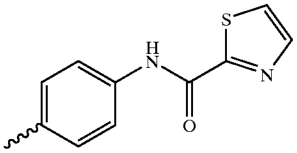 |
| 18 | 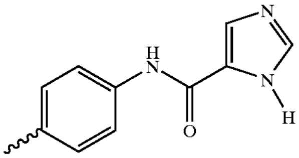 |
TABLE 45
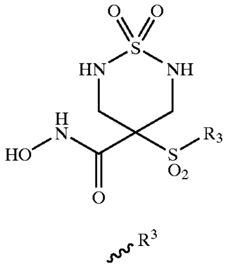
| | |
|---|---|
| 1 | 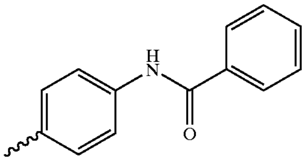 |
| 2 | 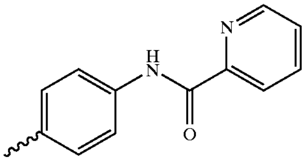 |
| 3 | 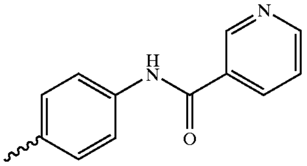 |

TABLE 45-continued
| | |
|---|---|
| | 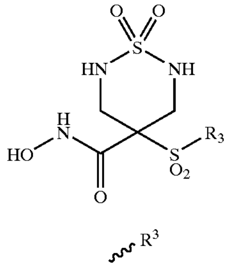 |
| 4 | 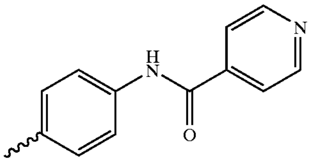 |
| 5 | 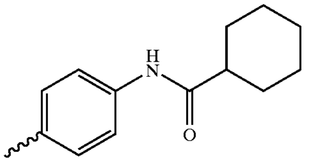 |
| 6 | 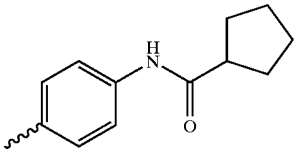 |
| 7 | 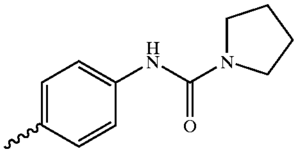 |
| 8 | 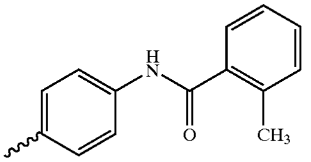 |
| 9 | 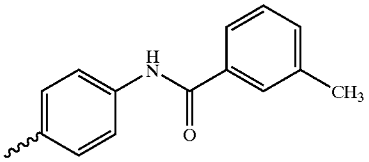 |
| 10 | 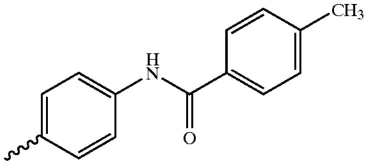 |
TABLE 45-continued
| | |
|---|---|
| | 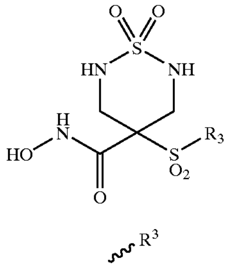 |
| 11 | 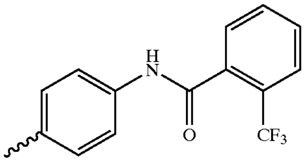 |
| 12 | 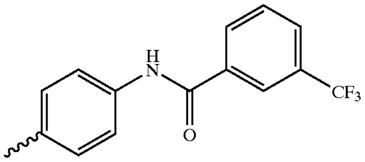 |
| 13 | 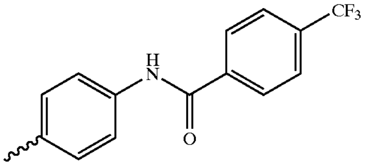 |
| 14 | 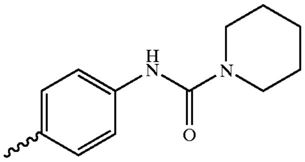 |
| 15 | 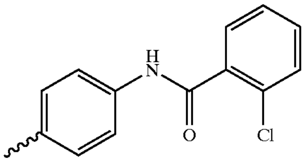 |
| 16 | 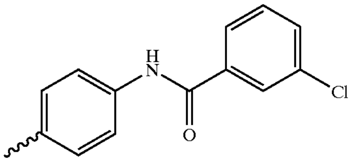 |
| 17 | 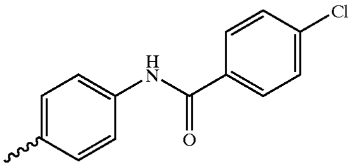 |

TABLE 45-continued
| | 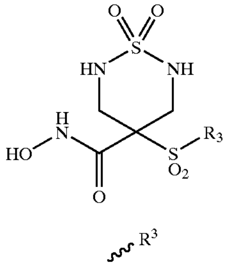 |
|---|---|
| 18 | 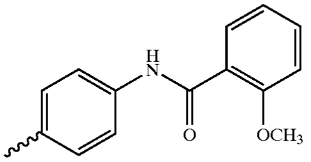 |
| 19 | 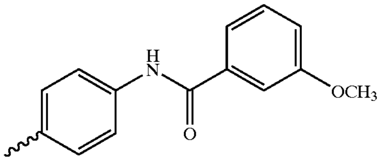 |
| 20 | 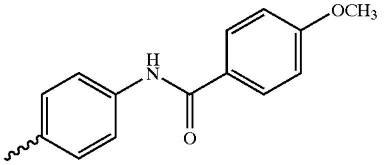 |
| 21 | 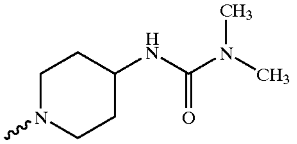 |
TABLE 46
| | 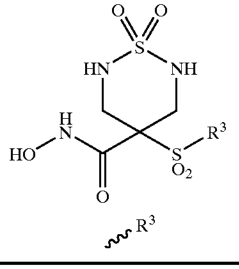 |
|---|---|
| 1 | 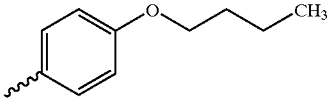 |
| 2 | 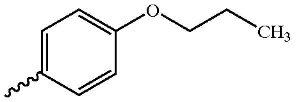 |
TABLE 46-continued
| | 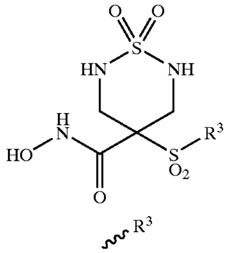 |
|---|---|
| 3 | 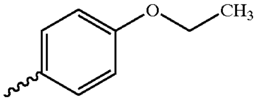 |
| 4 | 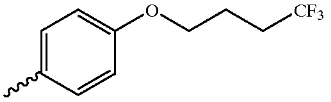 |
| 5 | 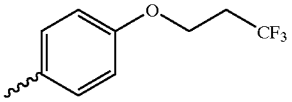 |
| 6 | 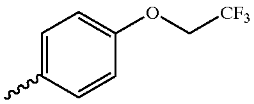 |
| 7 | 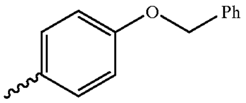 |
| 8 | 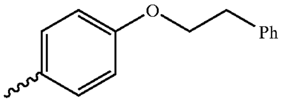 |
| 9 | 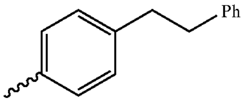 |
| 10 | 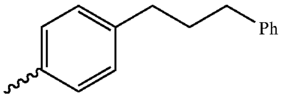 |
| 11 | 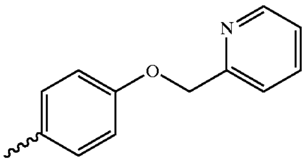 |
| 12 | 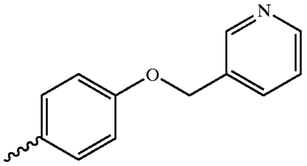 |

TABLE 46-continued
| | |
|---|---|
| 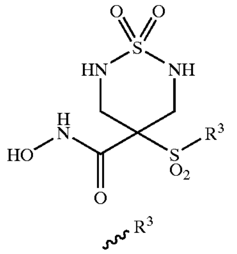 | |
| 13 | 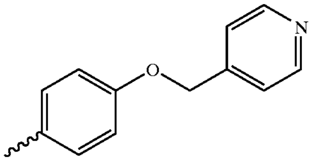 |
| 14 | 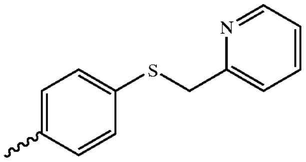 |
| 15 | 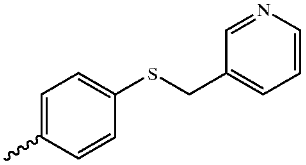 |
| 16 | 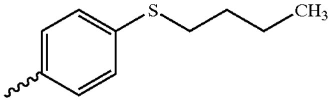 |
| 17 | 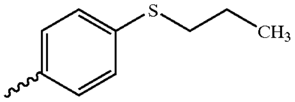 |
| 18 | 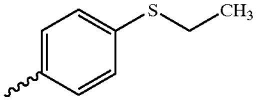 |
| 19 | 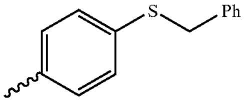 |
| 20 | 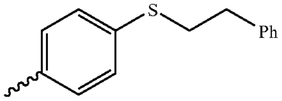 |
| 21 | 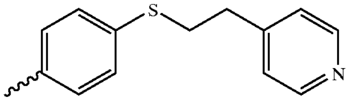 |
TABLE 46-continued
| | |
|---|---|
| 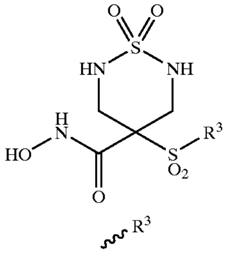 | |
| 22 | 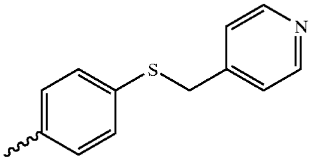 |
TABLE 47
| | |
|---|---|
| 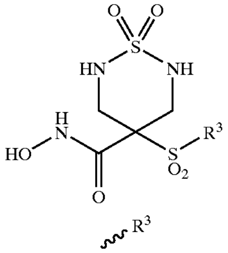 | |
| 1 | 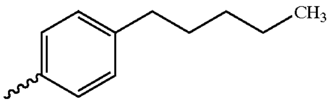 |
| 2 | 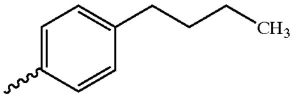 |
| 3 | 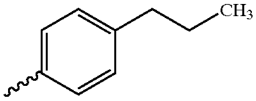 |
| 4 | 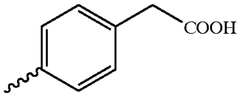 |
| 5 | 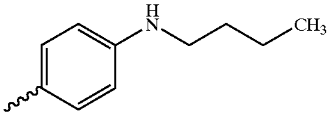 |
| 6 | 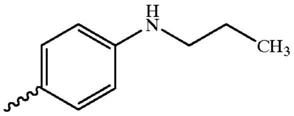 |

TABLE 47-continued
| | 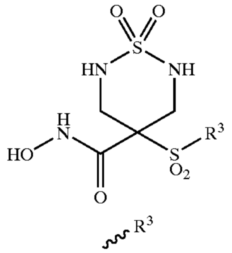 |
|---|---|
| 7 | 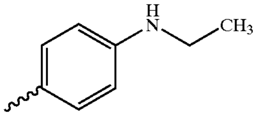 |
| 8 | 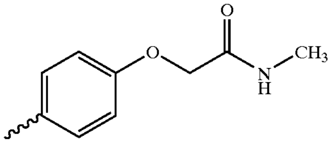 |
| 9 | 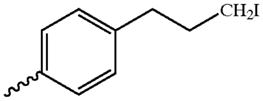 |
| 10 | 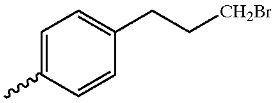 |
| 11 | 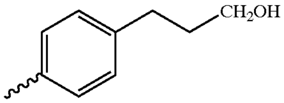 |
| 12 | 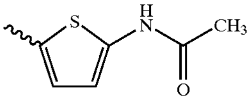 |
| 13 | 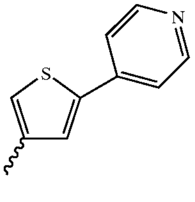 |
| 14 | 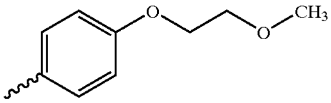 |
| 15 | 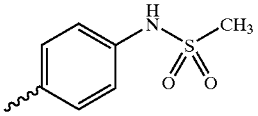 |
TABLE 47-continued
| | 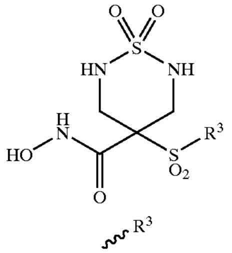 |
|---|---|
| 16 | 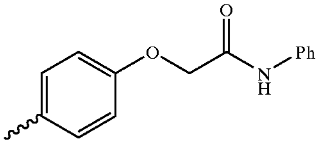 |
| 17 | 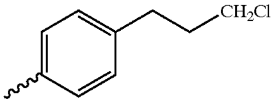 |
| 18 | 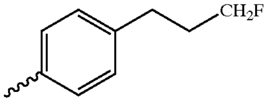 |
| 19 | 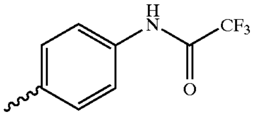 |
| 20 | 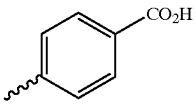 |
| 21 | 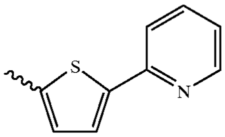 |
| 22 | 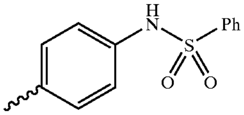 |
| 23 | 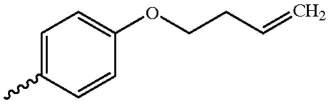 |
| 24 | 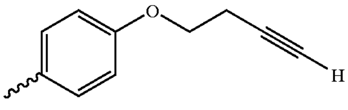 |
| 25 | 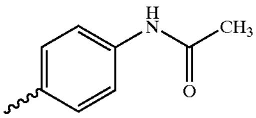 |

TABLE 47-continued
| | |
|---|---|
| 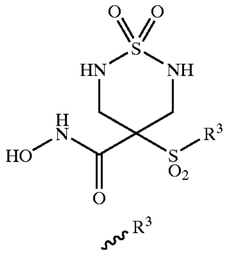 | |
| 26 | 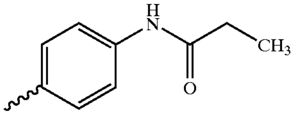 |
| 27 | 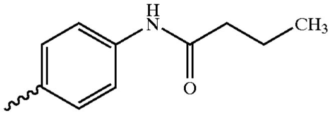 |
| 28 | 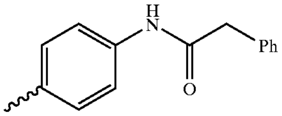 |
| 29 | 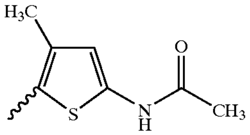 |
| 30 | 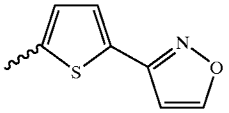 |
TABLE 48
| | |
|---|---|
| 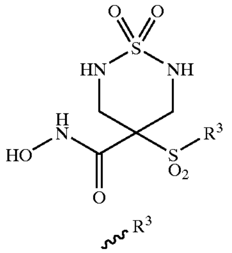 | |
| 1 | 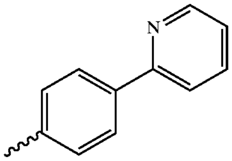 |
TABLE 48-continued
| | |
|---|---|
| 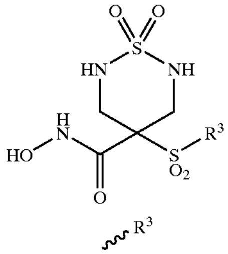 | |
| 2 | 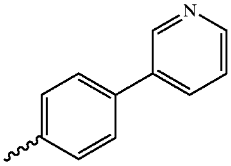 |
| 3 | 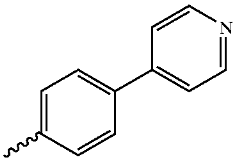 |
| 4 | 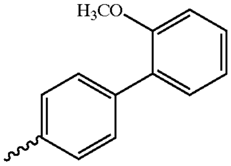 |
| 5 | 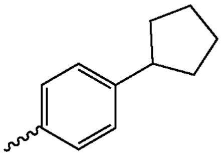 |
| 6 | 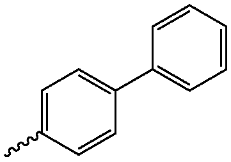 |
| 7 | 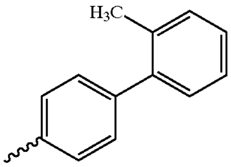 |
| 8 | 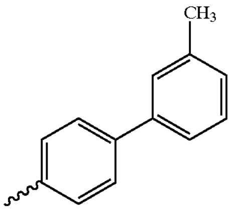 |

TABLE 48-continued
| |
|---|
| 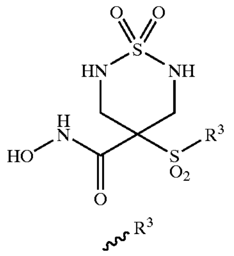 |
| 9 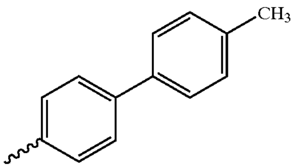 |
| 10 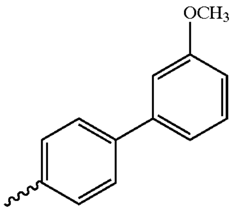 |
| 11 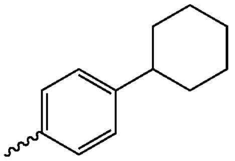 |
| 12 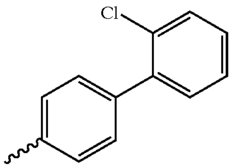 |
| 13 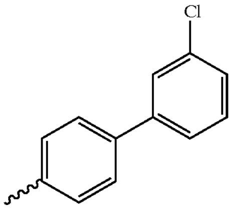 |
| 14 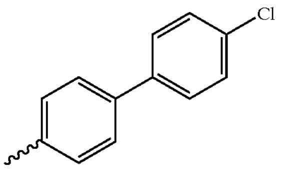 |
| 15 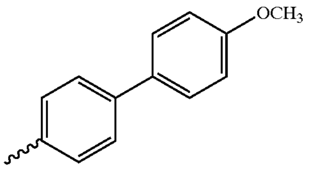 |
TABLE 48-continued
| |
|---|
| 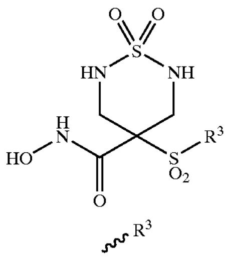 |
| 16 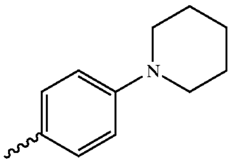 |
| 17 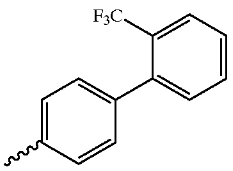 |
| 18 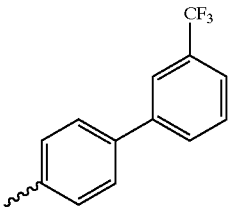 |
| 19 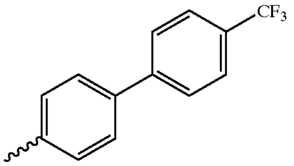 |
| 20 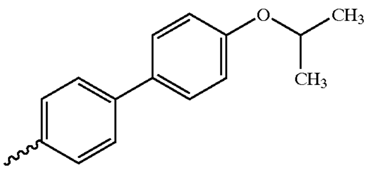 |
| 21 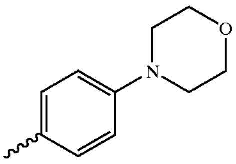 |

TABLE 49
| 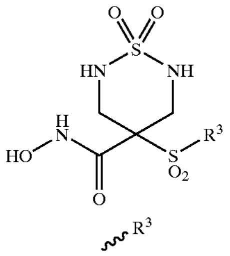 | |
|---|---|
| 1 | 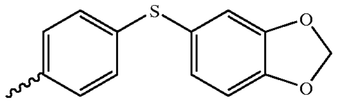 |
| 2 | 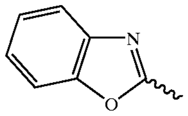 |
| 3 | 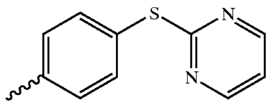 |
| 4 | 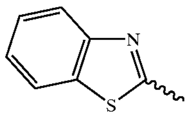 |
| 5 | 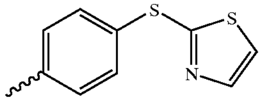 |
| 6 | 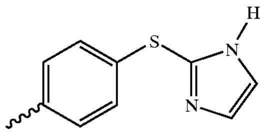 |
| 7 | 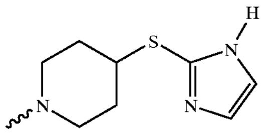 |
| 8 | 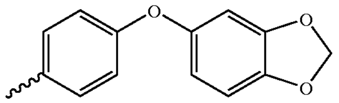 |
| 9 | 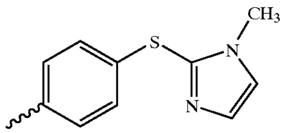 |
| 10 | 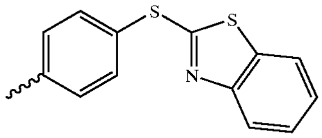 |
TABLE 49-continued
| 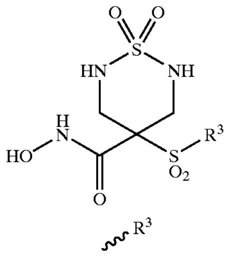 | |
|---|---|
| 11 | 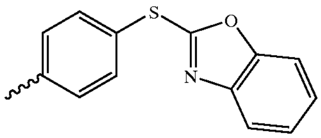 |
TABLE 50
| 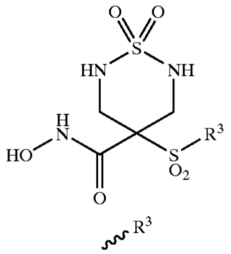 | |
|---|---|
| 1 | 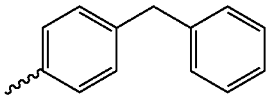 |
| 2 | 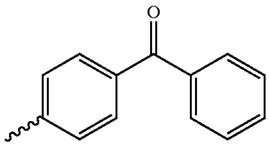 |
| 3 | 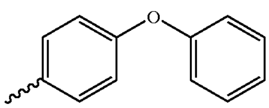 |
| 4 | 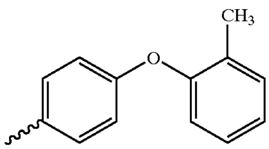 |
| 5 | 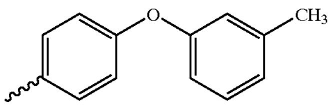 |

TABLE 50-continued
| | |
|---|---|
| | 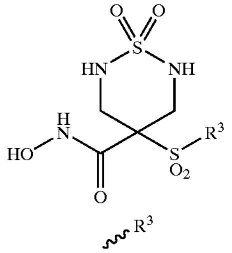 |
| 6 | 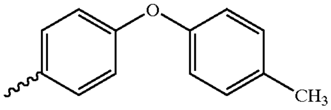 |
| 7 | 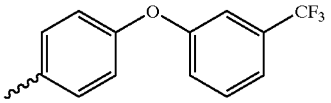 |
| 8 | 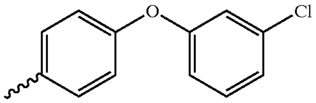 |
| 9 | 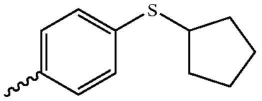 |
| 10 | 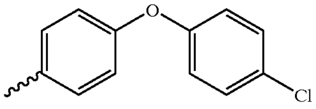 |
| 11 | 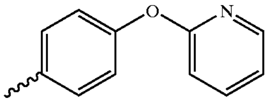 |
| 12 | 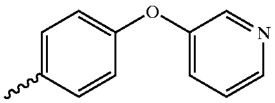 |
| 13 | 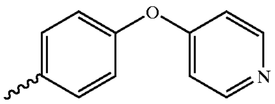 |
| 14 | 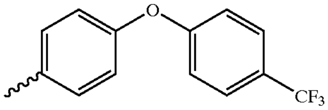 |
| 15 | 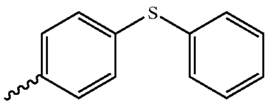 |
| 16 | 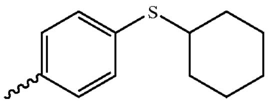 |
TABLE 50-continued
| | |
|---|---|
| | 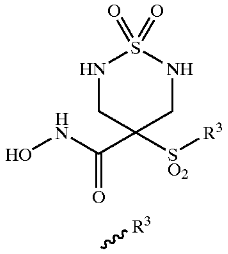 |
| 17 | 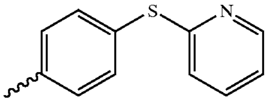 |
| 18 | 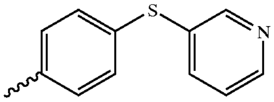 |
| 19 | 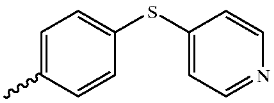 |
| 20 | 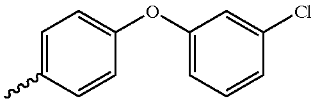 |
| 21 | 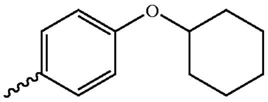 |
TABLE 51
| | |
|---|---|
| | 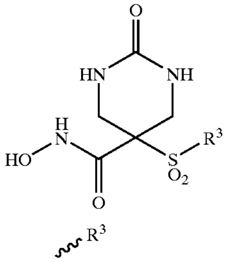 |
| 1 | 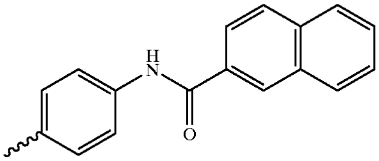 |
| 2 | 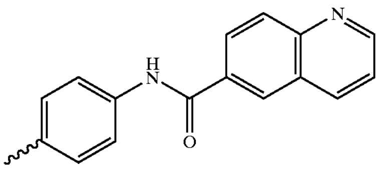 |

TABLE 51-continued
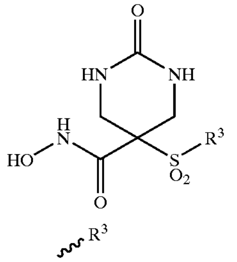
| | |
|---|---|
| 3 | 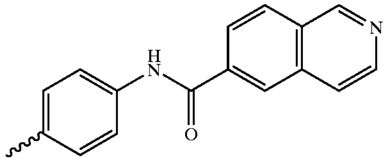 |
| 4 | 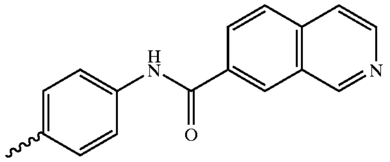 |
| 5 | 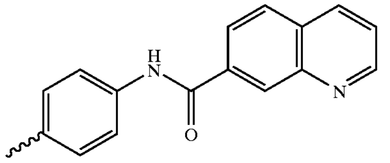 |
| 6 | 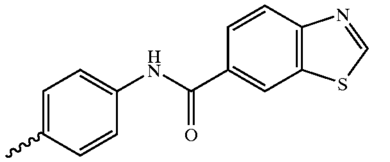 |
| 7 | 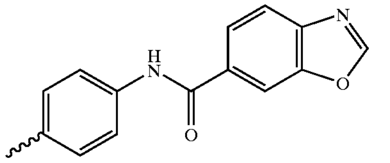 |
| 8 | 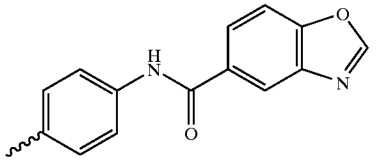 |
| 9 | 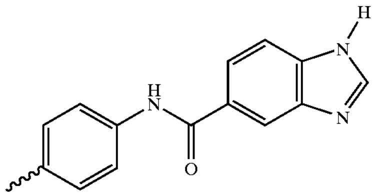 |
TABLE 51-continued
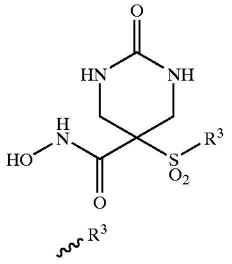
| | |
|---|---|
| 10 | 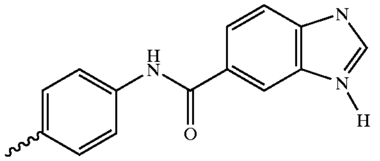 |
| 11 | 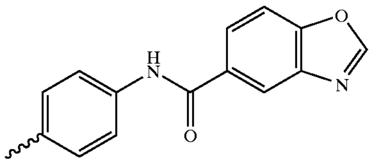 |
| 12 | 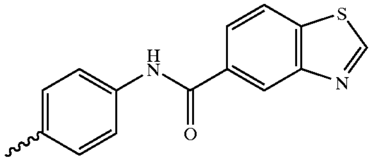 |
| 13 | 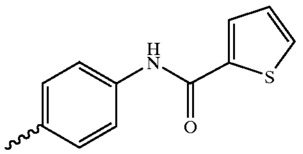 |
| 14 | 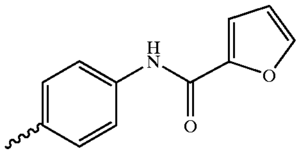 |
| 15 | 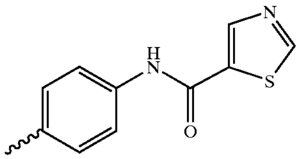 |
| 16 | 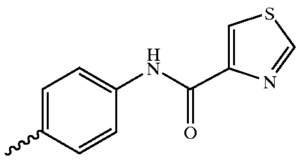 |

TABLE 51-continued
| 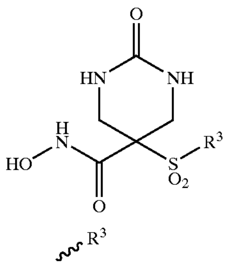 | |
|---|---|
| 17 | 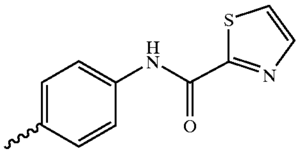 |
| 18 | 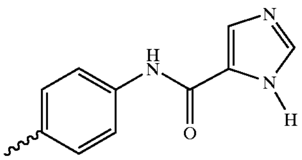 |
TABLE 52
| 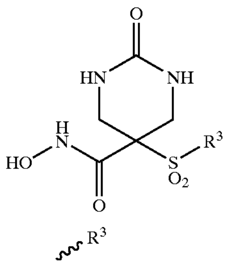 | |
|---|---|
| 1 | 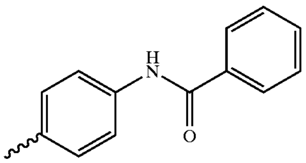 |
| 2 | 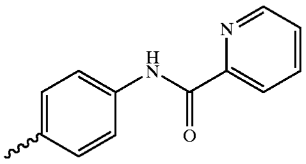 |
| 3 | 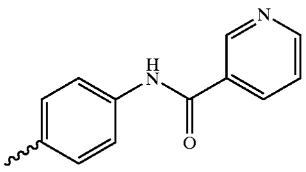 |
TABLE 52-continued
| 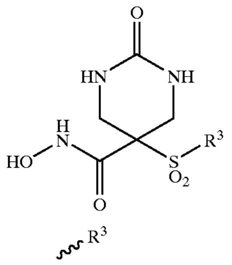 | |
|---|---|
| 4 | 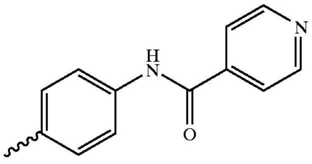 |
| 5 | 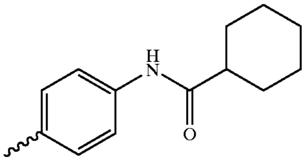 |
| 6 | 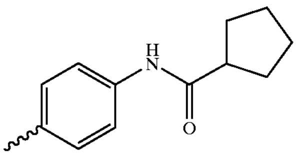 |
| 7 | 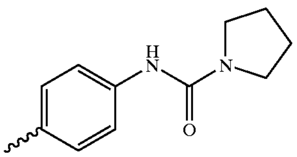 |
| 8 | 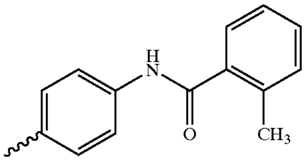 |
| 9 | 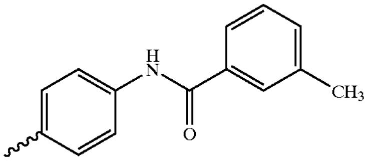 |
| 10 | 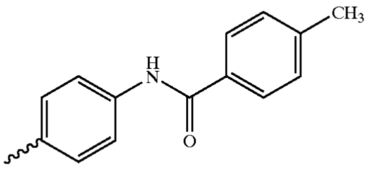 |

TABLE 52-continued
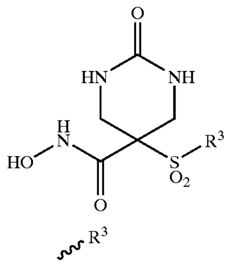
| | |
|---|---|
| 11 | 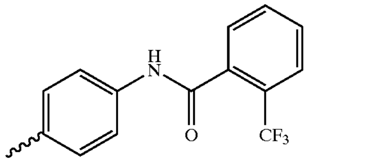 |
| 12 | 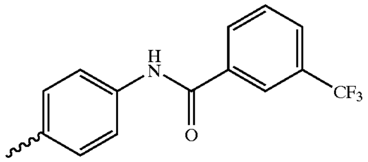 |
| 13 | 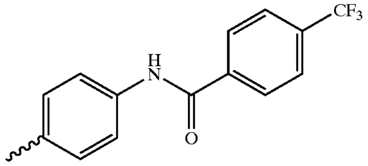 |
| 14 | 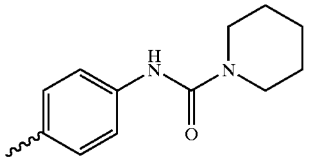 |
| 15 | 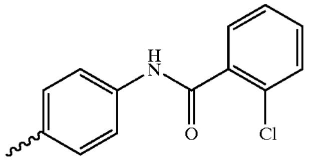 |
| 16 | 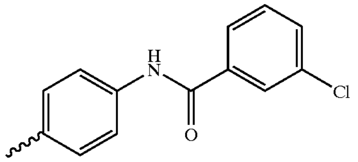 |
| 17 | 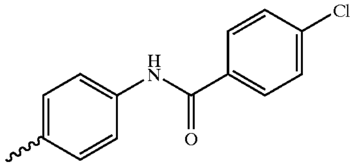 |
TABLE 52-continued
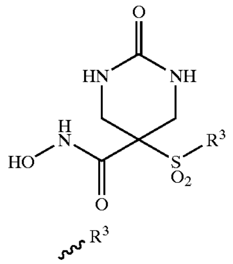
| | |
|---|---|
| 18 | 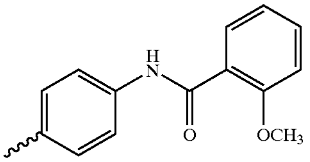 |
| 19 | 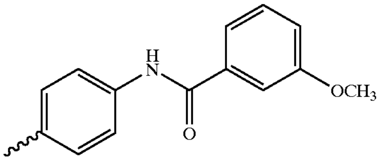 |
| 20 | 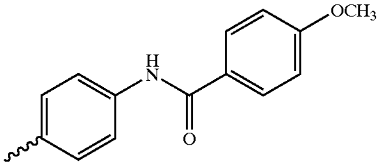 |
| 21 | 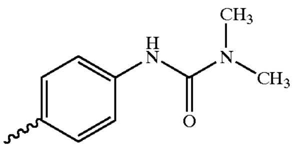 |
TABLE 53
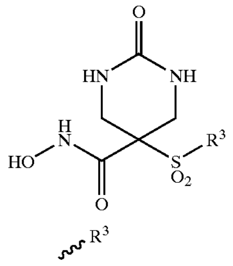
| | |
|---|---|
| 1 | 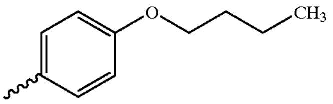 |
| 2 | 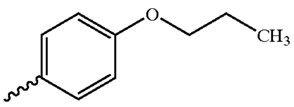 |

TABLE 53-continued
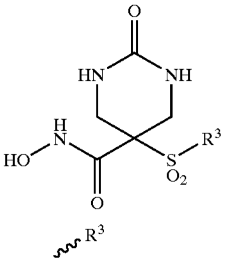
| | |
|---|---|
| 3 | 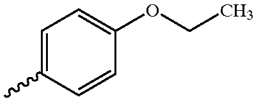 |
| 4 | 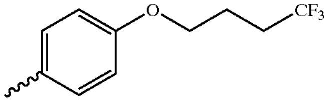 |
| 5 | 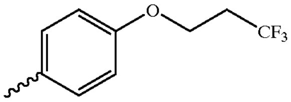 |
| 6 | 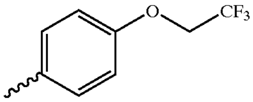 |
| 7 | 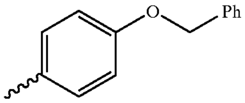 |
| 8 | 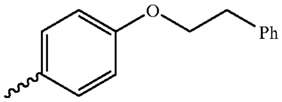 |
| 9 | 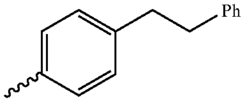 |
| 10 | 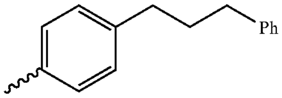 |
| 11 | 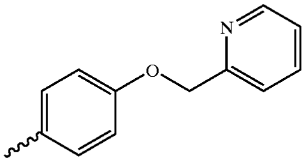 |
| 12 | 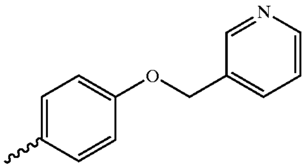 |
TABLE 53-continued
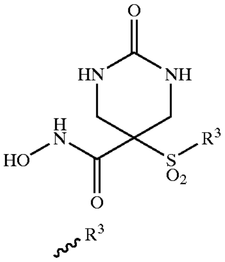
| | |
|---|---|
| 13 | 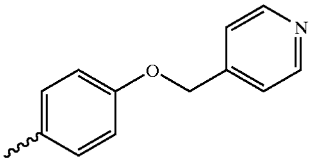 |
| 14 | 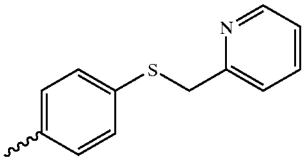 |
| 15 | 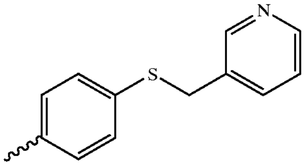 |
| 16 | 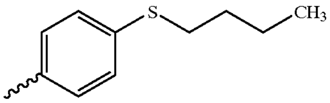 |
| 17 | 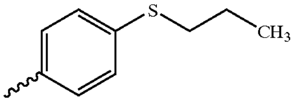 |
| 18 | 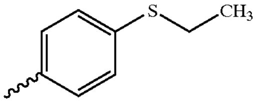 |
| 19 | 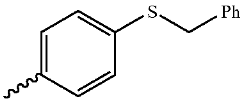 |
| 20 | 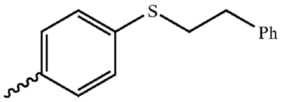 |
| 21 | 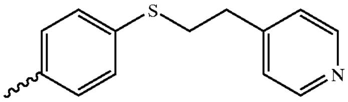 |

TABLE 53-continued
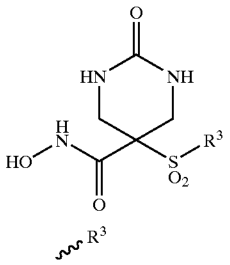
| | |
|---|---|
| 22 | 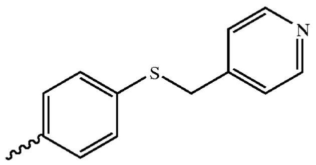 |
TABLE 54
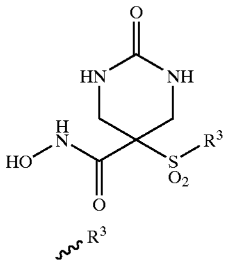
| | |
|---|---|
| 1 | 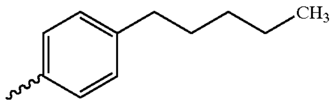 |
| 2 | 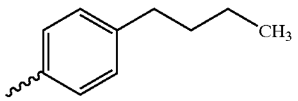 |
| 3 | 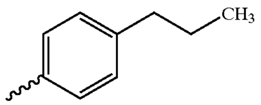 |
| 4 | 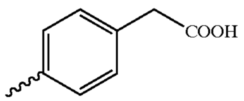 |
| 5 | 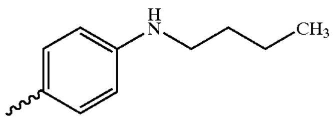 |
| 6 | 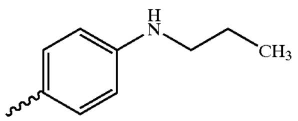 |
TABLE 54-continued
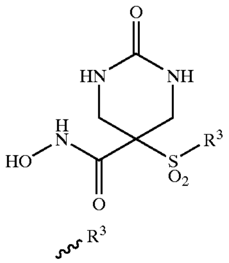
| | |
|---|---|
| 7 | 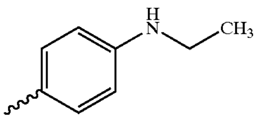 |
| 8 | 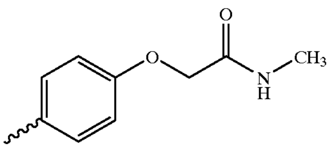 |
| 9 | 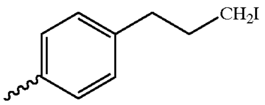 |
| 10 | 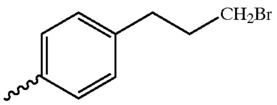 |
| 11 | 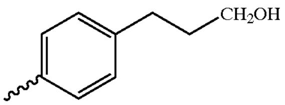 |
| 12 | 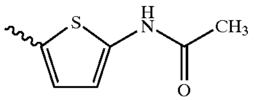 |
| 13 | 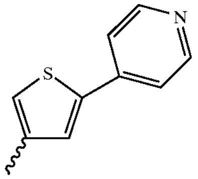 |
| 14 | 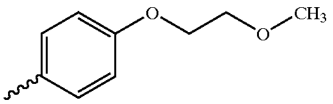 |
| 15 | 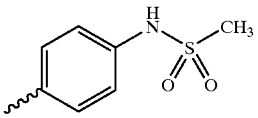 |

TABLE 54-continued
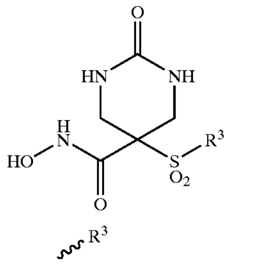
16 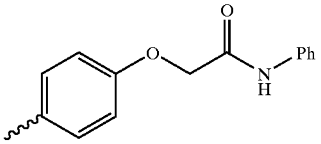
17 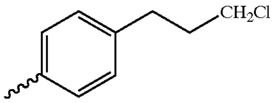
18 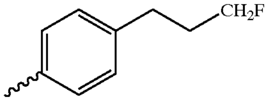
19 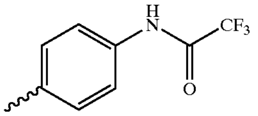
20 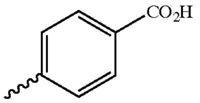
21 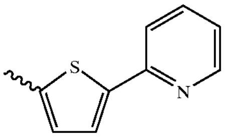
22 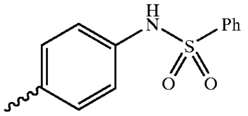
23 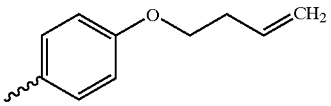
24 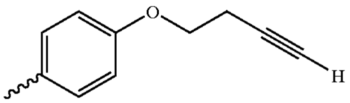
25 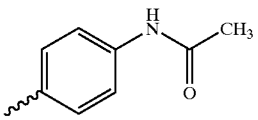
TABLE 54-continued
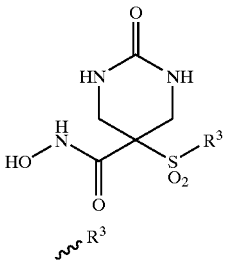
26 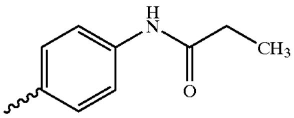
27 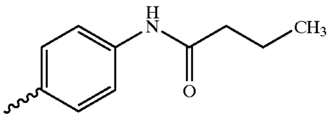
28 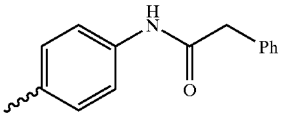
29 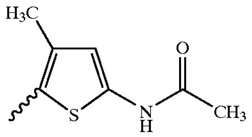
30 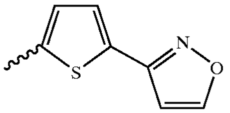
TABLE 55
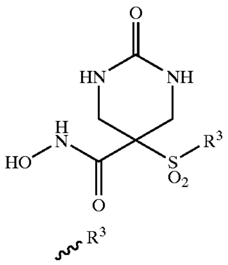
1 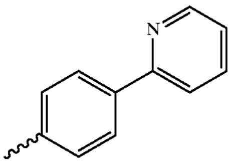

TABLE 55-continued
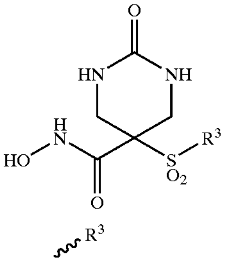
2
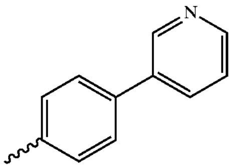
3
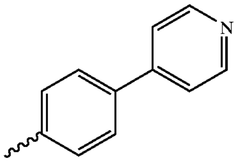
4
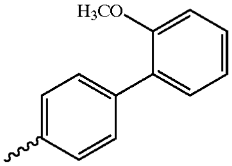
5
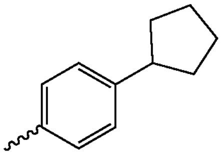
6
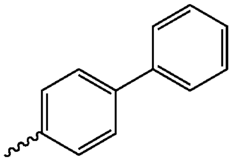
7
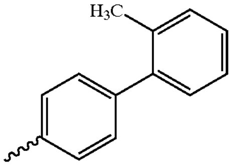
8
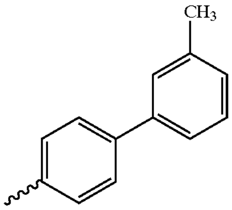
TABLE 55-continued
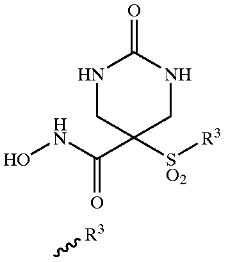
9
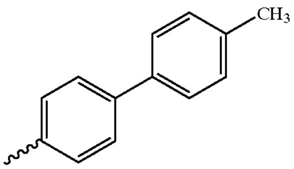
10
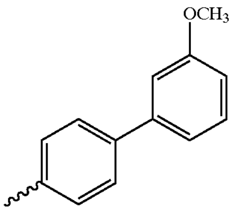
11
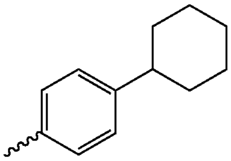
12
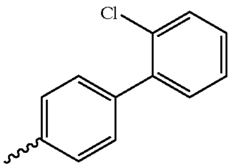
13
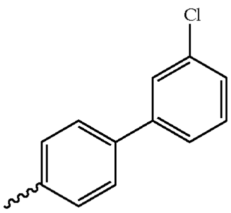
14
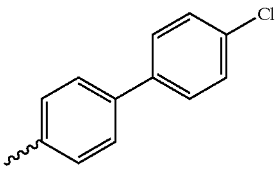
15
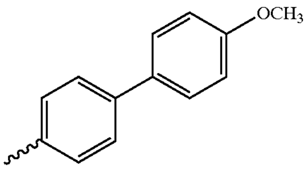

TABLE 55-continued
| | |
|---|---|
| 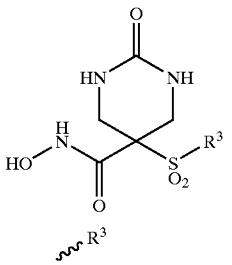 | |
| 16 | 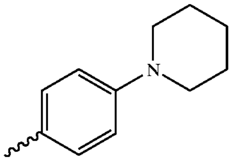 |
| 17 | 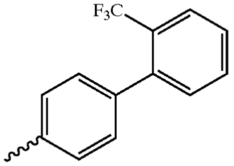 |
| 18 | 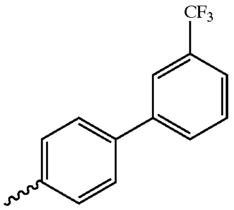 |
| 19 | 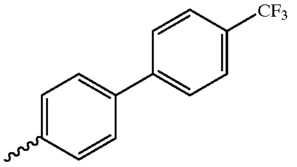 |
| 20 | 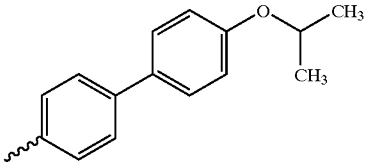 |
| 21 | 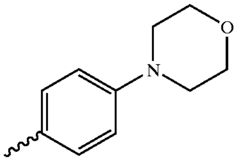 |
TABLE 56
| | |
|---|---|
| 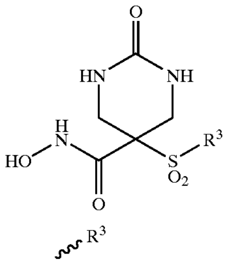 | |
| 1 | 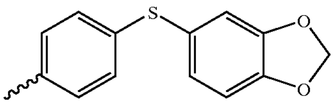 |
| 2 | 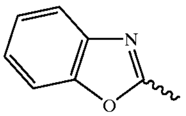 |
| 3 | 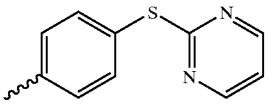 |
| 4 | 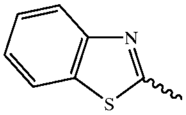 |
| 5 | 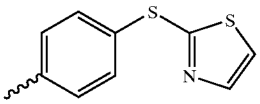 |
| 6 | 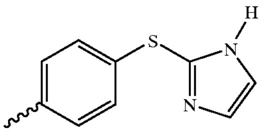 |
| 7 | 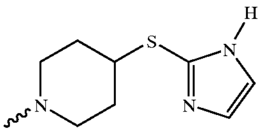 |
| 8 | 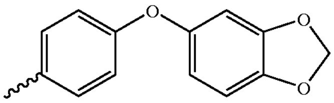 |
| 9 | 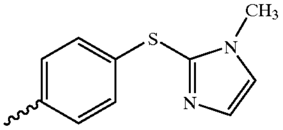 |
| 10 | 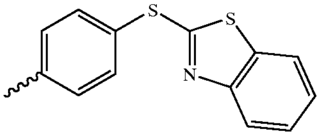 |

TABLE 56-continued
| | |
|---|---|
| | 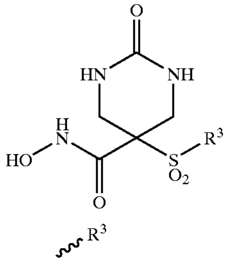 |
| 11 | 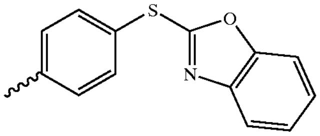 |
TABLE 57
| | |
|---|---|
| | 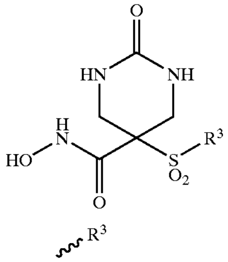 |
| 1 | 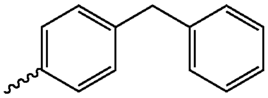 |
| 2 | 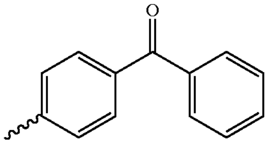 |
| 3 | 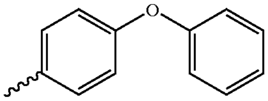 |
| 4 | 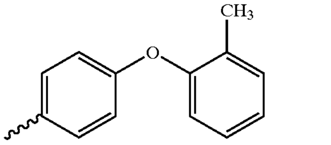 |
| 5 | 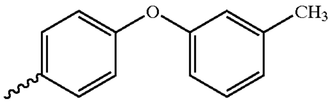 |
TABLE 57-continued
| | |
|---|---|
| | 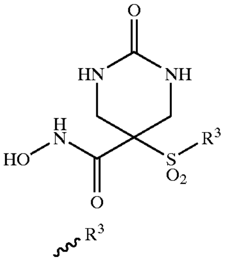 |
| 6 | 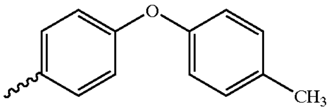 |
| 7 | 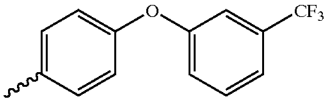 |
| 8 | 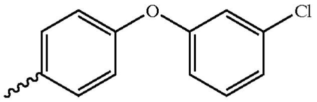 |
| 9 | 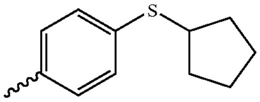 |
| 10 | 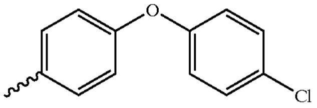 |
| 11 | 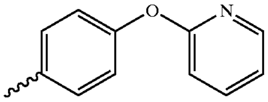 |
| 12 | 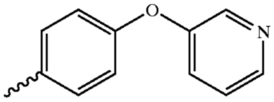 |
| 13 | 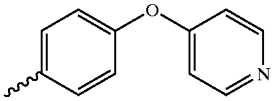 |
| 14 | 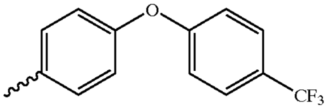 |
| 15 | 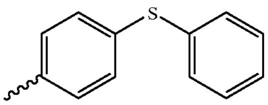 |
| 16 | 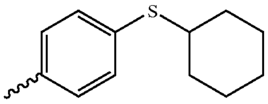 |

TABLE 57-continued
| 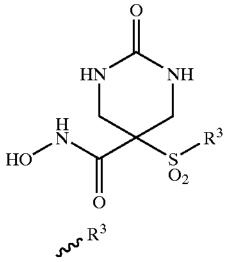 |  |
|---|---|
| 17 | 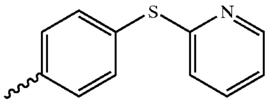 |
| 18 | 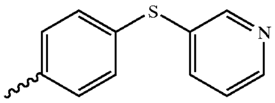 |
| 19 | 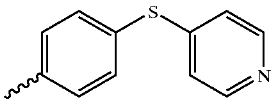 |
| 20 | 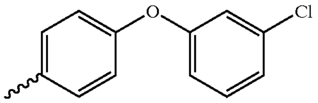 |
| 21 | 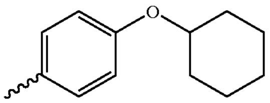 |
TABLE 58
| 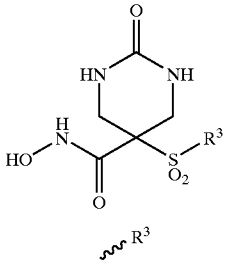 |  |
|---|---|
| 1 | 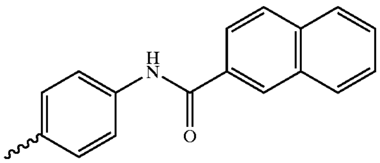 |
| 2 | 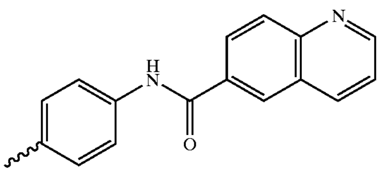 |
TABLE 58-continued
| 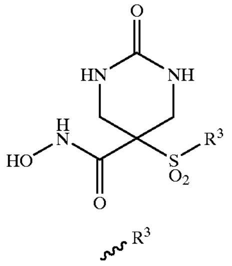 |  |
|---|---|
| 3 | 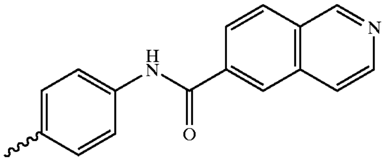 |
| 4 | 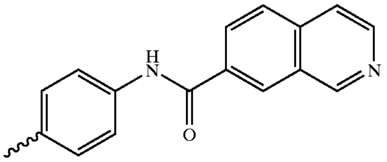 |
| 5 | 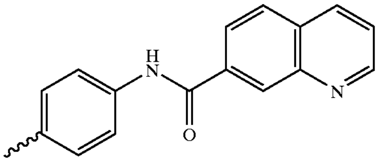 |
| 6 | 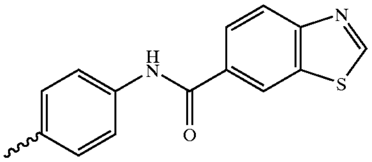 |
| 7 | 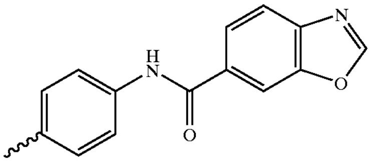 |
| 8 | 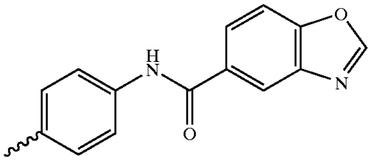 |
| 9 | 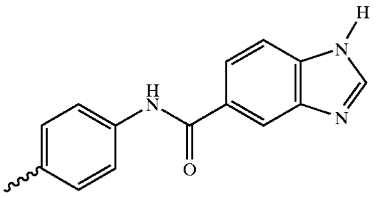 |

TABLE 58-continued
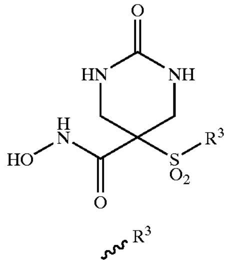
10
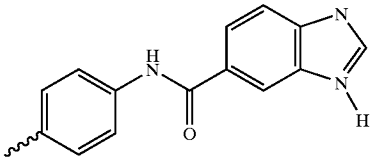
11
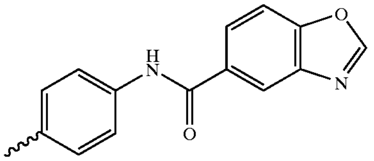
12
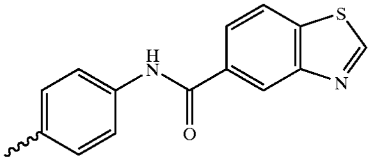
13
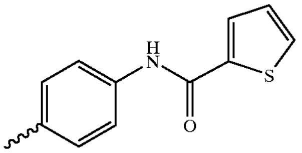
14
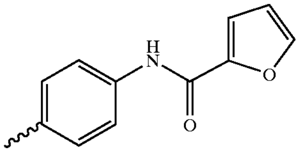
15
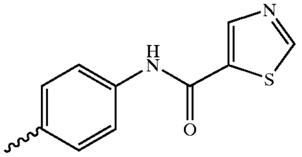
16
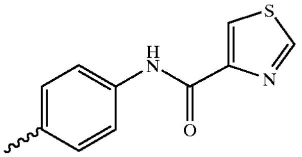
TABLE 58-continued
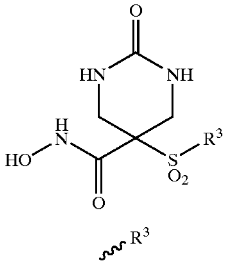
17
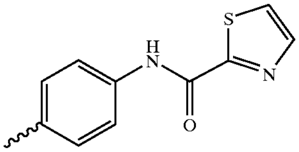
18
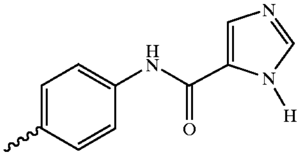
TABLE 59
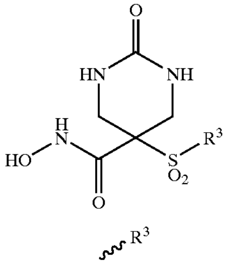
1
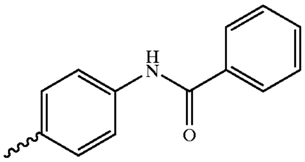
2
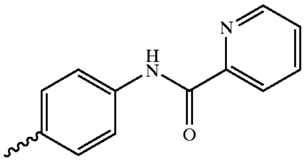
3
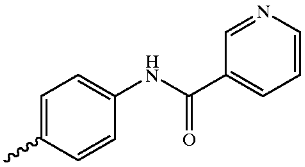

TABLE 59-continued
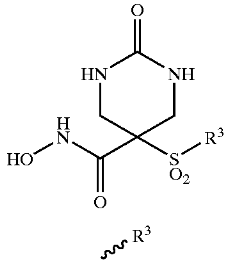
| | |
|---|---|
| 4 | 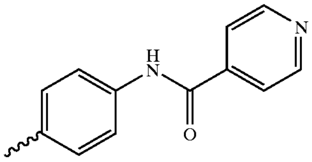 |
| 5 | 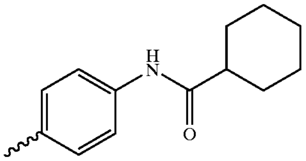 |
| 6 | 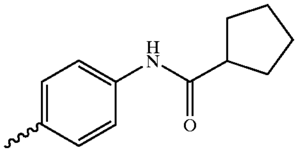 |
| 7 | 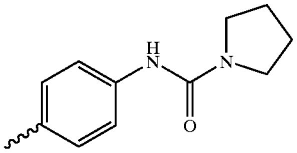 |
| 8 | 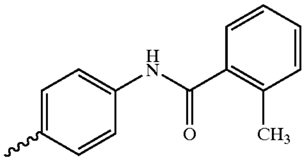 |
| 9 | 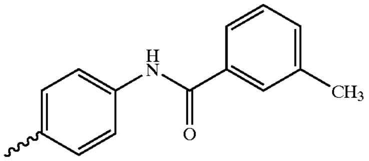 |
| 10 | 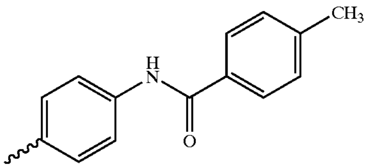 |
TABLE 59-continued
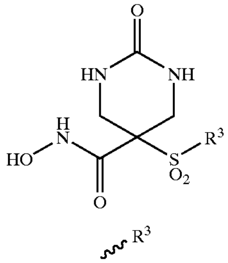
| | |
|---|---|
| 11 | 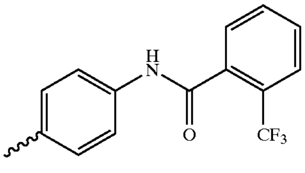 |
| 12 | 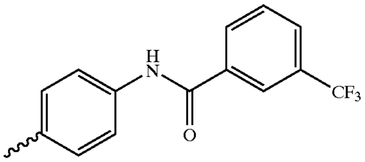 |
| 13 | 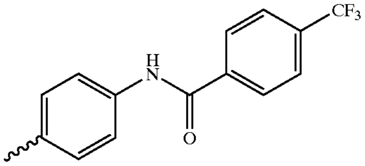 |
| 14 | 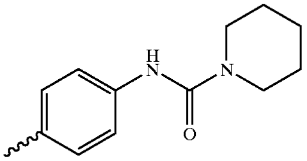 |
| 15 | 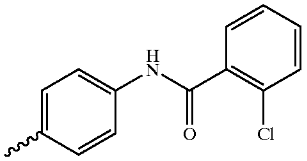 |
| 16 | 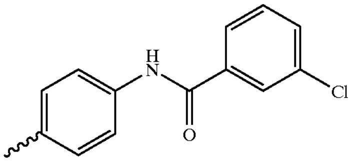 |
| 17 | 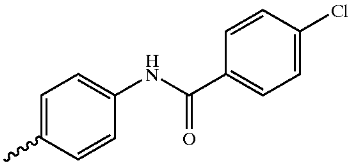 |

TABLE 59-continued
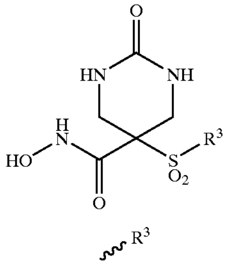
18 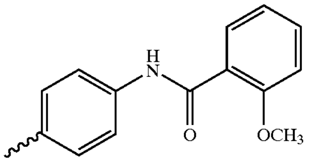
19 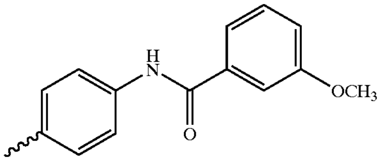
20 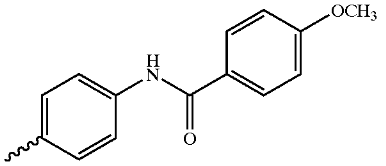
21 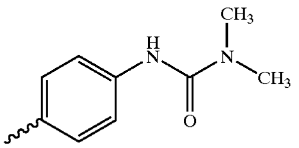
TABLE 60
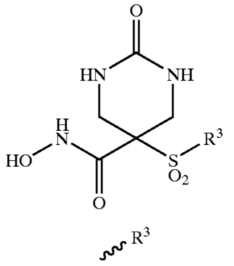
1 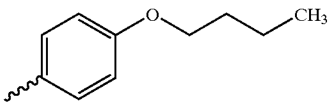
2 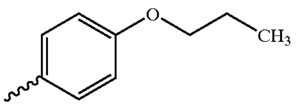
TABLE 60-continued
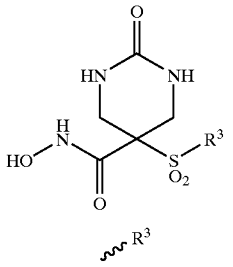
3 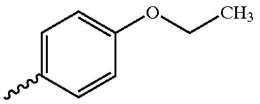
4 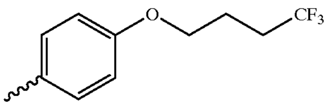
5 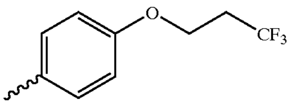
6 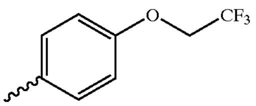
7 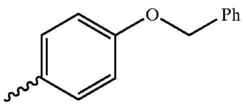
8 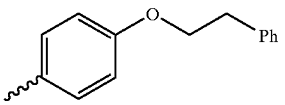
9 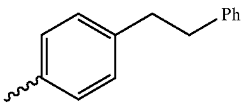
10 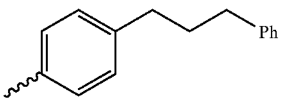
11 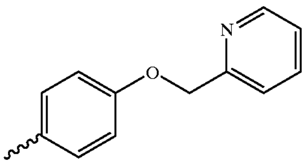
12 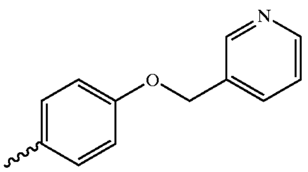

TABLE 60-continued
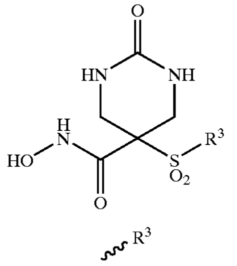
13
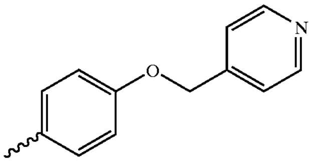
14
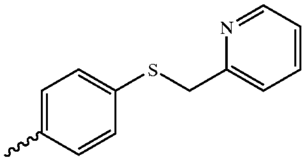
15
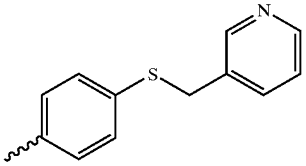
16
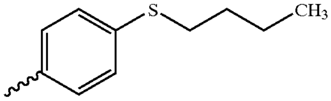
17
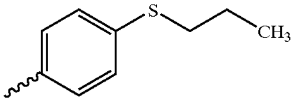
18
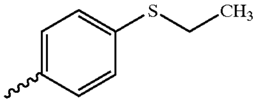
19
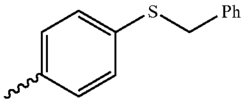
20
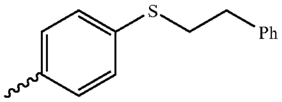
21
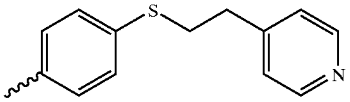
TABLE 60-continued
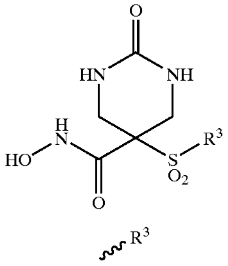
22
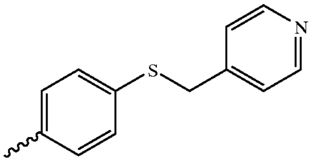
TABLE 61
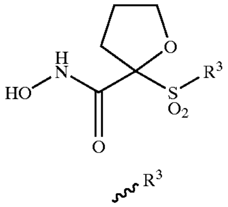
1
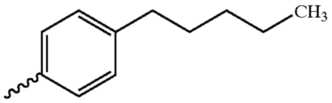
2
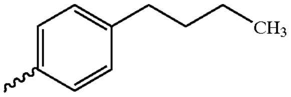
3
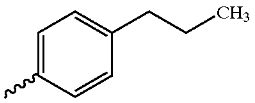
4
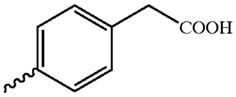
5
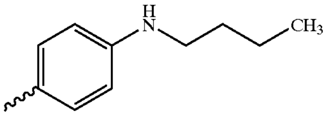
6

TABLE 61-continued
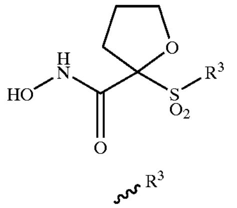
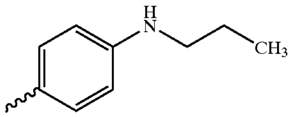
7
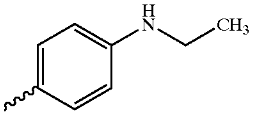
8
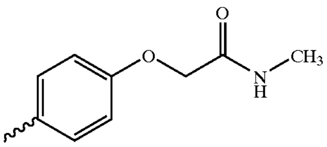
9
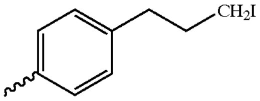
10
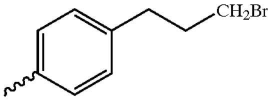
11
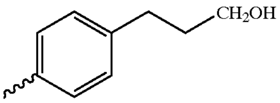
12
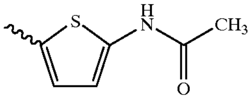
13
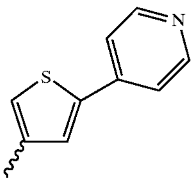
TABLE 61-continued
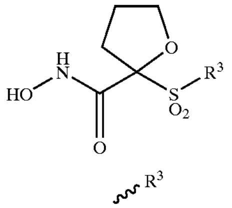
14
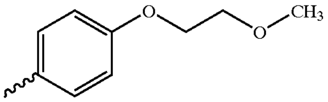
15
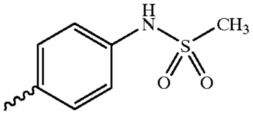
16
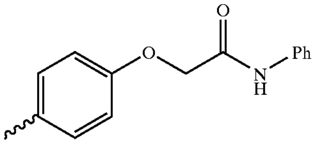
17
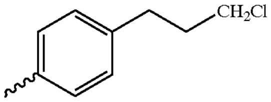
18
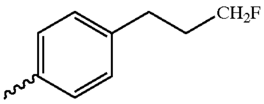
19
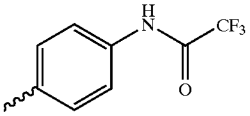
20
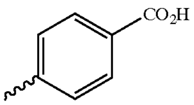
21
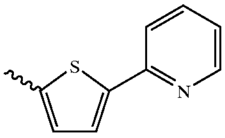

TABLE 61-continued
| 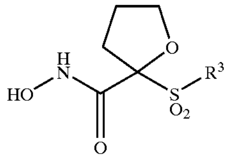 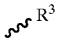 |
| --- |
| 22 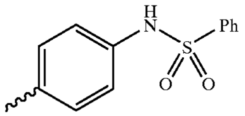 |
| 23 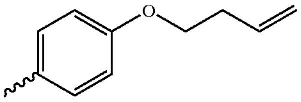 |
| 24 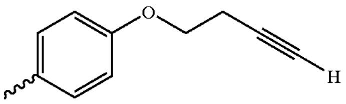 |
| 25 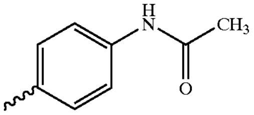 |
| 26 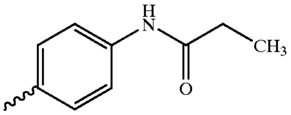 |
| 27 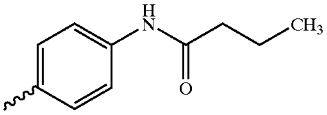 |
| 28 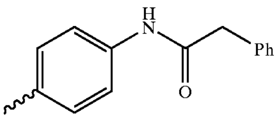 |
| 29 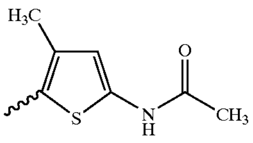 |
TABLE 61-continued
| 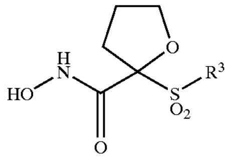 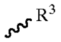 |
| --- |
| 30 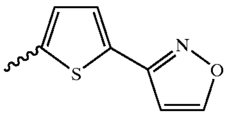 |
TABLE 62
| 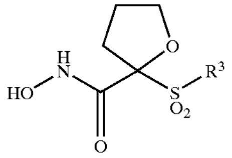 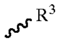 |
| --- |
| 1 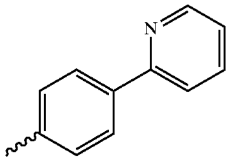 |
| 2 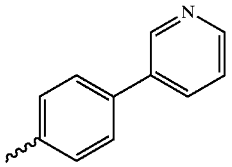 |
| 3 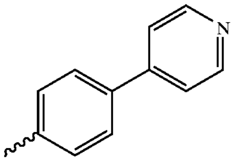 |
| 4 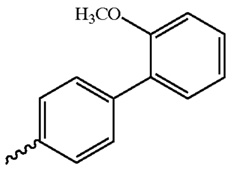 |
| 5 |

TABLE 62-continued
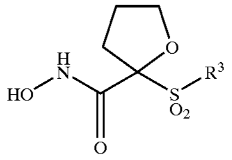
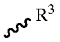
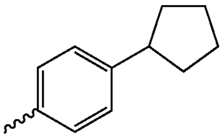
6
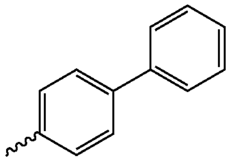
7
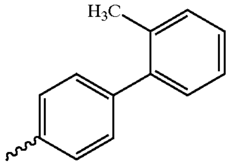
8
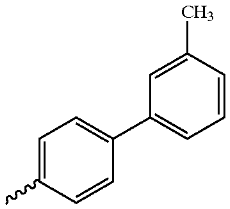
9
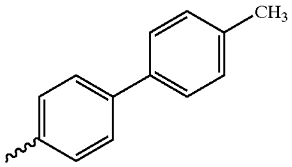
10
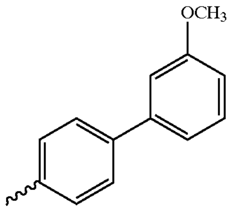
11
TABLE 62-continued
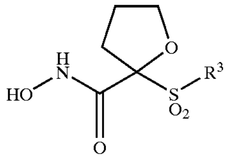
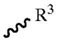
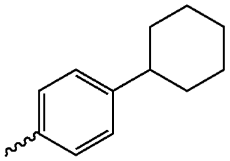
12
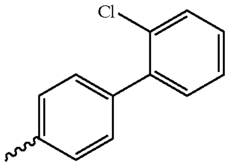
13
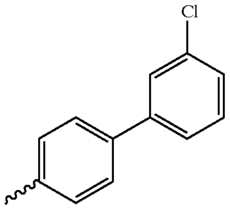
14
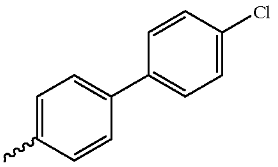
15
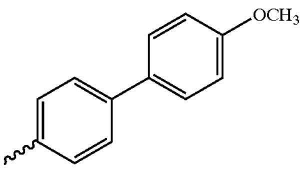
16
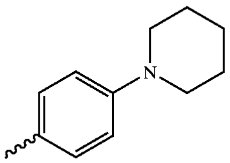
17

TABLE 62-continued
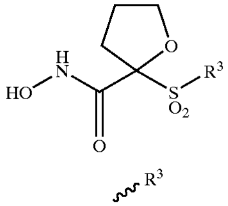
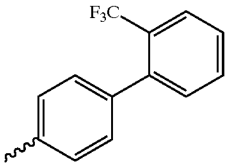
18
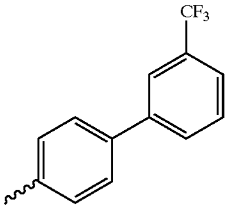
19
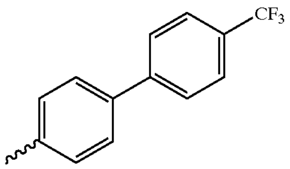
20
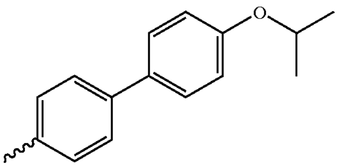
21
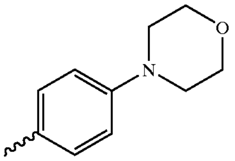
TABLE 63
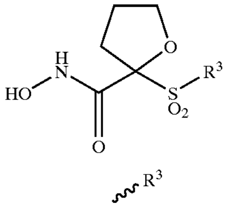
1
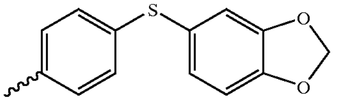
2
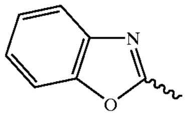
3
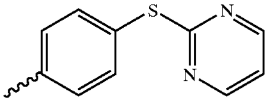
4
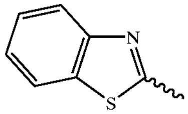
5
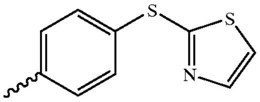
6
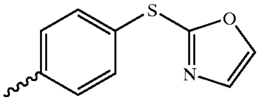
7
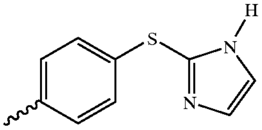
8
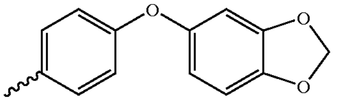
9

TABLE 63-continued
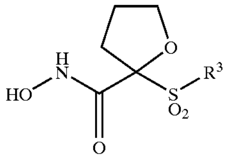
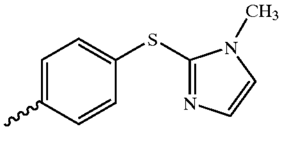
10
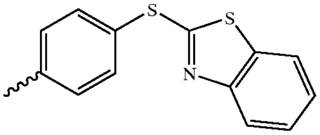
11
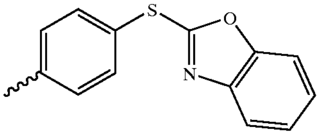
TABLE 64
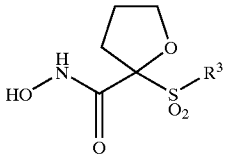
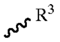
1
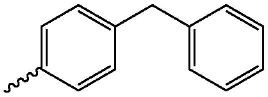
2
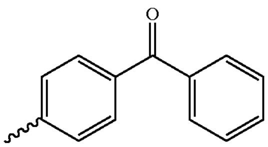
3
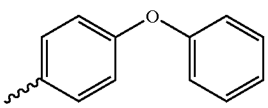
4
TABLE 64-continued
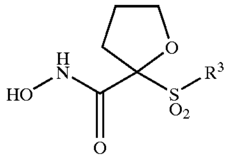
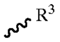
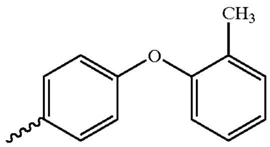
5
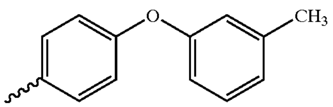
6
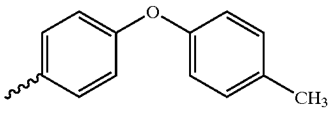
7
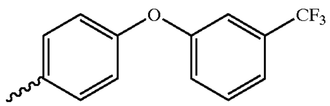
8
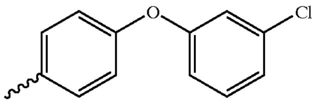
9
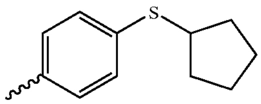
10
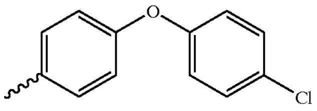
11
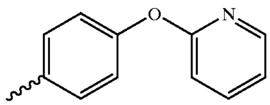
12

TABLE 64-continued
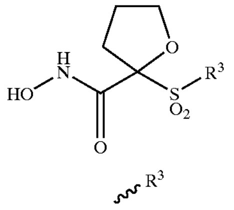
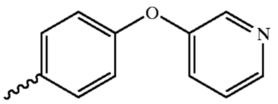
13
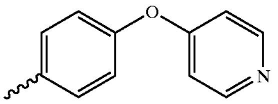
14
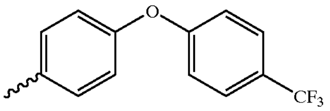
15
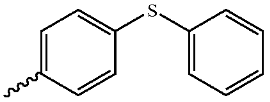
16
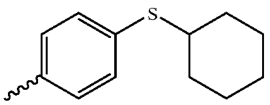
17
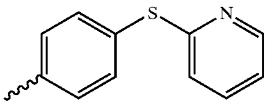
18
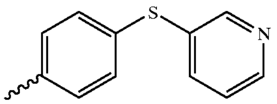
19
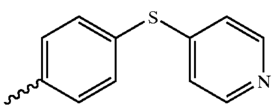
20
TABLE 64-continued
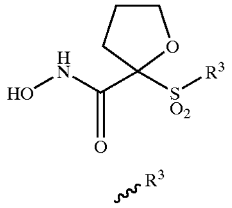
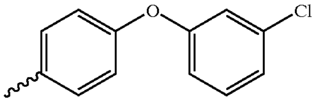
21
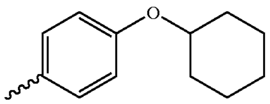
TABLE 65
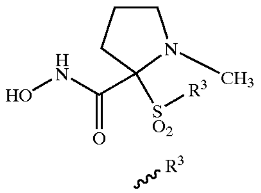
1
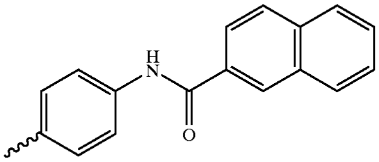
2
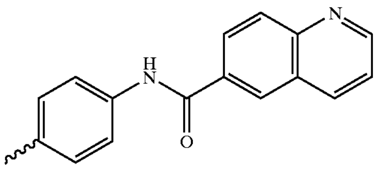
3
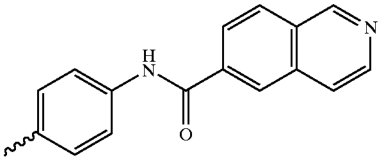
4

TABLE 65-continued
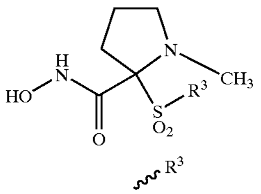
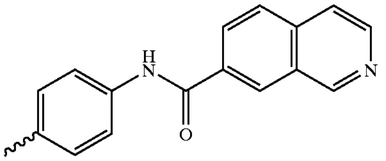
5
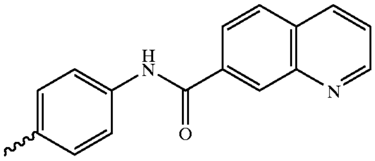
6
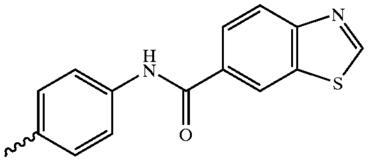
7
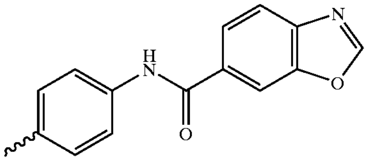
8
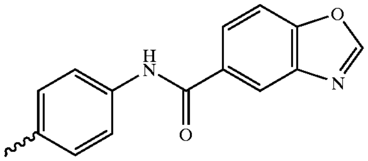
9
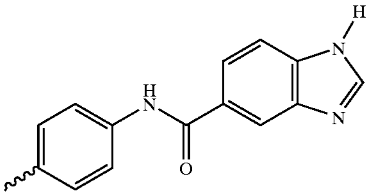
10
TABLE 65-continued
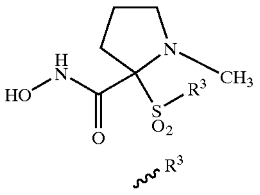
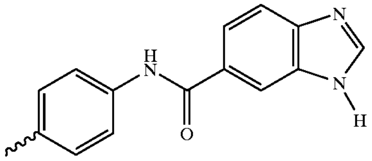
11
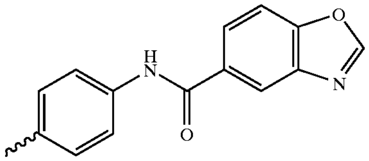
12
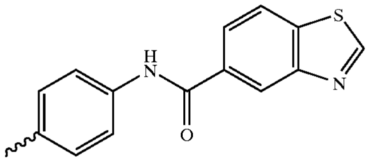
13
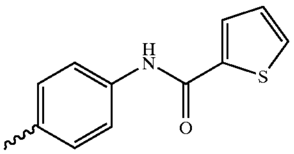
14
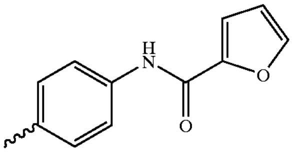
15
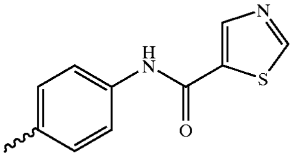
16

TABLE 65-continued
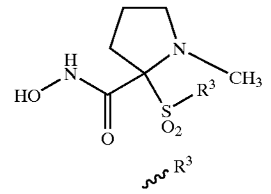
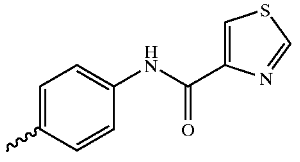
17
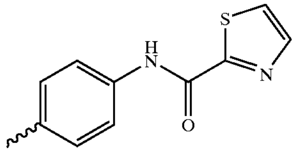
18
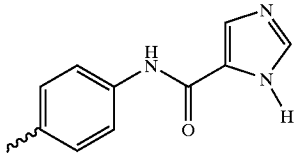
TABLE 66
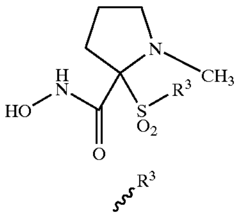
1
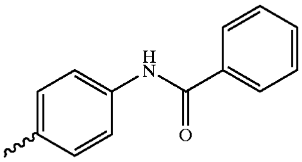
2
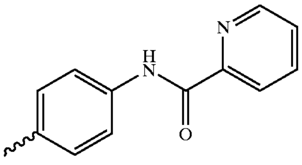
3
TABLE 66-continued
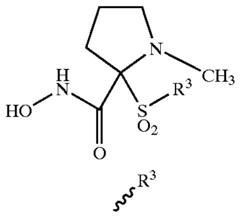
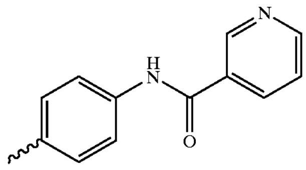
4
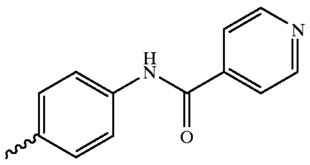
5
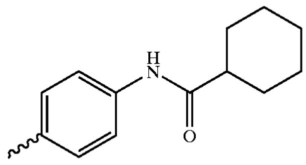
6
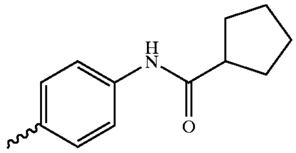
7
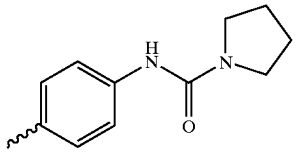
8
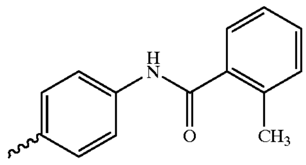
9

TABLE 66-continued
| 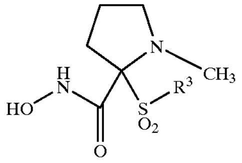 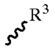 |
|---|
| 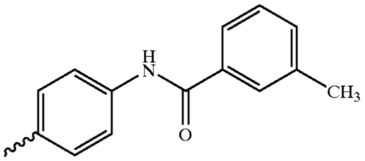 |
| 10 |
| 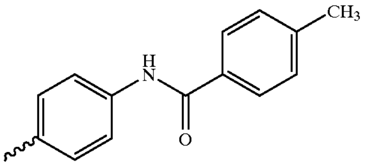 |
| 11 |
| 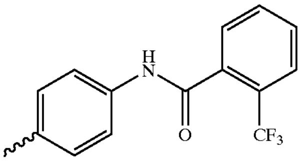 |
| 12 |
| 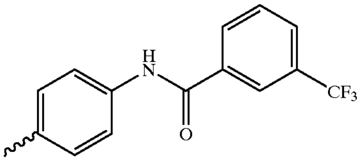 |
| 13 |
| 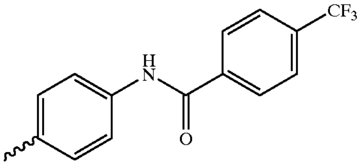 |
| 14 |
| 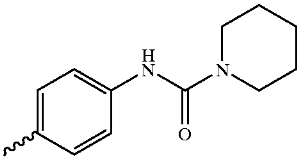 |
| 15 |
TABLE 66-continued
| 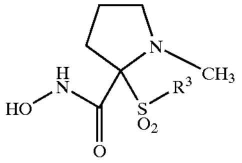 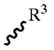 |
|---|
| 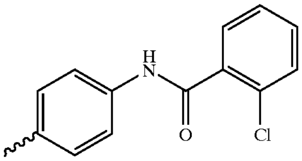 |
| 16 |
| 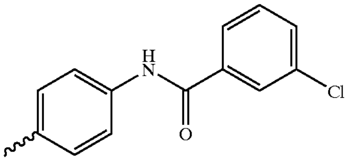 |
| 17 |
| 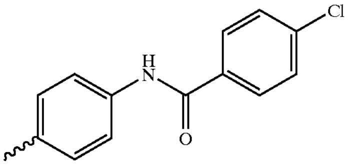 |
| 18 |
| 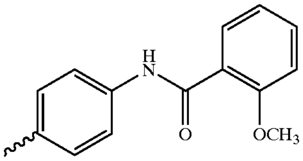 |
| 19 |
| 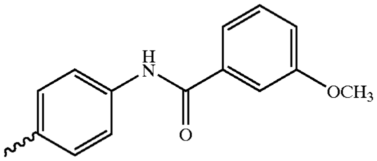 |
| 20 |
| 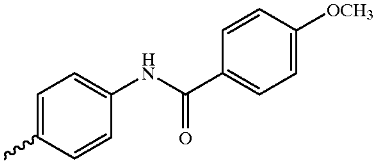 |
| 21 |

TABLE 66-continued
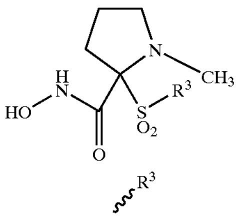
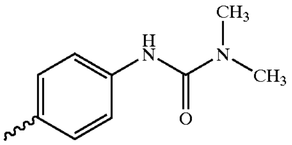
TABLE 67
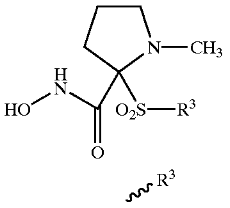
1
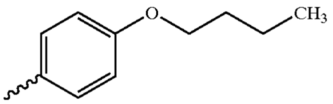
2
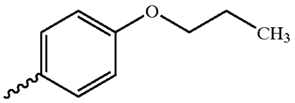
3
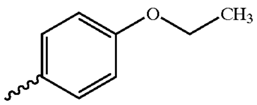
4
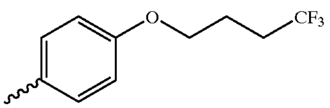
5
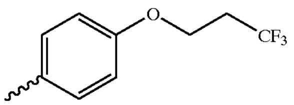
6
TABLE 67-continued
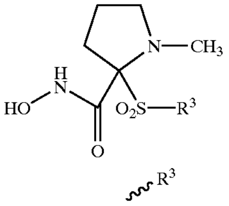
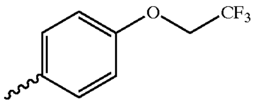
7
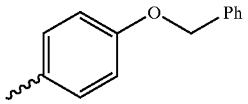
8
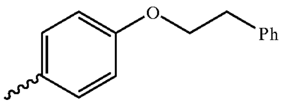
9
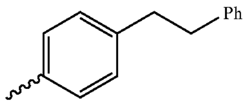
10
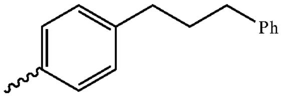
11
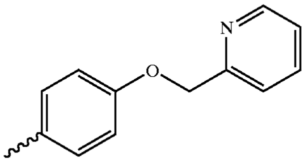
12
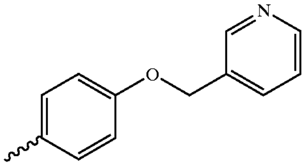
13

TABLE 67-continued
| 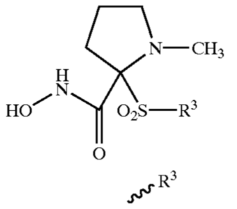 |
|---|
| 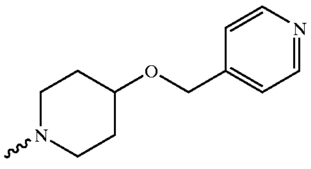 |
| 14 |
| 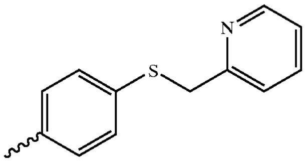 |
| 15 |
| 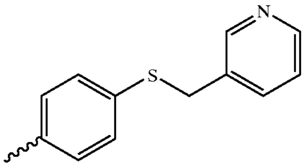 |
| 16 |
| 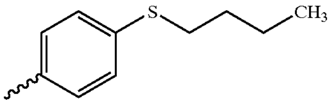 |
| 17 |
| 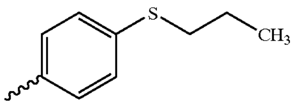 |
| 18 |
| 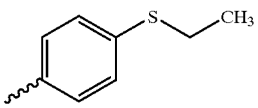 |
| 19 |
| 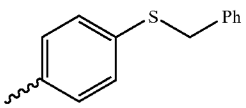 |
| 20 |
TABLE 67-continued
| 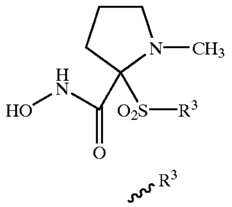 |
|---|
| 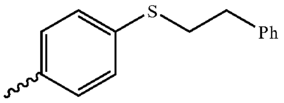 |
| 21 |
| 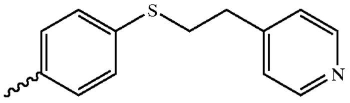 |
| 22 |
| 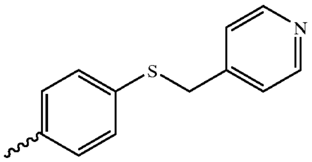 |
TABLE 68
| 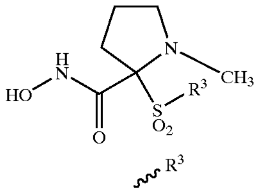 |
|---|
| 1 |
| 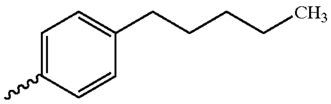 |
| 2 |
| 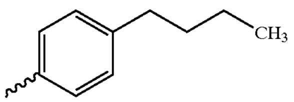 |
| 3 |
| 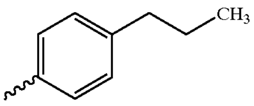 |
| 4 |

TABLE 68-continued
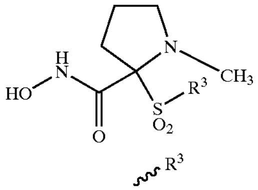
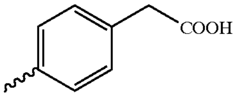
5
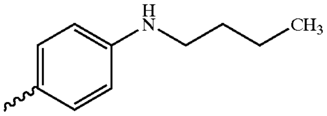
6
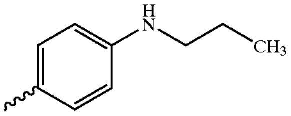
7
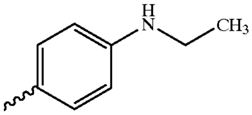
8
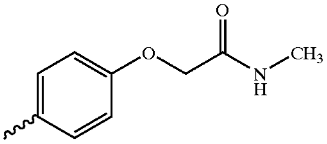
9
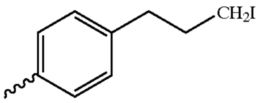
10
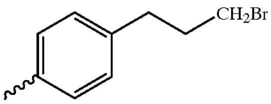
11
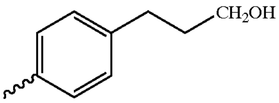
12
TABLE 68-continued
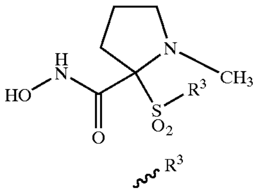
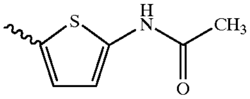
13
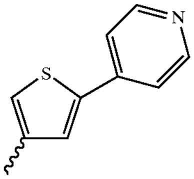
14
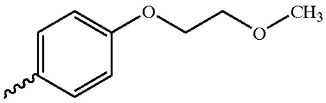
15
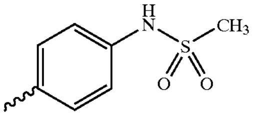
16
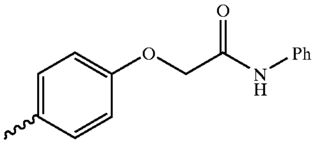
17
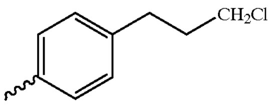
18
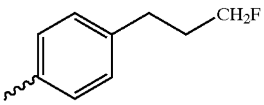
19
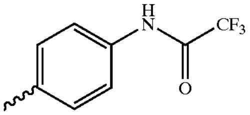
20

TABLE 68-continued
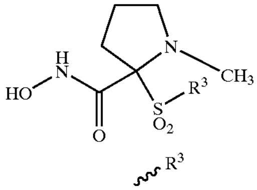
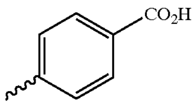
21
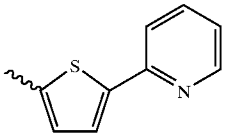
22
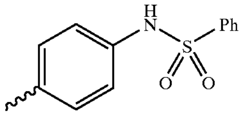
23
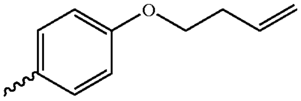
24
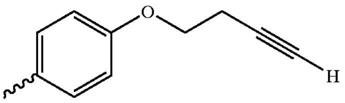
25
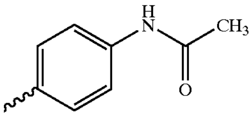
26
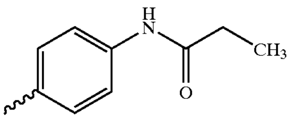
27
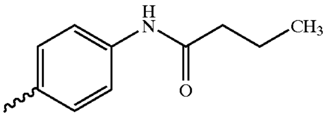
28
TABLE 68-continued
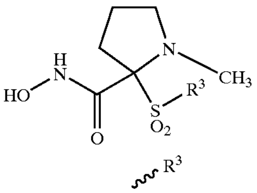
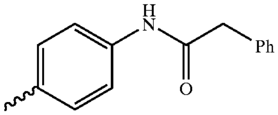
29
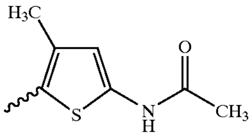
30
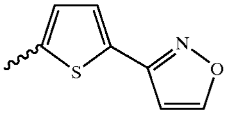
TABLE 69
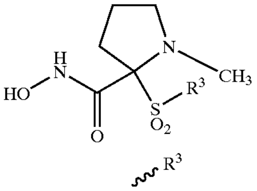
1
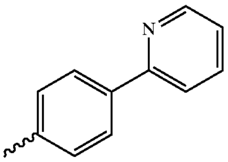
2
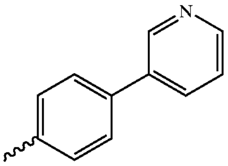
3

TABLE 69-continued
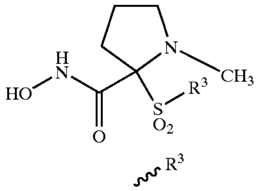
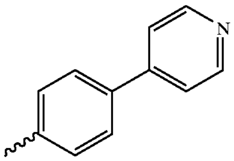
4
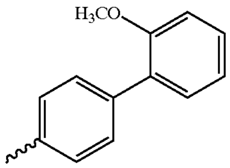
5
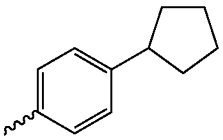
6
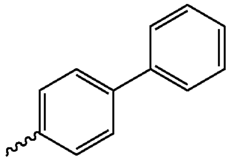
7
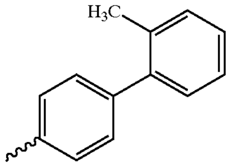
8
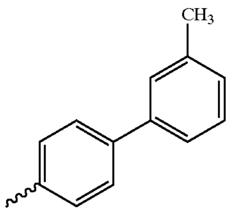
9
TABLE 69-continued
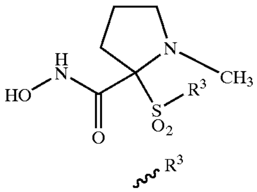
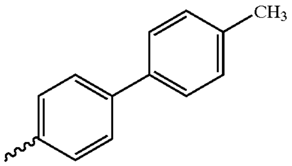
10
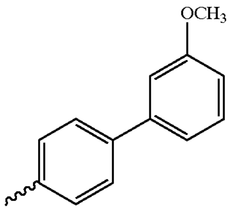
11
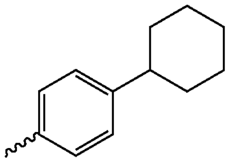
12
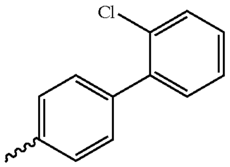
13
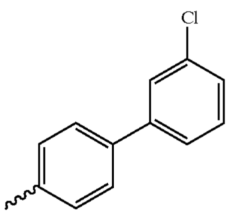
14
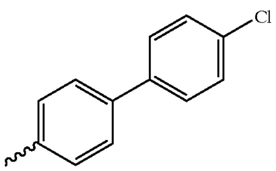
15

TABLE 69-continued
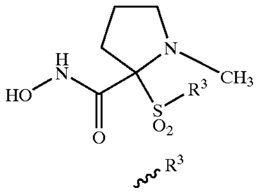
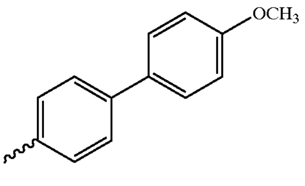
16
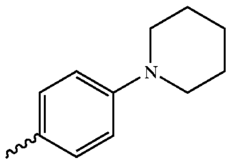
17
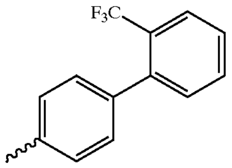
18
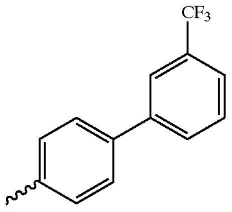
19
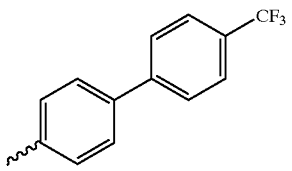
20
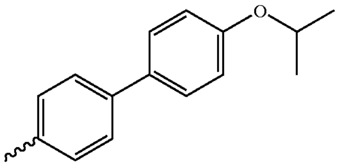
21
TABLE 69-continued
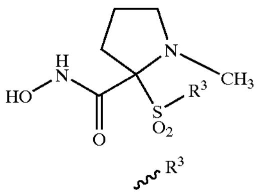
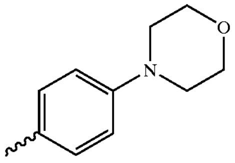
TABLE 70
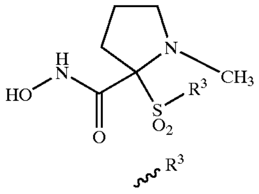
1
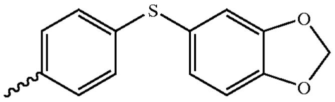
2
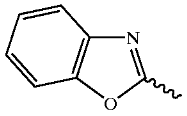
3
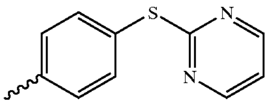
4
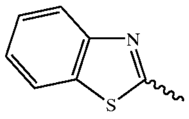
5
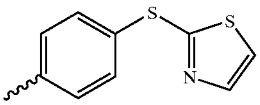
6

TABLE 70-continued
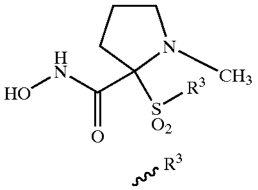
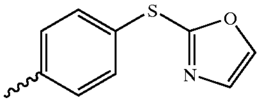
7
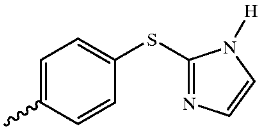
8
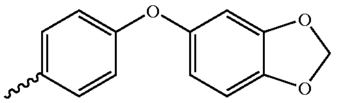
9
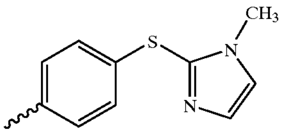
10
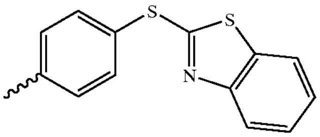
11
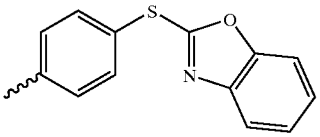
TABLE 71
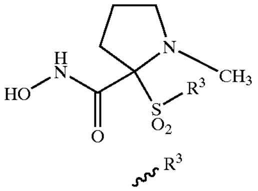
1
TABLE 71-continued
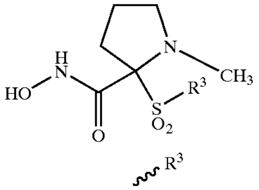
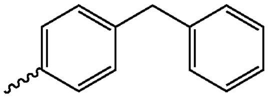
2
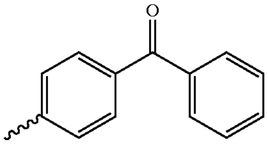
3
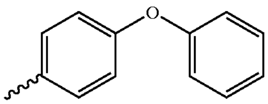
4
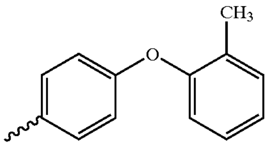
5
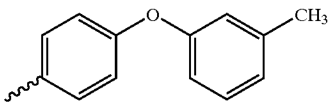
6
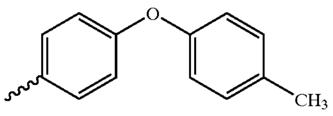
7
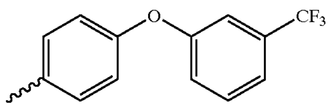
8
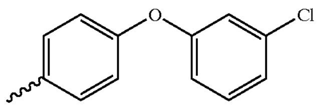
9

TABLE 71-continued
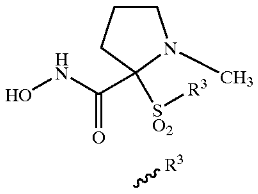
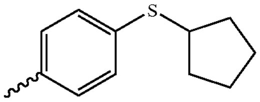
10
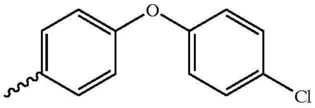
11
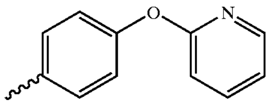
12
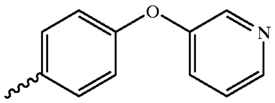
13
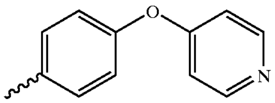
14
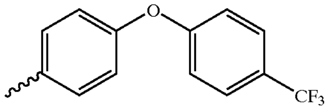
15
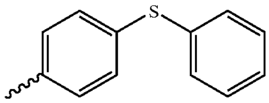
16
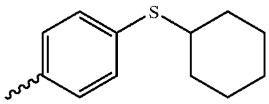
17
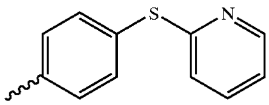
TABLE 71-continued
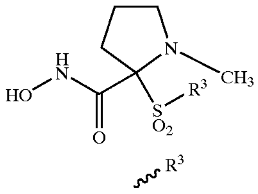
18
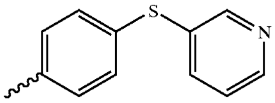
19
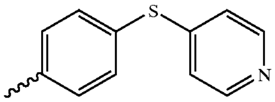
20
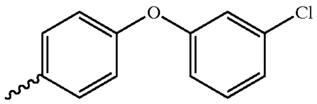
21
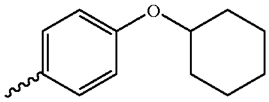
TABLE 72
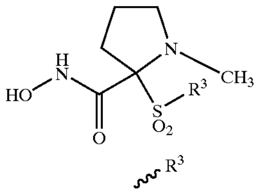
1
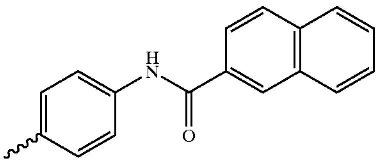
2
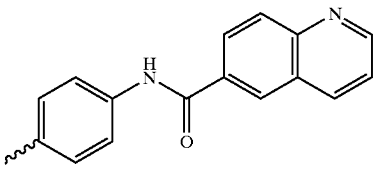

TABLE 72-continued
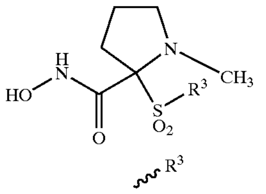
3
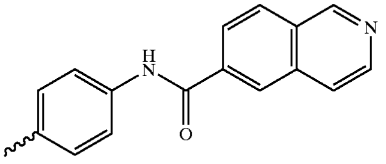
4
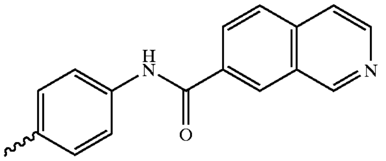
5
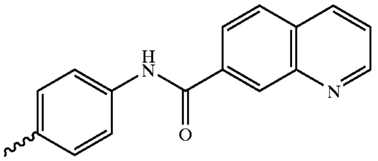
6
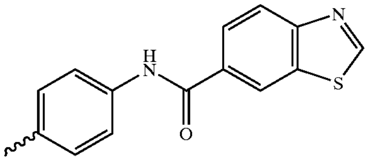
7
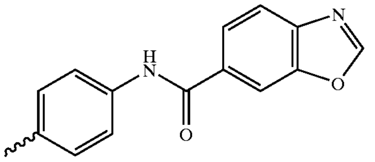
8
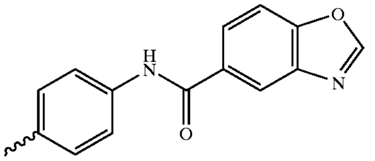
9
TABLE 72-continued
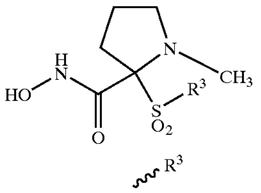
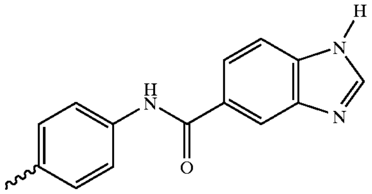
10
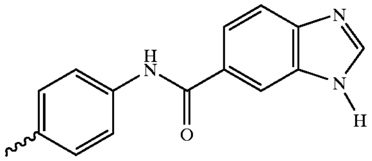
11
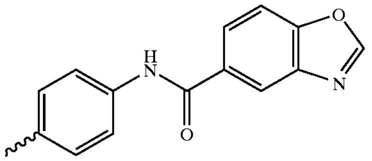
12
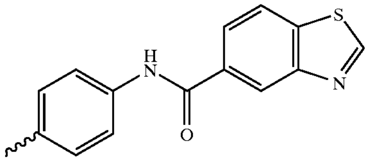
13
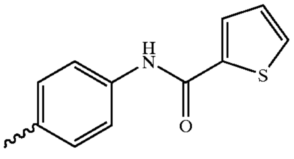
14
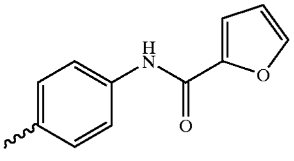
15

TABLE 72-continued
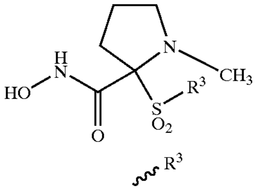
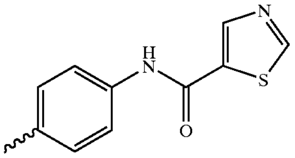
16
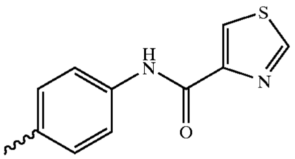
17
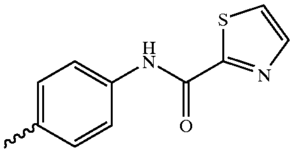
18
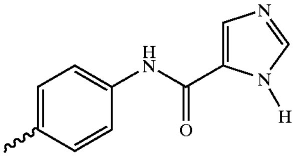
TABLE 73
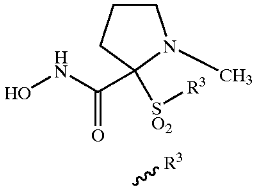
1
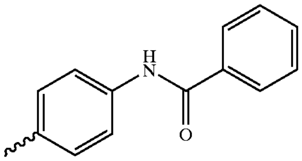
2
TABLE 73-continued
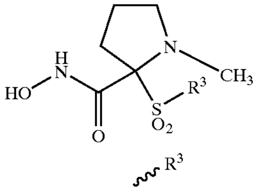
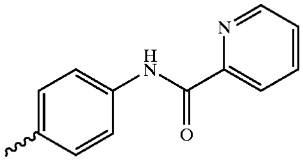
3
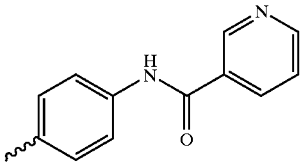
4
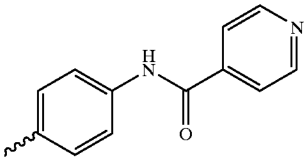
5
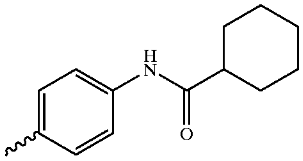
6
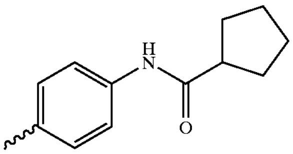
7
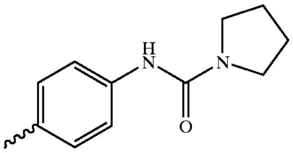
8

TABLE 73-continued
| 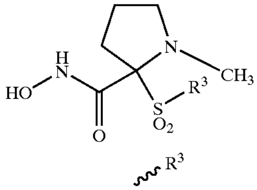 |
| --- |
| 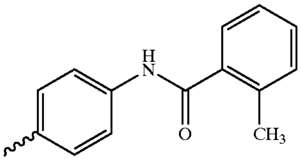 |
| 9 |
| 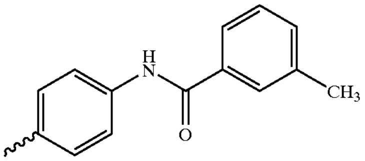 |
| 10 |
| 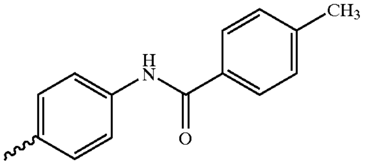 |
| 11 |
| 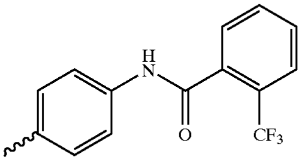 |
| 12 |
| 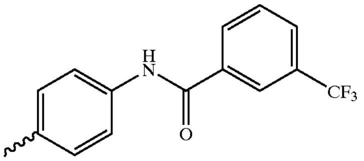 |
| 13 |
| 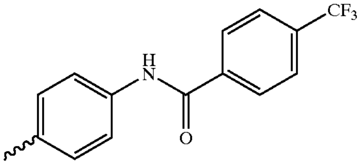 |
| 14 |
TABLE 73-continued
| 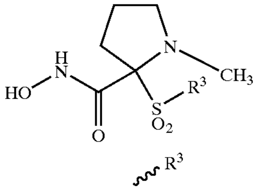 |
| --- |
| 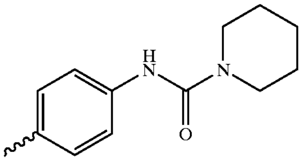 |
| 15 |
| 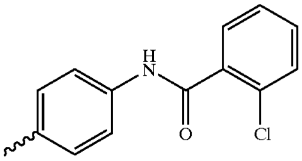 |
| 16 |
| 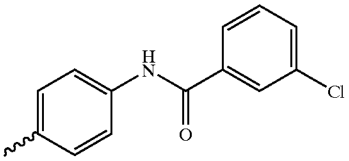 |
| 17 |
| 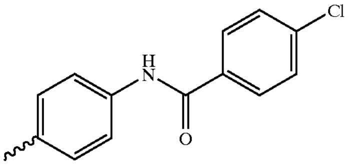 |
| 18 |
| 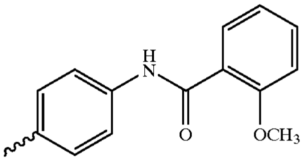 |
| 19 |
| 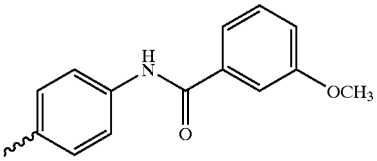 |
| 20 |

TABLE 73-continued
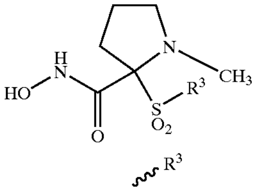
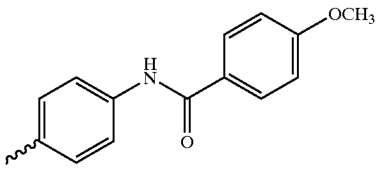
21
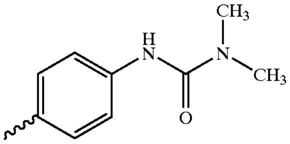
TABLE 74
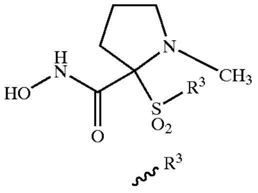
1
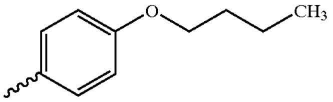
2
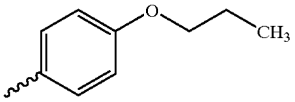
3
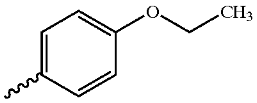
4
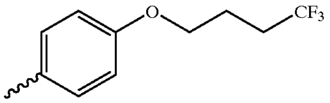
5
TABLE 74-continued
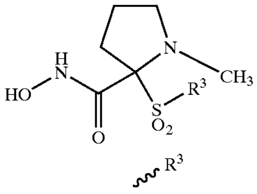
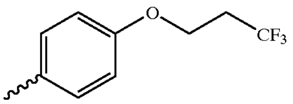
6
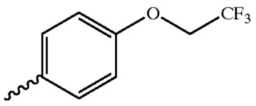
7
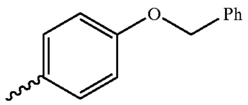
8
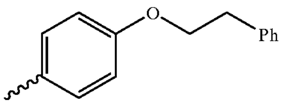
9
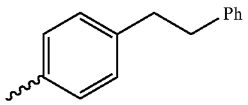
10
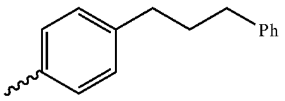
11
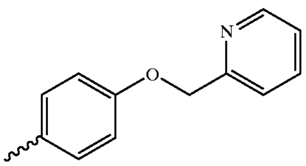
12
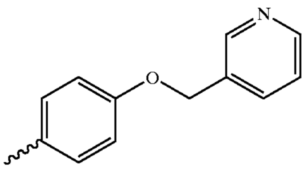
13

TABLE 74-continued
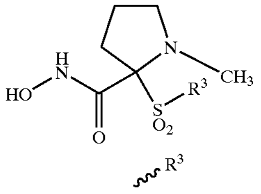
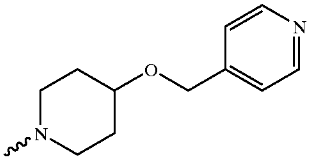
14
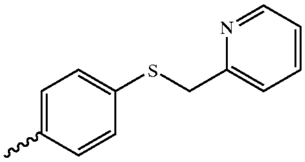
15
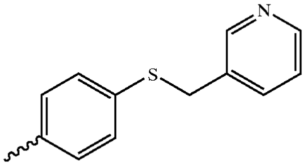
16
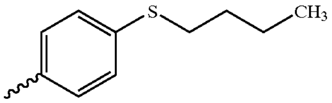
17
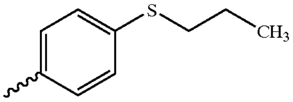
18
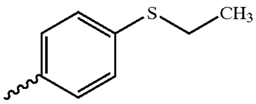
19
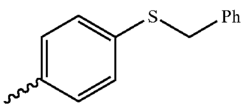
20
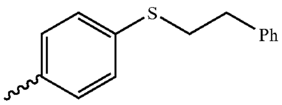
TABLE 74-continued
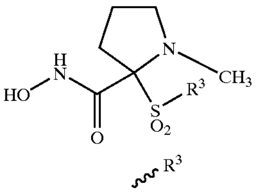
21
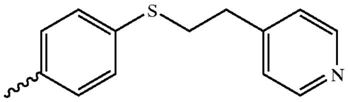
22
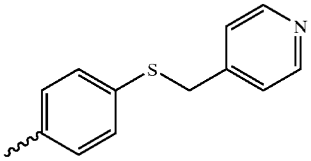
TABLE 75
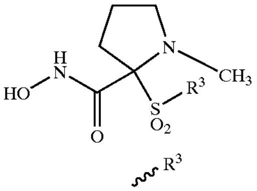
1
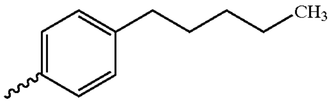
2
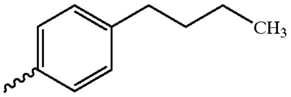
3
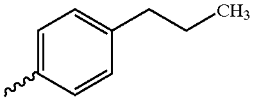
4
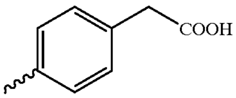
5

TABLE 75-continued
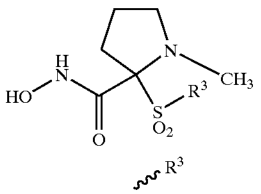
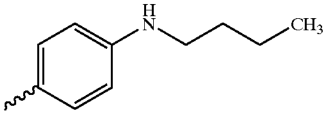
6
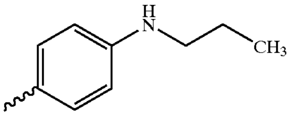
7
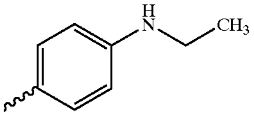
8
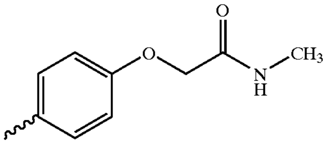
9
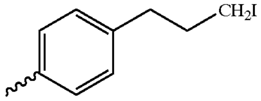
10
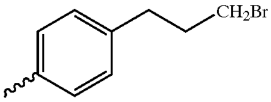
11
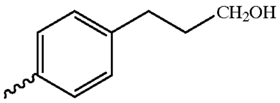
12
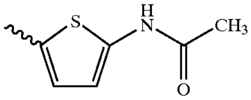
13
TABLE 75-continued
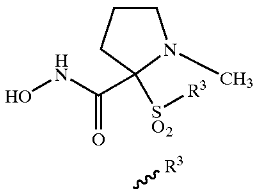
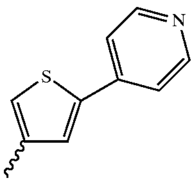
14
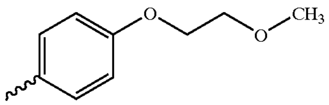
15
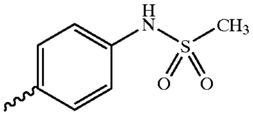
16
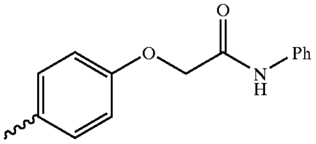
17
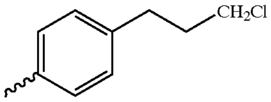
18
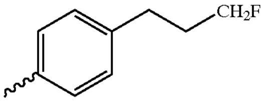
19
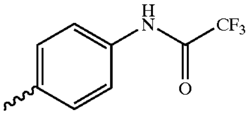
20
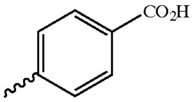
21

TABLE 75-continued
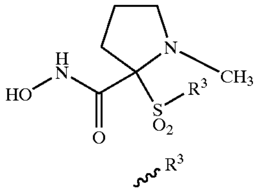
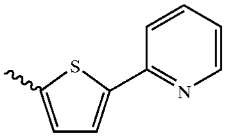
22
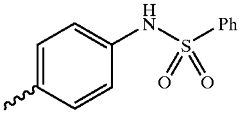
23
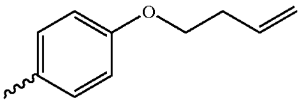
24
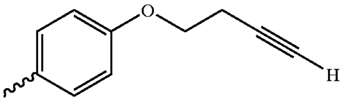
25
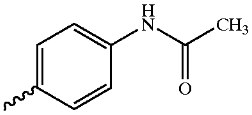
26
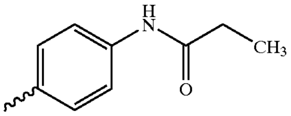
27
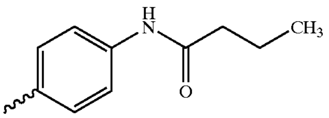
28
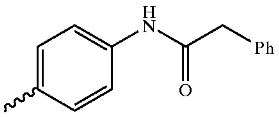
29
TABLE 75-continued
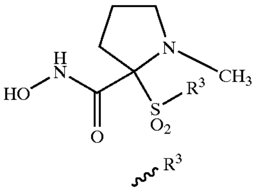
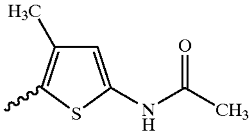
30
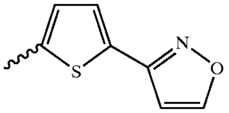
TABLE 76
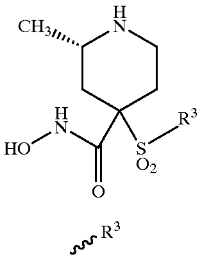
1
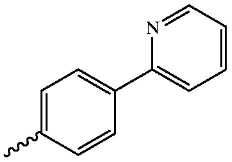
2
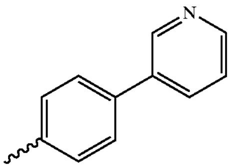
3
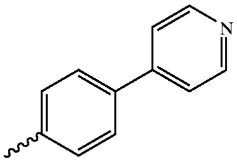
4
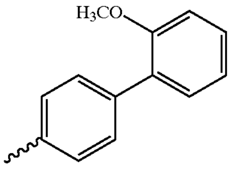

TABLE 76-continued
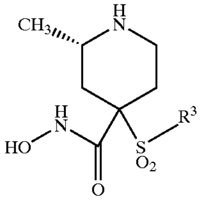
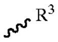
| | |
|---|---|
| 5 | 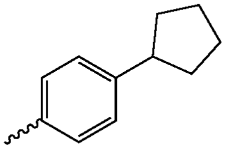 |
| 6 | 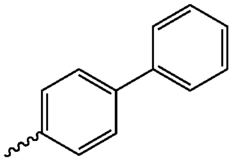 |
| 7 | 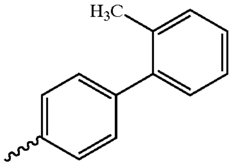 |
| 8 | 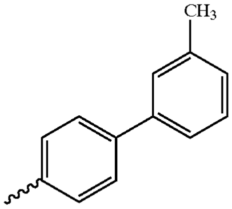 |
| 9 | 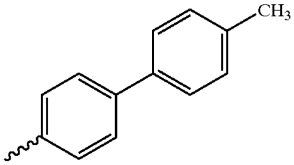 |
| 10 | 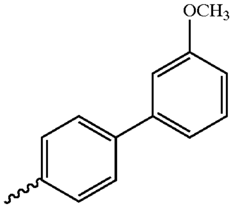 |
| 11 | 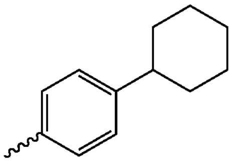 |
TABLE 76-continued
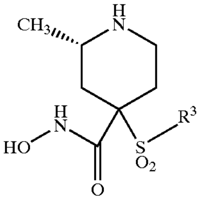
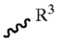
| | |
|---|---|
| 12 | 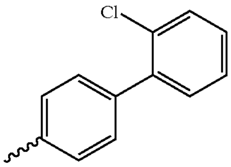 |
| 13 | 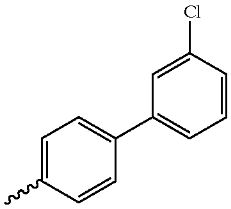 |
| 14 | 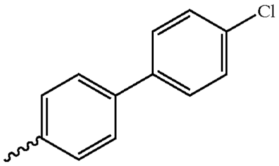 |
| 15 | 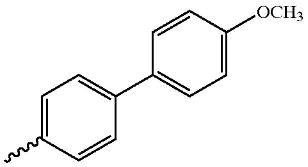 |
| 16 | 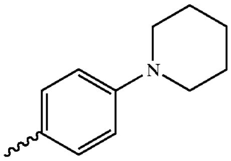 |
| 17 | 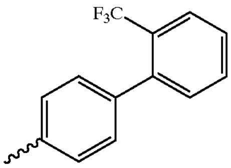 |
| 18 | 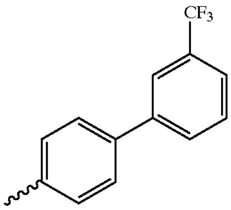 |

TABLE 76-continued
| | |
|---|---|
| | 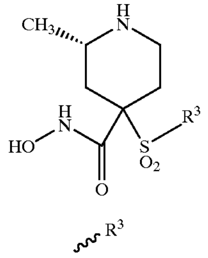 |
| 19 | 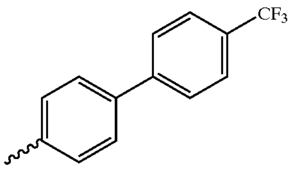 |
| 20 | 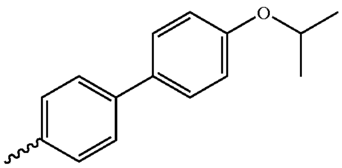 |
| 21 | 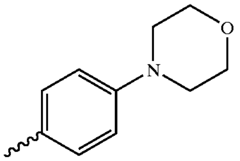 |
TABLE 77
| | |
|---|---|
| | 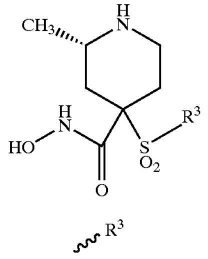 |
| 1 | 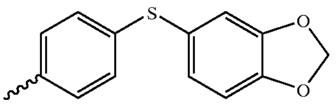 |
| 2 | 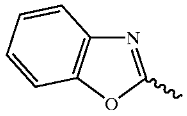 |
| 3 | 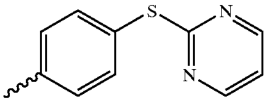 |
TABLE 77-continued
| | |
|---|---|
| | 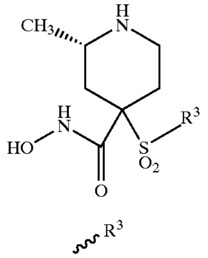 |
| 4 | 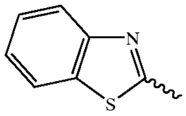 |
| 5 | 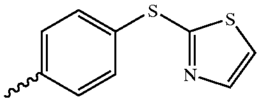 |
| 6 | 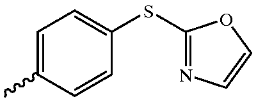 |
| 7 | 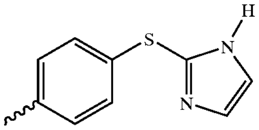 |
| 8 | 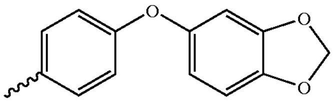 |
| 9 | 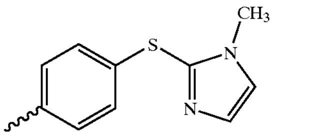 |
| 10 | 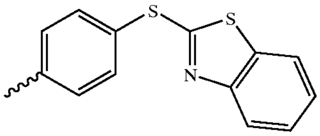 |
| 11 | 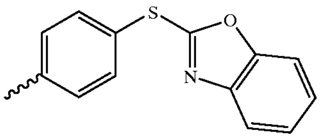 |

TABLE 78
| 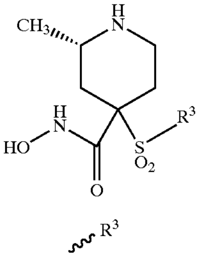 | |
|---|---|
| 1 | 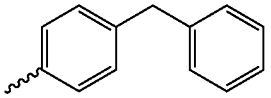 |
| 2 | 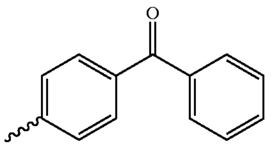 |
| 3 | 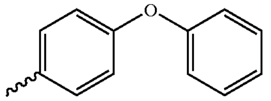 |
| 4 | 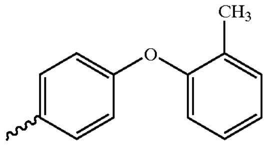 |
| 5 | 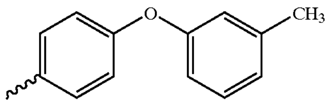 |
| 6 | 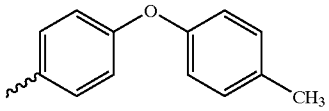 |
| 7 | 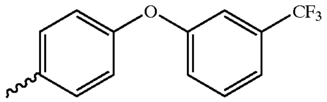 |
| 8 | 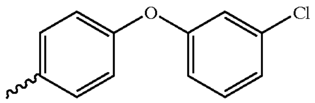 |
| 9 | 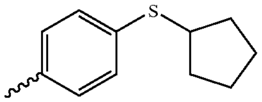 |
| 10 | 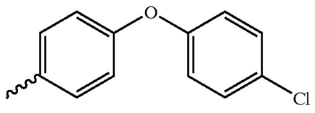 |
TABLE 78-continued
| 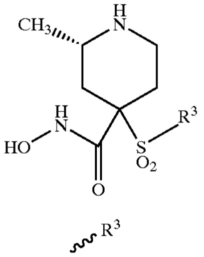 | |
|---|---|
| 11 | 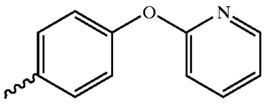 |
| 12 | 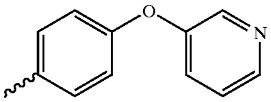 |
| 13 | 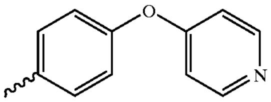 |
| 14 | 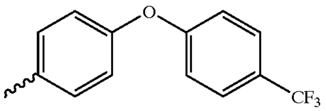 |
| 15 | 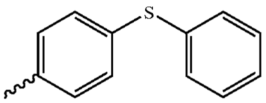 |
| 16 | 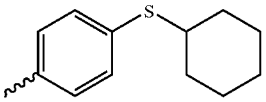 |
| 17 | 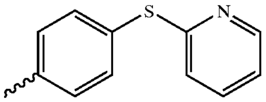 |
| 18 | 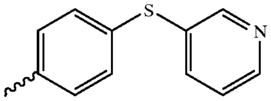 |
| 19 | 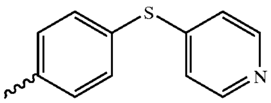 |
| 20 | 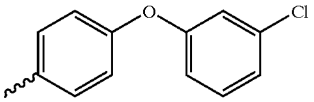 |
| 21 | 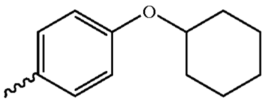 |

TABLE 79
| | |
|---|---|
| 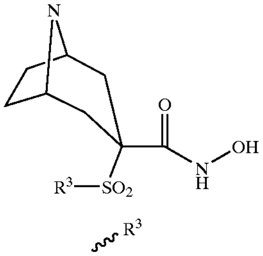 | |
| 1 | 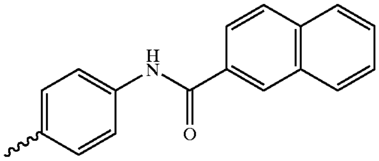 |
| 2 | 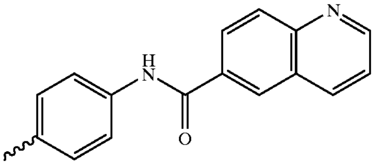 |
| 3 | 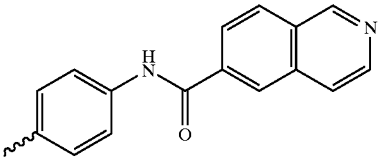 |
| 4 | 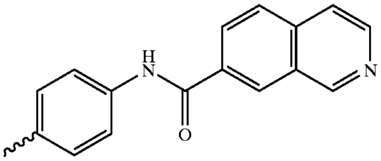 |
| 5 | 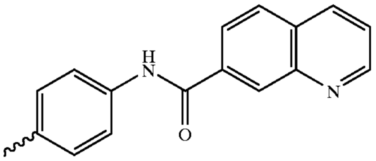 |
| 6 | 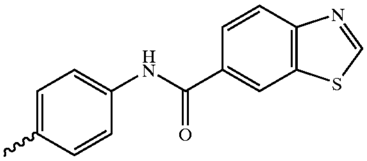 |
| 7 | 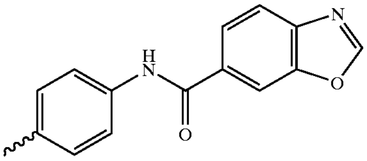 |
TABLE 79-continued
| | |
|---|---|
| 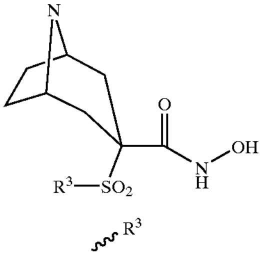 | |
| 8 | 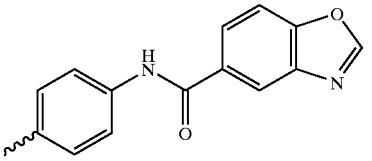 |
| 9 | 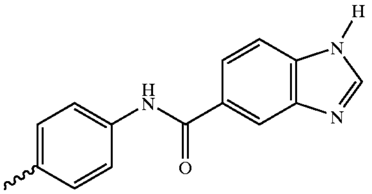 |
| 10 | 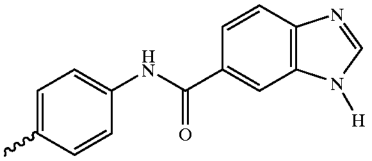 |
| 11 | 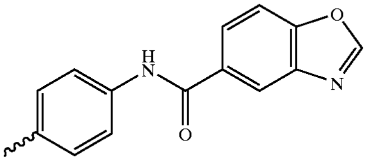 |
| 12 | 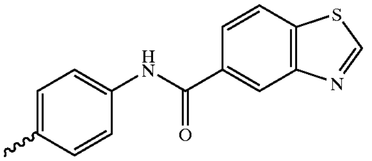 |
| 13 | 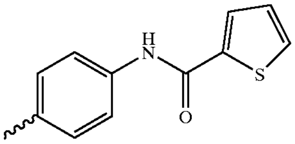 |
| 14 | 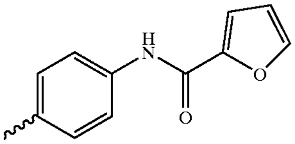 |

TABLE 79-continued
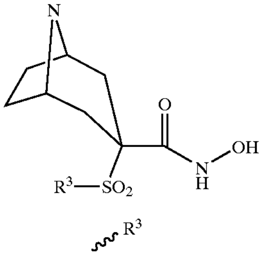
15
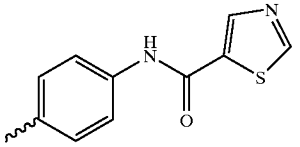
16
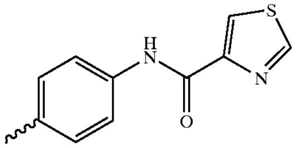
17
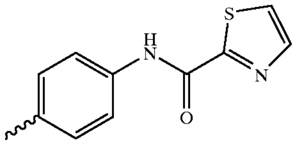
18
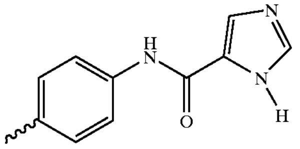
TABLE 80
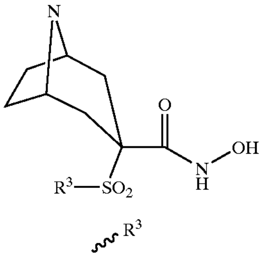
1
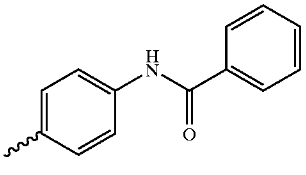
2
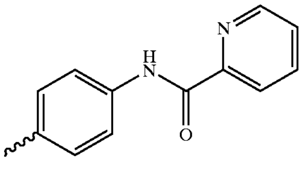
TABLE 80-continued
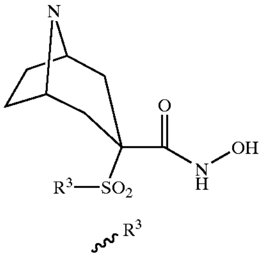
3
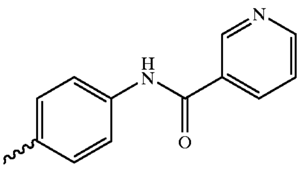
4
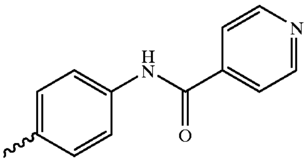
5
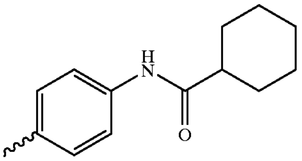
6
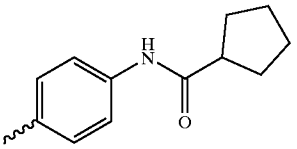
7
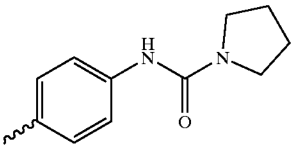
8
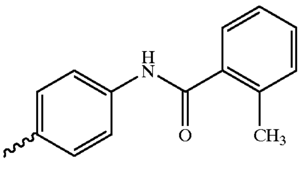
9
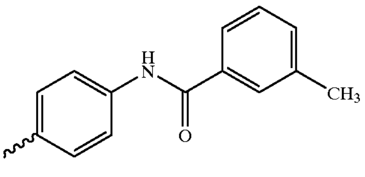

TABLE 80-continued
| 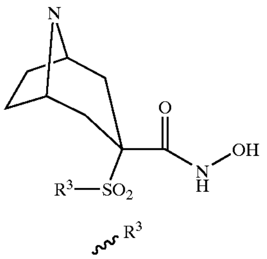 | |
|---|---|
| 10 | 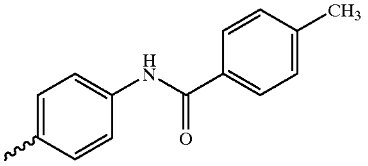 |
| 11 | 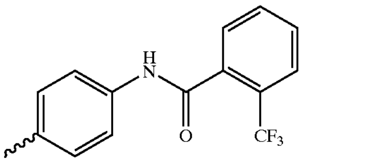 |
| 12 | 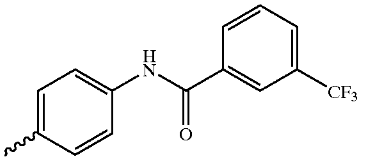 |
| 13 | 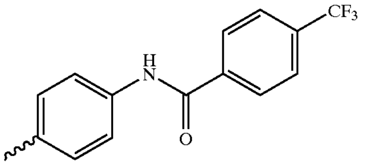 |
| 14 | 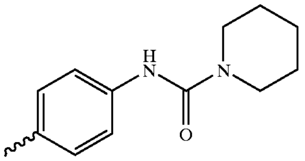 |
| 15 | 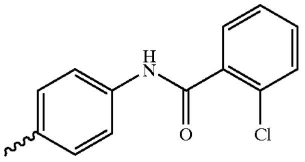 |
| 16 | 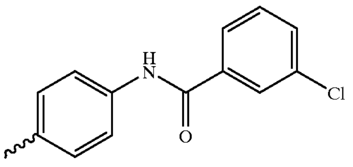 |
TABLE 80-continued
| 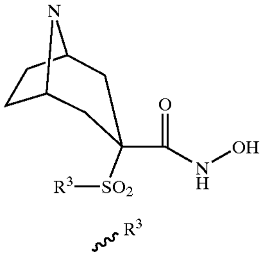 | |
|---|---|
| 17 | 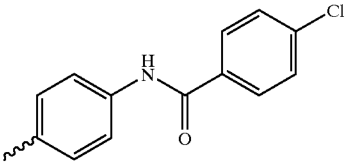 |
| 18 | 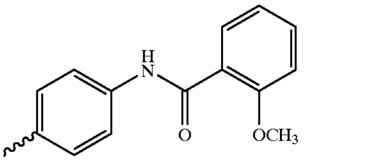 |
| 19 | 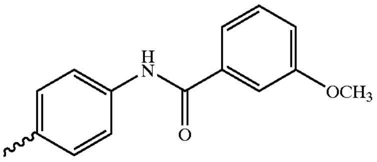 |
| 20 | 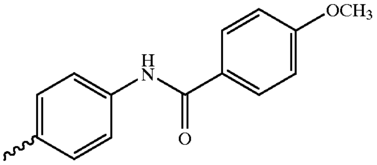 |
| 21 | 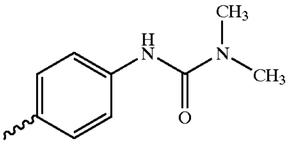 |
TABLE 81
| 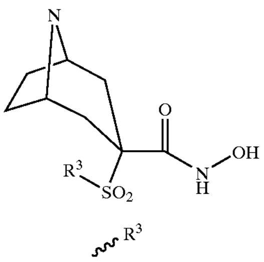 | |
|---|---|
| 1 | 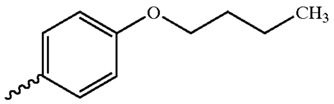 |

TABLE 81-continued
| | |
|---|---|
| | 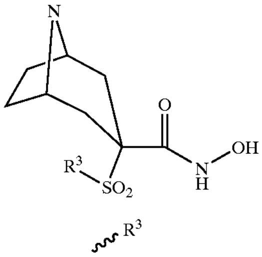 |
| 2 | 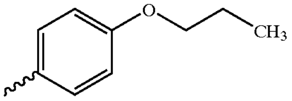 |
| 3 | 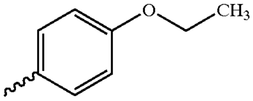 |
| 4 | 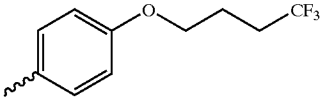 |
| 5 | 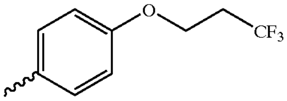 |
| 6 | 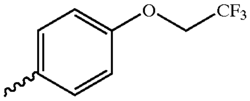 |
| 7 | 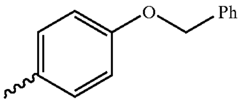 |
| 8 | 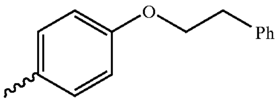 |
| 9 | 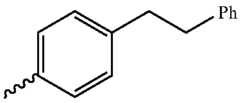 |
| 10 | 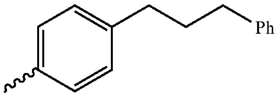 |
| 11 | 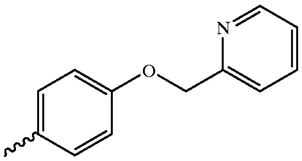 |
TABLE 81-continued
| | |
|---|---|
| | 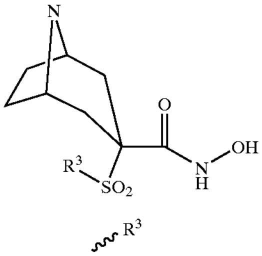 |
| 12 | 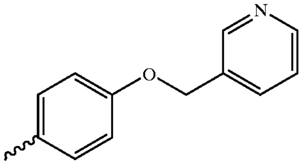 |
| 13 | 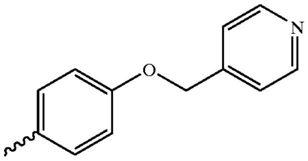 |
| 14 | 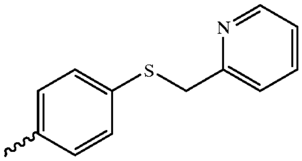 |
| 15 | 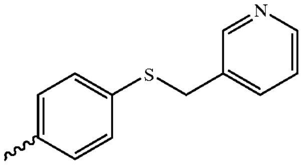 |
| 16 | 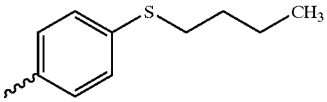 |
| 17 | 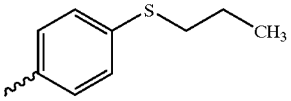 |
| 18 | 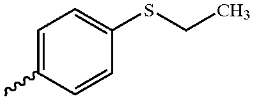 |
| 19 | 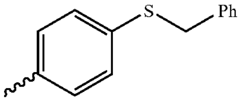 |
| 20 | 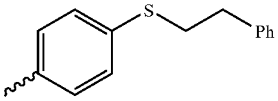 |

TABLE 81-continued
| | 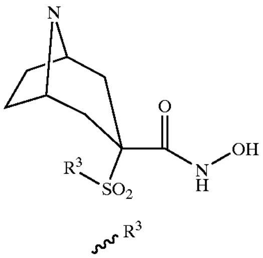 |
|---|---|
| 21 | 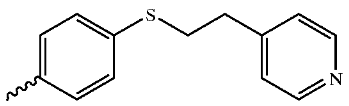 |
| 22 | 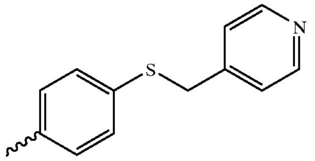 |
TABLE 82
| | 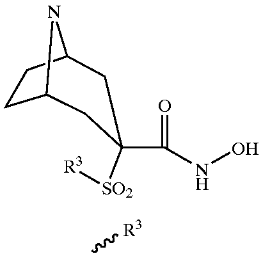 |
|---|---|
| 1 | 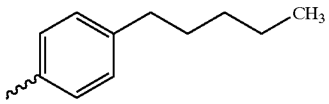 |
| 2 | 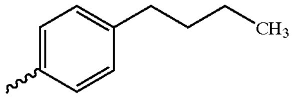 |
| 3 | 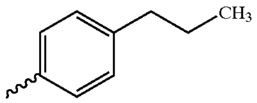 |
| 4 | 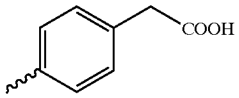 |
| 5 | 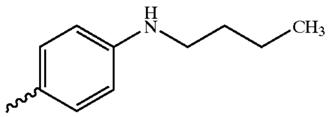 |
TABLE 82-continued
| | 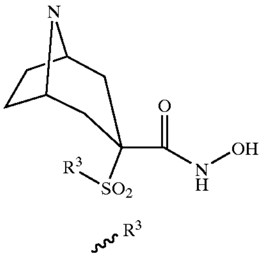 |
|---|---|
| 6 | 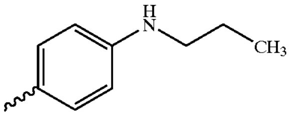 |
| 7 | 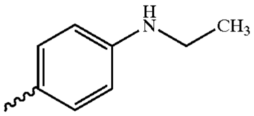 |
| 8 | 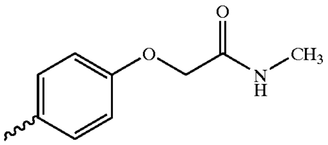 |
| 9 | 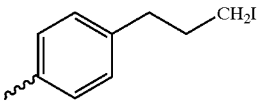 |
| 10 | 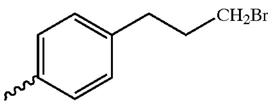 |
| 11 | 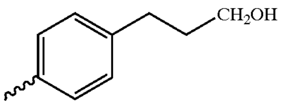 |
| 12 | 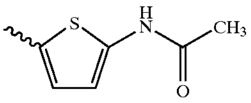 |
| 13 | 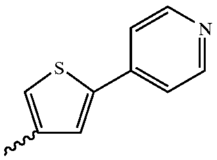 |
| 14 | 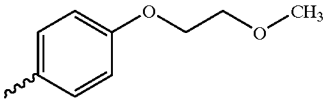 |
| 15 | 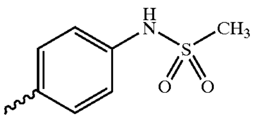 |

TABLE 82-continued
| | |
|---|---|
| | 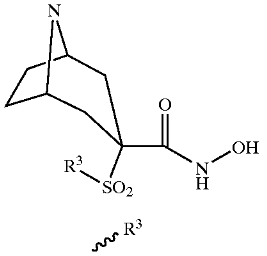 |
| 16 | 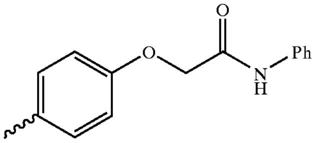 |
| 17 | 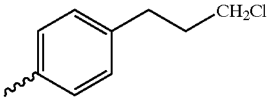 |
| 18 | 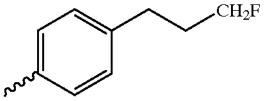 |
| 19 | 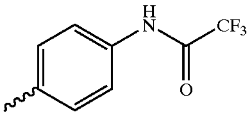 |
| 20 | 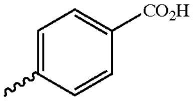 |
| 21 | 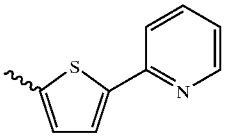 |
| 22 | 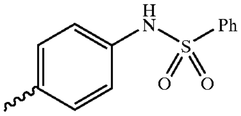 |
| 23 | 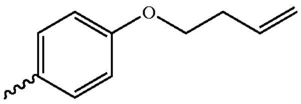 |
| 24 | 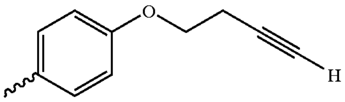 |
| 25 | 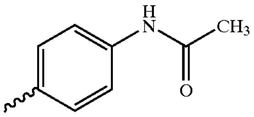 |
TABLE 82-continued
| | |
|---|---|
| | 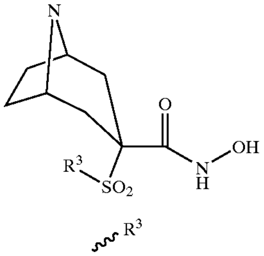 |
| 26 | 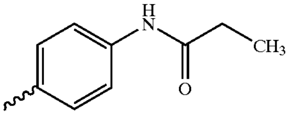 |
| 27 | 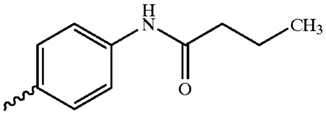 |
| 28 | 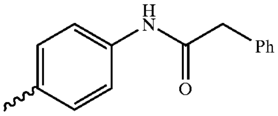 |
| 29 | 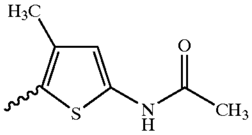 |
| 30 | 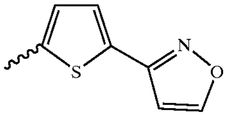 |
TABLE 83
| | |
|---|---|
| | 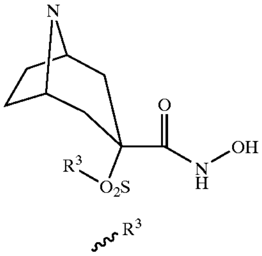 |
| 1 | 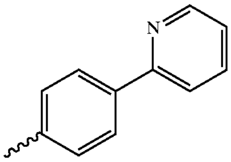 |

TABLE 83-continued
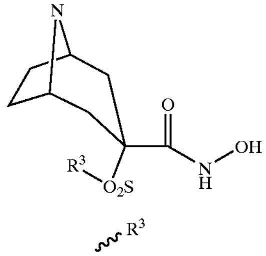
| | |
|---|---|
| 2 | 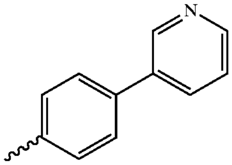 |
| 3 | 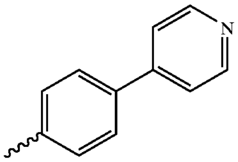 |
| 4 | 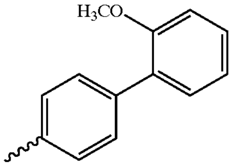 |
| 5 | 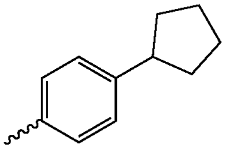 |
| 6 | 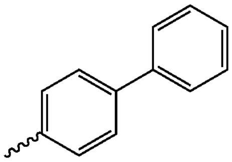 |
| 7 | 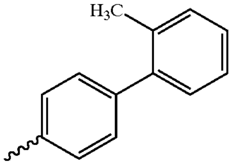 |
| 8 | 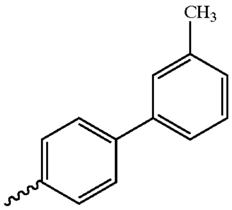 |
TABLE 83-continued
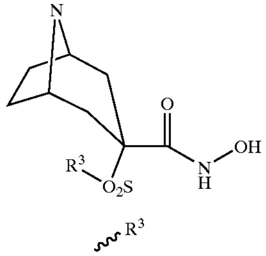
| | |
|---|---|
| 9 | 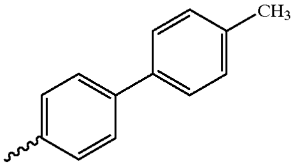 |
| 10 | 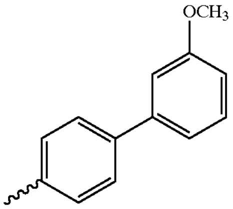 |
| 11 | 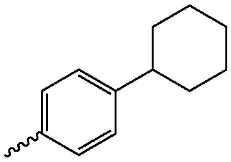 |
| 12 | 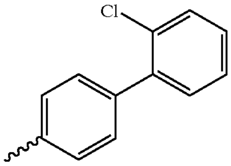 |
| 13 | 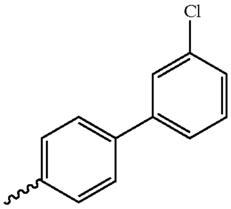 |
| 14 | 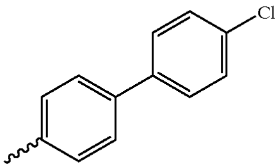 |
| 15 | 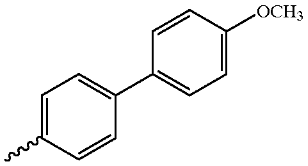 |

TABLE 83-continued
| | |
|---|---|
| | 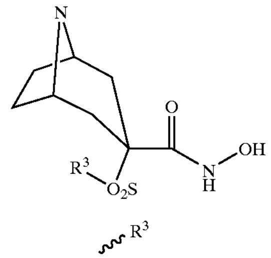 |
| 16 | 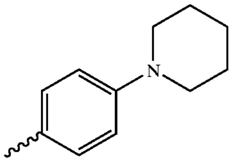 |
| 17 | 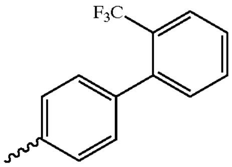 |
| 18 | 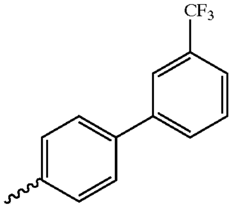 |
| 19 | 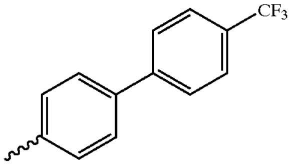 |
| 20 | 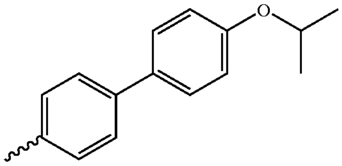 |
| 21 | 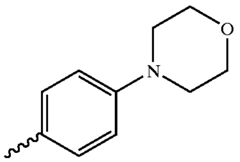 |
TABLE 84
| | |
|---|---|
| | 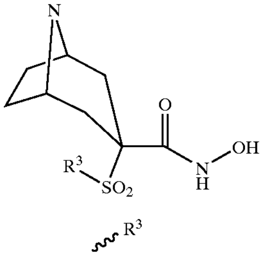 |
| 1 | 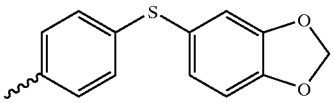 |
| 2 | 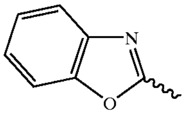 |
| 3 | 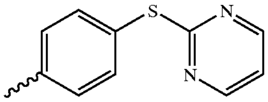 |
| 4 | 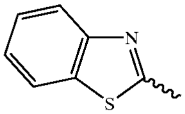 |
| 5 | 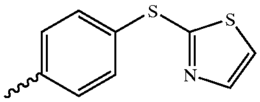 |
| 6 | 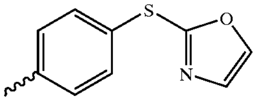 |
| 7 | 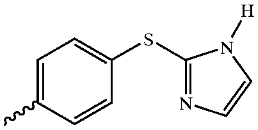 |
| 8 | 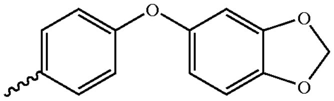 |
| 9 | 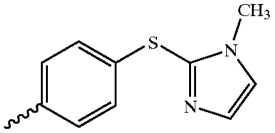 |
| 10 | 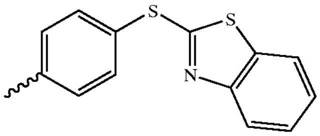 |

TABLE 84-continued
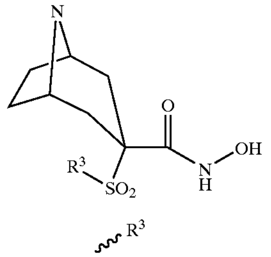
| | |
|---|---|
| 11 | 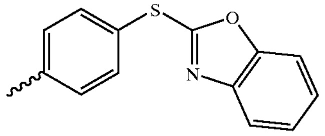 |
TABLE 85
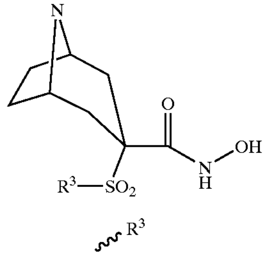
| | |
|---|---|
| 1 | 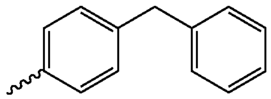 |
| 2 | 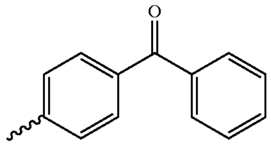 |
| 3 | 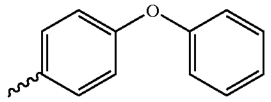 |
| 4 | 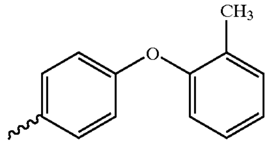 |
| 5 | 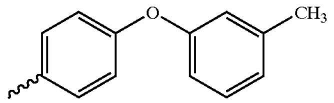 |
| 6 | 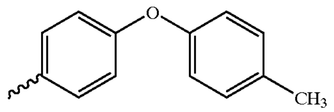 |
TABLE 85-continued
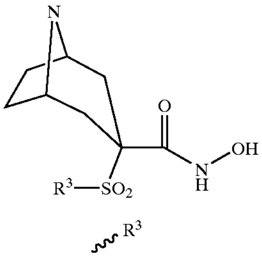
| | |
|---|---|
| 7 | 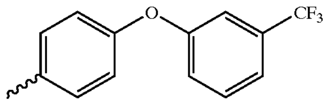 |
| 8 | 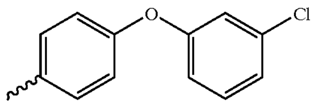 |
| 9 | 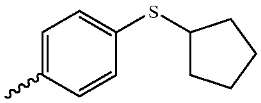 |
| 10 | 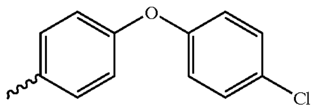 |
| 11 | 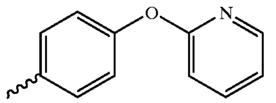 |
| 12 | 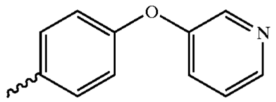 |
| 13 | 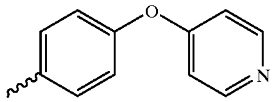 |
| 14 | 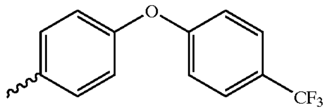 |
| 15 | 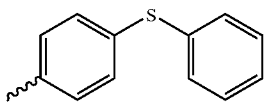 |
| 16 | 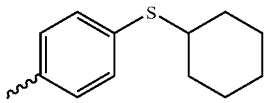 |
| 17 | 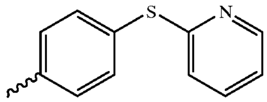 |

TABLE 85-continued
| | 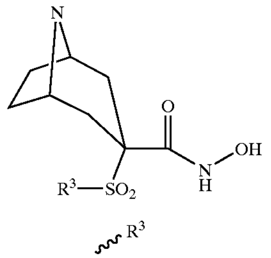 |
|---|---|
| 18 | 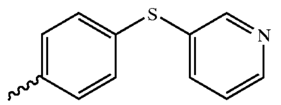 |
| 19 | 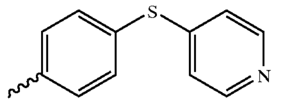 |
| 20 | 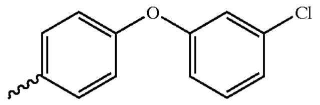 |
| 21 | 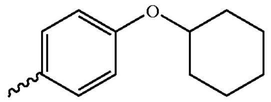 |
TABLE 86
| | 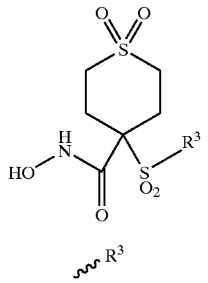 |
|---|---|
| 1 | 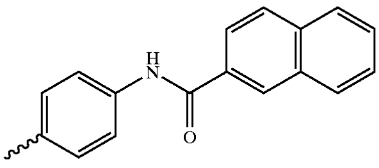 |
| 2 | 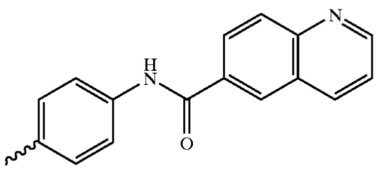 |
TABLE 86-continued
| | 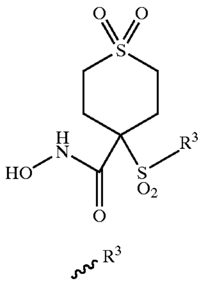 |
|---|---|
| 3 | 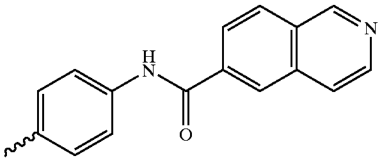 |
| 4 | 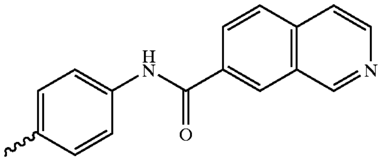 |
| 5 | 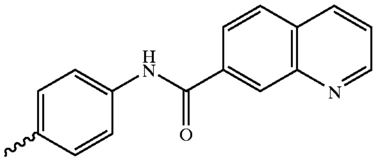 |
| 6 | 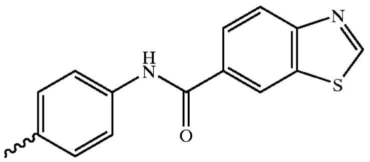 |
| 7 | 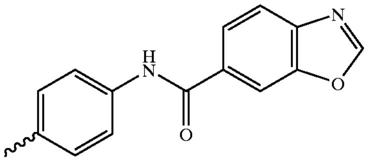 |
| 8 | 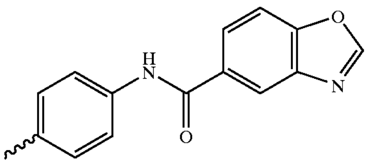 |
| 9 | 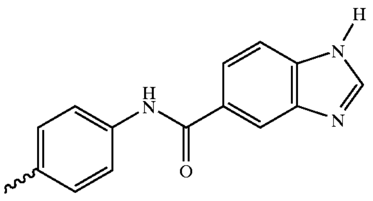 |

TABLE 86-continued
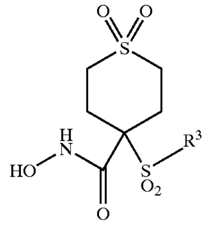
| | |
|---|---|
| 10 | 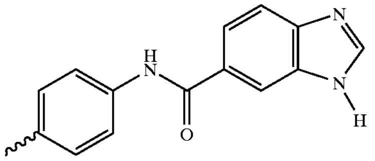 |
| 11 | 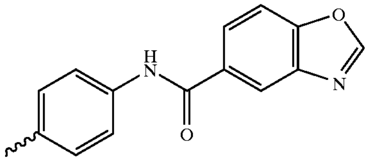 |
| 12 | 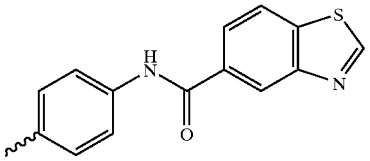 |
| 13 | 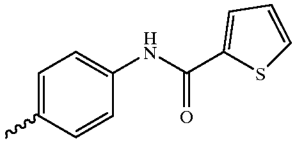 |
| 14 | 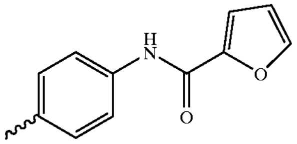 |
| 15 | 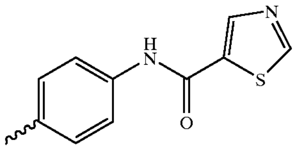 |
| 16 | 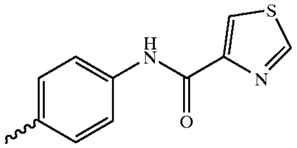 |
| 17 | 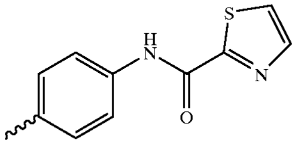 |
TABLE 86-continued
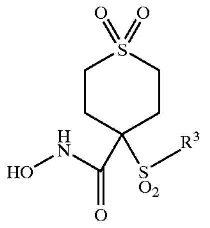
| | |
|---|---|
| 18 | 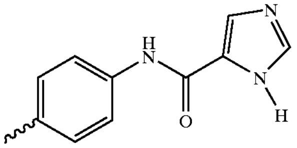 |
TABLE 87
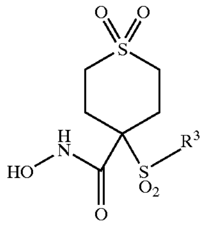
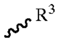
| | |
|---|---|
| 1 | 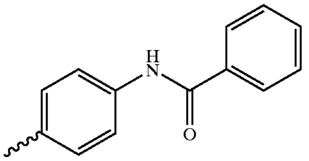 |
| 2 | 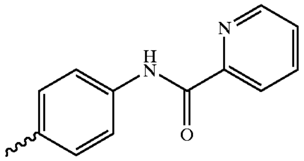 |
| 3 | 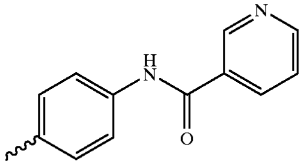 |
| 4 | 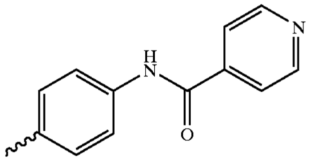 |

TABLE 87-continued
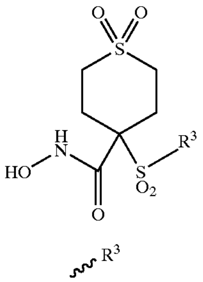
| | |
|---|---|
| 5 | 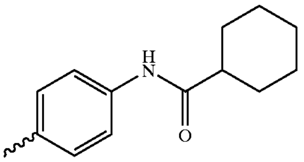 |
| 6 | 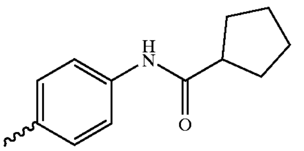 |
| 7 | 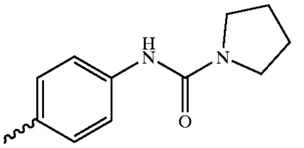 |
| 8 | 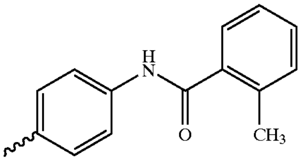 |
| 9 | 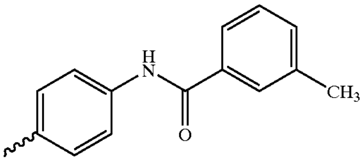 |
| 10 | 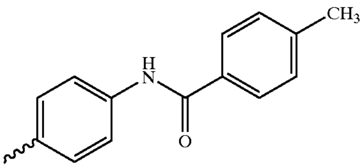 |
| 11 | 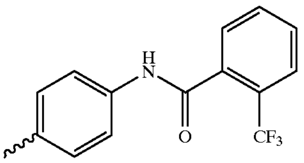 |
TABLE 87-continued
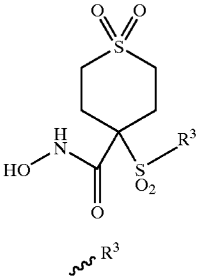
| | |
|---|---|
| 12 | 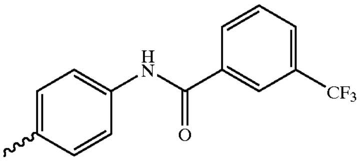 |
| 13 | 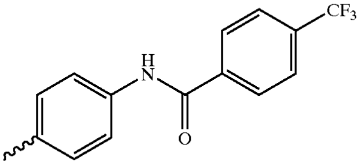 |
| 14 | 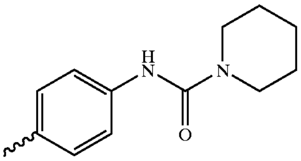 |
| 15 | 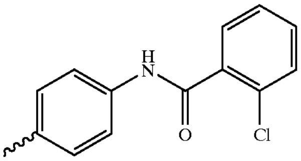 |
| 16 | 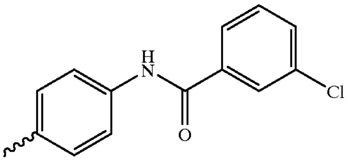 |
| 17 | 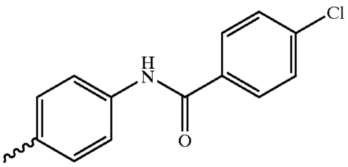 |
| 18 | 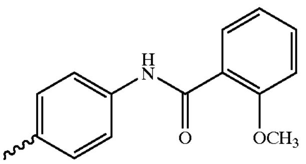 |

TABLE 87-continued
| 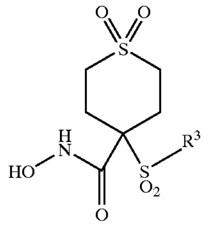 | |
|---|---|
| 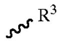 | |
| 19 | 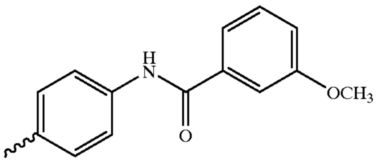 |
| 20 | 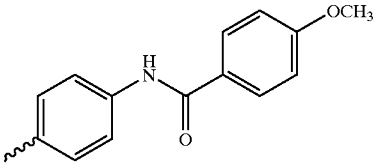 |
| 21 | 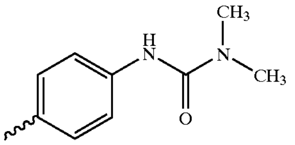 |
TABLE 88
| 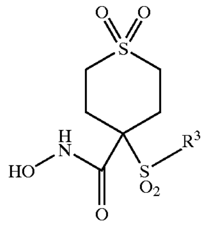 | |
|---|---|
| 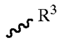 | |
| 1 | 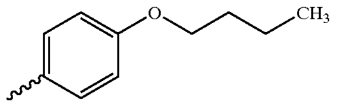 |
| 2 | 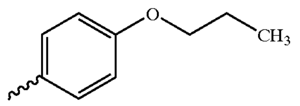 |
| 3 | 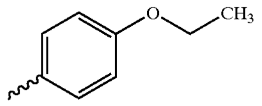 |
TABLE 88-continued
| 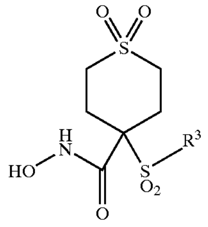 | |
|---|---|
| 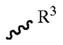 | |
| 4 | 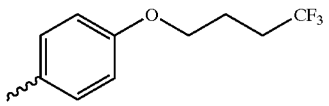 |
| 5 | 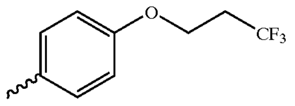 |
| 6 | 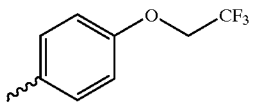 |
| 7 | 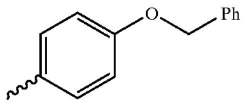 |
| 8 | 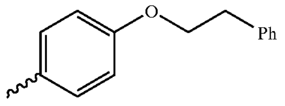 |
| 9 | 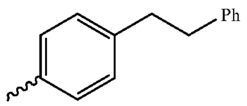 |
| 10 | 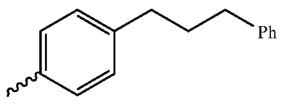 |
| 11 | 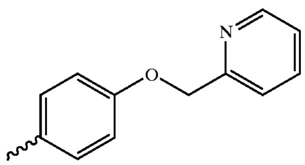 |
| 12 | 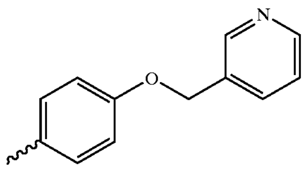 |

TABLE 88-continued
| 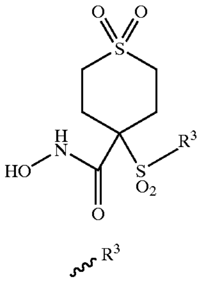 |
| --- |
| | |
| --- | --- |
| 13 | 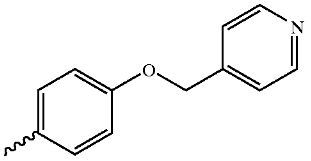 |
| 14 | 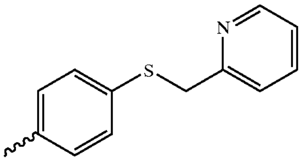 |
| 15 | 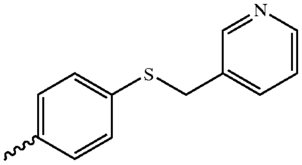 |
| 16 | 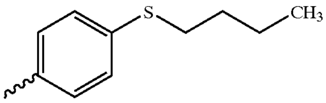 |
| 17 | 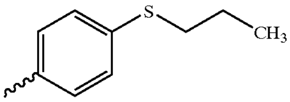 |
| 18 | 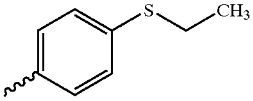 |
| 19 | 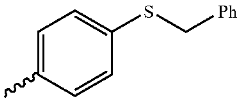 |
| 20 | 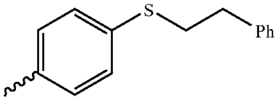 |
| 21 | 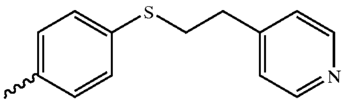 |
TABLE 88-continued
| 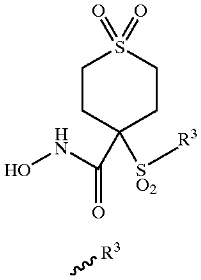 |
| --- |
| | |
| --- | --- |
| 22 | 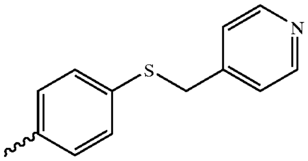 |
TABLE 89
| 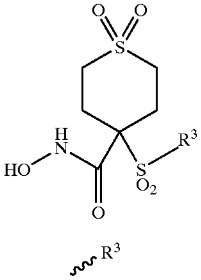 |
| --- |
| | |
| --- | --- |
| 1 | 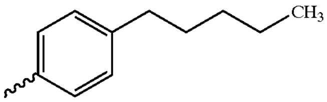 |
| 2 | 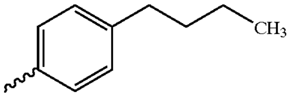 |
| 3 | 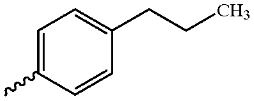 |
| 4 | 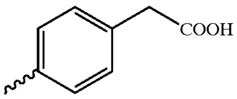 |
| 5 | 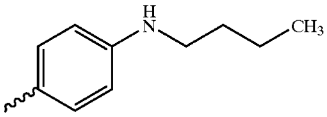 |
| 6 | 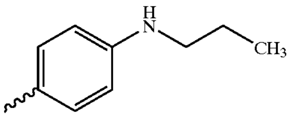 |

TABLE 89-continued
| | 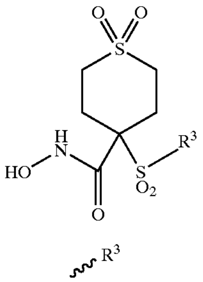 |
|---|---|
| 7 | 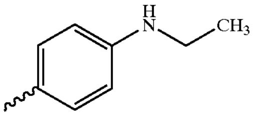 |
| 8 | 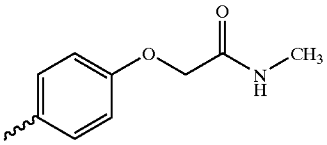 |
| 9 | 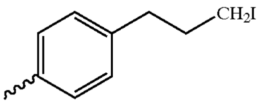 |
| 10 | 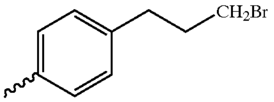 |
| 11 | 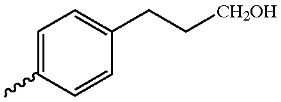 |
| 12 | 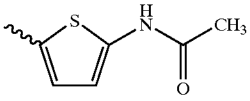 |
| 13 | 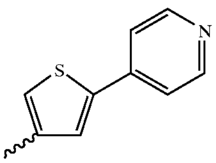 |
| 14 | 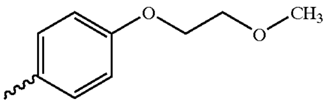 |
| 15 | 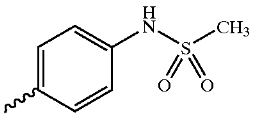 |
TABLE 89-continued
| | 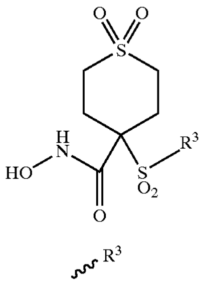 |
|---|---|
| 16 | 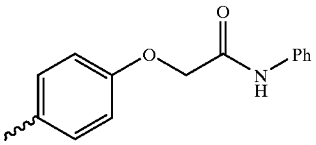 |
| 17 | 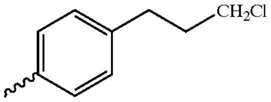 |
| 18 | 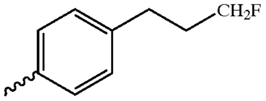 |
| 19 | 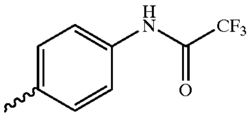 |
| 20 | 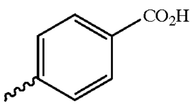 |
| 21 | 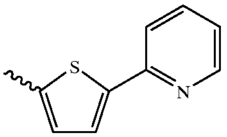 |
| 22 | 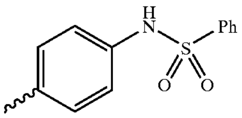 |
| 23 | 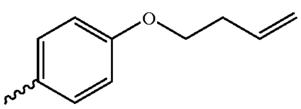 |
| 24 | 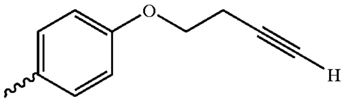 |
| 25 | 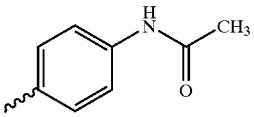 |

TABLE 89-continued
| | |
|---|---|
| | 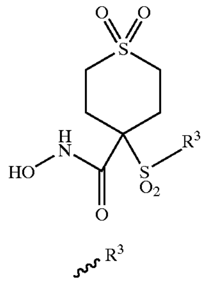 |
| 26 | 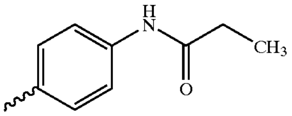 |
| 27 | 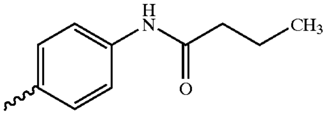 |
| 28 | 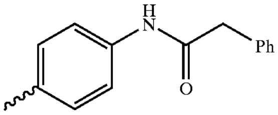 |
| 29 | 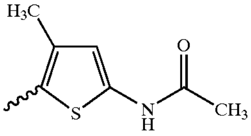 |
| 30 | 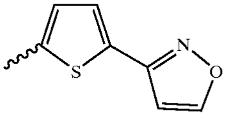 |
TABLE 90
| | |
|---|---|
| | 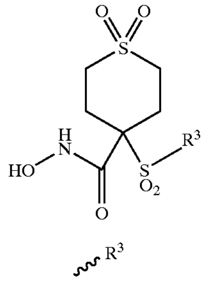 |
| 1 | 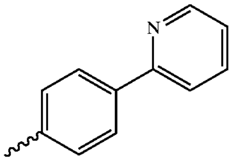 |
TABLE 90-continued
| | |
|---|---|
| | 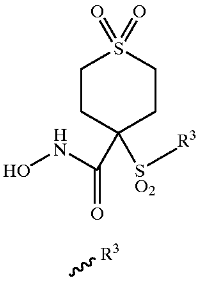 |
| 2 | 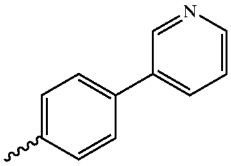 |
| 3 | 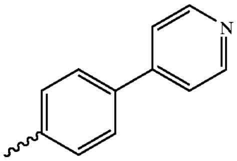 |
| 4 | 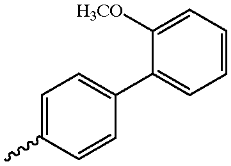 |
| 5 | 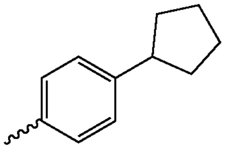 |
| 6 | 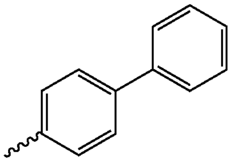 |
| 7 | 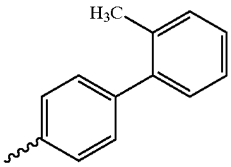 |
| 8 | 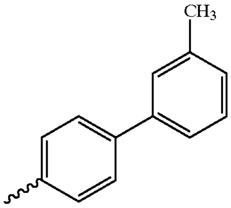 |

TABLE 90-continued
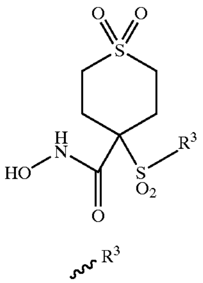
9 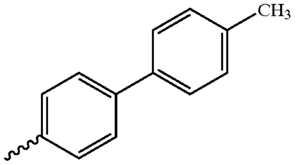
10 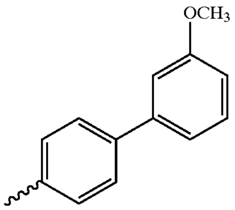
11 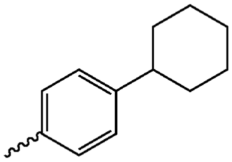
12 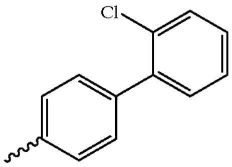
13 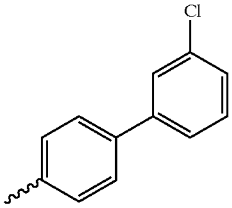
14 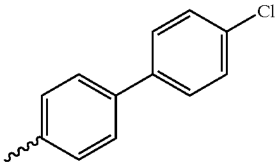
TABLE 90-continued
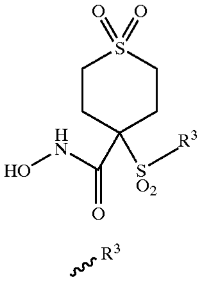
15 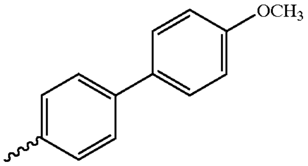
16 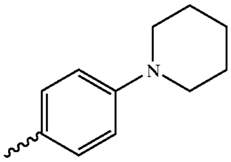
17 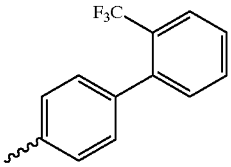
18 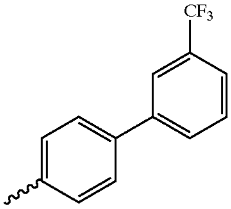
19 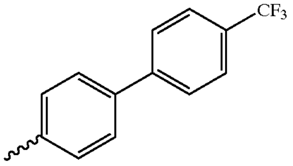
20 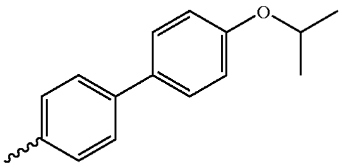
21 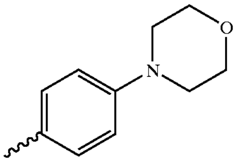

TABLE 91
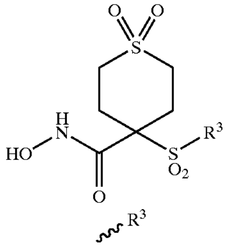
| | |
|---|---|
| 1 | 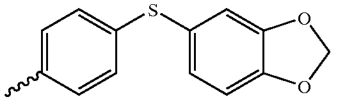 |
| 2 | 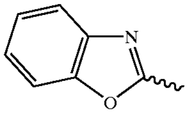 |
| 3 | 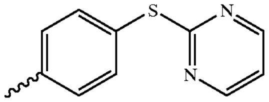 |
| 4 | 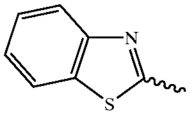 |
| 5 | 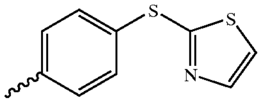 |
| 6 | 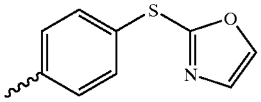 |
| 7 | 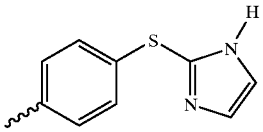 |
| 8 | 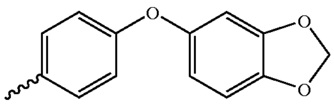 |
| 9 | 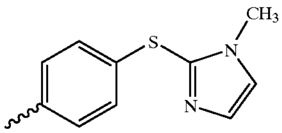 |
| 10 | 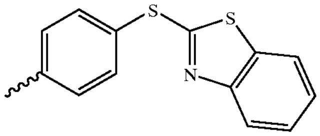 |
TABLE 91-continued
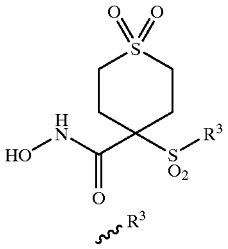
| | |
|---|---|
| 11 | 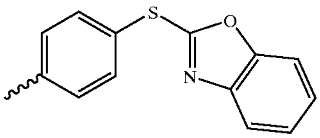 |
TABLE 92
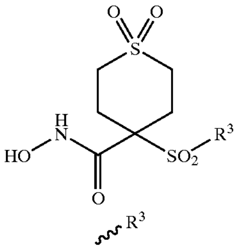
| | |
|---|---|
| 1 | 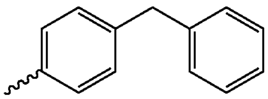 |
| 2 | 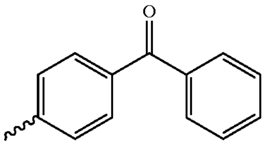 |
| 3 | 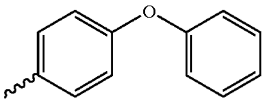 |
| 4 | 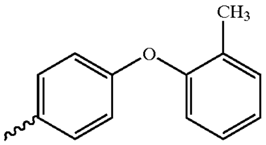 |
| 5 | 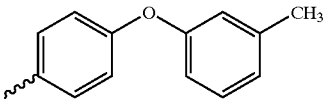 |
| 6 | 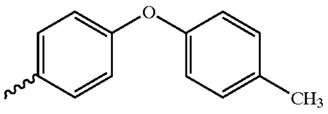 |

TABLE 92-continued
| | |
|---|---|
| | 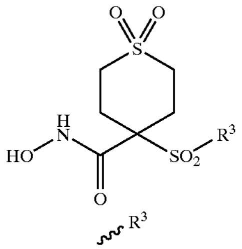 |
| 7 | 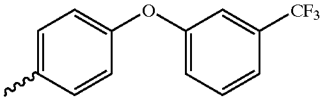 |
| 8 | 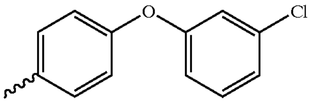 |
| 9 | 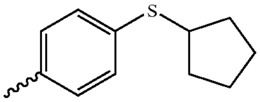 |
| 10 | 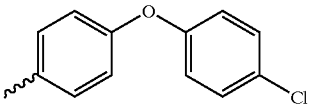 |
| 11 | 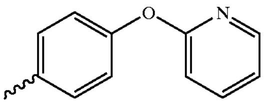 |
| 12 | 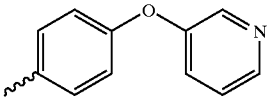 |
| 13 | 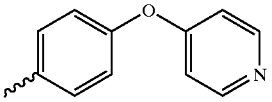 |
| 14 | 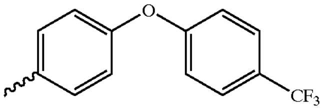 |
| 15 | 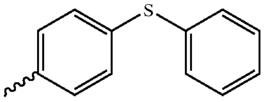 |
| 16 | 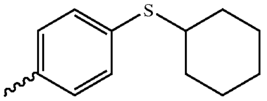 |
| 17 | 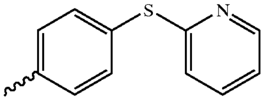 |
TABLE 92-continued
| | |
|---|---|
| | 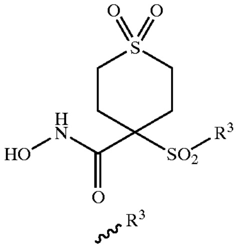 |
| 18 | 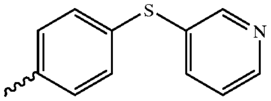 |
| 19 | 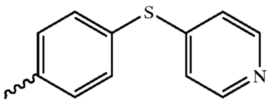 |
| 20 | 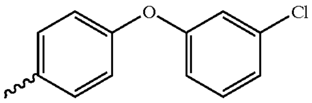 |
| 21 | 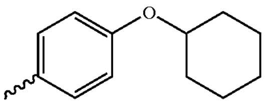 |
TABLE 93
| | |
|---|---|
| | 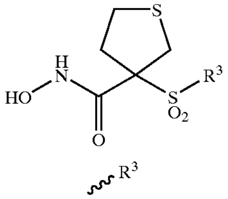 |
| 1 | 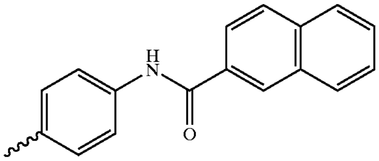 |
| 2 | 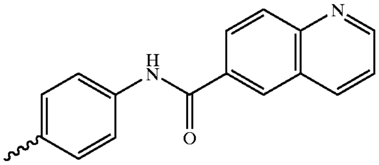 |
| 3 | 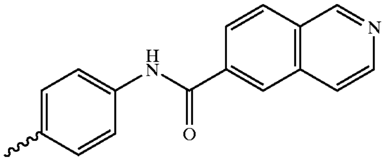 |

TABLE 93-continued
| | |
|---|---|
| | 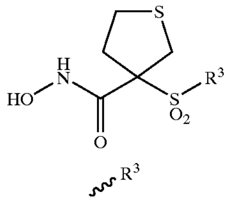 |
| 4 | 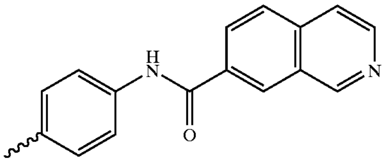 |
| 5 | 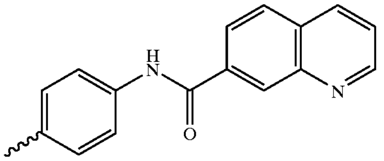 |
| 6 | 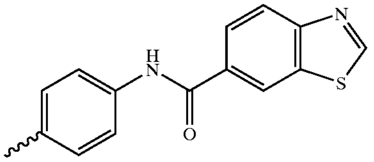 |
| 7 | 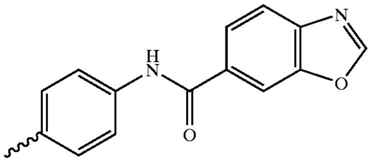 |
| 8 | 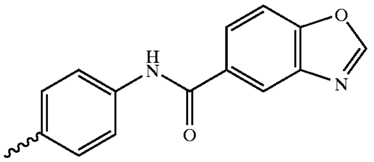 |
| 9 | 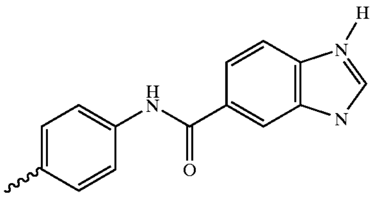 |
| 10 | 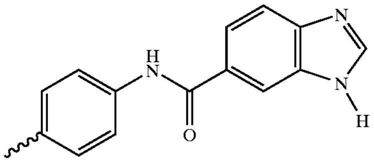 |
TABLE 93-continued
| | |
|---|---|
| | 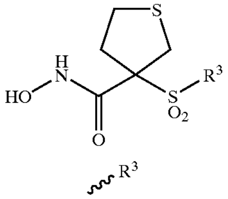 |
| 11 | 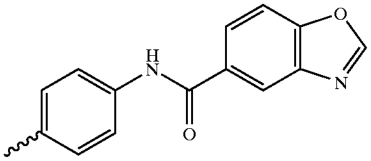 |
| 12 | 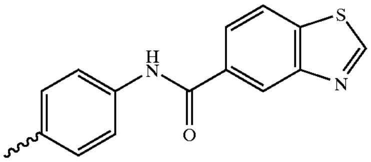 |
| 13 | 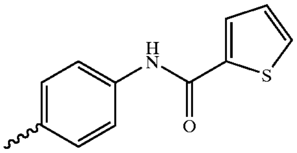 |
| 14 | 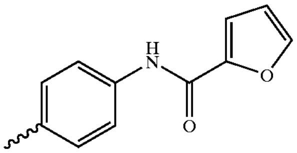 |
| 15 | 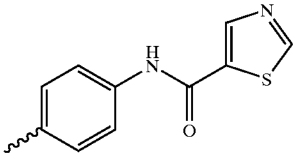 |
| 16 | 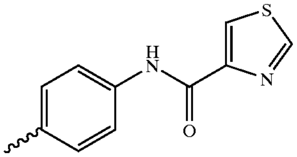 |
| 17 | 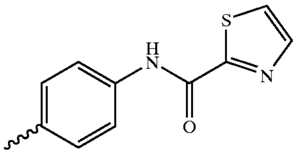 |
| 18 | 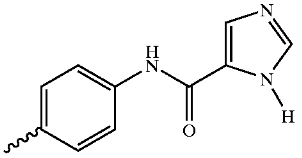 |

TABLE 94
| | |
|---|---|
| | 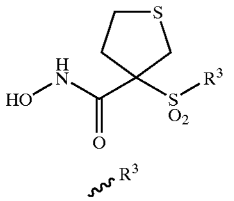 |
| 1 | 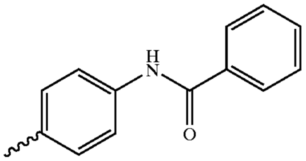 |
| 2 | 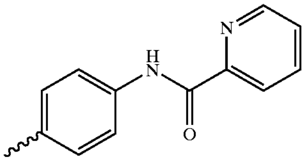 |
| 3 | 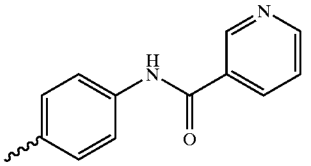 |
| 4 | 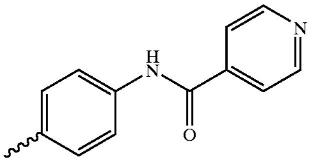 |
| 5 | 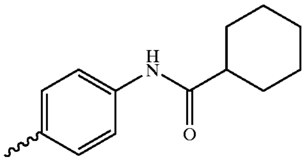 |
| 6 | 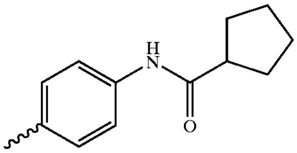 |
| 7 | 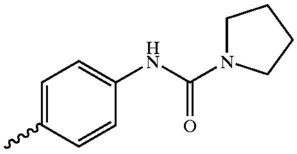 |
| 8 | 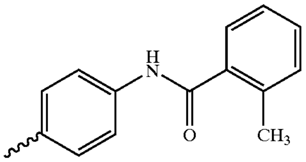 |
TABLE 94-continued
| | |
|---|---|
| | 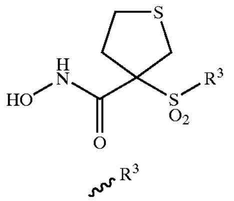 |
| 9 | 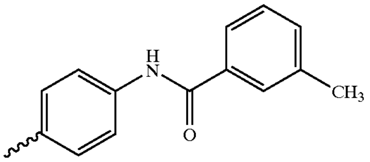 |
| 10 | 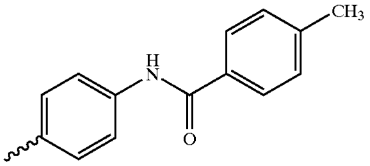 |
| 11 | 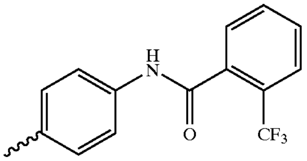 |
| 12 | 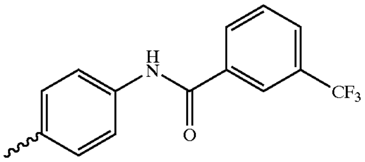 |
| 13 | 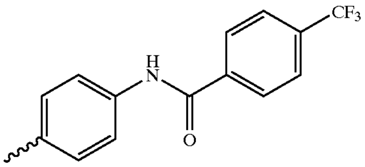 |
| 14 | 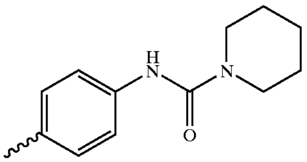 |
| 15 | 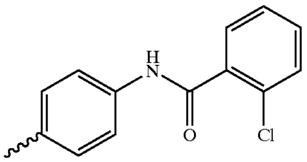 |
| 16 | 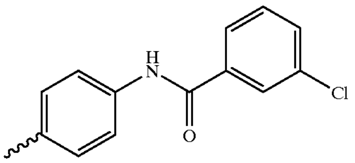 |

TABLE 94-continued
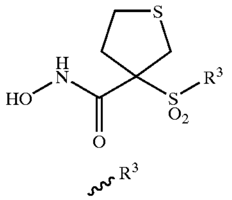
| | |
|---|---|
| 17 | 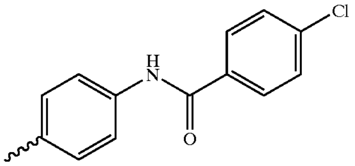 |
| 18 | 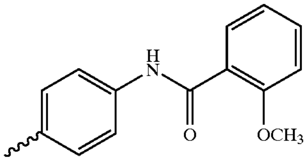 |
| 19 | 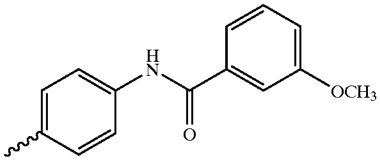 |
| 20 | 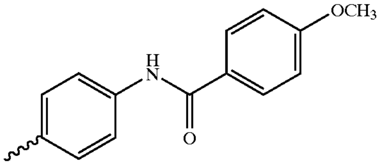 |
| 21 | 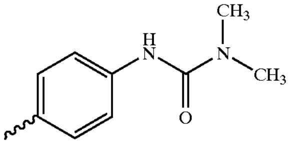 |
TABLE 95
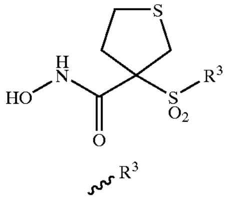
| | |
|---|---|
| 1 | 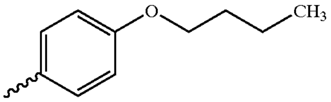 |
TABLE 95-continued
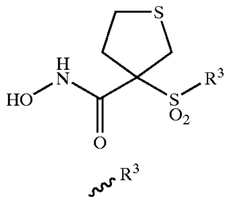
| | |
|---|---|
| 2 | 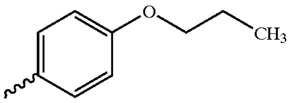 |
| 3 | 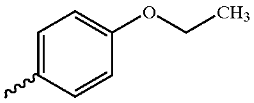 |
| 4 | 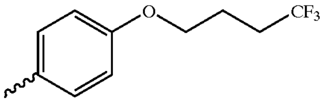 |
| 5 | 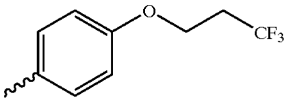 |
| 6 | 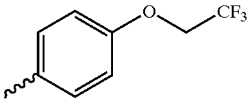 |
| 7 | 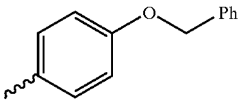 |
| 8 | 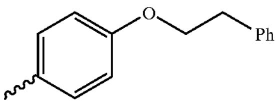 |
| 9 | 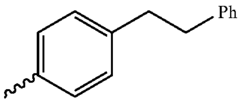 |
| 10 | 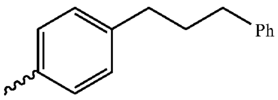 |
| 11 | 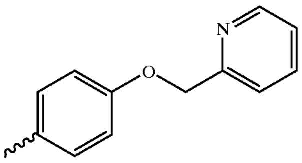 |

TABLE 95-continued
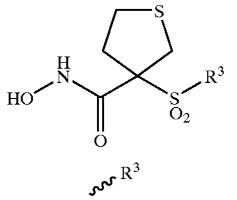
| | |
|---|---|
| 12 | 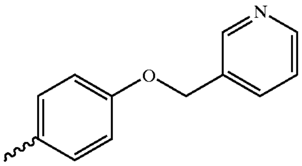 |
| 13 | 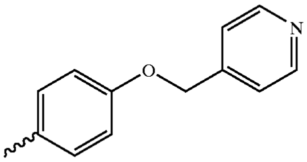 |
| 14 | 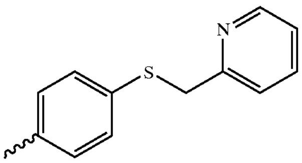 |
| 15 | 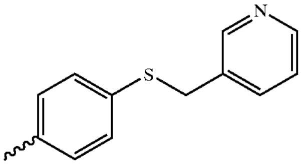 |
| 16 | 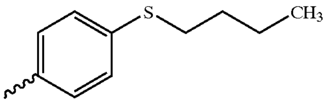 |
| 17 | 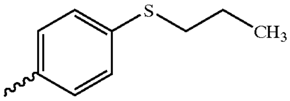 |
| 18 | 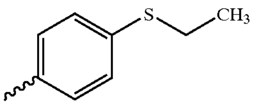 |
| 19 | 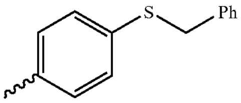 |
| 20 | 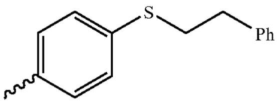 |
TABLE 95-continued
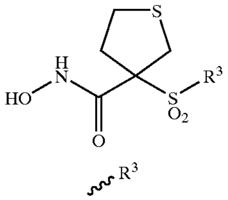
| | |
|---|---|
| 21 | 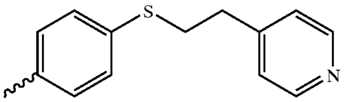 |
| 22 | 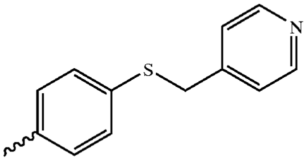 |
TABLE 96
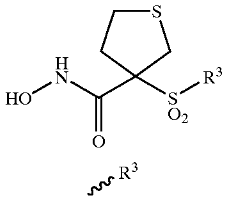
| | |
|---|---|
| 1 | 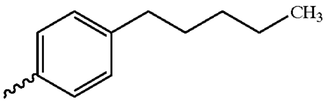 |
| 2 | 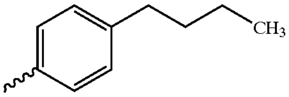 |
| 3 | 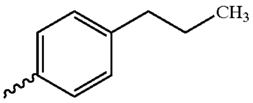 |
| 4 | 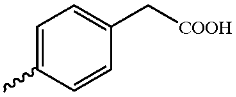 |
| 5 | 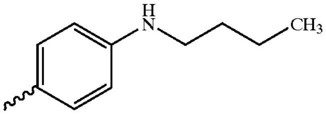 |
| 6 | 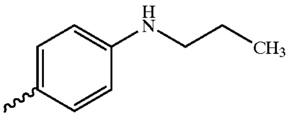 |

TABLE 96-continued
| | 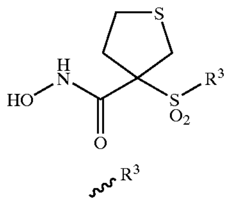 |
|---|---|
| 7 | 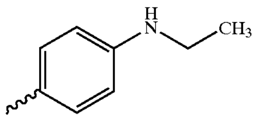 |
| 8 | 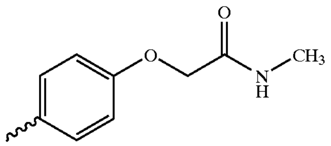 |
| 9 | 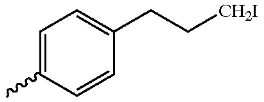 |
| 10 | 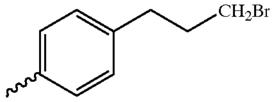 |
| 11 | 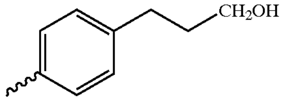 |
| 12 | 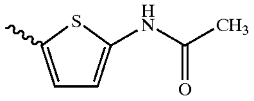 |
| 13 | 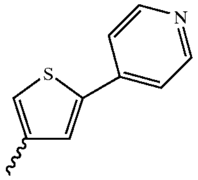 |
| 14 | 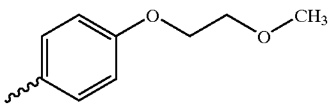 |
| 15 | 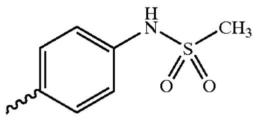 |
| 16 | 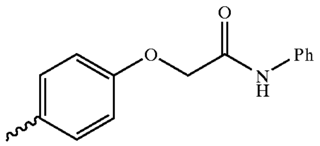 |
TABLE 96-continued
| | 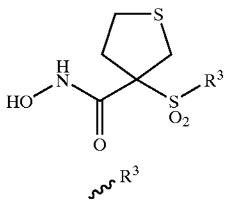 |
|---|---|
| 17 | 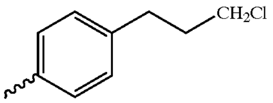 |
| 18 | 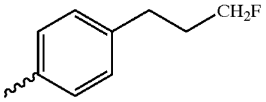 |
| 19 | 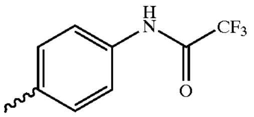 |
| 20 | 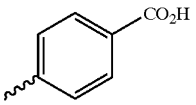 |
| 21 | 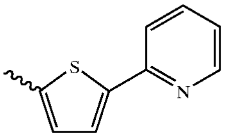 |
| 22 | 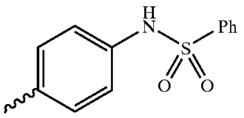 |
| 23 | 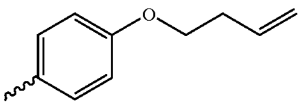 |
| 24 | 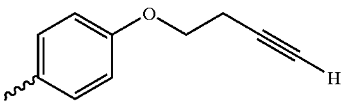 |
| 25 | 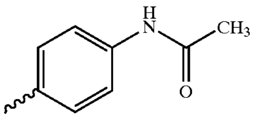 |
| 26 | 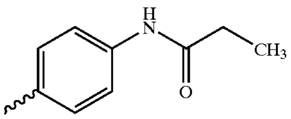 |
| 27 | 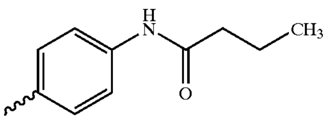 |

TABLE 96-continued
| | |
|---|---|
| | 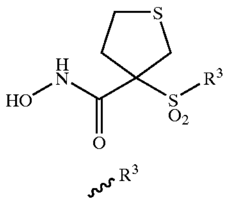 |
| 28 | 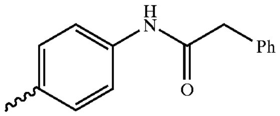 |
| 29 | 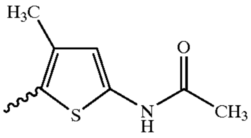 |
| 30 | 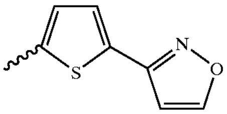 |
TABLE 97
| | |
|---|---|
| | 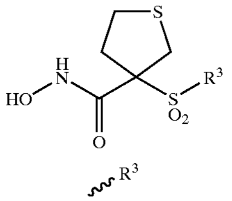 |
| 1 | 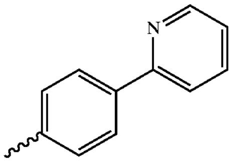 |
| 2 | 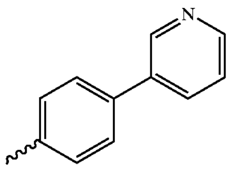 |
| 3 | 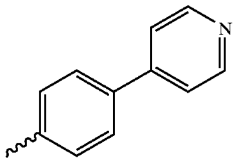 |
TABLE 97-continued
| | |
|---|---|
| | 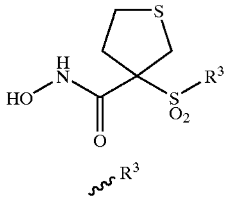 |
| 4 | 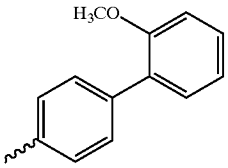 |
| 5 | 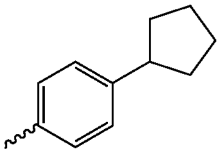 |
| 6 | 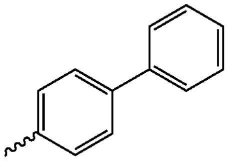 |
| 7 | 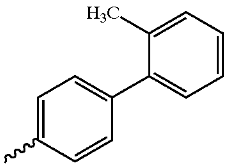 |
| 8 | 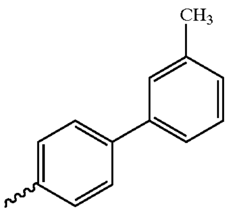 |
| 9 | 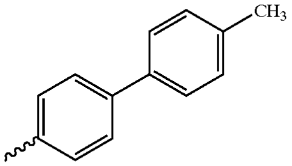 |
| 10 | 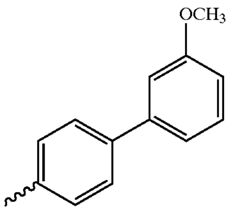 |

TABLE 97-continued
| | |
|---|---|
| 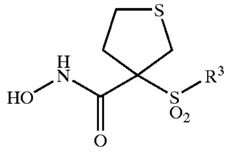 | |
| 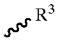 | |
| 11 | 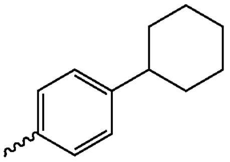 |
| 12 | 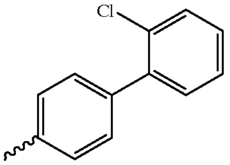 |
| 13 | 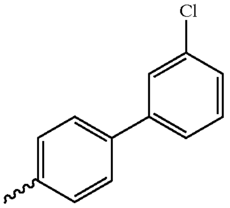 |
| 14 | 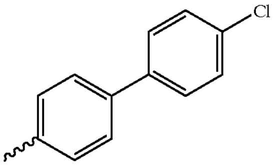 |
| 15 | 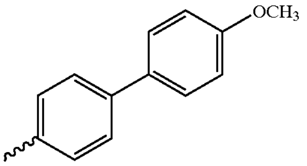 |
| 16 | 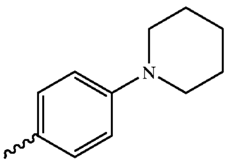 |
| 17 | 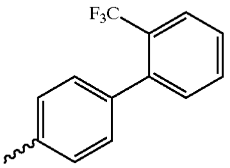 |
TABLE 97-continued
| | |
|---|---|
| 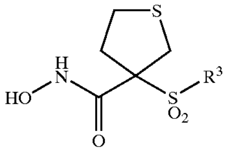 | |
| 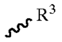 | |
| 18 | 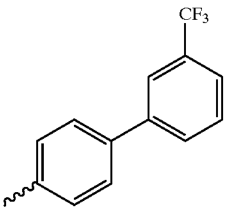 |
| 19 | 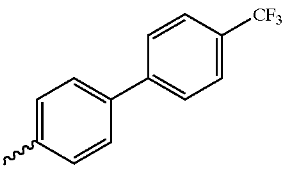 |
| 20 | 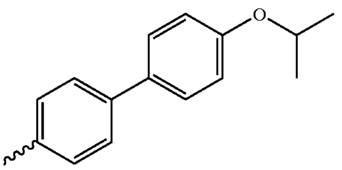 |
| 21 | 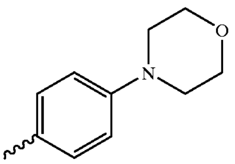 |
TABLE 98
| | |
|---|---|
| 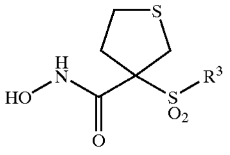 | |
| 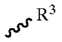 | |
| 1 | 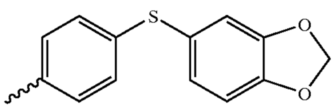 |
| 2 | 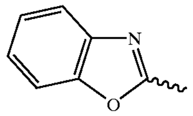 |

TABLE 98-continued
| | |
|---|---|
| | 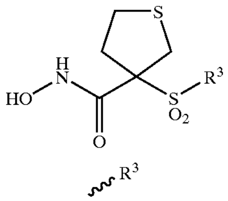 |
| 3 | 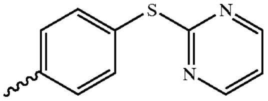 |
| 4 | 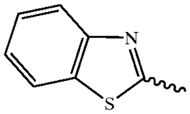 |
| 5 | 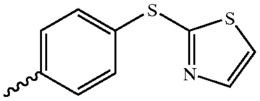 |
| 6 | 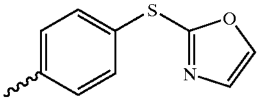 |
| 7 | 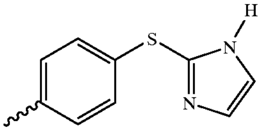 |
| 8 | 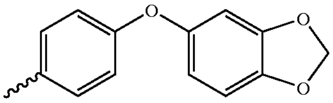 |
| 9 | 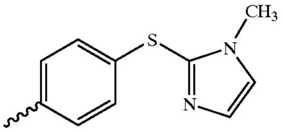 |
| 10 | 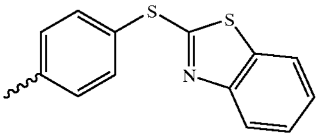 |
| 11 | 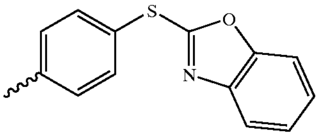 |
TABLE 99
| | |
|---|---|
| | 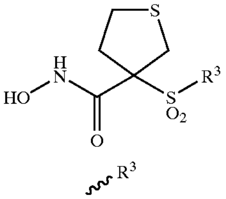 |
| 1 | 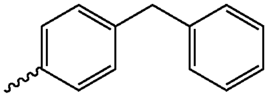 |
| 2 | 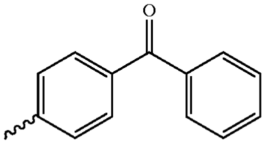 |
| 3 | 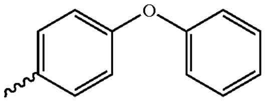 |
| 4 | 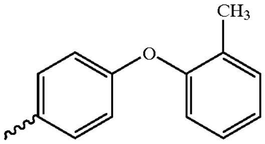 |
| 5 | 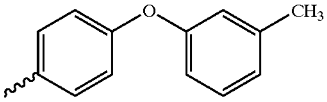 |
| 6 | 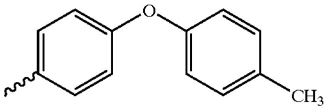 |
| 7 | 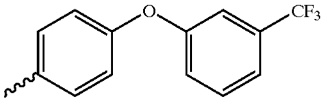 |
| 8 | 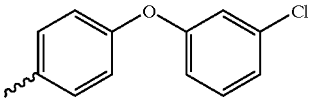 |
| 9 | 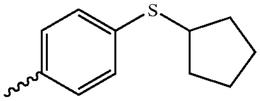 |
| 10 | 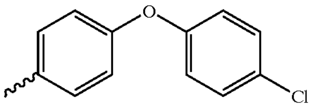 |
| 11 | 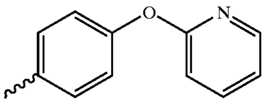 |

TABLE 99-continued
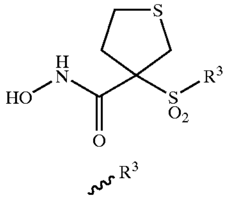
| | |
|---|---|
| 12 | 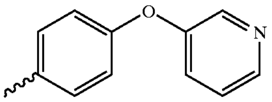 |
| 13 | 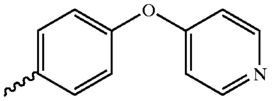 |
| 14 | 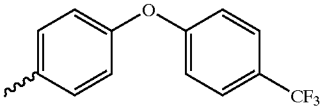 |
| 15 | 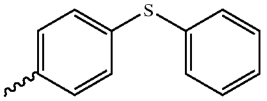 |
| 16 | 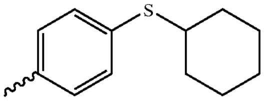 |
| 17 | 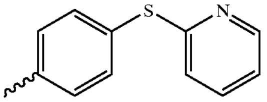 |
| 18 | 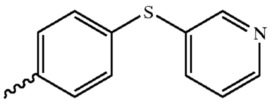 |
| 19 | 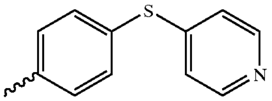 |
| 20 | 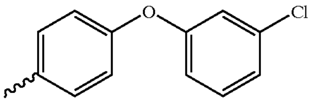 |
| 21 | 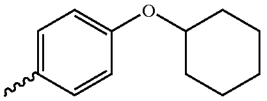 |
TABLE 100
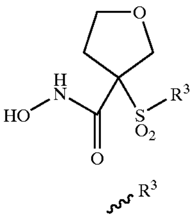
| | |
|---|---|
| 1 | 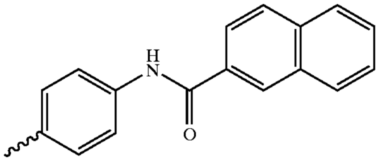 |
| 2 | 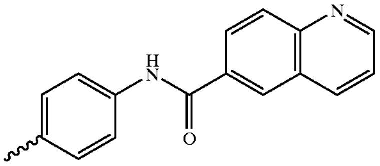 |
| 3 | 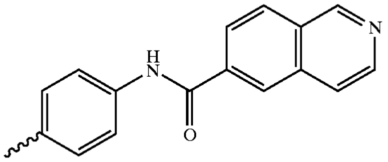 |
| 4 | 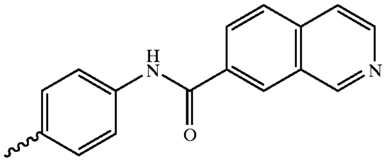 |
| 5 | 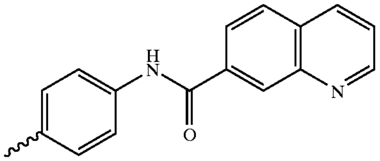 |
| 6 | 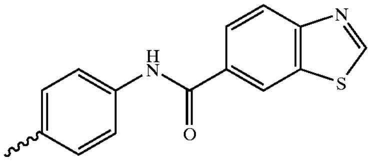 |
| 7 | 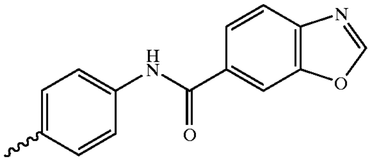 |

TABLE 100-continued
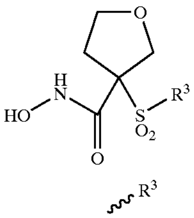
| | |
|---|---|
| 8 | 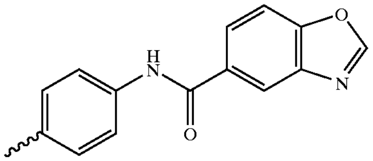 |
| 9 | 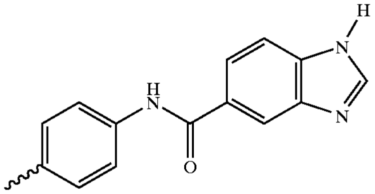 |
| 10 | 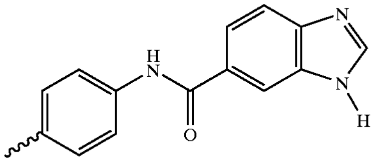 |
| 11 | 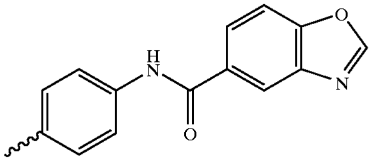 |
| 12 | 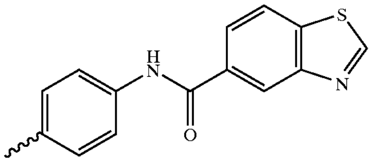 |
| 13 | 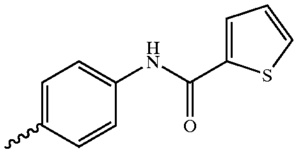 |
| 14 | 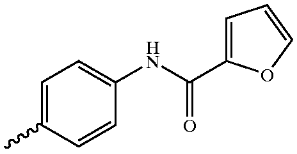 |
TABLE 100-continued
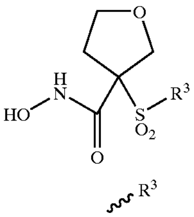
| | |
|---|---|
| 15 | 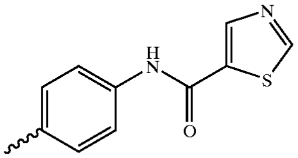 |
| 16 | 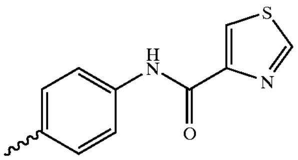 |
| 17 | 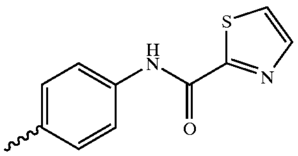 |
| 18 | 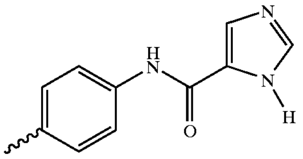 |
TABLE 101
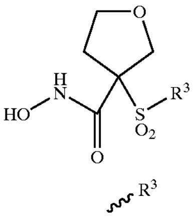
| | |
|---|---|
| 1 | 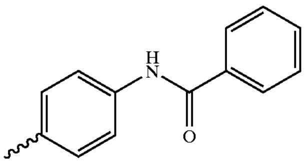 |
| 2 | 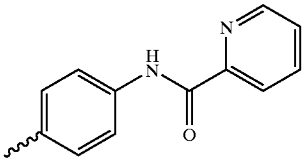 |

TABLE 101-continued
| 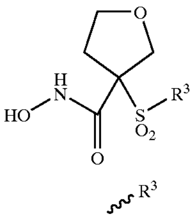 | |
|---|---|
| 3 | 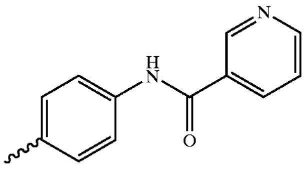 |
| 4 | 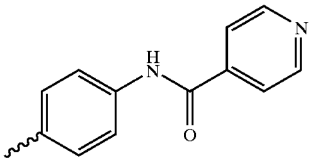 |
| 5 | 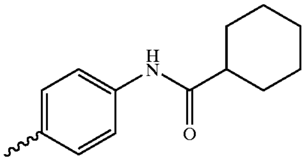 |
| 6 | 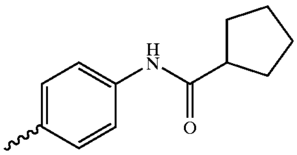 |
| 7 | 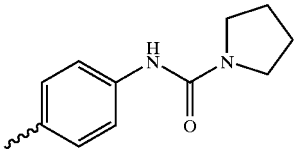 |
| 8 | 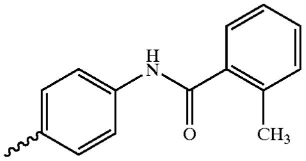 |
| 9 | 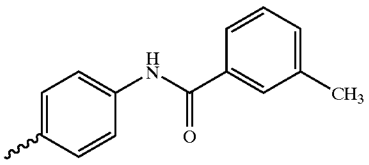 |
TABLE 101-continued
| 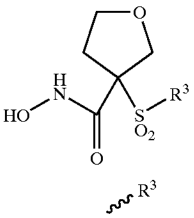 | |
|---|---|
| 10 | 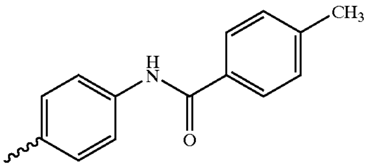 |
| 11 | 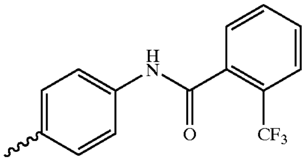 |
| 12 | 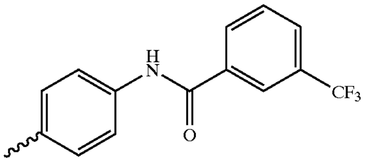 |
| 13 | 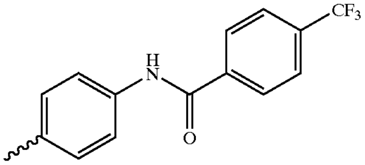 |
| 14 | 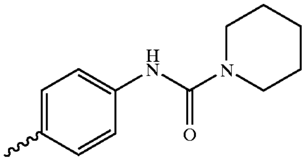 |
| 15 | 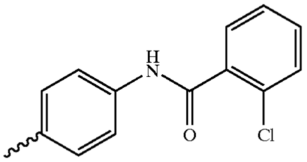 |
| 16 | 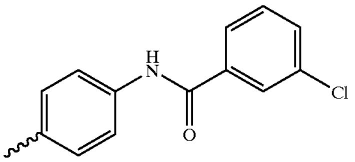 |

TABLE 101-continued
| | |
|---|---|
| | 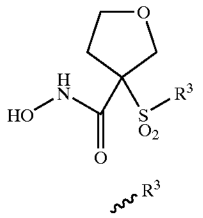 |
| 17 | 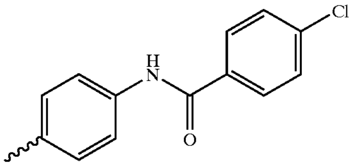 |
| 18 | 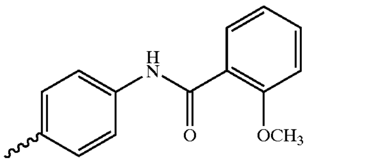 |
| 19 | 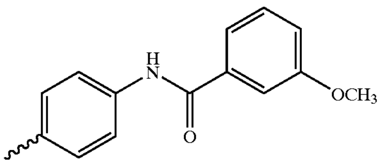 |
| 20 | 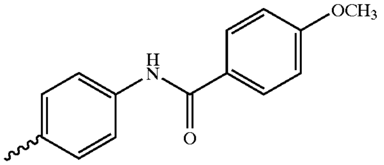 |
| 21 | 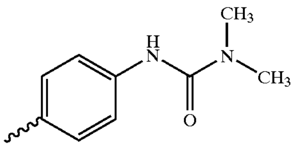 |
TABLE 102
| | |
|---|---|
| | 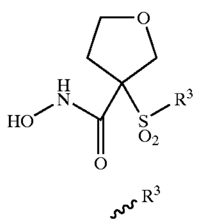 |
| 1 | 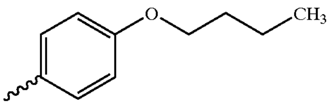 |
TABLE 102-continued
| | |
|---|---|
| | 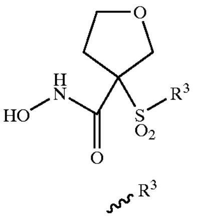 |
| 2 | 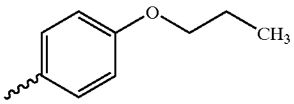 |
| 3 | 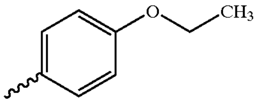 |
| 4 | 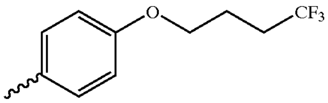 |
| 5 | 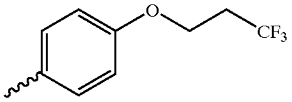 |
| 6 | 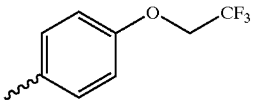 |
| 7 | 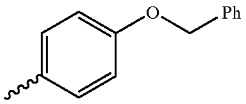 |
| 8 | 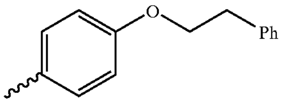 |
| 9 | 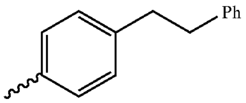 |
| 10 | 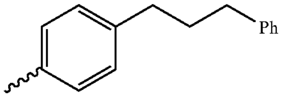 |
| 11 | 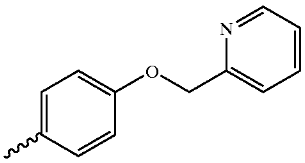 |

TABLE 102-continued
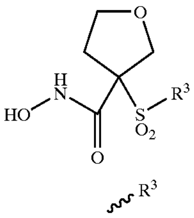
12
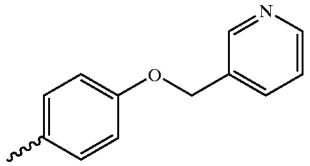
13
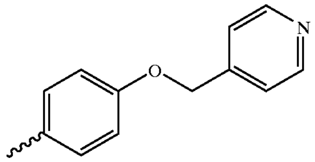
14
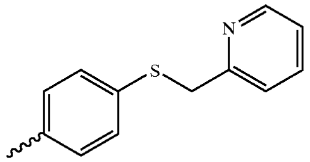
15
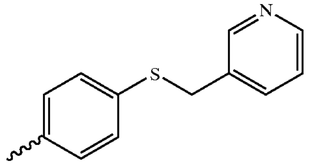
16
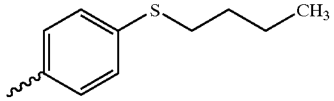
17
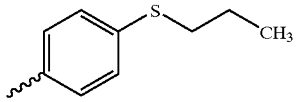
18
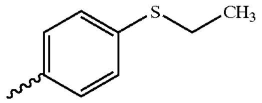
19
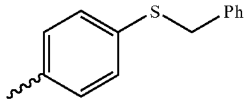
20
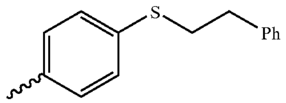
TABLE 102-continued
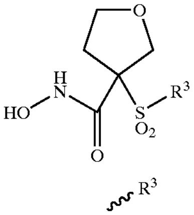
21
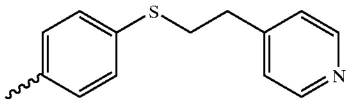
22
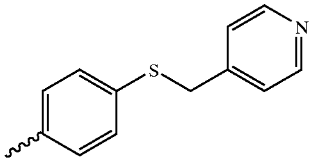
TABLE 103
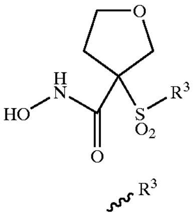
1
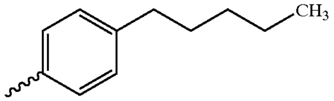
2
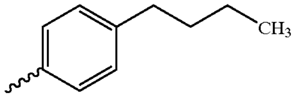
3
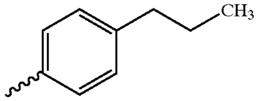
4
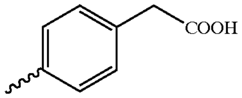
5
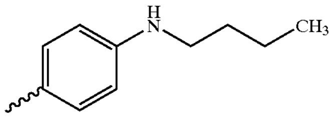
6
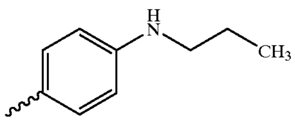

TABLE 103-continued
| | |
|---|---|
| | 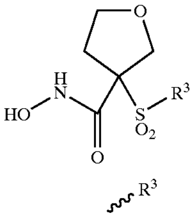 |
| 7 | 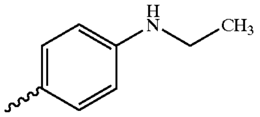 |
| 8 | 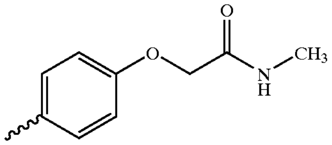 |
| 9 | 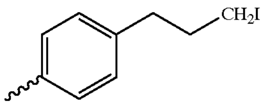 |
| 10 | 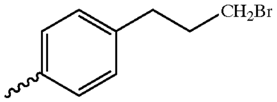 |
| 11 | 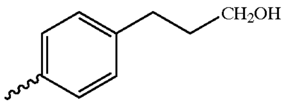 |
| 12 | 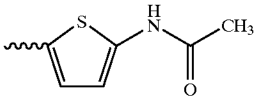 |
| 13 | 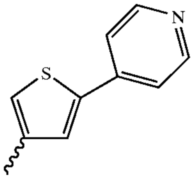 |
| 14 | 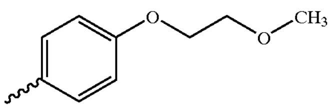 |
| 15 | 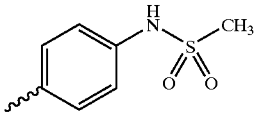 |
| 16 | 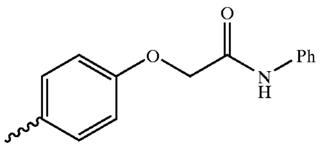 |
TABLE 103-continued
| | |
|---|---|
| | 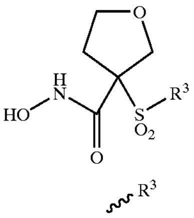 |
| 17 | 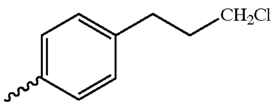 |
| 18 | 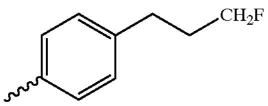 |
| 19 | 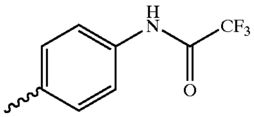 |
| 20 | 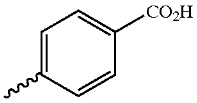 |
| 21 | 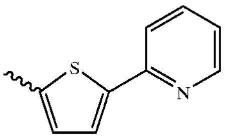 |
| 22 | 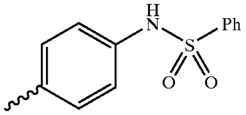 |
| 23 | 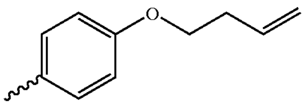 |
| 24 | 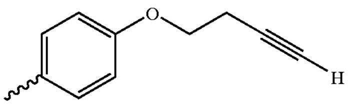 |
| 25 | 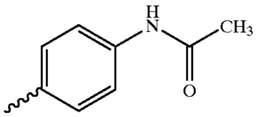 |
| 26 | 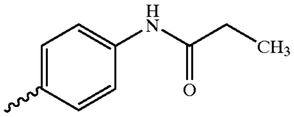 |

TABLE 103-continued
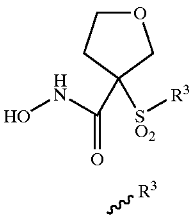
| | |
|---|---|
| 27 | 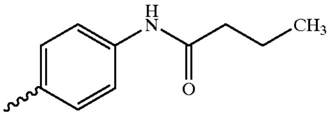 |
| 28 | 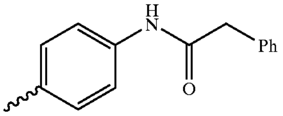 |
| 29 | 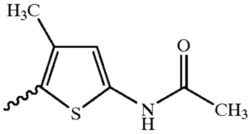 |
| 30 | 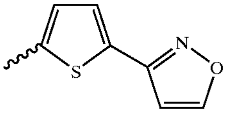 |
TABLE 104
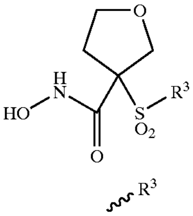
| | |
|---|---|
| 1 | 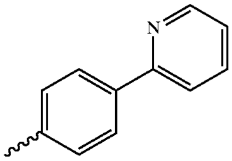 |
| 2 | 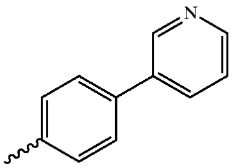 |
| 3 | 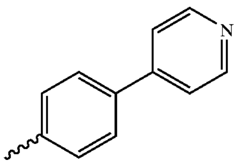 |
TABLE 104-continued
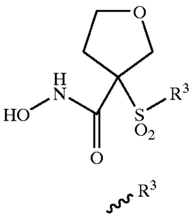
| | |
|---|---|
| 4 | 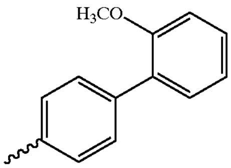 |
| 5 | 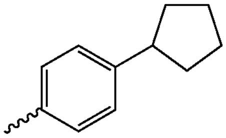 |
| 6 | 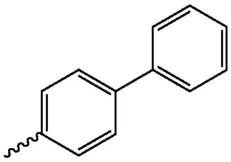 |
| 7 | 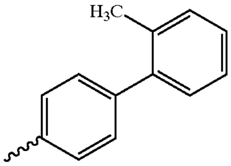 |
| 8 | 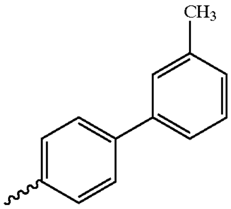 |
| 9 | 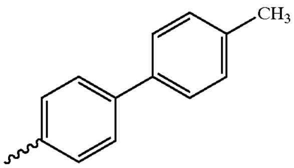 |
| 10 | 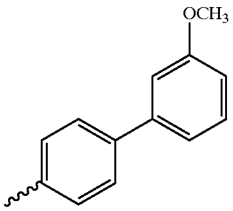 |

TABLE 104-continued
| | |
|---|---|
| 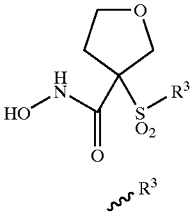 | |
| 11 | 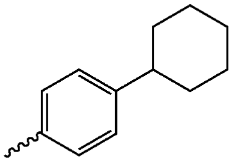 |
| 12 | 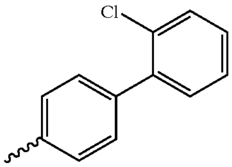 |
| 13 | 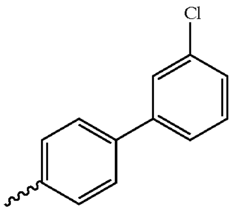 |
| 14 | 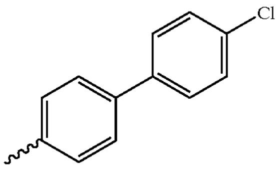 |
| 15 | 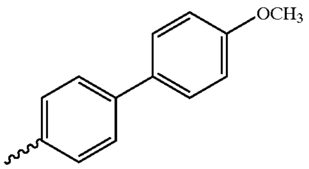 |
| 16 | 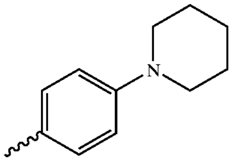 |
| 17 | 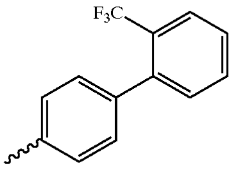 |
TABLE 104-continued
| | |
|---|---|
| 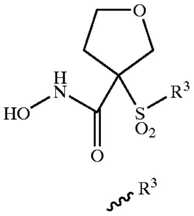 | |
| 18 | 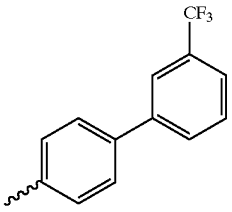 |
| 19 | 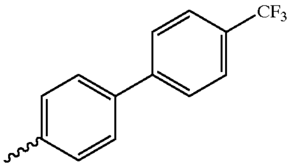 |
| 20 | 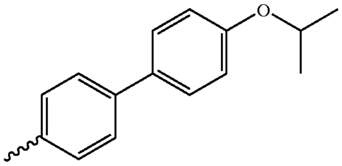 |
| 21 | 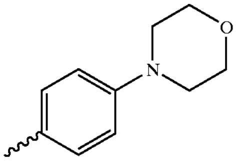 |
TABLE 105
| | |
|---|---|
| 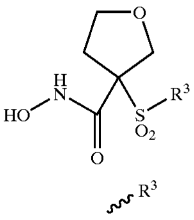 | |
| 1 | 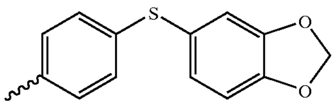 |
| 2 | 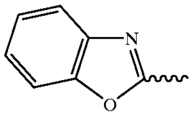 |

TABLE 105-continued
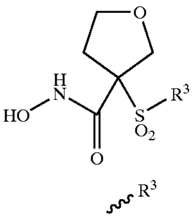
| | |
|---|---|
| 3 | 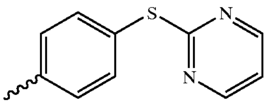 |
| 4 | 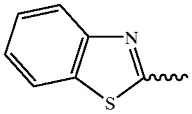 |
| 5 | 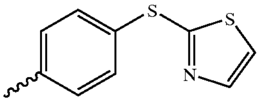 |
| 6 | 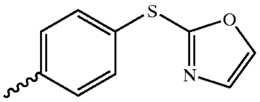 |
| 7 | 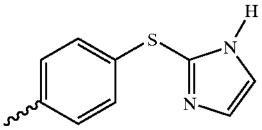 |
| 8 | 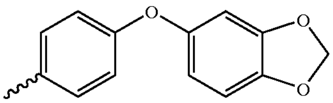 |
| 9 | 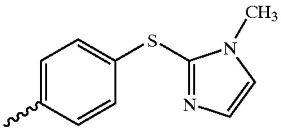 |
| 10 | 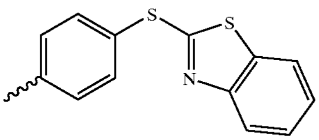 |
| 11 | 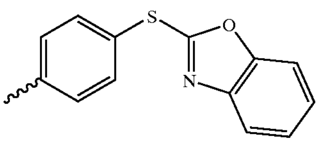 |
TABLE 106
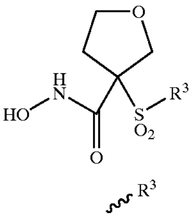
| | |
|---|---|
| 1 | 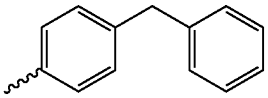 |
| 2 | 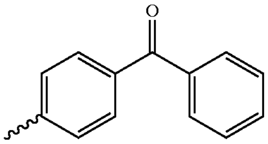 |
| 3 | 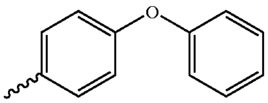 |
| 4 | 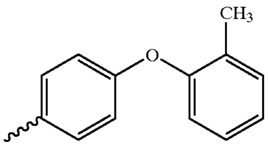 |
| 5 | 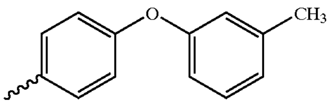 |
| 6 | 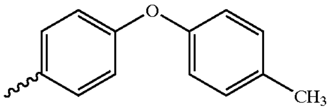 |
| 7 | 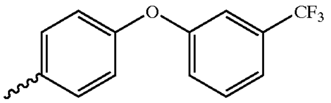 |
| 8 | 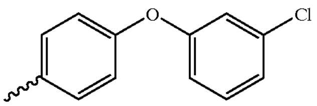 |
| 9 | 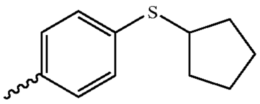 |
| 10 | 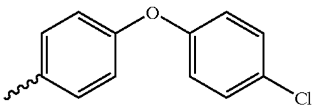 |

TABLE 106-continued
| | |
|---|---|
| | 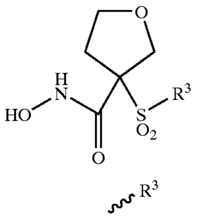 |
| 11 | 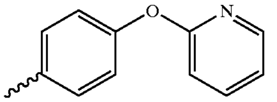 |
| 12 | 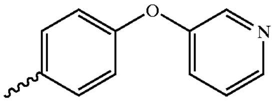 |
| 13 | 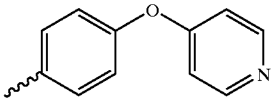 |
| 14 | 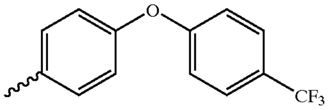 |
| 15 | 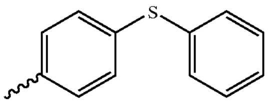 |
| 16 | 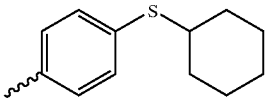 |
| 17 | 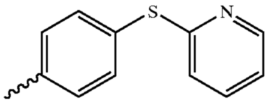 |
| 18 | 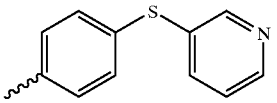 |
| 19 | 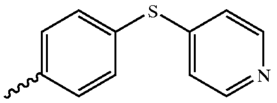 |
| 20 | 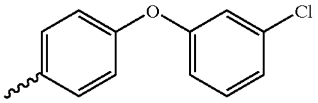 |
| 21 | 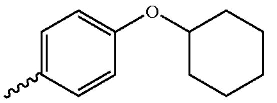 |
TABLE 107
| | |
|---|---|
| | 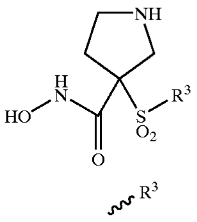 |
| 1 | 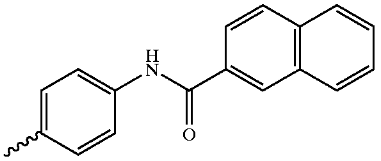 |
| 2 | 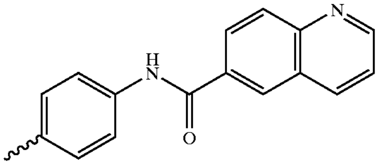 |
| 3 | 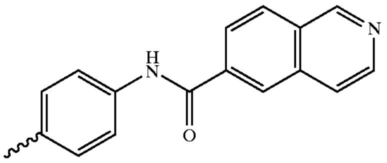 |
| 4 | 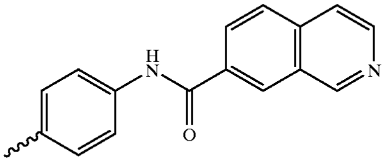 |
| 5 | 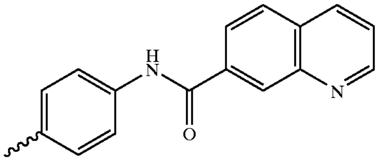 |
| 6 | 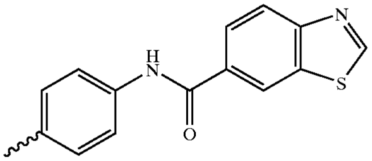 |
| 7 | 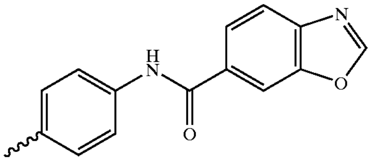 |

TABLE 107-continued
| 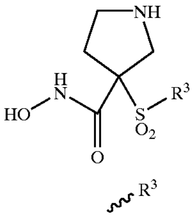 | |
|---|---|
| 8 | 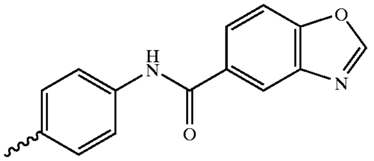 |
| 9 | 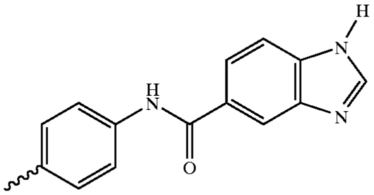 |
| 10 | 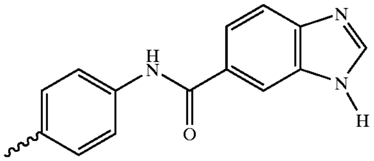 |
| 11 | 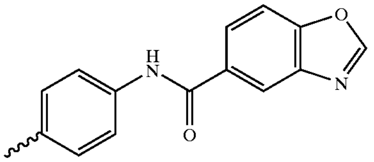 |
| 12 | 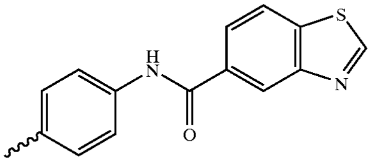 |
| 13 | 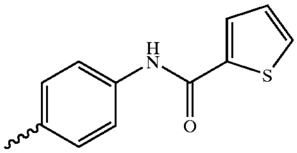 |
| 14 | 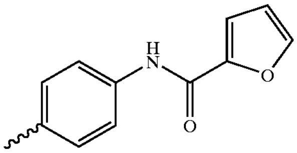 |
TABLE 107-continued
| 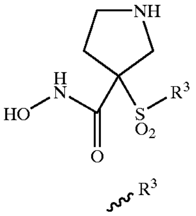 | |
|---|---|
| 15 | 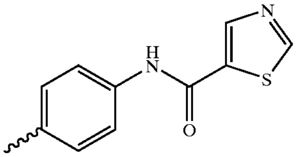 |
| 16 | 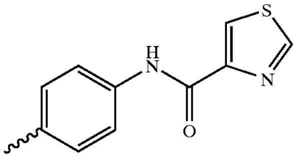 |
| 17 | 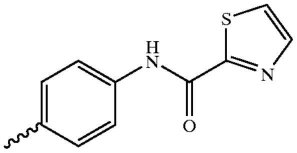 |
| 18 | 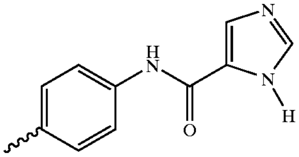 |
TABLE 108
| 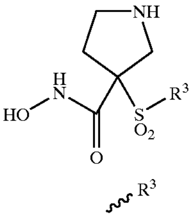 | |
|---|---|
| 1 | 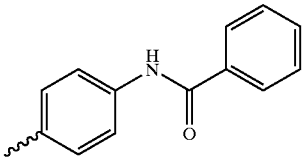 |
| 2 | 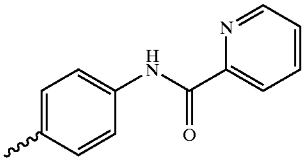 |

TABLE 108-continued
| | 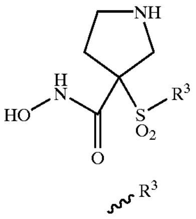 |
|---|---|
| 3 | 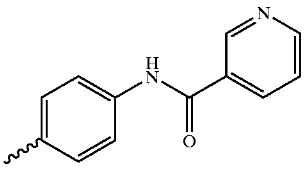 |
| 4 | 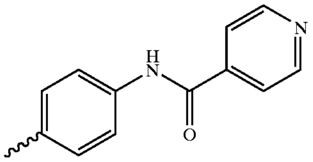 |
| 5 | 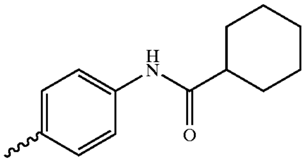 |
| 6 | 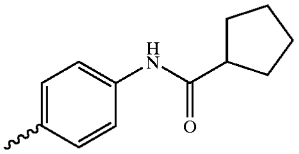 |
| 7 | 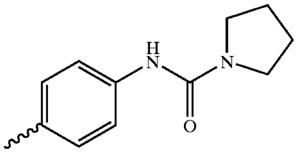 |
| 8 | 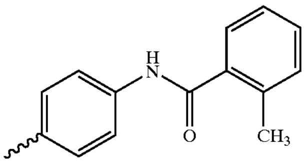 |
| 9 | 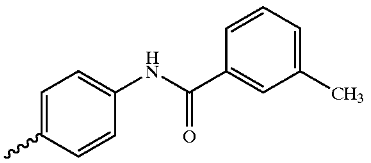 |
| 10 | 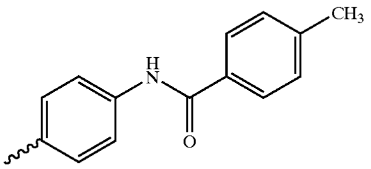 |
TABLE 108-continued
| | 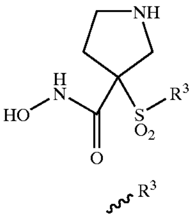 |
|---|---|
| 11 | 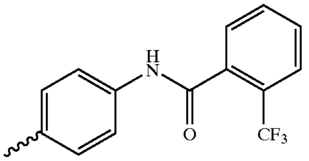 |
| 12 | 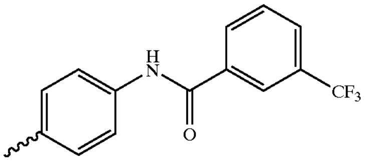 |
| 13 | 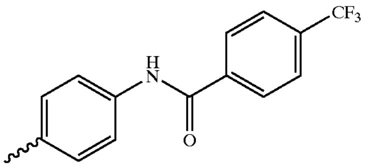 |
| 14 | 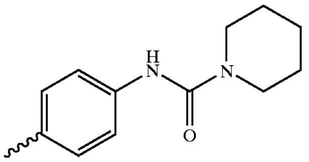 |
| 15 | 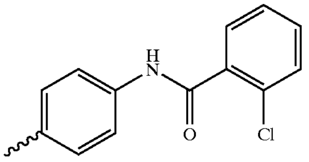 |
| 16 | 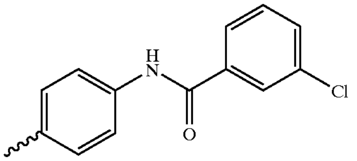 |
| 17 | 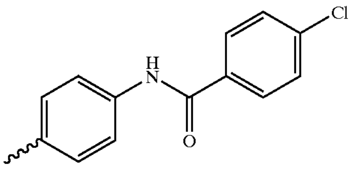 |

TABLE 108-continued
| 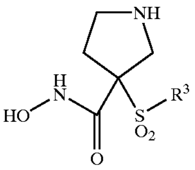 | |
|---|---|
| | 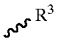 |
| 18 | 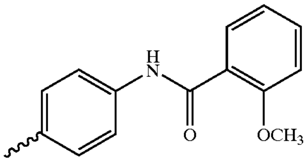 |
| 19 | 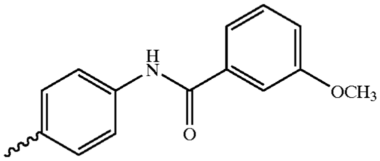 |
| 20 | 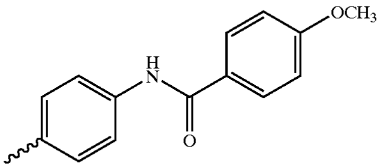 |
| 21 | 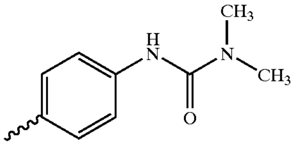 |
TABLE 109
| 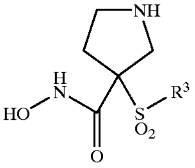 | |
|---|---|
| | 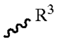 |
| 1 | 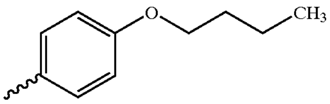 |
| 2 | 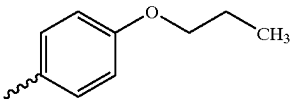 |
| 3 | 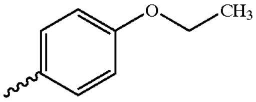 |
TABLE 109-continued
| 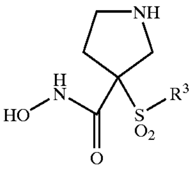 | |
|---|---|
| | 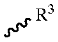 |
| 4 | 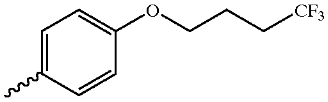 |
| 5 | 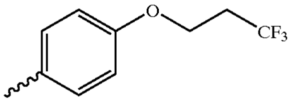 |
| 6 | 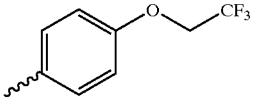 |
| 7 | 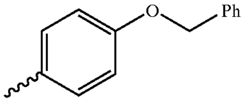 |
| 8 | 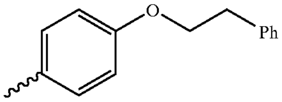 |
| 9 | 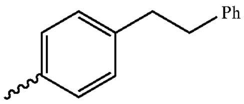 |
| 10 | 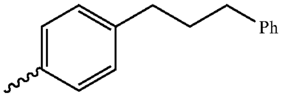 |
| 11 | 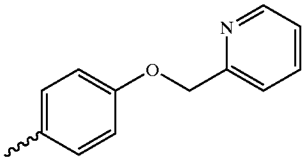 |
| 12 | 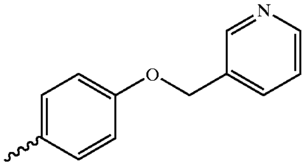 |
| 13 | 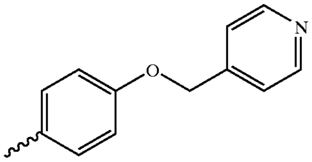 |

TABLE 109-continued
| | 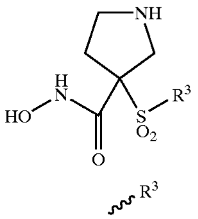 |
|---|---|
| 14 | 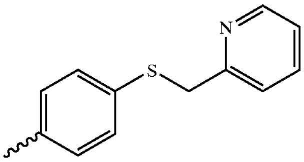 |
| 15 | 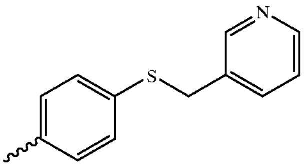 |
| 16 | 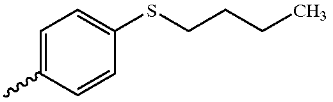 |
| 17 | 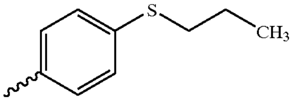 |
| 18 | 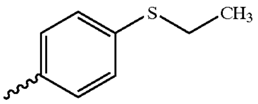 |
| 19 | 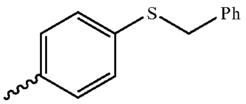 |
| 20 | 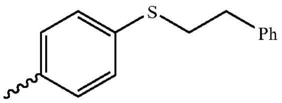 |
| 21 | 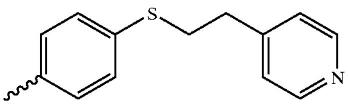 |
| 22 | 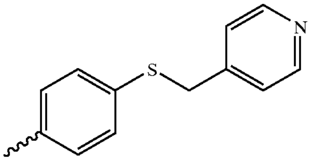 |
TABLE 110
| | 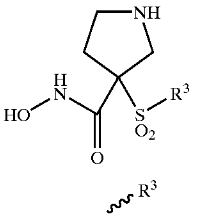 |
|---|---|
| 1 | 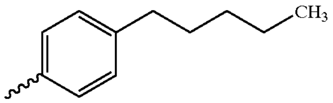 |
| 2 | 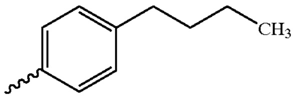 |
| 3 | 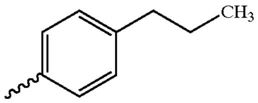 |
| 4 | 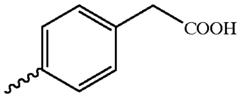 |
| 5 | 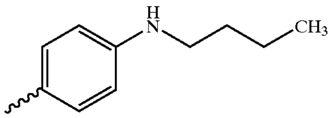 |
| 6 | 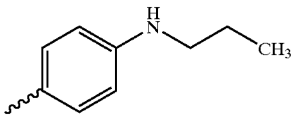 |
| 7 | 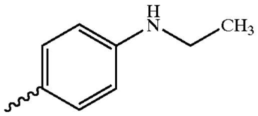 |
| 8 | 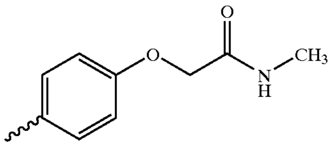 |
| 9 | 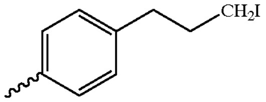 |
| 10 | 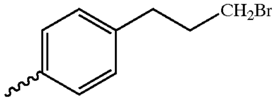 |
| 11 | 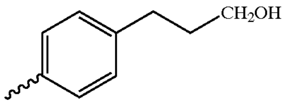 |

TABLE 110-continued
| | |
|---|---|
| | 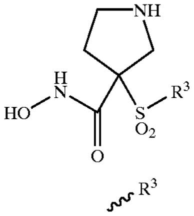 |
| 12 | 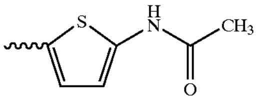 |
| 13 | 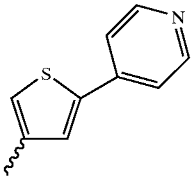 |
| 14 | 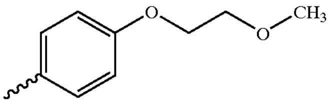 |
| 15 | 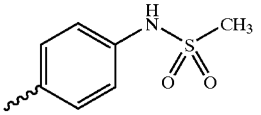 |
| 16 | 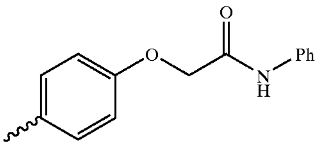 |
| 17 | 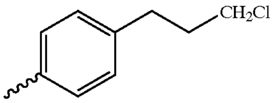 |
| 18 | 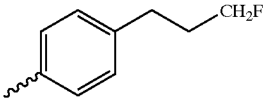 |
| 19 | 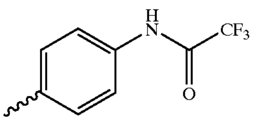 |
| 20 | 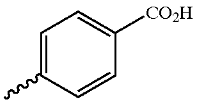 |
| 21 | 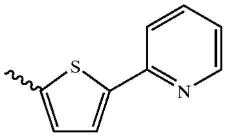 |
TABLE 110-continued
| | |
|---|---|
| | 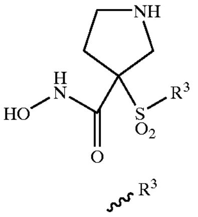 |
| 22 | 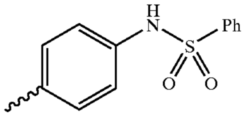 |
| 23 | 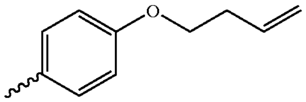 |
| 24 | 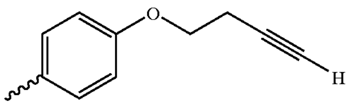 |
| 25 | 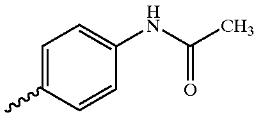 |
| 26 | 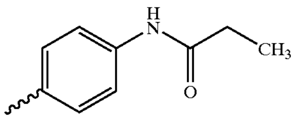 |
| 27 | 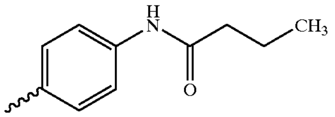 |
| 28 | 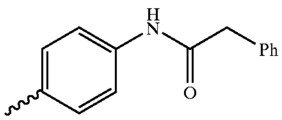 |
| 29 | 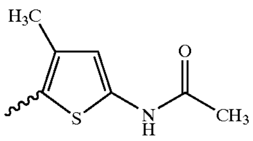 |
| 30 | 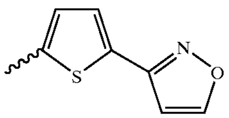 |

TABLE 111
| | |
|---|---|
| | 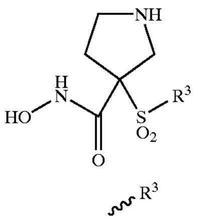 |
| 1 | 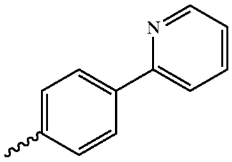 |
| 2 | 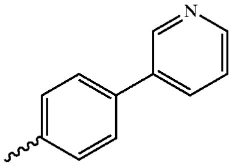 |
| 3 | 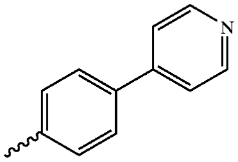 |
| 4 | 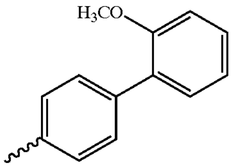 |
| 5 | 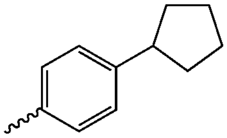 |
| 6 | 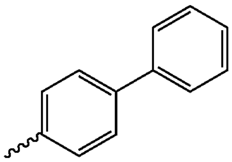 |
| 7 | 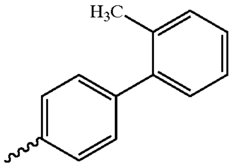 |
TABLE 111-continued
| | |
|---|---|
| | 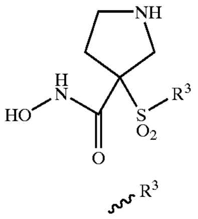 |
| 8 | 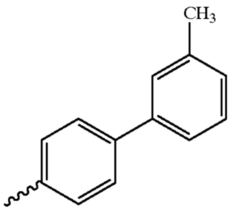 |
| 9 | 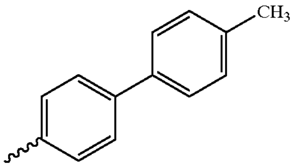 |
| 10 | 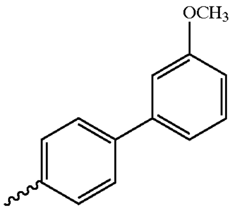 |
| 11 | 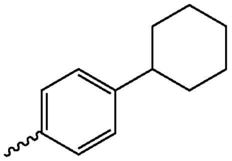 |
| 12 | 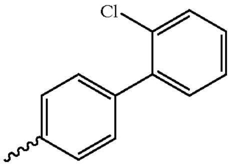 |
| 13 | 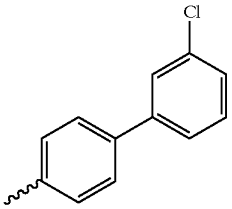 |
| 14 | 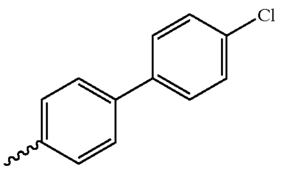 |

TABLE 111-continued
| | |
|---|---|
| | 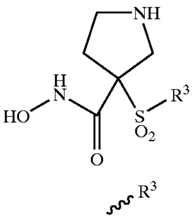 |
| 15 | 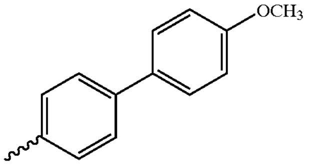 |
| 16 | 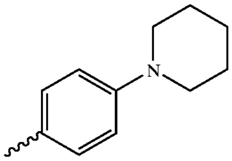 |
| 17 | 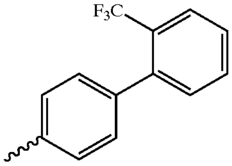 |
| 18 | 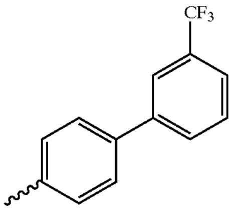 |
| 19 | 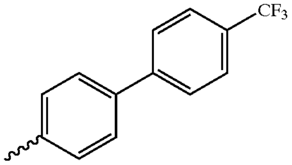 |
| 20 | 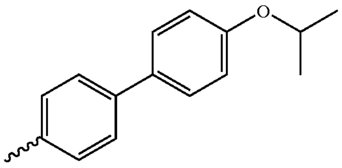 |
| 21 | 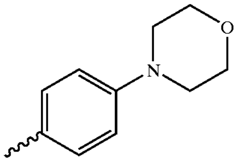 |
TABLE 112
| | |
|---|---|
| | 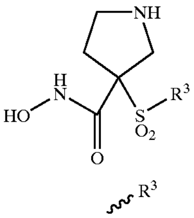 |
| 1 | 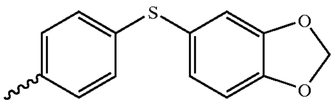 |
| 2 | 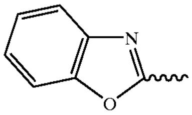 |
| 3 | 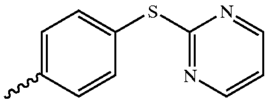 |
| 4 | 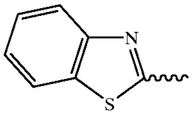 |
| 5 | 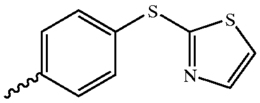 |
| 6 | 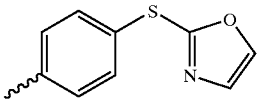 |
| 7 | 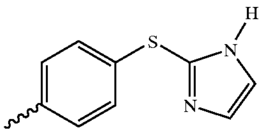 |
| 8 | 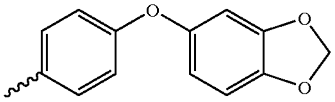 |
| 9 | 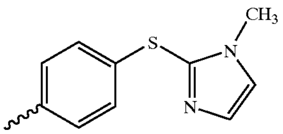 |
| 10 | 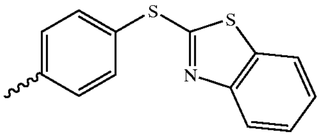 |

TABLE 112-continued
| | |
|---|---|
| | 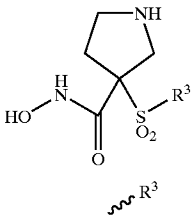 |
| 11 | 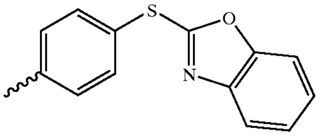 |
TABLE 113
| | |
|---|---|
| | 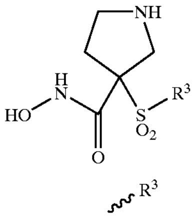 |
| 1 | 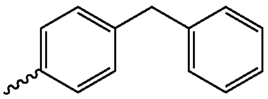 |
| 2 | 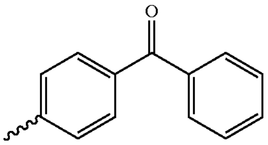 |
| 3 | 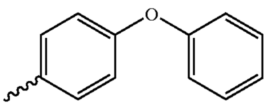 |
| 4 | 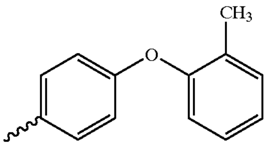 |
| 5 | 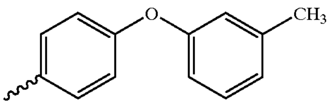 |
| 6 | 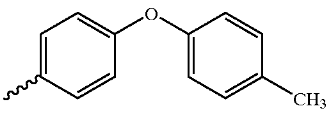 |
| 7 | 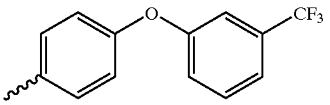 |
TABLE 113-continued
| | |
|---|---|
| | 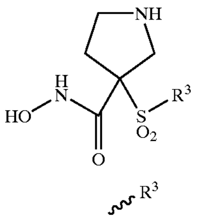 |
| 8 | 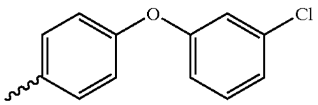 |
| 9 | 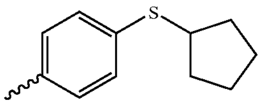 |
| 10 | 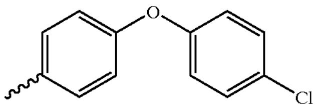 |
| 11 | 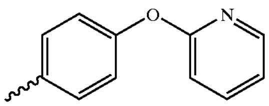 |
| 12 | 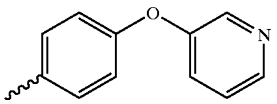 |
| 13 | 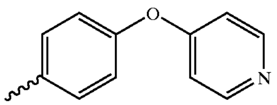 |
| 14 | 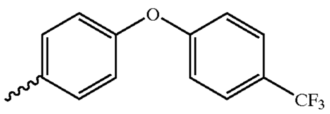 |
| 15 | 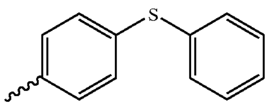 |
| 16 | 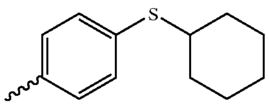 |
| 17 | 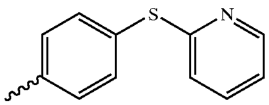 |
| 18 | 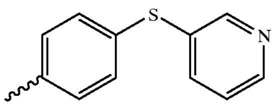 |

TABLE 113-continued
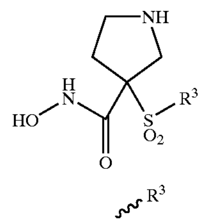
19
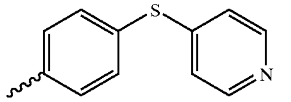
20
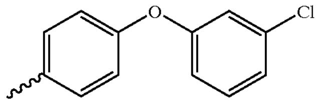
21
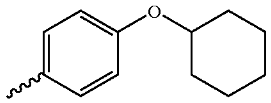
TABLE 114
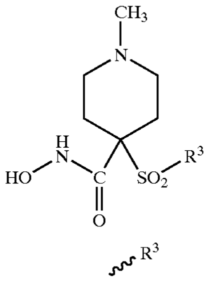
1
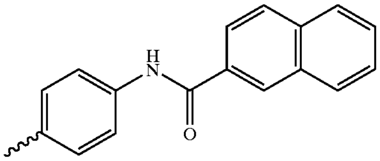
2
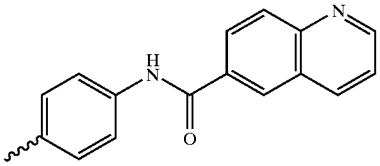
3
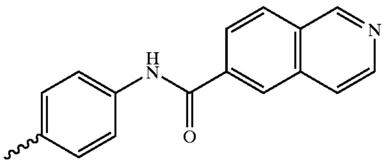
TABLE 114-continued
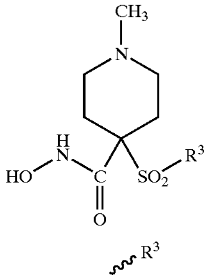
4
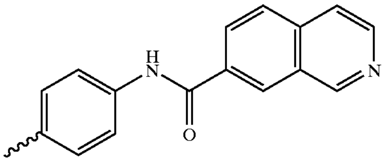
5
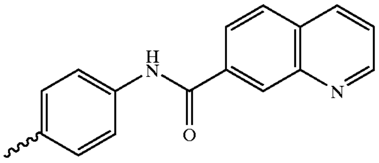
6
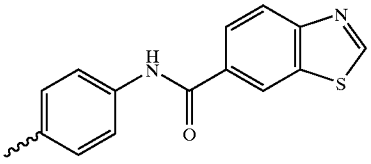
7
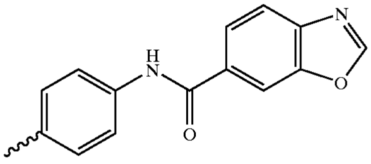
8
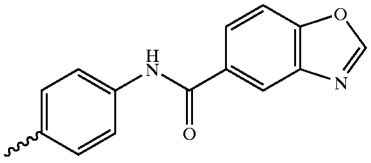
9
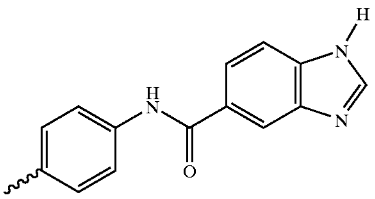
10
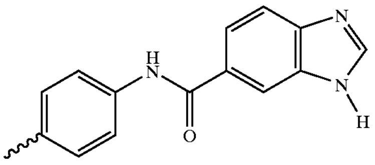

TABLE 114-continued
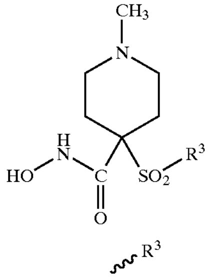
11 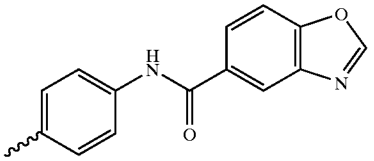
12 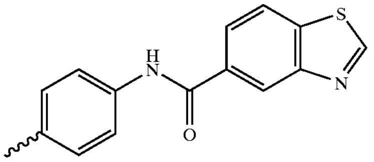
13 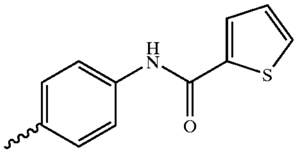
14 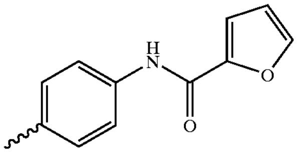
15 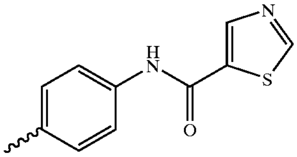
16 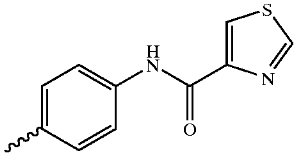
17 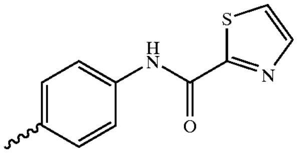
TABLE 114-continued
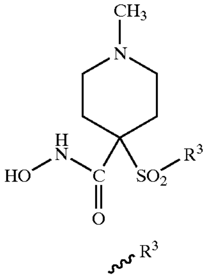
18 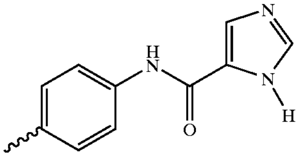
TABLE 115
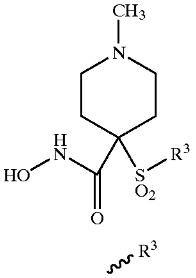
1 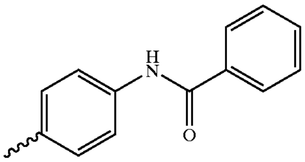
2 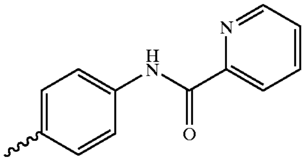
3 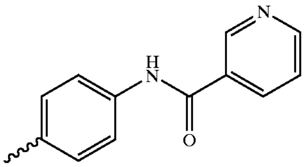
4 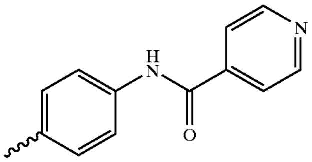

TABLE 115-continued
| | 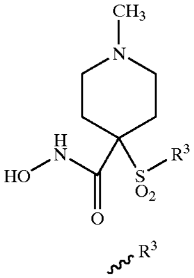 |
|---|---|
| 5 | 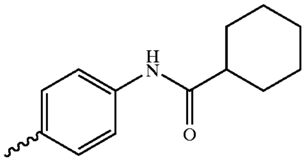 |
| 6 | 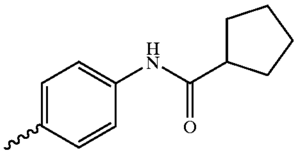 |
| 7 | 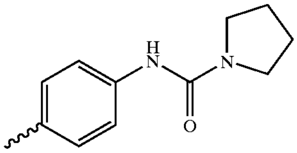 |
| 8 | 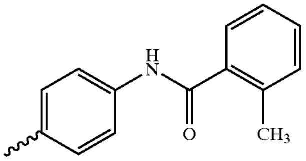 |
| 9 | 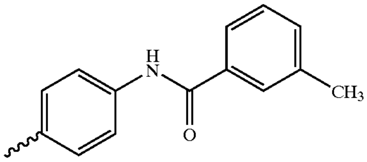 |
| 10 | 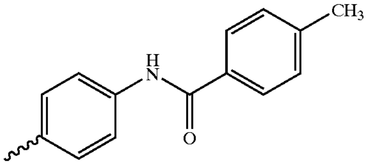 |
| 11 | 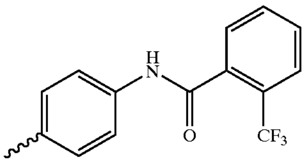 |
TABLE 115-continued
| | 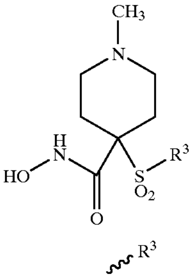 |
|---|---|
| 12 | 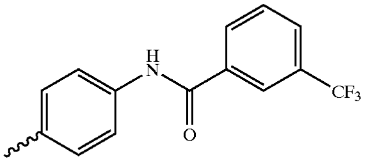 |
| 13 | 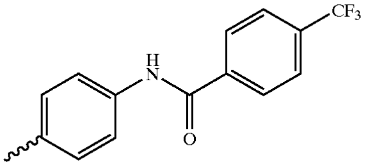 |
| 14 | 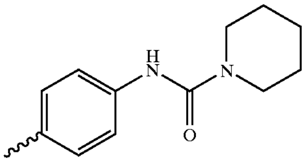 |
| 15 | 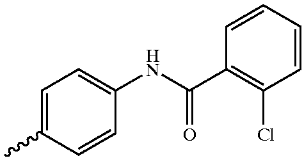 |
| 16 | 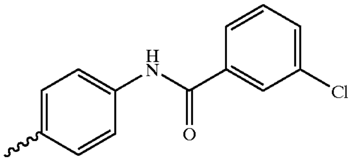 |
| 17 | 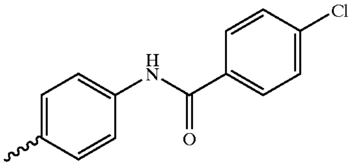 |
| 18 | 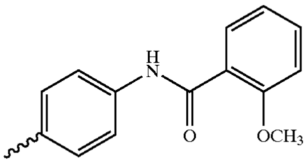 |

TABLE 115-continued
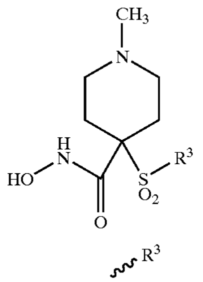
19
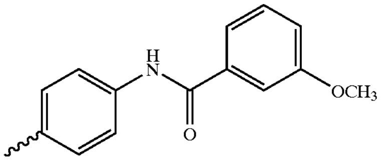
20
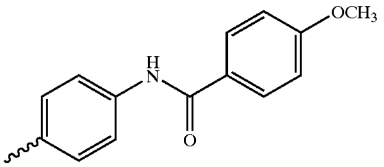
21
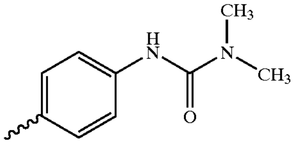
TABLE 116
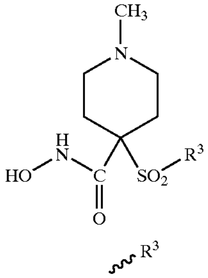
1
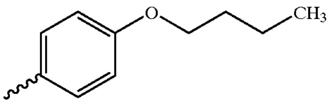
2
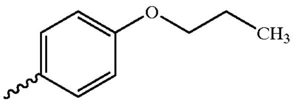
3
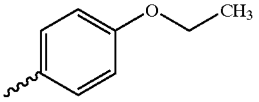
TABLE 116-continued
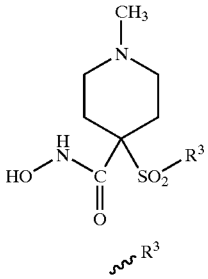
4
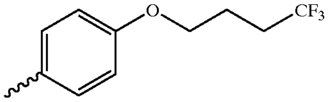
5
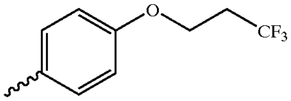
6
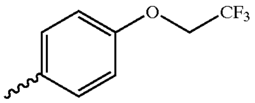
7
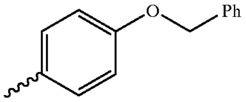
8
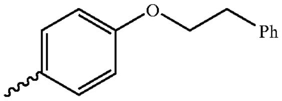
9
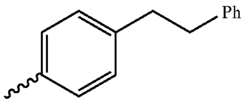
10
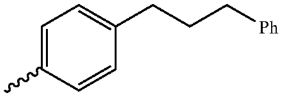
11
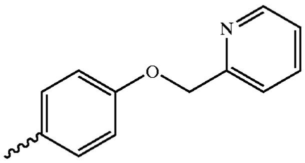
12
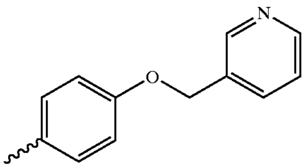

TABLE 116-continued
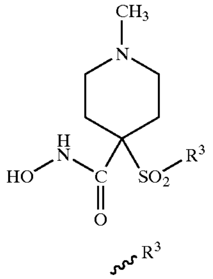
| | |
|---|---|
| 13 | 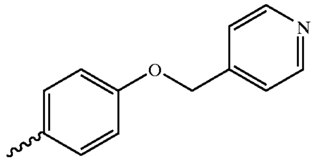 |
| 14 | 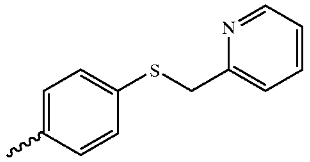 |
| 15 | 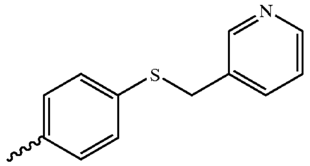 |
| 16 | 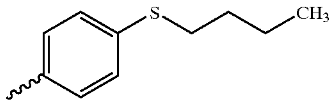 |
| 17 | 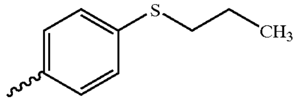 |
| 18 | 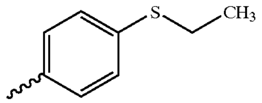 |
| 19 | 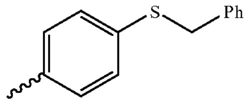 |
| 20 | 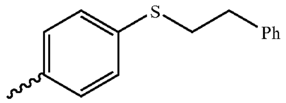 |
| 21 | 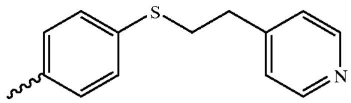 |
TABLE 116-continued
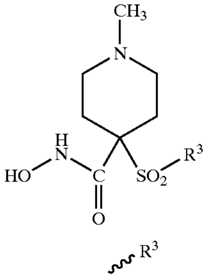
| | |
|---|---|
| 22 | 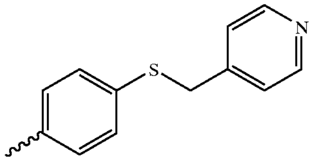 |
TABLE 117
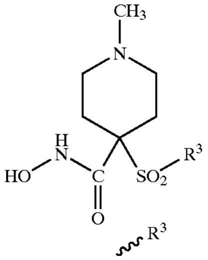
| | |
|---|---|
| 1 | 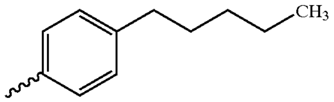 |
| 2 | 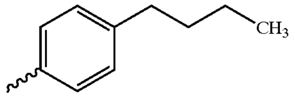 |
| 3 | 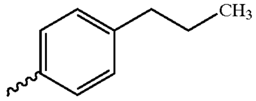 |
| 4 | 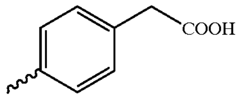 |
| 5 | 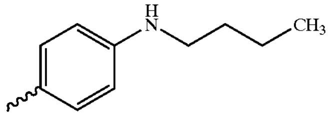 |
| 6 | 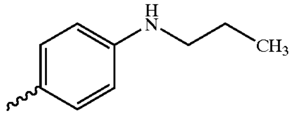 |

TABLE 117-continued
| | 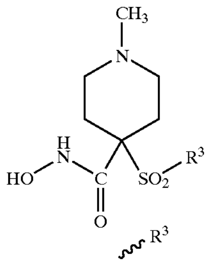 |
|---|---|
| 7 | 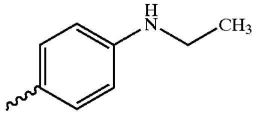 |
| 8 | 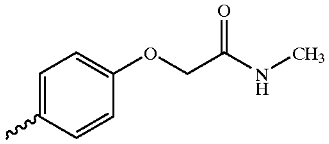 |
| 9 | 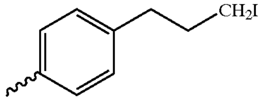 |
| 10 | 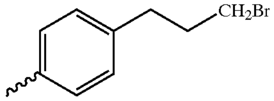 |
| 11 | 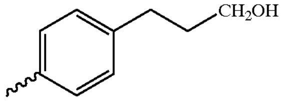 |
| 12 | 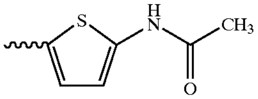 |
| 13 | 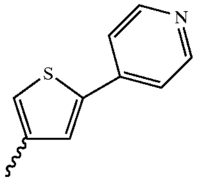 |
| 14 | 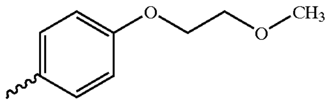 |
| 15 | 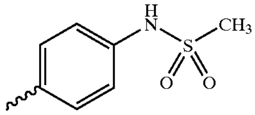 |
TABLE 117-continued
| | 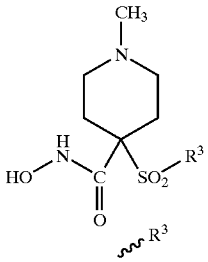 |
|---|---|
| 16 | 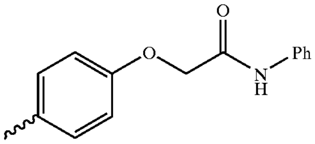 |
| 17 | 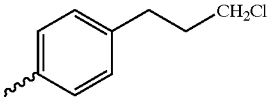 |
| 18 | 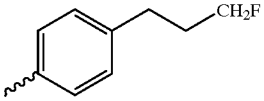 |
| 19 | 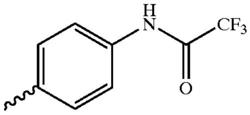 |
| 20 | 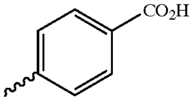 |
| 21 | 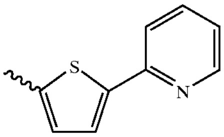 |
| 22 | 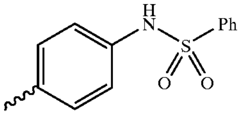 |
| 23 | 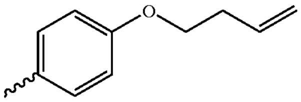 |
| 24 | 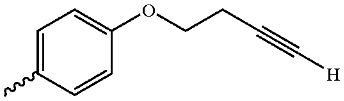 |
| 25 | 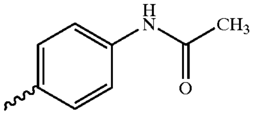 |

TABLE 117-continued
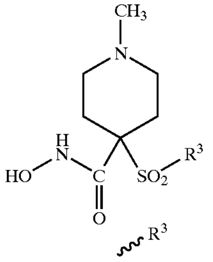
| | |
|---|---|
| 26 | 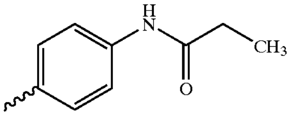 |
| 27 | 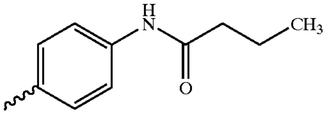 |
| 28 | 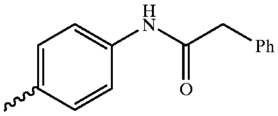 |
| 29 | 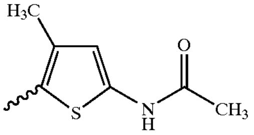 |
| 30 | 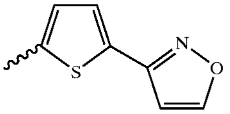 |
TABLE 118
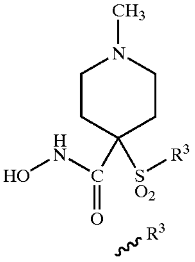
| | |
|---|---|
| 1 | 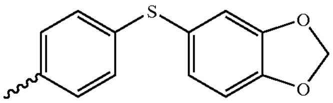 |
| 2 | 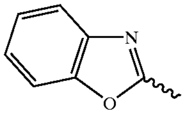 |
TABLE 118-continued
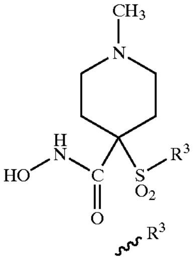
| | |
|---|---|
| 3 | 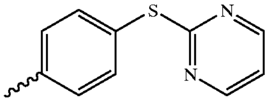 |
| 4 | 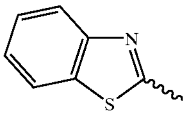 |
| 5 | 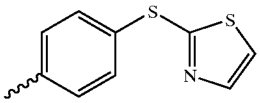 |
| 6 | 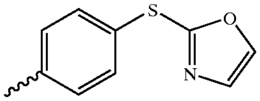 |
| 7 | 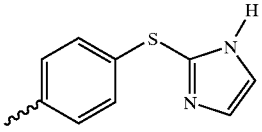 |
| 8 | 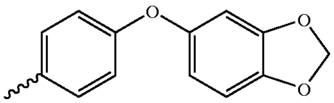 |
| 9 | 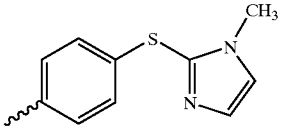 |
| 10 | 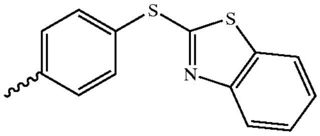 |
| 11 | 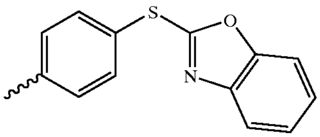 |

TABLE 119
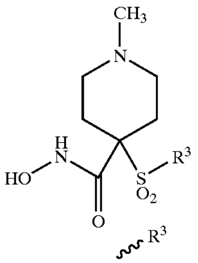
| | |
|---|---|
| 1 | 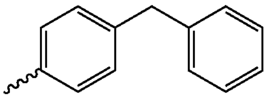 |
| 2 | 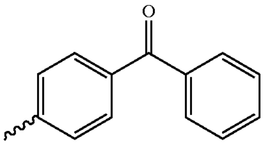 |
| 3 | 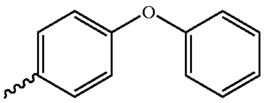 |
| 4 | 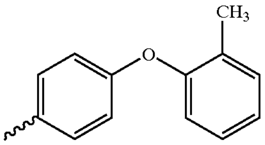 |
| 5 | 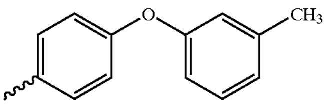 |
| 6 | 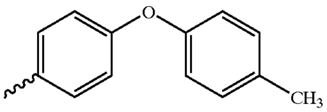 |
| 7 | 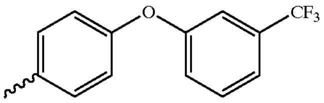 |
| 8 | 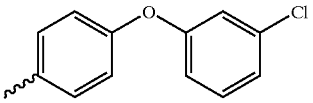 |
| 9 | 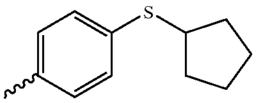 |
| 10 | 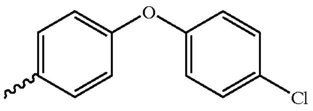 |
TABLE 119-continued
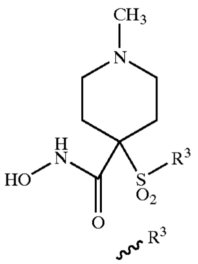
| | |
|---|---|
| 11 | 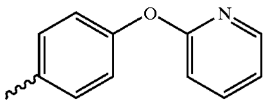 |
| 12 | 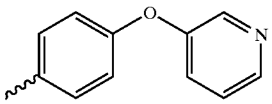 |
| 13 | 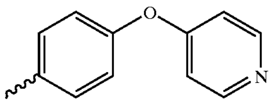 |
| 14 | 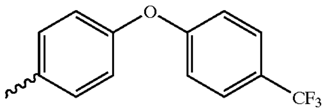 |
| 15 | 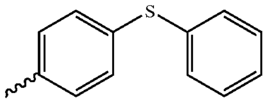 |
| 16 | 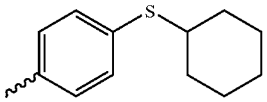 |
| 17 | 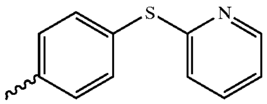 |
| 18 | 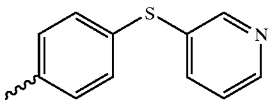 |
| 19 | 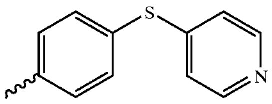 |
| 20 | 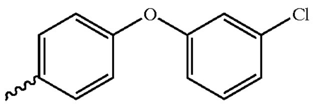 |
| 21 | 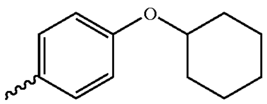 |

TABLE 120
| | 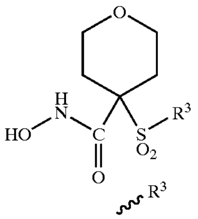 |
|---|---|
| 1 | 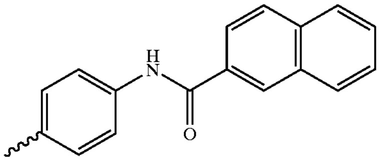 |
| 2 | 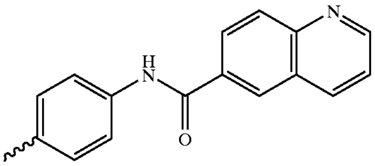 |
| 3 | 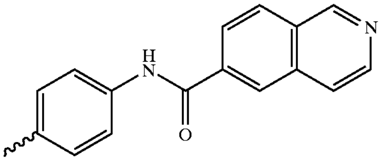 |
| 4 | 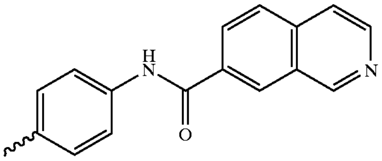 |
| 5 | 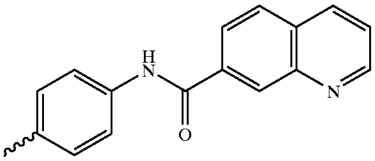 |
| 6 | 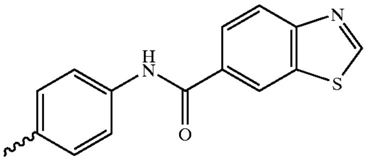 |
| 7 | 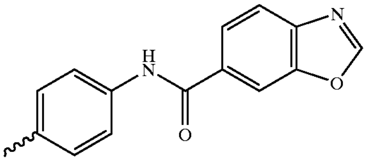 |
TABLE 120-continued
| | 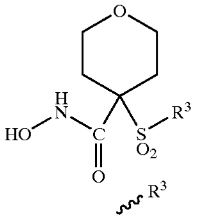 |
|---|---|
| 8 | 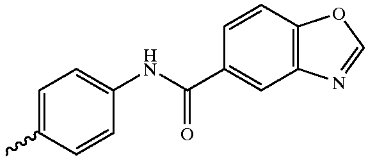 |
| 9 | 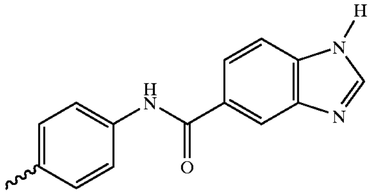 |
| 10 | 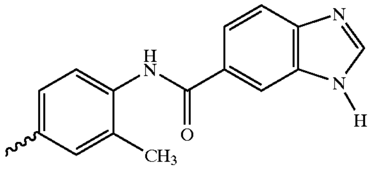 |
| 11 | 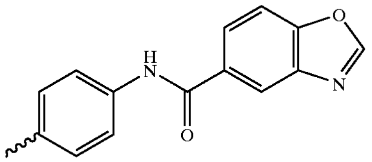 |
| 12 | 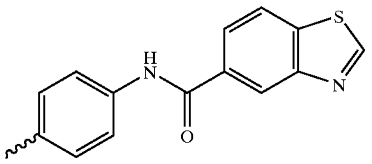 |
| 13 | 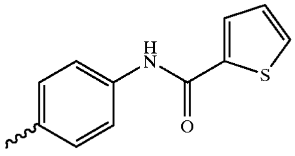 |
| 14 | 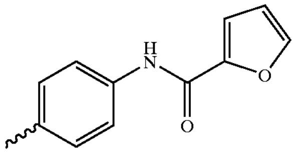 |

TABLE 120-continued
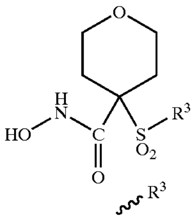
| | |
|---|---|
| 15 | 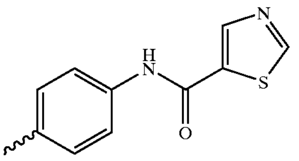 |
| 16 | 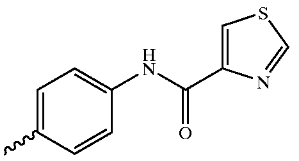 |
| 17 | 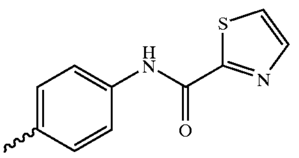 |
| 18 | 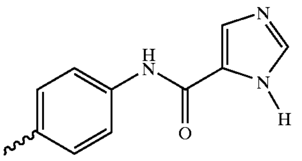 |
TABLE 121
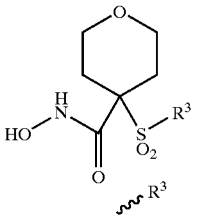
| | |
|---|---|
| 1 | 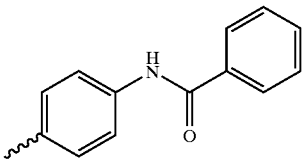 |
| 2 | 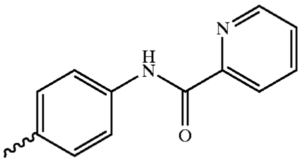 |
TABLE 121-continued
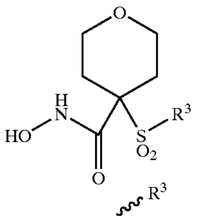
| | |
|---|---|
| 3 | 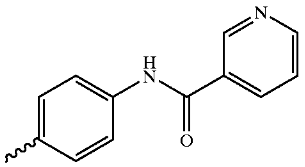 |
| 4 | 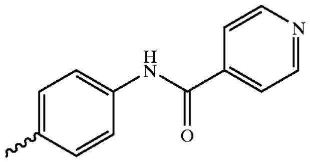 |
| 5 | 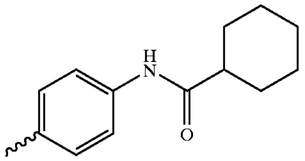 |
| 6 | 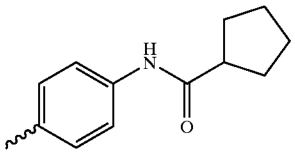 |
| 7 | 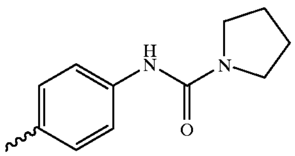 |
| 8 | 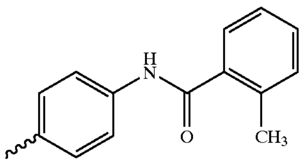 |
| 9 | 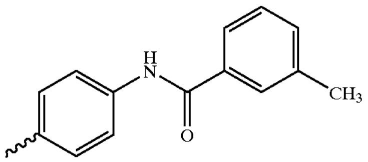 |

TABLE 121-continued
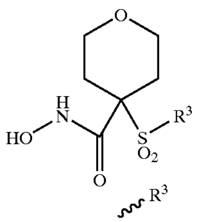
10
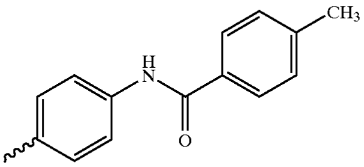
11
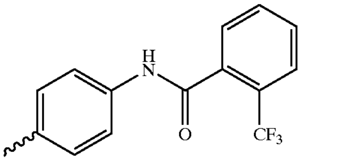
12
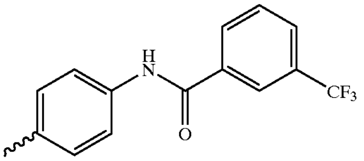
13
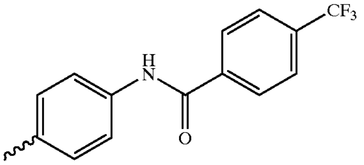
14
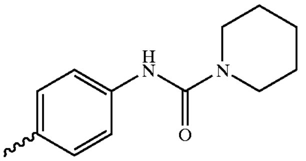
15
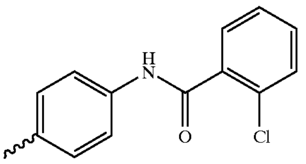
16
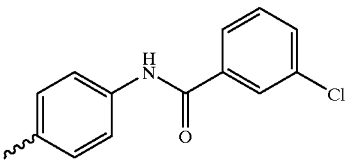
TABLE 121-continued
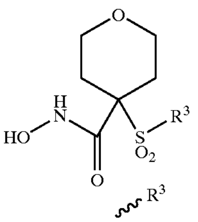
17
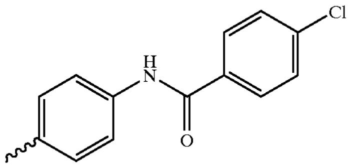
18
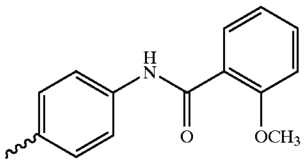
19
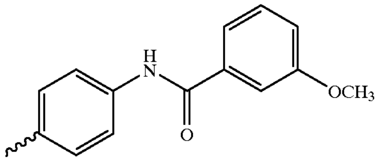
20
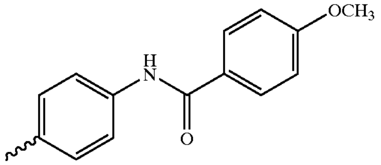
21
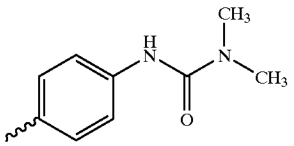
TABLE 122
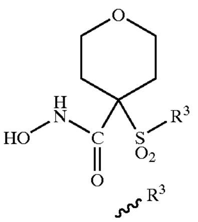
1
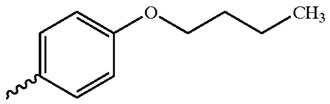

TABLE 122-continued
| | 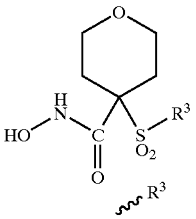 |
|---|---|
| 2 | 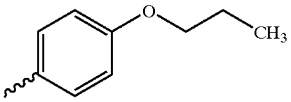 |
| 3 | 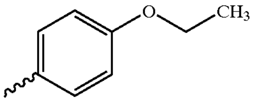 |
| 4 | 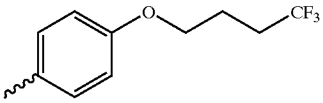 |
| 5 | 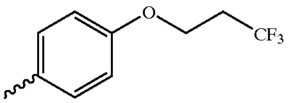 |
| 6 | 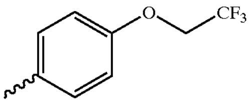 |
| 7 | 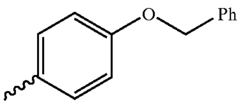 |
| 8 | 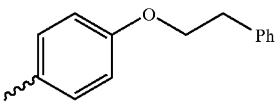 |
| 9 | 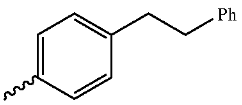 |
| 10 | 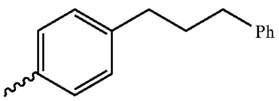 |
| 11 | 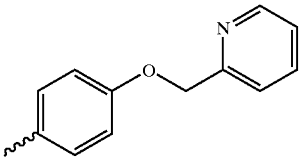 |
TABLE 122-continued
| | 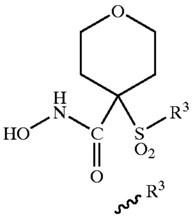 |
|---|---|
| 12 | 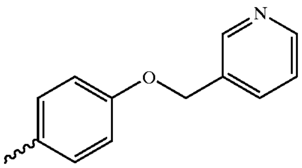 |
| 13 | 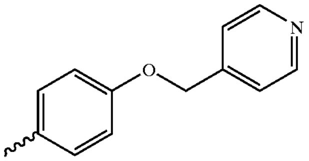 |
| 14 | 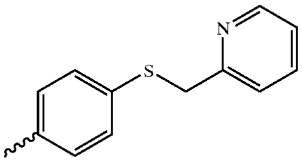 |
| 15 | 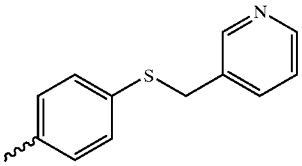 |
| 16 | 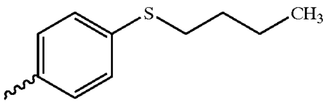 |
| 17 | 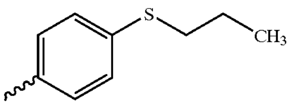 |
| 18 | 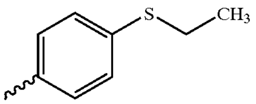 |
| 19 | 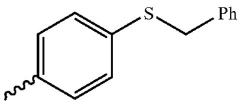 |
| 20 | 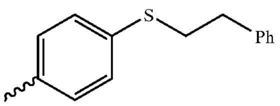 |

TABLE 122-continued
| | |
|---|---|
| | 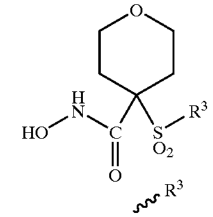 |
| 21 | 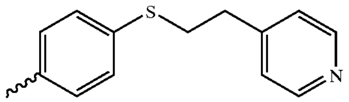 |
| 22 | 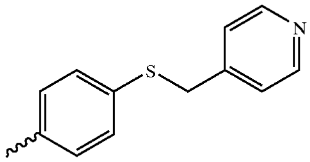 |
TABLE 123
| | |
|---|---|
| | 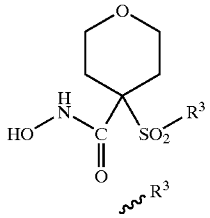 |
| 1 | 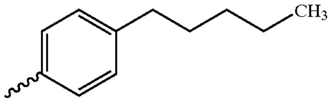 |
| 2 | 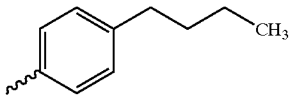 |
| 3 | 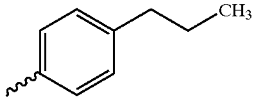 |
| 4 | 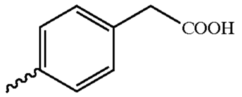 |
| 5 | 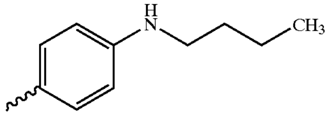 |
| 6 | 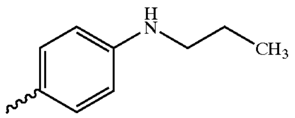 |
TABLE 123-continued
| | |
|---|---|
| | 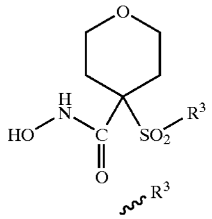 |
| 7 | 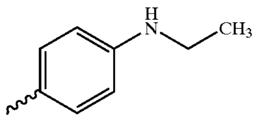 |
| 8 | 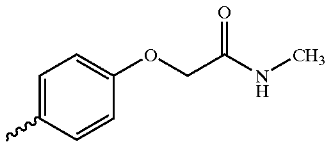 |
| 9 | 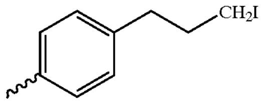 |
| 10 | 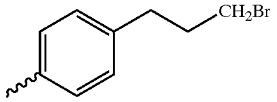 |
| 11 | 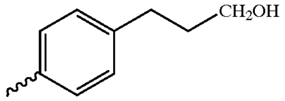 |
| 12 | 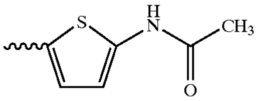 |
| 13 | 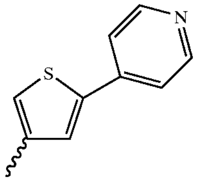 |
| 14 | 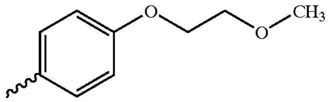 |
| 15 | 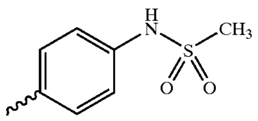 |
| 16 | 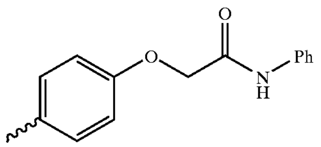 |

TABLE 123-continued
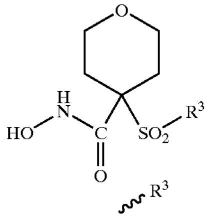
| | |
|---|---|
| 17 | 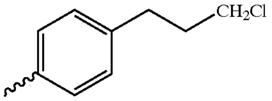 |
| 18 | 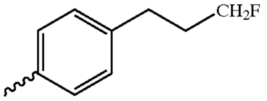 |
| 19 | 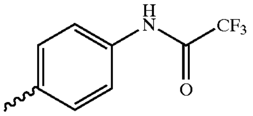 |
| 20 | 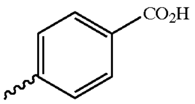 |
| 21 | 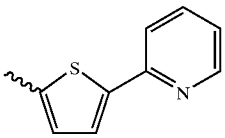 |
| 22 | 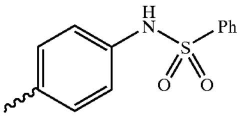 |
| 23 | 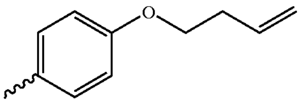 |
| 24 | 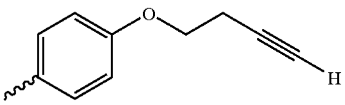 |
| 25 | 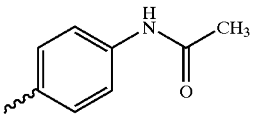 |
| 26 | 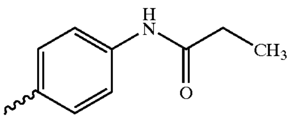 |
TABLE 123-continued
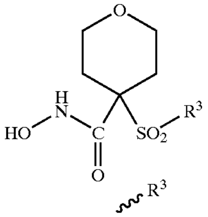
| | |
|---|---|
| 27 | 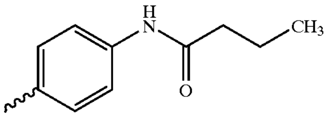 |
| 28 | 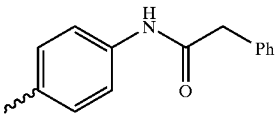 |
| 29 | 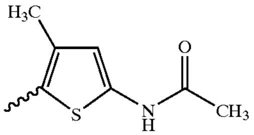 |
| 30 | 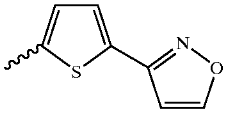 |
TABLE 124
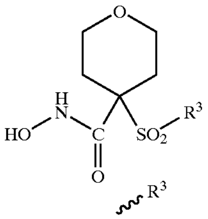
| | |
|---|---|
| 1 | 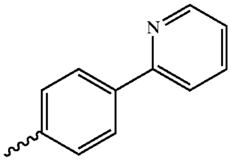 |
| 2 | 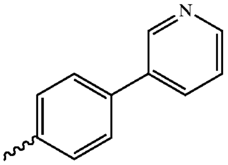 |
| 3 | 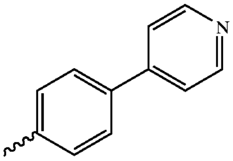 |

TABLE 124-continued
| 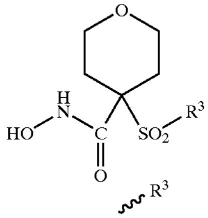 | |
|---|---|
| 4 | 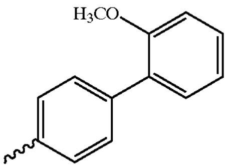 |
| 5 | 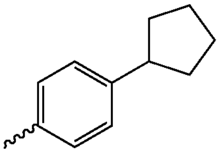 |
| 6 | 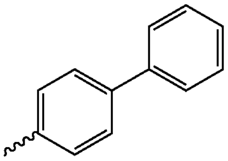 |
| 7 | 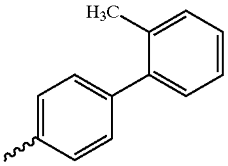 |
| 8 | 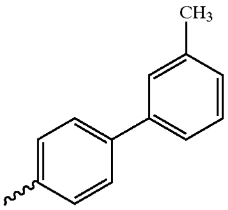 |
| 9 | 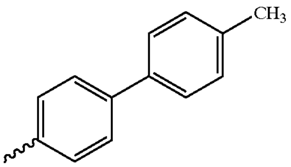 |
| 10 | 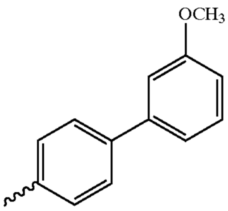 |
TABLE 124-continued
| 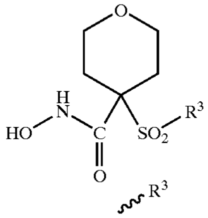 | |
|---|---|
| 11 | 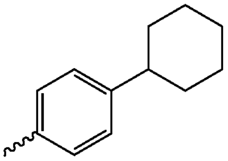 |
| 12 | 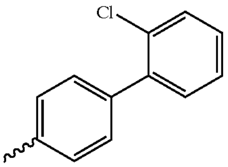 |
| 13 | 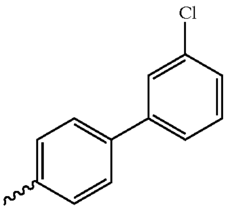 |
| 14 | 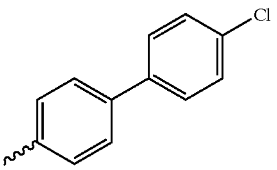 |
| 15 | 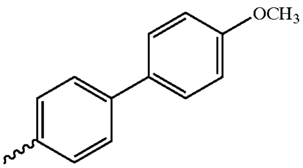 |
| 16 | 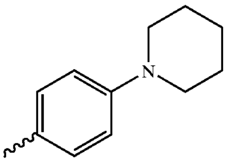 |
| 17 | 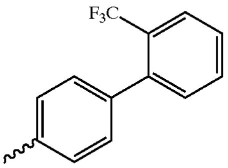 |

TABLE 124-continued
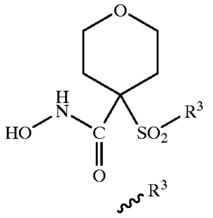
| | |
|---|---|
| 18 | 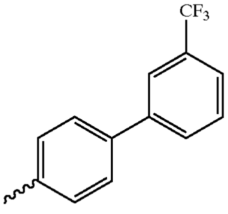 |
| 19 | 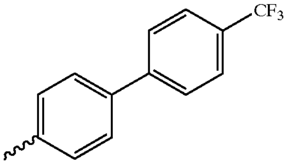 |
| 20 | 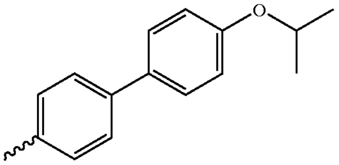 |
| 21 | 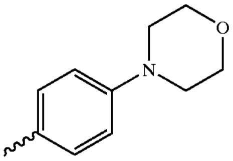 |
TABLE 125
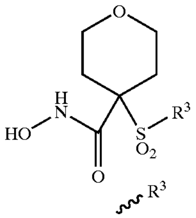
| | |
|---|---|
| 1 | 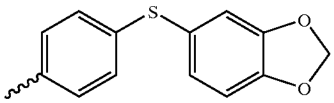 |
| 2 | 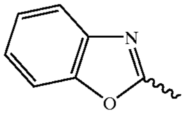 |
TABLE 125-continued
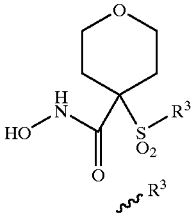
| | |
|---|---|
| 3 | 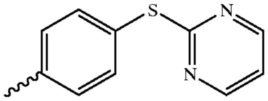 |
| 4 | 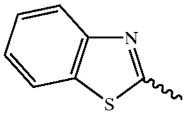 |
| 5 | 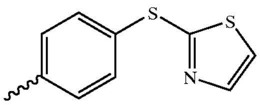 |
| 6 | 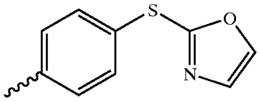 |
| 7 | 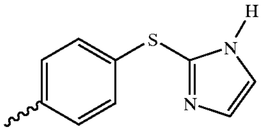 |
| 8 | 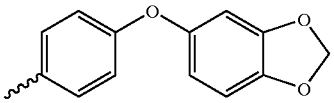 |
| 9 | 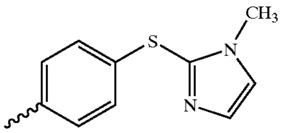 |
| 10 | 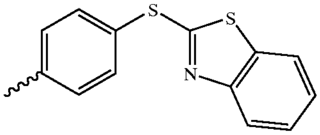 |
| 11 | 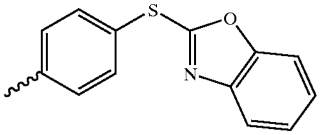 |

TABLE 126
| | |
|---|---|
| | 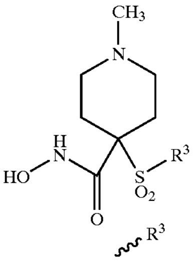 |
| 1 | 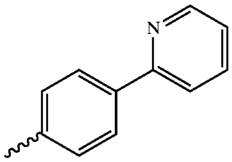 |
| 2 | 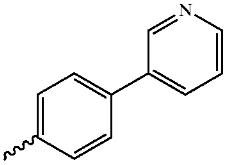 |
| 3 | 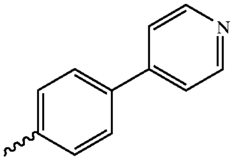 |
| 4 | 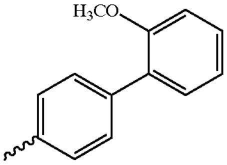 |
| 5 | 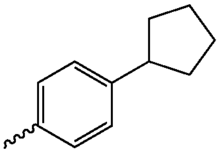 |
| 6 | 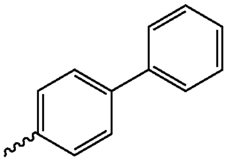 |
| 7 | 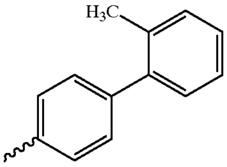 |
TABLE 126-continued
| | |
|---|---|
| | 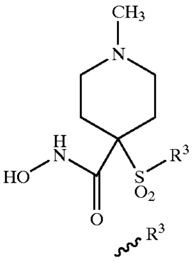 |
| 8 | 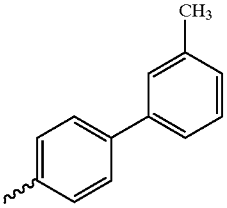 |
| 9 | 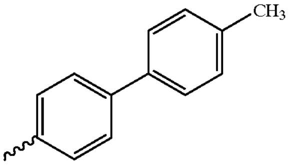 |
| 10 | 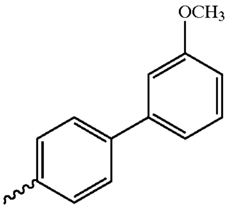 |
| 11 | 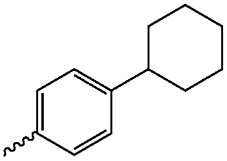 |
| 12 | 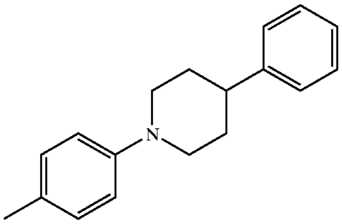 |
| 13 | 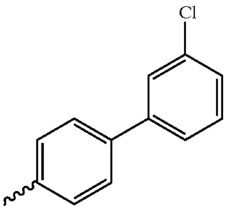 |

TABLE 126-continued
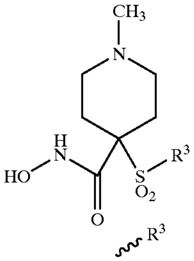
| | |
|---|---|
| 14 | 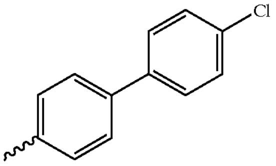 |
| 15 | 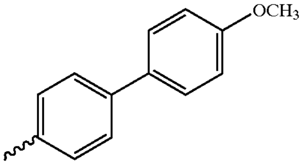 |
| 16 | 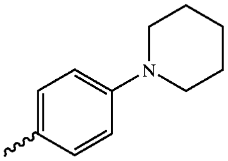 |
| 17 | 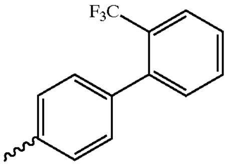 |
| 18 | 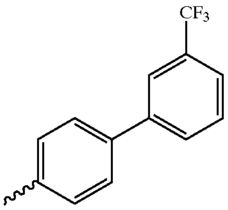 |
| 19 | 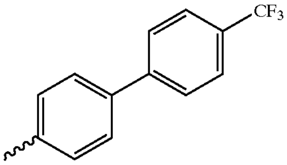 |
| 20 | 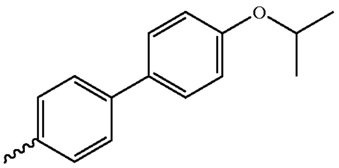 |
TABLE 126-continued
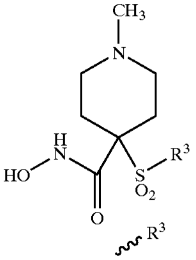
| | |
|---|---|
| 21 | 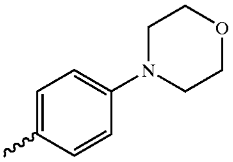 |
TABLE 127
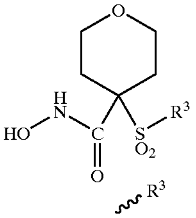
| | |
|---|---|
| 1 | 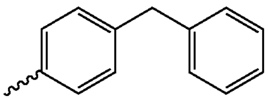 |
| 2 | 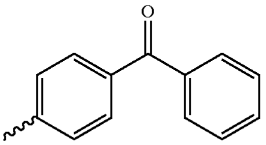 |
| 3 | 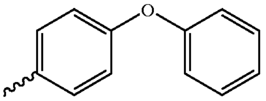 |
| 4 | 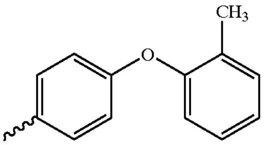 |
| 5 | 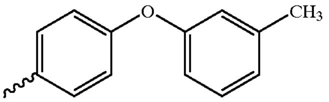 |
| 6 | 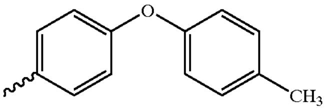 |

TABLE 127-continued
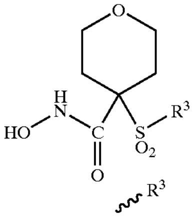
| | |
|---|---|
| 7 | 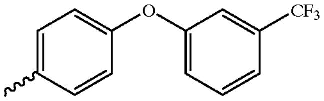 |
| 8 | 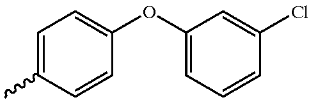 |
| 9 | 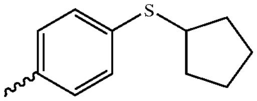 |
| 10 | 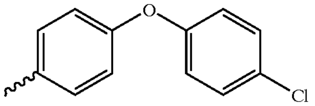 |
| 11 | 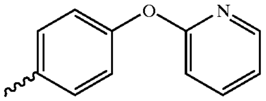 |
| 12 | 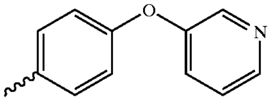 |
| 13 | 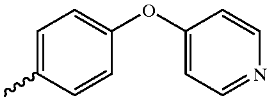 |
| 14 | 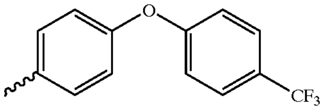 |
| 15 | 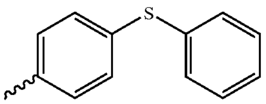 |
| 16 | 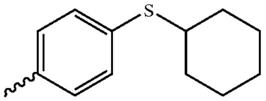 |
| 17 | 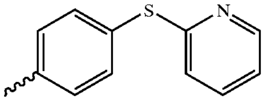 |
TABLE 127-continued
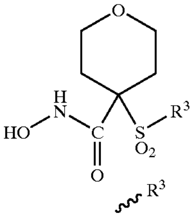
| | |
|---|---|
| 18 | 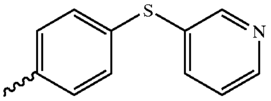 |
| 19 | 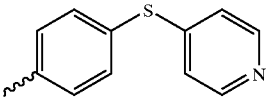 |
| 20 | 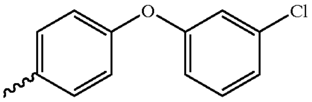 |
| 21 | 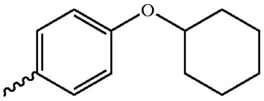 |
TABLE 128
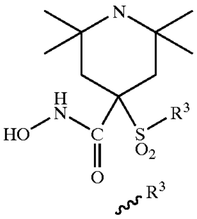
| | |
|---|---|
| 1 | 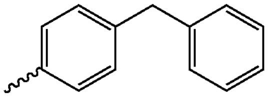 |
| 2 | 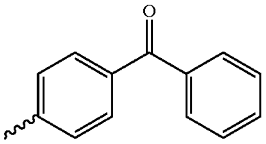 |
| 3 | 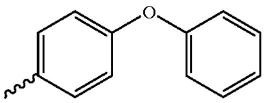 |
| 4 | 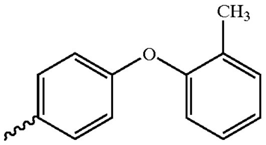 |

TABLE 128-continued
| | |
|---|---|
| | 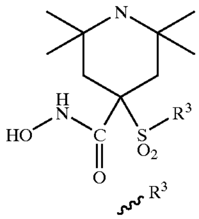 |
| 5 | 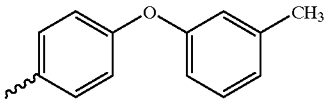 |
| 6 | 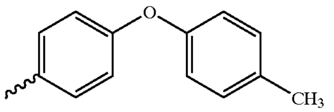 |
| 7 | 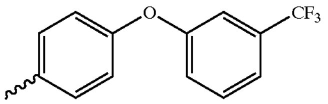 |
| 8 | 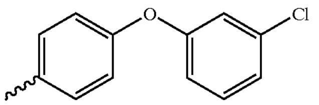 |
| 9 | 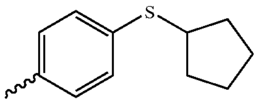 |
| 10 | 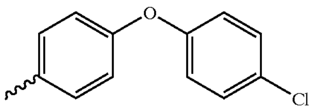 |
| 11 | 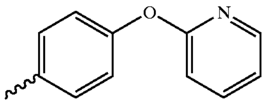 |
| 12 | 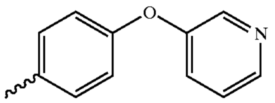 |
| 13 | 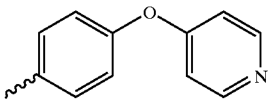 |
| 14 | 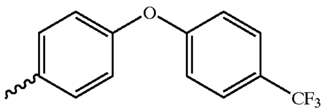 |
| 15 | 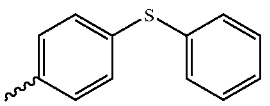 |
TABLE 128-continued
| | |
|---|---|
| | 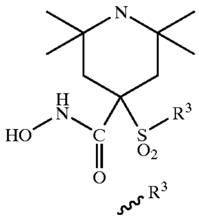 |
| 16 | 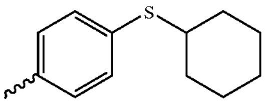 |
| 17 | 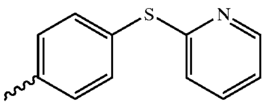 |
| 18 | 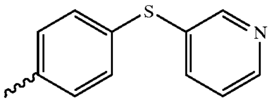 |
| 19 | 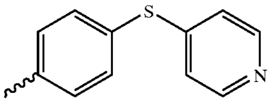 |
| 20 | 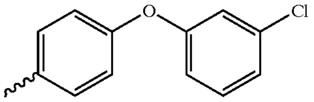 |
| 21 | 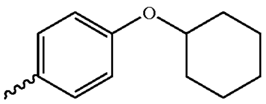 |
TABLE 129
| | |
|---|---|
| | 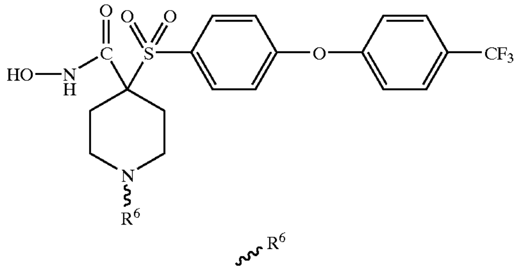 |
| 1 | 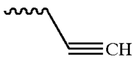 |
| 2 | 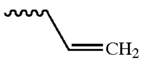 |
| 3 | 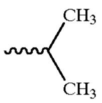 |

TABLE 129-continued
| | 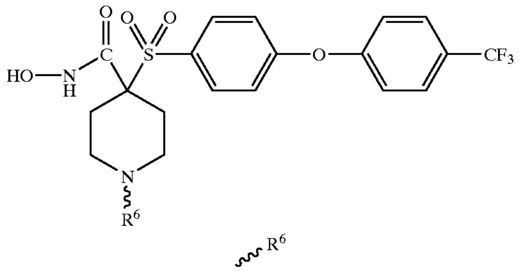 |
|---|---|
| 4 | 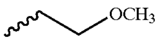 |
| 5 | 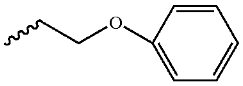 |
| 6 | 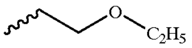 |
| 7 | 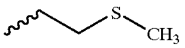 |
| 8 | 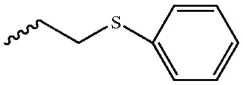 |
| 9 | 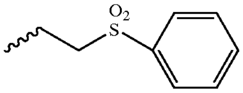 |
| 10 | 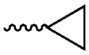 |
| 11 | 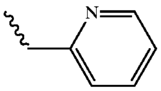 |
| 12 | 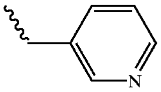 |
| 13 | 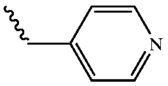 |
| 14 | 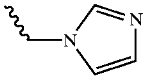 |
| 15 | 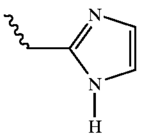 |
| 16 | 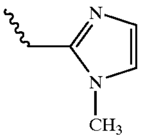 |
TABLE 129-continued
| | 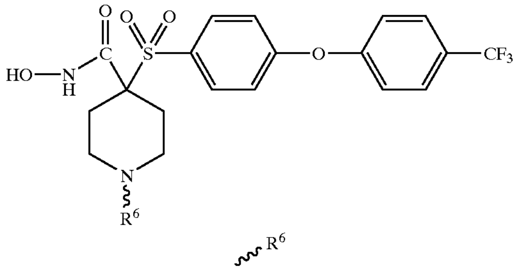 |
|---|---|
| 17 | 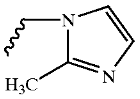 |
| 18 | 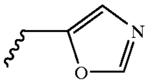 |
| 19 | 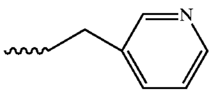 |
| 20 | 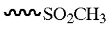 |
| 21 | 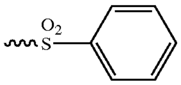 |
| 22 | 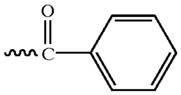 |
| 23 | 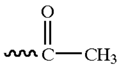 |
| 24 | 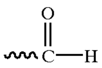 |
| 25 | 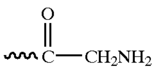 |
| 26 | 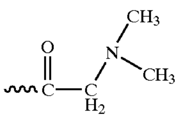 |

TABLE 130
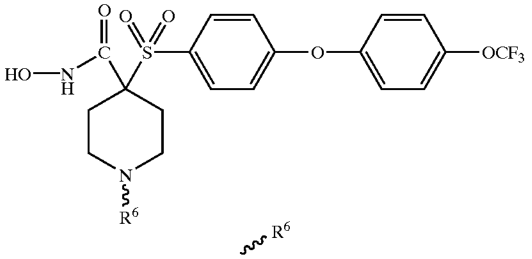
| | |
|---|---|
| 1 | 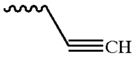 |
| 2 | 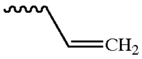 |
| 3 | 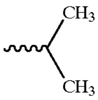 |
| 4 | 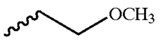 |
| 5 | 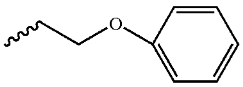 |
| 6 | 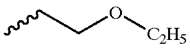 |
| 7 | 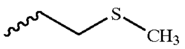 |
| 8 | 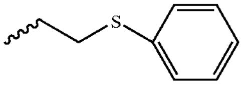 |
| 9 | 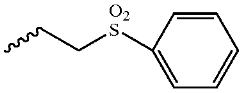 |
| 10 | 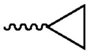 |
| 11 | 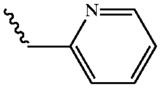 |
| 12 | 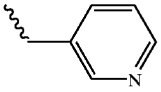 |
| 13 | 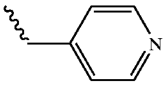 |
| 14 | 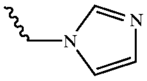 |
TABLE 130-continued
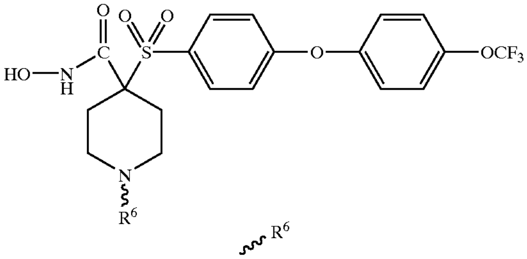
| | |
|---|---|
| 15 | 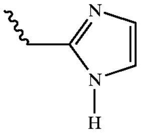 |
| 16 | 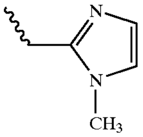 |
| 17 | 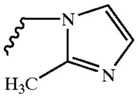 |
| 18 | 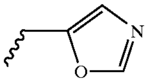 |
| 19 | 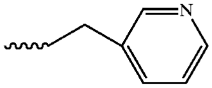 |
| 20 | 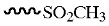 |
| 21 | 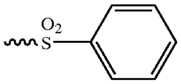 |
| 22 | 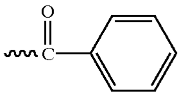 |
| 23 | 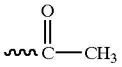 |
| 24 | 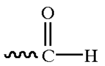 |
| 25 | 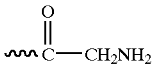 |
| 26 | 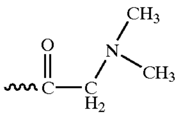 |

TABLE 131
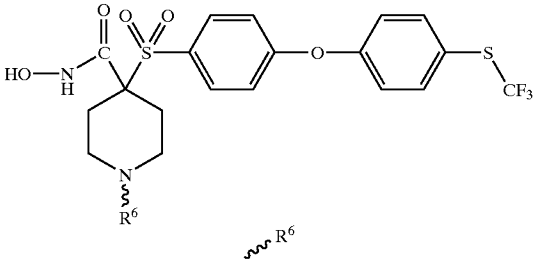
| | |
|---|---|
| 1 | 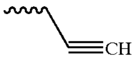 |
| 2 | 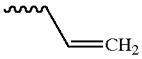 |
| 3 | 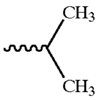 |
| 4 | 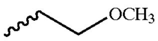 |
| 5 | 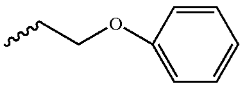 |
| 6 | 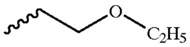 |
| 7 | 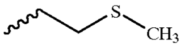 |
| 8 | 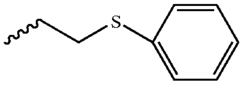 |
| 9 | 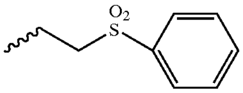 |
| 10 | 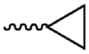 |
| 11 | 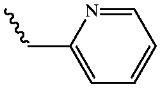 |
| 12 | 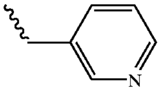 |
| 13 | 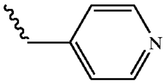 |
| 14 | 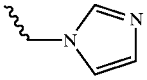 |
TABLE 131-continued
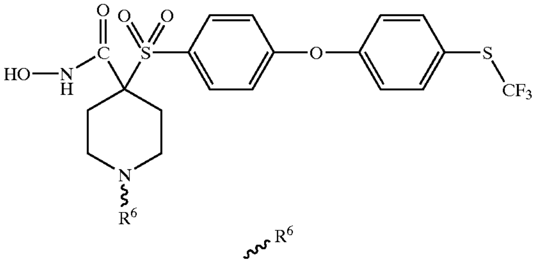
| | |
|---|---|
| 15 | 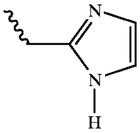 |
| 16 | 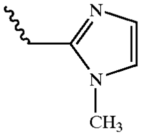 |
| 17 | 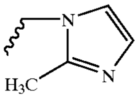 |
| 18 | 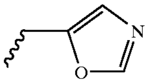 |
| 19 | 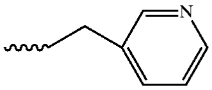 |
| 20 | ~~~$SO_2CH_3$ |
| 21 | 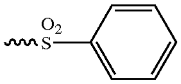 |
| 22 | 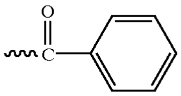 |
| 23 | 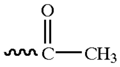 |
| 24 | 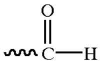 |
| 25 | 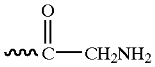 |
| 26 | 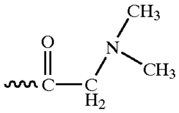 |

TABLE 132
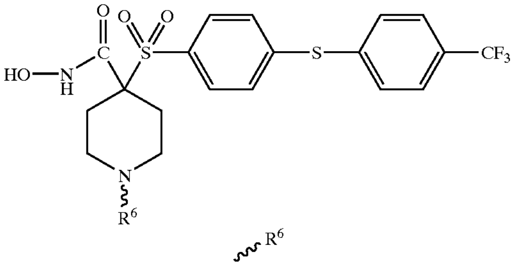
| | $R^6$ |
|---|---|
| 1 | 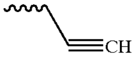 |
| 2 | 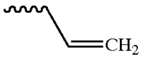 |
| 3 | 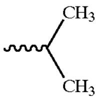 |
| 4 | 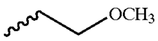 |
| 5 | 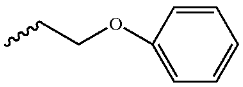 |
| 6 | 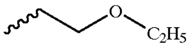 |
| 7 | 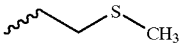 |
| 8 | 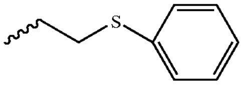 |
| 9 | 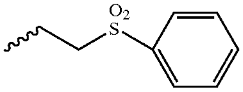 |
| 10 | 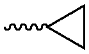 |
| 11 | 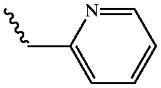 |
| 12 | 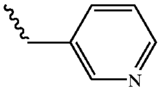 |
| 13 | 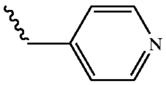 |
| 14 | 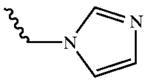 |
TABLE 132-continued
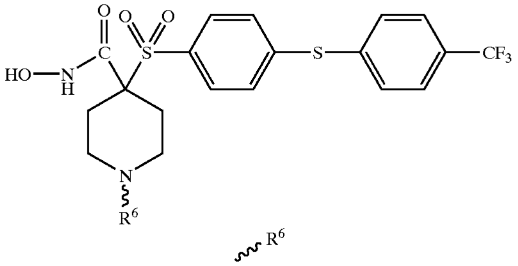
| | $R^6$ |
|---|---|
| 15 | 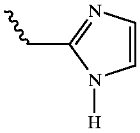 |
| 16 | 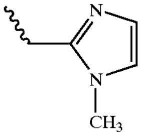 |
| 17 | 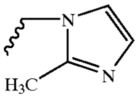 |
| 18 | 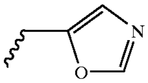 |
| 19 | 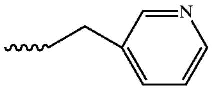 |
| 20 | $SO_2CH_3$ |
| 21 | 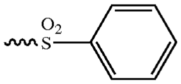 |
| 22 | 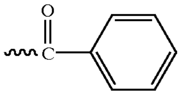 |
| 23 | 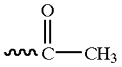 |
| 24 | 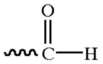 |
| 25 | 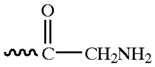 |
| 26 | 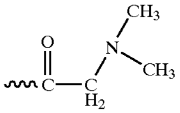 |

TABLE 133
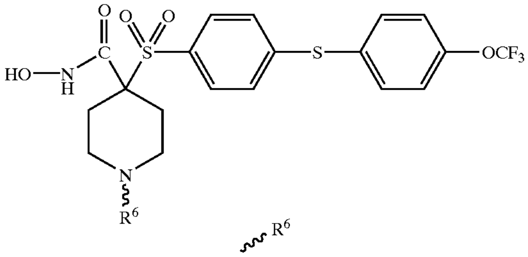
| | $R^6$ |
|---|---|
| 1 | 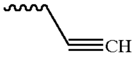 |
| 2 | 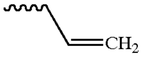 |
| 3 | 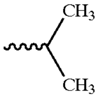 |
| 4 | 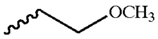 |
| 5 | 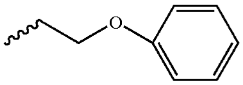 |
| 6 | 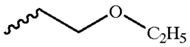 |
| 7 | 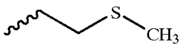 |
| 8 | 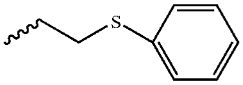 |
| 9 | 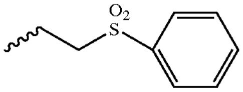 |
| 10 | 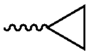 |
| 11 | 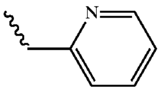 |
| 12 | 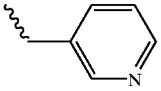 |
| 13 | 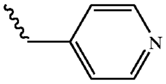 |
| 14 | 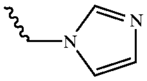 |
TABLE 133-continued
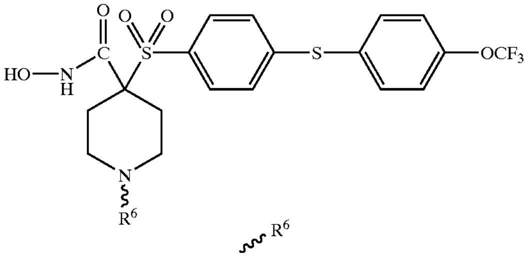
| | $R^6$ |
|---|---|
| 15 | 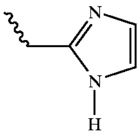 |
| 16 | 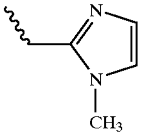 |
| 17 | 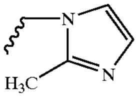 |
| 18 | 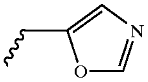 |
| 19 | 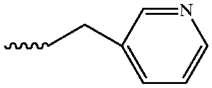 |
| 20 | $SO_2CH_3$ |
| 21 | 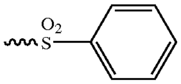 |
| 22 | 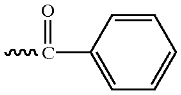 |
| 23 | 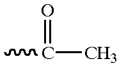 |
| 24 | 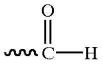 |
| 25 | 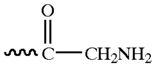 |
| 26 | 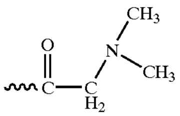 |

TABLE 134
| | |
|---|---|
| 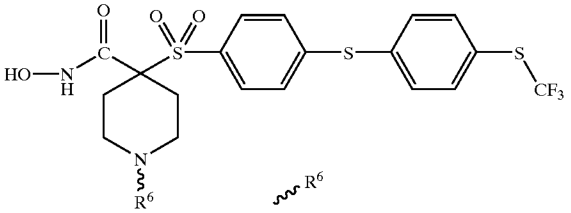 | |
| 1 | 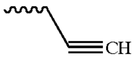 |
| 2 | 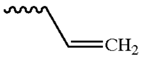 |
| 3 | 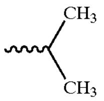 |
| 4 | 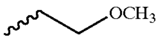 |
| 5 | 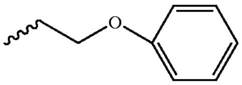 |
| 6 | 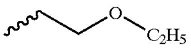 |
| 7 | 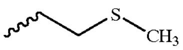 |
| 8 | 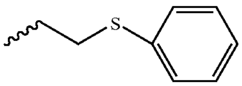 |
| 9 | 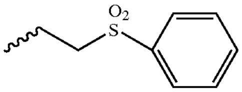 |
| 10 | 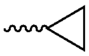 |
| 11 | 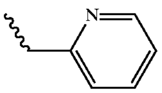 |
| 12 | 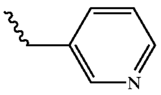 |
| 13 | 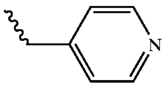 |
TABLE 134-continued
| | |
|---|---|
| 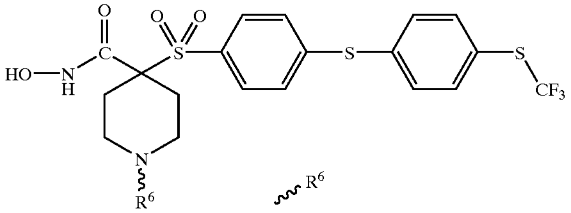 | |
| 14 | 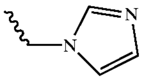 |
| 15 | 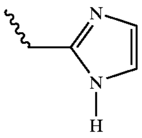 |
| 16 | 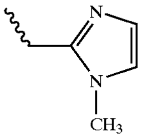 |
| 17 | 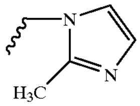 |
| 18 | 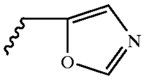 |
| 19 | 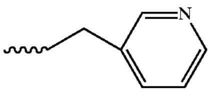 |
| 20 | 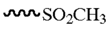 |
| 21 | 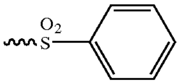 |
| 22 | 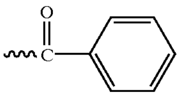 |
| 23 | 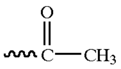 |
| 24 | 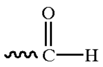 |
| 25 | 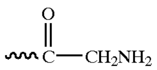 |
| 26 | 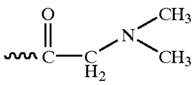 |

TABLE 135
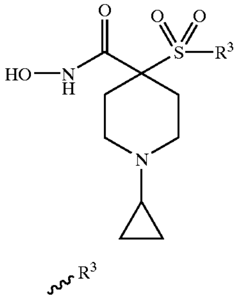
| | |
|---|---|
| 1 | 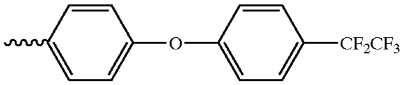 |
| 2 | 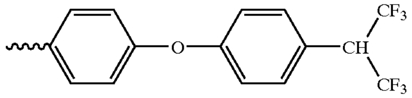 |
| 3 | 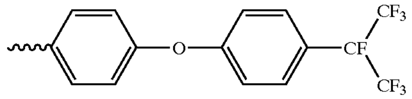 |
| 4 | 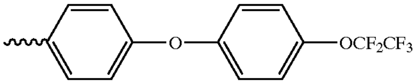 |
| 5 | 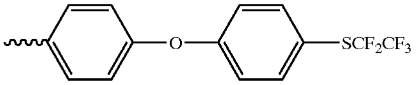 |
| 6 | 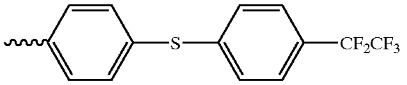 |
| 7 | 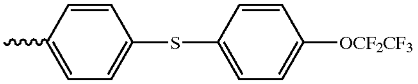 |
| 8 | 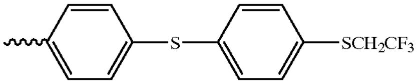 |
| 9 | 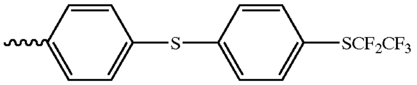 |
| 10 | 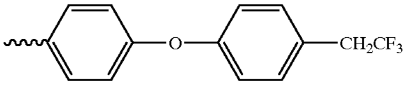 |
| 11 | 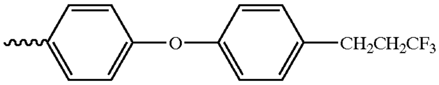 |
| 12 | 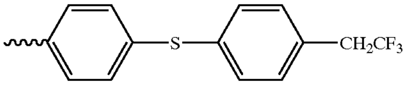 |
TABLE 135-continued
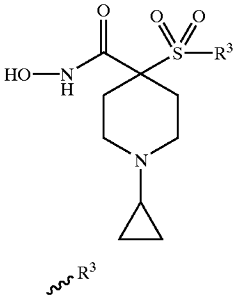
| | |
|---|---|
| 13 | 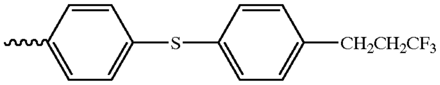 |
| 14 | 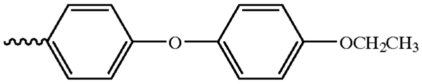 |
| 15 | 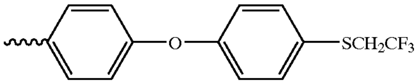 |
| 16 | 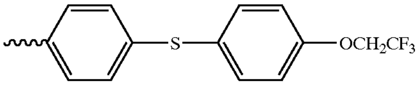 |
TABLE 136
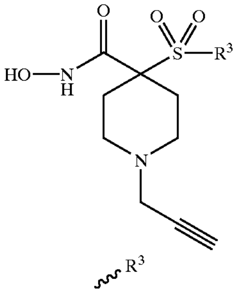
| | |
|---|---|
| 1 | 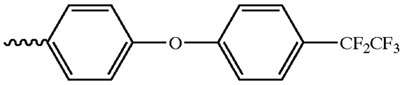 |
| 2 | 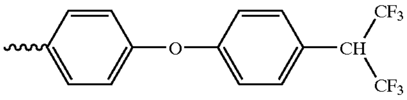 |
| 3 | 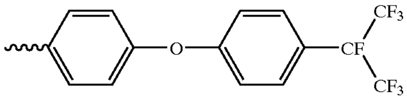 |
| 4 | 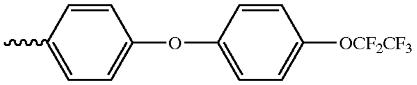 |

TABLE 136-continued
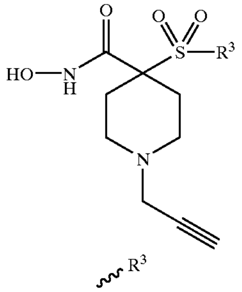
| | |
|---|---|
| 5 | 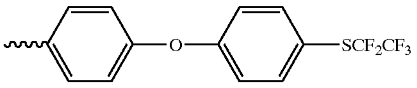 |
| 6 | 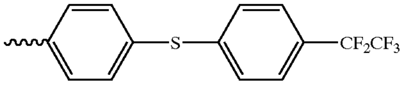 |
| 7 | 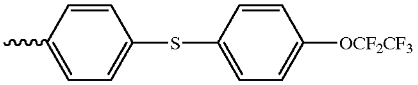 |
| 8 | 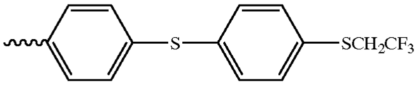 |
| 9 | 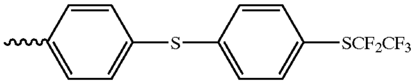 |
| 10 | 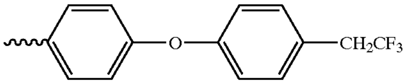 |
| 11 | 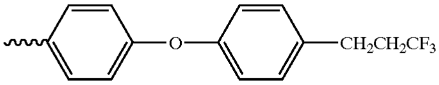 |
| 12 | 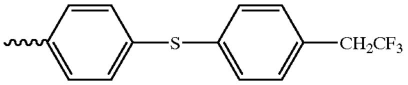 |
| 13 | 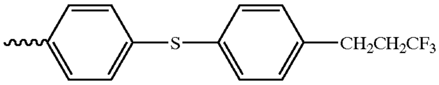 |
| 14 | 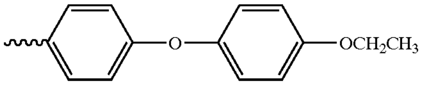 |
| 15 | 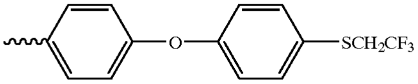 |
| 16 | 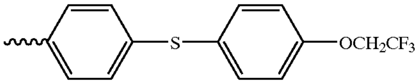 |
TABLE 137
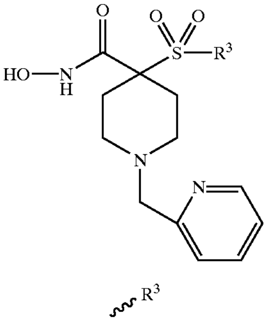
| | |
|---|---|
| 1 | 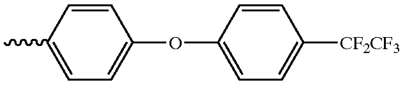 |
| 2 | 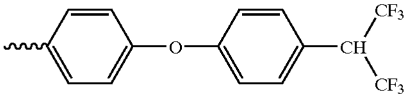 |
| 3 | 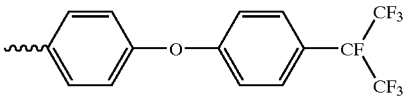 |
| 4 | 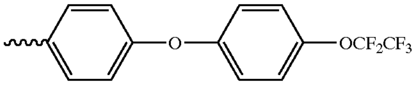 |
| 5 | 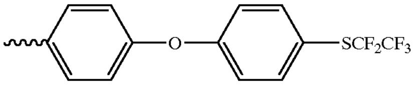 |
| 6 | 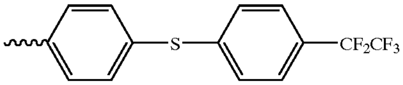 |
| 7 | 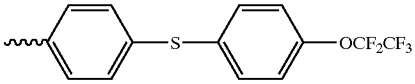 |
| 8 | 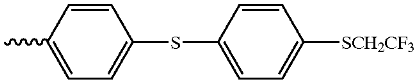 |
| 9 | 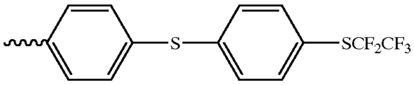 |
| 10 | 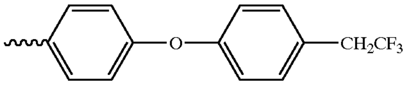 |
| 11 | 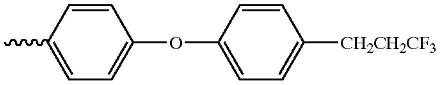 |
| 12 | 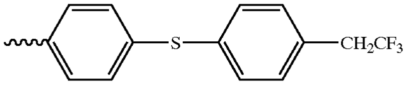 |

| | |
|---|---|
| 13 | 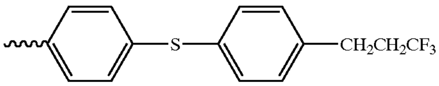 |
| 14 | 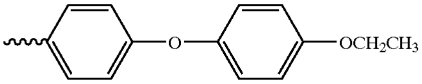 |
| 15 | 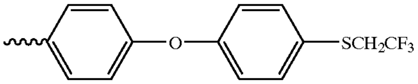 |
| 16 | 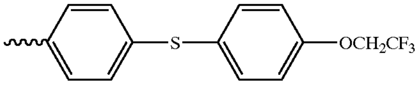 |
TABLE 138
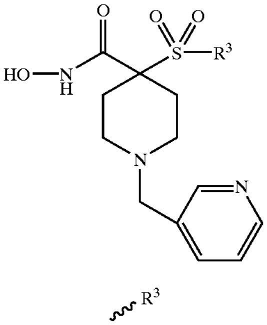
| | |
|---|---|
| 1 | 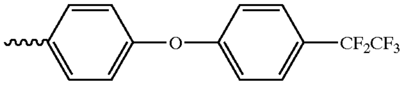 |
| 2 | 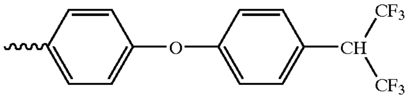 |
| 3 | 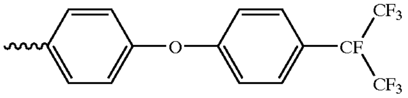 |
| 4 | 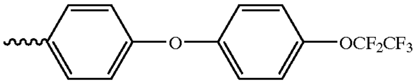 |
| 5 | 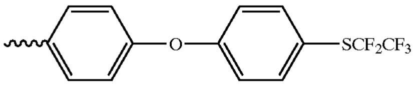 |
| 6 | 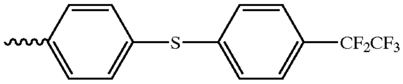 |
TABLE 138-continued
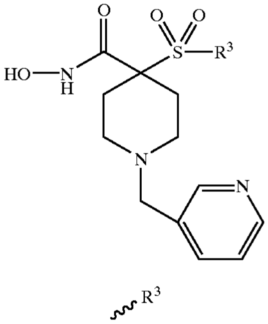
| | |
|---|---|
| 7 | 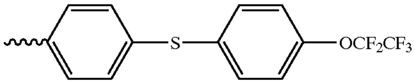 |
| 8 | 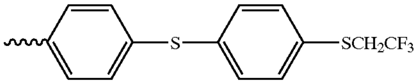 |
| 9 | 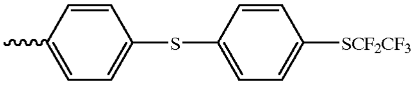 |
| 10 | 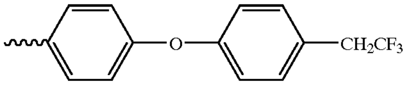 |
| 11 | 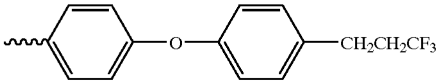 |
| 12 | 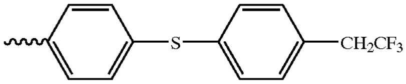 |
| 13 | 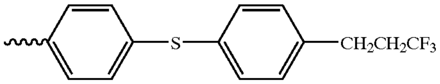 |
| 14 | 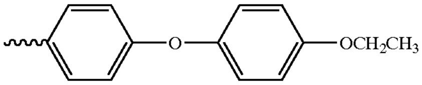 |
| 15 | 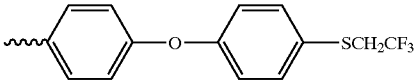 |
| 16 | 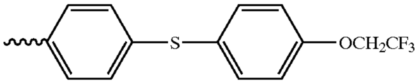 |

TABLE 139
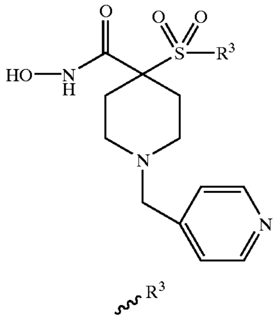
| | |
|---|---|
| 1 | 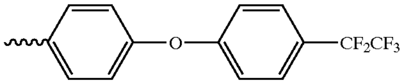 |
| 2 | 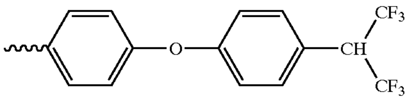 |
| 3 | 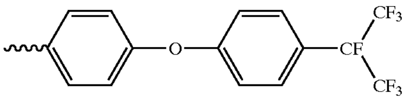 |
| 4 | 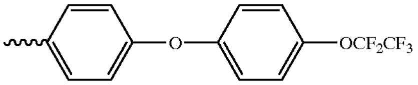 |
| 5 | 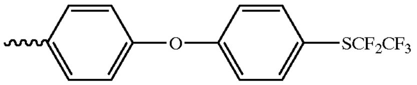 |
| 6 | 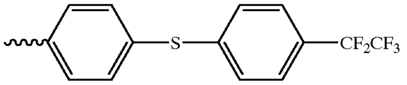 |
| 7 | 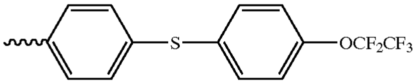 |
| 8 | 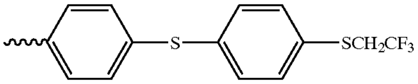 |
| 9 | 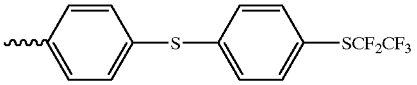 |
| 10 | 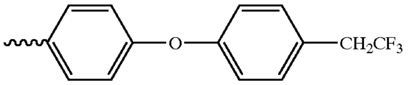 |
| 11 | 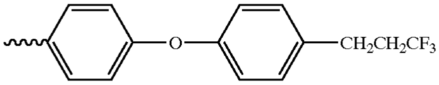 |
| 12 | 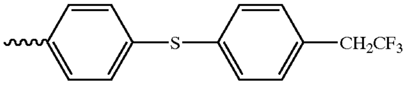 |
TABLE 139-continued
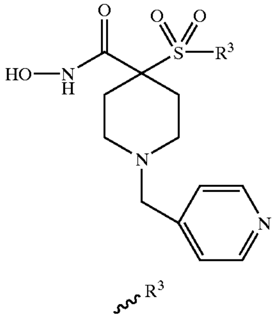
| | |
|---|---|
| 13 | 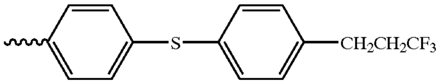 |
| 14 | 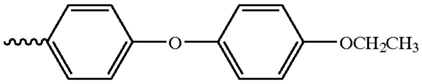 |
| 15 | 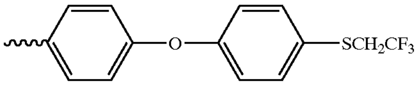 |
| 16 | 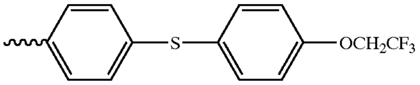 |
TABLE 140
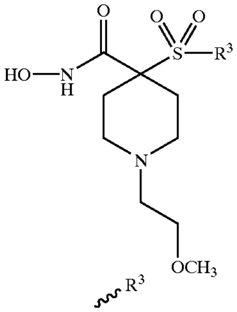
| | |
|---|---|
| 1 | 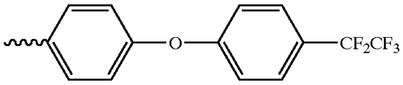 |
| 2 | 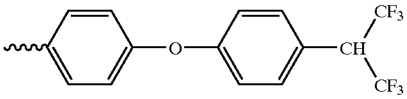 |
| 3 | 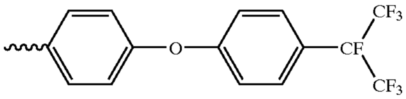 |
| 4 | 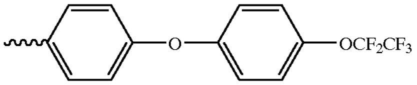 |

TABLE 140-continued
| | |
|---|---|
| | 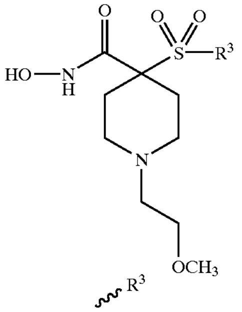 |
| 5 | 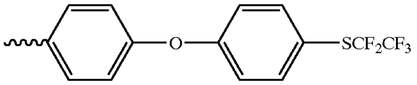 |
| 6 | 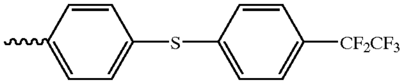 |
| 7 | 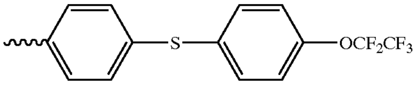 |
| 8 | 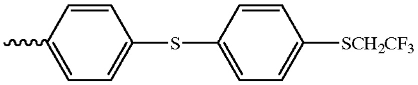 |
| 9 | 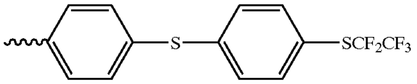 |
| 10 | 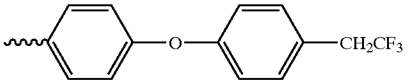 |
| 11 | 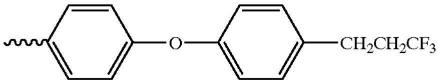 |
| 12 | 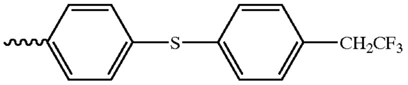 |
| 13 | 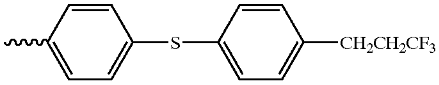 |
| 14 | 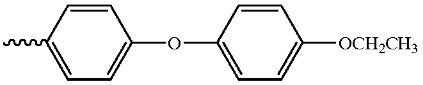 |
| 15 | 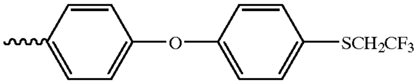 |
| 16 | 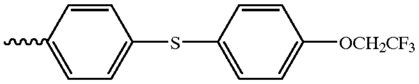 |
TABLE 141
| | |
|---|---|
| | 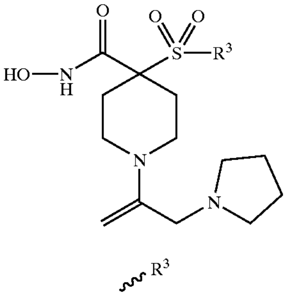 |
| 1 | 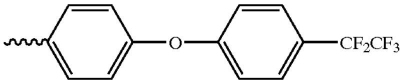 |
| 2 | 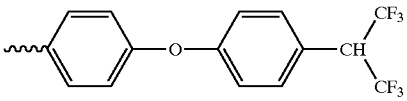 |
| 3 | 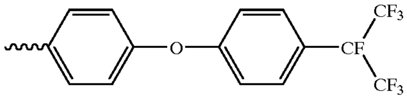 |
| 4 | 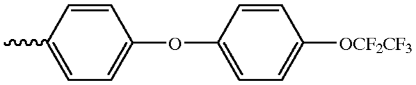 |
| 5 | 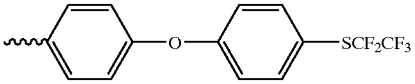 |
| 6 | 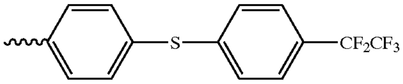 |
| 7 | 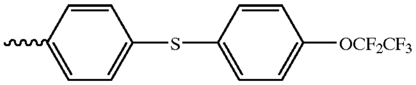 |
| 8 | 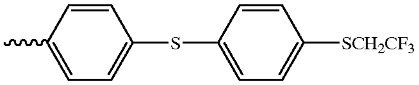 |
| 9 | 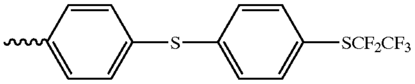 |
| 10 | 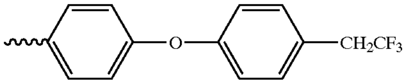 |
| 11 | 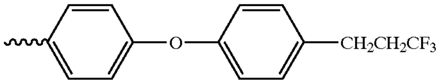 |
| 12 | 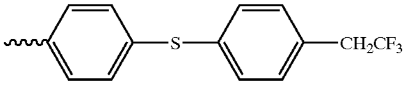 |

TABLE 141-continued
| | |
|---|---|
| | 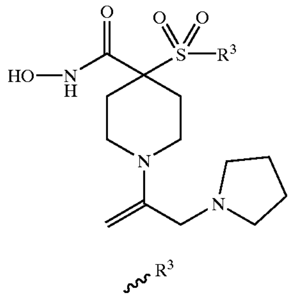 |
| 13 | 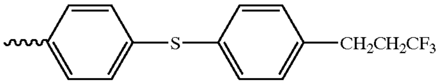 |
| 14 | 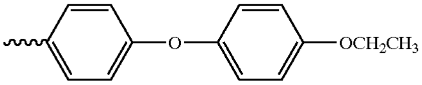 |
| 15 | 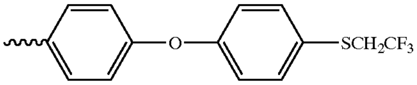 |
| 16 | 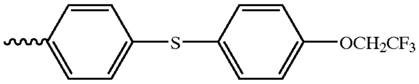 |
TABLE 142
| | |
|---|---|
| | 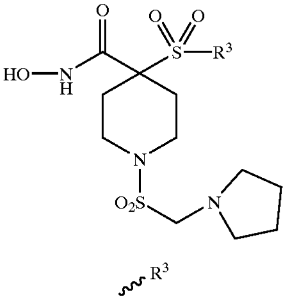 |
| 1 | 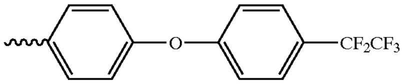 |
| 2 | 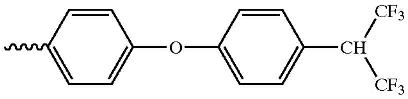 |
| 3 | 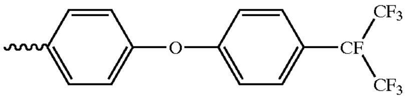 |
| 4 | 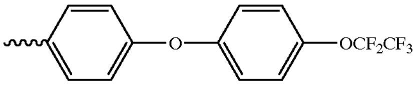 |
TABLE 142-continued
| | |
|---|---|
| | 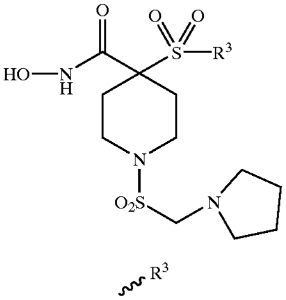 |
| 5 | 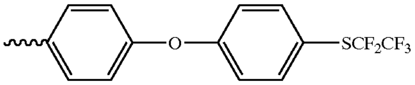 |
| 6 | 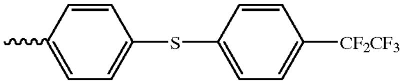 |
| 7 | 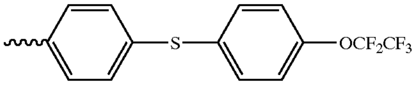 |
| 8 | 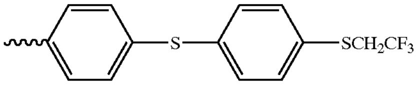 |
| 9 | 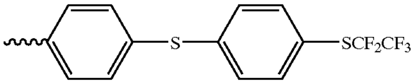 |
| 10 | 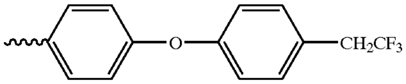 |
| 11 | 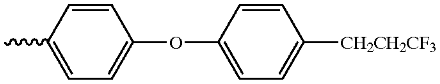 |
| 12 | 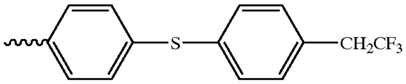 |
| 13 | 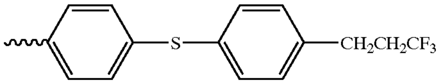 |
| 14 | 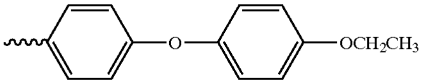 |
| 15 | 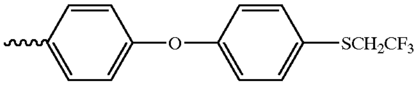 |
| 16 | 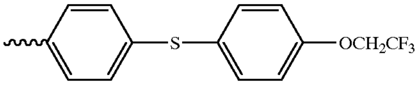 |

TABLE 143
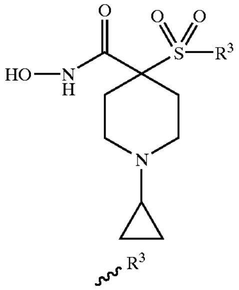
| | |
|---|---|
| 1 | 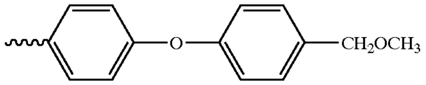 |
| 2 | 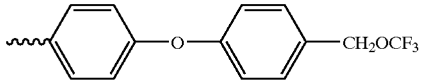 |
| 3 | 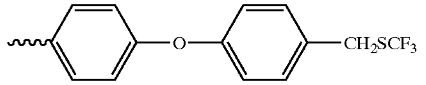 |
| 4 | 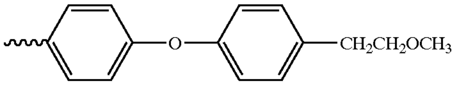 |
| 5 | 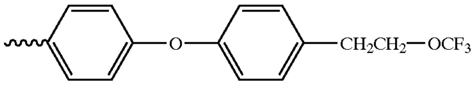 |
| 6 | 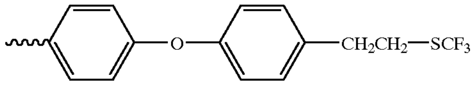 |
| 7 | 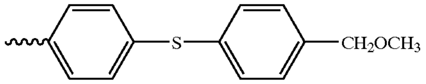 |
| 8 | 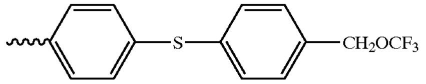 |
| 9 | 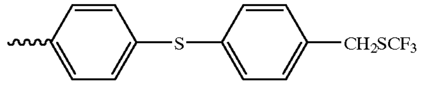 |
| 10 | 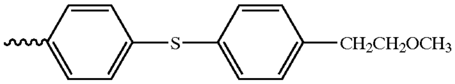 |
| 11 | 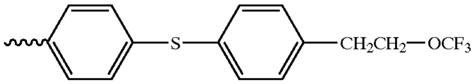 |
| 12 | 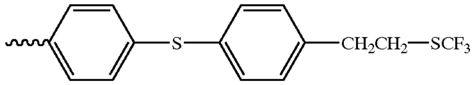 |
TABLE 144
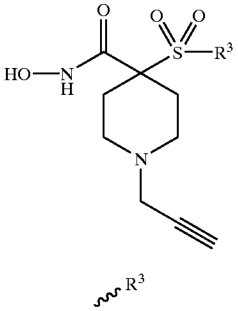
| | |
|---|---|
| 1 | 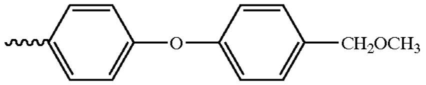 |
| 2 | 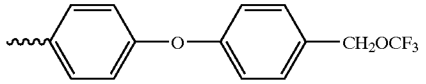 |
| 3 | 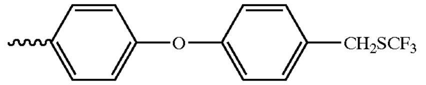 |
| 4 | 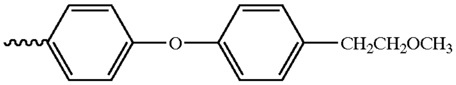 |
| 5 | 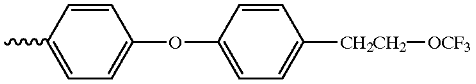 |
| 6 | 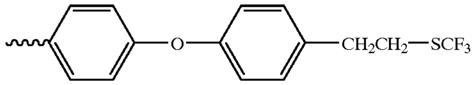 |
| 7 | 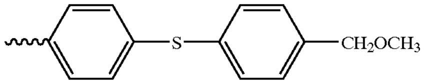 |
| 8 | 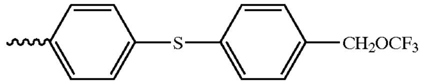 |
| 9 | 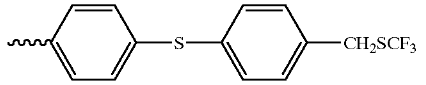 |
| 10 | 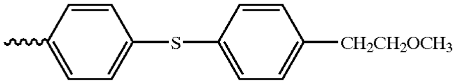 |
| 11 | 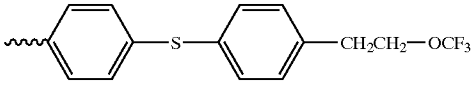 |
| 12 | 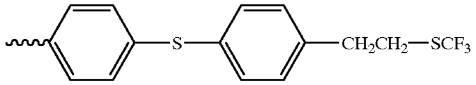 |

TABLE 145
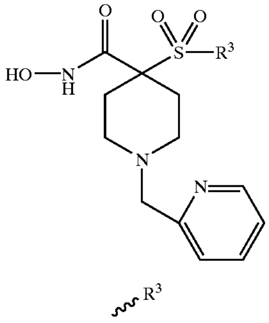
| | |
|---|---|
| 1 | 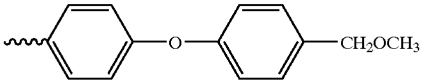 |
| 2 | 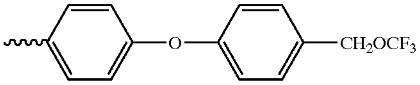 |
| 3 | 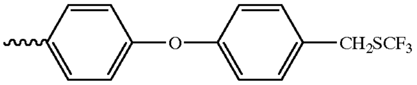 |
| 4 | 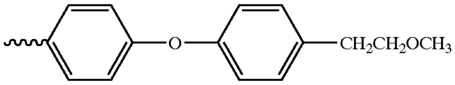 |
| 5 | 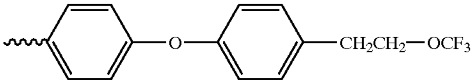 |
| 6 | 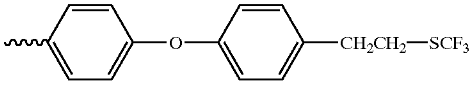 |
| 7 | 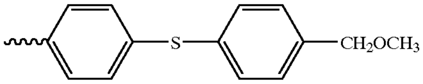 |
| 8 | 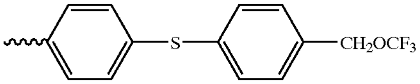 |
| 9 | 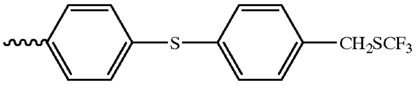 |
| 10 | 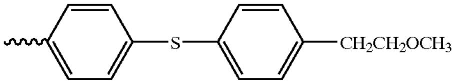 |
| 11 | 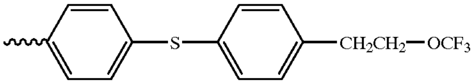 |
| 12 | 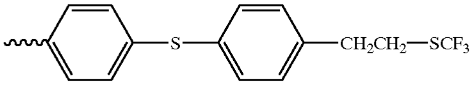 |
TABLE 146
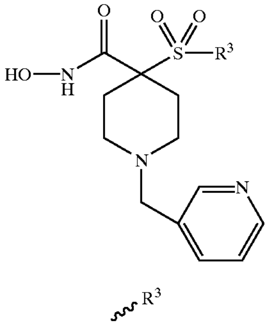
| | |
|---|---|
| 1 | 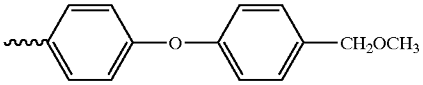 |
| 2 | 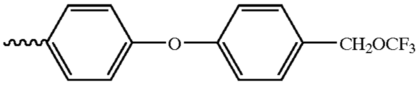 |
| 3 | 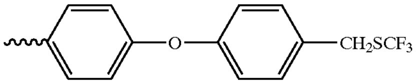 |
| 4 | 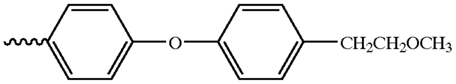 |
| 5 | 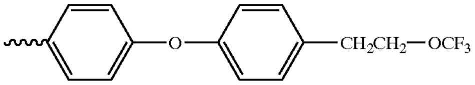 |
| 6 | 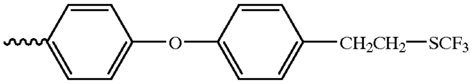 |
| 7 | 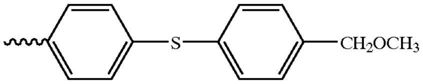 |
| 8 | 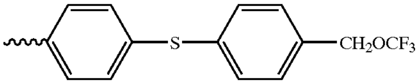 |
| 9 | 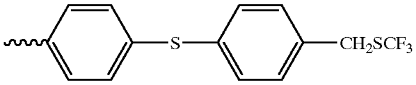 |
| 10 | 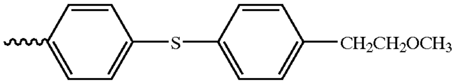 |
| 11 | 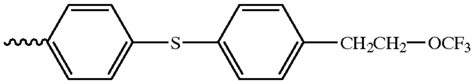 |
| 12 | 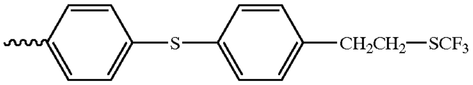 |

TABLE 147
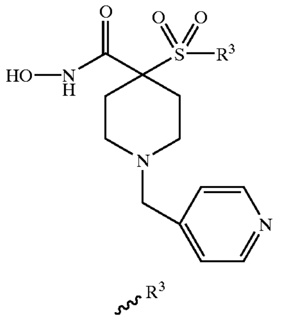
| | |
|---|---|
| 1 | 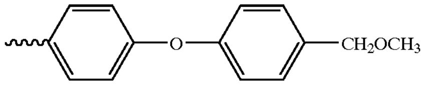 |
| 2 | 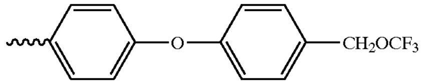 |
| 3 | 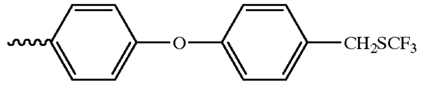 |
| 4 | 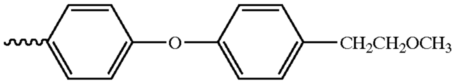 |
| 5 | 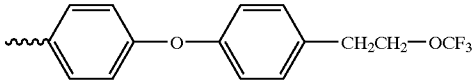 |
| 6 | 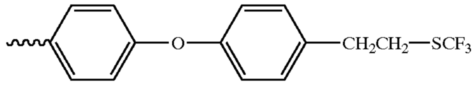 |
| 7 | 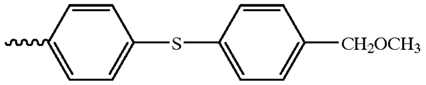 |
| 8 | 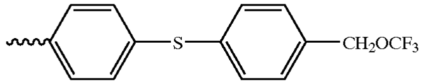 |
| 9 | 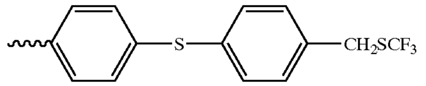 |
| 10 | 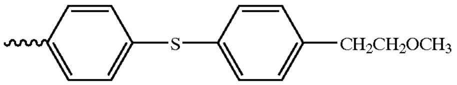 |
| 11 | 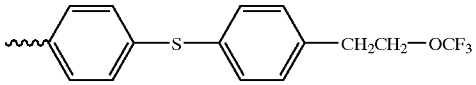 |
| 12 | 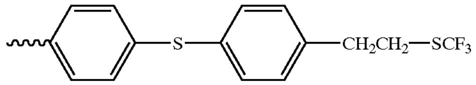 |
TABLE 148
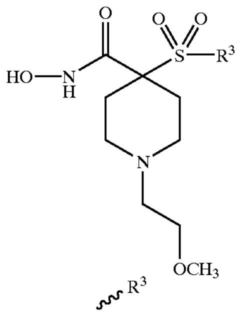
| | |
|---|---|
| 1 | 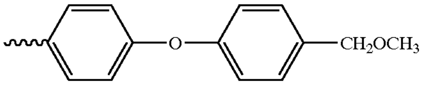 |
| 2 | 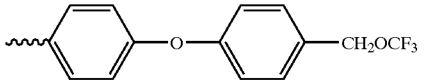 |
| 3 | 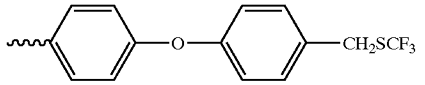 |
| 4 | 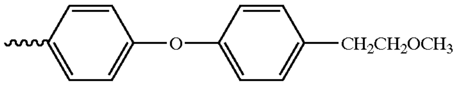 |
| 5 | 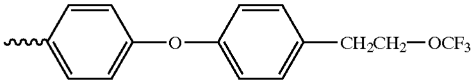 |
| 6 | 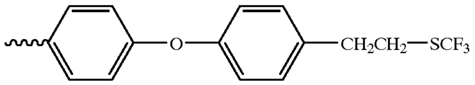 |
| 7 | 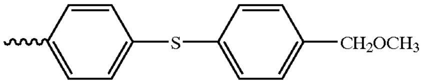 |
| 8 | 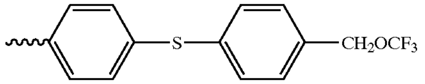 |
| 9 | 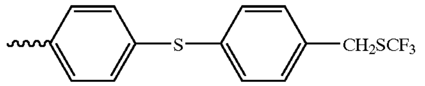 |
| 10 | 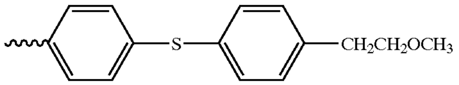 |
| 11 | 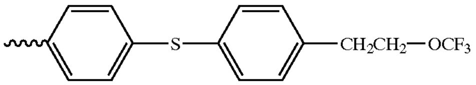 |
| 12 | 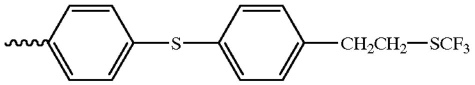 |

TABLE 149
| 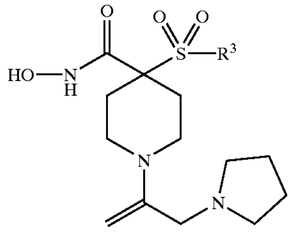 |
| --- |
| $R^3$ |
| 1 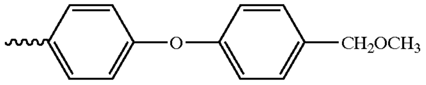 |
| 2 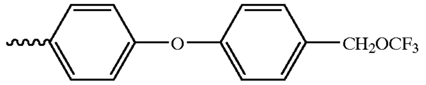 |
| 3 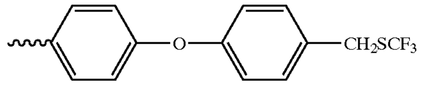 |
| 4 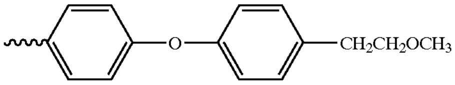 |
| 5 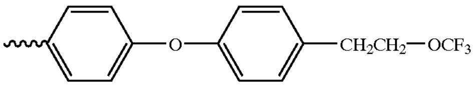 |
| 6 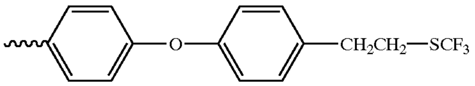 |
| 7 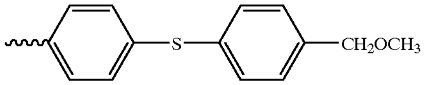 |
| 8 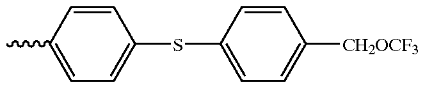 |
| 9 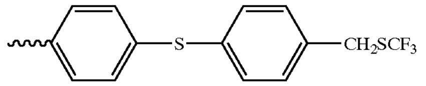 |
| 10 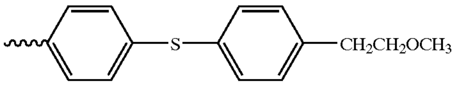 |
| 11 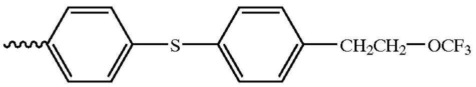 |
| 12 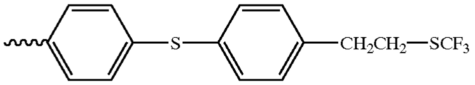 |
TABLE 150
| 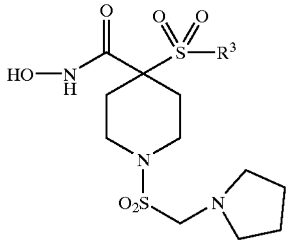 |
| --- |
| $R^3$ |
| 1 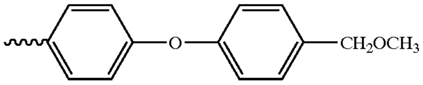 |
| 2 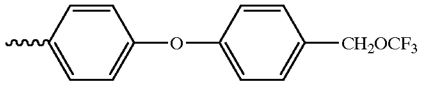 |
| 3 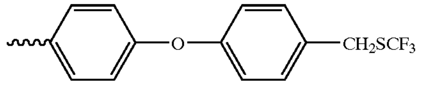 |
| 4 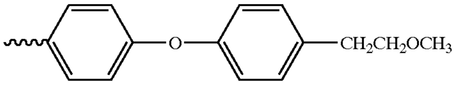 |
| 5 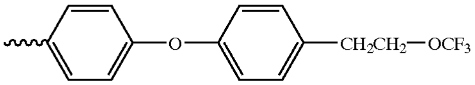 |
| 6 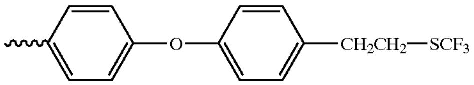 |
| 7 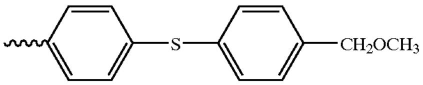 |
| 8 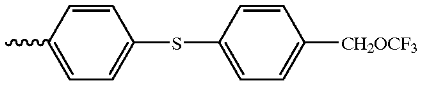 |
| 9 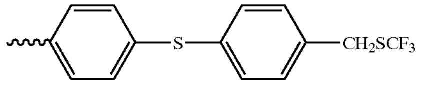 |
| 10 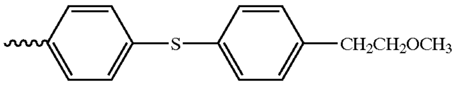 |
| 11 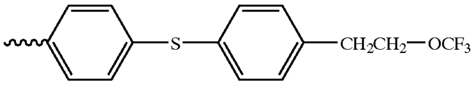 |
| 12 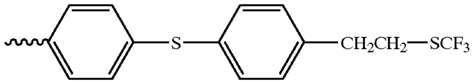 |
A contemplated inhibitor compound is used for treating a host mammal such as a mouse, rat, rabbit, dog, horse, primate such as a monkey, chimpanzee or human that has a condition associated with pathological matrix metalloprotease activity.

Also contemplated is use of a contemplated metalloprotease inhibitor compound in the treatment of a disease state that can be affected by the activity of metalloproteases TNF-α convertase. Exemplary of such disease states are the acute phase responses of shock and sepsis, coagulation responses, hemorrhage and cardiovascular effects, fever and inflammation, anorexia and cachexia.

In treating a disease condition associated with pathological matrix metalloproteinase activity, a contemplated MMP inhibitor compound can be used in the form of an amine salt derived from an inorganic or organic acid. Exemplary salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate.

Also, a basic nitrogen-containing group can be quaternized with such agents as lower alkyl halides, such as methyl, ethyl, propyl, and butyl chloride, bromides, and iodides; dialkyl sulfates like dimethyl, diethyl, dibuytl, and diamyl sulfates, long chain halides such as decyl, lauryl, myristyl and stearyl chlorides, bromides and iodides, aralkyl halides like benzyl and phenethyl bromides, and others to provide enhanced water-solubility. Water or oil-soluble or dispersible products are thereby obtained as desired. The salts are formed by combining the basic compounds with the desired acid.

Other compounds useful in this invention that are acids can also form salts. Examples include salts with alkali metals or alkaline earth metals, such as sodium, potassium, calcium or magnesium or with organic bases or basic quaternary ammonium salts.

In some cases, the salts can also be used as an aid in the isolation, purification or resolution of the compounds of this invention.

Total daily dose administered to a host mammal in single or divided doses can be in amounts, for example, for 0.001 to 30 mg/kg body weight daily and more usually 0.01 to 10 mg. Dosage unit compositions can contain such amounts or submultiples thereof to make up the daily dose. A suitable dose can be administered, in multiple sub-doses per day. Multiple doses per day can also increase the total daily dose, should this be desired by the person prescribing the drug.

The dosage regimen for treating a disease condition with a compound and/or composition of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed can vary widely and therefore can deviate from the preferred dosage regimen set forth above.

A compound of the present invention can be formulated as a pharmaceutical composition. Such a composition can then be administered orally, parenterally, by inhalation spray, rectally, or topically in dosage unit formulations containing conventional nontoxic pharmaceutically acceptable carriers, adjuvants, and vehicles as desired. Topical administration can also involve the use of transdermal administration such as transdermal patches or iontophoresis devices. The term parenteral as used herein includes subcutaneous injections, intravenous, intramuscular, intrasternal injection, or infusion techniques. Formulation of drugs is discussed in, for example, Hoover, John E., *Remington's Pharmaceutical Sciences,* Mack Publishing Co., Easton, Pa.; 1975 and Liberman, H. A. and Lachman, L., Eds., *Pharmaceutical Dosage Forms,* Marcel Decker, New York, N.Y., 1980.

Injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables. Dimethyl acetamide, surfactants including ionic and non-ionic detergents, polyethylene glycols can be used. Mixtures of solvents and wetting agents such as those discussed above are also useful.

Suppositories for rectal administration of the drug can be prepared by mixing the drug with a suitable nonirritating excipient such as cocoa butter, synthetic mono- di- or triglycerides, fatty acids and polyethylene glycols that are sold at ordinary temperatures but liquid at the rectal temperature and will therefore melt in the rectum and release the drug.

Solid dosage forms for oral administration can include capsules, tablets, pills, powders, and granules. In such solid dosage forms, the compounds of this invention are ordinarily combined with one or more adjuvants appropriate to the indicated route of administration. If administered per os, a contemplated aromatic sulfone hydroximate inhibitor compound can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from soerile powders or granules having one or more of the carriers or diluents mentioned for use in the formulations for oral administration. A contemplated aromatic sulfone hydroximate inhibitor compound can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The amount of active ingredient that can be combined with the carrier materials to produce a single dosage form varies depending upon the mammalian host treated and the particular mode of administration.

BEST MODE FOR CARRYING OUT THE INVENTION

Without further elaboration, it is believed that one skilled in the art can, using the preceding description, utilize the present invention to its fullest extent. The following preferred specific embodiments are, therefore, to be construed as merely illustrative, and not limiting of the remainder of the disclosure in any way whatsoever.

EXAMPLE 1

Preparation of N-hydroxy-2-[(4-phenoxyphenyl) sulfonyl]acetamide

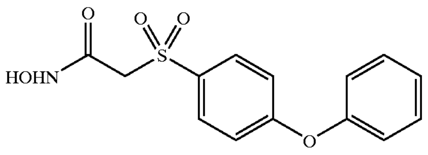

Part A: To a solution of 3-bromopyruvic acid hydrate (1.95 g, 11.7 mmol) cooled to zero degrees Celsius in methanol (50 mL) was added 4-(phenoxy)benzenethiol (2.35 g, 11.7 mmol). The solution was stirred for 15 minutes followed by concentration in vacuo. The residue was partitioned between ethyl acetate and $H_2O$ and the organic layer was dried over magnesium sulfate. Concentration in vacuo provided the crude sulfide as a yellow solid that was used without any additional purification.

Part B: To a solution of the crude sulfide of part A (1.2 g, <2.6 mmol) in methanol/$H_2O$ cooled to zero degrees Celsius was added Oxone® (3.5 g, 5.72 mmol). The solution was stirred for 1 hour followed by removal of excess Oxone® by filtration. The filtrate was concentrated and the residue was dissolved into ethyl acetate and washed with saturated $NaHCO_3$ and saturated NaCl and dried over magnesium sulfate. After concentration in vacuo the resulting residue was dissolved into methanol and thionyl chloride (1.9 mL, 26 mmol) was added. Chromatography (on silica, ethyl acetate/hexane) provided the sulfone as a solid (350 mg, 44%). MS(CI) $MH^+$ calculated for $C_{15}H_{14}O_5S$: 307, found 307.

Part C: To a solution of the sulfone (350 mg, 1.1 mmol) in methanol (2 mL) and THF (THF; 2 mL) was added 50 percent aqueous hydroxylamine (1 mL). The solution was stirred overnight. Trituration with ethyl acetate provided the title compound as a white solid (270 mg, 77%). HPLC purity: >97%. MS(CI) $MH^+$ calculated for $C_{14}H_{13}NO_5S$: 308, found 308.

EXAMPLE 2

Preparation of N-hydroxy-2-methyl-2-[(4-phenoxyphenyl)sulfonyl]propanamide

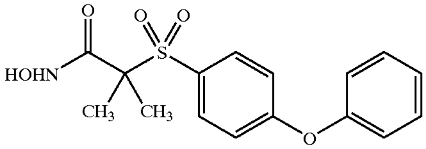

Part A: To a solution of 4-(phenoxy)benzenethiol (3.8 g, 18.8 mmol) in methanol (60 mL) cooled to zero degrees Celsius was added t-butyl bromoacetate (2.8 mL, 18.8 mmol) and triethylamine (2.6 mL, 19.0 mmol). The solution was stirred for 30 minutes and was then concentrated in vacuo. The residue was partitioned between ethyl acetate and $H_2O$ and the organic layer was washed with saturated NaCl and dried over magnesium sulfate. Concentration in vacuo provided the sulfide as an oil. To a solution of the sulfide in dichloromethane (85 mL) was added m-chloroperbenzoic acid (13.8 g, 43.2 mmol) over 15 minutes. The solution was stirred at ambient temperature for 2 hours. The reaction was quenched by the addition of aqueous $Na_2SO_3$. After 30 minutes the solution was filtered through Celite®. The filtrate was washed with 25 percent aqueous hydroxylamine, 1N HCl, and saturated NaCl and dried over magnesium sulfate. Chromatography (on silica, ethyl acetate/hexane) provided the sulfone as a white solid (4.0 g, 68%).

Part B: To a solution of the sulfone of part A (3.2 g, 9.2 mmol) in THF (65 mL) cooled to zero degrees Celsius was added sodium hydride (730 mg of a 60 percent dispersion in mineral oil, 18.4 mmol). After 10 minutes, methyl iodide (2.28 mL, 36.8 mmol) was added dropwise and the mixture was stirred for 18 hours at ambient temperature. The reaction was quenched with $H_2O$ and concentrated in vacuo. The aqueous residue was diluted with ethyl acetate and the organic phase was washed with $H_2O$ and dried over $Na_2SO_4$. Concentration in vacuo provided the dimethyl compound as an off-white solid (3.2 g, 92%). HPLC purity: 95%.

Part C: To a solution of the dimethyl compound of part B (3.2 g, 8.5 mmol) in anisole (10 mL) was added trifluoroacetic acid (30 mL) and the solution was stirred for 30 minutes. Concentration in vacuo followed by trituration (ethyl ether) provided the acid as a white solid (750 mg, 28%). HPLC purity: 99%. MS(CI) $MH^+$ calculated for $C_{16}H_{16}O_5S$: 321, found 321.

Part D: To a solution of the acid of part C (723 mg, 2.26 mmol) in DMF (DMF; 4.5 mL) was added N-hydroxybenzotriazole.$H_2O$ (HOBT; 366 mg, 2.71 mmol) and 1-(3-dimethylaminopropyl)-3-ethylcarbodiimide hydrochloride (EDC; 476 mg, 2.49 mmol). After the solution was stirred for 1 hour at ambient temperature 50 percent aqueous hydroxylamine (0.40 mL, 6.8 mmol) was added. After 15 minutes the solution was partitioned between ethyl acetate and $H_2O$. The organic layer was washed with $H_2O$ and saturated NaCl and dried over $Na_2SO_4$. Reverse phase chromatography (on silica, acetonitrile/$H_2O$) provided the title compound as a white foam (434 mg, 57%). HPLC purity: 99%. MS(CI) $M+Li^+$ calculated for $C_{16}H_{17}NO_5O$: 342, found 342.

EXAMPLE 3

Preparation of 1,1-dimethylethyl Ester 4-[(hydroxyamino)carbonyl]-4-[(phenoxyphenyl)-sulfonyl]-1-piperidinecarboxylic Acid

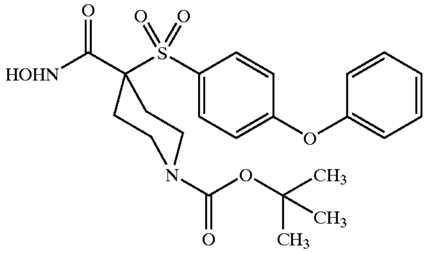

Part A: A solution of 4-(phenoxy)benzenethiol (2.03 g, 10.0 mmol) in DMSO (DMSO; 20 mL) was heated to sixty-five degrees Celsius for 5 hours. The solution remained at ambient temperature for 18 hours. The solution was extracted with ethyl acetate and the combined organic layers were washed with $H_2O$ and saturated NaCl and dried over magnesium sulfate. Concentration in vacuo provided the disulfide as a yellow oil (2.3 g, quantitative yield).

Part B: To a solution of ethyl isonipecotate (15.7 g, 0.1 mol) in THF (100 mL) was added a solution of di-tert-butyl dicarbonate (21.8 g, 0.1 mol) in THF (5 mL) dropwise over 20 minutes. The solution was stirred overnight at ambient temperature and concentrated in vacuo to yield a light oil. The oil was filtered through silica gel (7:3 ethyl acetate/hexanes) and concentrated in vacuo to give the BOC-piperidine compound (26.2 g, quantitative yield) as a clear, colorless oil.

Part C: To a solution of diisopropylamine (2.8 mL, 20 mmoL) in THF (30 mL), cooled to minus seventy-eight degrees Celsius, was added n-butyl lithium (12.5 mL, 20 mmol) dropwise. After 15 minutes, the BOC-piperidine compound of part B (2.6 g, 10 mmol) in THF (10 mL) was added dropwise. After 1.5 hours the solution was cooled to minus sixty degrees Celsius and the disulfide of part A (2.0 g, 10 mmol) in THF (7 mL). The solution was stirred at ambient temperature for 2 hours. The solution was diluted with $H_2O$ and extracted with ethyl acetate. The organic layer was washed with $H_2O$ and saturated NaCl and dried over magnesium sulfate. Chromatography (on silica, ethyl acetate/hexane) provided the sulfide as an oil (1.8 g, 40%).

Part D: To a solution of the sulfide of part C (1.8 g, 3.95 mmol) in dichloromethane (75 mL) cooled to zero degrees Celsius, was added m-chloroperbenzoic acid (1.7 g, 7.9 mmol). The solution was stirred for 1.5 hours followed by dilution with $H_2O$ and extraction with dichloromethane. The organic layer was washed with 10 percent $Na_2SO_4$, $H_2O$, and saturated NaCl and dried over magnesium sulfate. Chromatography (on silica, ethyl acetate/hexane) provided the sulfone as a solid (1.15 g, 59%).

Part E: To a solution of the sulfone of part D (800 mg, 1.63 mmol) in THF (9 mL) and ethanol (9 mL) was added NaOH (654 mg, 16.3 mmol) in $H_2O$ (3 mL). The solution was heated at sixty-five degrees Celsius for 18 hours. The solution was concentrated in vacuo and the residue was dissolved in $H_2O$. Following acidification with 2N HCl to pH 4, the solution was extracted with ethyl acetate and the organic layer was washed with saturated NaCl and dried over magnesium sulfate. Concentration in vacuo provided the acid as a white foam (790 mg, quantitative yield). Analytical calculated for $C_{23}H_{27}NO_7S$: C, 59.86; H, 5.90; N, 3.04; S, 6.95. Found: C, 59.49; H, 6.37; N, 2.81; S, 6.59.

Part F: To a solution of the acid of part G (730 mg, 1.58 mmol) in DMF (9 mL) was added HOBT (256 mg, 1.90 mmol) followed by EDC (424 mg, 2.21 mmol), 4-methylmorpholine (0.521 mL, 4.7 mmol) and 50 percent aqueous hydroxylamine (1.04 mL, 15.8 mmol). The solution was stirred for 20 hours and additional N-hydroxybenzotriazole.$H_2O$ (256 mg), EDC (424 mg) and 50 percent aqueous hydroxylamine (1.04 mL) were added. After an additional 24 hours of stirring the solution was diluted with $H_2O$ and extracted with ethyl acetate and the organic layer was washed with saturated NaCl and dried over magnesium sulfate. Reverse phase chromatography (on silica, acetonitrile/$H_2O$) provided the title compound as a white solid (460 mg, 61%). HPLC purity: >99%. Analytical calculated for $C_{23}H_{28}N_2O_7S$: C, 57.97; H, 5.92; N, 5.88; S, 6.73. Found: C, 57.95; H, 6.02; N, 5.81; S, 6.85.

EXAMPLE 4

Preparation of N-hydroxy-4-[(4-phenoxyphenyl) sulfonyl]-4-piperidinecarboxamide, Monohydrochloride

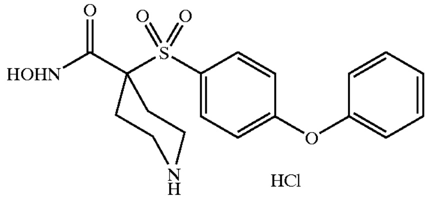

Part A: A solution of 4-(phenoxy)benzenethiol (2.03 g, 10.0 mmol) in DMSO (20 mL) was heated to sixty-five degrees Celsius for 5 hours. The solution remained at ambient temperature for 18 hours. The solution was extracted with ethyl acetate and the combined organic layers were washed with $H_2O$ and saturated NaCl and dried over magnesium sulfate. Concentration in vacuo provided the disulfide as a yellow oil (2.3 g, quantitative yield).

Part B: To a solution of ethyl isonipecotate (15.7 g, 0.1 mol) in THF (100 mL) was added a solution of di-tert-butyl dicarbonate (21.8 g, 0.1 mol) in THF (5 mL) dropwise over 20 minutes. The solution was stirred overnight at ambient temperature and concentrated in vacuo to yield a light oil. The oil was filtered through silica gel (on silica, ethyl acetate/hexane) and concentrated in vacuo to give the BOC-piperidine compound as a clear, colorless oil (26.2 g, quantitative yield).

Part C: To a solution of diisopropylamine (2.8 mL, 20 mmoL) in THF (30 mL), cooled to minus seventy-eight degrees Celsius, was added n-butyl lithium (12.5 mL, 20 mmol) dropwise. After 15 minutes, the BOC-piperidine compound of part B (2.6 g, 10 mmol) in THF (10 mT) was added dropwise. After 1.5 hours the solution was cooled to minus 60 degrees Celsius and the disulfide of part A (2.0 g, 10 mmol) in THF (7 mL) was added. The solution was stirred at ambient temperature for 2 hours. The solution was diluted with $H_2O$ and extracted with ethyl acetate. The organic layer was washed with $H_2O$ and saturated NaCl and dried over magnesium sulfate. Chromatography (on silica, ethyl acetate/hexane) provided the sulfide as an oil (1.8 g, 40%).

Part D: To a solution of the sulfide of part C (1.8 g, 3.95 mmol) in dichloromethane (75 mL) cooled to zero degrees C, was added m-chloroperbenzoic acid (1.7 g, 7.9 mmol). The solution was stirred for 1.5 hours followed by dilution with $H_2O$ and extraction with dichloromethane. The organic layer was washed with 10 percent $Na_2SO_3$, H2O, and saturated NaCl and dried over magnesium sulfate. Chromatography (on silica, ethyl acetate/hexane) provided the sulfone as a solid (1.15 g, 59%).

Part E: To a solution of the sulfone of part D (800 mg, 1.63 mmol) in THF (9 mL) and ethanol (9 mL) was added NaOH (654 mg, 16.3 mmol) in $H_2O$ (3 mL). The solution was heated at sixty-five degrees Celsius for 18 hours. The solution was concentrated in vacuo and the residue was dissolved in $H_2O$.

Following acidification with 2N HCl to pH 4, the solution was extracted with ethyl acetate and the organic layer was washed with saturated NaCl and dried over magnesium sulfate. Concentration in vacuo provided the acid as a white foam (790 mg, quantitative yield). analytical calculated for $C_{23}H_{27}NO_7S$: C, 59.86; H, 5.90; N, 3.04; S, 6.95. Found: C, 59.49; H, 6.37; N, 2.81; S, 6.59.

Part F: To a solution of the acid of part G (730 mg, 1.58 mmol) in DMF (9 mL) was added HOBT (256 mg, 1.90 mmol) followed by EDC (424 mg, 2.21 mmol), 4-methylmorpholine (0.521 mL, 4.7 mmol) and 50 percent aqueous hydroxylamine (1.04 mL, 15.8 mmol). The solution was stirred for 20 hours and additional HOBT (256 mg), EDC (424 mg) and 50 percent aqueous hydroxylamine (1.04 mL) were added. After an additional 24 hours of stirring the solution was diluted with $H_2O$, and extracted with ethyl acetate. The organic layer was washed with saturated NaCl and dried over magnesium sulfate. Reverse phase HPLC (acetonitrile/$H_2O$) provided the hydroxamate as a white solid (460 mg, 61%). HPLC purity: >99%. analytical calculated for $C_{23}H_{28}N_2O_7S$: C, 57.97; H, 5.92; N, 5.88; S, 6.73. Found: C, 57.95; H, 6.02; N, 5.81; S, 6.85.

Part G: Into a solution of the hydroxamate of part F (385 mg, 0.808 mmol) in ethyl acetate (25 mL), cooled to zero degrees Celsius, was bubbled HCl gas for 5 minutes. After standing for 30 minutes, the solution was concentrated in vacuo. Trituration with ethyl ether provided the title compound as a white solid (330 mg, quantitative yield). MS(CI) $MH^+$ calculated for $C_{18}H_{20}N_2O_5S$: 377, found 377. HRMS calculated for $C_{18}H_{20}N_2O_5S$: 377.1171, found 377.1170. analytical calculated for $C_{18}H_{20}N_2O_5S.1.1HCl.0.25H_2O$: C, 51.35; H, 5.17; N, 6.65; S, 7.62; Cl, 9.26. Found: C, 51.58; H, 5.09; N, 6.55; S, 8.02; Cl, 9.09.

EXAMPLE 5

Preparation of (E) N-hydroxy-2-[(4-phenoxyphenyl) sulfonyl]-3-phenyl-2-propenamide

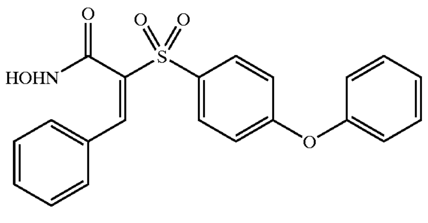

Part A: To a solution of 4-(phenoxy)benzenethiol (5.00 g, 24.7 mmol) in methanol (100 mL) cooled to zero degrees Celsius was added t-butylbromoacetate (3.99 mL, 24.7 mmol). Following the addition of triethylamine (3.60 mL, 25.8 mmol) the solution was stirred for 40 minutes The solution was concentrated in vacuo and the resulting residue was dissolved in ethyl acetate and washed with $H_2O$ and saturated NaCl and dried over $Na_2SO_4$. Concentration in vacuo provided the sulfide as an oil (7.9 g, quantitative yield).

Part B: To a solution of the sulfide of part A (7.9 g, 24.7 mmol) in methanol (180 mL) and $H_2O$ (20 mL) was added Oxone® (38.4 g, 62.5 mmol) and the mixture was stirred for 22 hours. The mixture was acidified to pH 4 with 2.5N NaOH and decanted to remove insoluble salts. The decantate was concentrated to one-half volume and partitioned between ethyl acetate and $H_2O$. The organic layer was washed with $H_2O$ and saturated NaCl and dried over $Na_2SO_4$. Chromatography (on silica, ethyl acetate/hexane) provided the sulfone as a yellow solid (5.79 g, 67%).

Part C: To a solution of the sulfone of part B (2.5064 g, 7.20 mmol) and benzaldehyde (0.748 mL, 7.36 mmol) in benzene (20 mL) were added acetic acid (0.15 mL) and piperidine (0.05 mL). The solution was heated to reflux for 2 hours and the condensate was collected via a Dean-Stark trap. After an additional 1.5 hours of reflux, the solution was returned to ambient temperature and stirred for 18 hours. The solution was diluted with ethyl acetate and washed with $H_2O$ and saturated NaCl and dried over $Na_2SO_4$. Chromatography (on silica, ethyl acetate/hexane) followed by trituration (ethyl ether/hexane) provided the unsaturated sulfone as a white solid (1.97 g, 73%). HPLC purity: >98%.

Part D: Into a solution of the unsaturated sulfone of part C (0.5053 g, 1.16 mmol) was bubbled HCl gas for 1 hour. The solution was concentrated in vacuo and the residue was dissolved into ethyl acetate and washed with $H_2O$ and dried over $Na_2SO_4$. Concentration in vacuo provided the acid as an oil (0.41 g, 93%).

Part E: To a solution of the acid of part D (461 mg, 1.21 mmol) was added thionyl chloride (3.0 mL) and the solution was heated to one hundred degrees Celsius for 1 hour. Concentration in vacuo provided the acid chloride as an amber oil (380 mg, 79%).

Part F: To a solution of the acid chloride of part E (380 mg, 0.95 mmol) in THF (20 mL) was added 50 percent aqueous hydroxylamine (1.7 mL, 9.5 mmol). The solution was stirred at zero degrees Celsius for 1 hour. The solution was diluted with ethyl acetate, washed with $H_2O$ and saturated NaCl, and dried over $Na_2SO_4$. Reverse phase chromatography (on silica, acetonitrile/$H_2O$) followed by trituration (ethyl ether/hexane) provided the title compound as a white solid (131 mg, 35%). HPLC purity: >97%.

EXAMPLE 6

Preparation of N-hydroxy-4-[(4-phenoxyphenyl) sulfonyl]-1-(2-propynyl)-4-piperidinecarboxamide, Monohydrochloride

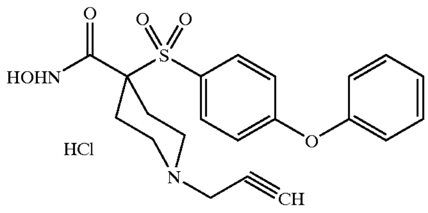

Part A: A solution of 4-(phenoxy)benzenethiol (2.03 g, 10.0 mmol) in DMSO (20 mL) was heated to 65 degrees Celsius for 5 hours. The solution remained at ambient temperature for 18 hours. The solution was extracted with ethyl acetate and the combined organic layers were washed with $H_2O$ and saturated NaCl, and dried over magnesium sulfate. Concentration in vacuo provided the disulfide as a yellow oil (2.3 g, quantitative yield).

Part B: To a solution of ethyl isonipecotate (15.7 g, 0.1 mol) in THF (100 mL) was added a solution of di-tert-butyl dicarbonate (21.8 g, 0.1 mol) in THF (5 mL) dropwise over 20 minutes. The solution was stirred overnight at ambient temperature and concentrated in vacuo to yield a light oil. The oil was filtered through silica gel (ethyl acetate/hexane) and concentrated in vacuo to give the BOC-piperidine compound as a clear, colorless oil (26.2 g, quantitative yield).

Part C: To a solution of diisopropylamine (2.8 mL, 20 mmoL) in THF (30 mL), cooled to minus seventy-eight degrees Celsius, was added n-butyl lithium (12.5 mL, 20 mmol) dropwise. After 15 minutes, the BOC-piperidine compound of part B (2.6 g, 10 mmol) in THF (10 mL) was added dropwise. After 1.5 hours the solution was cooled to minus sixty degrees Celsius and the disulfide of part A (2.0 g, 10 mmol) in THF (7 mL) was added. The solution was stirred at ambient temperature for 2 hours. The solution was diluted with $H_2O$ and extracted with ethyl acetate. The organic layer was washed with $H_2O$ and saturated NaCl and dried over magnesium sulfate. Chromatography (on silica, ethyl acetate/hexane) provided the sulfide as an oil (1.8 g, 40%).

Part D: To a solution of the sulfide of part C (1.8 g, 3.95 mmol) in dichloromethane (75 mL) cooled to zero degrees Celsius, was added m-chloroperbenzoic acid (1.7 g, 7.9 mmol). The solution was stirred for 1.5 hours followed by dilution with $H_2O$ and extraction with dichloromethane. The organic layer was washed with 10 percent $Na_2SO_4$, $H_2O$, and saturated NaCl and dried over magnesium sulfate. Chromatography (on silica, ethyl acetate/hexane) provided the sulfone as a solid (1.15 g, 59%)

Part E: Into a solution of the sulfone of part D (3.56 g, 7.0 mmol) in ethyl acetate (100 mL) cooled to zero degrees Celsius was bubbled HCl gas for 5 minutes. Concentration in vacuo followed by trituration with ethyl ether provided the amine hydrochloride salt as a white solid (3.5 g, quantitative yield). MS (CI) $MH^+$ calculated for $C_{20}H_{23}NO_5S$: 390, found 390.

Part F: To a solution of the amine hydrochloride salt of part E (2.6 g, 6 mmol) and $K_2CO_3$ (1.66 g, 12 mmol) in DMF (50 mL) was added propargyl bromide (892 mg, 6 mmol) and the solution was stirred at ambient temperature for 4 hours. The solution was diluted with $H_2O$ and extracted with ethyl acetate. The combined organic layers were washed with saturated NaCl and dried over magnesium sulfate. Chromatography (on silica, ethyl acetate/hexane) provided the propargyl amine as a white solid (2.15 g, 82%).

Part G: To a solution of the propargyl amine of part F (2.15 g, 5 mmol) in THF (30 mL) and ethanol (30 mL) was added NaOH (2.0 g, 50 mmol) and the solution was heated at 65 degrees Celsius for 48 hours. The solution was concentrated in vacuo and the aqueous residue was acidified to a pH value of 5. Vacuum filtration of the resulting precipitate provided the acid as a white solid (2.04 g, quantitative yield).

Part H: To a solution of the-acid of part G (559 mg, 1.4 mmol) in dichloromethane (5 mL) was added triethylamine (0.585 mL, 4.2 mmol) and 50 percent aqueous hydroxylamine (0.925 mL, 14.0 mmol) followed by bromotris (pyrrolidino)phosphonium hexafluourphosphate (PyBroP®; 718 mg, 1.54 mmol). The solution was stirred at ambient temperature for 4 hours. The solution was diluted with $H_2O$ and extracted with dichloromethane. The organic layer was washed with saturated NaCl and dried over magnesium sulfate. Reverse phase chromatography (on silica, acetonitrile/$H_2O$) provided the hydroxamate as a white solid (140 mg, 25%). Analytical calculation for $C_{21}H_{22}N_2O_5S$: C, 60.85; H, 5.37; N, 6.76; S, 7.74. Found: C, 60.47; H, 5.35; N, 6.61; S, 7.46.

Part I: To a solution of the hydroxamate of part H (121 mg, 0.292 mmol) in methanol (2 mL) cooled to zero degrees Celsius was added acetyl chloride (0.228 mL, 0.321 mmol) in methanol (1 mL). After stirring at ambient temperature for 30 minutes the solution was concentrated under a stream of $N_2$. Trituration with ethyl ether provided the title compound as a white solid (107 mg, 81%). Analytical calculation for $C_{23}H_{22}N_2O_5S.HCl.0.3H_2O$: C, 55.27; H, 5.21; N, 6.14. Found: C, 54.90; H, 5.37; N, 6.07.

EXAMPLE 7

Preparation of N-[4-[[2-(hydroxyamino)-2-oxoethyl] sulfonyl]phenyl]benzamide

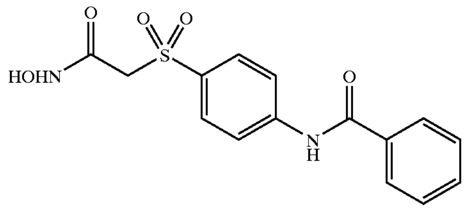

Part A: To a suspension of 2-(4-aminophenylthio)acetic acid (20.00 g, 0.109 mmol) in methanol (100 mL) cooled to zero degrees Celsius was added thionyl chloride (24.0 mL, 0.327 mmol) dropwise. Additional methanol was added (100 mL) and the suspension was heated to reflux for 2 hours. The solution was concentrated in vacuo and the residue was dissolved into $H_2O$ and neutralized with saturated $NaHCO_3$. The aqueous layer was extracted with ethyl acetate and the combined organic layers were washed with saturated NaCl and dried over $Na_2SO_4$. Concentration in vacuo provided the methyl ester as a dark purple oil (22.75 g, quantitative yield). HPLC purity: 99%.

Part B: To a solution of the methyl ester of part A (5.00 g, 25.35 mmol) and triethylamine (7.07 mL, 50.70 mmol) in dichloromethane (50 mL) was added benzoyl chloride (3.24 mL, 27.89 mmol) and the solution was stirred at ambient temperature for 2 hours. The solution was concentrated in vacuo and the residue was partitioned between ethyl acetate, THF and $H_2O$. The organic layer was washed with $H_2O$ and saturated NaCl and dried over $Na_2SO_4$. Concentration in vacuo provided the benzamide as a purple solid (7.06 g, 92%). HPLC purity: 98%. MS(CI) $M+Li^+$ calculated for $C_{16}H_{15}NO_3S$: 308, found 308.

Part C: To a solution of the benzamide of part B (4.00 g, 13.27 mmol) in THF (100 mL) and $H_2O$ (10 mL) cooled to zero degrees Celsius was added Oxone® (potassium monopersulfate; 24.47 g, 39.81 mmol). The slurry was stirred overnight (about eighteen hours) at ambient temperature. The mixture was filtered to remove excess Oxone® and the filtrate was concentrated in vacuo. The residue was dissolved into ethyl acetate and washed with $H_2O$ and saturated NaCl, and then dried over $Na_2SO_4$. Concentration in vacuo provided the sulfone as a pink solid (4.11 g, 93%). HPLC purity: 98%. MS(CI) M+Li$^+$ calculated for $C_{16}H_{15}NO_5S$: 340, found 340.

Part D: To a solution of the sulfone of part C (400 mg, 1.2 mmol) in THF (9 mL) was added 50 percent aqueous hydroxylamine (5.0 mL). The solution was stirred for 8 hours and was concentrated in vacuo. Trituration with hot ethyl ether provided the title compound as an off-white solid (348 mg, 78%). HPLC purity: 97%. MS (CI) MH$^+$ calculated for $C_{17}H_{14}N_2O_5S$: 335, found 335.

EXAMPLE 8

Preparation of N-[4-[[2-(hydroxyamino)-2-oxo-1-(piperidin-4-yl)ethyl)sulfonyl]-phenyl]-benzamide, Monohydrochloride

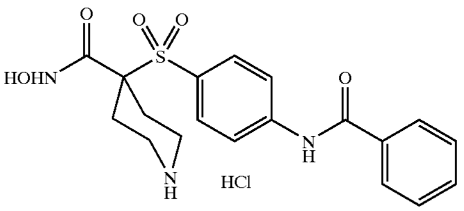

Part A: To a solution of diethanolamine (22.16 g, 0.211 mol) in THF (100 mL) cooled to zero degrees Celsius was added di-t-butyl dicarbonate (46.0 g, 0.211 mol) and the solution was stirred at ambient temperature for 20 hours. The solution was concentrated in vacuo and the resulting residue was filtered through a silica pad (5 percent methanol/95 percent dichloromethane) to provide the diol as a clear oil (45.06 g, quantitative yield). MS(CI) MH$^+$ calculated for $C_9H_{19}O_4S$: 206, found 206.

Part B: To a suspension of 2-(4-aminophenylthio)acetic acid (20.00 g, 0.109 mmol) in methanol (100 mL) cooled to zero degrees Celsius thionyl chloride (24.0 mL, 0.327 mmol) was added dropwise. After additional methanol was added (100 mL), the suspension was heated to reflux for 2 hours. The composition was concentrated in vacuo, the residue was dissolved in $H_2O$ and neutralized with saturated $NaHCO_3$. The aqueous layer was extracted with ethyl acetate and the combined organic layers were washed with saturated NaCl and dried over $Na_2SO_4$. Concentration in vacuo provided the methyl ester as a dark purple oil (22.75 g, quantitative yield). HPLC purity: 99%.

Part C: To a solution of the methyl ester of part B (5.00 g, 25.35 mmol) and triethylamine (7.07 mL, 50.70 mmol) in dichloromethane (50 mL) was added benzoyl chloride (3.24 mL, 27.89 mmol) and the solution was stirred at ambient temperature for 2 hours. The solution was concentrated in vacuo and the residue was partitioned between ethyl acetate, THF and $H_2O$. The organic layer was washed with $H_2O$ and saturated NaCl and dried over $Na_2SO_4$. Concentration in vacuo provided the benzamide as a purple solid (7.06 g, 92%). HPLC purity: 98%.

Part D: To a solution of the benzamide of part C (4.00 g, 13.27 mmol) in THF (100 mL) and $H_2O$ (10 mL) cooled to zero degrees Celsius was added Oxone® (24.47 g, 39.81 mmol). The slurry was stirred overnight (about eighteen hours) at ambient temperature. The mixture was filtered to remove excess Oxone® and the filtrate was concentrated in vacuo. The residue was dissolved into ethyl acetate and washed with $H_2O$ and saturated NaCl and dried over $Na_2SO_4$. Concentration in vacuo provided the sulfone as a pink solid (4.11 g, 93%). HPLC purity: 98%.

Part E: To a solution of the diol of part A (1.03 g, 5.00 mmol) and the methyl ester of part D (2.00 g, 6.00 mmol) in THF (100 mL) was added the 1,1'-(azodicarbonyl) dipiperidine (5.05 g, 20.00 mmol). To this slurry was added trimethyl phosphine (20.00 mL of a 1.0M solution in THF, 20.00 mmol). The mixture stirred for 1 hour at ambient temperature and then was heated at 40 degrees Celsius for 18 hours. After the slurry returned to ambient temperature, ethyl ether was added and the insoluble solids were removed by filtration. The filtrate was concentrated in vacuo and the resulting residue was dissolved into ethyl acetate, washed with $H_2O$ and saturated NaCl, and then dried over $Na_2SO_4$. Chromatography (on silica, ethyl acetate/hexane) provided the piperidine compound as a yellow solid (600 mg, 24%). MS(CI) MH$^+$ calculated for $C_{25}H_{30}N_2O_7S$: 503, found 503.

Part F: To a solution of the piperidine compound of part E (950 mg, 1.89 mmol) in THF (10 mL) was added potassium silanolate (970 mg, 7.56 mmol) and the solution was stirred at ambient temperature for 72 hours. The solution was diluted with $H_2O$, acidified to pH 2 with 1M HCl, and extracted with ethyl acetate. The combined organic layers were washed with saturated NaCl and dried over $Na_2SO_4$. Concentration in vacuo provided the acid as a yellow solid (772 mg, 84%).

Part G: To a solution of the acid of part F (772 mg, 1.48 mmol) in DMF (9 mL) was added HOBT (240 mg, 1.77 mmol), 4-methylmorpholine (0.488 mL, 4.44 mmol), O-tetrahydropyranyl hydroxyamine (538 mg, 4.54 mmol) and EDC (397 mg, 2.07 mmol). The solution stirred at ambient temperature for 2 hours. Following concentration in vacuo the residue was partitioned between ethyl acetate and $H_2O$. The organic layer was washed with saturated NaCl and dried over $Na_2SO_4$. Chromatography (on silica, ethyl acetate/hexane) provided the protected hydroxylamine as a white solid (608 mg, 70%). HPLC purity: >99%).

Part H: To a solution of the protected hydroxylamine of part G (596 g, 1.01 mmol) in dioxane (3 mL) and methanol (1 mL) was added 4M HCl in dioxane (2.50 mL, 10.14 mmol) and the solution stirred for 50 minutes at ambient temperature. Trituration with ethyl ether provided the title compound as a white solid (433 mg, 98%). HPLC purity: 98%. MS(CI) MH$^+$ calculated for $C_{19}H_{21}N_3O_5S$: 404, found 404.

EXAMPLE 9

Preparation of N-hydroxy-4-[[4-(phenylthio)phenyl] sulfonyl]-1-(2-propynyl)-4-piperidinecarboxamide, Monohydrochloride

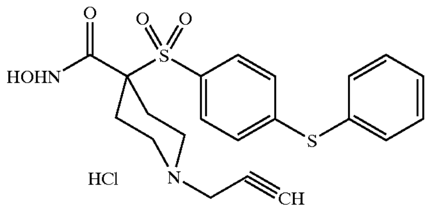

Part A: To a solution of ethyl isonipecotate (15.7 g, 0.1 mol) in THF (100 mL) was added a solution of di-tert-butyl dicarbonate (21.8 g, 0.1 mol) in THF (5 mL) dropwise over 20 minutes. The solution was stirred overnight (about eighteen hours) at ambient temperature and concentrated in vacuo to yield a light oil. The oil was filtered through silica gel (ethyl acetate/hexanes) and concentrated in vacuo to give the BOC-piperidine compound as a clear, colorless oil (26.2 g, quantitative yield).

Part B: A solution of 4-fluarothiophenol (50.29 g, 390 mmol) in DMSO (500 mL) was heated to 65 degrees Celsius for 6 hours. The reaction was quenched into wet ice and the resulting solid was collected by vacuum filtration to provide the disulfide as a white solid (34.4 g, 68.9%).

Part C: To a solution of the BOC-piperdine compound of part A (16 g, 62 mmol) in THF (300 mL) cooled to minus 50 degrees Celsius was added lithium diisopropylamide (41.33 mL, 74 mmol) and the solution was stirred for 1.5 hours at zero degrees Celsius. To this solution was added the disulfide of part B (15.77 g, 62 mmol), and the resulting solution was stirred at ambient temperature for 20 hours. The reaction was quenched with the addition of $H_2O$ and the solution was concentrated in vacuo. The aqueous residue was extracted with ethyl acetate and the organic layer was washed with 0.5N KOH, $H_2O$, and saturated NaCl. Chromatography (on silica, hexane/ethyl acetate) provided the sulfide as an oil (18.0 g, 75%).

Part D: To a solution of the sulfide of part C (16.5 g, 43 mmol) in dichloromethane (500 mL) cooled to zero degrees Celsius was added 3-chloroperbenzoic acid (18.0 g, 86 mmol) and the solution was stirred for 20 hours. The solution was diluted with $H_2O$ and extracted with dichloromethane. The organic layer was washed with 10 percent $Na_2SO_3$, $H_2O$, and saturated NaCl and dried overmagnesium sulfate. Chromatography (on silica, ethyl acetate/hexane) provided the sulfone as a solid (10.7 g, 60%).

Part E: Into a solution of the sulfone of part D (10 g, 24.0 mmol) in ethyl acetate (250 mL) was bubbled HCl gas for 10 minutes followed by stirring at ambient temperature for 4 hours. Concentration in vacuo provided the amine hydrochloride salt as a white solid (7.27 g, 86%).

Part F: To a solution of the amine hydrochloride salt of part E (5.98 g, 17.0 mmol) in DMF (120 mL) was added potassium carbonate (4.7 g, 34.0 mmol) followed by propargyl bromide (2.02 g, 17.0 mmol) and the solution was stirred for 4 hours at ambient temperature. The solution was partitioned between ethyl acetate and $H_2O$, and the organic layer was washed with $H_2O$ and saturated NaCl and dried over magnesium sulfate. Chromatography (on silica, ethyl acetate/hexane) provided the propargyl amine as a yellow oil (5.2 g, 86%).

Part G: To a solution of the propargyl amine of part F in DMF (15 mL) was added thiophenol (0.80 mL, 7.78 mmol) and $CSCO_3$ (2.79 g, 8.56 mmol) and the solution was heated to 70 degrees Celsius for 6 hours. The solution was partitioned between ethyl ether and $H_2O$. The organic layer was washed with $H_2O$ and saturated NaCl, and dried over magnesium sulfate. Chromatography (on silica, ethyl acetate/hexane) provided the S-phenoxyphenyl compound as an oil (1.95 g, 56%).

Part H: To a solution of the S-phenoxyphenyl of part G (1.81 g, 4.06 mmol) in ethanol (21 mL) and $H_2O$ (3.5 mL) was added KOH (1.37 g, 24.5 mmol) and the solution was heated to 105 degrees Celsius for 4.5 hours. The solution was acidified to a pH value of 1 with concentrated HCl solution and then concentrated to provide the acid as a yellow residue that was used without additional purification (1.82 g).

Part I: To a solution of the acid of part H (1.82 g, 4.06 mmol) in acetonitrile (20 mL) was added O-tetrahydro-2H-pyran-2-yl-hydroxylamine (723 mg, 6.17 mmol) and triethylamine (0.67 mL, 4.86 mmol). To this stirring solution was added EDC (1.18 g, 6.17 mmol) and the solution was stirred for 18 hours. The solution was partitioned between $H_2O$ and ethyl acetate. The organic layer was washed with $H_2O$, saturated $NaHCO_3$ and saturated NaCl and dried over magnesium sulfate. Chromatography (on silica, ethyl acetate/hexane) provided the protected hydroxamate as a white solid (1.32 g, 63%).

Part J: To a solution of the protected hydroxamate of part I (9.65 g, 18.7 mmol) in methanol (148 mL) cooled to zero degrees Celsius was added acetyl chloride (4.0 mL, 56.2 mmol), and the solution was stirred for 45 minutes at ambient temperature. Concentration in vacuo followed by trituration with ethyl ether provided the title compound as a white solid (8.10 g, 94%). MS(CI) $MH^+$ calculated for $C_{21}H_{22}N_2O_4S_2$: 431, found 431.

EXAMPLE 10

Preparation of 4-[[4-(1,3-benzodioxol-5-yloxy)phenyl]sulfonyl]-N-hydroxy-1-(2-propynyl)-4-piperidinecarboxamide, Monohydrochloride

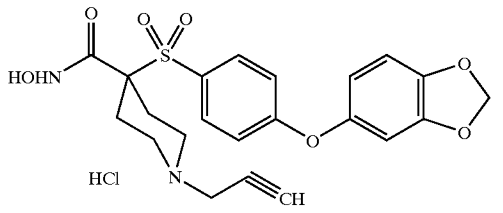

Part A: To a solution of the propargyl amine of Example 9, part F (7.0 g, 19.8 mmol) in DMF (30 mL) were added sesamol (5.52 g, 40 mmol) and potassium carbonate (5.52 g. 40 mmol), and the solution was heated to 85 degrees Celsius for 48 hours. The solution was partitioned between ethyl acetate and $H_2O$. The organic layer was dried over magnesium sulfate. Chromatography (on silica, ethyl acetate/hexane) provided the sulfide as an oil (9.38 g, quantitative yield).

Part B: To a solution of the sulfide of part A (2.72 g, 5.92 mmol) in ethanol (30 mL) and $H_2O$ (5 mL) was added potassium hydroxide (2.0 g, 36 mmol) and the solution was heated to reflux for 4 hours. The solution was acidified to pH=3 with concentrated HCl. The solution was concentrated in vacuo and the residue was dissolved in acetonitrile (30 mL). To this solution was added O-tetrahydro-2H-pyran-2-yl -hydroxylamine (1.05 g, 9.0 mmol), triethylamine (1 mL) and EDC (1.72 g, 9.0 mmol) and the solution was stirred at ambient temperature for 18 hours. The solution was concentrated in vacuo and diluted with saturated $NaHCO_3$ and extracted with ethyl acetate. The organic layer was dried over magnesium sulfate. Chromatography (on silica, ethyl acetate/hexane) provided the protected hydroxamate as an oil (2.86 g, 93%).

Part C: To a solution of the protected hydroxamate of part B (2.86 g, 5.27 mmol) in methanol (40 mL) was added acetyl chloride (1.13 mL, 15.8 mmol) and the solution was stirred for 3 hours. The solution was concentrated in vacuo. Reverse phase chromatography (on silica, acetonitrile/$H_2O$ (HCl)) provided the title compound as a white solid (2.2 g, 84%). MS(CI) $MH^+$ calculated for $C_{22}H_{22}N_2O_7S$: 459, found 459.

EXAMPLE 11

Preparation of Tetrahydro-N-hydroxy-4-[[4-(4-phenyl-1-piperidinyl)phenyl]sulfonyl]-2H-pyran-4-carboxamide, Monohydrochloride

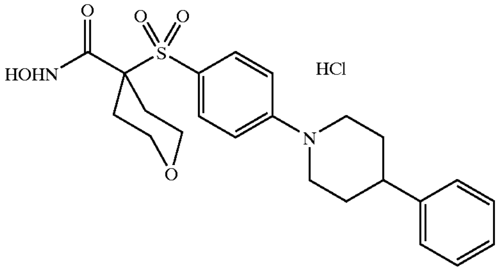

Part A: To a solution of Na (8.97 g, 390 mmol) in methanol (1 L) at zero degrees Celsius were added 4-fluorothiophenol (50 g, 390 mmol) and methyl chloroacetate (34.2 mL, 390 mmol), and the solution was stirred for 4 hours at ambient temperature. The solution was filtered to remove salts and the filtrate was concentrated in vacuo to provide the sulfide as a colorless oil (75.85 g, 97%).

Part B: To a solution of the sulfide of part A (75.85 g, 380 mmol) in methanol (1 L) and $H_2O$ (100 mL) was added Oxone® (720 g, 1.17 mol) and the solution was stirred for 2 hours. The reaction mixture was filtered to remove the excess salts and the filtrate was concentrated in vacuo. The residue was dissolved into ethyl acetate and washed with $H_2O$, saturated $NaHCO_3$ and saturated NaCl, and then dried over magnesium sulfate. Concentration in vacuo provide the sulfone as white solid (82.74 g, 94%)

Part C: To a solution of the sulfone of part B (28.5 g, 123 mmol) in N,N-dimethylacetamide (200 mL) were added potassium carbonate (37.3 g, 270 mmol), bis-(2-bromoethyl) ether (19.3 mL, 147 mmol), 4-dimethylaminopyridine (750 mg, 6 mmol) and tetrabutylammonium bromide (1.98 g, 6 mmol), and the solution was stirred at ambient temperature for 72 hours. The solution was poured into 1N HCl (300 mL) and the resulting precipitate was collected by vacuum filtration. Recrystallization (ethyl acetate/hexane) provided the tetrahydropyran compound as a beige solid (28.74 g, 77%).

Part D: To a solution of the tetrahydropyran compound of part C (1.21 g, 4.0 mmol) in DMSO (10 mL) were added $Cs_2CO_3$ (3.26 g, 10.0 mmol) and 4-phenylpiperidine (640 mg, 4.0 mmol), and the solution was heated to 90 degrees Celsius for 2 hours. The solution was diluted with H2O and extracted with ethyl acetate. The organic layer was washed with 5 percent aqueous $KHSO_4$, saturated $NaHCO_3$ and saturated NaCl and dried over magnesium sulfate. Concentration in vacuo provided the amine as a white solid (1.2 g, 67%).

Part E: To a solution of the amine of part D (815 mg, 1.84 mmol) in methanol (5 mL) and THF (5 mL) was added 50 percent aqueous NaOH (2 mL) and the solution was stirred for 18 hours at ambient temperature. The solution was concentrated in vacuo and the residue was diluted with $H_2O$ and acidified to a pH value of 7. The resulting precipitate was collected by vacuum filtration to provide the acid as a white solid (680 mg, 86%).

Part F: To a solution of the acid of part E (620 mg, 1.44 mmol) in dichloromethane (10 mL) and DMF (3 mL) were added PyBroP (810 mg, 1.73 mmol), N-methylmorpholine (0.5 mL, 4.3 mmol) and O-tetrahydro-2H-pyran-2-ylhydroxylamine (190 mg, 1.59 mmol) and the solution was stirred for 4 hours at ambient temperature. The solution was concentrated in vacuo, the residue dissolved into ethyl acetate and washed with $H_2O$ and saturated NaCl, and then dried over $Na_2SO_4$. Chromatography (on silica, ethyl acetate/hexane) provided the protected hydroxamate as a white solid (630 mg, 83%). MS (CI) $MH^+$ calculated for $C_{28}H_{36}N_2O_6S$: 529, found 529.

Part G: To a solution of the protected hydroxamate of part F (600 mg, 1.14 mmol) in dioxane (1.5 mL) and methanol (1.5 mL) was added 4N HCl in dioxane (1.5 mL), and the solution was stirred for 2 hours. The solution was poured into ethyl ether and the resulting precipitate was collected by vacuum filtration to provide the title compound as a beige solid (500 mg, 91%). MS(CI) $M+Li^+$ calculated for $C_{23}H_{28}N_2O_5S$: 445, found 445.

EXAMPLE 12

Preparation of 1-acetyl-N-hydroxy-4-[(4-phenoxyphenyl)sulfonyl]-4-piperidinecarboxamide

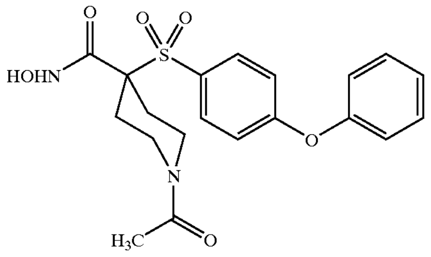

Part A: To a solution of the sulfone of Example 6, part D (2.75 g, 5.6 mmol) in THF (10 mL) and ethanol (10 mL) was added NaOH (2.25 g, 56 mmol), and the solution was heated to 70 degrees Celsius for 18 hours. The solution was concentrated in vacuo, the residue was dissolved into $H_2O$ and extracted with ethyl ether. The aqueous solution was acidified to a pH value of 2 and extracted with ethyl acetate. The organic layer was dried over magnesium sulfate. Concentration in vacuo provided the crude acid as a solid. A solution of the acid in dichloromethane (6 mL) and trifluoroacetic acid (6 mL) was stirred for 1 hour at ambient temperature. Concentration in vacuo provided the amine hydrochloride salt as a solid (2.3 g, quantitative yield).

Part B: To a solution of the amine hydrochloride salt of part A (2.3 g, <5.6 mmol) in acetone (10 mL) and $H_2O$ (10 mL) cooled to zero degrees Celsius were added triethylamine (1.17 mL, 8.4 mmol) and acetyl chloride (0.60 mL, 8.4 mmol), and the solution was stirred at ambient temperature for 18 hours. The solution was concentrated in vacuo to remove the acetone and the aqueous solution was extracted with ethyl ether. The aqueous layer was acidified to a pH value of 2 and extracted with ethyl acetate. The organic layer was dried over magnesium sulfate and concentration in vacuo provided the N-acetyl compound as a white solid (1.5 g, 65.2%).

Part C: To a solution of the N-acetyl compound of part B (0.6 g, 1.49 mmol) in DMF (10 mL) were added EDC (401 mg, 2.1 mmol) followed by 50 percent aqueous hydroxylamine (0.9 mL) and 4-methylmorpholine (0.7 mL, 6.4 mmol), and the solution was stirred for 18 hours at ambient temperature. The solution was concentrated in vacuo and the residue was dissolved into ethyl acetate. The organic layer was washed with $H_2O$ and dried over magnesium sulfate.

Reverse phase chromatography (on silica, acetonitrile/$H_2O$) provided the title compound as a white solid (101 mg, 16%). MS(CI) $MH^+$ calculated for $C_{20}H_{22}N_2O_6S$: 419, found 419.

EXAMPLE 13

Preparation of 4-[[4-(cyclohexylthio)-phenyl] sulfonyl]-N-hydroxy-1-(2-propynyl)-4-piperidinecarboxamide, Monohydrochloride

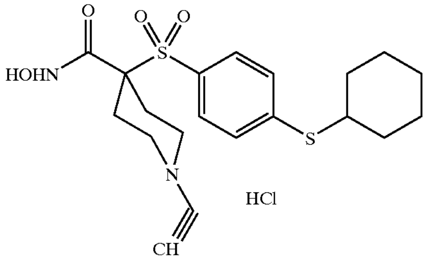

Part A: To a solution of the propargyl amine of Example 9, part F (6.5 g, 18.4 mmol) in DMF (10 mL) were added potassium carbonate (3.81 g, 27.6 mmol) and cyclohexyl mercaptan (3.37 mL, 27.6 mmol). The solution was heated to 100 degrees Celsius for 6.5 hours. The solution was diluted with $H_2O$ and extracted with ethyl acetate. The organic layers were dried over magnesium sulfate. Chromatography (on silica, hexane/ethyl acetate) provided the sulfide as a yellow oil (6.05 g, 73%).

Part B: To a solution of the sulfide of part B (612 mg, 1.4 mmol) in ethanol (8.4 mL) and $H_2O$ (1.4 mL) was added potassium hydroxide (470 mg, 8.4 mmol), and the solution was refluxed for 3 hours. The solution acidifed to a pH value of 3 and was concentrated in vacuo. The residue was dissolved into acetonitrile (10 mL) and to this solution were added O-tetrahydro-2H-pyran-2-yl-hydroxylamine (230 mg, 2.0 mmol) and triethylamine (0.5 mL) followed by EDC (380 mg, 2.0 mmol), and the solution was stirred at ambient temperature for 18 hours. The solution was concentrated in vacuo and the residue was diluted with saturated $NaHCO_3$ and extracted with ethyl acetate. The organic layer was dried over magnesium sulfate. Chromatography (on silica, ethyl acetate/hexane) provided the protected hydroxamate as an oil (246 mg, 34%).

Part C: To a solution of the protected hydroxamate of part B (246 mg, 0.47 mmol) in methanol (4 mL) was added acetyl chloride (0.11 mL, 1.5 mmol), and the solution was stirred at ambient temperature for 3 hours. After concentration in vacuo, reverse phase chromatography (on silica, acetonitrile/$H_2O$ (HCl)) provided the title compound as a white solid (223 mg, quantitative yield).

EXAMPLE 14

Preparation of N-hydroxy-1-methyl-4-[(phenoxyphenyl)sulfonyl]-4-piperidinecarboxamide, Monohydrochloride

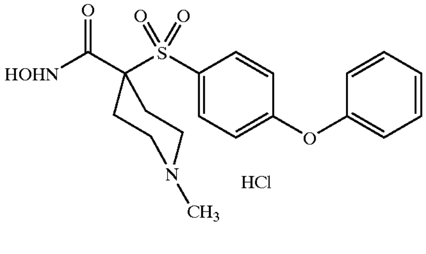

Part A: To a solution of the sulfone of Example 6, part D (2.67 g, 5.5 mmol) in dichloromethane (5 mL) was added trifluoroacetic acid (5 mL), and the solution was stirred at ambient temperature for 2 hours. The solution was concentrated in vacuo and the residue was triturated with ethyl ether to provide the crude amine trifluoroacetic acid salt. To a solution of the crude amine salt in methanol (10 mL) were added formaldehyde (37 percent aqueous solution, 2.0 mL, 27.5 mmol) and borane pyridine (2.2 mL, 22 mmol), and the solution was stirred at ambient temperature for 18 hours. The solution was concentrated in vacuo. The residue was dissolved into ethyl acetate, washed with $H_2O$ and dried over magnesium sulfate. Concentration in vacuo provided the N-methyl compound as a yellow oil (2.17 g, 98%).

Part B: To a solution of the N-methyl compound of part A (2.17 g, 5.4 mmol) in ethanol (10 mL) and THF (10 mL) was added NaOH (2.0 g, 50 mmol), and the reaction mixture was stirred at minus 65 degrees Celsius for 18 hours. The solution was concentrated in vacuo. The residue was dissolved into $H_2O$ and extracted with ethyl ether. The aqueous solution was acidified to a pH value of 2 and the resulting solid was collected by vacuum filtration to provide the acid as a white solid (1.8 g, 90%).

Part C: To a solution of the acid of part B (0.5 g, 1.3 mmol) in DMF (10 mL) were added EDC (1.06 g, 5.5 mmol) followed by O-tetrahydro-2H-pyran-2-yl-hydroxylamine (490 mg, 4.2 mmol) and 4-methylmorpholine (0.76 mL) and the solution was stirred at ambient temperature for 18 hours. The solution was concentrated in vacuo and the residue was dissolved into ethyl acetate, washed with $H_2O$ and dried over magnesium sulfate. Concentration in vacuo provided the crude protected hydroxamate. To a solution of the crude hydroxamate in methanol (10 mL) was added acetyl chloride (0.28 mL, 3.9 mmol), and the solution was stirred for 3 hours at ambient temperature. The solution was concentrated in vacuo. Reverse phase chromatography (on silica, acetonitrile/$H_2O$ (0.0125% HCl) provided the title compound as a white solid (261 mg, 46%). MS(CI) $MH^+$ calculated for $C_{19}H_{22}N_2O_5S$: 391, found 391.

EXAMPLE 15

Preparation of N-hydroxy-4-[[4-(4-methoxyphenoxy)phenyl]sulfonyl]1-(2-propynyl)-4-piperidinecarboxamide, Monohydrochloride

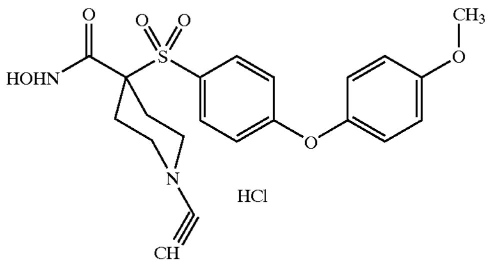

Part A: To a solution of the propargyl amine of Example 9, part F (2.00 g, 5.66 mmol) in DMF (10 mL) were added cesium carbonate (4.7 g, 14.5 mmol) and 4-methoxythiophenol (1.80 g, 14.5 mmol), and the solution was heated to 95 degrees Celsius for 24 hours. The solution was diluted with ethyl acetate and washed with 1N NaOH and saturated NaCl, and then dried over magnesium sulfate. Chromatography (on silica, ethyl acetate/hexane) provided the phenoxy compound as a solid (2.67 g, quantitative yield).

Part B: To a solution of the phenoxy compound of part A (2.40 g, 5.25 mmol) in ethanol (30 mL) and $H_2O$ (6 mL) was added potassium hydroxide (2.0 g, 31.37 mmol), and the solution was heated to reflux for 4 hours. The solution was acidified with concentrated HCl to a pH value of 3 and the residue was collected by vacuum filtration to provide the crude acid that was carried on without additional purification.

Part C: To a solution of the acid of part B (2.25 g, 5.25 mmol) in acetonitrile (30 mL) were added triethylamine (1 mL) and O-tetrahydro-2H-pyran-2-yl-hydroxylamine (1.34 g, 9.0 mmol). After the solution was stirred for 15 minutes, EDC (1.72 g, 9.0 mmol) was added the solution was stirred at ambient temperature for 18 hours. The solution was concentrated in vacuo and the residue was dissolved into ethyl acetate. The ethyl acetate solution was washed with saturated $NaHCO_3$, $H_2O$ and saturated NaCl and dried over magnesium sulfate. Chromatography (on silica, ethyl acetate/hexane) provided the protected hydroxamate as a white solid (0.93 g, 33%).

Part D: To a solution of the protected hydroxamate of part C (0.93 g, 1.7 mmol) in methanol (15 mL) was added acetyl chloride (0.36 mL, 5.1 mmol) and the solution was stirred for 3 hours. The solution was concentrated in vacuo to provide the title compound as a white solid (650 mg, 82%). Analytical calculation for $C_{22}H_{24}N_2O_6S$ HCl: C, 54.84; H, 5.24; N, 5.82; S, 6.67; Cl, 6.67. Found: C, 53.10; H, 5.07; N, 5.59; S, 7.04; Cl, 6.32.

EXAMPLE 16

Preparation of 4-[[4-(4-butoxy-1-piperidinyl)phenyl]sulfonyl]-tetrahydro-N-hydroxy-2H-pyran-4-carboxamide, Monohydrochloride

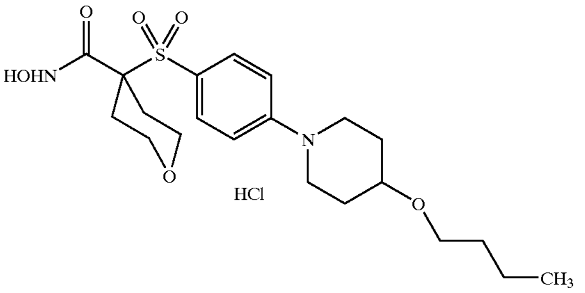

Part A: To a solution of the tetrahydropyran compound of Example 11, part C (1.95 g, 6.46 mmol) in DMSO (25 mL) were added $Cs_2CO_3$ (7.4 g, 22.6 mmol) and 4-butoxypiperidine (1.25 g, 6.46 mmol) and the solution was heated to 90 degrees Celsius for 1 hour. The solution was quenched with $H_2O$ and extracted with ethyl acetate. The organic layer was washed with 5 percent aqueous $KHSO_4$, saturated $NaHCO_3$ and saturated NaCl, and dried over magnesium sulfate. Chromatography (on silica, ethyl acetate/dichloromethane) provided the amine as a yellow oil (1.85 g, 65%).

Part B: To a solution of theamine of part A (1.65 g, 3.76 mmol) in THF (10 mL) was added potassium trimethylsilanolate (530 mg, 4.13 mmol), and the solution was stirred for 22 hours at ambient temperature. The solution was concentrated in vacuo and the crude residue was used as is in the next reaction.

Part C: To a solution of the crude acid of part B (1.74 g, 3.76 mmol) in dichloromethane (10 mL) were added PyBroP (2.10 g, 4.51 mmol), N-methylmorpholine (1.24 mL, 11.3 mmol) and O-tetrahydro-2H-pyran-2-yl-hydroxylamine (484 mg, 4.14 mmol), and the solution was stirred for 30 minutes at ambient temperature. The solution was concentrated in vacuo. The residue was dissolved into ethyl acetate and washed with $H_2O$ and saturated NaCl, and dried over magnesium sulfate. Chromatography (on silica, ethyl acetate/hexane/methanol) provided the protected hydroxamate as a colorless oil (1.5 g, 76% over two steps).

Part D: To a solution of the protected hydroxamate of part C (1.25 g, 2.4 mmol) in dioxane (3 mL) was added 4N HCl in dioxane (3 mL), and the solution was stirred for 15 minutes. After methanol (3 mL) was added the solution was stirred for 5 hours at ambient temperature. The solution was poured into ethyl ether and the resulting precipitate was collected by vacuum filtration to provide the title compound as a white solid (1.0 g, 88%). MS(CI) $MH^+$ calculated for $C_{21}H_{32}N_2O_6S$: 441, found 441.

EXAMPLE 17

Preparation of 1-cyclopropyl-N-hydroxy-4-[(4-phenoxyphenyl)sulfonyl]-4-piperidinecarboxamide, Monohydrochloride

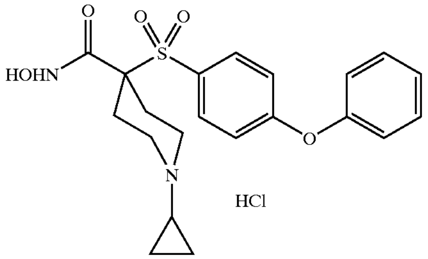

Part A: To a solution of the amine hydrochloride salt of Example 6, part E (2.13 g, 5.0 mmol) in methanol (25 mL) was added 3A molecular sieves, acetic acid (2.86 mL, 50 mmol) and the solution was stirred for 5 minutes. To this solution was added ((1-ethyoxycyclopropyl)oxy)-trimethylsilane (6.08 mL, 30 mmol) followed by sodium cyanoborohydride (1.41 g, 22.0 mmol), and the solution was heated to reflux for 18 hours. The excess salts and sieves were collected by filtration and the filtrate was concentrated in vacuo. The residue was diluted with ethyl acetate and washed with 1N NaOH, $H_2O$ and saturated NaCl, and dried over magnesium sulfate. Chromatography (on silica, ethyl acetate/hexane) provided the cyclopropyl amine as a white solid (1.90 g, 86%).

Part B: To a solution of the cyclopropyl amine of part A (1.9 g, 4.2 mmol) in THF (12 mL) and ethanol (12 mL) was added NaOH (1.71 g, 4.3 mmol) in $H_2O$ (10 mL), and the solution was heated to 62 degrees Celsius for 20 hours. The solution was concentrated in vacuo and the residue was diluted with $H_2O$ and acidified to a pH value of 5 with 1N HCl. The resulting solid was collected by vacuum filtration to provide the acid as a white solid (1.49 g, 82%). MS(CI) $MH^+$ calculated for $C_{21}H_{23}NO_5S$: 402, found 402. HRMS calculated for $C_{21}H_{23}NO_5S$: 402.1375, found 402.1350.

Part C: To a solution of the acid of part C (1.49 g, 3.4 mmol) in dichloromethane (50 mL) was added triethylamine (1.42 mL, 10.21 mmol) followed by 50 percent aqueous hydroxylamine (2.25 mL, 34.0 mmol) and PyBroP (3.17 g, 6.8 mmol), and the solution was stirred for 72 hours. The mixture was diluted with $H_2O$ and the organic layer was separated, washed with saturated NaCl and dried over magnesium sulfate. Concentration in vacuo followed by reverse phase chromatography (on silica, acetonitrile/$H_2O$) provided the hydroxamate.

The hydrochloride salt was prepared by dissolving the free base (830 mg, 2.0 mmol) in methanol (20 mL) followed by the addition of acetyl chloride (0.17 mL, 2.0 mmol). The solution was stirred for 10 minutes at zero degrees Celsius. The resulting white solid was collect by vacuum filtration and washed with cold ethyl ether to provide the title compound (595 mg, 66%). HRMS calculated for $C_{21}H_{24}N_2O_5S$: 416.1407, found 416.1398. Analytical calculation for $C_{21}H_{24}N_2O_5S$: C, 55.68; H, 5.56; N, 6.18; S, 7.08; Cl, 7.83. Found: C,55.39; H, 5.72; N, 6.15; S, 7.29; Cl, 8.17.

EXAMPLE 18

Preparation of N-hydroxy-1-(methylsulfonyl)-4-(phenoxyphenyl)-sulfonyl]-4-piperidinecarboxamide

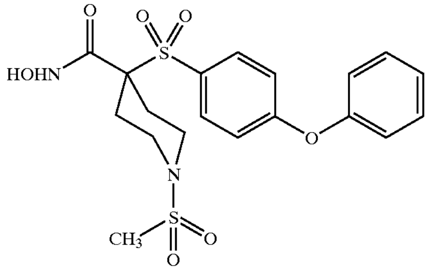

Part A: To a solution of the amine hydrochloride salt of Example 6, part E (1.06 g, 2.5 mmol) in dichloromethane (10 mL) were added triethylamine (0.76 mL, 5.5 mmol) and methanesulfonyl chloride (0.23 mL, 3.0 mmol), and the solution was stirred for 18 hours at ambient temperature. The solution was concentrated in vacuo and the residue was partitioned between ethyl acetate and $H_2O$. The organic layer was washed with $H_2O$ and saturated NaCl and dried over magnesium sulfate. Chromatography (on silica, ethyl acetate/hexane) provided the methanesulfonamide as a solid (2.1 g, 58%).

Part B: To a solution of the methanesulfonamide of part A (2.0 g, 4.15 mmol) in ethanol (12 mL) and $H_2O$ (12 mL) was added NaOH (1.66 g, 41.5 mmol), and the solution was heated to 65 degrees Celsius for 18 hours. The solution was concentrated in vacuo and the remaining aqueous solution was acidified to a pH of 4. The solution was extracted with ethyl acetate and the organic layer was washed with saturated NaCl and dried over magnesium sulfate. Concentration in vacuo provided the acid as a yellow foam (1.46 g, 80%).

Part C: To a solution of the acid of part B (1.46 g, 3.38 mmol) in dichloromethane (50 mL) were added triethylamine (1.41 mL, 10.1 mmol), 50 percent aqueous hydroxylamine (2.2 mL, 33.8 mmol) and PyBroP (3.16 g, 6.76 mmol), and the solution was stirred at ambient temperature for 72 hours. The solution was diluted with $H_2O$ and the organic layer was separated and washed with saturated NaCl, and then dried over magnesium sulfate. Reverse phase chromatography (on silica, acetonitrile/$H_2O$) followed by trituration with ethyl ether provide the title compound as a white solid (160 mg, 11%). Analytical calculation for $C_{19}H_{22}N_2O_7S_2$: C, 50.21; H, 4.88; N. 6.16; S, 14.11. Found: C, 48.72; H, 5.36; N, 5.61; S, 12.81.

EXAMPLE 19

Preparation of 4-[[4-(cyclohexylthio)-phenyl] sulfonyl]-N-hydroxy-4-piperidinecarboxamide, Monohydrochloride

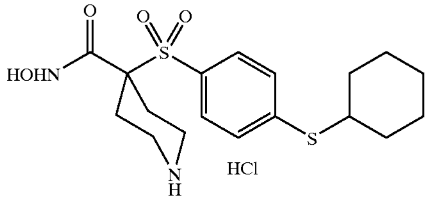

Part A: To a solution of the sulfone of Example 9, part D (10.1 g, 24.0 mmol) in DMF (20 mL) were added $K_2CO_3$ (5.0 g, 36.0 mmol) and cyclohexylmercaptan (4.4 mL, 36.0 mmol), and the solution was heated at 85 degrees Celsius for 6.5 hours. The solution was partitioned between ethyl acetate and $H_2O$. The organic layer was washed with saturated NaCl and dried over magnesium sulfate. Chromatography (on silica, ethyl acetate/hexane) provided the sulfide as a oil (8.2 g, 67%).

Part B: To a solution of the sulfide (2.32 g, 4.5 mmol) in ethanol (10 mL) and THF (10 mL) was added NaOH (1.81 g, 45 mmol) in $H_2O$ (10 mL), and the solution was heated to 65 degrees Celsius for 18 hours. The solution was concentrated in vacuo and the aqueous residue was acidified to a pH value of 2. The solution was extracted with dichloromethane and dried over magnesium sulfate. Concentration in vacuo provided the acid as a white solid (830 mg, 38%).

Part C: To a solution of the acid of part B (2.0 g, 4.0 mmol) in dichloromethane (25 mL) were added N-methylmorpholine (1.32 mL, 12.0 mmol), PyBroP (2.12 g, 2.12 mmol) and 50 percent aqueous hydroxylamine (2.6 mL, 40 mmol), and the solution was stirred for 18 hours at ambient temperature. The solution was diluted with $H_2O$ and the layers were separated. The organic layer was washed with saturated NaCl and dried over magnesium sulfate. Chromatography (on silica, ethyl acetate/methanol) provided the hydroxamate as a white solid (1.4 g, 70%).

Part D: Into a solution of the hydroxamate of part C (1.31 g, 2.63 mmol) in ethyl acetate (70 mL) cooled to zero degrees Celsius was bubbled HCl gas for 30 minutes. The solution was concentrated in vacuo. Reverse phase chromatography (on silica, acetonitrile/$H_2O$ (HCl)) provided the title compound as a white solid (378 mg, 33%). Analytical calculation for $C_{18}H_{26}N_2O_4S_2$: C, 49.70; H, 6.26; N, 6.44; S, 14.74; Cl, 8.15. Found: C, 48.99; H, 6.34; N, 6.24; S,14.66; Cl, 8.56.

EXAMPLE 20

Preparation of tetrahydro-N-hydroxy-4-[[4-(4-phenyl-1-piperazinyl)phenyl]sulfonyl]-2H-pyran-4-carboxamide Dihydrochloride

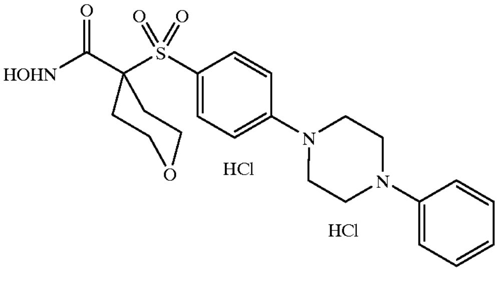

Part A: To a solution of the tetrahydropyran compound of Example 11, part C (1.96 g, 6.5 mmol) in DMSO (20 mL) were added $Cs_2CO_3$ (4.9 g, 15 mmol) and 4-phenylpiperazine (1.1 mL, 7.15 mmol), and the solution was heated to 90 degrees Celsius for 45 minutes. The solution was quenched by the addition of $H_2O$ and was extracted with ethyl acetate. The organic layer was washed with 5 percent aqueous $KHSO_4$, saturated $NaHCO_3$ and saturated NaCl and dried over magnesium sulfate. Concentration in vacuo provided the amine as a beige solid (1.7 g, 59%).

Part B: To a solution of the amine of part A (1.5 g, 3.38 mmol) in THF (20 mL) was added potassium trimethylsilanolate (480 mg, 3.72 mmol), and the solution was stirred at ambient temperature for 22 hours. Concentration in vacuo provided the crude acid salt to be used without purification in the next step.

Part C: To a solution of the acid salt of part B (1.58 g, 3.38 mmol) in dichloromethane (10 mL) and DMF (3 mL) were added PyBroP (1.89 g, 4.06 mmol), N-methylmorpholine (1.1 mL, 10.1 mmol) and O-tetrahydro-2H-pyran-2-yl-hydroxylamine (435 mg, 3.72 mmol), and the solution was stirred at ambient temperature for 18 hours. The solution was concentrated in vacuo and the residue was partitioned between ethyl acetate and $H_2O$ and the organic layer was washed with $H_2O$ and saturated NaCl, and then dried over magnesium sulfate. Chromatography (on silica, dichloromethane/methanol) provided the protected hydroxamate as a white foam (1.7 g, 95% over two steps).

Part D: To a solution of the protected hydroxamate of part C (1.28 g, 2.4 mmol) in dioxane (5 mL) and methanol (5 mL) was added 4N HCl in dioxane (5 mL), and the solution was stirred for 2 hours at ambient temperature. The solution was poured into ethyl ether and the resulting precipitate was collected by vacuum filtration to provide the title compound as a white solid (900 mg, 73%). MS(CI) $MH^+$ calculated for $C_{22}H_{27}N_3O_5S$: 446, found 446.

EXAMPLE 21

Preparation of 4-[[4-(cyclohexylthio)-phenyl] sulfonyl]-1-cyclopropyl)-N-hydroxy-4-piperidine Carboxamide, Monohydrochloride

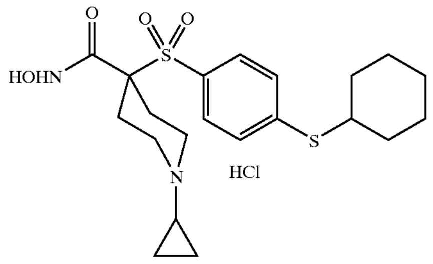

Part A: To a solution of the sulfone of Example 9, part D (10.1 g, 24.0 mmol) in DMF (20 mL) were added $K_2CO_3$ (5.0 g, 36.0 mmol) and cyclohexylmercaptan (4.4 mL, 36.0 mmol), and the solution was heated at 85 degrees Celsius for 6.5 hours. The solution was partitioned between ethyl acetate and $H_2O$. The organic layer was washed with saturated NaCl and dried over magnesium sulfate. Chromatography (on silica, ethyl acetate/hexane) provided the sulfide as a oil (8.2 g, 67%).

Part B: HCl gas was bubbled for 30 minutes into a solution of the sulfide of part B (8.2 g, 17.0 mmol) in ethyl acetate (100 mL) cooled to zero degrees Celsius. The solution was concentrated in vacuo to provide the amine as a white solid (5.99 g, 79%). MS(CI) $MH^+$ calculated for $C_{20}H_{29}NO_4S$: 412, found 412.

Part C: To a solution of the amine of part B (2.24 g, 5.0 mmol) in methanol (20 mL) was added acetic acid (2.86 mL, 50 mmol) followed by (1-ethoxycyclopropyl) oxytrimethylsilane (6.03 mL, 30 mmol) and sodium borohydride (1.41 g, 22.5 mmol), and the solution was refluxed for 18 hours. The solution was concentrated in vacuo and the residue was dissolved into ethyl acetate and washed with 1N NaOH, $H_2O$ and saturated NaCl and dried over magnesium sulfate. Chromatography (on silica, ethyl acetate/hexane) provided the cyclopropyl amine as a white solid (1.97 g, 87%).

Part D: To a solution of the cyclopropyl amine of part C (1.9 g, 4.2 mmol) in ethanol (10 mL) and THF (10 mL) was added NaOH (1.68 g, 42.0 mmol) in $H_2O$ (10 mL) and the solution was heated at sixty-eight degrees Celsius for 18 hours. The solution was concentrated in vacuo and the aqueous residue was acidified to a pH value of 2. The resulting solid was collected and washed with ethyl ether to provide the acid as a white solid (1.61 g, 81%). HRMS calculated for $C_{21}H_{29}NO_4S_2$: 424.1616, found 424.1615.

Part E: To a solution of the acid of part D (1.61 g, 3.0 mmol) in dichloromethane (30 mL) were added N-methylmorpholine (1.0 g, 9.0 mmol), PyBroP (1.54 g, 3.3 mmol) and 50 percent aqueous hydroxylamine (2.0 mL, 30 mmol), and the solution was stirred for 18 hours at ambient temperature. The solution was concentrated in vacuo. The residue was partitioned between ethyl acetate and $H_2O$, the organic layer washed with $H_2O$ and saturated NaCl, and then dried over magnesium sulfate. Filtration through a silica pad (ethyl acetate/methanol) gave the hydroxamate as a white solid (1.07 g, 80%).

Part F: To a solution of the hydroxamate of part F (1.07 g, 2.4 mmol) in cold methanol (2 mL) was added acetyl chloride (0.27 mL, 3.6 mmol), and the solution was stirred for 30 minutes. The solution was concentrated in vacuo. Reverse phase chromatography (acetonitrile/$H_2O$ (HCl)) provided the title compound as a white solid (245 mg, 21%).

EXAMPLE 22

Preparation of 4-[[4-[(4-fluorophenyl)thio]phenyl] sulfonyl]-N-hydroxy-4-piperidinecarboxamide, Monohydrochloride

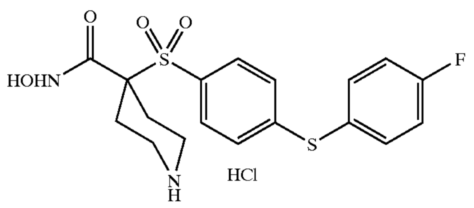

Part A: To a solution of the sulfone of Example 9, part D (6.0 g, 14.4 mmol) in DMF (30 mL) were added potassium carbonate (2.39 mg, 17.3 mmol) and 4-fluorothiophenol (3.0 mL, 28.1 mmol), and the solution was stirred at ambient temperature for 18 hours. The solution was diluted with ethyl acetate and washed with 1N NaOH and saturated NaCl, and thrn dried over magnesium sulfate. Chromatography (on silica, ethyl acetate/hexane) provided the sulfide as a solid (6.6 g, 87%).

Part B: To a solution of the sulfide of part A (6.6 g, 12.6 mmol) in ethanol (90 mL) and $H_2O$ (20 mL) was added sodium hydroxide (5.04 g, 126 mmol), and the solution was heated at 70 degrees Celsius for 18 hours. The mixture was acidified to a pH value of 4 and the solution was extracted with ethyl acetate. The organic layer was washed with saturated NaCl and dried over magnesium sulfate. Chromatography (on silica, ethyl acetate/ethanol) provided the solid acid (4.8 g, 79%).

Part C: To a solution of the acid of part B (4.8 g, 10.0 mmol) in DMF (30 mL) was added 4-methylmorpholine (3.03 g, 30.0 mmol) followed by 0-tetrahydro-2H-pyran-2-yl-hydroxylamine (7.45 g, 50.0 mmol) and PyBroP (5.59 g, 12.0 mmol), and the solution was stirred for 18 hours at ambient temperature. The solution was concentrated in vacuo. The residue was dissolved into ethyl acetate and washed with $H_2O$ and saturated NaCl, and then dried over magnesium sulfate. Chromatography (on silica, ethyl acetate/hexane) provided the protected hydroxamate as a white solid (4.0 g, 67%).

Part D: HCl gas was bubbled for 5 minutes into a solution of the protected hydroxamate of part D (4.0 g, 6.7 mmol) in ethyl acetate (120 mL) followed by stirring at ambient temperature for 1.5 hours. The resulting solid was collected by vacuum filtration to provide the title compound as a white solid (1.90 g, 64%) . MS (CI) $MH^+$ calculated for $C_{18}H_{19}N_2O_4S_2F$: 411, found 411.

EXAMPLE 23

Preparation of N-hydroxy-4-[[4-[4-(1H-imidazol-1-yl)phenoxy]phenyl]sulfonyl]-1-(2-propynyl)-4-piperidinecarboxamide, Dihydrochloride

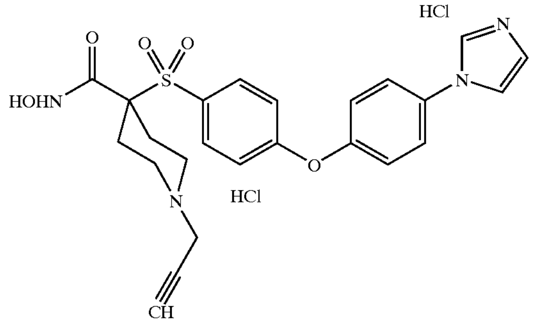

Part A: To a solution of the amine hydrochloride salt of Example 9, part F (3.00 g, 8.49 mmol) in DMF (13 mL) were added $K_2CO_3$ (2.35 g, 17.0 mmol) and 4-(imidazol-1-yl) phenol (2.72 9, 17.0 mmol), and the solution was heated to 85 degrees Celsius for 64 hours. The solution was concentrated and the residue was partitioned between ethyl acetate and $H_2O$. The organic layer was washed with $H_2O$ and saturated NaCl and dried over magnesium sulfate. Chromatography (on silica, chloroform/methanol) provided the ethyl ester as a white foam (2.36 g, 56%).

Part B: To a solution of the ethyl ester of part A (2.36 g, 5.33 mmol) in ethanol (2.8 mL) and $H_2O$ (4.6 mL) was added KOH (1.80 g, 32.1 mmol), and the solution was heated to 100 degrees Celsius for 4.5 hours. The solution was acidified to a pH value of 1 with concentrated HCl solution and then concentrated to provide the acid as a tan solid that was used without additional purification (2.87 g).

Part C: To a solution of the acid of part B (2.87 g, 5.33 mmol) in acetonitrile (24 mL) were added O-tetrahydro-2H-pyran-2-yl-hydroxylamine (870 mg, 7.45 mmol), EDC (1.43 g, 7.45 mmol) and N-methylmorpholine (1.21 mL, 11.0 mmol) and the solution was stirred for 18 hours at ambient temperature. The solution was concentrated and the residue was diluted with $H_2O$ and extracted with ethyl acetate. The organic layer was washed with $H_2O$ and saturated NaCl and dried over magnesium sulfate. Chromatography (chloroform, methanol) provided the protected hydroxylamine as a white solid (1.62 g, 53%).

Part D: To a solution of the protected hydroxylamine of part C (1.60 g, 2.83 mmol) in methanol (23 mL) was added acetyl chloride (0.61 mL, 8.52 mmol), and the solution was stirred for 1 hour. The solution was concentrated in vacuo. Reverse phase chromatography (on silica, acetonitrile/$H_2O$) provided the title compound as a white solid (975 mg, 62%).

MS(CI) $MH^+$ calculated for $C_{24}H_{25}N_4O_5S$: 481, found 481. Analytical calculation for $C_{24}H_{25}N_4O_5S$ 2HCl: C, 52.08; H, 4.73; N, 10.12; S, 5.79; Cl, 12.81. Found: C, 51.59; H, 4.84; N, 10.93; S, 5.51; Cl, 11.98.

EXAMPLE 24

Preparation of 4-[[4-[(4-fluorophenyl)thiophenyl] sulfonyl]-N-hydroxy-1-(2-propynyl)-4-piperidinecarboxamide, Monohydrochloride

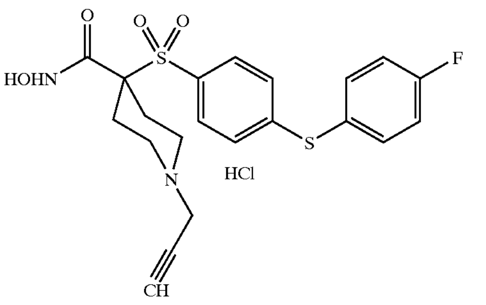

Part A: To a solution of the propargyl amine of Example 9, part F (4.06 g, 11.49 mmol) in DMF (20 mL) were added potassium carbonate (3.18 g, 22.98 mmol) and 4-fluorothiophenol (2.95 g, 22.98 mmol), and the solution was stirred for 18 hours at ambient temperature. The solution was diluted with ethyl acetate, washed with 1N NaOH and saturated NaCl, and dried over magnesium sulfate. Chromatography (on silica, ethyl acetate/hexane) provided the sulfide as a solid (4.46 g, 84%).

Part B: To a solution of the sulfide of part A (4.46 g, 9.7 mmol) in tetrahydropyran (90 ML), $H_2O$ (30 mL) and ethanol (30 mL) was added NaOH (3.86 g, 97.0 mmol), and the solution was heated to 65 degrees Celsius for 2 hours. The solution was concentrated in vacuo and the residue was dissolved into $H_2O$ and acidified to a pH value of 4 with 2N HCl. The resulting residue was collected by vacuum filtration to provide the acid as a white solid (4.0 g, 95%).

Part C: To a solution of the acid of part B (4.0 g, 9.2 mmol) in DMF (50 mL) and 4-methylmorpholine (2.8 g, 27.7 mmol) was added O-tetrahydro-2H-pyran-2-yl-hydroxylamine (6.88 g, 46.1 mmol) and PyBroP (5.16 g, 11.1 mmol), and the solution was stirred at ambient temperature for 18 hours. The solution was concentrated in vacuo and the residue was dissolved into ethyl acetate. The solution was washed with $H_2O$ and saturated NaCl, and dried over magnesium sulfate. Chromatography (on silica, ethyl acetate/hexane) provided the protected hydroxamate as a white solid (2.8 g, 56%).

Part D: HCl gas was bubbled for 10 minutes into a solution of the protected amine of part C (2.8 g, 5.1 mmol) in ethyl acetate (100 mL), and the solution was then stirred for 1 hour. The solution was concentrated in vacuo and the solid recrystallized (ethanol) to provide the title compound as a white solid (1.12 g, 45%). MS(CI) $MH^+$ calculated for $C_{21}H_{21}N_2O_4S_2F$: 449, found 449.

EXAMPLE 25

Preparation of 4-[[4-[(4-chlorophenyl)-thio]phenyl] sulfonyl]tetrahydro-N-hydroxy-2H-pyran-4-carboxamide

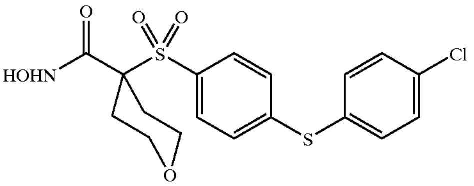

Part A: To a solution of the tetrahydropyran compound of Example 11, part C (8.0 g, 26.5 mmol) in THF (250 mL) was added potassium trimethylsilonate (10.2 g, 79.5 mmol), and the solution was stirred for 1.5 hours. The reaction was quenched by the addition of $H_2O$, acidified to a pH value of 2.5, and the solution was extracted with ethyl acetate. The organic layer was washed with saturated NaCl and dried over $Na_2SO_4$. Concentration in vacuo provide the acid salt as a white solid (5.78 g, 76%).

Part B: To a solution of the acid salt of part A (5.4 g, 18.7 mmol) in DMF (35 mL) were added HOBT (3.04 g, 22.5 mmol), N-methylmorpholine (6.2 mL, 56.2 mmol), O-tetrahydro-2H-pyran-2-yl-hydroxylamine (6.8 g, 58.1 mmol) and EDC (5.0 g, 26.2 mmol), and the solution was stirred for 3 hours at ambient temperature. The solution was concentrated in vacuo, the residue partitioned between ethyl acetate and $H_2O$, and the organic layer was washed with 5 percent aqueous $KHSO_4$, $H_2O$, saturated $NaHCO_3$ and saturated NaCl, and then dried over $Na_2SO_4$. Concentration in vacuo provided the protected hydroxamate as a white solid (6.34 g, 87%).

Part C: To a solution of p-chlorothiophenol (2.71 g, 18.7 mmol) in DMF (10 mL) was added $K_2CO_3$ (2.6 g, 18.7 mmol) followed by the protected hydroxamate of part B (2.9 g, 7.5 mmol) and the solution was heated at 75 degrees Celsius for 5 hours. The solution was concentrated in vacuo, the residue partitioned between ethyl acetate and $H_2O$, the organic layer was washed with saturated NaCl, and dried over $Na_2SO_4$. Chromatography (on silica, ethyl acetate/hexane/methanol) provided the sulfide as a white foam (3.56 g, 93%) .MS(CI) $MH^+$ calculated for $C_{23}H_{26}ClNO_6S_2$: 512, found 512.

Part D: To a solution of the sulfide of part C (3.5 g, 6.8 mmol) in dioxane (10 mL) was added 4N HCl in dioxane (10 mL). After 10 minutes of stirring, methanol (10 mL) was added with continued stirring for one hour. The solution was concentrated in vacuo. Recrystallization (acetone/hexane) provided the title compound as a white solid (2.4 g, 83%). MS(CI) $MH^+$ calculated for $C_{18}H_{18}ClNO_5S$: 428, found 428.

EXAMPLE 26

Preparation of Tetrahydro-N-hydroxy-4-[[4-[4-(1H-1,2,4-triazol-1-yl) phenoxy]-phenyl]-sulfonyl]-2H-pyran-4-, carboxamide, Monohydrochloride

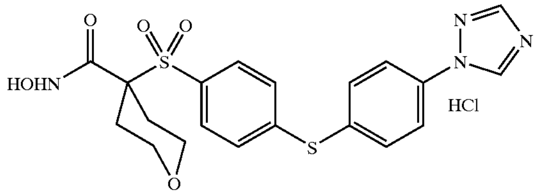

Part A: To a solution of the protected hydroxamate of Example 25, part B (2.9 g, 7.5 mmol) in DMF (10 mL) was added 4-(1,2,4-triazol-1-yl)phenol (2.47 g, 15 mmol) in DMF (5 mL) followed by $Cs_2CO_3$ (7.33 g, 22.5 mmol), and the solution was heated at 95 degrees Celsius for 5 hours. The solution was concentrated in vacuo and the residue was partitioned between ethyl acetate and $H_2O$. The organic layer was washed with saturated NaCl and dried over $Na_2SO_4$. Chromatography (on silica, ethyl acetate/hexane/methanol) provided the phenol as a white solid (3.16 g, 80%).

Part B: To a solution of the phenol of part A (2.8 g, 5.3 mmol) in dioxane (10 mL) was added 4N HCl in dioxane (10 mL). After 5 minutes of stirring, methanol (10 mL) was added and stirring was continued for 1 hour. The solution was then poured into ethyl ether, and the resulting precipitate was collected by vacuum filtration to provide the title compound as a white solid (2.44 g, 96%). MS(CI) $MH^+$ calculated for $C_{20}H_{20}N_4O_6S$: 445, found 445.

EXAMPLE 27

Preparation of 1-cyclopropyl-4-[[4-[(4-fluorophenyl)thio]phenyl]sulfonyl]-N-hydroxy-4-piperidinecarboxamide, Monohydrochloride

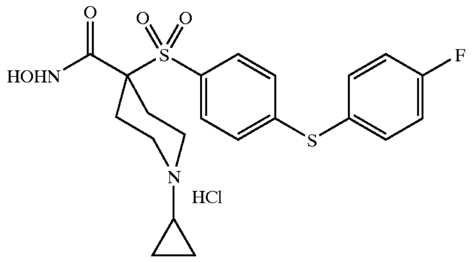

Part A: HCl gas was bubbled for 7 minutes into a solution of the sulfide of Example 9, part D (7.06 g, 13.5 mmol) in ethyl acetate (150 mL), and the solution was stirred for 15 minutes at zero degrees Celsius. The solution was concentrated in vacuo to provide the amine as a white solid (6.43 g, quantitative yield).

Part B: To a solution of the amine of part A (6.4 g, 13.9 mmol) in methanol (65 mL) was added acetic acid (7.96 mL, 139 mmol) and a scoop of 3A molecular sieves. To this mixture was added (1-ethoxycyclopropyl)-oxytrimethylsilane (16.8 mL, 84 mmol) followed by sodium cyanoborohydride (3.9 g, 62 mmol). The solution was heated to reflux for 6 hours. The solution was filtered and the filtrate was concentrated in vacuo. The residue was dissolved into ethyl acetate, washed with $H_2O$, 2N NaOH and saturated NaCl, and dried over magnesium sulfate. Filtration through a pad of silica (hexane/ethyl acetate) provided the cyclopropyl amine as a white solid (6.49 g, quantitative yield).

Part C: To a solution of the cyclopropyl amine of part B (6.4 g, 13.8 mmol) in ethanol (30 mL) and THF (30 mL) was added NaOH (5.5 g, 138 mmol) in $H_2O$ (23 mL), and the solution was heated to 65 degrees Celsius for 12 hours. The solution was concentrated in vacuo and the aqueous layer was acidified to a pH value of 2 with 2N HCl. The resulting white precipitate was collected by filtration to provide the acid as a white solid (5.2 g, 87%). MS(CI) $MH^+$ calculated for $C_{21}H_{22}NO_4S_2F$: 436, found 436.

Part D: To a solution of the acid of part C (2.27 g, 5.2 mmol) in DMF (60 mL) was added HOBT (845 mg, 6.2 mmol) followed by N-methylmorpholine (1.71 mL, 15.6 mmol), EDC (1.40 g, 7.28 mmol) and O-tetrahydro-2H-pyran-2-yl-hydroxylamine (913 mg, 7.8 mmol), and the solution was stirred at ambient temperature for 72 hours. The solution was concentrated in vacuo, the residue was dissolved into dichloromethane and washed with $H_2O$ and saturated NaCl, and then dried over magnesium sulfate. Chromatography (on silica, hexane/ethyl acetate) provided the protected hydroxamate as a white solid (1.95 g, 70%).

Part E: To a solution of the protected hydroxamate of part D (3.2 g, 6.0 mmol) in cold methanol (100 mL) was added acetyl chloride (1.3 mL, 18.0 mmol) in methanol (30 mL), and the solution was stirred at ambient temperature for 4 hours. The solution was concentrated in vacuo and the residue was triturated with ethyl ether to provide the title compound as a white solid (2.86 g, 98%). MS(CI) $MH^+$ calculated for $C_{21}H_{23}N_2O_4S_2F$: 451, found 451. Analytical calculation for $C_{21}H_{23}N_2O_4S_2F$ $0.25H_2O$ HCl: C, 51.32; H, 5.02; N, 5.70; S, 13.05; Cl, 7.21. Found: C, 50.99; H, 4.91; N, 5.65; S, 13.16; Cl, 7.83.

EXAMPLE 28

Preparation of N-hydroxy-4-[[4-(phenylthio)phenyl]sulfonyl]-1(2-propenyl)-4-piperidine Carboxamide, Monohydrochloride

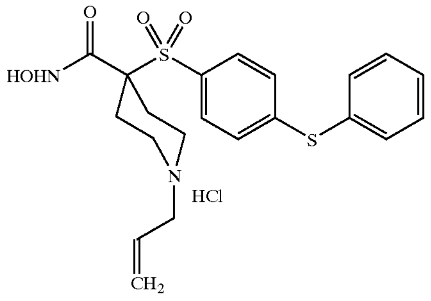

Part A: To a solution of the amine hydrochloride salt of Example 9, part E (4.78 g, 10.8 mmol) in DMF (25 mL) were added $K_2CO_3$ (2.98 g, 21.6 mmol) and allyl bromide (0.935 mL, 10.8 mmol), and the solution was stirred for 5 hours at ambient temperature. The solution was partitioned between ethyl acetate and $H_2O$, and the organic layer was washed with $H_2O$ and saturated NaCl, and dried over magnesium sulfate. Filtration through a pad of silica (hexane/ethyl acetate) provided the allyl amine as an oil (4.80 g, quantitative yield).

Part B: To a solution of the allyl amine of part A (4.8 g, 10.8 mmol) in ethanol (25 mL) and THF (25 mL) was added NaOH (4.3 g, 108 mmol) in $H_2O$ (20 mL), and the solution was heated to 65 degrees Celsius for 18 hours. The solution was concentrated in vacuo and diluted with $H_2O$. The aqueous solution was acidified to a pH value of 3. The resulting precipitate was collected by vacuum filtration to provide the acid as a beige solid (4.1 g, 84%). MS(CI) $MH^+$ calculated for $C_{21}H_{23}NO_4S_2$: 418, found 418.

Part C: To a solution of the acid of part B (4.1 g, 9.0 mmol) in DMF (90 mL) was added HOBT(1.46 g, 11.0 mmol) followed by N-methylmorpholine (2.97 mL, 2.7 mmol), O-tetrahydro-2H-pyran-2-yl-hydroxylamine (1.58 g, 13.5 mmol) and EDC (2.42 g, 13.0 mmol), and the solution was stirred for 72 hours. The solution was concentrated in vacuo. The residue was dissolved in dichloromethane and washed with $H_2O$ and saturated NaCl, and then dried over magnesium sulfate. Chromatography (on silica, ethyl acetate/methanol) provided the protected hydroxylamine as a white solid (4.11 g, 88%).

Part D: To a solution of the protected hydroxylamine of part C (4.11 g, 8.0 mmol) in ethyl acetate (100 mL) cooled to zero degrees Celsius was added acetyl chloride (1.71 mL, 24.0 mmol), and the solution was stirred for 4 hours at ambient temperature. The solution was concentrated in vacuo and trituration with ethyl ether provided the title compound as a white solid (3.53 g, 95%). Analytical calculation for $C_{21}H_{24}N_2O_4S_2$ HCl $0.5H_2O$: C, 52.76; H, 5.48; N, 5.86; S, 13.42; Cl, 7.42. Found: C, 52.57; H, 5.69; N, 6.29; S, 12.59; Cl, 7.80.

EXAMPLE 29

Preparation of 1-(cyclopropylmethyl)-N-hydroxy-4-[(4-phenoxyphenyl)sulfonyl]-4-piperidine Carboxamide, Monohydrochloride

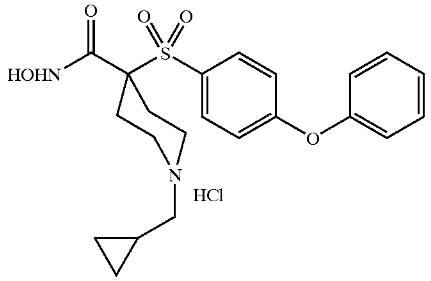

Part A: To a solution of the amine hydrochloride salt of Example 6, part E (2.13 g, 5.0 mmol) in DMF (10 mL) were added $K_2CO_3$ (1.4 g, 10.0 mmol) and bromomethylcyclopropane (0.48 mL, 5.0 mmol), and the solution was stirred for 18 hours at ambient temperature. The solution was partitioned between ethyl acetate and $H_2O$, the organic layer was washed with $H_2O$ and saturated NaCl, and then dried over magnesium sulfate. Chromatography (on silica, ethyl acetate/hexane) provided the solid cyclopropylmethylamine (2.09 g, 91%).

Part B: To a solution of the cyclopropylmethylamine of part A (2.0 g, 4.4 mmol) in ethanol (12 mL) and THF (12 mL) was added NaOH (1.75 g, 44 mmol) in $H_2O$ (10 mL), and the solution was heated to 65 degrees Celsius for 18 hours. The solution was concentrated in vacuo and the aqueous residue was acidified to a pH value of 5. The resulting precipitate was collected by vacuum filtration to provide the acid as a white solid (1.58 g, 79%). HRMS calculated for $C_{22}H_{25}NO_5S$: 414.1375, found 414.1334.

Part C: To a solution of the acid of part B (1.58 g, 3.5 mmol) in dichloromethane (50 mL) was added triethylamine (1.46 mL, 10.5 mmol) followed by 50 percent aqueous hydroxylamine (2.3 mL, 35 mmol) and PyBroP (3.26 g, 6.99 mmol), and the solution was stirred at ambient temperature for 72 hours. The solution was washed with $H_2O$ and saturated NaCl, and dried over magnesium sulfate. Reverse phase chromatography (on silica, acetonitrile/$H_2O$) provided the hydroxamate as a white solid (3.2 g, quantitative yield).

Part D: To a solution of the hydroxamate of part C (1.5 g, 3.5 mmol) in cold methanol (20 mL) was added acetyl chloride (0.25 mL, 3.5 mmol) in methanol (5 mL) and the solution was stirred at zero degrees Celsius for 15 minutes. After the solution had stirred for an additional 30 minutes at ambient temperature, it was concentrated in vacuo. Trituration with ethyl ether provided the title compound as a white solid (229 mg, 7%).

EXAMPLE 30

Preparation of N-hydroxy-1-(2-methoxyethyl)-4-[(4-phenoxyphenyl)-sulfonyl]-4-piperidine Carboxamide, Monohydrchloride

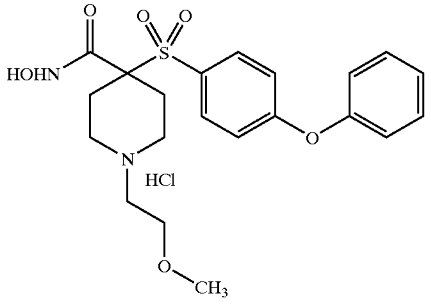

Part A: To a solution of the amine HCl salt of part E, Example 6 (2.5 g, 5.87 mmol) and $K_2CO_3$ (1.6 g, 11.57 mmol) in N,N-dimethylformamide (25 mL) was added 2-bromoethyl methyl ether (0.66 mL, 7.0 mmol) and then stirred at ambient temperature for 18 hours. Then N,N-dimethylformamide was evaporated under high vacuum and residue was diluted with ethyl acetate. The organic layer was washed with water and dried over $Mg_2SO_4$. Concentration in vacuo provided the methoxyl ethyl amine as light yellow gel (2.63 g, quantitative yield).

Part B: To a solution of the methoxyl ethyl amine of part A (2.63 g, 5.87 mmol) in tetrahydrofuran (18 mL) and ethanol (18 mL) was added NaOH (2.1 g, 5.25 mmol) in water (6 mL). The solution was heated to reflux for 12 hours. The solution was concentrated in vacuo and diluted with water. The aqueous layer was extracted with ether (2×100 mL) and was acidified to pH=2. Vacuum filtration of the resulting precipitation provided the acid as a white solid (2.4 g, quantitative yield).

Part C: To a solution of the acid of part B (2.0 g, 4.33 mmol), also containing N-methyl morpholine (1.8 mL, 16.4 mmol), and O-tetrahydro-2H-pyran-yl-hydroxylamine (0.767 g, 6.44 mmol) in N,N-dimethylformamide (20 mL) was added 1-[3-(dimethylamino)propyl]-3-ethylcarbodiimide hydrochloride (3.1 g, 16.2 mmol), and solution was stirred at ambient temperature for 20 hours. The solution was concentrated under high vacuum and the residue was dissolved in ethyl acetate. The organic layer was washed with $H_2O$ and dried over $Mg_2SO_4$. Concentration in vacuo provided the amide as off white foam (1.60 g, 71.1%).

Part D: To a solution of the amide of part C (1.58 g, 3.05 mmol) in methanol (20 mL) cooled to zero degrees Celsius was added acetyl chloride (0.65 mL, 9.15 mmol) and the resulting solution was stirred at the same temperature for 3 hours. The solution was concentrated and reverse phase chromatography (on C-18 silica, acetonitrile/$H_2O$ with 0.01% HCl) provided hydroxamate HCl salt as a white solid (0.65 g, 45.5%). Analytical calculation for $C_{21}H_{26}N_2O_6S.HCl.0.75H_2O$: C, 52.06; H, 5.93; N, 5.78; S, 6.62. Found: C, 51.94; H, 5.67; N, 5.91; S, 6.66. HSMS calculated for $C_{21}H_{26}N_2O_6S$: 435.1590, found 435.1571.

EXAMPLE 31

Preparation of N-hydroxy-4-[(4-phenoxyphenyl) sulfonyl]-1-(1-pyrrolidinylacetyl)-4-piperidine Carboxamide, Monohydrochloride

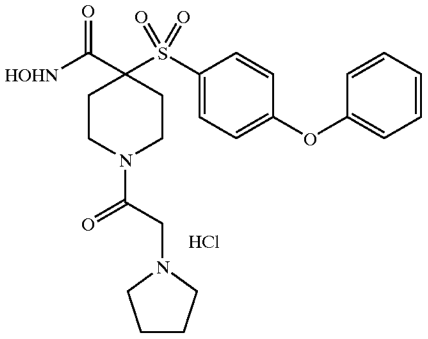

Part A: To a solution of the sulfone of part D, Example 6 (2.75g, 5.6mmol) in tetrahydrofuran (10 mL) and ethanol (10 mL) was added NaOH (2.25g, 56mmol) in $H_2O$ (20 mL), and the solution was heated to 70 degrees Celsius for 20 hours. The solution was concentrated in vacuo and the dry residue was dissolved in $H_2O$. The aqueous layer was extracted with ether and was acidified to pH=2 followed by the extraction with ethyl acetate. The combined organic layers were washed again with $H_2O$ and dried over $Mg_2SO_4$. Concentration in vacuo provided the BOC-acid as white foam (2.39, 88.8%)

Part B: To a solution of BOC-acid of part A (2.3 g, 4.98 mmol) in dichloromethane (6 mL) was added trifluroacetic acid (6 mL, 77.8 mmol), and the resulting solution was stirred at ambient temperature for 1 hour. Concentration in vacuo provided the amine as white foam (2.44 g, quantitative yield).

Part C: To the solution of the amine of part B (2.4 g, 4.9 mmol) and triethylamine (3.5 mL, 24.4 mmol) in acetone (15 mL) and $H_2O$ (15 mL) was added chloroacetyl chloride (1.2 mL, 14.7 mmol), and solution was stirred at ambient temperature for 20 hours. Then acetone was evaporated and aqueous layer was acidified to pH=2. The aqueous layer was extracted with ethyl acetate and the organic layer was washed with water and dried over $Mg_2SO_4$. Concentration in vacuo provided the chloroacetyl amide as light yellow gel (2.78 g, quantitative yield).

Part D: To the solution of the chloroacetyl amide of part C (2.78 g, 4.93 mmol) and $K_2CO_3$ (5 g, 36 mmol) in N,N-dimethylformamide (20 mL) was added pyrolidine (3 mL, 36 mmol). The solution was then stirred at ambient temperature for 18 hours. Then N,N-dimethylformamide was evaporated under high vacuum and reverse phase chromatography (on C-18 silica, acetonitrile/$H_2O$ with 0.01% HCl) provided pyrolidine acetyl amide (0.25 g, 10.7%).

Part E: To a solution of the pyrolidine acetyl amide of part D (0.25 g, 0.53 mmol), also containing N-methyl morpholine (0.14 mL, 1.27 mmol), 1-hydroxybenzotriazole (0.17 g, 1.2 mmol) and O-tetrahydro-2H-pyran-yl-hydroxylamine (0.15 g, 1.26 mmol) in N,N-dimethylformamide (4 mL) was added 1-[3-(dimethylamino)propyl]-3-ethylcarbodiimide hydrochloride (0.23 g, 1.2 mmol). The solution was then stirred at ambient temperature for 18 hours. The solution was concentrated under high vacuum and the residue was dissolved in ethyl acetate. The organic layer was washed with saturated $NaHCO_3$, $H_2O$ and dried over $Mg_2SO_4$. Concentration in vacuo provided the THP amide as white foam (0.25 g, 83.3%).

Part F: To a solution of the amide of part E (0.25 g, 0.437 mmol) in methanol (4 mL) cooled to zero degrees Celsius was added acetyl chloride (0.075 mL, 1.05 mmol), and the resulting solution was stirred at ambient temperature for 2.5 hours. The solution was concentrated and reverse phase chromatography (on C-18 silica, acetonitrile/$H_2O$ with 0.01% HCl) provided hydroxamate HCl salt as a white solid (80 mg, 29%). Analytical calculation for $C_{24}H_{29}N_3O_6S.HCl.0.9H_2O$: C, 53.36; H, 5.98; N, 7.78. Found: C, 53.61; H, 5.71; N, 7.94. HSMS calculated for $C_{24}H_{29}N_3O_6S$: 488.1855, found 488.1835.

EXAMPLE 32

Preparation of 1-cyclopropyl-N-hydroxy-4-[[4-(phenylthio)phenyl]sulfonyl]-4-piperidine Carboxamide, Monohydrochloride

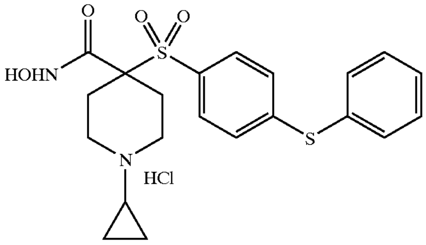

Part A: A solution of 4-flurothiophenol (50.29 g, 0.39 mmol) in dimethylsulfoxide (500 mL) was heated to 65 degrees Celsius for 5 hours. The solution was cooled to ambient temperature and poured into vigorously stirred ice water. The precipitate was filtered and washed twice with water. Drying under high vacuum provided the disulfide as a yellow oil (34.39 g, 68.9%) at ambient temperature.

Part B: A solution of di-tert-butyl dicarbonate (21.8 g, 0.1 mol) in tetrahydrofuran (5 mL) was added dropwise over 20 minutes to a solution of ethyl isonipecotate (15.7 g, 0.1 mol) in tetrahydrofuran (100 mL). The resulting solution was stirred overnight (about eighteen hours) at ambient temperature and concentrated in vacuo to yield a light oil. The oil was filtered through silica gel (ehyl acetate/hexane) and concentrated in vacuo to give the BOC-piperidine compound as a clear, colorless oil (26.2 g, quantitative yield).

Part C: To a solution of BOC-piperidine compound of part B (15.96 g, 62 mmol) in tetrahydrofuran (300 mL), cooled to minus forty degrees Celsius, was added lithium diisopropylamide (41.33 mL, 74 mmol). The solution was then stirred at minus forty degrees C. for one hour and zero degreec C. for one-half hour. Then the solution was cooled to minus forty degrees Celsius again and the disulfide of part A (15.77 g, 62 mmol) in tetrahydrofuran (20 mL) was added. The resulting solution as stirred at ambient temperature for 18 hours. The solution was diluted with $H_2O$ and extracted with ethyl acetate. The organic layer was washed with $H_2O$ and saturated NaCl and dried over $MgSO_4$. Chromatography (on silica, ethyl acetate/hexane) provided the sulfide as an oil (18 g, 75%).

Part D: To a solution of the sulfide of part C (16.5 g, 43 mmol) in dichloromethane (500 mL) cooled to zero degrees Celsius, was added m-chloroperbenzoic acid (18.5 g, 107 mmol). After 2 hours, the solution was diluted with dichloromethane and washed with 1N KOH, H2O and dried over $MgSO_4$. Concentration in vacuo provided the sulfone as a solid (21 g, quantitative yield).

Part E: To a solution of sulfone (40 g, 96 mmol) of part D and powdered $K_2CO_3$ (26 g, 188 mmol) in N,N-dimethylformamide (200 mL) cooled to zero degrees Celsius was added thiolphenol (19.8 mL, 192 mmol), and the reculting composition was then stirred at ambient temperature for 36 hours. That solution was concentrated under high vacuum and the residue was dissolved in ethyl acetate. The organic layer was washed with $H_2O$ and dried over magnesium sulfate. Chromatography (on silica, ethyl acetate/hexane) provided phenyl thiophenyl Boc-sulfone as white solid (44.34 g, 91%).

Part F: To a solution of phenyl thiophenyl Boc-sulfone of part E (8.6 g, 17 mmol) in dichloromethane (30 mL) cooled to zero degrees Celsius was added trifluroacetic acid (TFA; 30 mL), and the resulting solution was stirred at ambient temperature for 2 hours. Concentration in vacuo provided the amine TFA salt as a light yellow gel (8.7 g, quantitative yield).

Part G: To a solution of amine TFA salt of part F (6 g, 11.9 mmol) was added acetic acid (6.8 mL, 119 mmol). After 5 minutes stirring at ambient temperature, (1-ethoxylcyclopropyl)oxytriomethylsilane (14.3 mL, 71.4 mmol) was added followed 5 minutes later by the addition of sodium cyanoboran hydrate (3.35 g, 53.55 mmol). Then the solution was heated to reflux for 18 hours. Methanol was evaporated and residue was dissolved in ethyl acetate. The organic layer was washed with 1N NaOH, $H_2O$ and dried over $Mg_2SO_4$. Concentration in vacuo gave the cyclopropylamine as an off-white powder (4.9 g, 92.6%).

Part H: To a solution of the cyclopropylamine of part G (4.88 g, 10.95 mmol) in tetrahydrofuran (12.5 mL) and ethanol (12.5 mL) was added NaOH (4.3 g, 100 mmol) in water (25 mL). The solution was then heated to 50–55 degrees Celsius for 12 hours and was stirred at ambient temperature for 18 hours. Solution was acidified to pH=2 and concentration in vacuo provided the acid as white solid together with NaCl in the mixture. To a solution of this mixture in acetonitrile (50 mL) were added O-tetrahydropyronylamine (1.95 g, 16.3 mmol), N-methylmorpholine (2.4 mL, 21.9 mmol), and 1-[3-(dimethylamino)propyl]-3-ethylcarbodiimide hydrochloride (3.14 g, 16.3 mmol) in sequence. The solution was then stirred at ambient temperature for 18 hours. The solution was concentrated in vacuo and the residue was dissolved in ethyl acetate. The organic layer was washed with $H_2O$ and dried over $Mg_2SO_4$. Concentration in vacuo provided the tetrehyrdopyronyl (THP) amide as white solid (3.0 g, 53.1%).

Part I: To a solution of the THP amide of part H (3 g, 5.8 mmol) in methanol (45 mL) cooled to zero degrees Celsius was added acetyl chloride (1.5 mL, 21.1 mmol), and the solution was stirred at ambient temperature for 2.5 hours. Vacuum filtration of the precipitate provided hydroxamate HCl salt as a white solid (1.844 g, 68.3%). Analytical calculation for $C_{21}H_{24}N_2O_4S_2$.HCl: C, 53.78; H, 5.37; N, 5.97; S, 13.67. Found: C, 53.40; H, 5.26; N, 5.95; S, 13.68.

EXAMPLE 33

Preparation of N-hydroxy-1-methyl-4-[[4-(phenylthio)phenyl]sulfonyl]-4-piperidinecarboxamide, Monohydrochloride

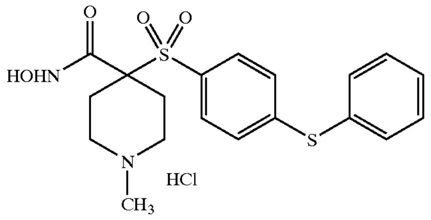

Part A: To a solution of amine TFA salt of part F, Example 32 (2.67 g, 5.14 mmol) and 37% formaldehyde in aqueous solution (2.0 mL, 25.7 mmol) in methanol (20 mL) was added borane pyridine (2.6 mL, 25.7 mmol) at ambient temperature. The solution was then stirred at ambient temperature for 18 hours. The solution was acidified to destroy excess reagent. Methanol was evaporated and the residue was partitioned between NaHCO, aqueous solution and ethyl acetate. The $NaHCO_3$ aqueous layer was extracted with ethyl acetate. The combined organic layers were washed with $H_2O$ and dried over $Mg_2SO_4$. Concentration in vacuo gave the methyl amine as off white foam (1.6 g, 76%).

Part B: To a solution of the methyl amine of part A (1.63 g, 3.88 mmol) in ethanol (20 mL) was added KOH (1.31 g, 23.2 mmol) in water (4 mL), and the resulting solution was heated to 50 degrees Celsius for 8 hours, 70 degree Celsius for 4 hours and stirred at ambient temperature for 18 hours. The solution was acidified and concentrated in vacuo providing the acid as white solid together with NaCl in the mixture. To a solution of this mixture in N,N-dimethylformamide (50 mL) were added ) O-tetrahydropyronylamine (0.92 g, 7.76 mmol), N-methylmorpholine (1.05 mL, 7.76 mmol), and 1-[3-(dimethylamino)propyl]-3-ethylcarbodiimide hydrochloride (1.5 g, 7.76 mmol) in sequence. The solution was stirred at ambient temperature for 72 hours. The solution was concentrated in high vacuum and the residue was dissolved in ethyl acetate. The organic layer was washed with saturated $NaHCO_3$, $H_2O$ and dried over $Mg_2SO_4$. Concentration in vacuo and chromatography (silica, dichloromethane/methanol) provided the THP amide as white solid (0.46 g, 24.2%).

Part C: To a solution of the THP amide of part B (0.22 g, 0.45 mmol) in methanol (5 mL) cooled to zero degrees Celsius was added acetyl chloride (0.096 mL, 13.5 mmol), and the resulting solution was stirred at ambient temperature for 3 hours. The solution was concentrated in vacuo and reverse phase chromatography (on C-18 silica, acetonitrile/$H_2O$ with 0.01% HCl) provided hydroxamate HCl salt as a white solid (0.12 g, 60.6%). HSMS calculated for $C_{19}H_{22}N_2O_4S_2$: 407.1099, found 407.1105.

EXAMPLE 34

Preparation of N-hydroxy-1-(1-methylethyl)-4-[[4-(phenylthio)phenyl]sulfonyl]-4-piperidinecarboxamide, Monohydrochloride

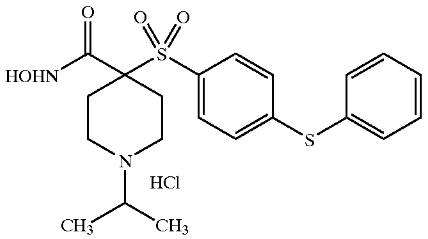

Part A: Into a solution of BOC-sulfone of part E, Example 32 (11.19 g, 22.12 mmol) in ethyl acetate (150 mL) cooled to zero degrees Celsius was bubbled HCl gas for 20 minutes. The solution was stirred at the same temperature for another 40 minutes. Concentration in vacuo and titration with ether provided the amine HCl salt (9.88 g, quantitative yield).

Part B: To a solution of amine HCl salt of part A (4.7 g, 10.6 mmol), triethylamine (2.0 mL, 14.4 mmol) and acetone (2.0 mL, 27.2 mmol) in dichloromethane (100 mL) were added sodium triacetoxylborohydride (5.7 g, 26.9 mmol) followed by acetic acid (1.5 mL, 26.9 mmol) at ambient temperature. The solution was stirred for 18 hours and then partitioned in 1N NaOH and ether. The aqueous layer was extracted with ether and combined organic layers were washed with 1N NaOH, $H_2O$ and dried over $Mg_2SO_4$. Concentration in vacuo gave the isopropyl amine as white foam (4.58 g, 96.2%).

Part C: To a solution of the isopropyl amine of part B (4.58 g, 10.2 mmol) in tetrahydrofuran (10 mL) and ethanol (10 mL) was added NaOH (2.1 g, 5.25 mmol) in water (20 mL). The solution was heated to 60 degrees Celsius for 13.5 hours, then stirred at ambient temperature for 18 hours. The solution was acidified and concentrated in vacuo providing the acid as white solid together with NaCl in the mixture. To a solution of this mixture in N,N-dimethylformamide (75 mL) were added 1-hydroxybenzotriazole (1.94 g, 14.4 mmol), O-tetrahydropyronylamine (1.8 g, 15.1 mmol), N-methylmorpholine (3.37 mL, 30.7 mmol), and 1-[3-(dimethylamino)propyl]-3-ethylcarbodiimide hydrochloride (2.74 g, 14.3 mmol) in sequence. The solution was stirred at ambient temperature for 48 hours. The solution was concentrated in high vacuum and the residue was dissolved in ethyl acetate. The organic layer was washed with saturated $NaHCO_3$, $H_2O$ and dried over $Mg_2So_4$. Concentration in vacuo and chromatography (silica, dichloromethane/methanol) provided the THP amide as white solid (3.78 g, 71.3%).

Part D: To a solution of the THP amide of part C (1.15 g, 2.2 mmol) in methanol (20 mL) was added acetyl chloride (0.096 mL, 13.5 mmol), and the resulting solution was stirred at ambient temperature for 2.5 hours. The solution was concentrated in vacuo and reverse phase chromatography (on C-18 silica, acetonitrile/$H_2O$ with 0.01% HCl) provided hydroxamate HCl salt as a white solid (0.69 g, 66.3%). Analytical calculation for $C_{21}H_{26}N_2O_4S_2$.HCl.$H_2O$: C, 51.58; H, 5.98; N, 5.73; S, 13.11. Found: C, 51.76; H, 5.47; N, 5.72; S, 12.68.

EXAMPLE 35

Preparation of N-hydroxy-1-(2-methoxyethyl)-4-[[4-(phenylthio)phenyl)-sulfonyl]-4-piperidinecarboxamide, Monohydrochloride

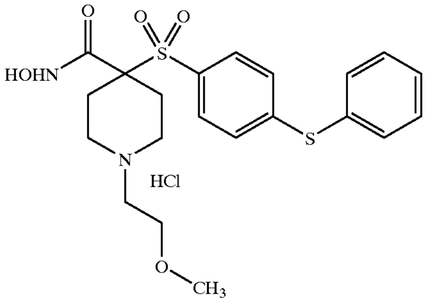

Part A: To the solution of the amine HCl salt of part A, Example 34 (4.3 g, 9.43 mmol) and $K_2CO_3$ (2.62 g, 19.0 mmol) in N,N-dimethylformamide (40 mL) was added 2-bromoethyl methyl ether (1.9 mL, 20.2 mmol). The solution was stirred at ambient temperature for 48 hours. Then N,N-dimethylformamide was evaporated under high vacuum and the residue was diluted with ethyl acetate. The organic layer was washed with water and dried over $Mg_2SO_4$. Concentration in vacuo provided the methoxyl ethyl amine as white foam (4.26 g, 95.3%).

Part B: To a solution of the methoxyl ethyl amine of part A (4.26 g, 9.2 mmol) in tetrahydrofuran (5 mL) and ethanol (5 mL) was added NaOH (3.7 g, 92.5 mmol) in water (9 mL). The solution resulting was heated to 60 degrees Celsius for 12 hours and stirred at ambient temperature for 18 hours. The solution was concentrated in vacuo and diluted with water. The aqueous layer was extracted with ether (2×100 mL) and was acidified to pH=2. Vacuum filtration of the resulting precipitate provided the acid as a while solid (3.5 g, 87.5%).

Part C: To a solution of the acid of part B (3.4 g, 7.8 mmol), also containing N-methyl morpholine (2.6 mL, 23.4 mmol), 1-hydroxybenzotriazole (3.16 g, 23.4 mmol), and O-tetrahydro-2H-pyran-2-yl-hydroxylamine (1.85 g, 15.5 mmol) in N,N-dimethylformamide (20 mL) was added 1-[3-(dimethylamino)propyl]-3-ethylcarbodiimide hydrochloride (4.47 g, 23.4 mmol). The solution was stirred at ambient temperature for 36 hours. The solution was concentrated under high vacuum and the residue was dissolved in ethyl acetate. The organic layer was washed with saturated $NaHCO_3$, H2O and dried over $Mg_2SO_4$. Concentration in vacuo provided the amide as off white solid (2.98 g, 71.5%).

Part D: To a solution of the amide of part C (2.98 g, 5.6 mmol) in methanol (40 mL) cooled to zero degrees Celsius was added acetyl chloride (1.19 mL, 16.8 mmol), and the resulting solution was stirred at the ambient temperature for 3 hours. The solution was concentrated and reverse phase chromatography (on C-18 silica, acetonitrile/$H_2O$ with 0.01% HCl) provided hydroxamate HCl salt as a white solid (2.29 g, 84.6%). Analytical calculation for $C_2H_{26}N_2O_6S$.HCl.0.9$H_2O$: C, 50.12; H, 5.77; N, 5.57; S, 12.74. Found: C, 50.41; H, 5.85; N, 5.73; S, 12.83.

EXAMPLE 36

Preparation of 1-acetyl-N-hydroxy-4-[[4-(phenylthio)phenyl]sulfonyl]-4-piperidinecarboxamide, Monohydrochloride

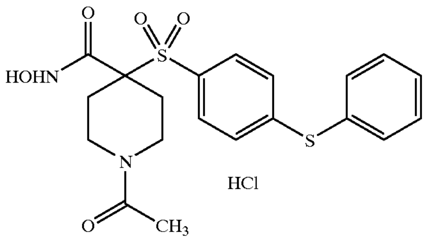

Part A: To a solution of the phenyl thiophenyl BOC-sulfone of part E, Example 32 (7 g, 1.29 mmol) in tetrahydrofuran (25 mL) and ethanol (25 mL) was added NaOH (5.1 g, 12.9 mmol) in $H_2O$ (50 mL). The solution was heated to reflux for 20 hours. On cooling, the solution was concentrated in vacuo and the dry residue was dissolved in $H_2O$. The aqueous layer was extracted with ether and was acidified to pH=2 followed by the extraction with ethyl acetate. The combined organic layers were washed again with $H_2O$ and dried over $Mg_2SO_4$. Concentration in vacuc provided the BOC-acid as white foam (3.9 g, 60%).

Part B: To a solution of BOC-acid of part A (2.3 g, 4.98 mmol) in dichloromethane (6 mL) was 5 added trifluroacetic acid (6 mL, 77.8 mmol), and the solution was stirred at ambient temperature for 1 hour. Concentration in vacuo provided the amine as white foam (2.44 g, quantitative yield).

Part C: To a solution of the amine of part B (5.0 g, 12.08 mmol) and triethylamine (8.7 mL, 60.4 mmol) in acetone (20 mL) and $H_2O$ (20 mL) cooled to zero degrees Celsius was added acetyl chloride (4.6 mL, 36 mmol), and the solution was stirred at ambient temperature for 40 hours. The acetone was evaporated and the aqueous layer was acidified to pH=2. The aqueous layer was extracted with ethyl acetate and the combined organic layers were washed with water and dried over $Mg_2SO_4$. Concentration in vacuo provided the acetyl amide as light yellow foam (5 g, quantitative yield).

Part D: To a solution of acetyl amide of part C (5 g, 11.9 mmol), also containing N-methyl morpholine (5.3 mL, 47.6 mmol), 1-hydroxybenzotriazole (4.8 g, 35.7 mmol) and O-tetrahydro-2H-pyran-yl-hydroxylamine (2.8 g, 23.5 mmol) in N,N-dimethylformamide (50 mL) was added 1-[3(dimethylamino)propyl]-3-ethylcarbodiimide hydrochloride (6.8 g, 35.7 mmol), and the solution was stirred at ambient temperature for 20 hours. The solution was concentrated under high vacuum and the residue was dissolved in ethyl acetate. The organic layer was washed with saturated $NaHCO_3$, $KHSO_4$, $H_2O$ and dried over $Mg_2So_4$. Concentration in vacuo provided the THP amide as white foam (6.07 g, 98.2%).

Part E: To a solution of the THP amide of part D (6.07 g, 11.7 mmol) in methanol (100 mL) cooled to zero degrees Celsius was added acetyl chloride (2.5 mL, 35.1 mmol), and the solution was stirred at ambient temperature for 3 hours. The solution was concentrated and chromatography (on silica, methanol/dichloromethane) provided hydroxamate HCl salt as a white solid (3.3 g, 65%). Analytical calculation for $C_{24}H_{29}N_3O_6S.HCl.0.9H_2O$: C, 53.36; H, 5.98; N, 7.78. Found: C, 53.61; H, 5.71; N, 7.94. HSMS calculated for $C_{24}H_{29}N_3O_6S$: 488.1855, found 488.1835.

EXAMPLE 37

Preparation of 1-acetyl-4-[(4-(1,3-benzodioxol-5-yloxy)phenyl)sulfonyl]-N-hydroxy-4-piperidinecarboxamide, Monohydrochloride

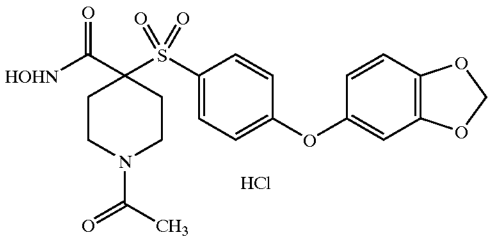

Part A: To a solution of sulfone from Part D, Example 32 (25 g, 67.3 mmol) and powdered $K_2CO_3$ (23.3 g, 16.9 mmol) in N,N-dimethylformamide was added sesamol (23.24 g, 16.8 mmol) at ambient temperature, and solution was heated to ninety degrees Celsius for 24 hours. The solution was concentrated under high vacuum and the residue was dissolved in ethyl acetate. The organic layer was washed with 1N NaOH, $H_2O$ and dried over $MgSO_4$. Chromatography (on silica, ethyl acetate/hexane) provided sesamol BOC-sulfone as a white foam (33.6 g, 93.6%).

Part B: To a solution of sesamol BOC-sulfone of part E (29.31 g, 54.93 mmol) in ethanol (60 mL) and tetrahydrofuran (60 mL) was added NaOH (21.97 g, 544 mmol) from addition funnel over 20 minutes at ambient temperature. The solution was then heated to sixty degrees Celsius for 9 hours, then ambient temperature for 12 hours. The solution was concentrated in vacuo and diluted with water. The aqueous layer was extracted with ether and acidified to pH=2. It was then extracted with ethyl acetate and the combined organic layers were washed with $H_2O$ and dried over $MgSO_4$. Concentration in vacuc provided the acid as white solid (25.3, 91%).

Part C: HCl gas was bubbled into a solution of the acid of part F (20.3 g, 40.15 mmol) in ethyl acetate cooled to zero degrees Celsius. After 1.5 hours, vacuum filtration of white precipitate provided the amine HCl salt as a white solid (16 g, 93.6%).

Part D: To the solution of the amine HCl salt of part G (8.1 g, 19.01 mmol) and triethylamine (13.2 mL, 95.05 mmol) in acetone (150 mL) and $H_2O$ (150 mL) cooled to zero degrees Celsius was added acetyl chloride (5.4 mL, 76 mmol). The solution was stirred at ambient temperature for 18 hours. The acetone was evaporated and aqueous layer was acidified to pH=2. The aqueous layer was extracted with ethyl acetate and the combined organic layers were washed with water and dried over $Mg_2SO_4$. Concentration in vacuo provided the acetyl amide as light yellow foam (9.24 g, quantitative yield).

Part E: To the solution of the acetyl amide of part D (9.1 g, 20.33 mmol), N-methyl morpholine (6.7 mL, 61 mmol), 1-hydroxybenzotriazole (8.2 g, 60 mmol) and O-tetrahydro-2H-pyran-yl-hydroxylamine (4.85 g, 40 mmol) in N,N-dimethylformamide (40 mL) was added 1-[3-(dimethylamino)propyl]-3-ethylcarbodiimide hydrochloride (11.65 g, 60 mmol). The resulting solution was stirred at ambient temperature for 20 hours. The solution was then concentrated under high vacuum and the residue was dissolved in ethyl acetate. The organic layer was washed with saturated $NaHCO_3$, $KHSO_4$, $H_2O$ and dried over $Mg_2SO_4$. Concentration in vacuo and chromatography (on silica, ethyl acetate/hexane) provided the THP amide as white a foam (10 g, 89.7%).

Part F: To a solution of 4N HCl in dioxane (20 mL) was added a solution of the amide of part E (5.0 g, 9.1 mmol) in methanol (5 mL) and dioxane (15 mL). That solution was stirred at ambient temperature for 30 minutes. Vacuum filtration of the white precipitate provided the hydroxamate HCl salt as a white solid (3.3 g, 65%). Analytical calculation for $C_{21}H_{22}N_2O_8S$.HCl: C, 54.34; H, 5.15; N, 5.49; S, 6.43. Found: C, 54.54; H, 4.79; N, 6.06; S, 6.93. HSMS calculated for $C_{21}H_{22}N_2O_8S$: 463.1175, found 463.118.

EXAMPLE 38

Preparation of 4-[[4-(3,4-dimethoxyphenoxy)phenyl]sulfonyl]-N-hydroxy-1-(2-propynyl)-4-piperidinecarboxamide, Monohydrochloride

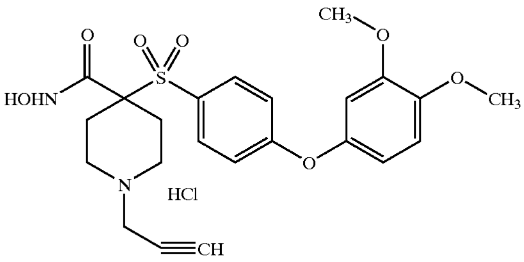

Part A: HCl gas was bubbled into a solution of the sulfone of part D, Example 32 (10 g, 24 mmol) in ethyl acetate cooled to zero degrees Celsius. After 4 hours, vacuum filtration of the white precipitate provided the amine HCl salt as a white solid (7.27 g, 86%).

Part B: To a solution of the amine HCl salt of part A (5.98 g, 17 mmol) and powered $K_2CO_3$ (4.7 g, 34 mmol) in N,N-dimethylformamide (120 mL) was added propargyl bromide (2.022 g, 17 mmol) at ambient temperature, followed by stirring for 4 hours. The solution was diluted with ethyl acetate and washed with $H_2O$, saturated NaCl and dried over $Mg_2SO_4$. Concentration in vacuo and chromatography (on silica, ethyl acetate/hexane) provided the propargyl amine as a white solid (5.2 g, 86%).

Part C: To a solution of the propargyl amine of part B (8 g, 22.63 mmol) and powdered $K_2CO_3$ (8.8 g, 56.6 mmol) in N,N-dimethylformamide (150 mL) was added 3,4-dimethoxyphenol (6.98 g, 45 mmol) at ambient temperature. The composition was heated to 90 degrees Celsius for 36 hours. The solution was concentrated under high vacuum and the residue was dissolved in ethyl acetate. The organic layer was washed with 1N NaOH, $H_2O$ and dried over $MgSO_4$. Chromatography (on silica, ethyl acetate/hexane) provided phenoxy propargyl amine as light yellow gel (10 g, 90.9%).

Part D: A solution of NaOH (8.2 g, 200 mmol) in $H_2O$ (30 mL) from addition funnel was added to a solution of the phenoxy propargyl amine of part C (10 g, 20.5 mmol) in ethanol (15 mL) and tetrahydrofuran (15 mL) at ambient temperature. The resulting solution was then heated to 60 degrees Celsius for 48 hours and at ambient temperature for 48 hours. The solution was concentrated in vacuo and diluted with water. The aqueous layer was extracted with ether and acidified to pH=2. Vacuum filtration of the white precipitate provided the acid as a white solid (9.4 g, quantitative yield).

Part E: To a solution of the acid of part D (9.4 g, 20.5 mmol), N-methyl morpholine (6.8 mL, 62 mmol), 1-hydroxybenzotriazole (8.3 g, 60 mmol) and O-tetrahydro-2H-pyran-yl-hydroxylamine (4.8 g, 40 mmol) in N,N-dimethylformamide (50 mL) was added 1-[3-(dimethylamino)propyl]-3-ethylcarbodiimide hydrochloride (11.7 g, 60 mmol). The resulting solution was then stirred at ambient temperature for 20 hours. The solution was concentrated under high vacuum and the residue was dissolved in ethyl acetate. The organic layer was washed with saturated $NaHCO_3$, $H_2O$ and dried over $Mg_2SO_4$. Concentration in vacuo and chromatography (on silica, ethyl acetate/hexane) provided the THP amide as white foam (10 g, 89.7%).

Part F: To a solution of 4N HCl in dioxane (38 mL, 152 mmol)) was added a solution of the amide of part E (8.5 g, 15.2 mmol) in methanol (8 mL) and dioxane (24 mL).The resulting composition was stirred at ambient temperature for 80 minutes. Concentration in vacuo and titration with ether provided hydroxamate HCl salt as a white solid (7.7 g, quantitative yield). HSMS calculated for $C_{23}H_{26}N_2O_7S$: 475.1461, found 475.1539.

EXAMPLE 39

Preparation of 4-[[4-(3,5-dimethoxyphenoxy)phenyl]sulfonyl]-N-hydroxy-1-(2-propynyl)-4-piperidinecarboxamide, Monohydrochloride

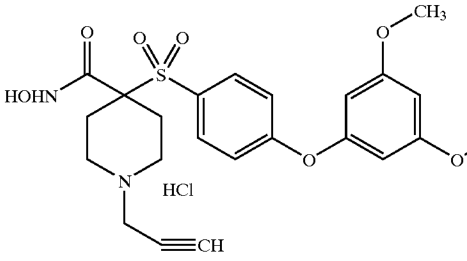

Part A: To a solution of the propargyl amine of Part B. Example 38 (2 g, 5.6 mmol) and powdered $K_2CO_3$ (1.9 g, 13.7 mmol) in N,N-dimethylformamide (20 mL) was added 3,5-dimethoxyphenol (2.18 g, 13.7 mmol) at ambient temperature. The resulting composition was heated to 90 degrees Celsius for 36 hours. The solution was concentrated under high vacuum and the residue was dissolved in ethyl acetate. The organic layer was washed with 1N NaOH, $H_2O$ and dried over $MgSO_4$. Chromatography (on silica, ethyl acetate/hexane) provided phenoxy propargyl amine as light yellow gel (2.76 g, quantitative yield).

Part 2: To a solution of the phenoxy propargyl amine of part A (2.75 g, 5.6 mmol) in ethanol (5 mL) and tetrahydrofuran (5 mL) was added NaOH (2.3 g, 56 mmol) in $H_2O$ (10 mL) at ambient temperature. The solution was then heated to 60 degrees Celsius for 18 hours. The solution was concentrated in vacuo and diluted with water. The aqueous layer was extracted with ether and acidified to pH=2. Vacuum filtration of white precipitate provided the acid as white solid (2 g, 77.2%).

Part C: To a solution of the acid of part B (2 g, 4.3 mmol), also containing N-methyl morpholine (1.9 mL, 17.2 mmol), 1-hydroxybenzotriazole (1.74 g, 13.2 mmol) and O-tetrahydro-2H-pyran-yl-hydroxylamine (1.02 g, 8.6 mmol) in N,N-dimethylformamide (20 mL) was added 1-[3-(dimethylamino)propyl]-3-ethylcarbodiimide hydrochloride (2.47 g, 12.9 mmol). The resulting composition was stirred at ambient temperature for 20 hours. The solution was concentrated under high vacuum and the residue was dissolved in ethyl acetate. The organic layer was washed with saturated $NaHCO_3$, $H_2O$ and dried over $Mg_2SO_4$. Concentration in vacuo and chromatography (on silica, ethyl acetate/hexane) provided the THP amide as white foam (2.4 g, quantitative yield).

Part D: To a solution of 4N HCl in dioxane (13 mL, 52 mmol)) was added a solution of the THP amide of part C (2.43 g, 4.35 mmol) in methanol (2 mL) and dioxane (6 mL), and the composition was stirred at ambient temperature for 80 minutes. Vacuum filtration of the precipitate and washing with ether provided the hydroxamate HCl salt as a white solid (1.25 g, 56.3%). Analytical calculation for $C_{23}H_{26}N_2O_7S.1.5HCl$: C, 52.20; H, 5.24; N, 5.29. Found: C, 52.00; H, 5.05; N, 5.17.

EXAMPLE 40

Preparation of 4-[[4-(1,3-benzodioxol-5-yloxy) phenyl]sulfonyl]-N-hydroxy-4-piperidinecarboxamide, Monohydrochloride

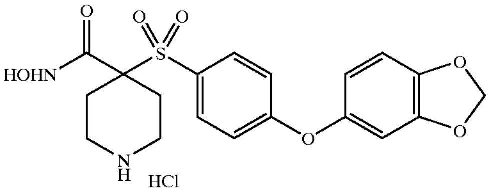

Part A: To a solution of the N-BOC carboxylic acid compound of part B, Example 37 (1.25 g, 2.47 mmol), N-methylmorpholine (1.00 g, 9.89 mmol) and 1-hydroxybenzotriazole hydrate (0.40 g, 2.96 mmol) in N,N-dimethylformamide (8 mL) at ambient temperature was added 1-(3-dimethylaminopropyl)-3-ethylcarbodiimide hydrochloride (0.616 g, 3.21 mmol). After 5 minutes a solution of O-tetrahydro-2H-pyran-2-yl-hydroxylamine (0.39 g, 3.33 mmol) in N,N-dimethylformamide (2 mL) was added. After 2 days the pale yellow solution was concentrated in vacuo to afford a residue which was dissolved in ethyl acetate and washed successively with water (3×) and brine and dried over sodium sulfate. Concentration afforded a residue that was chromatographed on silica gel eluting with ethyl acetate/hexane (20/80) to afford the THP-protected hydroxamate as an oil (1.54 g, 100%).

Part B: To a solution of THP-protected hydroxamate of part A (1.49 g, 2.46 mmol) in dioxane (9 mL) and methanol (3 mL) was added 4 N HCl in dioxane (10 mL, 40 mmol). After 1.5 hours at ambient temperature the suspension was treated with diethyl ether (15 mL) and filtered to afford the title hydroxamate (1.00 g, 89%) as a colorless powder. MS (CI) $MH^+$ calculated for $C_{19}H_{20}N_2SO_7$: 421, found 421. Analytical calculation for $C_{19}H_{20}N_2SO_7.HCl$: C, 49.95; H, 4.63; N, 6.13; Cl, 7.76; S, 7.02. Found: C, 49.82; H, 4.60; N, 5.98; Cl, 17.38; S, 7.10.

EXAMPLE 41

Preparation of N-hydroxy-4-[[4-(3-methylphenoxy) phenyl]sulfonyl]-1-(2-propynyl)-4-piperidinecarboxamide, Monohydrochloride

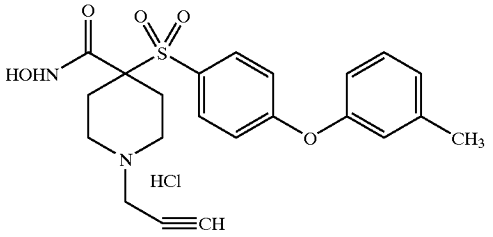

Part A: To a solution of propargylamine of part F, Example 9 (8.0 gm, 22.6 mmol) and $K_2CO_3$ in N,N-dimethylformamide (30 mL) was added m-cresol (3.5 g, 33.9 mmol) and the solution was stirred at 90 degrees Celsius for 18 hours. The solution was diluted with $H_2O$ and extracted with ethyl acetate. The combined organic layers were washed with saturated NaCl and dried over $MgSO_4$. Chromatography (on silica, eluting with 10% ethyl acetate/hexane) provided the 3-methyl phenoxyphenyl compound as a solid (10.3 g, 98%). Cal'd MS for $C_{24}H_{28}NSO_5$ 441.1688, found 442.1697.

Part B: To a solution of 3-methyl phenoxyphenyl compound of part A (10.3 g, 22.0 mmol) in tetrahydrofuran (50 mL) and ethanol (50 mL) was added NaOH (8.9 g, 22.3 mol) and the solution was heated at 65 degrees Celsius for 24 hours. The solution was concentrated in vacuo and the aqueous residue was acidified to pH=3. Vacuum filtration of the resulting precipitate provided the acid as a white solid (9.0 g, 91%). MS cal'd for $C_{22}H_{24}NSO_5$=414.1375. Found =414.1389.

Part C: To a solution of the acid of part B (9.0 g, 19.5 mmol) was added 1-hydroxybenzotriazole (3.24 g, 23.9 mmol), N-methylmorpholine (6.58 mL, 59.9 mmol), O-tetrahydro-2H-pyran-yl-hydroxylamine (3.5 g, 29.9 mmol) followed by 1-3-(dimethylamino)propyl]-3-ethylcarbodimmide hydrochloride (5.35 g, 27.9 mmol). The solution was stirred at ambient temperature for 18 hours. The solution was diluted with $H_2O$ (400 mL) and extracted with ethyl acetate. The organic layer was washed with saturated NaCl and dried over $MGSO_4$. Chromatography (on silica, eluting with 40% ethyl acetate/hexane) provided the desired THP-protected hydroxamate as a solid (6.9 g, 67%). Analytical calculation for $C_{27}H_{33}N_2SO_6$:0.1 $H_2O$: C, 62.92, H, 6.49, N, 5.43, S, 6.23. Found: C, 62.69, H, 6.47, N, 5.57, S, 6.33. Cal'd MS for $C_{27}H_{33}N_2SO_6$: 513.2059. Found 513.2071.

Part D: To a solution of THP-protected hydroxamate of part C (6.4 gm, 12.5 mmol) in dioxane (56 mL) and methanol (19 mL) was added 4 N HCl/dioxane (40 mL). After stirring at ambient temperature for 1 hours, the solution was concentrated in vacuo. Trituration with ethyl ether provided the title compound as a white solid (5.66 g, 97.4%). Cal'd MS for $C_{22}H_{24}N_2SO_5$+1: 429.1484. Found M+1: 429.1493

EXAMPLE 42

Preparation of 4-([4-(1,3-benzodioxol-5-yloxy) phenyl]sulfonyl)-N-hydroxy-1-(methylsulfonyl)-4-piperidinecarboxamide

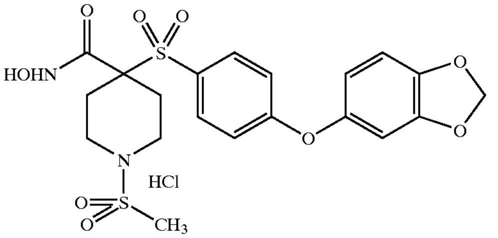

Part A: To a solution of sulfone of part D, Example 32 (25. g, 67.3 mmol) in N,N-dimethylformamide was added potassium carbonate (23.3 g, 0.169 mol) and sesamol (23.2 g, 0.164 mol). The. solution was submerged in an oil bath at 90° C. and stirred for 25 hours. Ethyl acetate was added to the solution, and the organic phase was washed with water, 1N NaOH and water, dried over magnesium sulfate, filtered and concentrated in vacuo. Chromatography on silica, eluting with ethyl acetate/hexane (15/85) provided the ethyl ester compound as an oil (29.3 g, 82%).

Part 8: To a solution of ethyl ester from part A (29.3 gm, 54.93 mmol) in ethanol (60 mL) and tetrahydrofuran (60 mL) was added a solution of NaOH (21.9 g, 0.549 mol) in water 120 mL) and the solution was heated at 65 degrees Celsius for 10 hours. The solution was concentrated in vacuo and the aqueous residue was acidified to pH=3. The solution was extracted with ethyl acetate. The solution was dried over magnesium sulfate, filtered and concentrated in vacuo to give the acid as a yellow foam (25.6 g 92.1%).

Part C: To a solution of the acid of Part B (20.3 g, 40.15 mmol) in ethyl acetate at zero degrees C. was bubbled gas HCl for 20 minutes. The solution stirred at Zero degrees Celsius for 1.5 hours. The precipitate formed was filtered and washed with ether to give the amine hydrochloride as a white solid (16.0 g, 93.5%)

Part D: To a solution of amine hydrochloride of part C (7.5 g, 17.0 mmol) in methylene chloride (200 mL) was added methanesulfonyl chloride (2.0 g, 25.0 mol) and the solution was stirred at ambient temperature for 18 hours. The solution was washed with water and saturated NaCl, dried over magnesium sulfate, concentrated in vacuo to provide the acid as a white solid (6.97 g, 85%).

Part E: To a solution of the acid of part D (7.37 g, 15.0 mmol) was added 1-hydroxybenzotriazole (2.43 g, 18.0 mmol), N-methylmorpholine (4.94 mL, 45.0 mmol), O-tetrahydro-2H-pyran-yl-hydroxylamine (2.65 g, 22.5 mmol) followed by 1-3-(dimethylamino)propyl]-3-ethylcarbodimmide hydrochloride (4.02 g, 21.0 mmol). The solution was stirred at ambient temperature for 18 hours. The solution was diluted with $H_2O$ (400 mL) and extracted with ethyl acetate. The organic layer was washed with saturated NaCl and dried over $MgSO_4$. Chromatography (on silica, eluting with 50% ethyl acetate/hexane) provided the desired THP-protected hydroxamate as a solid (7.54 g, 85%).

Part F: To a solution of THP-protected hydroxamate of part E (6.32 gm, 10.8 mmol) in dioxane (75 mL) and methanol (25 mL) was added 4 N HCl/dioxane (30 mL). After stirring at ambient temperature for 1 hour, the solution was concentrated in vacuo. Trituration with ethyl ether provided the title compound. Chromatography (on silica, 5% methanol/ethyl acetate) provided the hydroxamate as a white solid (4.32 g, 80%) Cal'd MS for $C_{22}H_{22}N_2S_2O_9$+1: 499.0845. Found 499.0848.

EXAMPLE 43

Preparation of 4-[[4-(3,4-Dimethylphenoxyl)phenyl] sulfonyl]-N-hydroxy-1-(2-propynyl)-4-piperidinecarboxamide, Monhydrochloride

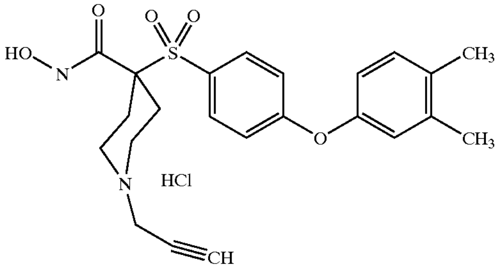

Part A: A mixture of the fluoro compound from part F, Example 9 (2.0 g, 5.66 mmol), 3,4-dimethylphenol (2.0 g, 16.5 mmol), and potassium carbonate (2.3 g, 16.5 mmol) in N,N-dimethylformamide (15 mL) was heated at 90 degrees Celsius overnight (about 18 hours) under an atmosphere of nitrogen. The brown mixture was concentrated in vacuo and purified by chromatography (on silica, ethyl acetate/hexane) to afford the 3,4-dimethylphenoxy phenyl compound as a clear, yellow oil (2.0 g, 79% yield). Analytical calculation for $C_{25}H_{29}NO_5S$: C, 65.91; H, 6.42; N, 3.04; S, 7.04. Found: C, 65.76; H, 6.37; N, 3.03; S, 7.00.

Part B: A solution of the 3,4-dimethylphenoxy phenyl compound of part A (2.0, 4.93 mmol) and potassium hydroxide (1.7 g, 29.7 mmol) in a mixture of ethanol (25 mL) and water (4 mL) was stirred at reflux for four hours under a nitrogen atmosphere. The solution was cooled with an ice bath, subsequently acidified with concentrated hydrochloric acid, and concentrated to a crude residue. The crude residue, O-tetrahydo-2H-pyran-2-yl-hydroxylamine (0.88 g, 7.50 mmol), triethylamine (0.81 mL, 5.81 mmol), and 1-(3-dimethylaminopropyl)-3-ethylcarbodiimide hydrochloride in acetonitrile (24 mL) was stirred at ambient temperature overnight. The mixture was diluted with water and extracted with ethyl acetate. The organic layer was washed with water, a saturated sodium bicarbonate solution, water, and a saturated salt solution. After drying over magnesium sulfate, the filtrate, as the THP-protected hydroxamate, was concentrated to a yellow foam.

Part C: The THP-protected hydroxamate (920 mg, 1.75 mmol) of part B was dissolved in methanol (16 mL). Acetyl chloride (0.37 mL, 5.3 mmol) was added. After three hours, concentration followed by reverse phase HPLC afforded the title compound as a white solid (611 mg, 79%). MS (EI) $MH^+$ calculated for $C_{23}H_{26}N_2O_5S$: 443, found 443.

EXAMPLE 44

Preparation of 4-[[4-(4-chlorophenyl)thiolphenyl] sulfonyl]-1-(propynyl)-4-piperidinecarboxylic Acid, Monohydrochloride and 4-[[4-(4-chlorophenyl) thiolphenyl]sulfonyl]-N-hydroxy-l-(propynyl)-4-piperidinecarboxamide, Monohydrochloride

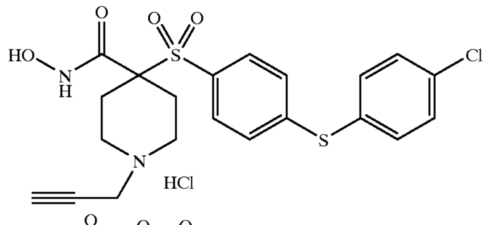

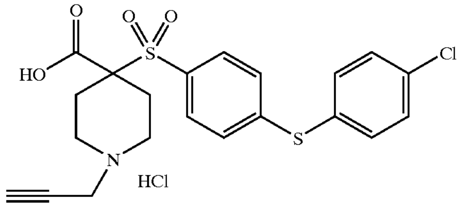

Part A: A mixture of the fluoro compound from part F, Example 9 (2.0 g, 5.66 mmol), 4-chlorothiophenol (1.0 g, 6.94 mmol), and potassium carbonate (1.1 g, 8.00 mmol) in N,N-dimethylformamide (12 mL) was stirred overnight (about 18 hours) under an atmosphere of nitrogen at ambient temperature. The mixture was concentrated in vacuo. The residue was diluted with water and extracted with ethyl acetate. The organic layer was washed with water and a saturated salt solution, dried over magnesium sulfate, and concentrated in vacuo to a yellow oil. The oil was purified by chromatography (on silica, ethyl acetate/hexane) to afford the 4-chlorophenylthiolphenyl compound as a white solid (2.0 g, 75% yield). Analytical calculation for $C_{23}H_{24}NO_4S_2C_1$: C, 57.791; H, 5.06; N, 2.93; S, 13.42; Cl, 7.42. Found: C, 57.57; H, 5.11; N, 2.94; S, 13.19; Cl, 7.73.

Part B: The chorophenylthiophenyl compound from part A (2.04 g, 4.27 mmol) was diluted with ethanol (30 mL) and water (5mL). Potassium hydroxide (1.55 g, 27.7 mmol) was added, and the mixture was heated at reflux for 3 hours. After complete reaction, the solution was cooled and was acidified to pH=1–3 with concentrated HCl. The solvent was removed by rotary evaporation and the residue was azeotroped to dryness by repeated addition of acetonitrile. The acid hydrochloride was further dried on a vacuum line, then carried as is through the coupling reaction. The saponification was presumed to be quantitative.

Part C: The carboxylic acid hydrochloride from the previous step (4.27 mmol) was suspended in acetonitrile (20 mL). N-Methylmorpholine (about 1.0 mL) was added, followed by O-tetrahydro-2H-pyran-2-yl-hydroxylamine (585 mg, 5 mmol). After 5 minutes, 1-[3-(dimethylamino) propyl]-3-ethylcarbodiimide hydrochloride (EDC; 955 mg, 5 mmol) was added. The mixture was stirred overnight (about 18 hours), then solvent was removed by rotary evaporation, the residue was diluted with half-saturated $NaHCO_3$ solution (50 mL), and the product was extracted into ethyl acetate (2×100 mL). In this example, an intractable emulsion complicated compound recovery. The combined organic layers were dried over $MgSO_4$, filtered through silica, concentrated, and subjected to chromatography (flash silica, ethyl acetate/hexane) affording, on concentration, the title O-THP-protected hydroxamate (162 mg, 7%, from ester) as a foam. MS (EI) $MH^+$ calculated for $C_{21}H_{22}N_2O_4S_2Cl$: 450, found 450. Because mass recovery was poor, the silica filter cake was extracted with 1:1 methanol:ethyl actetate affording 4-[[4-(4-chlorophenyl) thiolphenyl]sulfonyl]-1-(propynyl)-4-piperidinecarboxylic acid, monohydrochloride (540 mg, 26%).

Part D: The O-THP-protected hydroxamate of part C (441 mg, 0.80 mmol) was dissolved in methanol (2 mL). Acetyl chloride (0.2 mL, 3 mmol) was added. After three hours, concentration followed by reverse phase HPLC afforded the title hydroxamate compound as a pink solid (162 mg, 44%). MS (EI) $MH^+$ calculated for $C_{21}H_{22}N_2O_4S_2$: 465, found 465.

EXAMPLE 45

Preparation of 4-[[4-(Cyclopentylthio)-phenyl] sulfonyl]-N-hydroxy-1-(2-propynyl)-4-piperidinecarboxamide, Monohydrochloride

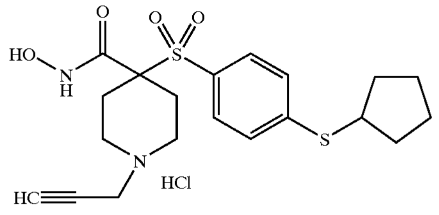

Part A: The propargyl amine of part F, Example 9 (3.05 g, 8.5 mmol) was combined with $K_2CO_3$ (1.38 g, 10 mmol), N,N-dimethylformamide (6 mL) and cyclopentyl mercaptan (1.02 mL, 10 mmol). The mixture was heated to 80 degrees Celsius for 4 hours and 95 degrees Celsius for 2.5 hours, monitoring by TLC. Aqueous workup was accomplished using water (10 mL) and ethyl acetate (2×100 mL). The combined organic layers were dried over magnesium sulfate, concentrated, and chromatographed (flash silica; ethyl acetate/hexane eluant) affording the cyclopentylmercaptyl compound as an oil (3.2 g, 86%).

Part 3: The cyclopentylmercaptyl compound from part A (3.12 g 7.13 mmol) was diluted with ethanol (50 mL) and water (8 mL). Potassium hydroxide (2.59 g, 46.3 mmol) was added, and the mixture was heated at reflux for 3.5 hours. After complete reaction, the solution was cooled and was acidified to pH=1–3 with concentrated HCl. The solvent was removed by rotary evaporation and the residue was azeotroped to dryness by repeated addition of acetonitrile. The carboxylic acid hydrochloride was further dried on a vacuum line, then carried as is through the coupling reaction. The saponification was presumed to be quantitative.

Part C: The carboxylic acid hydrochloride from Part B (7.13 mmol) was suspended in acetonitrile (50 mL). N-Methylmorpholine (ca. 2.0 mL) was added, followed by O-tetrahydro-2H-pyran-2-yl-hydroxylamine (1.05 g, 9 mmol). After 5 minutes, EDC (1.72 g, 9 mmol) was added. The mixture was stirred overnight (about 18 hours), then solvent was removed by rotary evaporation. The residue was diluted with half-saturated $NaHCO_3$ solution (50 mL), and the product was extracted into ethyl acetate (2×100 mL). The combined organic layers were dried over $MgSO_4$, filtered through silica, concentrated, and subjected to chromatography (flash silica, ethyl acetate/hexane) affording, on concentration, the O-THP-protected hydroxamate (2.0 g, 51%, from ester) as a foam.

Part D: The O-THP-protected hydroxamate from Part D (2.00 g, 3.95 mmol) was dissolved in methanol (16 mL). Acetyl chloride (0.86 mL, 12 mmol) was added over 2 minutes. The reaction was stirred at ambient temperature for 4 hours, then concentrated, with repeated addition of chloroform and acetonitrile to effect drying. The title compound precipitated as a white solid (1.77 g, 98%). MS (EI) $MH^+$ calculated for $C_{20}H_{26}N_2O_4S_2$: 422, found 422.

EXAMPLE 47

Preparation of N-hydroxy-4-[[4-(phenylthio)phenyl] sulfonyl]-1-(2-propynyl)-4-piperidinecarboxamide, 1-oxide and N-hydroxy-4-[[4-(phenylsulfinyl)-phenyl]sulfonyl-1-(2-propynyl)-4-piperidinecarboxamide

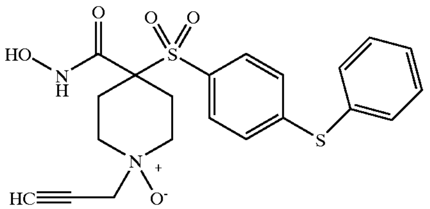

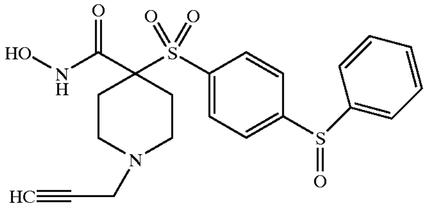

m-Chloroperbenzoic acid (57–86%, 120 mg) was added to a solution of N-hydroxy-4-([4-(phenylthio)phenyl]-sulfonyl]-1-(2-propynyl)-4-piperidinecarboxamide (title compound, Example 9)(215 mg, 0.5 mmol) in methanol (5 mL) at zero degrees Celsius. The reaction was permitted to warm slowly to ambient temperature and after 16 hours, the mixture was passed through a micron filter and concentrated. Reverse phase HPLC (Delta Pak 50×300 mm; 15 micron $C_{18}$ 100 Angstrom; 30 minute gradient method starting with dilute HCl (0.5 mL/4 L): acetonitrile 80:20, ending with 50:50) separated 5 major components. The first and second peaks off the column afforded, upon concentration, 14 (6%) and 16 mg (7%) of two compounds, which were assigned as diastereomers of N-Hydroxy-4-[[4-(phenylsulfinyl)-phenyl]sulfonyl-1-(2-propynyl)-4-piperidinecarboxamide on the basis of their NMR spectra. The third peak was unidentified. The 4th peak was assigned by NMR as N-hydroxy-4-[[4-(phenylthio)phenyl]sulfonyl]-1-(2-propynyl)-4-piperidinecarboxamide, 1-oxide (147 mg, 66%) MS (EI) $MH^+$ calculated for $C_{21}H_{22}N_2O_5S_2$: 447, found 447. The last peak contained 73 mg of recovered 3-chlorobenzoic acid.

EXAMPLE 48

Preparation of N-hydroxy-2,2-dimethyl-5-[(4-phenoxyphenyl)sulfonyl]-1,3-dioxane-4-carboxamide

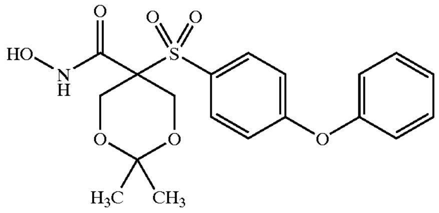

Part A: A fresh sodium methoxide solution was prepared by slowly adding hexane-washed sodium spheres (9.4 g, 410 mmol) to methanol (1.0 L) at zero degrees Celcius. To this cooled solution was added the 4-fluorothiophenol (50.0 g, 390 mmol) followed by methyl 2-chloro acetate (42.3 g, 390 mmol). After warming to ambient temperature the reaction was stirred overnight (about 18 hours). The methanol was removed in vacuo and the residue was taken up in ethyl acetate (300 mL). The organic layer was washed with water (2×-200 mL) and dried over $MgSO_4$. Concentrating afforded the methyl ester sulfide product as a clear oil (71.8 g, 92%).

Part B: To a solution of the methyl ester sulfide product of part A (71.8 g, 358 mmol) in 70% methanol/$H_2O$ (1.0 L) was slowly added Oxone™ (660 g, 1.08 mol). The mixture stirred overnight (about 18 hours) at ambient temperature. The excess Oxone™ was filtered off and the methanol was removed from the filtrate in vacuo. The remaining aqueous solution was extracted with ethyl acetate (3×300 mL). The organic layers were washed with water (2×-300 mL) and dried over $MgSO_4$. Concentrating afforded the sulfone product as a tan oil (82 g, 98%).

Part C: To a prepared slurry of potassium bicarbonate (1.0 g, 9.8 mmol) in 37% formaldehyde solution was added the sulfone product of part B (28.6 g, 123 mmol). The reaction was stirred for one hour and then a saturated solution of sodium sulfate (20 mL) was added. After stirring for thirty minutes, the mixture was extracted with diethyl ether (4×-100 mn). The organic layers were dried over $MgSO_4$. Chromatography (on silica, ethyl acetate/hexane) provided the sulfone diol product as a clear oil (15.3 g, 42%).

Part D: The sulfone diol product of Part C (1.3 g, 4.5 mmol) was dissolved in acetone (40 mL) along with 2,2-dimethoxypropane (1.1 mL, 9.0 mmol) and p-toluenesulfonic acid monohydrate (0.03 mg, 0.14 mmol) and the resulting composition was refluxed for 30 6 hours. After cooling, the mixture was neutralized with solid $Na_2CO_3$ (pH-7), filtered, and concentrated. The residue was dissolved in chloroform (50 mL) and washed with water (2×-30 mL). Drying over $MgSO_4$ and concentrating gave the dimethyl ketal product as an opaque oil (1.4 g, 94%).

Part E: Phenol (0.6 g, 6.3 mmol) and cesium carbonate (2.0 g, 6.3 mmol) were added to a solution of the dimethyl ketal product (1.4 g, 4.2 mmol) of part D in N,N-dimethylformamide (20 mL ). The mixture was heated at 90 degrees Celsius for five hours, diluted with water (20 mL), and extracted with ethyl acetate (4×-100 mL). The organic layers were washed with brine (1×-100 mL) and water (1×-100 mL). Concentrating afforded the phenol-O-phenol dimethyl ketal as a dark brown oil (1.51 g, 88%).

Part F: To a solution of the phenol-O-phenol dimethyl ketal product (1.5 g, 3.4 mmol) of part E in tetrahydrofuran (10 mL) was added an aqueous lithium hydroxide solution (0.34 g, 14.8 mmol, in 5 mL of $H_2O$). The reaction was stirred for two hours and then was diluted with water (15 mL) and acidified via 30% $HCl_{aq}$ to pH=3. The acidic solution was extracted with diethyl ether (3×-100 mL). Drying over $MgSO_4$ and concentrating afforded the carboxylic acid product as a brown oil (1.5 g, quantitative yield).

Part G: To a solution of the carboxylic acid product of Part F (1.3 g, 3.3 mmol) and N-hydroxybenzotriazole hydrate (0.54 g, 4.0 mmol) in DMF (15 mL) was added 4-methylmorpholine (1.67 g, 16.5 mmol), O-tetrahrdro-2H-pyran-2-yl-hydroxylamine (1.2 g, 10.2 mmol), and EDC (0.88 g, 4.6 mmol), respectively. After stirring overnight, the DMF was removed in vacuo and the residue was taken up in ethyl acetate/water (1:1, 50 mL). The organic layer was washed with brine (1×-20 mL) and water (1×-20 mL) and dried over $MgSO_4$. Chromatography (on silica, ethyl acetate/hexane) provided the THP-protected hydroxylamine product as a white solid (0.36 g, 22%) as well as the decarboxylated by-product (0.27 g, 24%).

Part H: To a solution of the THP-protected hydroxylamine product of Part G (0.36 g, 0.73 mmol) in dioxane (3 mL) and methanol (1 mL) was added 4 N HCl in dioxane (2 mL). The reaction was stirred for five minutes and then the solvents were removed in vacuo. Chromatography (reverse phase C-18, acetonitrile/water) gave the title compound as a white solid (0.13 g, 44%). MS (FAB) $M^+H$ calculated for $C_{19}H_{21}NO_7S$: 408, found 408.

EXAMPLE 49

Preparation of tetrahydro-N-hydroxy-4-[[4-(phenylthio)phenyl]sulfonyl]-2H-thiopyran-4-carboxamide

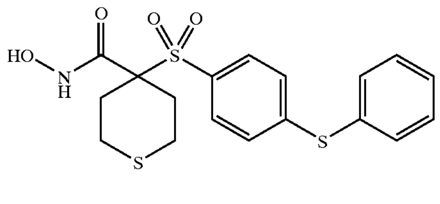

Part A: To a solution of methyl 2-chloroacetate (322 g, 2.96 mol) in N,N-dimethylacetamide(1.0 L) were added thiophenol (400 g, 3.12 mol) and potassium carbonate (408 g, 2.96 mol). The reaction was stirred at ambient temperature overnight (about 18 hours). After diluting with a minimal amount of water (800 mL), the mixture was extracted with ethyl acetate (4×-1 L). The organic layers were washed with water (1×-800 mL), dried over $MgSO_4$, and concentrated to afford the sulfide product as a clear oil (614 g, quantitative yield).

Part B: To a solution of the sulfide from part A (75.85 g, 0.38 mol) in methanol (1000 mL) was added water (100 mL) and Oxone® (720 g, 1.17 mol) at twenty degrees Celsius. An exotherm to 67 degrees Celsius was noted. After two hours, the reaction was filtered and the cake washed well with methanol. The filtrate was concentrated in vacuo. The residue was taken up in ethyl acetate and washed with brine, dried over $MgSO_4$, filtered, and concentrated in vacuo to give the sulfone as a crystalline solid (82.74 g, 94%).

Part C: To a solution of the sulfone of part B (60.0 g, 258 mmol) in DMA (350 mL) was added the dibromoethylthioether (76.9 g, 310 mmol), followed by potassium carbonate (78.3 g, 568 mmol). The mixture was stirred five minutes before adding catalytic amounts of 4-dimethylaminopyridine and tetrabutylammonium bromide. The reaction was stirred overnight (about 18 hours), after which it was poured into a stirring solution of 10% $HCl_{aq}$ (2.5 L). The resulting precipitate was filtered and washed with hexane to remove the excess thioether. Drying in vacuo overnight (about 18 hours) yielded the methylester thiopyran —Ph-p-F as a yellow powder (76.1 g, 93%).

Step D: To a solution of the methylester thiopyran —Ph-p-F of part C (4.0 g, 12.6 mmol) in N,N-dimethylacetamide (25 mL) were added cesium carbonate (6.1 g, 18.9 mmol) and thiophenol (2.1 g, 18.9 mmol). The mixture was stirred 2 hours at 90 degrees Celsius. The mixture was diluted with water (30 mL) and extracted with ethyl acetate (3×-100 mL). The organic layers were washed with brine (1×-75 mL) and water (1×-75 mL) and was then dried over $MgSO_4$. Chromatography (on silica, ethyl acetate/hexane) provided the phenyl-S-phenyl methyl ester as a yellowish solid (3.6 g, 71%).

Step E: Potassium trimethylsilonate (1.24 g, 9.7 mmol) was added to a solution of the phenyl-S-phenyl methyl ester of part D (3.6 g, 8.8 mmol) in tetrahydrofuran (15 mL). The mixture was stirred 2–3 hours at ambient temperature or until a solid precipitate developed. After the hydrolysis was complete, N-methylmorpholine (2.9 mL, 26.4 mmol) was added followed by PyBrop (4.9 g, 10.6 mmol). The solution was stirred for 10 minutes. Aqueous hydroxylamine (0.32 g, 9.7 mmol) was added and the mixture stirred for an additional 2 hours. After completion, the solvent was removed in vacuo. Chromatography (reverse phase C-18, acetonitrile/water) of the residue provided the title compound as an off white solid (0.82 g, 23%). MS (FAB) $M^+H$ calculated for $C_{18}H_{19}NO_4S_3$: 410, found 410.

EXAMPLE 50

Preparation of 4-[(4-fluorophenyl)-sulfonyl] tetrahydro-N-[(tetrahydro-2H-pyran-2-yl)oxy]-2H-thiopyran-4-carboxamide

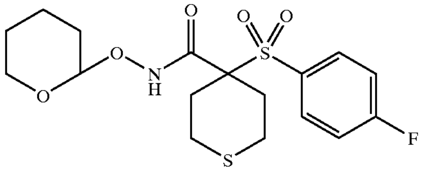

Part A: Thiophenol (400 g, 3.12 mol) and potassium carbonate (408 g, 2.96 mol) were added to a solution of methyl 2-chloroacetate (322 g, 2.96 mol) in N,N-dimethylacetamide (1.0 L). The reaction was stirred at ambient temperature overnight (about 18 hours). After diluting with a minimal amount of water (800 mL), the mixture was extracted with ethyl acetate (4×-1 L). The organic layers were washed with water (1×-800 mL), dried over $MgSO_4$, and concentrated to afford the sulfide product as a clear oil (614 g, quantitative yield).

Part B: To a solution of the sulfide from part A (75.85 g, 0.38 mol) in methanol (1000 mL) was added water (100 mL) and Oxone® (720 g, 1.17 mol) at 20 degrees Celsius. An exotherm to 67 degrees Celsius was noted. After two hours, the reaction was filtered and the cake was washed well with methanol. The filtrate was concentrated in vacuo. The residue was taken up in ethyl acetate and washed with brine, dried over $MGSO_4$, filtered, and concentrated in vacuo to give the methyl ester sulfone as a crystalline solid (82.74 g, 94%).

Part C: To a solution of the methyl ester sulfone product of part B (60.0 g, 258 mmol) in N,N-dimethylacetamide (350 mL) was added 2,2-dibromoethylthioether (76.9 g, 310 mmol) followed by potassium carbonate (78.3 g, 568 mmol). The mixture was stirred five minutes before adding catalytic amounts of 4-dimethylaminopyridine and tetrabutylammonium bromide. The reaction was stirred overnight (about 18 hours), after which it was poured into a stirring solution of 10% $HCl_{aq}$ (2.5 L). The resulting precipitate was filtered and washed with hexane to remove the excess thioether. Drying in vacuo overnight (about 18 hours) yielded the thiopyran methyl ester as a yellow powder (76.1 g, 93%).

Step D: To a solution of the thiopyran methyl ester of part C (30.0 g, 94 mmol) in tetrahydrofuran (250 mL) was added potassium trimethylsilonate (28.9 g, 226 mmol). The mixture was stirred 2–3 hours at ambient temperature or until a solid precipitate developed. After the hydrolysis was complete, the solvent was removed in vacuo. Water (200 mL) was added and the mixture was washed with diethyl ether (1×-200 mL). The aqueous layer was cooled to zero degrees Celsius and 10% $HCl_{aq}$ was slowly added until a precipitate formed. The solid was collected and dried in vacuo with phosphorous pentoxide to afford the thiopyran carboxylic acid as a yellow solid (17.8 g, 62%).

Part E: To a solution of the thiopyran carboxylic acid of part D (17.8 g, 58.5 mmol) in N,N-dimethylformamide (100 mL) was added N-methylmorpholine (19.3 mL, 176 mmol) followed by N-hydroxybenzotriazole hydrate(9.5 g, 70.2 mmol), O-tetrahydro-2H-pyran-2-yl-hydroxylamine (10.3 g, 87.8 mmol), and 1-(3-dimethylaminopropyl)-3-ethylcarbodiimide hydrochloride (16.8 g, 87.8 mmol). The mixture was stirred three hours and was then diluted with water (100 mL). The mixture was extracted with ethyl acetate (4×-200 mL). Organic layers were washed with an aqueous saturated potassium carbonate solution (1×-200 mL), 1% $HCl_{aq}$, and brine (1×-200 mL). Drying over $MgSO_4$ and concentrating in vacuo afforded the title compound as an off white solid (30.8 g, quantitative yield). MS (FAB) $M^+H$ calculated for $C_{17}H_{22}FNO_5S_2$: 404, found 404.

EXAMPLE 51

Preparation of Tetrahydro-N-hydroxy-4-[[4-[(4-methoxypheny)thiolphenyl]sulfonyl]-2H-thionyran-4-carboxamide

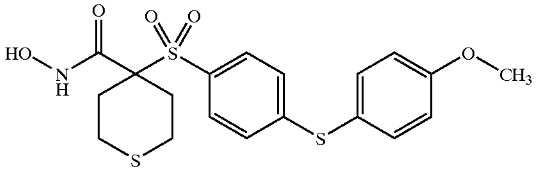

Part A: To a solution of the title compound of Example 50 (6.0 g, 14.9 mmol) in N,N-dimethylacetamide (25 mL) was added 4-methoxy thiophenol (2.5 g, 17.8 mL), followed by potassium carbonate (6.2 g, 44.7 mmol). The reaction was heated at 60 degrees Celsius for three hours. The reaction mixture was diluted with water (25 mL) and extracted with ethyl acetate (4×-100 mL). The organic layers were washed with water (2×-50 mL) and dried over $MgSO_4$. Concentrating in vacuo provided the THP-protected-Phenyl-S-pPhenyl-OMe product as a yellowish solid (9.2 g, quantitative yield).

Part B: To a solution of the THP-protected-Phenyl-S-pPhenyl-OMe product from part A (9.2 g, 14.9 mmol) in dioxane was slowly added 4N HCl in dioxane (10 mL). After stirring overnight (about 18 hours), the solvent was removed. Chromatography on the resultant residue (reverse phase C-18, acetonitrile/water) gave the title compound as a white solid (1.84 g, 28.3%). MS (FAB) $M^+H$ calculated for $C_{19}H_{21}NO_5S_3$: 440, found 440.

EXAMPLE 52

Preparation of Tetrahydro-N-hydroxy-4-[(4-phenylthio)phenyl]sulfonyl]-2H-thiopyran-4-carboxamide 1,1-dioxide

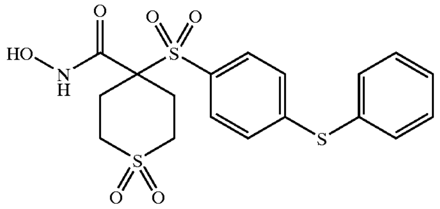

Part A: To a solution of the title compound of Example 50 (13.0 g, 24.5 mmol) in methylene chloride(100 mL) cooled to zero degrees Celsius was slowly added 50–60% m-chloroperbenzoic acid (17.1 g, 49.5 mmol). The mixture was stirred one hour at zero degrees Celsius followed by an additional 3 hours as the temperature rose to ambient conditions. Water (200 mL) was added and the mixture was neutralized with 10% ammonium hydroxide (100 mL). The organic layer was washed with water (1×-200 mL) and dried over $MgSO_4$. Concentrating in vacuo provided an orangish oil (3.5 g, 33%). The water/10% ammonium hydroxide solution was saturated with sodium chloride and extracted with ethyl acetate (2×-400 mL). Organic layer was dried over $MgSO_4$ and concentrated to afford the THP-protected sulfone-thiopyran-p-F compound as an orange foam (6.1 g, 57%).

Part B: To a solution of the THP-protected sulfone-thiopyran-p-F from Part A (9.6 g, 22 mmol) in N,N-diemthylacetamide (120 mL) was added thiophenol (2.9 g, 26.4 mL), followed by potassium carbonate (9.1 g, 66 mmol). The reaction was heated at 60 degrees Celsius for four hours. The reaction mixture was diluted with water (25 mL) and extracted with ethyl acetate (4×-100 mL). The organic layers were washed with water (2×-50 mL) and dried over $MgSO_4$. Chromatography (on silica, ethyl acetate/hexane) provided the THP-protected-phenyl-S-phenyl product as an orange oil (5.1 g, 43%).

Part C: To a solution of the THP-protected-phenyl-S-phenyl product from part B (5.1 g, 9.4 mmol) in dioxane was slowly added 4N HCl in dioxane (10 mL). After stirring overnight (about 18 hours), the solvent was removed. Chromatography of the resultant residue (reverse phase C-18, acetonitrile/water) gave the title compound as a pink solid (1.2 g, 29%). MS (FAB) $M^+H$ calculated for $C_{18}H_{19}NO_6S_3$: 442, found 442.

EXAMPLE 53

Preparation of Tetrahydro-N-hydroxy-4-[[4-[4-(1H-1,2,4-triazol-1-yl) phenoxy]-phenyl]-sulfonyl]-2H-thiopyran-4-carboxamide 1,1-dioxide, Monohydrochloride

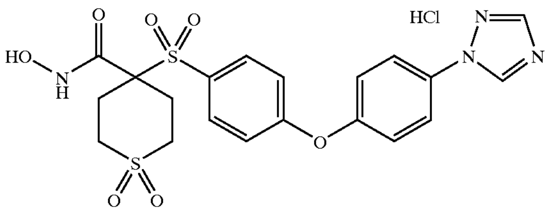

Part A: To a solution of the title compound of Example 50 (13.0 g, 24.5 mmol) in methylene chloride (100 mL) cooled to zero degrees Celsius was slowly added 50–60% m-chloroperbenzoic acid (17.1 g, 49.5 mmol). The mixture was stirred one hour at zero degrees Celsius followed by an additional 3 hours as the temperature rose to ambient conditions. Water (200 mL) was added and the mixture was neutralized with 10% ammonium hydroxide (100 mL). The organic layer was washed with water (1×-200 mL) and dried over $MgSO_4$. Concentrating in vacuo provided an orangish oil (3.5 g, 33%). The water/10% ammonium hydroxide solution was saturated with sodium chloride and extracted with ethyl acetate (2×-400 mL). Organic layer was dried over $MgSO_4$ and concentrated to afford the THP-protected sulfone-thiopyran-p-F as an orange foam (6.1 g, 57%).

Part B: To a solution of the THP-protected sulfone-thiopyran-p-F from A (6.0 g, 13.8 mmol) in N,N-dimethylformamide (25 mL) was added 4-(1H-1,2,4-triazol-1-yl)phenol (4.4 g, 27.5 mmol), followed by cesium carbonate (13.4 g, 41.4 mmol). The reaction was heated at 95 degrees Celsius for five hours. The reaction mixture was diluted with water (25 mL) and extracted with ethyl acetate (4×-100 mL). The organic layers were washed with water (2×-50 mL) and dried over $MgSO_4$. Concentrating afforded the THP-protected phenyl-O-phenyl triazole product as a tan solid (9.7 g, quantitative yield).

Part C: To a solution of the crude THP-protected phenyl-O-phenyl triazole product from B (8.0 g, 13.8 mmol) in acetonitrile (40 mL) was slowly added 10% $HCl_{aq}$ (100 mL). After stirring overnight (about 18 hours), the acetonitrile was removed. The resultant precipitate was collected, giving the title compound as a tan solid (1.3 g, 18%). MS (FAB) $M^+H$ calculated for $C_{20}H_{21}ClN_4O_7S_2$: 493, found 493.

EXAMPLE 54

Preparation of 4-[[4-[4-(2-aminoethyl))-phenoxy] phenyl]sulfonyl]tetrahydro-N-hydroxy-2H-thiopyran-4-carboxamide 1,1-dioxide Monohydrochloride

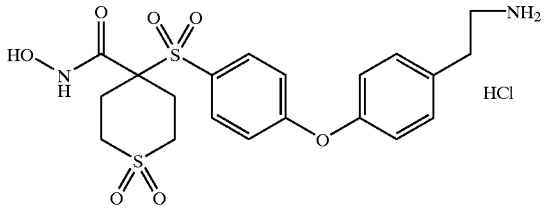

Part A: To a solution of the title compound of Example 50 (13.0 g, 24.5 mmol) in methylene chloride (100 mL) cooled to zero degrees Celsius was slowly added 50–60% m-chloroperbenzoic acid (17.1 g, 49.5 mmol). The mixture was stirred one hour at zero degrees Celsius followed by an additional 3 hours as the temperature rose to ambient conditions. Water (200 mL) was added and the mixture was neutralized with 10% ammonium hydroxide (100 mL). The organic layer was washed with water (1×-200 mL) and dried over $MGSO_4$. Concentrating in vacuo provided an orangish oil (3.5 g, 33%). The water/10% ammonium hydroxide solution was saturated with sodium chloride and extracted with ethyl acetate (2×-400 mL). The organic layer was dried over $MgSO_4$ and concentrated to afford the THP-protected sulfone-thiopyran-p-F as an orange foam (6.1 g, 57%).

Part D: To a solution of the THP-protected sulfone-thiopyran-p-F from A (6.0 g, 13.8 mmol) in N,N-dimethylacetamide (25 mL) was added tyramine (3.8 g, 28 mmol) followed by cesium carbonate (13.6 g, 42 mmol). The reaction was heated at 95 degrees Celsius for five hours. Removing the N,N-dimethylacetamide in vacuo afforded a brown solid (20 g). Chromatography (reverse phase, C-18, acetonitrile/water) gave the THP-protected tyramine product as a tan oil (1.0 g, 13%).

Part C: To a solution of the crude THP-protected tyramine product from part B (1.0 g, 1.8 mmol) in acetonitrile (40 mL) was slowly added 10% HClaq (100 mL). After stirring overnight (about 18 hours), the acetonitrile was removed. The resultant precipitate was collected, giving the title compound as a tan solid (0.9 g, 99%). MS (FAB) $M^+H$ calculated for $C_{20}H_{25}ClN_2O_7S_2$: 469, found 469.

EXAMPLE 55

Preparation of 4-[(4-fluorophenyl)-sulfonyl] tetrahydro-N-[(tetrahydro-2H-pyran-2-yl)oxy]-2H-pyran-4-carboxamide

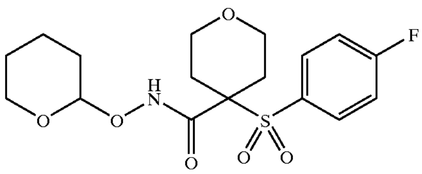

Part A: In dry equipment under nitrogen, sodium metal (8.97 g, 0.39 mol) was added to methanol (1000 mL) at two degrees Celsius. The reaction was stirred at ambient temperature for forty five minutes at which time the sodium had dissolved. The solution was chilled to five degrees Celsius and p-fluorothiophenol (41.55 mL, 0.39 mmol) was added, followed by methyl 2-chloroacetate (34.2 mL, 0.39 mol). The reaction was stirred at ambient temperature for four hours, filtered, and concentrated in vacuo to give the sulfide as a clear colorless oil (75.85 g, 97%).

Part B: To a solution of the sulfide from part A (75.85 g, 0.38 mol) in methanol (1000 mL) were added water (100 mL) and Oxone® (720 g, 1.17 mol) at 20 degrees Celsius. An exotherm to 67 degrees Celsius was noted. After two hours, the reaction was filtered and the cake was washed well with methanol. The filtrate was concentrated in vacuo. The residue was taken up in ethyl acetate and washed with brine, dried over $MgSO_4$, filtered, and concentrated in vacuo to give the sulfone as a crystalline solid (82.74 g, 94%).

Part C: To a solution of the sulfone from part B (28.5 g, 0.123 mol) in N,N-dimethylacetamide (200 mL) were added potassium carbonate (37.3 g, 0.27 mol), bis-(2-bromoethyl) ether (19.3 mL, 0.147 mol), 4-dimethylaminopyridine (0.75 g, 6 mmol), and tetrabutylammonium bromide (1.98 g, 6 mmol). The reaction was stirred overnight (about 18 hours) at ambient temperature. The reaction was slowly poured into 1N HCl (300 mL), the resultant solid filtered and the cake washed well with hexanes. The solid was recrystallized from ethyl acetate/hexanes to give the pyran compound as a beige solid (28.74 g, 77%). MS (ES+) MH+ calculated for $C_{13}H_{15}O_5S_1F_1$: 303, found 303.

Part D: In dry equipment under nitrogen, the pyran compound from part C (8.0 g, 26.5 mmol) was dissolved in dry tetrahydrofuran (250 mL) and a solution of potassium trimethylsilonate (10.2 g, 79.5 mmol) in dry tetrahydrofuran (15 mL) was added at ambient temperature. After ninety minutes, water (100 mL) was added and the solution concentrated in vacuo. The residue was taken up in water and extracted with ethyl acetate to remove unreacted starting material. The aqueous solution was treated with 6N HCl until pH=1. The slurry was extracted with ethyl acetate and the combined extracts washed with water, dried over $Na_2SO_4$, filtered, and concentrated in vacuo. The residue was heated in diethyl ether, the solid filtered and dried to give the carboxylic acid as a crystalline solid (5.78 g, 76%). HRMS (ES−) M−H calculated for $C_{12}H_{13}O_5\ S_1F_1$: 287.04, found 287.04.

Part E: In dry equipment under nitrogen, the carboxylic acid from part D (9.1 g, 31.6 mmol) was dissolved in dry N,N-dimethylformamide (70 mL) and the remaining reagents were added to the solution in the following order: N-hydroxybenzotriazole hydrate (5.1 g, 37.9 mmol), N-methylmorpholine (10.4 mL, 94.8 mmol), O-tetrahydro-2H-pyran-2-yl-hydroxylamine (11.5 g, 98 mmol), and 1-(3-dimethylaminopropyl)-3-ethylcarbodiimide hydrochloride (8.48 g, 44.2 mmol). After three hours at ambient temperature, the reaction was concentrated in vacuo. The residue was taken up in ethyl acetate, washed with water, 5% $KHSO_4$, saturated $NaHCO_3$, brine, dried over $Na_2SO_4$, filtered, and concentrated in vacuo. Chromatography (on silica, ethyl acetate/hexanes) provided the title compound as a crystalline solid (9.7 g, 80%). HRMS (ES+) MH+ calculated for $C_{17}H_{22}NO_6\ S_1F_1$: 388.12, found 388.12.

EXAMPLE 56

Preparation of 4-[[4-(3,4-difluorophenoxy)-phenyl]sulfonyl]tetrahydro-N-hydroxy-2H-pyran-4-carboxamide

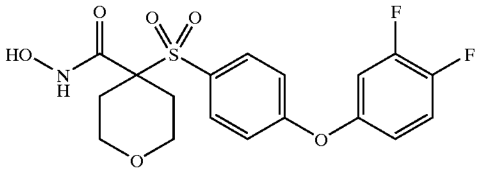

Part A: To a solution of the title compound of Example 55 (2.0 g, 5.2 mmol) in N,N-dimethylacetamide (6 mL) was added 3,4-difluorophenol (1.0 g, 7.7 mmol), followed by cesium carbonate (6.6 g, 20.2 mmol). The reaction was heated at 95 degrees Celsius for five hours. Removing the N,N-dimethylacetamide in vacuo afforded a brown solid (8.3 g, quantitative). Chromatography (reverse phase, C-18, acetonitrile/water) gave the THP-protected difluoro product in solution.

Part B: To the collected THP-protected difluoro product from A in acetonitrile/ water (50 mL) was slowly added 10% $HCl_{aq}$ (100 mL). After stirring overnight (about 18 hours), the acetonitrile was removed. The resultant precipitate was collected, giving the title compound as a white solid (1.02 g, 48.6%). MS (FAB) $M^+H$ calculated for $C_{18}H_{17}FNO_6S$: 414, found 414.

EXAMPLE 57

Prepartion of Tetrahydro-N-hydroxy-4-[[4-(4-iodophenoxy) phenyl]sulfonyl]-2H-pyran-4-carboxamide

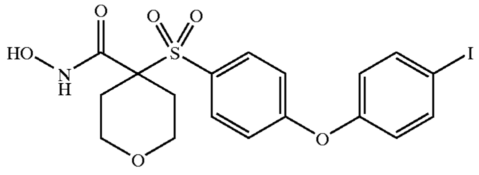

Part A: To a solution of the title compound of Example 55 (2.0 g, 5.2 mmol) in N,N-dimethylacetamide (6 mL) was added 4-iodophenol (1.7 g, 7.8 mmol), followed by cesium carbonate (6.6 g, 20.2 mmol). The reaction was heated at 95 degrees Celsius for five hours. Removing the N,N-dimethylacetamide in vacuo afforded a brown solid (5.7 g, quantitative) Chromatography (reverse phase, C-18, acetonitrile/water) gave the THP-protected iodo product in solution.

Part B: To the solution of the crude THP-protected iodo product from A in acetonitrile/water (40 mL) was slowly added 10% $HCl_{aq}$ (100 mL). After stirring overnight (about 18 hours), the acetonitrile was removed. The resultant precipitate was collected, giving the title compound as a white solid (2.6 g, 99%). MS (FAB) $M^+H$ calculated for $C_{18}H_{18}INO_6S$: 504, found 504.

EXAMPLE 58

Preparation of Tetrahydro-N-hydroxy-4-[[4-(2,4,5-trifluorophenoxy)phenyl)-sulfonyl]-2H-pyran-4-carboxamide

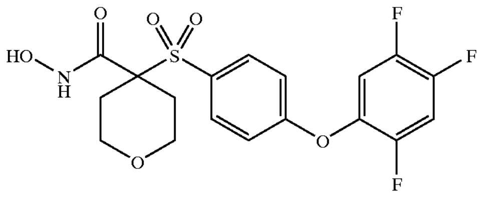

Part A: To a solution of the title compound of Example 55 (2.0 g, 5.2 mmol) in N,N-dimethylacetamide(6 mL) was added 2,4,5-trifluorophenol (1.2 g, 7.8 mmol), followed by cesium carbonate (10.1 g, 31.0 mmol). The reaction was heated at 95 degrees Celsius for thirty-two hours. Removinging the N,N-dimethylacetamide in vacuo afforded a brown solid (5.7 g, quantitative). Chromatography (reverse phase, C-18, acetonitrile/water) gave the THP-protected phenol product (1.2 g, 44%).

Part By: To the solution of the crude THP-protected phenol product from Part A (1.2 g, 2.3 mmol)in acetonitrile/water (40 mL) was slowly added 10% $HCl_{aq}$ (100 mL). After stirring overnight (about 18 hours), the acetonitrile was removed. The resultant precipitate was collected, giving the title compound as a white solid (0.79 g, 79%). MS (FAB) $M^{-}H$ calculated for $C_{18}H_{16}F_3NO_6S$: 430, found 430.

EXAMPLE 59

Preparation of 4-[[4-(3,5-dichlorophenoxy) -phenyl] sulfonyl]-tetrahydro-N-hydroxy-2H-pyran-4-carboxamide

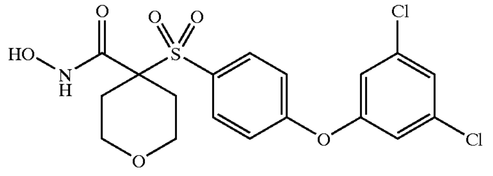

Part A: To a solution of the title compound of Example 55 (2.0 g, 5.2 mmol) in N,N-dimethylacetamide (6 mL) was added 3,5-dichlorophenol (1.3 g, 7.8 mmol), followed by cesium carbonate (6.6 g, 20.2 mmol). The reaction was heated at 95 degrees Celsius for twelve hours. Removing the N,N-dimethylacetamide in vacuo afforded a brown solid (5.7 g, quantitative). The residue was taken up in acetonitrile/water (20 mL) and acidified to pH=6. A white precipitate formed and was collected affording the THP-protected product as a white cake (1.8 g, 64%).

Part B: To the THP-protected product from Part A (1.8 g, 3.4 mmol) in acetonitrile/water (20 mL) was slowly added 10% $HCl_{aq}$ (40 mL). After stirring overnight (about 18 hours), the acetonitrile was removed. The resultant precipitate was collected, giving the title compound as a white solid (0.71 g, 47%). MS (FAB) $M^{+}H$ calculated for $C_{18}H_{17}Cl_2NO_6S$: 447, found 447.

EXAMPLE 59

Preparation of Tetrahydro-N-hydroxy-4-[[4-[[5-(trifluoromethyl)-2-pyridinyl]-thio]phenyl]sulfonyl]-2H-pyran-4-carboxamide Monohydrochloride

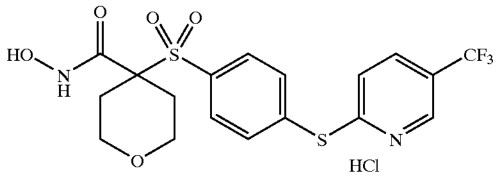

Part A: To a solution of the title compound of Example 55 (2.0 g, 5.2 mmol) in N,N-dimethylacetamide (6 mL) was added 5-(trifluoromethyl)-2-pyridinyl thiophenol (1.4 g, 7.8 mmol), followed by potassium carbonate (2.2 g, 15.6 mmol). The reaction was heated at 65 degrees Celsius for twelve hours. Removing the N,N-dimethylacetamide in vacuo afforded a brown solid (5.4 g, quantitative). Chromatography (reverse phase, C-18, acetonitrile/water) gave the THP-protected product in solution.

Part B: To the solution of the crude THP-protected product from Part A in acetonitrile/water (40 mL) was slowly added 10% $HCl_{aq}$ (40 mL). After stirring overnight (about 18 hours), the acetonitrile was removed. The resultant precipitate was collected, giving the title compound as a white solid (0.20 g, 8%). MS (FAB) $M^{+}H$ calculated for $C_{18}H_{17}N_2O_5S_2$: 463, found 463.

EXAMPLE 60

Preparation of 4-[[4-(3,4-dichlorophenyl]-thio] phenyl]sulfonyl]-tetrahydro-N-hydroxy-2H-pyran-4-carboxamide

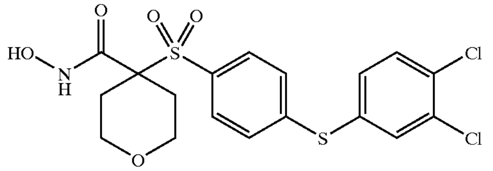

Part A: To a solution of the title compound of Example 55 (2.0 g, 5.2 mmol) in N,N-dimethylacetamide (6 mL) was added 3,4-dichlorothiophenol (1.4 g, 7.8 mmol) followed by potassium carbonate (2.2 g, 15.6 mmol). The reaction was heated at 70 degrees Celsius for six hours. Removing the N,N-dimethylacetamide in vacuo afforded a brown solid (5.6 g, quantitative). Chromatography (reverse phase, C-18, acetonitrile/water) gave the THP protected product in solution.

Part B: To the solution of the THP-protected product from Part A in acetonitrile/water (40 mL) was slowly added 10% $HCl_{aq}$ (40 mL). After stirring overnight (about 18 hours), the acetonitrile was removed. The resultant precipitate was collected, giving the title compound as a white solid (1.5 g, 62%). MS (FAB) $M^{+}H$ calculated for $C_{18}H_{17}Cl_2NO_5S$: 463, found 463.

EXAMPLE 61

Preparation of 4-[[4-[[2-amino-4-(trifluoromethyl) phenyl]thio]phenyl]-sulfonyl]-tetrahydro-N-hydroxy-2H-pyran-4-carboxamide, Monohydrochloride

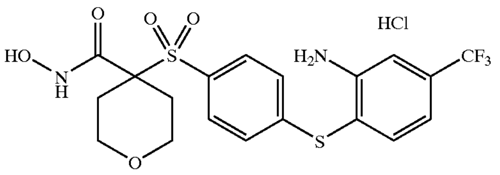

Part A: To a solution of the title compound of Example 55 (2.0 g, 5.2 mmol) in N,N-dimethylacetamide (6 mL) was added 2-amino-4-(trifluoromethyl)thiophenol hydrochloride (1.8 g, 7.8 mmol), followed by potassium carbonate (3.6 g, 26 mmol). The reaction was heated at 70 degrees Celsius for eight hours. Removing the dimethylacetamide in vacuo afforded a brown solid (14 g, quantitative). Chromatography (reverse phase, C-18, acetonitrile/water) gave the THP protected product in solution.

Part B: To the solution of the THP-protected product in acetonitrile/water (40 mL) was slowly added 10% $HCl_{aq}$ (40 mL). After stirring overnight (about 18 hours), the acetonitrile was removed. The resultant precipitate was collected, giving the title compound as a white solid (1.3 g, 52%). MS (FAB) $M^+H$ calculated for $C_{18}H_{17}Cl_2NO_6S$: 477, found 477.

EXAMPLE 62

Preparation of Tetrahydro-4[[4-(4-phenyl-1-piperidinyl)phenyl]sulfonyl]-2H-pyran-4-carboxamide, Monohydrochloride

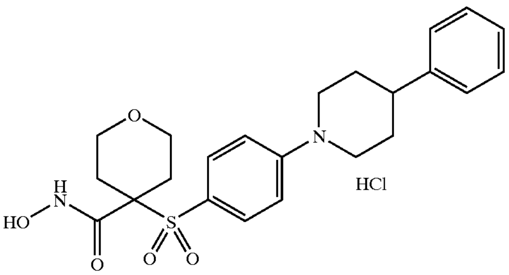

Part A: In dry equipment under nitrogen, sodium metal (8.97 A, 0.39 mol) was added to methanol (1000 mL) at two degrees Celsius. The reaction was stirred at ambient temperature for forty-five minutes at which time the sodium had dissolved. The solution was chilled to five degrees Celsius and p-fluorothiophenol (41.55 mL, 0.39 mmol) was added, followed by methyl 2-chloroacetate (34.2 mL, 0.39 mol). The reaction was stirred at ambient temperature for four hours, filtered, and concentrated in vacuo to give the sulfide as a clear colorless oil (75.85 g, 97%).

Part B: To a solution of the sulfide from part A (75.85 g, 0.38 mol) in methanol (1000 mL) was added water (100 mL) and Oxone® (720 g, 1.17 mol) at 20 degrees Celsius. An exotheym to 67 degrees Celsius was noted. After two hours, the reaction was filtered and the cake was washed well with methanol. The filtrate was concentrated in vacuo. The residue was taken up in ethyl acetate and washed with brine, dried over $MgSO_4$, filtered, and concentrated in vacuo to give the sulfone as a crystalline solid (82.74 g, 94%).

Part C: To a solution of the sulfone from part B (28.5 g, 0.123 mol) in N,N-dimethylacetamide (200 mL) were added potassium carbonate (37.3 g, 0.27 mol), bis-(2-bromoethyl) ether (19.3 mL, 0.147 mol), 4-dimethylaminopyridine (0.75 g, 6 mmol), and tetrabutylammonium bromide (1.98 g, 6 mmol). The reaction was stirred overnight (about 18 hours) at ambient temperature. The reaction was slowly poured into 1N HCl (300 mL), the resultant solid filtered and the cake washed well with hexanes. The solid was recrystallized from ethyl acetate/hexanes to give the pyran compound as a beige solid (28.74 g, 77%). MS (ES+) MH+ calculated for $C_{13}H_{15}O_5S_1F_1$: 303, found 303.

Part D: To a solution of the pyran compound from part C (1.21 g, 4.0 mmol) in dimethyl sulfoxide (10 mL) were added cesium carbonate (3.26 g, 10 mmol) and 4-phenylpiperidine (0.64 g, 4.0 mmol) in methyl sulfoxide (10 mL). The slurry was stirred at 90 degrees Celsius for two hours. The reaction was cooled, diluted with water and extracted with ethyl acetate. The combined organic layers were washed with 5% $KHSQ_4$, saturated $NaHCO_3$, brine, dried over $Na_2SO_4$, filtered, and concentrated in vacuo. The resultant solid was slurried in diethyl ether, filtered and dried to give the N-substituted piperidine as a white solid (1.2 g, 67%). MS (FAB+) MH+ calculated for $C_{24}H_{29}N_1O_5S_1$: 444, found 444.

Part E: To a slurry of the N-substituted piperidine from part D (815 mg, 1.84 mmol) in methanol (5 mL) and tetrahydrofuran (5 mL) was added 50% sodium hydroxide (3 mL). After twenty-four hours at ambient temperature, the reaction was concentrated in vacuo. The slurry was diluted with water (10 mL) and 6N HCl was added until the pH=7. Vacuum filtration of the resulting precipitate provided the acid as a white solid (705 mg, 89%). MS (FAB+) MH+ calculated for $C_{23}H_{27}N_1O_5S_1$: 430, found 430.

Part F: In dry equipment under nitrogen, the carboxylic acid from part E (620 mg, 1.44 mmol) was slurried in methylene chloride (10 mL) and N,N-dimethylformamide (3 mL) and the remaining reagents were added to the slurry in the following order: bromo-tris-pyrrolidino-phosphonium hexafluorophosphate (810 mg, 1.73 mmol), N-methylmorpholine (0.5 mL, 4.34 mmol), and O-tetrahydro-2H-pyran-2-yl-hydroxylamine (190 mg, 1.59 mmol). After four hours at ambient temperature, the reaction was concentrated in vacuo. The residue was taken up in ethyl acetate, washed with water, brine, dried over $Na_2SO_4$, filtered, and concentrated in vacuo. Chromatography (on silica, ethyl acetate/hexanes) provided the THP-protected hydroxamate as a white solid (630 mg, 83%). MS (FAB+) MH+ calculated for $C_{28}H_{22}N_2O_6$ $S_1$: 529, found 529.

Part G: To a slurry of the THP-protected hydroxamate from part F (600 mg, 1.14 mmol) in dioxane (1.5 mL) was added a 4N HCl dioxane solution (1.5 mL) and methanol (1.5 mL). After two hours at ambient temperature the reaction was poured into diethyl ether (100 mL). Vacuum filtration of the resulting precipitate provided the title compound as a light beige solid (500 mg, 91%). MS (FAB+) M+Li calculated for $C_{23}H_{28}N_2O_5S_1$: 445, found 445.

EXAMPLE 63

Preparation of 4-[[4-[4-(1,3-Benzodioxol-5-yloxy)-1-piperidinyl]phenyl]sulfonyl]-tetrahydro-N-hydroxy-2H-pyran-4-carboxamide, Monohydrochloride

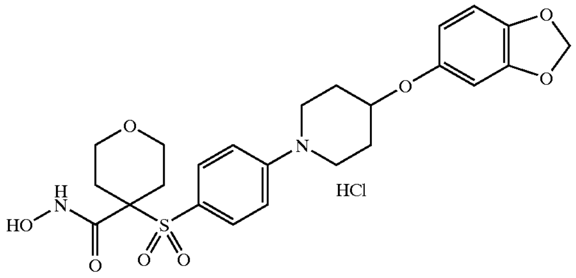

Part A: In dry equipment under nitrogen, 4-hydroxypiperidine (20.2 g, 0.2 mol) was dissolved in tetrahydrofuran (200 mL) and triethylamine (29 mL, 0.21 mol). A solution of di-t-butyldicarbonate (43.65 g, 0.2 mol) was added at such a rate that the temperature remained below 30 degrees Celsius. After stirring at ambient temperature for four hours, the reaction was concentrated in vacuo. The residue was taken up in ethyl acetate, washed with water, 5% $KHSO_4$, saturated $NaHCO_3$, brine, dried over $Na_2SO_4$, filtered, and concentrated in vacuo to give the BOC piperidine as a white solid (37.7 g, 94%).

Part B: In dry equipment under nitrogen, the BOC piperidine from part A (5.0 g, 24.8 mmol) in dry tetrahydrofuran (100 mL) was cooled to zero degrees Celsius and triphenylphosphine (9.77 g, 37.3 mmol) was added. After fifteen minutes of stirring at zero degrees Celsius, sesamol (5.15 g, 37.3 mmol) was added to the reaction followed by the dropwise addition of diethylazodicarboxylate (5.87 mL, 37.7 mmol). The reaction was stirred for thirty minutes at zero degrees Celsius and then at ambient temperature for twenty hours. The reaction was concentrated in vacuo. The residue was slurried in diethyl ether, the triphenyl phosphine oxide filtered off and the filtrate concentrated in vacuo. Chromatography (on silica, ethyl acetate/hexanes) provided the substituted BOC piperidine as a white solid (3.14 g, 39%).

Part C: To a slurry of the substituted BOC piperidine from part B (3.14 g, 9.8 mmol) in dioxane (15 mL) was added a 4N HCl dioxane solution (15 mL). After three hours at ambient temperature, the reaction was concentrated in vacuc. The residue was slurried in diethyl ether and vacuum filtration of the resulting precipitate provided the hydrochloride salt as a white solid (2.3 g, 100%).

Part D: To a slurry of the hydrochloride salt from part C (0.93 g, 3.6 mmol) in N,N-dimethylformamide (10 mL) were added cesium carbonate (2.93 g, 9 mmol) and the title compound of Example 55 (1.16 g, 3.0 mmol). The slurry was stirred at 90 degrees Celsius for twenty four hours. The reaction was concentrated in vacuo. The residue was taken up in ethyl acetate, washed with water, 5% $KHSO_4$, saturated $NaHCO_3$, brine, dried over $Na_2SO_4$, filtered, and concentrated in vacuo. Chromatography (on silica, ethyl acetate/hexanes) provided the substituted THP-protected hydroxamate as a white solid (640 mg, 36%). MS (FAB+) MH+ calculated for $C_{29}H_{36}N_2O_9$ $S_1$: 589, found 589.

Part E: To a slurry of the THP-protected hydroxamate from part D (600 mg, 1.02 mmol) in dioxane (3 mL) were added a 4N HCl dioxane solution (3 mL) and methanol (3 mL). After one hour at ambient temperature, the reaction was poured into diethyl ether (100 mL). Vacuum filtration of the resulting precipitate provided the title compound as a light beige solid (440 mg, 80%). HRMS (ES+) MH+ calculated for $C_{24}H_{28}N_2O_8S_1$: 505.16, found 505.16.

EXAMPLE 64

Preparation of Tetrahydro-N-hydroxy-4-[[4-(4-methoxyphenoxy)phenyl]sulfonyl]-2H-pyran-4-carboxamide

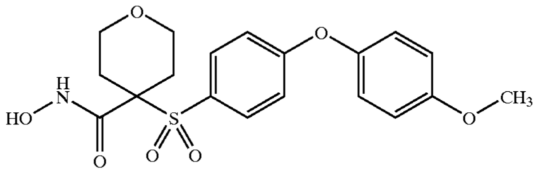

Part A: To a solution of the title compound of Example 55 (3.48 g, 9 mmol) in N,N-dimethylformamide (20 mL) were added cesium carbonate (8.8 g, 27 mmol) and p-methoxyphenol (2.23 g, 18 mmol) . The slurry was stirred at 95 degrees Celsius for twenty four hours. The reaction was concentrated in vacuo. The residue was taken up in ethyl acetate, washed with brine, dried over $Na_2SO_4$, filtered, and concentrated in vacuo. Chromatography (on silica, ethyl acetate/hexanes) provided the substituted THP-protected hydroxamate as a beige foam (3.82 g, 86%). MS (FAB+) MH+ calculated for $C_{24}H_{29}N_1O_8$ $S_1$: 492, found 492.

Part B: To a slurry of the THP-protected hydroxamate from part A (3.6 g, 7.33 mmol) in dioxane (18 mL) were added a 4N HCl dioxane solution (18 mL) and methanol (18 mL). After fifteen minutes at ambient temperature, the reaction was diluted with ethyl acetate and washed with water, dried over $Na_2SO_4$, filtered, and concentrated in vacuo. The product was recrystallized (acetone/hexanes) to give the title compound as a white solid (2.1 g, 70%). HRMS (ES+) MH+ calculated for $C_{19}H_{21}N_1O_7S_1$: 408.11, found 408.11.

EXAMPLE 65

Preparation of Tetrahydro-N-hydroxy-4-[[4-(4-methoxyphenylthio)phenyl]-sulfonyl]-2H-pyran-4-carboxamide

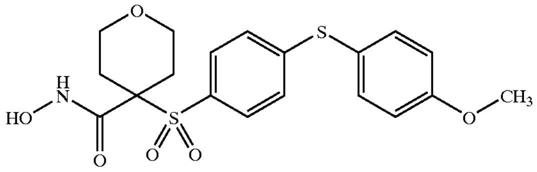

Part A: To a solution of the title compound of Example 55 (3.1 g, 8 mmol) in N,N-dimethylformamide (20 mL) were added potassium carbonate (1.33 g, 9.6 mmol) and p-methoxybenzenethiol (1.48 mL, 12 mmol). The slurry was stirred at 65 degrees Celsius for twenty-four hours. The reaction was concentrated in vacuo. The residue was taken up in ethyl acetate, washed with brine, dried over $Na_2SO_4$, filtered, and concentrated in vacuo. Chromatography (on silica, ethyl acetate/hexanes) provided the substituted THP-protected hydroxamate as a white foam (4.1 g, 100%).

HRMS (ES+) M+$NH_4^+$ calculated for $C_{24}H_{29}N_1O_7S_2$: 525.17, found 525.17.

Part B: To a slurry of the THP-protected hydroxamate from part A (4.0 g, 7.9 mmol) in dioxane (20 mL) was added a 4N HCl dioxane solution (20 mL) and methanol (20 mL). After fifteen minutes at ambient temperature, the reaction was diluted with ethyl acetate, washed with water, dried over $Na_2SO_4$, filtered, and concentrated in vacuo. The product was recrystallized (acetone/hexanes) to give the title compound as a white solid (2.21 g, 67%). HRMS (ES+) MH+ calculated for $C_{19}H_{21}N_1O_6S_2$: 424.09, found 424.09.

EXAMPLE 66

Preparation of 4-[(4-fluorophenyl)-sulfonyl] tetrahydro-N-hydroxy-2H-pyran-4-carboxamide

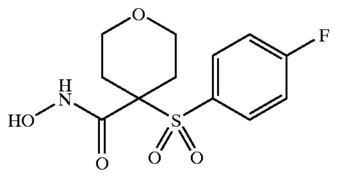

Part A: To a slurry of the title compound of Example 55 (530 mg, 1.38 mmol) in dioxane (5 mL) was added a 4N HCl dioxane solution (5 mL) and methanol (5 mL). After fifteen minutes at ambient temperature the reaction was concentrated in vacuo. Reverse phase chromatography (on silica, acetonitrile/water) provided the title compound as a beige solid (140 mg, 34%). HRMS (ES+) M+ $NH_4^+$ calculated for $C_{12}H_{14}N_1O_5S_1F_1$: 321.09, found 321.09.

EXAMPLE 67

Preparation of tetrahydro-N-hydroxy-4-[[4-(4-piperidinyloxy)phenyl]sulfonyl]-2H-pyran-4-carboxamide, Monohydrochloride

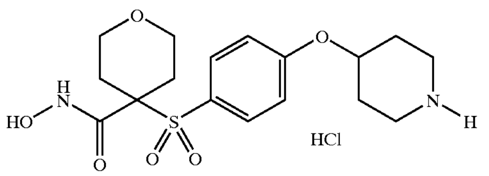

Part A: In dry equipment under nitrogen, 4-hydroxy-N-t-(butoxycarbonyl)piperidine (844 mg, 4.2 mmol) was added to 60% sodium hydride (210 mg, 5.25 mmol) in dry N,N-dimethylformamide (10 mL) at zero degrees Celsius. The slurry was stirred for two hours at ambient temperature. At five degrees Celsius, the title compound of Example 55(1.35 g, 3.5 mmol) was added and the reaction heated to 50 degrees Celsius for three hours. The reaction was cooled, quenched with water, and concentrated in vacuo. The residue was taken up in ethyl acetate, washed with brine, dried over $Na_2SO_4$, filtered, and concentrated in vacuo. Chromatography (on silica, ethyl acetate/hexanes) provided the substituted THP-protected hydroxamate as a white foam (283 mg, 14%). MS (FAB+) MH+ calculated for $C_{27}H_{40}N_2O_9S_1$: 569, found 569.

Part B: To a slurry of the THP-protected hydroxamate from part A (530 mg, 0.93 mmol) in dioxane (5 mL) were added a 4N HCl dioxane solution (5 mL) and methanol (5 mL). After fifteen minutes at ambient temperature the reaction was concentrated in vacuo. Reverse phase chromatography (on silica, acetonitrile /water buffered with 0.01%HCl) provided the title compound as a beige solid (240 mg, 62%). HRMS (ES+) MH+ calculated for $C_{17}H_{24}N_2O_6S_1$: 385.14, found 385.14.

EXAMPLE 68

Preparation of tetrahydro-N-hydroxy-4-[[4-[(4-phenylmethyl)amino]phenyl]-sulfonyl]-2H-pyran-4-carboxamide, Monohydrochloride

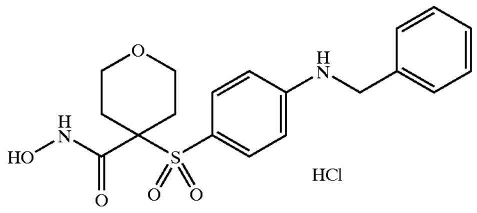

Part A: In a solid phase reaction vessel, benzylamine (11.0 mL, 100 mmol) was added to Resin II (in a procedure described hereinafter; 5.0 g, 4.55 mmol) swollen in dry 1-methyl-2-pyrrolidinone (40 mL). The reaction was heated to 100 degrees Celsius for forty-eight hours with good shaking. The resin was transferred to a frit and washed four times with N,N-dimethylformamide (30 mL), four times with methanol (30 mL), four times with methylene chloride (30 mL), and dried. The dried resin was transferred to a flask and a solution of 95% trifluoroacetic acid/5%water (50 mL) was added. The slurry was stirred for one hour, filtered and the cake was washed with methylene chloride. The combined filtrates were concentrated in vacuo. The residue was dissolved in ethyl acetate and saturated sodium bicarbonate solution was added until pH=7. The organic layer was dried over $Na_2SO_4$, filtered, and concentrated in vacuo. Reverse phase chromatography (on silica, acetonitrile/water buffered with 0.01%HCl) provided the title compound as a reddish solid (1.01 g, 52%). HRMS (ES+) M+ $NH_4^+$ calculated for $C_{19}H_{22}N_2O_5S_1$: 408.16, found 408.16.

EXAMPLE 69

Preparation of Tetrahydro-N-hydroxy-4-[[4-[4-trifluoromethoxy)phenoxy)phenyl]-sulfonyl]-2H-pyran-4-carboxamide

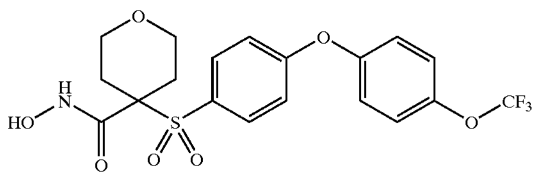

Part A: To a solution of the title compound of Example 55 (3.1 g, 8 mmol) in N,N-dimethylacetamide (20 mL) were added cesium carbonate (8.8 g, 27 mmol) and p-(trifluoromethoxy)phenol (2.1 mL, 16 mmol). The slurry was stirred at 95 degrees Celsius for nineteen hours. The reaction was concentrated in vacuo. The residue was taken up in ethyl acetate, washed with brine, dried over $Na_2SO_4$, filtered, and concentrated in vacuo. Chromatography (on silica, ethyl acetate/hexanes) provided the substituted THP-protected hydroxamate as a white foam (4.2 g, 96%). HRMS (ES+) MH+ calculated for $C_{24}H_{26}N_1O_8S_1F_3$: 546.14, found 546.14.

Part B: To a slurry of the THP-protected hydroxamate from part A (4.0 g, 7.3 mmol) in dioxane (20 mL) were added a 4N HCl dioxane solution (20 mL) and methanol (20 mL). After fifteen minutes at ambient temperature, the reaction was diluted with ethyl acetate and washed with water, dried over $Na_2SO_4$, filtered, and concentrated in vacuo. The product was recrystallized (acetone/hexanes) to give the title compound as a white solid (2.2 g, 65%). HRMS (ES+) M+ $NH_4^+$ calculated for $C_{19}H_{18}N_1O_7S_1F_3$: 479.11, found 479.11.

EXAMPLE 70

Preparation of 4-[[4-(3,5-difluorophenoxy)phenyl] sulfonyl]tetrahydro-N-hydroxy-2H-pyran-4-carboxamide

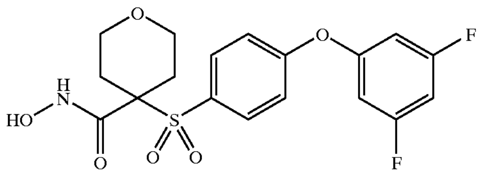

Part A: To a solution of the title compound of Example 55 (3.1 g, 8 mmol) in N,N-dimethylacetamide (20 mL) were added cesium carbonate (8.8 g, 27 mmol) and 3,5-difluorophenol (2.1 g, 16 mmol). The slurry was stirred at 95 degrees Celsius for forty-eight hours. The reaction was concentrated in vacuo. The residue was taken up in ethyl acetate, washed with brine, dried over $Na_2SO_4$, filtered, and concentrated in vacuo. Chromatography (on silica, ethyl acetate/hexanes) provided the substituted THP-protected hydroxamate as a beige foam (3.23 g, 81%). HRMS (ES+) MH+ calculated for $C_{23}H_{25}N_1O_7$ $S_1F_2$: 498.14, found 498.14.

Part B: To a slurry of the THP-protected hydroxamate from part A (3.2 g, 6.3 mmol) in dioxane (20 mL) were added a 4N HCl dioxane solution (20 mL) and methanol (20 mL). After fifteen minutes at ambient temperature the reaction was diluted with ethyl acetate and washed with water, dried over $Na_2SO_4$, filtered, and concentrated in vacuo. The residue was slurried in diethyl ether and vacuum filtration of the resulting precipitate provided the title compound as a white solid (1.5 g, 57%). HRMS (ES+) M+$NH_4^+$ calculated for $C_{18}H_{17}N_1O_6$ $S_1F_2$: 431.11, found 431.11.

EXAMPLE 71

Preparation of 4-[[4-(3,4-dichlorophenoxy)-phenyl] sulfonyl]-tetrahydro-N-hydroxy-2H-pyran-4-carboxamide

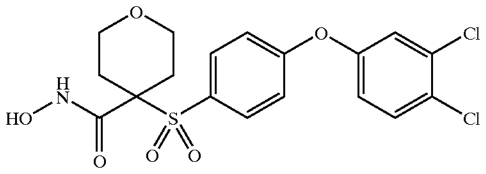

Part A: To a solution of the title compound of Example 55 (3.1 g, 8 mmol) in N,N-dimethylacetamide (20 mL) were added cesium carbonate (8.8 g, 27 mmol) and 3,4-dichlorophenol (2.61 g, 16 mmol). The slurry was stirred at 95 degrees Celsius for forty-one hours. The reaction was concentrated in vacuo. The residue was taken up in ethyl acetate, washed with brine, dried over $Na_2SO_4$, filtered, and concentrated in vacuo. Chromatography (on silica, ethyl acetate/hexanes) provided the substituted THP-protected hydroxamate as a white foam (4.17 g, 98%). HRMS (ES+) M+ $NH_4^+$ calculated for $C_{23}H_{25}N_1O_7$ $S_1Cl_2$: 547.11, found 547.10.

Part B: To a slurry of the THP-protected hydroxamate from part A (3.5 g, 6.6 mmol) in dioxane (20 mL) were added a 4N HCl dioxane solution (20 mL) and methanol (20 mL). After fifteen minutes at ambient temperature the reaction was diluted with ethyl acetate and washed with water, dried over $Na_2SO_4$, filtered, and concentrated in vacuo. The residue was slurried in diethyl ether and vacuum filtration of the resulting precipitate provided the title compound as a white solid (2.98 g, 100%). HRMS (ES+) M+ $NH_4^+$ calculated for $C_{18}H_{17}N_1O_6$ $S_1Cl_2$: 463.05, found 463.05.

EXAMPLE 72

Preparation of tetrahydro-N-hydroxy-4-[[4-[4-[(phenylmethyl)oxy]phenoxy]-phenyl]-sulfonyl]-2H-pyran-4-carboxamide

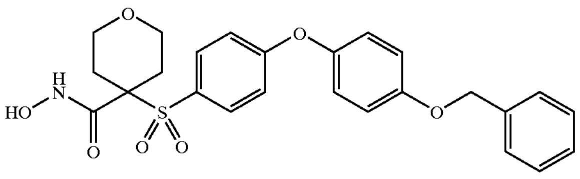

Part A: To a solution of the title compound of Example 55 (2.7 g, 7 mmol) in N,N-dimethylacetamide (20 mL) were added cesium carbonate (6.84 g, 21 mmol) and 4-(benzyloxy)phenol (2.8 g, 14 mmol). The slurry was stirred at 95 degrees Celsius for six hours. The reaction was concentrated in vacuo. The residue was taken up in ethyl acetate, washed with brine, dried over $Na_2SO_4$, filtered, and concentrated in vacuo. Chromatography (on silica, ethyl acetate/hexanes) provided the substituted THP-protected hydroxamate as a white foam (3.94 g, 99%). HRMS (ES+) M+ $NH_4^+$ calculated for $C_{30}H_{33}N_1O_8$ $S_1$: 585.23, found 585.23.

Part B: To a slurry of the THP-protected hydroxamate from part A (1.42 g, 2.5 mmol) in dioxane (6.3 mL) were added a 4N HCl dioxane solution (6.3 mL) and methanol (6.3 mL). After fifteen minutes at ambient temperature the reaction was diluted with ethyl acetate and washed with water, dried over $Na_2SO_4$, filtered, and concentrated in vacuo. The product was recrystallized (acetone/hexanes) to give the title compound as a white solid (0.56 g, 46%). found 484.14.

EXAMPLE 73

Preparation of tetrahydro-N-hydroxy-4-[[4-[4-(trifluoromethoxy)phenylthio]-phenyl]-sulfonyl]-2H-pyran-4-carboxamide

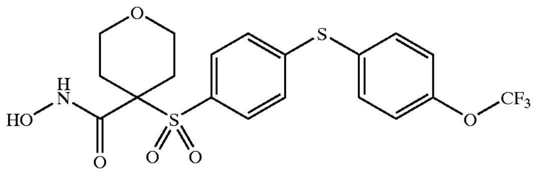

Part A: To a solution of the title compound of Example 55 (3.1 g, 8 mmol) in N,N-dimethylformamide (20 mL) were added potassium carbonate (2.21 g, 16mmol) and p-(trifluoromethoxy)benzenethiol (2.33 g, 12 mmol). The slurry was stirred at 70 degrees Celsius for two hours The reaction was concentrated in vacuo. The residue was taken up in ethyl acetate, washed with brine, dried over $Na_2SO_4$, filtered, and concentrated in vacuo. Chromatography (on silica, ethyl acetate/hexanes) provided the substituted THP-protected hydroxamate as a white solid (4.4 g, 98%). HRMS (ES+) $M+NH_4^+$ calculated for $C_{24}H_{26}N_1O_7S_2F_3$: 579.14, found 579.14.

Part B: To a slurry of the THP-protected hydroxamate from part A (4.15 g, 7.4 mmol) in dioxane (20 mL) were added a 4N HCl dioxane solution (20 mL) and methanol (20 mL). After fifteen minutes at ambient temperature the reaction was diluted with ethyl acetate and washed with water, dried over $Na_2SO_4$, filtered, and concentrated in vacuo. The product was recrystallized (acetone/hexanes) to give the title compound as a white solid (3.0 g, 85%). HRMS (ES+) $M+NH_4^+$ calculated for $C_{19}H_{18}N_1O_6\ S_2F_3$: 495.09, found 495.09.

EXAMPLE 74

Preparation of phenylmethyl-[4-[[2-(hydroxyamino)-2-oxoethyl]-sulfonyl]phenyl] carbamate

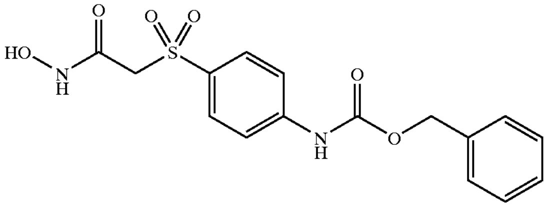

Part A: To a suspension of 2-(4-aminophenylthio) acetic acid (20.0 g, 0.11 mol) in methanol (100 mL), cooled to zero degrees Celsius, was slowly added thionyl chloride (24.0 mL, 0.33 mol). Additional methanol (100 mL) was added and the cooling bath was removed. The resulting mixture was heated at reflux for 2 hours. The reaction mixture was then cooled to ambient temperature and concentrated in vacuo. The residue was dissolved in $H_2O$ and neutralized with saturated $NaHCO_3$. The aqueous reaction mixture was extracted with ethyl acetate. The organic layer was washed with saturated NaCl and dried over $Na_2SO_4$. Concentration in vacuo provided the methyl ester sulfide as a dark purple oil (22.75 g, quantitative yield).

Part B: To a solution of the methyl ester sulfide of part A (10.0 g, 50.7 mmol) in dichloromethane (100 mL) was added N-methylmorpholine (11.2 mL, 101.4 mmol), followed by N-(benzyloxycarbonyloxy) succinimide (12.6 g, 50.7 mmol). The resulting mixture was stirred at ambient temperature overnight (about 18 hours) and then concentrated in vacuo. The residue was dissolved in ethyl acetate and then washed with $H_2O$, 5% $KHSO_4$, saturated NaCl and dried over $Na_2SO_4$. Concentration in vacuo provided the benzyloxy carbamate sulfide as a dark oil (16.2 g, 96%).

Part C: To a solution of the benzyloxy carbamate sulfide of part B (16.2 g, 48.7 mmol) in tetrahydrofuran (100 mL) and $H_2O$ (10 mL) was added Oxone® (90.0 g, 146.4 mmol), and the resulting mixture was stirred at ambient temperature for 16 hours. The reaction mixture was then filtered and the filtrate was concentrated in vacuo. The residue was dissolved in ethyl acetate, washed with $H_2O$, saturated NaCl and dried over $Na_2SO_4$. Concentration in vacuo provided the benzyloxy carbamate sulfone as a tan solid (15.6 g, 88%).

Part D: To a solution of the benzyloxy carbamate sulfone of part C (0.25 g, 0.69 mmol) in tetrahydrofuran (3 mL) was added 50% aqueous hydroxylamine (1.5 mL). The resulting mixture was stirred at ambient temperature for 24 hours. The mixture was then diluted with ethyl acetate (30 mL), washed with $H_2O$, saturated NaCl and dried over $Na_2SO_4$. Concentration in vacuo followed by washing with hot diethyl ether provided the title compound as a pale pink solid (0.20 g, 80%). MS $MH^+$ calculated for $C_{16}H_{17}O_6N_2S$: 365, found 365.

EXAMPLE 75

Preparation of N-hydroxy-2-[[4-[[(phenylamino) carbonyl]amino]-phenyl]sulfonyl]acetamide

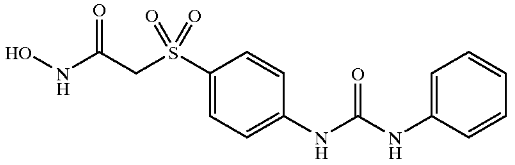

Part A: Hydrogen gas was bubbled into a suspension of the benzyloxy carbamate sulfone of part C, Example 74 (13.4 g, 36.8 mmol) and 4% Pd/C in tetrahydrofuran (100 mL). After the uptake of $H_2$ ceased the mixture was purged with $N_2$ and then filtered through a pad of Celite® washing with tetrahydrofuran. The filtrate was concentrated in vacuo to give the aniline as a brown solid (8.1 g, 96%).

Part B: To a suspension of the aniline of part A (0.50 g, 2.2 mmol) in dichloromethane (4 mL) was added phenyl isocyanate (0.36 mL, 3.3 mmol). The mixture was stirred at ambient temperature overnight (about 18 hours) and then diluted with dichloromethane (50 mL). The mixture was then washed with $H_2O$, saturated NaCl and dried over $Na_2SO_4$. Chromatography (on silica, ethyl acetate/hexane) provided the urea as a white solid (0.59 g, 78%).

Part C: To a solution of the urea of part B (0.32 g, 0.92 mmol) in tetrahydrofuran (3 mL) was added 50% aqueous hydroxylamine (1.5 mL). The resulting mixture was stirred at ambient temperature for 24 hours. The mixture was then diluted with ethyl acetate (30 mL), washed with $H_2O$, saturated NaCl and dried over $Na_2SOo_4$. Concentration in vacuo, followed by washing with hot diethyl ether provided the title compound as a pale pink solid (0.24 g, 76%). MS $MH^+$ calculated for $C_{15}H_{16}O_5N_3S$: 350, found 350.

EXAMPLE 78

Preparation of 5-[4-(3,4-dimethylphenoxy)phenyl]sulfonyl-$N^5$-hydroxy-1,3-dimethylhexahydro-5-pyrimidinecarboxamide, Dihydrochloride

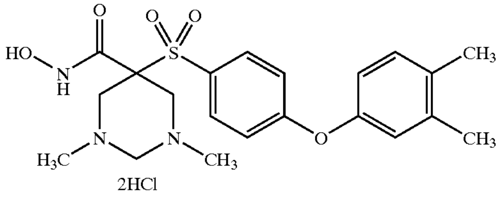

Part A: To a solution of part B, Example 55 (2.00 g, 8.61 mmol) and 1,3,5-trimethylhexahydro-1,3,5-triazine (1.21 mL, 8.61 mmol) in benzene (20 mL) was slowly added trifluoroacetic acid (0.66 mL, 8.61 mmol). The resulting mixture was heated at reflux for 1 hour and then cooled to ambient temperature. The mixture was then extracted with 2N HCl. The aqueous layer was neutralized with saturated $NaHCO_3$ and then extracted with diethyl ether. The organic layers were washed with saturated NaCl and dried over $Na_2SO_4$. Concentration in vacuo provided the tetrahydro-pyrimidine as a clear oil (2.31 g, 81%).

Part B: To a solution of the tetrahydopyrimidine of part A (1.26 g, 3.81 mmol) in N,N-dimethylformamide (5.0 mL) were added 3,4-dimethylphenol (0.559 g, 4.58 mmol) and $Cs_2CO_3$ (3.72 g, 11.43 mmol). The resulting mixture was heated at 90 degrees Celsius for 16 hours. After cooling to ambient temperature, the reaction was diluted with $H_2O$ and extracted with ethyl acetate. The organic layers were washed with saturated NaCl and dried over $Na_2SO_4$. Chromatography (on silica, ethyl acetate) gave the biaryl ether as a pale amber oil (1.40 g, 85%).

Part C: To a solution of the biaryl ether of part B (0.936 g, 2.16 mmol) in tetrahydrofuran (5.0 mL) was added potassium trimethylsilanolate (0.360 g, 2.81 mmol). The resulting mixture was stirred at ambient temperature for 48 hours and then the solvent was removed. The resulting residue was dissolved in dichloromethane (5.0 mL) then, N-methylmorpholine (0.712 mL, 6.48 mmol) and O-tetrahydro-2H-pyran-2-yl-hydroxylamine (0.278 g, 2.38 mmol) were added. After stirring at ambient temperature for 10 minutes, PyBroP® (1.21 g, 2.59 mmol) was added. The resulting mixture was stirred at ambient temperature overnight (about 18 hours), then diluted with dichloromethane (50 mL) and washed with $H_2O$. The organic layer was removed and washed with saturated NaCl and dried over $Na_2SO_4$. Chromatography (on silica, ethyl acetate) provided the hydroxamate as a white solid (0.970 g, 87%).

Part F: To a suspension of the hydroxamate of part E (0.667 g, 1.29 mmol) in dioxane (3.0 mL) and methanol (1.0 mL) was added a solution of 4N HCl in dioxane (3.22 mL, 12.9 mmol). After stirring at ambient temperature for 30 minutes, the reaction mixture was concentrated in vacuo. Reverse phase chromatography (on silica, acetonitrile/$H_2O$/trifluoroacetic acid) provided the title compound as a white solid (0.379 g, 58%). MS $MH^+$ calculated for $C_{21}H_{28}O_5N_3S$: 434, found 434.

EXAMPLE 79

Preparation of 4-[[4-(4-chloro-3-methylphenoxy)phenyl]sulfonyl]-N-hydroxy-4-piperidinecarboxamide, Monohydrochloride

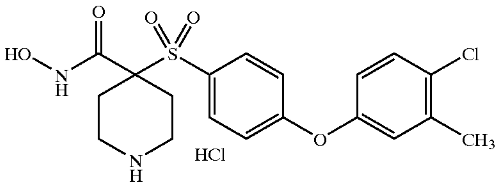

Part A: To a suspension of isonipectic acid (50.0 g, 0.39 mol) in methanol (300 mL) cooled to zero degrees Celsius was slowly added dropwise thionyl chloride (85.0 mL, 1.16 mol). Once the addition was complete the cooling bath was removed and the mixture was heated at reflux for 2 hours. After cooling to ambient temperature the reaction mixture was concentrated in vacuo. The resulting solids were suspended in ethyl acetate and then washed with saturated $NaHCO_3$. The aqueous layer was concentrated in vacuo and the resulting solids were dissolved in hot ethyl acetate and decanted from the salts. The organic layers were then concentrated in vacuo to give the methyl ester as a white solid (55.4 g, quantitative yield).

Part B: To a solution of di-tert-butyl dicarbonate (15.3 g, 70.0 mmol) in tetrahydrofuran (100 mL) was added the methyl ester of part A (10.0 g, 70.0 mmol). The resulting mixture was stirred at ambient temperature overnight (about 18 hours) and then concentrated in vacuo. Chromatography (on silica, ethyl acetate/hexane) provided the Boc-piperidine methyl ester as a pale yellow oil (10.1 g, 59%).

Part C: To a solution of the Boc-piperidine methyl ester of part B (23.31 g, 0.096 mol) in tetrahydrofuran (500 mL), cooled to minus 40 degrees Celsius, was slowly added lithium diisopropylamide (57.5 mL, 2.0 M in THF, 0.115 mol). The resulting mixture was stirred at minus 40 degrees Celsius for 1 hour and then at zero degrees Celsius for 30 minutes. The mixture was then recooled to minus 40 degrees Celsius and a solution of the disulfide from Part A, Example 6 (24.37 g, 0.096 mol) in tetrahydrofuran (60 mL) was slowly added. The resulting mixture was slowly warmed to ambient temperature overnight (about 18 hours) and then $H_2O$ (200 mL) was added. The mixture was then concentrated in vacuo and the aqueous layer was extracted with ethyl acetate. The organic layers were washed with 0.5 M NaOH, $H_2O$, saturated NaCl and dried over $Na_2SO_4$. Chromatography (on silica, ethyl acetate/hexane) gave the sulfide as an amber oil (28.1 g, 79%).

Part D: To a solution of the sulfide of part C (28.2 g, 0.076 mol) in dichloromethane (250 mL), cooled to zero degrees Celsius, was added m-chloroperoxy-benzoic acid (48 g, 0.152 mol). The resulting mixture was stirred at zero degrees Celsius for 1 hour, and then at ambient temperature for 2.5 hours. The mixture was then diluted with $H_2O$ and 10% $NH_4OH$. The organic layer was washed with 10% $NH_4OH$, $H_2O$ and dried over $Na_2SO_4$. Chromatography (on silica, ethyl acetate/hexane) provided the sulfone as a white solid (24.7 g, 81%).

Part E: To a solution of the sulfone of part D (3.00 g, 7.47 mmol) in N,N-dimethylformamide (15 mL) were added 4-chloro-3-methylphenol (1.28 g, 8.96 mmol) and $Cs_2CO_3$ (7.30 g, 22.42 mmol). The resulting mixture was heated at 80 degrees Celsius for 8 hours. The mixture was then concentrated in vacuo, and the residue was partitioned between $H_2O$ and ethyl acetate. The organic layer was washed with saturated NaCl and dried over $Na_2SO_4$. Chromatography (on silica, ethyl acetate/hexane) gave the biaryl ether as a clear oil (3.26 g, 83%).

Part F: To a solution of the biaryl ether of part E (3.17 g, 6.05 mmol) in tetrahydrofuran (30 mL) was added potassium trimethylsilanolate (1.01 g, 7.87 mmol) The resulting mixture was stirred at ambient temperature for 20 hours. Additional tetrahydrofuran (40 mL) was added and the mixture was stirred at ambient temperature for 36 hours. Additional potassium trimethylsilanolate (0.233 g, 1.82 mmol) was added and the mixture was stirred at ambient temperature for 23 hours. The tetrahydrofuran was removed and the resulting residue was suspended in dichloromethane (30 mL). To the suspension was added N-methylmorpholine (2.00 mL, 18.15 mmol) and O-tetrahydro-2H-pyran-2-yl-hydroxylamine (0.780 g, 6.66 mmol) followed by PyBroP® (3.38 g, 7.26 mmol). The mixture was stirred at ambient temperature for 24 hours and then concentrated in vacuo. The residue was partitioned between $H_2O$ and ethyl acetate. The organic layer was washed with $H_2O$, saturated NaCl and dried over $Na_2SO_4$. Chromatography (on silica, ethyl acetate/hexane) provided the hydroxamate as an off-white foam (2.98 g, 81%).

Part G: To a solution of the hydroxamate of part F (2.98 g, 4.89 mmol) in dioxane (14 mL) and methanol (6 mL) was added a solution of 4N HCl in dioxane (10 mL). The resulting mixture was stirred at ambient temperature for 3.5 hours, then diethyl ether (40 mL) was added and the precipitate was collected by filtration to provide the title compound as a light pink solid (2.00 g, 88%). MS $MH^+$ calculated for $C_{19}H_{22}O_5N_2ClS$: 425, found 425.

EXAMPLE 80

Preparation of 4-[[4-(4-chloro-3-methylphenoxy) phenyl]sulfonyl]-4-(hydroxyamino)carbonyl]-1-piperidineacetic Acid, Monohydrochloride

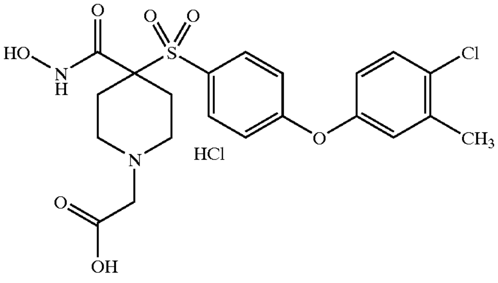

Part A: To a suspension of the title compound of Example 80 (0.250 g, 0.542 mmol) in acetonitrile (4.0 mL) were added tert-butylbromoacetate (0.088 mL, 0.542 mmol) and $K_2CO_3$ (0.150 g, 1.08 mmol). The resulting mixture was stirred at ambient temperature for 18 hours, then filtered through a pad of Celite®, washing with ethyl acetate. The filtrate was then concentrated in vacuo. Reverse phase chromatography (on silica, acetonitrile/$H_2O$/trifluoroacetic acid) provided the tert-butyl ester as a white solid (0.156 g, 53%).

Part B: The tert-butyl ester of part A (0.156 g, 0.289 mmol) was treated with a solution of 4N HCl in dioxane (1.5 mL) and the resulting mixture was stirred at ambient temperature for 3.5 hours at which time additional dioxane (2 mL) was added. After stirring at ambient temperature for 8 hours the reaction mixture was concentrated in vacuo. The residue was treated again with a solution of 4N HCl in dioxane (1.5 mL) at ambient temperature for 4 hours. Diethyl ether was added to the reaction mixture and the precipitate was collected by filtration to give the title compound as an off-white solid (0.111 g, 74%). MS $MH^+$ calculated for $C_{21}H_{24}O_7N_2SCl$: 483, found 483.

EXAMPLE 81

Preparation of 4-[[4-(4-chloro-3-methylphenoxy) phenyl]sulfonyl]-N-hydroxy-1-(2-propynyl)-4-piperidinecarboxamide, Monohydrochloride

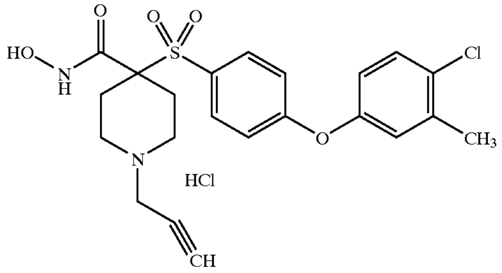

Part A: To a suspension of the title compound of Example 79 (0.500 g, 1.08 mmol) in acetonitrile (8.0 mL) were added propargyl bromide (0.126 mL, 80% solution in toluene, 1.13 mmol) and $K_2CO_3$ (0.300 g, 2.17 mmol). The resulting mixture was stirred at ambient temperature for 24 hours, then filtered through a pad of Celite®, washing with methanol and the filtrate was then concentrated in vacuo. Chromatography (on silica, ethyl acetate) provided the N-propargyl hydroxamate as a tan solid (0.200 g, 40%).

Part B: To a solution of the N-propargyl hydroxamate of part A (0.200 g, 0.432 mmol) in acetonitrile (3.0 mL) and $H_2O$ (0.5 mL) was added concentrated HCl (0.05 mL). The resulting mixture was stirred at ambient temperature for 5 minutes and the concentrated in vacuo to provide the title compound as a pink solid (0.200 g, 93%). MS $MH^+$ calculated for $C_{22}H_{24}O_5N_2SCl$: 463, found 463.

EXAMPLE 82

Preparation of 4-[[4-(4-chloro-3-methylphenoxy) phenyl]sulfonyl]-N-hydroxy-1-(2-propenyl)-4-piperidinecarboxamide, Monohydrochloride

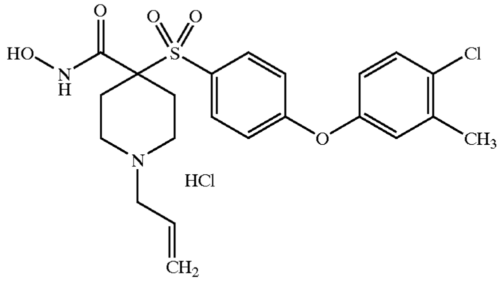

Part A: To a suspension of the title compound of Example 79 (0.500 g, 1.08 mmol) in acetonitrile (8.0 mL) were added allyl bromide (0.093 mL, 1.08 mmol) and $K_2CO_3$ (0.300 g, 2.17 mmol). The resulting mixture was stirred at ambient temperature for 22 hours. Additional allyl bromide (0.054 mL, 1M in acetonitrile, 0.054 mmol) was added and stirring was continued at ambient temperature for 6 hours. The resulting mixture was filtered through a pad of Celite®, washing with ethyl acetate and the filtrate was concentrated in vacuo. Chromatography (on silica, methanol/ethyl acetate) provided the N-allyl hydroxamate as an off-white solid (0.080 g, 15%).

Part B: To a solution of the N-allyl hydroxamate of part A (0.080 g, 0.172 mmol) in acetonitrile (3.0 mL) and $H_2O$ (1.0 mL) was added concentrated HCl (0.05 mL). The resulting mixture was stirred at ambient temperature for ten minutes and then concentrated in vacuo to provide the title compound as a white solid (0.100 g, quantitative yield). MS $MH^+$ calculated for $C_{22}H_{26}O_5N_2SCl$: 465, found 465.

EXAMPLE 83

Preparation of 4-[[4-(4-fluoro-3-methylphenoxy) phenyl]sulfonyl]-N-hydroxy-4-piperidine Carboxamide, Monohydrochloride

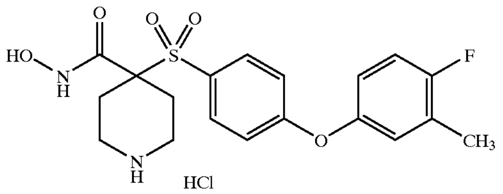

Part A: To a solution of the sulfone of part D, Example 79 (5.00 g, 12.45 mmol) in tetrahydrofuran (100 mL) was added potassium trimethylsilanolate (4.79 g, 37.36 mmol). The resulting mixture was stirred at ambient temperature for 1.5 hours, diluted with $H_2O$ and diethyl ether (100 mL). The aqueous layer was extracted with diethyl ether and the combined organic layers were washed with $H_2O$. The aqueous layers were combined and acidified with 2N HCl (pH=2) and then extracted with ethyl acetate. The combined organic layers were washed with saturated NaCl and dried over $Na_2SO_4$ to provide the acid as an off-white solid (4.61 g, 96%).

Part B: To a suspension of the acid of part A (0.830 g, 2.14 mmol) in dichloromethane (10 mL) was added N-methylmorpholine (0.706 mL, 6.42 mmol) and O-tetrahydro-2H-pyran-2-yl-hydroxylamine (0.276 g, 2.35 mmol). After stirring at ambient temperature for 5 minutes, PyBroP® (1.20 g, 2.57 mmol) was added and the resulting mixture was stirred at ambient temperature for 19 hours. The mixture was concentrated in vacuo and the residue was partitioned between $H_2O$ and ethyl acetate. The aqueous layer was further extracted with ethyl acetate and the combined organic layers were washed with saturated NaCl and dried over $Na_2SO_4$. Chromatography (on silica, ethyl acetate/hexane) provided the p-fluorosulfone as a white crystalline solid (0.993 g, 95%).

Part C: To a solution of the p-fluorosulfone of part B (0.485 g, 0.996 mmol) in N,N-dimethylformamide (5 mL) were added 4-fluoro-3-methylphenol (0.133 mL, 1.20 mmol) and $Cs_2CO_3$ (0.973 g, 2.99 mmol). The resulting mixture was heated at 60 degrees Celsius for 17 hours. Additional 4-fluoro-3-methylphenol (0.055 mL, 0.498 mmol) was added and the temperature of the reaction mixture was increased to 80 degrees Celsius for 4 hours and then to 100 degrees Celsius for 3 hours. Additional 4-fluoro-3-methylphenol (0.133 mL, 1.20 mmol) was added and the reaction mixture was heated at 100 degrees Celsius for 7.5 hours. Additional $Cs_2CO_3$ was added and heating continued at 100 degrees Celsius for 17 hours. The reaction was cooled to ambient temperature and then concentrated in vacuo. The residue was partitioned between $H_2O$ and ethyl acetate. The organic layer was washed with saturated NaCl and dried over $Na_2SO_4$. Chromatography (on silica, ethyl acetate/hexane) provided the protected hydroxamate as an off-white solid (0.490 g, 83%).

Part D: To a solution of the protected hydroxamate of part C (0.479 g, 0.808 mmol) in dioxane (3 mL) and methanol (1 mL) was added a solution of 4N HCl in dioxane (2.02 mL, 8.08 mmol). The resulting mixture was stirred at ambient temperature for 1.5 hours. Diethyl ether (5 mL) was added and the precipitate was collected by filtration to give the title compound as an off-white solid (0.323 g, 90%). MS $MH^+$ calculated for $C_{19}H_{22}O_5N_2SF$: 409, found 409.

EXAMPLE 84

Preparation of 4-[[4-(3-chloro-4-fluorophenoxy) phenyl]sulfonyl]-N-hydroxy-4-piperidine Carboxamide, Monohydrochloride

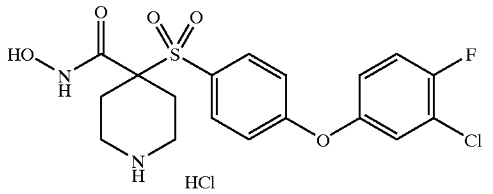

Part A: To a solution of the p-fluorosulfone of Part B, Example 83 (0.485 g, 0.996 mmol) in N,N-dimethylformamide (5.0 mL) were added 4-fluoro-3-chlorophenol (0.176 g, 1.20 mmol) and $Cs_2CO_3$ (0.973 g, 2.99 mmol). The resulting mixture was heated at 60 degrees Celsius for 17 hours, then additional 4-fluoro-3-chlorophenol (0.073 g, 0.498 mmol) was added and the reaction mixture was heated at 80 degrees Celsius for 24 hours then increased to 90 degrees Celsius. After heating 90 degrees Celsius for 7 hours additional 4-fluoro-3-chlorophenol (0.176 g, 1.20 mmol) was added and heating was contiued at 90 degrees Celsius for 7.5 hours. Additional $Cs_2CO_3$ (0.973 g, 2.99 mmol) was added and the mixture was heated at 90 degrees Celsius for 24 hours. After cooling to ambient temperature, the reaction mixture was concentrated in vacuo. The residue was partitioned between $H_2O$ and ethyl acetate. The organic layer was washed with saturated NaCl and dried over $Na_2SO_4$. Chromatography (on silica, ethyl acetate/hexane) provided the protected hydroxamate as an off-white solid (0.550 g, 90%).

Part B: To a solution of the protected hydroxamate of part A (0.530 g, 0.864 mmol) in dioxane (3 mL) and methanol (1 mL) was added a solution of 4N HCl in dioxane (2.00 mL, 8.00 mmol). The resulting mixture was stirred at ambient temperature for 1.5 hours. Diethyl ether (5 mL) was added and the precipitate was collected by filtration to give the title compound as an off-white solid (0.377 g, 94%). MS $MH^+$ calculated for $C_{19}H_{19}O_5N_2SFCl$: 429, found 429.

EXAMPLE 85

Preparation of 4-[[4-(4-chlorophenoxy)-phenyl] sulfonyl]-N-hydroxy-1-(2-propynyl)-4-piperidinecarboxamide, Monohydrochloride

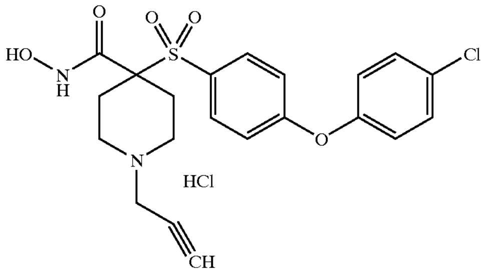

Part A: To a solution of sulfone of part D, Example 79 (4.53 g, 11.28 mmol) in N,N-dimethylformamide (20 mL) were added 4-chlorophenol (4.41 g, 13.54 mmol) and $Cs_2CO_3$ (11.03 g, 33.85 mmol) The resulting mixture was heated at 90 degrees Celsius for 5 hours. After cooling to ambient temperature, the reaction mixture was concentrated in vacuo. The residue was partitioned between $H_2O$ and ethyl acetate. The organic layer was washed with saturated NaCl and dried over $Na_2SO_4$. Chromatography (on silica, ethyl acetate/hexane) provided the biaryl ether as a white solid (4.60 g, 78%).

Part B: To a solution of the biaryl ether of part A (4.57 g, 8.96 mmol) in dioxane (10 mL) was added a solution of 4N HCl in dioxane (10 mL). The resulting mixture was stirred at ambient temperature for 2.5 hours and then additional dioxane (10 mL) was added. After stirring at ambient temperature for 1.5 hours the mixture was concentrated in vacuo. The resulting solid was suspended in dioxane (20 mL) and retreated with a solution of 4N HCl in dioxane (10 mL). The mixture was stirred at ambient temperature for 1 hour, methanol (1 mL) was added and stirring was continued at ambient temperature. After 1 hour, the mixture was concentrated in vacuo to give the amine as a white solid (4.09 g, quantitative yield).

Part C: To a suspension of the amine of part B (4.00 g, 8.96 mmol) in acetonitrile (20 mL) were added propargyl bromide (1.05 mL, 80% solution in toluene, 9.41 mmol) and $K_2CO_3$ (2.60 g, 18.82 mmol). The resulting mixture was stirred at ambient temperature for 18 hours, filtered through a pad of Celite®, washing with ethyl acetate, and then the filtrate was concentrated in vacuo to provide the N-propargyl amine as a sticky foam (4.14 g, quantitative yield).

Part D: To a suspension of the N-propargyl amine of part C (4.14 g, 8.96 mmol) in tetrahydrofuran (20 mL) was added potassium trimethylsilanolate (1.26 g, 9.86 mmol). The resulting mixture was stirred at ambient temperature for 17 hours and additional tetrahydrofuran (5 mL) and potassium trimethylsilanolate (0.350 g, 2.73 mmol) were added. After stirring at ambient temperature for 4 hours, additional tetrahydrofuran (5 mL) was added and stirring was continued at ambient temperature for 24 hours. Additional potassium trimethylsilanolate (0.115 g, 0.896 mmol) was added and the mixture was stirred at ambient temperature for 24 hours, at which time, additional potassium trimethylsilanolate was added and the resulting mixture was stirred at ambient temperature for another 24 hours. The tetrahydrofuran was removed and the residue was suspended in dichloromethane (20 mL).

To the dichloromethane suspension were added N-methylmorpholine (2.96 mL, 26.9 mmol) and O-tetrahydro-2H-pyran-2-yl-hydroxylamine (1.15 g, 9.86 mmol), followed by PyBroP® (5.01 g, 10.75 mmol). The resulting mixture was stirred at ambient temperature overnight and then concentrated in vacuo. The residue was partitioned between $H_2O$ and ethyl acetate. The organic layer was washed with saturated NaCl and dried over $Na_2SO_4$. Chromatography (on silica, ethyl acetate/hexane) provided the protected hydroxamate as an off-white foam (3.29 g, 69%).

Part E: To a solution of the protected hydroxamate of part D (3.27 g, 6.13 mmol) in dioxane (21 mL) and methanol (7 mL) was added a solution of 4N HCl in dioxane (10 mL). The resulting mixture was stirred at ambient temperature for 4 hours and then diethyl ether (75 mL) was added. The solids were collected by filtration, washing with diethyl ether, to give the title compound as an off-white solid (2.95 g, 99%). MS $MH^+$ calculated for $C_{21}H_{22}O_5N_2SCl$: 449, found 449.

EXAMPLE 86

Preparation of 4-[[4-(phenylthio)-phenyl]-sulfonyl]-N-hydroxy-4-piperidine-carboxamide, Monohydrochloride

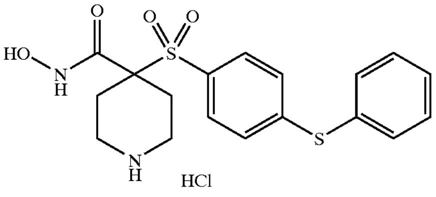

Part A: To a solution of the sulfone of part D, Example 79 (0.500 g, 1.25 mmol) in N,N-dimethylformamide (3.0 mL) were added thiophenol (0.154 mL, 1.50 mmol) and $K_2CO_3$ (0.518 g, 3.75 mmol). The resulting mixture was stirred at ambient temperature for 24 hours and then concentrated in vacuo. The residue was partitioned between $H_2O$ and ethyl acetate. The organic layers were washed with saturated NaCl and dried over $Na_2SO_4$. Chromatography (on silica, ethyl acetate/hexane) provided the biaryl thioether as a clear sticky oil (0.480 g, 78%).

Part B: To a solution of the biaryl thioether of part A( 2.01 g, 4.09 mmol) in tetrahydrofuran (40 mL) was added potassium trimethylsilanolate (0.682 g, 5.21 mmol) . The resulting mixture was stirred at ambient temperature for 23 hours and then concentrated in vacuo. The residue was then suspended in dichloromethane (20 mL) then N-methylmorpholine (1.35 mL, 12.27 mmol) and 50% aqueous hydroxylamine (0.265 mL, 4.50 mmol) were added, followed by PyBrOP® (2.29 g, 4.91 mmol). The resulting mixture was stirred at ambient temperature for 16 hours and then concentrated in vacuo. The residue was partitioned between ethyl acetate and $H_2O$. The organic layer was washed with saturated NaCl and dried over $Na_2SO_4$. A portion of the sample was subjected to reverse phase chromatography (on silica, acetonitrile/$H_2O$/trifluoroacetic acid) to give the hydroxamate as an off-white solid (0.190 g).

Part C: To a solution of the hydroxamate of part B (0.181 g, 0.367 mmol) in dioxane (5 mL) and methanol (1 mL) was added a solution of 4N HCl in dioxane (3 mL). The resulting mixture was stirred at ambient temperature for 3 hours and then concentrated in vacuo to give the title compound as an off-white solid (0.170 g, quantitative yield). MS $MH^+$ calculated for $C_{18}H_{21}O_4N_2S_2$: 393, found 393.

EXAMPLE 87

Preparation of 4-[(hydroxyamino)-carbonyl]-4-[[4-(phenylthio)phenyl]-sulfonyl]-1-piperidineacetic Acid, Monohydrochloride

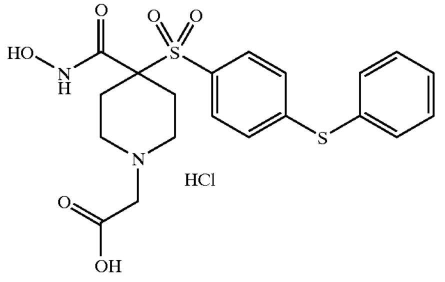

Part A: To a solution of the compound of Example 86 (0.322 g, 0.751 mmol) in acetonitrile (4.0 mL) were added tert-butylbromoacetate (0.121 mL, 0.751 mmol) and $K_2CO_3$ (0.207 g, 1.50 mmol). The resulting mixture was stirred at ambient temperature for 18 hours, filtered through a pad of Celite®, washing with ethyl acetate, and the filtrate was concentrated in vacuo. Reverse phase chromatography (on silica, acetonitrile/$H_2O$/trifluoroacetic acid) provided the tert-butyl ester as an off-white solid (0.150 g, 40%).

Part B: The tert-butyl ester of part A (0.145 g, 0.286 mmol) was treated with a solution of 4N HCl in dioxane (3.0 mL). The resulting mixture was stirred at ambient temperature for 7 hours, diethyl ether was added and the precipitate was collected by filtration. Reverse phase chromatography (on silica, acetonitrile/$H_2O$/HCl) provided the title compound as an off-white solid (0.060 g, 43%). MS $MH^+$ calculated for $C_{20}H_{23}O_6N_2S_2$: 451, found 451.

EXAMPLE 88

Preparation of 4-[[4-(4-chlorophenoxy)-phenyl]sulfonyl]-4-[(hydroxyamino)-carbonyl]-1-piperidineacetic acid, Monohydrochloride

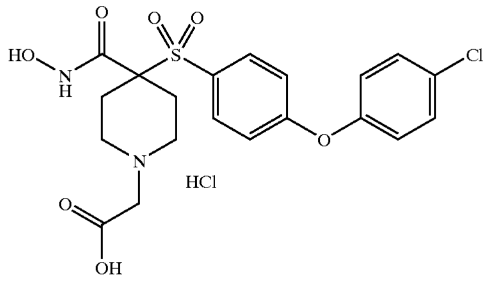

Part A: To a suspension of 4-bromopiperidine hydrobromide (40.0 g, 0.16 mol) in tetrahydrofuran (200 mL) was slowly added triethylamine (45.4 mL, 0.33 mol), followed by di-tert-butyl dicarbonate (37.4 g, 0.17 mol), which was added in several portions. The resulting mixture was stirred at ambient temperture for 17 hours then filtered and concentrated in vacuo. The solids were washed with hexanes and then collected by filtration to give the Boc-piperidine compound as an amber oil (45.8 g, >100%).

Part B: To a solution of 4-fluorophenol (25.0 g, 0.20 mol) in acetone (150 mL), degassed with $N_2$. was added $Cs_2CO_3$ (79.7 g, 0.25 mol). After degassing the resulting mixture with $N_2$ for 5 minutes, the Boc-piperidine compound of part A (43.1 g, 0.16 mol) was added. The resulting mixture was stirred at ambient temperature for 22 hours and then filtered through a pad of Celite®, washing with acetone. The residue was washed with diethyl ether and the solids were collected by filtration to provide the sulfide as a yellow oil (47.6 g, 93%).

Part C: To a solution of the sulfide of part B (47.3 g, 0.15 mol) in dichloromethane (350 mL), cooled to zero degrees Celsius, was added m-chloroperoxy-benzoic acid (80 g, 57–86%). Additional dichloromethane (50 mL) was added and the mixture was stirred at zero degrees Celsius for 1 hour and then for 1.5 hours at ambient temperature The reaction mixture was diluted with $H_2O$ and aqueous sodium meta-bisulfite (4.0 g in SO mL) was added. The mixture was concentrated in vacuo and then extracted with diethyl ether and ethyl acetate. The combined organic layers were washed with 10% $NH_4OH$, saturated NaCl and dried over $Na_2SO_4$. Recrystallization from ethyl acetate provided the sulfone as a white solid (18.9 g, 36%).

Part D: To a solution of the sulfone of part C (8.00 g, 23.3 mmol) in N,N-dimethylformamide (40 mL) were added 4-chlorophenol (3.59 g, 27.96 mmol) and $K_2CO_3$ (22.77 g, 69.90 mmol). The resulting mixture was heated at 60 degrees Celsius for 4 hours and then increased to 80 degrees Celsius for 7 hours. The reaction was cooled to ambient temperature and then concentrated in vacuo. To the residue was added $H_2O$ (100 mL) and the solids were collected by filtration to give the biaryl ether as an off-white solid (10.5 g, 99%).

Part E: To a solution of the biaryl ether of part D (5.00 g, 11.1 mmol) in tetrahydrofuran (50 mL), cooled to zero degrees Celsius, was added lithium bis(trimethylsilyl)amide (13.3 mL, 1M in tetrahydrofuran, 13.3 mmol), at such a rate that the temperature of the reaction mixture never exceeded 2 degrees Celsius. The resulting mixture was stirred at zero degrees Celsius for 30 minutes, then dimethyl carbonate (1.40 mL, 16.6 mmol) was slowly added at such a rate that the temperature of the reaction mixture never exceeded 2 degrees Celsius. The resulting mixture was then slowly permitted to warm to ambient temperature.

After 17 hours, the reaction was recooled to zero degrees Celsius and additional lithium bis(trimethylsilyl)amide (5.50 mL, 1M in tetrahydrofuran, 5.50 mmol) was slowly added at a rate such that the temperature of the reaction never exceeded 2 degrees Celsius. After stirring for 30 minutes, dimethyl carbonate (0.048 mL, 0.570 mmol) was added and stirring was continued at zero degrees Celsius for 45 minutes. Additional lithium bis(trimethylsilyl)amide (0.500 mL, 1M in tetrahydrofuran, 0.500 mmol) was slowly added and after 1 hour additional dimethyl carbonate (0.010 mL, 0.119 mmol) was added. After stirring at zero degrees Celsius for 20 minutes, saturated $NH_4Cl$ was added and the reaction mixture was then concentrated in vacuo. The residue was diluted with $H_2O$ and extracted with ethyl acetate. The combined organic layers were washed with saturated NaCl and dried over $Na_2SO_4$. Recrystallization from methanol provided the methyl ester as a white crystalline solid (3.56 g, 63%).

Part F: To a solution of the methyl ester of part E (3.54 g, 6.94 mmol) in dioxane (18 mL) and methanol (6 mL) was added a solution of 4N HCl in dioxane (10 mL). The resulting mixture was stirred at ambient temperature for 5 hours and then concentrated in vacuo to provide the amine as an off-white solid (3.10 g, quantitative yield).

Part G: To a solution of the amine o. part F (1.50 g, 3.36 mmol) in acetonitrile (15 mL) were added tert-butylbromoacetate (0.570 mL, 3.53 mmol) and $K_2CO_3$ (1.16 g, 8.40 mmol). The resulting mixture was stirred at ambient temperature for 3 hours, then filtered through a pad of Celite®, washing with ethyl acetate. The filtrate was concentrated in vacuo to provide the tert-butyl ester as a pale yellow oil (1.83 g, >100%).

Part H: To a solution of the tert-butyl ester of part G (1.76 g, 3.36 mmol) in tetrahydrofuran (15 mL) was added potassium trimethylsilanolate (0.475 g, 3.70 mmol). The resulting mixture was stirred at ambient temperature overnight (about 18 hours) and additional tetrahydrofuran (10 mL) was added. After stirring at ambient temperature overnight (about 18 hours), additional potassium trimethylsilanolate (0.475 g, 3.70 mmol) was added. The resulting mixture was stirred at ambient temperature for 4 hours then diluted with $H_2O$. The reaction mixture was acidified (pH-7) with 1N HCl and then concentrated in vacuo. The solids were washed with diethyl ether and then with $H_2O$ to provide the acid as an off-white solid (0.597 g, 32%).

Part I: To a suspension of the acid of part H (0.597 g, 1.17 mmol) in dichloromethane (5 mL) was added N-methylmorpholine (0.386 mL, 3.51 mmol) and O-tetrahydro-2H-pyran-2-yl-hydroxylamine (0.151 g, 1.29 mmol), followed by PyBroP® (0.655 g, 1.40 mmol). The resulting mixture was stirred at ambient temperature overnight (about 18 hours) and then concentrated in vacuo. The residue was partitioned between $H_2O$ and ethyl acetate. The organic layer was washed with saturated NaCl and dried over $Na_2SO_4$. Chromatography (on silica, ethyl acetate/hexane) provided the protected hydroxamate as a white foam (0.510 g, 72%).

Part J: The protected hydroxamate of part I (0.510 g, 0.837 mmol) was treated with a solution of 4N HCl in dioxane (10 mL). The resulting mixture was stirred at ambient temperature for 24 hours, then diethyl ether (20 mL) was added and the solids were collected by filtration to provide the title compound as a white solid (0.370 g, 87%). MS $MH^+$ calculated for $C_{20}H_{22}O_7N_2SCl$: 469, found 469.

EXAMPLE 89

Preparation of 4-[[4-(4-chlorophenoxy)-phenyl]sulfonyl]-N-hydroxy-1-[2-(4-morpholinyl)ethyl]-4-piperidine-carboxamide, Dihydrochloride

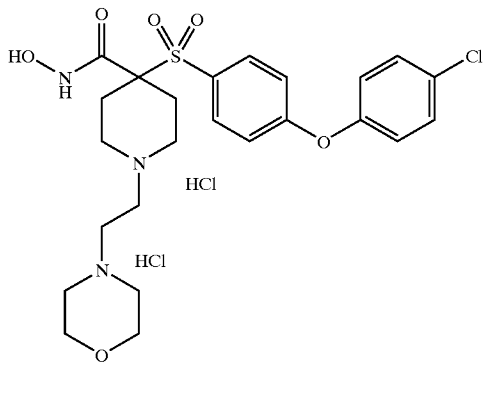

Part A: To a solution of the amine of part F, Example 88 (1.00 g, 2.24 mmol) in acetonitrile (10 mL) were added 4-(2-chloroethyl)morpholine (0.438 g, 2.35 mmol) and $K_2CO_3$ (1.24 g, 8.96 mmol). The resulting mixture was stirred at ambient temperature for 1.5 hours then a catalytic amount of NaI was added and stirring was continued at ambient temperature for 21 hours. The temperature of the reaction mixture was then increased to 60 degrees Celsius for 29 hours. After cooling to ambient temperature, the reaction mixture was filtered through a pad of Celite®, washing with ethyl acetate. The filtrate was concentrated in vacuo to provide the ester as an oily solid (1.15 g, 98%).

Part B: To a solution of the ester of part A (1.15 g, 2.20 mmol) in tetrahydrofuran (10 mL) was added potassium trimethylsilanolate (0.579 g, 4.51 mmol). The reaction mixture was stirred at ambient temperature for 4 hours then additional tetrahydrofuran (10 mL) was added and stirring was continued at ambient temperature overnight (about 18 hours). The reaction mixture was diluted with $H_2O$ (10 mL) and acidified (pH-7) with 1N HCl. The resulting precipitate was collected by filtration to provide the acid as a gray solid (0.753 g, 72%).

Part C: To a suspension of the acid of part B (0.750 g, 1.47 mmol) in dichloromethane (7 mL) were added N-methylmorpholine (0.500 mL, 4.55 mmol), and O-tetrahydro-2H-pyran-2-yl-hydroxylamine (0.198 g, 1.62 mmol), followed by PyBroP® (0.822 g, 1.76 mmol). The resulting mixture was stirred at ambient temperature for 24 hours then additional N-methylmorpholine (0.242 mL, 2.21 mmol), O-tetrahydro-2H-pyran-2-yl-hydroxylamine (0.052 g, 0.441 mmol) and PyBroP® (0.343 g, 0.735 mmol) were added. The resulting mixture was stirred at ambient temperature for 23 hours and then additional O-tetrahydro-2H-pyran-2-yl-hydroxylamine (0.017 g, 0.145 mmol) and PyBroP® (0.073 g, 0.157 mmol) were added. The resulting mixture was stirred at ambient temperature overnight (about 18 hours) and then concentrated in vacuo. The residue was partitioned between $H_2O$ and ethyl acetate. The organic layer was washed with saturated NaCl and dried over $Na_2SO_4$. Chromatography (on silica, methanol/chloroform) provided the protected hydroxamate as an off-white solid (0.750 g, 84%).

Part D: The protected hydroxamate of part C (0.730 g, 1.20 mmol) was treated with a solution of 4N HC1 in dioxane (10 mL) and methanol (1 mL). The resulting mixture was stirred at ambient temperature for 1 hour, then diethyl ether (20 mL) was added and the solids were collected by filtration to provide the title compound as a pale yellow solid (0.625 g, 87%). MS $MH^+$ calculated for $C_{24}H_{31}O_6N_3SCl$: 525, found 525.

EXAMPLE 90

Preparation of 4-[[4-(4-chlorophenoxy)-phenyl]sulfonyl]-$N^4$-hydroxy-$N^1$-(1-methylethyl)-1,4-piperidine Dicarboxamide

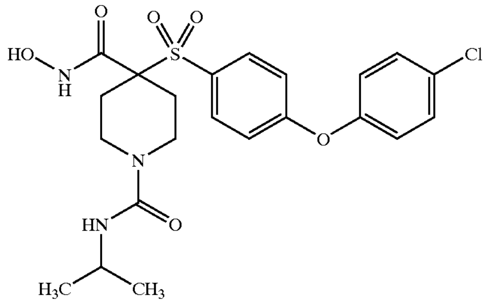

Part A: To a suspension of the amine of part F, Example 88 (0.600 g, 1.34 mmol) in dichloromethane (5 mL) were added triethylamine (0.411 mL, 2.95 mmol) and isopropyl isocyanate (0.198 mL, 2.01 mmol). The resulting mixture was stirred at ambient temperature for 2 hours then diluted with dichloromethane (50 mL). The mixture was washed with $H_2O$, saturated NaCl and dried over $Na_2SO_4$ to give the urea as an off-white solid (0.670 g, >100%).

Part B: To a solution of the urea of part A (0.640 g, 1.29 mmol) in tetrahydrofuran (10 mL) was added potassium trimethylsilanolate (0.199 g, 1.55 mmol). The resulting mixture was stirred at ambient temperature for 17 hours at which time additional potassium trimethylsilanolate (0.015 g, 0.117 mmol) was added. The resulting mixture was stirred for an additional 24 hours then the tetrahydrofuran was removed by blowing N. over the mixture. To a suspension of the residue in dichloromethane (5 mL) were added N-methylmorpholine (0.426 mL, 3.87 mmol) and O-tetrahydro-2H-pyran-2-yl-hydroxylamine (0.181 g, 1.55 mmol), followed by PyBroP® (0.902 g, 1.94 mmol). The resulting mixture was stirred at ambient temperature for 7 hours and then concentrated in vacuo. The residue was partitioned between $H_2O$ and ethyl acetate. The organic layer was washed with saturated NaCl and dried over $Na_2SO_4$. Chromatography (on silica, ethyl acetate/hexane) provided the protected hydroxamate as an off-white solid (0.330 g, 44%).

Part C: To a solution of the protected hydroxamate of part B (0.330 g, 0.569 mmol) in dioxane (3 mL) and methanol (1 mL) was added a solution of 4N HCl in dioxane (10 mL). The resulting mixture was stirred at ambient temperature for 3.5 hours then diethyl ether was added. The solids were collected by filtration to give the title compound as a white solid (0.259 g, 92%). MS $MH^+$ calculated for $C_{22}H_{27}O_6N_3SCl$: 496, found 496.

EXAMPLE 91

Preparation of 4-[(4'-chloro[1,1'-biphenyl]-4-yl) sulfonyl]-N-hydroxy-4-piperidinecarboxamide, Monohydrochloride

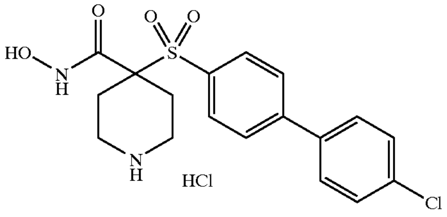

Part A: To a solution of 4-bromothiophenol (16.98 g, 89.80 mmol) in acetone (200 mL), degassed with $N_2$, was added $K_2CO_3$ (12.41 g, 89.80 mmol). After degassing the resulting mixture with $N_2$ for 5 minutes, the Boc-piperidine compound of part A, Example 88 (21.57 g, 81.64 mmol) was added. The resulting mixture was stirred at ambient temperature for 19 hours and then filtered through a pad of Celite®, washing with acetone. The residue was washed with diethyl ether and the solids were collected by filtration to provide the sulfide as a green oil (31.7 g, >100%).

Part B: To a solution of the sulfide of part A (31.68 g, 81.64 mmol) in dichloromethane (200 mL), cooled to zero degrees Celsius, was added m-chloroperoxybenzoic acid (56.35 g, 50-60%, 163.28 mmol). The resulting mixture became very thick, and additional dichloromethane (100 mL) was added. The mixture was stirred at zero degrees Celsius for 1.5 hours and then at ambient temperature for 1.5 hours. The reaction mixture was diluted with $H_2O$ (300 mL) and aqueous sodium meta-bisulfte (8.00 g, 42.08 mmol in 50 mL of $H_2O$) was added. The dichloromethane was removed in vacuo and the aqueous reaction mixture was extracted with ethyl acetate. The combined organic layers were washed with 10% $NH_4OH$, saturated NaCl and dried over $Na_2SO_4$. Concentration in vacuo provided the sulfone as a yellow oil (33.42 g, >100%).

Part C: To a solution of the sulfone of part B (7.80 g, 19.34 mmol) in tetrahydrofuran (100 mL), cooled to zero degrees Celsius, was added lithium bis(trimethylsilyl)amide (23.8 mL, 1M in tetrahydrofuran, 23.8 mmol) at such a rate that the temperature of the reaction never exceeded 2 degrees Celsius. After stirring at zero degrees Celsius for 30 minutes a solution of methyl chloroformate (2.30 mL, 29.8 mmol) in tetrahydrofuran (5 mL) was added at such a rate that the temperature of the reaction never exceeded 2 degrees Celsius. The resulting mixture was then slowly allowed to warm to ambient temperature. The mixture was diluted with saturated $NH_4Cl$ and the tetrahydrofuran was removed in vacuo. The aqueous layer was extracted with ethyl acetate. The combined organic layers were washed with saturated NaCl and dried over $Na_2SO_4$. Chromatography (on silica, ethyl acetate/hexane) provided the ester as a yellow solid (6.33 g, 69%).

Part D: To a solution of the ester of part C (4.74 g, 10.28 mmol) in dimethoxyethane (50 mL) were added 4-chlorophenylboronic acid (1.77 g, 11.30 mmol), aqueous $Cs_2CO_3$ (25 mL, 2.0 M, 50.0 mmol) and tetrakis (triphenylphosphine)palladium (0) (1 g). The resulting mixture was stirred at ambient temperature for 3 days. The reaction mixture was filtered through a pad of Celite®, washing with ethyl acetate, and the filtrate was concentrated in vacuo. Chromatography (on silica, ethyl acetate/hexane) provided the biphenyl compound as an off-white solid (4.16 g, 82%).

Part E: To a solution of the biphenyl compound of part D (1.50 g, 3.04 mmol) in tetrahydrofuran (10 mL) was added potassium trimethylsilanolate (0.468 g, 3.65 mmol). The resulting mixture was stirred at ambient temperature for 1 hour, additional tetrahydrofuran (5 mL) was added and the reaction mixture was stirred at ambient temperature overnight (about 18 hours). Additional tetrahydrofuran (15 mL) was added and the mixture was stirred for another 26 hours at ambient temperature. Additional potassium trimethylsilanolate (0.040 g, 0.304 mmol) was added and the mixture was stirred at ambient temperature overnight (about 18 hours) and then the solvent was removed by blowing $N_2$ over the reaction mixture.

To a suspension of the residue in dichloromethane (20 mL) were added added N-methylmorpholine (1.00 mL, 9.12 mmol), O-tetrahydro-2H-pyran-2-yl-hydroxylamine (0.427 g, 3.65 mmol), followed by PyBrop® (2.13 g, 4.56 mmol). The resulting mixture was stirred at ambient temperature for 24 hours and then concentrated in vacuo. The residue was partitioned between $H_2O$ and ethyl acetate. The organic layer was washed with saturated NaCl and dried over $Na_2SO_4$. Chromatography (on silica, ethyl acetate/hexane) provided the protected hydroxamate as a white solid (1.25 g, 71%).

Part F: To a solution of the protected hydroxamate of part E (1.25 g, 2.16 mmol) in dioxane (3 mL) and methanol (1 mL) was added a solution of 4N HCl in dioxane (10 mL). The resulting mixture was stirred at ambient temperature for 3.5 hours, then diethyl ether (20 mL) was added. The solids were collected by filtration to give the title compound as a white solid (0.900 g, 97%). MS $MH^+$ calculated for $C_{18}H_{20}O_4N_2SCl$: 395, found 395.

EXAMPLE 92

Preparation of N-hydroxy-4-[[4-(methylphenylamino)phenyl]sulfonyl]-4-piperidinecarboxamide, Monohydrochloride

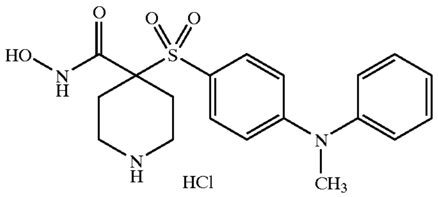

Part A: To a solution of the ester of part C, Example 91 (1.00 g, 2.17 mmol) in toluene (4 mL) were added N-methylaniline (0.282 mL, 2.60 mmol), $Cs_2CO_3$ (0.990 g, 3.04 mmol), tris(dibenzylideneacetone)-dipalladium(o) (0.018 g, 0.02 mmol) and (R)-(+)-2,2'-bis (diphenylphosphino)1,1'-binaphthyl (BINAP; 0.021 g, 0.033 mmol). The resulting mixture was heated to 100 degrees Celsius for 20 hours. After cooling to ambient temperature, diethyl ether was added, the mixture was filtered through a pad of Celite®, washing with diethyl ether, and the filtrate was concentrated in vacuo. Chromatography (on silica, ethyl acetate/hexane) provided the aniline as a yellow sticky gum (0.930 g, 88%).

Part B: To a solution of the aniline of part A (0.930 g, 1.90 mmol) in tetrahydrofuran (10 mL) was added potassium trimethylsilanolate (0.293 g, 2.28 mmol). The resulting mixture was stirred at ambient temperature for 19 hours and then additional potassium trimethylsilanolate (0.024 g, 0.190 mmol) was added. After stirring at ambient temperature overnight (about 18 hours) the solvent was removed by blowing $N_2$ over the mixture.

To a suspension of the residue in dichloromethane (10 mL) were added added N-methylmorpholine (0.627 mL, 5.70 mmol), O-tetrahydro-2H-pyran-2-yl-hydroxylamine (0.267 g, 2.28 mmol), followed by PyBroP® (1.33 g, 2.85 mmol). The resulting mixture was stirred at ambient temperature for 2 days and then concentrated in vacuo. The residue was partitioned between $H_2O$ and ethyl acetate. The organic layer was washed with saturated NaCl and dried over $Na_2SO_4$. Chromatography (on silica, ethyl acetate/hexane) provided the protected hydroxamate as a white solid (0.860 g, 79%).

Part C: To a solution of the protected hydroxamate of part B (0.890 g, 1.55 mmol) in dioxane (3 mL) and methanol (1 mL) was added a solution of 4N HCl in dioxane (5 mL). The resulting mixture was stirred at ambient temperature for 1 hour, then diethyl ether (15 mL) was added. The solids were collected by filtration to give the title compound as a white solid (0.529 g, 80%). MS $MH^+$ calculated for $C_{19}H_{24}O_4N_3S$: 390, found 390.

EXAMPLE 93

Preparation of 4-[[4-(4-chlorophenoxy)-phenyl]sulfonyl]-N-hydroxy-4-piperidinecarboxamide, Monohydrochloride

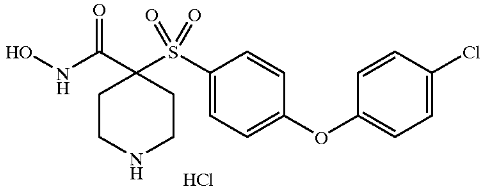

Part A: To a suspension of resin I (4.98 g, 5.87mmol) in 1-methyl-2-pyrrolidinone (45 mL), in a peptide flask, were added the acid of part A, Example 83 (4.55 g, 11.74 mmol), benzotriazole-1-yl-oxy-tris-pyrrolidino-phosphonim hexafluorophosphate (6.11 g, 11.74 mmol) and N-methylmorpholine (2.58 mL, 23.48 mmol). The resulting mixture was agitated at ambient temperature for 14 hours. The resin was then collected by filtration, the filtrate was removed and set aside, and the resin was washed with N,N-dimethylformamide, $H_2O$, N,N-dimethylformamide, methanol, dichloromethane and finally with diethyl ether. The resin was dried in vacuo at ambient temperature to give the resin bound p-fluorosulfone as a yellow solid (6.72 g, 95%).

The filtrate was diluted with $H_2O$ and extracted with ethyl acetate. The aqueous layer was acidified (pH-2.0) with 2N HCl and then extracted with ethyl acetate. The organic layer was washed with saturated NaCl and dried over $Na_2SO_4$. The resulting residue was dissolved in 1-methyl-2-pyrrolidinone (40 mL), the above resin was added, followed by N-methylmorpholine (1.50 mL, 13.64 mmol) and benzotriazole-1-yl-oxy-tris-pyrrolidino-phosphonim hexafluorophosphate (3.05 g, 5.86 mmol). The resulting mixture was agitated at ambient temperature for 3.5 hours. The resin was then collected by filtration and washed with N,N-dimethylformamide, $H_2O$, N,N-dimethylformamide, methanol, dichloromethane and finally with diethyl ether. The resin was dried in vacuo at ambient temperature to give the resin bound p-fluorosulfone as a pale orange solid (6.34 g, 89%). The loading (0.78 mmol/g) was determined by cleaving a small portion of the resin bound p-fluorosulfone with 95% trifluoroacetic acid/$H_2O$.

Part B: To a suspension of the resin bound p-fluorosulfone (0.700 g, 0.546 mmol) in 1-methyl-2-pyrrolidinone (3 mL) was added p-chlorophenol (0.702 g, 5.46 mmol) and $Cs_2CO_3$ (1.78 g, 5.46 mmol). The resulting mixture was heated to 110 degrees Celsius for 13 hours. The resin was then collected by filtration and washed consecutively with N,N-dimethylformamide, $H_2O$, N,N-dimethylformamide, 2N HCl N,N-dimethylformamide, methanol, and dichloromethane. The resulting resin was resubjected to the above reaction conditions for 3 hours. The resin was then collected by filtration and washed consecutively with N,N-dimethylformamide, $H_2O$, N,N-dimethylformamide, 2N HCl, N,N-dimethylformamide, methanol, and dichloromethane. The solid was dried in vacuo at ambient temperature to provide the resin bound hydroxamate as an orange solid (0.692 g, 91%).

Part C: The resin bound hydroxamate of part B (0.692 g, 0.540 mmol) was treated with 95% trifluoroacetic acid/$H_2O$ (3 mL) for 1 hour at ambient temperature. The resin was filtered and washed with 95% trifluoroacetic acid/$H_2O$ (3 mL) and then dichloromethane (2×3 mL). The filtrate was then evaporated. Reverse phase chromatography (on silica, acetonitrile/$H_2O$/trifluoroacetic acid) provided the hydroxamate. The resulting solid was dissolved in acetonitrile (5 mL) and $H_2O$ (0.5 mL) and treated with concentrated HCl. The resulting mixture was stirred at ambient temperature for 5 minutes and the concentrated in vacuo to provide the title compound as an off-white solid (0.220 g, 91%). MS $MH^+$ calculated for $C_{18}H_{20}O_5N_2SCl$: 411, found 411.

EXAMPLE 94

Preparation of Tetrahydro-N-hydroxy-4-[(4-phenoxyphenyl)sulfonyl]-2H-pyran-4-carboxamide

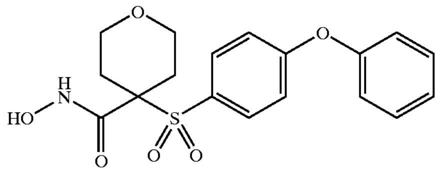

Part A: To a stirred solution of the methyl ester compound of Example 55, part C, (0.96 g, 3.2 mmol) in N,N-dimethylformamide (30 mL) was added phenol (0.3 g, 3.2 mmol), followed by cesium carbonate (3.2 g, 10 mmol). The resulting composition was heated to 70 degrees Celsius for 5 hours. The solution remained at ambient temperature for 18 hours, was diluted with $H_2O$ and extracted with 10 ethyl acetate. The organic layer was washed with half-saturated NaCl and dried over sodium sulfate.

The solvent was removed by rotary evaporation to yield the desired phenoxy compound (1.1 g, 92%).

Part B: Sodium hydroxide (1 g, 25 mmol) was added to a solution of the phenoxy compound of part A (1.1 g, 2.9 mmol) in THF (10 mL) and ethanol (10 mL). The resulting solution was stirred at ambient temperature for 1 hour. The solution was then heated to 80 degrees Celsius for 1 hour. The solvent was removed by rotary evaporation and the resulting sodium salt was acidified with 1 N HCl (50 mL) and extracted with ethyl acetate. The organic layer was dried over $Na_2SO_4$. The solvent was removed by rotary evaporation to yield the desired phenoxy carboxylic acid (1.1 g, 99%).

Part C: To a stirred solution of the phenoxy carboxylic acid of part B (1.1 g, 3 mmol) in DMF (7 mL) was added N-hydroxybenzotriazole-$H_2O$ (0.623 g, 4.6 mmol), followed by 1-[3-(dimethylamino)propyl]-3-ethylcarbodiimide hydrochloride (0.634 g, 3.3 mmol). After 10 minutes, a 50% aqueous hydroxylamine solution was added (2 mL, 30 mmol) and the solution was stirred at ambient temperature for 18 hours. The solution was diluted with saturated sodium bicarbonate and extracted with ethyl acetate. The organic layer was washed with $H_2O$ and followed by half-saturated NaCl and then dried over $Na_2SO_4$. Reverse phase chromatography (on silica, acetonitrile/$H_2O$) provided the title compound as a white solid (0.37 g, 33%). HRMS ($ES^+$) $MH^+$ for $C_{18}H_{19}NO_6S$ 378.1011. Found: 378.0994.

EXAMPLE 95

Preparation of Tetrahydro-N-hydroxy-4-[[4-(phenylthio)phenyl]sulfonyl]-2H-pyran-4-carboxamide

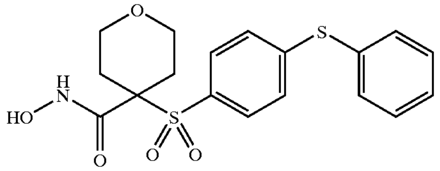

Part A: To a stirred solution under a nitrogen atmosphere of the methyl ester of Example 55, part C, (1.02 g, 3.4 mmol) in N,N-dimethylformamide (20 mL) was added thiophenol (0.37 g, 3.4 mmol), followed by cesium carbonate (3.3 g, 10.1 mmol) and the solution was heated to 70 degrees Celsius for 17 hours. The solution remained at ambient temperature for 1 hour, was diluted with $H_2O$ and extracted with ethyl acetate. The organic layer was washed with half-saturated NaCl and dried over $Na_2SO_4$. Chromatography (on silica, ethyl acetate/hexane) provided the S-phenyl compound (0.6 g, 41%).

Part B: To a stirred solution of the S-phenyl compound of part A (0.6 g, 1.4 mmol) in THF (10 mL) and ethanol (10 mL) was added NaOH (0.8 g, 20 mmol). The solution was heated to 80 degrees Celsius for 1 hour. The solution remained at ambient temperature for 18 hours. The solvent was removed by rotary evaporation, the resulting sodium salt was acidified with 1 N HCl (25 mL), extracted with ethyl acetate, and the organic layer was dried over sodium sulfate. The solvent was removed by rotary evaporation to yield the desired S-phenyl carboxylic acid (0.6 g, quantitative yield).

Part C: To a stirred solution of the S-phenyl carboxylic acid of part B (0.6 g, 1.5 mmol) in DMF (6 mL) was added N-hydroxybenzotriazole-$H_2O$ (0.30 g, 2.2 mmol), followed by 1-[3-(dimethylamino)-propyl]-3-ethylcarbodiimide hydrochloride (0.32 g, 1.6 mmol). After 10 minutes, a 50% aqueous hydroxylamine solution was added (1.5 mL, 22 mmol) and the solution was stirred at ambient temperature 42 hours. The solution was diluted with saturated sodium bicarbonate and extracted with ethyl acetate. The organic layer was washed with $H_2O$, followed by half-saturated NaCl and dried over sodium sulfate. Reverse phase chromatography (on silica, acetonitrile/$H_2O$) provided the title compound as a white solid (0.15 g, 26%). HRMS ($ES^+$) $MH^+$ for $C_{18}H_{19}NO_5S_2$ 394.0783. Found: 394.0753.

EXAMPLE 96

Preparation of 4-[[4-(3,4-dimethyl-phenoxy)phenyl]sulfonyl]tetrahydro-N-hydroxy-2H-pyran-4-carboxamide

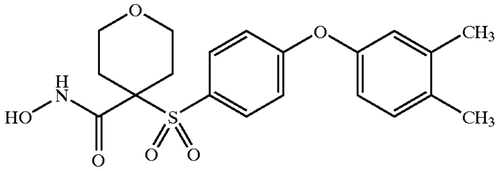

Part A: To a stirred solution of the methyl ester Example 55, part C, (1.04 g, 3.3 mmol) in N,N-dimethylformamide (30 mL) was added 3,4-dimethylphenol (0.4g, 3.3 mmol), followed by cesium carbonate (3.2 g, 10 mmol). The resulting solution was heated to 88 degrees Celsius for 5 hours. The solution was concentrated by rotary evaporation, diluted with $H_2O$ and extracted with ethyl acetate. The organic layer dried over $MgSO_4$. The solvent was removed by rotary evaporation to yield the desired dimethylphenoxy compound (1.2 g, 91%).

Part B: To a solution of the dimethylphenoxy compound of part A (1.2 g, 3 mmol) in THF (10 mL) and ethanol (10 mL) was added NaOH (1 g, 25 mmol). The resulting solution was heated to 80 degrees Celsius for 1 hour. The solvent was removed by rotary evaporation, the resulting sodium salt was acidified with 1 N HCl (50 mL) and extracted with ethyl acetate. The organic layer was dried over sodium sulfate. The solvent was removed by rotary evaporation to yield the desired dimethylphenoxy carboxylic acid (1.2 g, quantitative yield).

Part C: To a stirred solution of the dimethylphenoxy carboxylic acid of part B (1.2 g, 3 mmol) in DMF (7 mL) was added N-hydroxybenzotriazole-$H_2O$ (0.623 g, 4.6 mmol), followed by 1-[3-(dimethylamino)propyl]-3-ethylcarbodiimide hydrochloride (0.634 g, 3.3 mmol). After 10 minutes, a 50% aqueous hydroxylamine solution was added (2 mL, 30 mmol) and the solution was stirred at ambient temperature 18 hours. The solution was diluted with saturated sodium bicarbonate and extracted with ethyl acetate. The organic layer was washed with $H_2O$ and followed half-saturated NaCl and dried over $Na_2SO_4$. Reverse phase chromatography (on silica, acetonitrile/$H_2O$) provided the title compound as a white solid (0.52 g, 43%). HRMS ($ES^+$) $MH^+$ for $C_{20}H_{23}NO_6S$ 406.1324. Found: 406.1302.

EXAMPLE 97

Preparation of Tetrahydro-N-hydroxy-4-[[4-[(6-methyl-3-pyridinyl)oxy]phenyl)-sulfonyl]-2H-pyran-4-carboxamide, Monohydrochloride

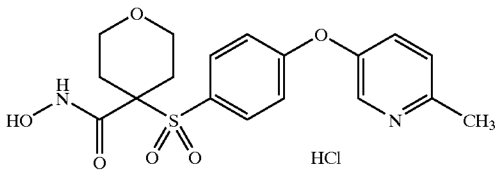

Part A: To a stirred solution of the methyl ester of Example 55, Part C, (1.02 g, 3.4 mmol) in N,N-dimethylformamide (20 mL) was added 5-hydroxy-2-methyl-pyridine (0.54 g, 5 mmol), followed by cesium carbonate (3.2 g, 10 mmol). The resulting solution was heated to 70 degrees Celsius for 5 hours. The solution remained at ambient temperature for 4 days, then was diluted with $H_2O$ and extracted with ethyl acetate. The organic layer was washed with half-saturated NaCl and dried over sodium sulfate. The solvent was removed by rotary evaporation to yield a heavy oil from which the desired white methyl pyridine compound crystallized at ambient temperature in vacuo (1.2 g, 94%).

Part B: To a solution of the methyl pyridine compound of part A (1.2 g, 3.2 mmol) in THF (13 mL) was added potassium trimethylsilanoate (0.5 g, 3.5 mmol). The resulting solution was stirred at ambient temperature for 18 hours, during which time a gel formed. The solvent was removed by rotary evaporation to yield the desired methyl pyridine carboxylic acid (1.4 g, quantitative yield).

Part C: To a stirred solution of the methyl pyridine carboxylic acid of part B (1.4 g, 3.2 mmol) in methylene chloride (10 mL) was added bromo-tris-pyrrolidino-phosphonium hexafluorophosphate (1.79 g, 3.8 mmol), followed by 4-methylmorpholine (0.97 g, 9.6 mmol), followed by O-tetrahydro-2H-pyran-yl-hydroxylamine (0.41 g, 3.5 mmol) and the solution was stirred at ambient temperature for 1.5 hours. The solution was filtered to remove a precipitate and the solvent was removed by rotary evaporation. Chromatography (on silica, ethyl acetate/hexane) provided the O-tetrahydropyran methyl pyridine as a white solid (1.48 g, 97%).

Part D: Methanol (3 mL) was added to a stirred solution of the O-tetrahydropyran methyl pyridine of part C (1.48 g, 3.1 mmol) in 4 N HCl in dioxane (5 mL). The solution was stirred at ambient temperature for 3 hours and poured into ethyl ether. The resulting precipitate was collected by vacuum filtration. Reverse phase chromatography (on silica, acetonitrile/$H_2O$/HCl ) provided the title compound as a white solid (0.64 g, 53%). HRMS ($ES^+$) $MH^+$ for $C_{18}H_{20}N_2O_6S$ 393.1120. Found: 393.1110.

EXAMPLE 98

Preparation of Tetrahydro-N-hydroxy-4-[[4-[(6-methyl-2-pyridinyl)oxy]phenyl]-sulfonyl]-2H-pyran-4-carboxamide

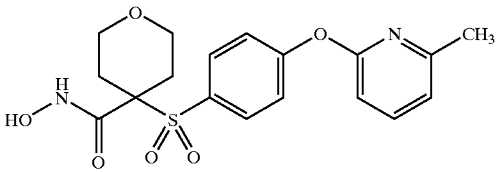

Part A: To a stirred solution of the methyl ester of Example 55, part C, (1.0 g, 3.3 mmol) in N,N-dimethylformamide (20 mL) was added 2-hydroxy-6-methyl-pyridine (0.54 g, 5 mmol), followed by cesium carbonate (3.2 g, 10 mmol). The resulting solution was heated to 70 degrees Celsius for 5 hours. The solution remained at ambient temperature for 11 hours, at which time additional 2-hydroxy-6-methyl-pyridine (0.3 g, 2.7 mmol) was added to the stirred solution and the resulting solution was heated to 70 degrees Celsius for 3 hours. The solution was concentrated by rotary evaporation, diluted with saturated NaCl in $H_2O$ and extracted with ethyl acetate. The organic layer was dried over sodium sulfate. The solvent was removed by rotary evaporation and chromatography (on silica, ethyl acetate/methanol) provided the desired methyl pyridine as a white solid (0.63 g, 49%).

Part B: To a solution of the methyl pyridine compound of part A (0.63 g, 1.6 mmol) in THF (13 mL) was added potassium trimethylsilanoate (0.5 g, 3.5 mmol). The resulting solution was stirred at ambient temperature for 18 hours. The precipitate that formed was removed by filtration, washed with methylene chloride and dried in vacuo to provide the methyl pyridine carboxylic acid potassium salt (0.4 g, 55%).

Part C: To a stirred solution of the methyl pyridine carboxylic acid potassium salt of part B (0.4 g, 0.9 mmol)in N,N-dimethylformamide (5 mL) was added bromo-tris-pyrrolidino-phosphonium hexafluorophosphate (0.5 g, 1 mmol), followed by 4-methylmorpholine (0.27 g, 2.6 mmol), followed by a 50% aqueous hydroxylamine solution (0.6 mL, 9 mmol). The resulting solution was stirred at ambient temperature 32 hours. The solution was concentrated by rotary evaporation and reverse phase chromatography (on silica, acetonitrile/$H_2O$) provided the title compound as a white solid (0.162 g, 47%). HRMS ($ES^+$) $MH^+$ for $C_{18}H_{20}N_2O_6S$ 393.1120. Found: 393.1119.

EXAMPLE 99

Preparation of tetrahydro-N-hydroxy-4-[[4-[4-(1H-imidazol-1-yl)phenoxy]phenyl]-sulfonyl]-2H-pyran-4-carboxamide, Monohydrochloride

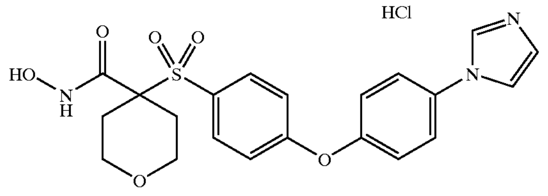

Part A: To a solution of the THP pyranfluoro compound of Example 55, part C, (2.0 g, 5.2 mmol ) in N,N-dimethylacetamide (6 mL) was added 4-(1,3-imidazole) phenol (12.9 g, 33.3 mmol), followed by cesium carbonate (32.5 g, 99.9 mmol). The reaction was heated at 65 degrees Celsius for twelve hours. Removing the dimethylacetamide in vacuo afforded a brown solid. Reverse phase chromatography (on silica, acetonitrile/water) gave the THP-protected product in solution.

Part B: A solution of 10% $HCl_{aq}$ (100 mL) was slowly added to the solution of the crude THP-protected product from A in acetonitrile/water (100 mL). After stirring overnight (about 18 hours), the acetonitrile was removed. The resultant precipitate was collected, giving the title compound as a brown solid (6.0 g, 41%). MS (FAB) $M^+H$ calculated for $C_{218}H_{21}N_3O_6S_1$: 444, found 444.

EXAMPLE 100

Preparation of 4-[[4-(4-chlorophenoxy)-phenyl] sulfonyl]-tetrahydro-N-hydroxy-2H-pyran-4-carboxamide

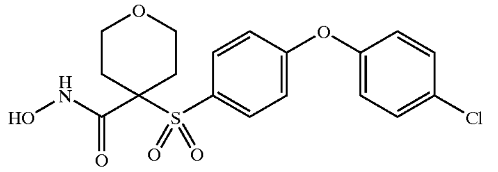

Part A: To a stirred solution of the THP pyranfluoro compound of Example 55, Part C, (2.9 g, 7.5 mmol) in N,N-dimethylformamide (15 mL) was added p-chlorophenol (1.93 g, 15 mmol), followed by cesium carbonate (7.3 g, 22.5 mmol). The resulting composition was heated to 90 degrees Celsius for 1.5 hours. The solution remained at ambient temperature for 18 hours with stirring, and dimethylformamide (20 mL) was added to the stirred solution, followed by cesium carbonate (2 g, 6.2 mmol). The resulting composition was heated to 95 degrees Celsius for 3 hours. The solution then remained at ambient temperature 20 hours, at which time it was diluted with $H_2O$ and extracted with ethyl acetate. The organic layer was washed with half-saturated NaCl and dried over sodium sulfate. The solvent was removed by rotary evaporation. Chromatography (on silica, ethyl acetate/hexane) provided the p-chloro phenoxyphenyl THP-protected hydroxamate compound (2.9 g, 78%).

Part B: To a solution of the p-chloro phenoxyphenyl THP-protected hydroxamate compound of part A (2.9 g, 5.7 mmol) in dioxane (5 mL) was added 4N HCl in dioxane (5 mL, 20 mmol), followed by methanol (7.5 mL). The resulting solution was stirred at ambient temperature for 1 hour. The solvent was removed by rotary evaporation. Reverse phase chromatography (on silica, acetonitrile/$H_2O$) provided the title compound as a white solid (1.35 g, 58%). MS (FAB) $MH^+$ for $C_{18}H_{18}NO_6SCl$ 412. Found: 412.

EXAMPLE 101

Preparation of 4-[[4-(3-chlorophenoxy)-phenyl] sulfonyl]tetrahydro-N-hydroxy-2H-pyran-4-carboxamide

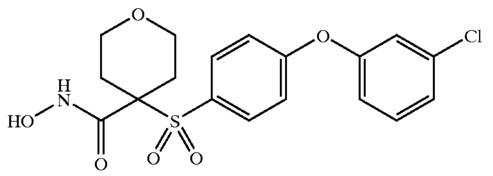

Part A: To a stirred solution of the THP pyranfluoro compound of Example 55, Part C, (5.0 g, 13 mmol) in N,N-dimethylformamide (20 mL) was added p-chlorophenol (5 g, 39 mmol), followed by cesium carbonate (17 g, 52 mmol). The resulting solution was heated to 95 degrees Celsius for 7 hours. The solution was maintained at ambient temperature for 7 hours, diluted with $H_2O$ and extracted with ethyl acetate. The organic layer was washed with half-saturated NaCl and dried over sodium sulfate. The solution was concentrated by rotary evaporation. Chromatography (on silica, ethyl acetate/hexane) provided the m-chloro phenoxyphenyl THP-protected hydroxamate compound (5.2 g, 82%).

Part B: To a solution of the m-chloro phenoxyphenyl THP-protected hydroxamate compound of part A (5.2 g, 10 mmol) in dioxane (5 mL) was added 4N HCl in dioxane (5 mL, 20 mmol), followed by methanol (10 mL). The resulting solution was stirred at ambient temperature for 1 hour. The solvent was removed by rotary evaporation to provide the title compound as a white solid (3.4 g, 79%). HRMS ($ES^+$) $M+NH_4^+$ for $C_{18}H_{18}NO_6SCl$ 429.0887. Found: 429.0880.

EXAMPLE 102

Preparation of methyl 4-[4-[(tetrahydro-4-[(hydroxyamino)carbonyl]-2H-pyran-4-yl]sulfonyl]-phenoxy]benzenepropanoate

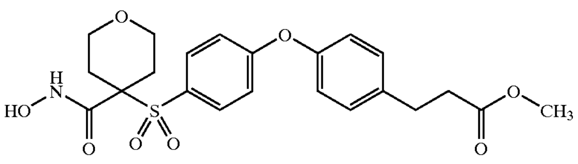

Part A: To a stirred solution of the THP pyranfluoro compound of Example 55, part C, (5.0 g, 13 mmol) in N,N-dimethylformamide (45 mL) was added methyl 3-(4-hydroxyphenyl)-propanoate (7 g, 39 mmol), followed by cesium carbonate (17 g, 52 mmol). The resulting composition was heated to 95 degrees Celsius for 7 hours. The solution then remained at ambient temperature for 7 hours. The solution was thereafter diluted with $H_2O$ and extracted with ethyl acetate. The organic layer was washed with half-saturated NaCl and dried over sodium sulfate. The solution was concentrated by rotary evaporation. Chromatography (on silica, ethyl acetate/hexane) provided the methyl propanoate phenoxyphenyl THP-protected hydroxamate compound (5.6 g, 79%).

Part B: To a solution of the methyl propanoate phenoxyphenyl THP-protected hydroxamate compound of part A (5.6 g, 10 mmol) in methanol (5 mL) was added 4N HCl in dioxane (5 mL, 20 mmol). The resulting solution was stirred at ambient temperature for 0.5 hours. The solvent was removed by rotary evaporation. The residue was dissolved in methylene chloride/ethyl acetate and the compound precipitated with hexane. The precipitate was washed with hexane and dried in vacuo to provide the title compound as a white solid (3.8 g, 80%). HRMS ($ES^+$) $M^+$ for $C_{22}H_{25}NO_8S$ 464.138. Found: 464.135.

EXAMPLE 103

Preparation of 4-[[4-[(4-fluorophenyl)-thio]phenyl] sulfonyl]tetrahydro-N-hydroxy-2H-pyran-4-carboxamide

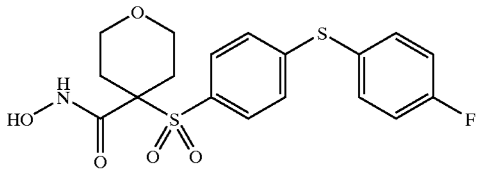

Part A: To a stirred solution under a nitrogen atmosphere of the THP pyranfluoro compound of Example 55, part C, (2.9 g, 7.5 mmol) in N,N-dimethylformamide (25 mL) was added cesium carbonate (4.9 g, 15 mmol), followed by 4-fluoro-thiophenol (1.9 g, 15 mmol). The resulting composition was heated to 95 degrees Celsius for 7 hours. Cesium carbonate was added (1.2 g, 3.8 mmol) after 1 hour of heating and again at two hours. The solution remained at ambient temperature for 9 hours, was concentrated by rotary evaporation, diluted with $H_2O$ containing 30% brine and extracted with ethyl acetate. The organic layer was washed with half-saturated NaCl and dried over sodium sulfate. The solution was concentrated by rotary evaporation. Chromatography (on silica, ethyl acetate/hexane) followed by reverse phase chromatography (acetonitrile/$H_2O$) provided the p-fluoro-phenyl-S-phenyl THP-protected hydroxamate compound (1.9 g, 55%).

Part B: To a solution of the p-fluoro-phenyl-S-phenyl THP-protected hydroxamate compound of part A (1.9 g, 4 mmol) in methanol (5 mL) was added 4N HCl in dioxane (5 mL, 20 mmol. The resulting solution was stirred at ambient temperature for 0.5 hours. The solvent was removed by rotary evaporation, the residue was dissolved in methylene chloride and precipitated with hexane. The precipitate was and dried in vacuo to provide the title compound as a white solid (1.5 g, 89%). HRMS ($ES^+$) $M+NH_4^+$ for $C_{18}H_{18}NO_5S_2F$ 429.0954. Found: 429.0948.

EXAMPLE 104

Preparation of Tetrahydro-N-hydroxy-4-[[4-(4-pyridinylthio)phenyl]sulfonyl]-2H-pyran-4-carboxamide, Monohydrochloride

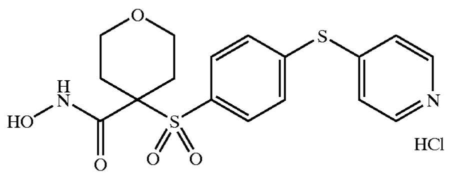

Part A: To a stirred solution of the THP pyranfluoro compound of Example 55, Part C, (2.9 g, 7.5 mmol) in N,N-dimethylformamide (20 mL) was added potassium carbonate (2.6 g, 19 mmol), followed by 4-mercaptopyridine (1.7 g, 15 mmol). The resulting composition was heated to 75 degrees Celsius for 5 hours. Potassium carbonate was added (0.26 g, 1.9 mmol) after 1 hour of heating and again at two hours. The solution remained at ambient temperature for 14 hours. The solution was concentrated by rotary evaporation, diluted with $H_2O$ containing 30% brine and extracted with ethyl acetate. The organic layer was washed with half-saturated NaCl and dried over $Na_2SO_4$. The solution was concentrated by rotary evaporation. Chromatography (on silica, ethyl acetate/hexane) provided the mercaptopyridine THP-protected hydroxamate compound (1.2 g, 33%).

Part B: To a solution of the mercaptopyridine THP-protected hydroxamate compound of part A (1.2 g, 2.5 mmol) in acetonitrile (20 mL) was added 12.5 N HCl (0.4 mL, 5 mmol), followed by methanol (3 mL). The resulting solution was stirred at ambient temperature for 1 hour. The precipitate was filtered, washed with methanol followed by ethyl ether and dried in vacuo to provide the title compound as a white solid (0.92 g, 86%). HRMS ($ES^+$) $M+NH_4^+$ for $CH_{17}H_{18}N_2O_5S_2$ 395.0735. Found: 395.0734.

EXAMPLE 105

Preparation of 4-[4-[[tetrahydro-4-[(hydroxyamino) carbonyl]-2H-pyran-4-yl]sulfonyl]phenoxy] benzenepronanoic Acid

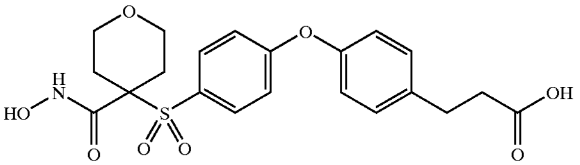

Part A: To a stirred solution of the title compound of Example 102 (0.1 g, 0.2 mmol) in methanol (0.5 mL) was added aqueous 1 M $Li(OH)_2$ (0.43 mL, 0.43 mmol). After standing at ambient temperature 24 hours, the solution was refluxed 20 hours. The solution was lyophilized to dryness and reverse phase chromatography provided the title compound as a white solid (9 mg, 9%). MS (FAB) $M+Li^+$ for $C_{21}H_{23}NO_8S$ 456. Found: 456.

EXAMPLE 106

Preparation of Tetrahydro-N-hydroxy-4-[[4-[1-(2-propynyl)-4-piperidinyl)-oxy]phenyl]sulfonyl]-2H-pyran-4-carboxamide, Monohydrochloride

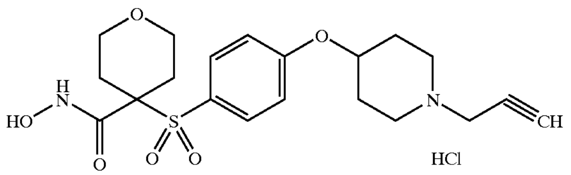

Part A: To a heat dried three-neck flask under a nitrogen atmosphere was added NaH (1.59 g of 60%, 40 mmol) slurried in N,N-dimethylformamide (50 mL). The slurry was chilled to zero degrees Celsius using an ice bath and N-Boc-4-hydroxy piperidine was added (8 g, 40 mmol) followed by a N,N-dimethylformamide rinse (10 mL). The ice bath was removed and the stirred solution permitted to reach ambient temperature over two hours. The stirred solution was again chilled to zero degrees Celsius and the methyl ester compound of Example 55, part C, (10 g, 33 mmol) dissolved in N,N-dimethylformamide (40 mL) was added. The ice bath was removed and the solution stirred at ambient temperature 48 hours. The solution was concentrated by rotary evaporation. The solution was diluted with $H_2O$ and extracted with ethyl acetate. The organic layer was dried over sodium sulfate. After chromatography (on silica, ethyl acetate/hexane/methanol), the crude N-Boc methyl ester was treated with 1 N HCl in methanol. The solvent was removed by rotary evaporation. The residue was then dissolved in acetonitrile (21 mL) to which $H_2O$ was added (21 mLs). Reverse phase chromatography (on silica, acetonitrile/$H_2O$) afforded the purified piperidine methyl ester as the HCl salt (4.9 g, 35%).

Part B: To a stirred suspension of the piperidine methyl ester HCl salt of part A (1.8 g, 4 mmol) in acetonitrile (24 mL) and was added potassium carbonate (1.8 g, 13 mmol), followed by propargyl bromide (0.58 mL of 80% solution, 5.2 mmol). The mixture was stirred at ambient temperature for 18 hours. The solution was concentrated by rotary evaporation, diluted with $H_2O$ and extracted with ethyl acetate. The organic layer was dried over $Na_2SO_4$ and concentrated by rotary evaporation. Chromatography (on silica, methylene chloride/methanol) provided the propargyl piperidine methyl ester compound (1.1 g, 63%).

Part C: To a solution of the propargyl piperidine methyl ester compound of part B (1.1 g, 2.7 mmol) in THF (3 mL) was added potassium trimethylsilanoate (0.57 g, 4 mmol). After 5 minutes, THF was added (12 mL), followed by a second addition of THF (15 mL) after 10 more minutes. The resulting solution was stirred at ambient temperature for 18 hours, during which a gel formed. The solvent was removed by rotary evaporation, and the residue was diluted with $H_2O$ and washed with ethyl acetate. The aqueous layer was acidified and chromatographed (on silica, acetonitrile/$H_2O$) to provide the desired propargyl piperidine carboxylic acid after lyophilization (0.64 g, 59%).

Part D: To a stirred solution of propargyl piperidine carboxylic acid of part C (0.64 g, 1.6 mmol) in N,N-dimethylformamide (5 mL) was added 1-hydroxybenzotriazole (0.3 g, 2.3 mmol), followed by 1-[3-(dimethylamino)propyl]-3-ethylcarbodiimide hydrochloride (0.33 g, 1.7 mmol), followed by O-tetrahydro-2H-pyran-2-yl-hydroxylamine (0.57 g, 4.8 mmol). The solution was stirred at ambient temperature 42 hours, concentrated by rotary evaporation, diluted with $H_2°$ and extracted with ethyl acetate. The organic layer was washed with saturated sodium bicarbonate, followed by brine and dried over $Na_2SO_4$. The solution was concentrated by rotary evaporation and chromatographed on reverse phase (on silica, acetonitrile/$H_2O$) to provide the title compound as a white solid upon lyophilization (0.2 g, 30%). HRMS ($ES^+$) $MH^+$ for $C_{20}H_{26}N_2O_6S$ 423.159. Found: 423.159.

EXAMPLE 107

Preparation of 4-[[4-[(l-acetyl-4-piperidinyl)oxy]phenyl]-sulfonyl]tetrahydro-N-hydroxy-2H-pyran-4-carboxamide

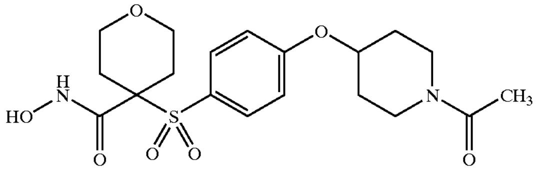

Part A: Acetic anhydride (1.7 g, 16 mmol) was added to a stirred suspension of the piperidine methyl ester HCl salt of Example 106, part A, (1.8 g, 4 mmol) in pyridine (2 mL). The mixture was stirred at ambient temperature for 20 minutes. The solution was concentrated by rotary evaporation and chromatographed (on silica, ethyl acetate/methanol) to provide the acetyl piperidine methyl ester compound (1.5 g, 83%).

Part B: To a solution of the acetyl piperidine methyl ester compound of part A (1.5 g, 3.3 mmol) in THF (5 mL) was added potassium trimethylsilanoate (0.86 g, 6 mmol). After 5 minutes, THF was added (15 mL), followed by a second addition of THF (15 mL) after 10 more minutes. The resulting solution was stirred at ambient temperature for 18 hours. The precipitate was isolated by filtration to provide the desired acetyl piperidine carboxylic acid (1.5 g, 98).

Part C: To a stirred solution of acetyl piperidine carboxylic acid of part B (0.9 g, 2 mmol) in dimethylacetamide (5 mL) was added bromo-tris-pyrrolidino-phosphonium hexafluorophosphate (1 g, 2.3 mmol), followed by 4-methylmorpholine (0.6 g, 6 mmol), followed by aqueous O-tetrahydro-2H-pyran-2-yl-hydroxylamine (1.5 mL, 23 mmol) and the solution was stirred at ambient temperature 48 hours.

Reverse-phase chromatography (on silica, $H_2O$/acetonitrile) provided title compound as a white solid (0.1 g, 12%). MS (FAB) $MH^+$ for $C_{19}H_{26}N_2O_7S$ 427. Found: 427.

EXAMPLE 108

Preparation of 4-[[4-(3-chloro-4-fluorophenoxy) phenyl]sulfonyl]-tetrahydro-N-hydroxy-2H-pyran-4-carboxamide

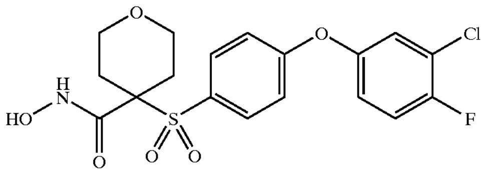

Part A: To a stirred solution of the THP pyranfluoro compound of Example 55, part C, (3.2 g, 7.7 mmol ) in N,N-dimethylacetamide (15 mL) was added the 3-chloro-4-fluorophenol (1.7 mL, 12 mmol), followed by cesium carbonate (5 g, 15.5 mmol). The reaction was heated at 95 degrees Celsius for 2 hours. Cesium carbonate (2.5 g, 8 mmol) was added, and the reaction was heated at 95 degrees Celsius for 6 hours. The solution remained at ambient temperature for 8 hours. The crude reaction was then filtered to remove the cesium chloride and precipitated product. The filter cake was suspended in $H_2O$ and acidified with HCl to pH=6. After foaming ceased, the precipitate was removed by filtration, washed with $H_2O$, dissolved in $H_2O$/acetonitrile and chromatographed over a reverse phase HPLC column ($H_2O$/aceronitrile) to give the 3-chloro-4-fluoro phenoxy THP-protected hydroxamate (1.4 g, 35%).

Part B: To a stirred solution of the 3-chloro-4-fluoro phenoxy THP-protected hydroxamate from part A (1.4 g, 2.7 mmol) in acetonitrile (10 mL) was added 1N aqueous HCl (10 mL). The solution was stirred at ambient temperature for 1 hour. The acetonitrile was evaporated off at ambient temperature under a steady stream of nitrogen until a heavy precipitate formed. The precipitate was filtered and the cake was washed with $H_2O$ followed by diethyl ether and dried under vacuum, giving the title compound as a white solid (12.5g, 96%). The compound was recrystallized from acetone/hexane, giving white crystals (10.9 g, 86%). HRMS (ES) $M+NH_4^+$ for $C_{18}H_{19}NO_6SFCl$ 447.079. Found: 447.080.

EXAMPLE 109

Preparation of tetrahydro-N-hydroxy-4-[[4-(4-phenoxy)phenyl]sulfonyl 2H-thiopyran-4-carboxaide

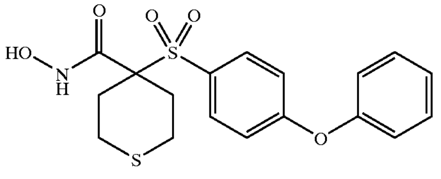

Part A: To a solution of the methylester thiopyran compound of Part C, Example So (MW 318, 3 g, 1.0 equivalents) in N,N-dimethylacetamide (DMA; 40 mL) were added cesium carbonate (12 g, 1.5 equivalents) and phenol (1.5 g). The mixture was heated to 95 degrees Celsius for 6 hours. After the reaction was cooled to ambient temperature, the reaction mixture was filtered and the N,N-dimethylacetamide was then removed via rotary evaporation. The residue was dissolved in 10% aqueous HCl (100mL) and extracted with ethyl acetate (2×). The ethyl acetate extract was dried over sodium sulfate and removed under reduced pressure to give an oil. The oil was purified on silica gel to give 2 g of methyl ester. The $^1H$ NMR, MS, and HPLC were consistent with the desired compound.

Part B: To a solution of the methyl ester compound of Part A (MW 392, 2 g) in THF (20 mL) was added potassium trimethylsilanoate (MW 128,1.6 g, 1.2 equivalents). The mixture stirred 2–3 hours at ambient temperature until a solid precipitate developed. After the hydrolysis was complete, N-methylmorpholine (2 mL) was added followed by PyBrop (2.3 g, 1.2 equivalents). The solution was stirred for 10 minutes, then aqueous hydroxylamine was added and stirring for an additional 2 hours. After complete reaction (2 hours) the solvent was removed via rotary evaporation. The residue was dissolved in water/acetonitrile, made acidic with TFA (pH=2), then purified on prep RPHPLC to give 1 g the title compound as a white solid. The $^1H$ NMR, MS, and HPLC were consistent with the desired compound. MS (CI) M+H calculated for $C_{18}H_{19}NO_5S_2$: 393, found 393.

EXAMPLE 110

Preparation of tetrahydro-N-hydroxy-4-[[4-(4-phenoxy)phenyl]sulfonyl 2H-sulfonyl pyran-4-carboxamide

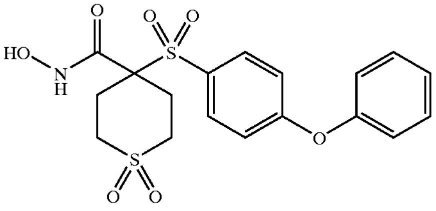

Part A: Water (50 mL) was added to a solution of the compound of Example 109, part A, (2 g) in tetrahydrofuran (50 mL). To this vigorously stirred mixture was added Oxone® (8 g, 3 equivalents) . The course of the reaction was monitored by RPHPLC. After 3 hours, water was added and the product was extracted with ethyl acetate (100 mL, 2×). The ethyl acetate was dried over sodium sulfate. After solvent was removed via reduced pressure, 1.8 g of the phenoxy methyl ester compound was obtained as a white solid. The $^1H$ NMR, MS, and HPLC were consistent with the desired compound.

Part B: To a solution of the phenoxy methyl ester compound of part A (MW 590, 2 g) in tetrahydrofuran (20 mL) was added potassium trimethylsilanoate (MW 128, 1.2 g, 1.2 equivalents). The mixture was stirred 2–3 hours until a solid precipitate developed. After the hydrolysis was complete, N-methylmorpholine (2 mL) was added followed by PyBrop (2.3 g, 1.2 equivalents). The solution was stirred for 10 minutes then aqueous hydroxylamine was added and with stirring for an additional 2 hours. After complete reaction, (2 hours) the solvent was removed via rotary evaporation. The residue was dissolved in water/acetonitrile, made acidic with trifluoroacetic acid (pH=2), then purified on prep RPHPLC to give 500 mg of the title compound as a white solid. The $^1H$ NMR, MS, and HPLC were consistent with the desired compound. MS (CI) M+H calculated for $C_{18}H_{19}NO_7S_2$: 425, found 425.

EXAMPLE 111

Preparation of tetrahydro-N-hydroxy-4-[[4-(4-phenoxy)phenyl]sulfonyl2H-sulfoxyl pyran-4-carboxamide

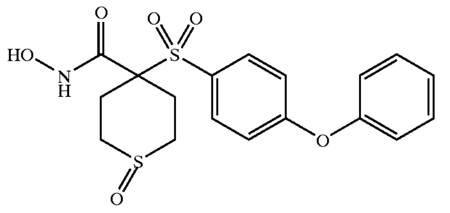

Part A: To a solution of methyl ester of Example 109, part A, (2 g) in acetic acid/water (25/5mL) was added hydrogen peroxide(2mL, 30% solution) . The course of this vigorously stirred solution was monitored by RPHPLC. After 3 hours, water was added and the product was extracted with ethyl acetate (100 mnL, 2×) . The ethyl acetate was dried over sodium sulfate. After solvent was removed via reduced pressure, 2.1 grams of the methylester sulfoxidepyran Phenyl-O-phenyl compound was obtained as a white solid. The $^1$H NMR, MS, and HPLC were consistent with the desired compound.

Part B: To a solution of the methylester sulfoxidepyran Phenyl-O-phenyl compound of Part A (MW 578, 1.8 g) in tetrahydrofuran (25 mL) was added potassium trimethylsilanoate (MW 128, 1.2 g, 1.2 equivalents). The mixture was stirred 2–3 hours until a solid precipitate developed. After the hydrolysis was complete, N-methyl morpholine (2 ML) was added followed by PyBrop (2.3 g, 1.2 equivalents). The solution was stirred for 10 minutes then aqueous hydroxylamine was added, with stirring for an additional 2 hours. After complete reaction (12 hours) the solvent was removed via rotary evaporation. The residue was dissolved in water/acetonitrile, made acidic with trifluoroacetic acid (pH=2), then purified on prep RPHPL( to give 500 milligram s of the title compound as a white solid. The $^1$H NMR, MS, and HPLC were consistent with the desired compound. MS (CI) M+H calculated for $C_{18}H_{19}NO_6S_2$: 409, found 409.

EXAMPLE 112

Preparation of tetrahydro-N-hydroxy-4-(4-( m-acetyl-4-(4-piperazine-phenoxy)phenyl]sulfonyl2H-thiotyran-4-carboxamide

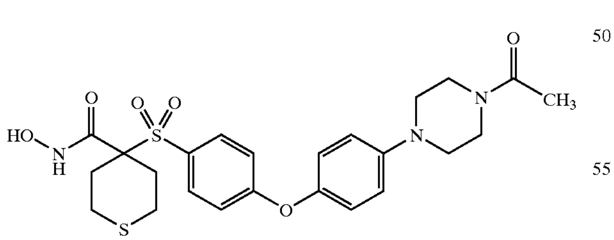

Part A: To a solution of the methylester thiopyran compound of Example 50, part C, (MW 318, 5 g, 1.0 equivalents) in N,N-dimethylacetaminde (7 mL) were added cesium carbonate (MW 5.5g, 1.5 equivalents), tetrabutylammonium fluoride (2 mL, 2 M in THF) and 1-acetyl-4-(4-hydroxyphenyl)piperazine (4.9 g). The mixture was stirred and heated at 90 degrees Celsius for 6 hours. The reaction mixture was filtered and the N,N-dimethylacetamide was then removed via rotary evaporation. The residue was dissolved in water (100 mL) and extracted with ethyl acetate (2×). The ethyl acetate was dried over sodium sulfate and removed under reduced pressure to give an oil. The oil was purified on silica gel to give 3 g of methyl ester. The $^1$H NMR, MS, and HPLC were consistent with the desired compound.

Step B: To a solution of the methyl ester compound of Part A (MW 433, 3 g) in tetrahydrofuran (50 mL) was added potassium trimethylsilanoate (MW 128, 0.9 g, 1.2 equivalents). The mixture was stirred 2–3 hours until a solid precipitate developed. After the hydrolysis was complete N-methyl morpholine (2 mL) was added followed by PyBrop (3.5 g, 1.2 equivalents). The solution was stirred for 10 minutes then aqueous hydroxylamine was added with stirring for an additional 2 hours. After complete reaction (2 hours) the solvent was removed via rotary evaporation. The residue was dissolved in water/acetonitrile, made acidic with trifluoroacetic acid (pH=2), then purified on prep RPHPLC to give 1.2 g of the title compound as a white solid. The $^1$H NMR, MS, and HPLC were consistent with the desired compound. MS (CI) M+H calculated for $C_{24}H_{29}N_3O_6S_2$: 5191 found 519.

EXAMPLE 113

Preparation of tetrahydro-N-hydroxy-4-[[4-(4-thiophenoxy)phenyl]sulfonyl2H-thionyran-4-carboxamide

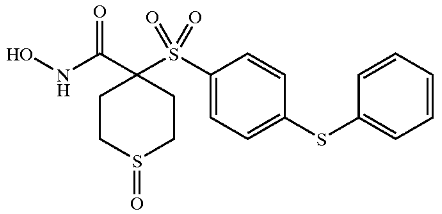

Part A: To a solution of the methylester thiopyran compound of Example 50, part C, (5 g.) in acetic acid (40mL) was added water/hydrogen peroxide(8 mL,4 mL/4 mL, 30% solution). The course of this vigorously stirred solution was monitored by RPHPLC. After 3 hours at ambient temperature, water was added and the product was extracted with ethyl acetate (100 mL, 2×). The ethyl acetate was dried over sodium sulfate. After solvent was removed via reduced pressure 4.5 g of the methylester sulfoxidepyran Ph-p-F was obtained as a white solid. The $^1$H NMR, MS, and HPLC were consistent with the desired compound.

Part B: To a solution of the methylester sulfoxidepyran Ph-p-F of Part A(MW 318, 5 g, 1.0 equivalents) in DMA (70 mL) were added cesium carbonate (MW 4.5 g, 1.1 equivalents) and thiophenol (1.5 g, 1.05 equivalents). The mixture was stirred 2 hours at room temperature. The reaction mixture was filtered and the N,N-dimethylacetamide was then removed via rotary evaporation. The residue was dissolved in water (100 mL) and extracted with ethyl acetate (2×). The ethyl acetate was dried over sodium sulfate and removed under reduced pressure to give an oil. The oil was purified on prep RPHPLC to give 2 g of methyl ester sulfoxidepyran Phenyl-S-Ph compound. The $^1$H NMR, MS, and HPLC were consistent with the desired compound.

Part C: To a solution of the methylester sulfoxidepyran Phenyl-S-Ph of Part B (MW 590, 5 g) in tetrahydrofuran (100 mL) was added potassium trimethylsilanoate (MW 128,1.5 g, 2 equivalents). The mixture was stirred 2–3 hours at ambient temperature until a solid precipitate developed. After the hydrolysis was complete, N-methyl morpholine (6 mL) was added followed by PyBrop (4 g, 1.1 equivalents). The solution was stirred for 10 minutes then aqueous hydroxylamine was added with stirring for an additional 2 hours. After complete reaction (12 hours), the solvent was removed via rotary evaporation. The residue was dissolved in water/acetonitrile, made acidic with trifluoroacetic acid (pH=2), then purified on prep RPHPLC to give 1.9 g of the title compound as a white solid. The $^1$H NMR, MS, and HPLC were consistent with the desired compound. MS (CI) M+H calculated for $C_{18}H_{19}NO_5S_3$: 425, found 425.

EXAMPLE 114

Preparation of tetrahydro-N-hydroxy-4-[[4-[4-(4-hydroxyphenyl)thiophenoxy)-phenyl]sulfonyl 2H-thiopyran-4-carboxamide

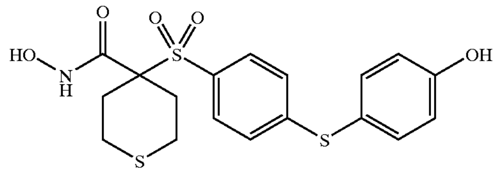

Part A: To a solution of the title compound of Example 50 (MW 402, 5 g, 1.0 equivalent) in N,N-dimethylacetamide (70 mL) was added the 4-hydroxythiophenol (MW 126, 1.6 g, 1.3 equivalents) followed by potassium carbonate (MW 138, 5 g, 2.0 equivalents). The reaction was heated at 65 degrees Celsius for 3 hours, until HPLC indicated the reaction had finished. The reaction mixture was filtered, the N,N-dimethylacetamide was removed in vacuo. The residue was dissolved in water (100 mL) and extracted with ethyl acetate (2×). The ethyl acetate was dried over sodium sulfate and removed under reduced pressure to give the p-OH thiophenoxy compound as a crude oil. The $^1$H NMR, MS, and HPLC were consistent with the desired compound.

Part B: The crude p-OH thiophenoxy compound from Part A was stirred in HCl/dioxane (50 mL) for 2 hours. The solvent was removed and the residue was dried and dissolved in water/acetonitrile, made acidic with trifluoroacetic acid (pH=2), then purified on prep RPHPLC to give 2.1 g of the title compound as a yellow solid. The $^1$H NMR, MS, and HPLC were consistent with the desired compound. MS (CI) M+H calculated for $C_{18}H_{19}NO_5S_3$: 425, found 425.

EXAMPLE 115

Preparation of tetrahydro-N-hydroxy-4-[[4-[4-aminophenyl)thiophenoxy]phenyl]sulfonyl 2H-thiopyran-4-carboxamide

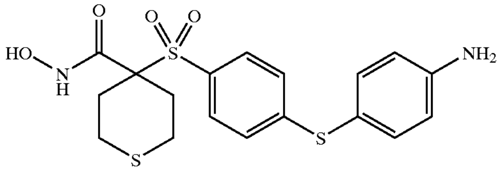

Part A: To a solution of the title compound of Example 50 (MW 402, 5 g, 1.0 equivalents) in N,N-dimethylacetamide (70 mL) was added the 4-aminothiophenol (MW 126, 1.6 g, 1.3 equivalents) followed by potassium carbonate (MW 138, 5 g, 2.0 equivalents). The reaction was heated at 65° C. for 3 hours, until HPLC indicated the reaction had finished. The reaction mixture was filtered, and the N,N-dimethylacetamide was removed in vacuo. The residue was dissolved in water (100 mL) and extracted with ethyl acetate (2×). The ethyl acetate was dried over sodium sulfate and removed under reduced pressure to give the p-$NH_2$ thiophenoxy compound as a crude oil. The $^1$H NMR, MS, and HPLC were consistent with the desired compound.

Part B: The crude p-$NH_2$ thiophenoxy compound of Part A was stirred in HCl/dioxane (50 mL) for 2 hours. The solvent was removed and the residue was dried and dissolved in water/acetonitrile, made acidic with trifluoroacetic acid (pH=2), then purified on prep RPHPLC to give 2.1 g of the title compound as a yellow solid. The $^1$H NMR, MS, and HPLC were consistent with the desired compound. MS (CI) M+H calculated for $C_{18}H_{20}N_2O_4S_3$ $C_2HF_3O_2$: 538, found 538.

EXAMPLE 116

Preparation of tetrahydro-N-hydroxy-4-[[4-[4-tyramine)phenoxy]phenyl]sulfonyl 2H-thioryran-4-carboxamide

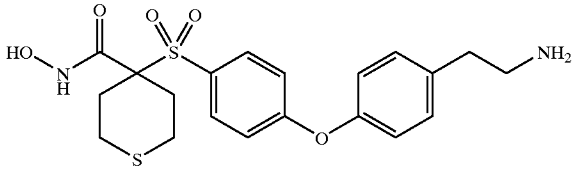

Step A: To a solution of title compound of Example 50 (MW 402, 5 g, 1.0 equivalents) in N,N-dimethylacetamide (50 mL) was added the trypamine (3 g, 2 equivalents), followed by cesium carbonate (10 g, 2.0 equivalents). The reaction was heated at 95 degrees Celsius for 5 hours, until HPLC indicated the reaction had finished. The reaction mixture was filtered, the N,N-dimethylacetamide was removed in vacuo. The solvent was removed and the residue was dried and dissolved in water/acetonitrile, made acidic with trifluoroacetic acid (TFA; pH=2), then purified on prep RPHPLC to give 2.5 g of the crude methyl ester as a yellow solid. The $^1$H NMR, MS, and HPLC were consistent with the desired compound.

Step B: The crude methyl ester from reaction Step A was stirred in aqueous HCl (50 mL) for 1 hour. The solvent was removed and the residue was dried and dissolved in water/acetonitrile, made acidic with TFA (pH=2), then purified on prep RPHPLC to give 2.2 g of yellow foam solid as the trifluoroacetic acid salt of the title compound. The $^1$H NMR, MS, and HPLC were consistent with the desired compound. MS (CI) M+H calculated for $C_{20}H_{24}N_2O_5S_2$ C2HF3O2: 550, found 550.

EXAMPLE 117

Preparation of tetrahydro-N-hydroxy-4-[[4-[4-hydroxyphenyl glycine)]phenyl]sulfonyl 2H-thiopyran-4-carboxamide

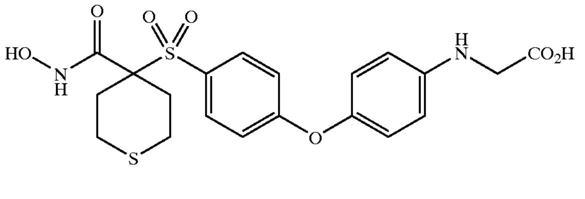

Step A: To a solution of the title compound of Example 50 (MW 402, 5 g, 1.0 equivalents) in N,N-dimethylacetamide (50 mL) was added hydroxyphenylglycine (3 g, 2 equivalents), followed by cesium carbonate (10 g, 2.0 equivalents). The reaction was heated at 95 degrees Celsius for 5 hours, until HPLC indicated the reaction had finished. The reaction mixture was filtered, the N,N-dimethylacetamide was removed in vacuo. The solvent was removed, the residue was dried and dissolved in water/acetonitrile, made acidic with trifluoroacetic acid (pH=2), then purified on prep RPHPLC to give 2.0 g of the crude methyl ester as a tan solid. The $^1$H NMR, MS, and HPLC were consistent with the desired compound.

Step B: The crude methyl ester from reaction Step A was stirred in aqueous HCl (50 mL) for 1 hour. The solvent was removed and the residue was dried and dissolved in water/acetonitrile, made acidic with trifluoroacetic acid (pH=2), then purified on prep RPHPLC to give 2.2 g of tan foam/solid as the trifluoroacetic acid salt of the title compound. The $^1$H NMR, MS, and HPLC were consistent with the desired compound. MS (CI) M+H calculated for $C_{20}H_{22}N_2O_7S_2$ $C_2HF_3O$ $_2$: 580, found 580.

EXAMPLE 118

Preparation of tetrahydro-N-hydroxy-4-[[4-[4-hydroxyphenyl glycine)]phenyl]sulfonyl 2H-thiopyran-4-carboxamide

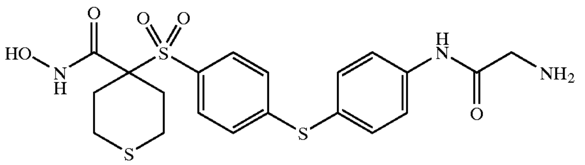

Step A: A solution of the title compound of Example 115 (MW 518, 2.5 g, 1.0 equivalents) in THF (25 mL)and N-Boc N-hydroxysuccinyl glycine (2.1 g, 2 equivalents) containing N-methylmorpholine (2 mL) and 4-dimethylaminopyridine (250 mg) was stirred for 12 hours. After RPHPLC indicated complete reaction at this time, the solvent was removed under reduced pressure to give an oil. Hydrochloric acid 10% aqueous solution was added with stirring for an additional 1–2 hours. The solution was then purified on prep RPHPLC to give 1.2 g of white foam/solid as the trifluoroacetic acid salt. The $^1$H NMR, MS, and HPLC were consistent with the desired compound. The solid was dried under reduced pressure, then suspended in ethyl ether followed by addition of 4N HCl/dioxane (20 mL). The HCl salt was filtered and washed with ethyl ether to give the title compound as a tan solid (1. 1 g). The $^1$H NMR, MS, and HPLC were consistent with the desired compound. MS (CI) M+H calculated for $C_{20}H_{23}N_3O_5S_3$ $C_2HF_3O_2$: 595, found 595.

EXAMPLE 119

Preparation of tetrahydro-N-hydroxy-4-[[4-(4-pyridinylthio)-phenyl]sulfonyl]-2H-thiopyran-4-carboxamide, monohydrochloride

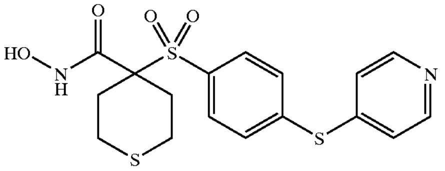

Step A: To a solution of the title compound of Example 50 (MW 402, 5 g, 1.0 equivalents) in N,N-dimethylacetamide (50 d) were added 4-thiopyridine (3 g, 2 equivalents), followed by cesium carbonate (10 g, 2.0 equivalents). The reaction mixture was heated at 75 degrees Celsius for 5 hours, until HPLC indicated the reaction had finished. The reaction mixture was filtered, and the N,N-dimethylacetamide was removed in vacuo. The residue was dried and dissolved in water/acetonitrile, made acidic with trifluoroacetic acid (pH=2), then purified on prep RPHPLC to give 2.0 g of the crude —S-pyridyl THP-protected thiopyran compound as a brown solid. The $^1$H NMR, MS, and HPLC were consistent with the desired compound.

Step B: The —S-pyridyl THP-protected thiopyran compound from Step A was stirred in aqueous HCl (50 mL) for 1 hour. The solvent was removed and the residue was dried and dissolved in water/acetonitrile, made acidic with trifluoroacetic acid (pH=2), then purified on prep RPHPLC to give 1.8 g of tan foam/glass as the trifluoroacetic acid salt of the title compound. The $^1$H NMR, MS, and HPLC were consistent with the desired compound. MS (CI) M+H calculated for $C_{17}H_{18}N_2O_4S_3$ HCl: 447, found 447.

EXAMPLE 120

Preparation of 4-[[4-[(4-aminophenyl)thio]phenyl]-sulfonyl]tetrahydro-N-hydroxy-2H-pyran-4-carboxamide

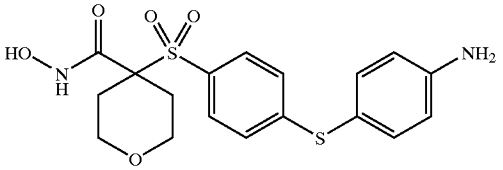

Step A: To a solution of the title compound of Example 55 (MW 387, 5 g, 1.0 equivalents) in N,N-dimethylacetamide (50 mL) were added the 4-aminothiophenol (3 g, 2 equivalents) followed by potassium carbonate (10g, 2.0 equivalents). The reaction was heated at 60 degrees Celsius for 5 hours, until HPLC indicated the reaction had finished. The reaction mixture was filtered, the DMA was removed in vacuo. The solvent was removed and the residue was dried and dissolved in water/acetonitrile, made acidic with trifluoroacetic acid (pH=2), then purified on prep RPHPLC to give 2.0 g of the crude 4-amino-S-Ph THP-protected thiopyran as a brown solid. The $^1$H NMR, MS, and HPLC were consistent with the desired compound.

Step B: The 4-amino-S-Ph THP-protected thiopyran compound of Step A was stirred in aqueous HCl (50 mL) for 1 hour. The solvent was removed and the residue was dried and dissolved in water/acetonitrile, made acidic with trifluoroacetic acid (pH=2), then purified on prep RPHPLC to give 1.4 g of tan foam/glass as the trifluoroacetic acid salt of the title compound. The $^1$H NMR, MS, and HPLC were consistent with the desired compound. MS (CI) M+H calculated for $C_{18}H_{20}N_2O_5S_2$: 408, found 408.

EXAMPLE 121

Preparation of tetrahydro-N-hydroxy-4-[[4-[(2-methyl-5-benzothiazolyl)-oxy]phenyl]sulfonyl]-2H-pyran-4-carboxamide

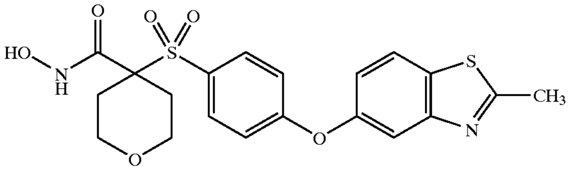

Step A: To a solution of the title compound of Example 55 (MW 387, 10 g, 1.0 equivalents) in DMA (SOmL) were added hydroxymethyl benzothiazole (8 g, 1.5 equivalents) followed by cesium carbonate (20 g, 2.0 equivalents). The reaction was heated at 90 degrees Celsius for 5 hours, until HPLC indicated the reaction had finished. The reaction mixture was cooled then filtered, the N,N-dimethylacetamide was discarded. The filter cake was placed in 10% aqueous HCl and stirred for 30 minutes to remove the cesium salts. The desired solid separated out of solution as a gum. This gum was dissolved in ethyl aceatate (100 mL) and was washed with water and dried over sodium sulfate. The solvent was removed in vacuo to give an oil that was dissolved in water/acetonitrile, made acidic with trifluoroacetic acid (pH=2), then purified on prep RPHPLC to give the 2-methyl-5-benzothiazolyloxy compound. The $^1$H NMR, MS, and HPLC were consistent with the desired compound.

Step B: The 2-methyl-5-benzothiazolyloxy compound of Step A was stirred in aqueous HCl (20 mL)/acetonitrile(20 mL) for 1 hour. The solvent was concentrated and the solid that separated was filtered to give 6.5 g of the title compound. The $^1$H NMR, MS, and HPLC were consistent with the desired compound. MS (CI) M+H calculated for $C_{20}H_{20}N_2O_6S_2$: 448, found 448.

EXAMPLE 122

Preparation of 4-[[4-(4-chloro-3-fluorophenoxy) phenyl]sulfonyl]-tetrahydro-N-hydroxy-2H-pyran-4-carboxamide

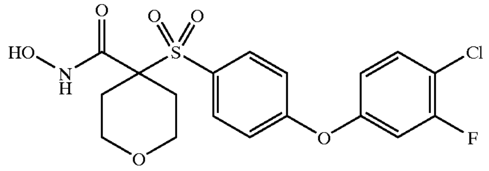

Step A: To a solution of the title compound of Example 55 (MW 387, 10 g, 1.0 equivalents) in N,N-dimethylacetamide (50 mL) were added 4-chloro-3-flourophenol (7 g, 1.4 equivalents) followed by cesium carbonate (20g, 2.0 equivalents). The reaction was heated at 90 degrees Celsius for 5 hours, until HPLC indicated the reaction had finished. The reaction mixture was cooled then filtered, the DMA was discarded. The filter cake was placed in 10% aqueous HCl and stirred for 30 minutes to remove the cesium salts. The desired 4-chloro-3-fluorophenoxy compound (11 g) separated out of solution and was filtered. The $^1$H NMR, MS, and HPLC were consistent with the desired compound.

Step B: The 4-chloro-3-fluorophenoxy compound (3.4 g) of Step A was stirred in aqueous HCl (20 mL)/acetonitrile (20 mL) for 1 hour. The solvent was concentrated and the solid that separated was filtered to give 2.0 g of the title compound. The $^1$H NMR, MS, and HPLC were consistent with the desired compound. MS (CI) M+H calculated for $C_{18}H_{17}ClFNO_6S$: 429, found 429.

EXAMPLE 123

Preparation of 4-([4-[4-(4-acetyl-1-piperazinyl) phenoxy]phenyl]sulfonyl]-tetrahydro-N-hydroxy-2H-pyran-4-carboxamide, Trifluoroacetic Acid Salt

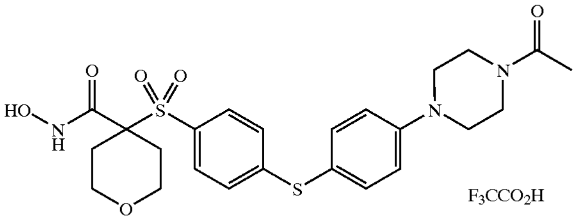

Step A: To a solution of the title compound of Example 55 (MW 387, 5 g, 1.0 equivalents) in DMA (50 mL) were added 1-acetyl-4-(4-hydroxy-phenyl)piperazine (3 g, 2 equivalents) followed by cesium carbonate (10 g, 2.0 equivalents). The reaction was heated at 90 degrees Celsius for 5 hours, until HPLC indicated the reaction had finished. The reaction mixture was filtered, the DMA was removed in vacuo. The residue was dissolved in water/acetonitrile, made acidic with TFA (pH=2), then purified on prep RPHPLC to give 3.1 g of the crude 4-acetyl-1-piperazinylphenoxy compound as a brown solid. The $^1$H NMR, MS, and HPLC were consistent with the desired compound.

Step B: The 4-acetyl-1-piperazinylphenoxy compound from reaction Step A was stirred in aqueous HCl (50 mL) for 1 hour. The solvent was removed and the residue was dried and dissolved in water/acetonitrile, made acidic with TFA (pH=2), then purified on prep RPHPLC to give 2.0 g of tan foam as the trifluoroacetic acid salt of the title compound. The $^1$H NMR, MS, and HPLC were consistent with the desired compound. MS (CI) M+H calculated for $C_{24}H_{29}N_3O_7S$ $C_2HF_3O_2$: 617, found 617.

EXAMPLE 124

Preparation of N,N-dimethyl-5-[4-[[tetrahydro-4-[(hydroxyamino)-carbonyl]-2H-pyran-4-yl]sulfonyl]-phenoxy]-1H-indole-2-carboxamide, Trifluoroacetic Acid Salt

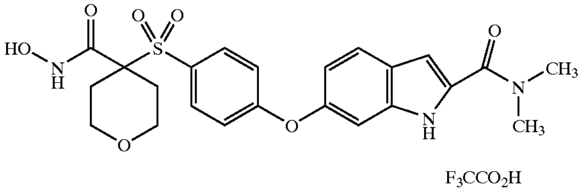

Step A: To a solution of the title compound of Example 55 (MW 387, 5 g, 1.0 equivalents) in DMA (50 mL) were added the 5-hydroxy-2-indole dimethylcarboxylate (3 g, 2 equivalents) followed by $Cs_2CO_3$ (10 g, 2.0 equivalents). The reaction was heated at 90 degrees Celsius for 5 hours, until HPLC indicated the reaction had finished. The reaction mixture was filtered, the DMA was removed in vacuo. The residue was dissolved in water/acetonitrile, made acidic with TFA (pH=2), then purified on prep RPHPLC to give 2.1 g of the crude THP-protected pyran hydroxamate compound as a brown solid. The $^1H$ NMR, MS, and HPLC were consistent with the desired compound.

Step B: The THP-protected pyran hydroxamate compound from Step A was stirred in aqueous HCl (50 mL) for 1 hour. The solvent was removed and the residue was dried and dissolved in water/acetonitrile, made acidic with TFA (pH=2), then purified on prep RPHPLC to give 1.5 g of tan solid as the trifluoroacetic acid salt of the title compound. The $^1H$ NMR, MS, and HPLC were consistent with the desired compound. MS (CI) M+H calculated for $C_{23}H_{25}N_3O_7S$: 487, found 487.

EXAMPLE 125

Preparation of tetrahydro-N-hydroxy-4-[[4-[4-(1-methylethyl)phenoxy]phenyl]sulfonyl]-2H-pyran-4-carboxamide

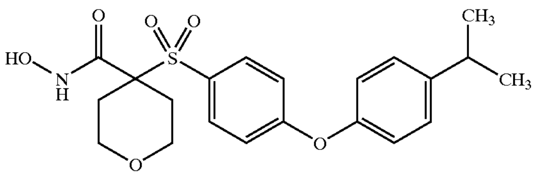

Step A: To a solution of the title compound of Example 55 (MW 387, 5 g, 1.0 equivalents) in DMA (50 mL) was added the 4-isopropylphenol (3 g, 2 equivalents), followed by cesium carbonate (10 g, 2.0 equivalents). The reaction mixture was heated at 90 degrees Celsius for 8 hours, until HPLC indicated the reaction had finished. The reaction mixture was filtered, the DMA portion was discarded. The filter cake was placed in 10% aqueous HCl and stirred for 30 minutes to remove the cesium salts. The solid (3.5 g) isopropylphenoxyphenyl THP-protected hydroxamate separated and was filtered. The $^1H$ NMR, MS, and HPLC were consistent with the desired compound.

Step B: Into a stirred solution of aqueous HCl (20 mL) and acetonitrile (20 mL) was added the crude isopropylphenoxyphenyl THP-protected hydroxamate from Step A and the resulting mixture was stirred for 1–2 hours. The solvent was concentrated via a stream of nitrogen over the surface of the solution. The solid was filtered and dried to give 2.2 g of the title compound as a tan solid. The $^1H$ NMR, MS, and HPLC were consistent with the desired compound. MS (CI) M+H calculated for $C_{21}H_{25}NO_6S$: 419, found 419.

EXAMPLE 126

Preparation of Resin II

Step 1: Attachment of Compound of Example 55, Part D, to Resin I

A 500 mL round-bottomed flask was charged with of resin I [Floyd et al., *Tetrahedron Lett.* 1996, 37, 8045–8048] (8.08 g, 9.7 mmol) and 1-methyl-2-pyrrolidinone (50 mL). A magnetic stirring bar was added, and the resin slurry slowly stirred. A separate solution of the compound of Part D, Example 55 (5.58 g, 19.4 mmol) in 1-methyl-2-pyrrolidinone (35 mL) was added to the slurry followed by addition of benzotriazole-1-yl-oxy-tris-pyrrolidino-phosphonium hexafluorophosphate (10.1 g, 19.4 mmol) in one portion. Once the hexafluorophosphate salt had dissolved, 4-methylmorpholine (4.26 mL, 39 mmol) was added dropwise. The reaction slurry was stirred at room temperature for 24 hours, then the resin was collected in a sintered-disc funnel and washed with N,N-dimethylformamide, methanol, methylene chloride and diethyl ether (3×30 mL each solvent). The resin was dried in vacuo to yield 10.99 g polymer-bound hydroxymate as a tan polymeric solid. Theoretical loading on polymer was 0.91 mmol/g. FTIR microscopy showed bands at 1693 and 3326 $cm^{-1}$ indicative of the hydroxamate carbonyl and nitrogen-hydrogen stretches, respectively.

Step 2: Preparation of Resin III: Reaction of Resin II With Nucleophiles

Resin II (50 mg, 0.046 mmol) was weighed into an 8 mL glass vial, and a 0.5 M solution of a nucleophile in 1-methyl-2-pyrrolidinone (1 mL) was added to the vessel. In the case of phenol and thiophenol nucleophiles, cesium carbonate (148 mg, 0.46 mmol) was added, and in the case of substituted piperazine nucleophiles, potassium carbonate (64 mg, 0.46 mmol) was added. The vial was capped and heated to 70 to 155 degrees Celsius for 24–48 hours, then cooled to room temperature. The resin was drained and washed with 1-methyl-2-pyrrolidinone, 1-methyl-2-pyrrolidinone/water (1:1), water, 10% acetic acid/water, methanol, and methylene chloride (3×3 mL each solvent).

Step 3: Cleavage of Hydroxamic Acids from The Polymer-Support

Resin III was treated with a trifluoroacetic acid/water mixture (19:1, 1 mL) for 1 hour at room temperature. During that time, the resin became a deep red color. The resin was then drained and washed with trifluoroacetic acid/water (19:1) and methylene chloride (2×1 mL each solvent), collecting the combined filtrates in a tared vial. The volatiles were removed in vacuo, then a toluene/methylene chloride mixture (2 mL each) was added to the residue. The mixture was again concentrated in vacuo. The product was characterized by electrospray mass spectroscopy.

The following hydroxamic acids were synthesized from resin II using the conditions of Step 2 with the indicated nucleophile, followed by release from the polymer using Step 3 reaction conditions.

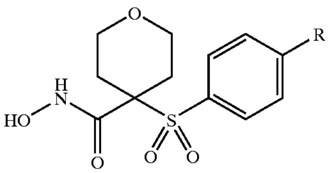
| Example Number | R | Nucleophile | MS (ES) m/z |
|---|---|---|---|
| 126-1 | 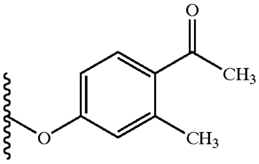 | 4'-hydroxy-2'-methylacetophenone | 451 (M + $NH_4$) |
| 126-2 | 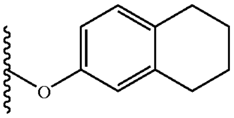 | 5,6,7,8-tetrahydro-2-naphthol | 455 (M + $NH_4$) |
| 126-3 | 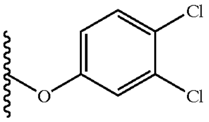 | 3,4-dichlorophenol | 462 (M + $NH_4$) |
| 126-4 | 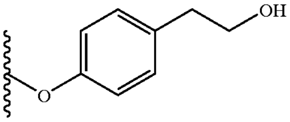 | 4-hydroxyphenethyl alcohol | 439 (M + $NH_4$) |
| 126-5 | 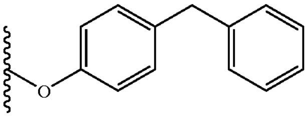 | 4-hydroxy diphenylmethane | 485 (M + $NH_4$) |
| 126-6 | 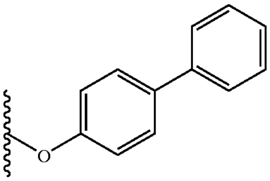 | 4-phenylphenol | 471 (M + $NH_4$) |
| 126-7 | 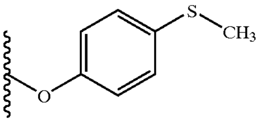 | 4-(methylthio)phenol | 441 (M + $NH_4$) |
| 126-8 | 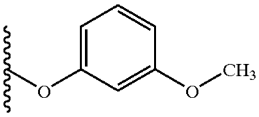 | 3-methoxyphenol | 425 (M + $NH_4$) |
| 126-9 | 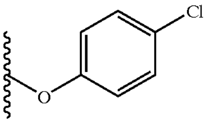 | 4-chlorophenol | 429 (M + $NH_4$) |

-continued
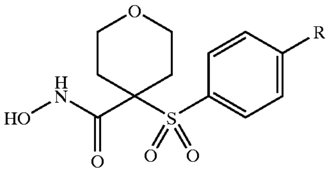
| Example Number | R | Nucleophile | MS (ES) m/z |
|---|---|---|---|
| 126-10 | 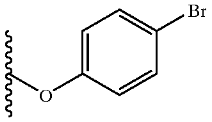 | 4-bromophenol | 590 (M + Cs) |
| 126-11 | 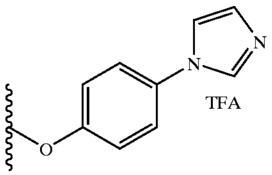 TFA | 4-(imidazol-1-yl)-phenol | 444 (M + H) |
| 126-12 | 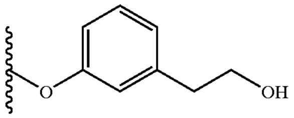 | 3-hydroxyphenethyl alcohol | 439 (M + $NH_4$) |
| 126-13 | 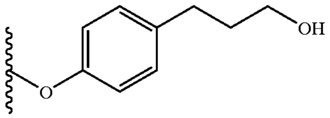 | 3-(4-hydroxy-phenyl)-1-phenol | 453 (M + $NH_4$) |
| 126-14 | 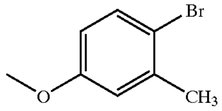 | 4-bromo-3-methylphenol | 487 (M + $NH_4$) |
| 126-15 | 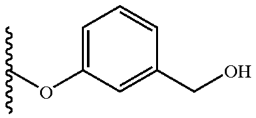 | 3-hydroxybenzyl alcohol | 425 (M + $NH_4$) |
| 126-16 | 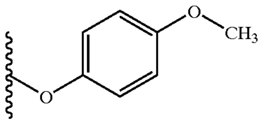 | 4-methoxyphenol | 425 (M + $NH_4$) |
| 126-17 | 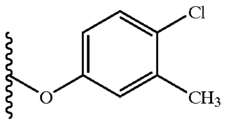 | 4-chloro-3-methylphenol | 558 (M + Cs) |
| 126-18 | 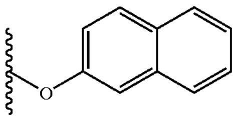 | 2-naphthol | 560 (M + Cs) |

-continued
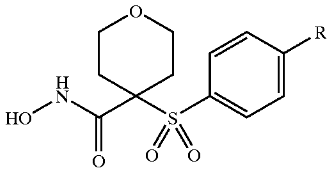
| Example Number | R | Nucleophile | MS (ES) m/z |
|---|---|---|---|
| 126-19 | 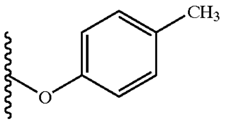 | p-cresol | 409 ($M + NH_4$) |
| 126-20 | 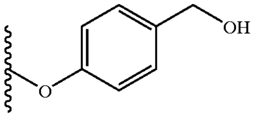 | 4-hydroxybenzyl alcohol | 408 (M + H) |
| 126-21 | 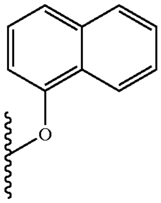 | 1-naphthol | 445 ($M + NH_4$) |
| 126-22 | 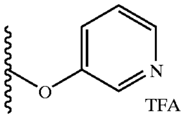 | 3-hydroxypyridine | 379 (M + H) |
| 126-23 | 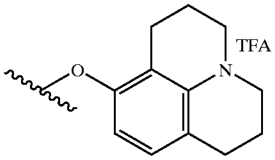 | 8-hydroxyjulolidine | 473 (M + H) |
| 126-24 | 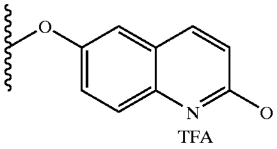 | 2,6-quinolinediol | 445 (M + H) |
| 126-25 | 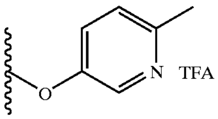 | 5-hydroxy-2-methylpyridine | 393 (M + H) |
| 126-26 | 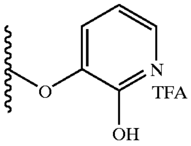 | 2,3-dihydroxy-pyridine | 412 (M + H) |

-continued
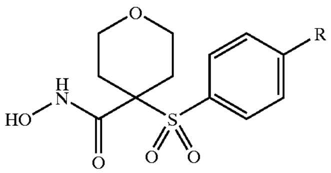
| Example Number | R | Nucleophile | MS (ES) m/z |
|---|---|---|---|
| 126-27 | 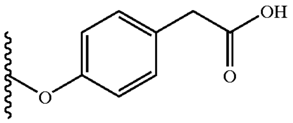 | 4-hydroxyphenyl acetic acid | 453 (M + $NH_4$) |
| 126-28 | 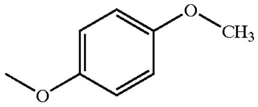 | 4-amino-m-cresol | 407 (M + H) |
| 126-29 | 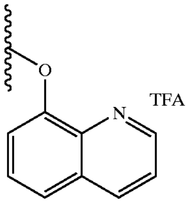 | 8-quinolinol | 429 (M + H) |
| 126-30 | 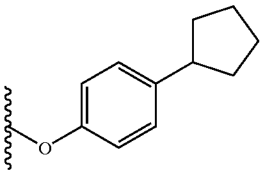 | 4-cyclopentylphenol | 463 (M + $NH_4$) |
| 126-31 | 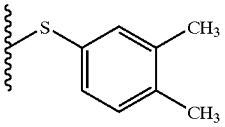 | 3,4-dimethyl-thiophenol | 439 (M + $NH_4$) |
| 126-32 | 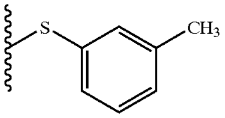 | m-thiocresol | 425 (M + $NH_4$) |
| 126-33 | 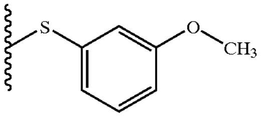 | 3-methoxythiophenol | 441 (M + $NH_4$) |
| 126-34 | 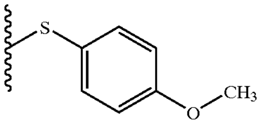 | 4-methoxythiophenol | 441 (M + $NH_4$) |
| 126-35 | 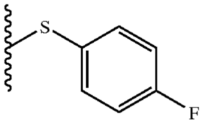 | 4-fluorothiophenol | 429 (M + $NH_4$) |

-continued
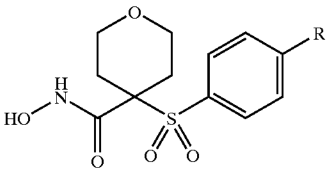
| Example Number | R | Nucleophile | MS (ES) m/z |
|---|---|---|---|
| 126-36 | 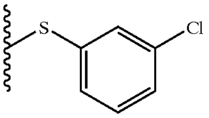 | 3-chlorothiophenol | 445 ($M + NH_4$) |
| 126-37 | 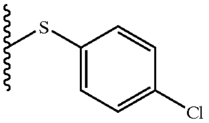 | 4-chlorothiophenol | 445 ($M + NH_4$) |
| 126-38 | 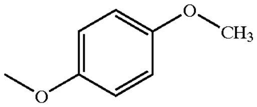 | 4-aminothiophenol | 426 ($M + NH_4$) |
| 126-39 | 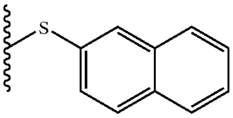 | 2-naphthalenethiol | 461 ($M + NH_4$) |
| 126-40 | 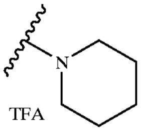 | piperidine | |
| 126-41 | 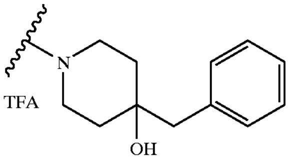 | 4-benzyl-4-hydroxypiperidine | 475 (M + H) |
| 126-42 | 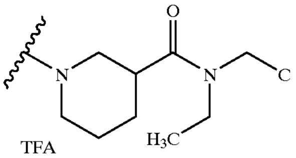 | nipecotamide | 468 (M + H) |
| 126-43 | 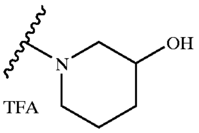 | 3-hydroxypiperidine | 385 (M + H) |

-continued
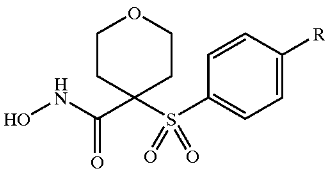
| Example Number | R | Nucleophile | MS (ES) m/z |
|---|---|---|---|
| 126-44 | 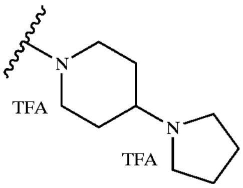 | 4-(1-pyrrolidinyl)-piperidine | 438 (M + H) |
| 126-45 | 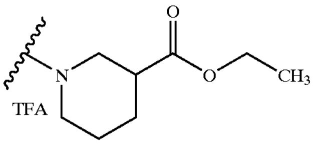 | ethyl nipecotate | 441 (M + H) |
| 126-46 | 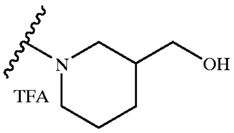 | 3-piperidinyl-methanol | 512 (M + TFA) |
| 126-47 | 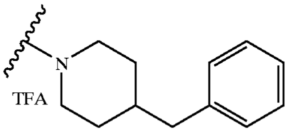 | 4-benzylpiperidine | 459 (M + H) |
| 126-48 | 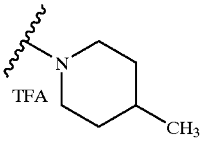 | 4-methylpiperidine | 383 (M + H) |
| 126-49 | 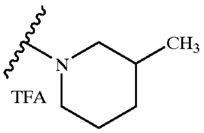 | 3-methylpiperidine | 383 (M + H) |
| 126-50 | 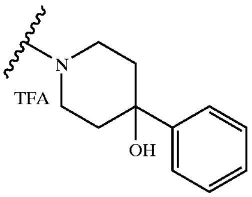 | 4-hydroxy-4-phenylpiperidine | 461 (M + H) |
| 126-51 | 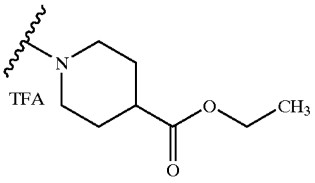 | ethyl isonipecotate | 441 (M + H) |

-continued
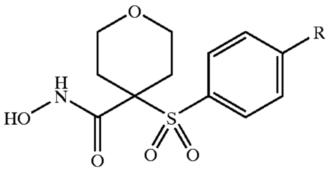
| Example Number | R | Nucleophile | MS (ES) m/z |
|---|---|---|---|
| 126-52 | 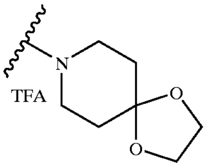 | 1,4-dioxa-8-azaspiro(4,5)decane | 427 (M + H) |
| 126-53 | 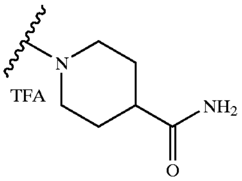 | isonipecotamide | 412 (M + H) |
| 126-54 | 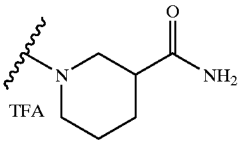 | nipecotamide | 412 (M + H) |
| 126-55 | 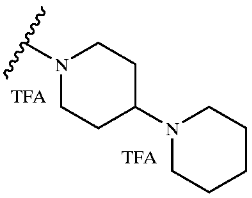 | 4-piperidino-piperidine | 452 (M + H) |
| 126-56 | 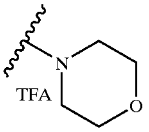 | morpholine | 388 ($M + NH_4$) |
| 126-57 | 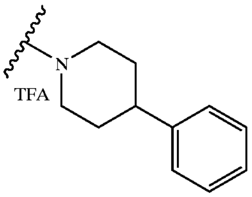 | 4-phenylpiperidine | 445 (M + H) |
| 126-58 | 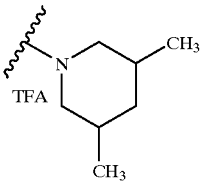 | 3,5-dimethyl-piperidine | 414 ($M + NH_4$) |

-continued
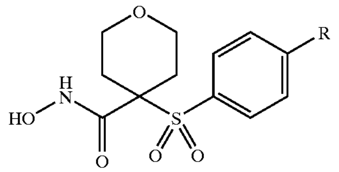
| Example Number | R | Nucleophile | MS (ES) m/z |
| --- | --- | --- | --- |
| 126-59 | 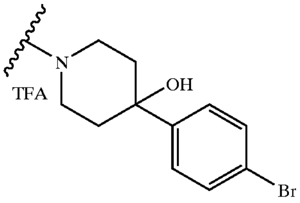 | 4-(4-bromophenyl)-4-piperidinol | 539 (M + H) |
| 126-60 | 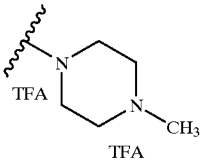 | 1-methylpiperazine | 384 (M + H) |
| 126-61 | 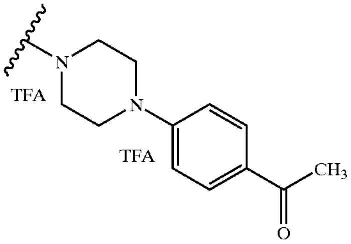 | 4-piperazino-acetophenone | 488 (M + H) |
| 126-62 | 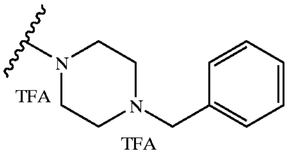 | 1-benzylpiperazine | 460 (M + H) |
| 126-63 | 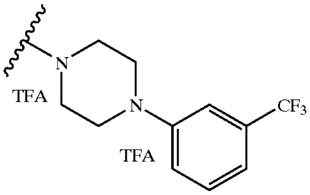 | N-(α,α,α-trifluoro-m-tolyl)piperazine | 514 (M + H) |
| 126-64 | 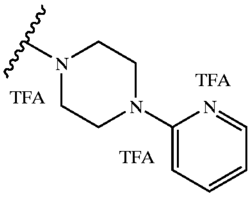 | 1-(2-pyridyl)-piperazine | 447 (M + H) |

-continued
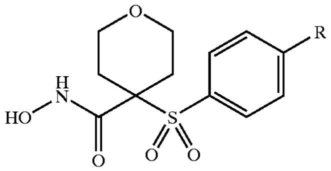
| Example Number | R | Nucleophile | MS (ES) m/z |
|---|---|---|---|
| 126-65 | 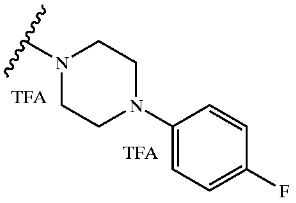 | 1-(4-fluorophenyl)-piperazine | 464 (M + H) |
| 126-66 | 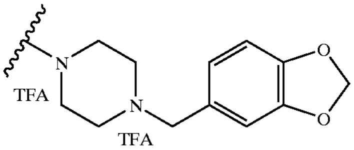 | 1-piperonyl-piperazine | 504 (M + H) |
| 126-67 | 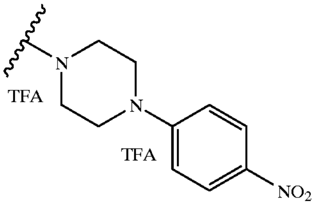 | 1-(4-nitrophenyl)-piperazine | 491 (M + H) |
| 126-68 | 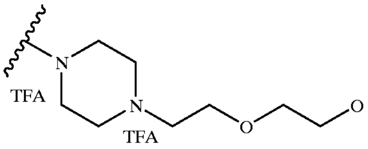 | 1-hydroxyethyl-ethoxypiperazine | 458 (M + H) |
| 126-69 | 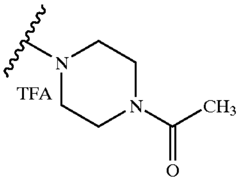 | 1-acetylpiperazine | 412 (M + H) |
| 126-70 | 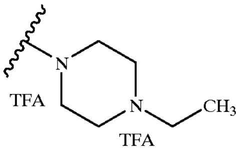 | 1-ethylpiperazine | 398 (M + H) |
| 126-71 | 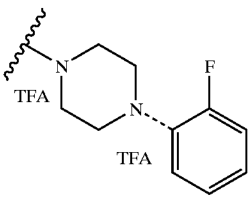 | 1-(2-fluorophenyl)-piperazine | 464 (M + H) |

-continued

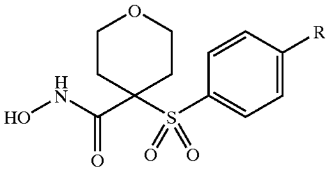

| Example Number | R | Nucleophile | MS (ES) m/z |
|---|---|---|---|
| 126-72 | 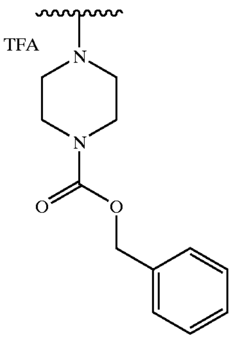 | benzyl-1-piperazine carboxylate | 504 (M + H) |
| 126 | 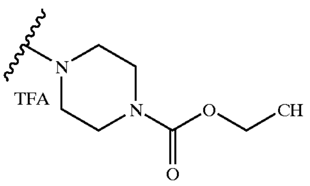 | ethyl-N-piperazine carboxylate | 442 (M + H) |
| 127 | 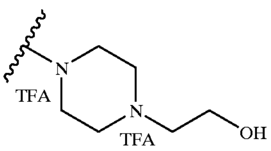 | N-(2-hydroxyethyl)-piperazine | 414 (M + H) |
| 128 | 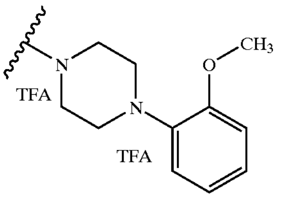 | 1-(2-methoxy-phenyl)piperazine | 476 (M + H) |

EXAMPLE XX

Large Scale Preparation of Resin IIIa

Resin II (5 g, 0.91 mmol) was weighed into an oven-dried three-necked round bottom flask fitted with a temperature probe, an overhead stirring paddle, and a nitrogen inlet. Anhydrous 1-methyl-2-pyrrolidinone (35 mL) was added to the flask followed by ethyl isonipecotate (7.0 mL, 45.5 mmol). The resin slurry was stirred slowly with the overhead stirrer, and the mixture was heated to 80 degrees Celsius with a heating mantle for 65 hours. The flask was thereafter cooled to room temperature.

The resin was collected in a sintered-disk glass funnel and washed with N,N-dimethylformamide, methanol and methylene chloride (3x30 mL each solvent). The resin was dried in vacuo to provide 5.86 g of resin IIIa as off-white resin beads. The theoretical loading of the polymer was 0.81 mmol/g. TFA cleavage performed on 50 mg of resin IIIa as described in step 3 yielded 10.4 mg of off-white solid spectroscopically indistinguishable from the reaction product using ethyl isonipecotate of Example 211.

EXAMPLE YY

Large Scale Preparation of Resin IIIb

Preparation of resin IIIb followed the procedure described for preparation of resin IIIa, except ethyl nipecotate was substituted for ethyl isonipecotate. The yield after drying in vacuo was 5.77 g of resin IIIb as pale yellow resin beads. The theoretical loading of the polymer was 0.81 mmol/g. TFA cleavage performed on 50 mg of resin IIIb as described in step 3 yielded 14.7 mg of off-white solid spectroscopically indistinguishable from the reaction product using ethyl nipecotate of Example 212.

Step 4: Hydrolysis of Polymer-Bound Ester: Preparation of Resin IVa

Resin IIIa (5.8 g, 4.5 mmol) was weighed into a three-necked round bottomed flask fitted with an overhead stirring paddle. 1,4-Dioxane was added to the flask, and the resin slurry was stirred for 15 minutes. Then, a 4 M solution of KOH (5 mL, 20 mmol) was added, and the mixture was stirred for 44 hours. The resin was thereafter collected in a sintered-disk glass funnel and washed with dioxane/water (9:1), water, 10% acetic acid/water, methanol and methylene chloride (3x30 mL each solvent). The resin was dried in vacuo co yield 5.64 g of resin IVa as off-white polymer beads. FTIR microscopy showed bands at 1732 and 1704 $cm^{-1}$ and a broad band from 2500–3500 $cm^{-1}$. The theoretical loading of the polymer-bound acid was 0.84 mmol/g.

Preparation of Resin Ivb

Using the procedure described in Step 4, resin IIIb (5.71 g, 4.5 mmol) was converted into 5.61 g of resin IVb. FTIR microscopy showed bands at 1731 and 1705 $cm^{-1}$ and a broad band from 2500–3500 $cm^{-1}$. The theoretical loading of the polymer-bound acid was 0.84 mmol/g.

Step 5: Amide Bond Formation: Preparation of Resin V

Into a fritted reaction vessel was weighed either resin IVa or resin IVb (50 mg, 0.042 mmol), and the vessel was capped under nitrogen. A 0.5 M solution of hydroxybenzotriazole in 1-methyl-2-pyrrolidinone (0.3 mL, 0.15 mmol) was added followed by a 0.5 M solution of diisopropylcarbodiimide in 1-methyl-2-pyrrolidinone (0.3 mL, 0.15 mmol). The resin was stirred using a tabletop stirring plate for 15 minutes, then a 0.7 M solution of the amine in 1-methyl-2-pyrrolidinone (0.3 mL, 0.21 mmol) was added. The reaction mixture was stirred for 6 hours, then the resin was drained and washed with 1-methyl-2-pyrrolidinone (3x1 mL). The reaction was repeated using the same amounts of reagents described above. The reaction mixture was stirred for 16 hours, then the resin was drained and washed with 1-methyl-2-pyrrolidinone, methanol and methylene chloride (3x1 mL each solvent).

The following hydroxamic acids were synthesized using the indicated polymer-bound acid and the indicated amine in Step 5 reaction conditions followed by release from the polymer using Step 3 reaction conditions.

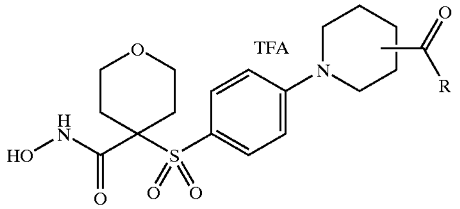

| Example Number | Resin | Amine | R | Position | MS (ES) m/z |
|---|---|---|---|---|---|
| 129 | IVa | — | 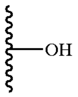 | 4 | |
| 130 | IVa | methylamine | 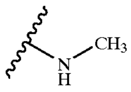 | 4 | |
| 131 | IVa | morpholine | 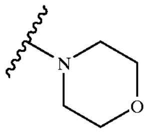 | 4 | 482 (M + H) |
| 132 | IVa | ethanolamine | 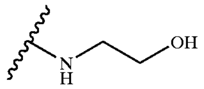 | 4 | 456 (M + H) |
| 133 | IVa | 1,3-diamino-propane | 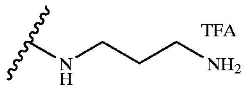 | 4 | 469 (M + H) |
| 134 | IVa | ethylamine | 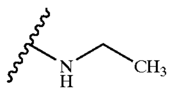 | 4 | 440 (M + H) |
| 135 | IVa | glycine t-butyl ester HCl | 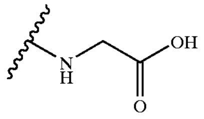 | 4 | 470 (M + H) |

-continued
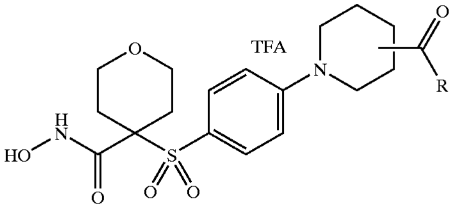
| Example Number | Resin | Amine | R | Position | MS (ES) m/z |
|---|---|---|---|---|---|
| 136 | IVa | L-histidine methyl ester HCl | 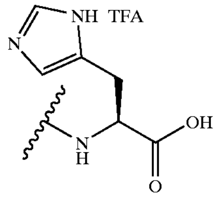 | 4 | 564 (M + H) |
| 137 | IVa | 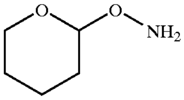 | 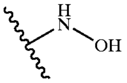 | 4 | 428 (M + H) |
| 138 | IVb | — | 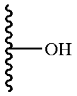 | 3 | |
| 139 | IVb | methylamine | 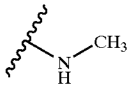 | 3 | 426 (M + H) |
| 140 | IVb | morpholine | 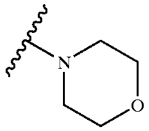 | 3 | 482 (M + H) |
| 141 | IVb | ethanolamine | 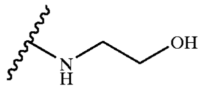 | 3 | 456 (M + H) |
| 142 | IVb | 1,3-diamino-propane | 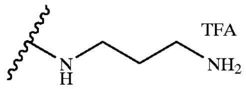 | 3 | 469 (M + H) |
| 143 | IVb | ethylamine | 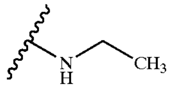 | 3 | 440 (M + H) |
| 144 | IVb | glycine t-butyl ester HCl | 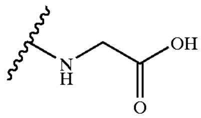 | 3 | 470 (M + H) |

-continued
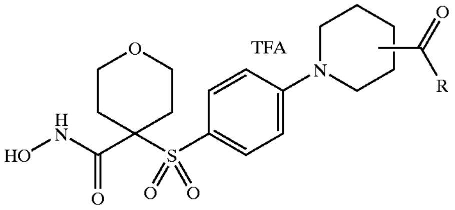
| Example Number | Resin | Amine | R | Position | MS (ES) m/z |
|---|---|---|---|---|---|
| 145 | IVb | L-histidine methyl ester HCl | 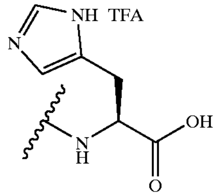 | 3 | 564 (M + H) |
| 146 | IVb | 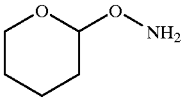 | 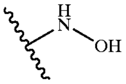 | 3 | 428 (M + H) |
| 147 | IVa | dimethylamine | 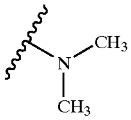 | 4 | 440 (M + H) |
| 148 | IVa | diethylamine | 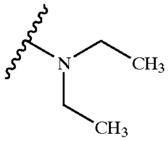 | 4 | 468 (M + H) |
| 149 | IVa | piperidine | 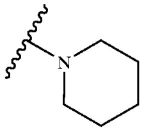 | 4 | 480 (M + H) |
| 150 | IVa | 1-methyl-piperazine | 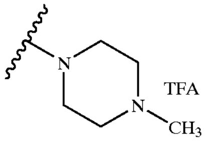 | 4 | 495 (M + H) |
| 151 | IVa | N-Boc-piperazine | 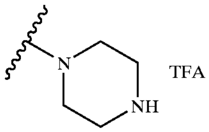 | 4 | 481 (M + H) |
| 152 | IVa | ethyl isonipecotate | 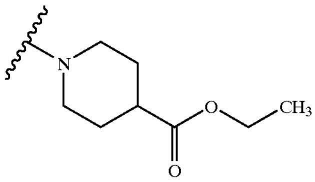 | 4 | 552 (M + H) |

-continued
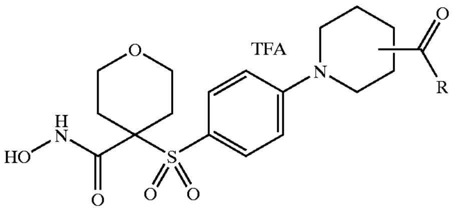
| Example Number | Resin | Amine | R | Position | MS (ES) m/z |
|---|---|---|---|---|---|
| 153 | IVa | ethyl nipecotate | 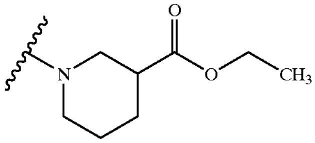 | 4 | 552 (M + H) |
| 154 | IVa | ethyl pipecolate | 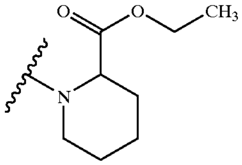 | 4 | 552 (M + H) |
| 155 | IVb | dimethylamine | 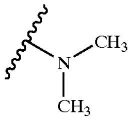 | 3 | 440 (M + H) |
| 156 | IVb | piperidine | 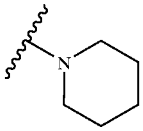 | 3 | 480 (M + H) |
| 157 | IVb | 1-methyl-piperazine | 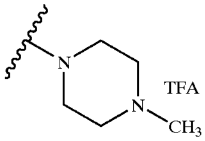 | 3 | 495 (M + H) |
| 158 | IVb | N-Boc-piperazine | 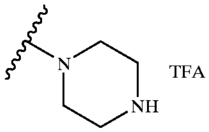 | 3 | 481 (M + H) |
| 159 | IVb | ethyl isonipecotate | 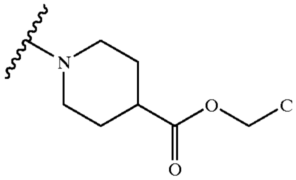 | 3 | 552 (M + H) |
| 160 | IVb | ethyl nipecotate | 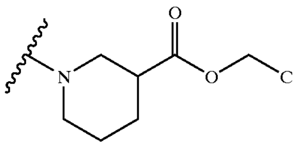 | 3 | 552 (M + H) |

-continued
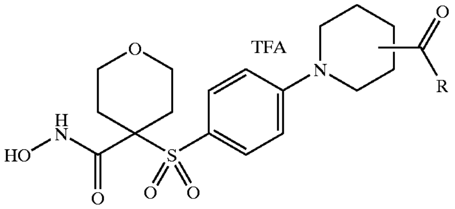
| Example Number | Resin | Amine | R | Position | MS (ES) m/z |
|---|---|---|---|---|---|
| 161 | IVb | ethyl pipecolate | 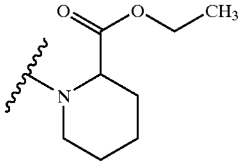 | 3 | 552 (M + H) |
| 162 | IVb | hexamethylene-imine | 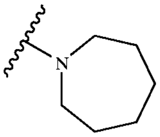 | 3 | 494 (M + H) |
| 163 | IVb | 1,3,3-tri-methyl-6-aza-bicyclo [3.2.1]-octane | 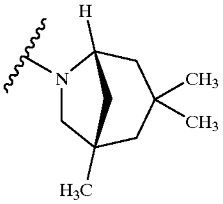 | 3 | 548 (M + H) |
| 164 | IVa | 1,3,3-tri-methyl-6-aza-bicyclo [3.2.1]-octane | 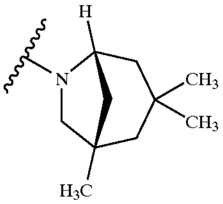 | 4 | 548 (M + H) |
| 165 | IVa | hexamethylene-imine | 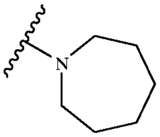 | 4 | 494 (M + H) |
| 166 | IVb | 3-pyrrolidinol | 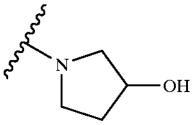 | 3 | 482 (M + H) |
| 167 | IVb | (3S)-(−)-3-(dimethyl amino)-pyrrolidine | 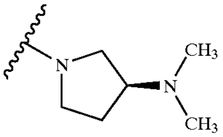 TFA | 3 | 509 (M + H) |

-continued
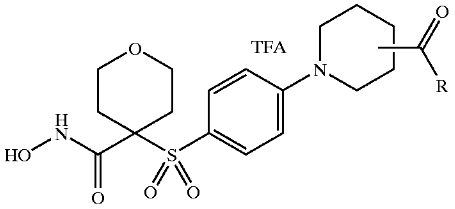
TFA
| Example Number | Resin | Amine | R | Posi-tion | MS (ES) m/z |
|---|---|---|---|---|---|
| 168 | IVb | (3S)-(−)-3-(t-butoxy-carbonylamino)-pyrrolidine | 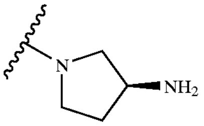 TFA | 3 | 481 (M + H) |
| 169 | IVb | cis-2,6-dimethyl-morpholine | 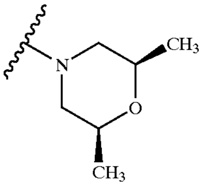 | 3 | 510 (M + H) |
| 170 | IVb | decahydro-quinoline | 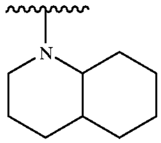 | 3 | 534 (M + H) |
| 171 | IVb | 4-(1-pyrrolidinyl)-piperidine | 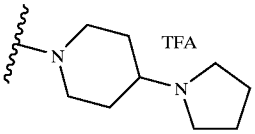 TFA | 3 | 549 (M + H) |
| 172 | IVb | pyrrolidine | 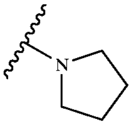 | 3 | 466 (M + H) |
| 173 | IVa | 3-pyrrolidinol | 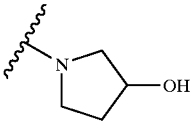 | 4 | 482 (M + H) |
| 174 | IVa | (3S)-(−)-3-(dimethyl amino)-pyrrolidine | 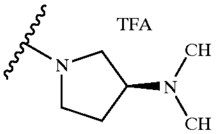 TFA | 4 | 509 (M + H) |
| 175 | IVa | (3S)-(−)-3-(t-butoxy-carbonylamino)-pyrrolidine | 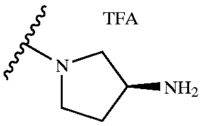 TFA | 4 | 481 (M + H) |

-continued
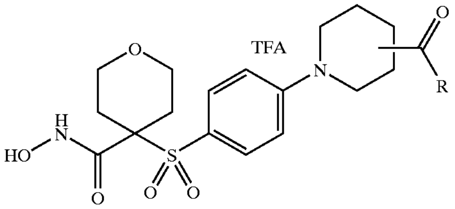
| Example Number | Resin | Amine | R | Position | MS (ES) m/z |
|---|---|---|---|---|---|
| 176 | IVa | cis-2,6-dimethyl-morpholine | 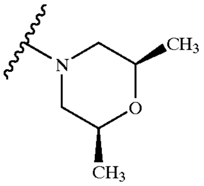 | 4 | 510 (M + H) |
| 177 | IVa | decahydro-quinoline | 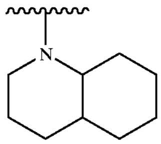 | 4 | 534 (M + H) |
| 178 | IVa | 4-(1-pyrrolidinyl)-piperidine | 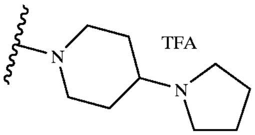 | 4 | 549 (M + H) |
| 179 | IVa | pyrrolidine | 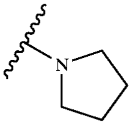 | 4 | 466 (M + H) |
| 180 | IVa | 2,2,2-tri-fluoroethyl-amine | 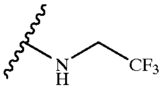 | 4 | 494 (M + H) |
| 181 | IVa | butylamine | 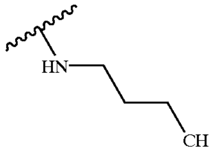 | 4 | 468 (M + H) |
| 182 | IVa | diallylamine | 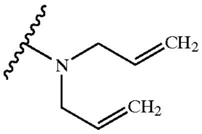 | 4 | 492 (M + H) |
| 183 | IVa | 3,3'-imino-bis(N,N-di-methylpropyl-amine) | 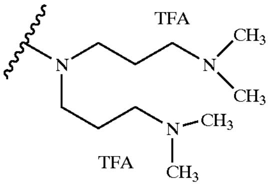 | 4 | 582 (M + H) |

-continued
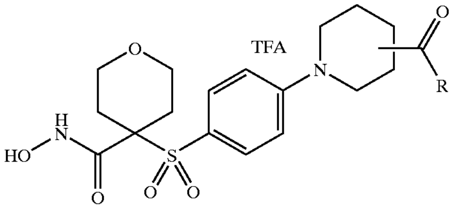
| Example Number | Resin | Amine | R | Position | MS (ES) m/z |
|---|---|---|---|---|---|
| 184 | IVa | iso-propylamine | 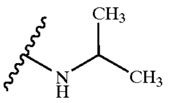 | 4 | 454 (M + H) |
| 185 | IVa | 4-amino-morpholine | 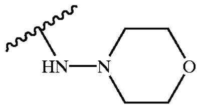 | 4 | 497 (M + H) |
| 186 | IVa | 3-(amino-methyl)-pyridine | 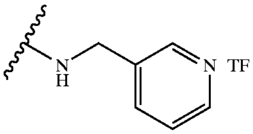 | 4 | 503 (M + H) |
| 187 | IVa | cyclohexyl-amine | 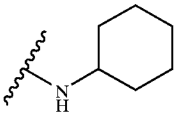 | 4 | 494 (M + H) |
| 188 | IVa | 1-aminoindane | 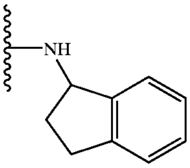 | 4 | 528 (M + H) |
| 189 | IVa | 2-thiophene-methylamine | 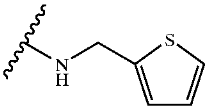 | 4 | 508 (M + H) |
| 190 | IVa | 4-methyl-piperidine | 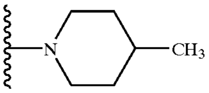 | 4 | 494 (M + H) |
| 191 | IVa | 4-benzyl-piperidine | 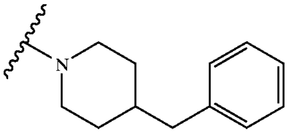 | 4 | 570 (M + H) |
| 192 | IVa | 4-phenyl-piperidine | 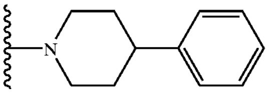 | 4 | 556 (M + H) |

-continued

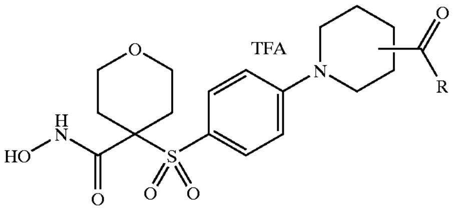

| Example Number | Resin | Amine | R | Position | MS (ES) m/z |
|---|---|---|---|---|---|
| 193 | IVa | 4-benzyl-4-hydroxy-piperidine | 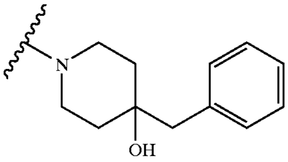 | 4 | 586 (M + H) |
| 194 | IVa | cycloheptyl-amine | 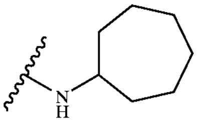 | 4 | 508 (M + H) |
| 195 | IVa | 4-aminomethyl-pyridine | 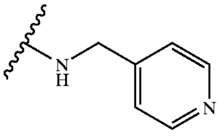 TFA | 4 | 503 (M + H) |
| 196 | IVa | 2-aminomethyl-pyridine | 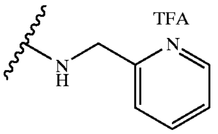 TFA | 4 | 503 (M + H) |
| 197 | IVa | 4-fluoro-benzylamine | 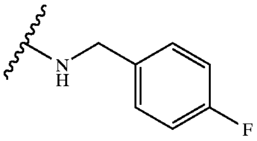 | 4 | 520 (M + H) |
| 198 | IVa | dibenzylamine | 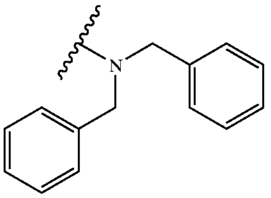 | 4 | 592 (M + H) |
| 199 | IVa | 1,2,3,4-tetrahydro-isoquinoline | 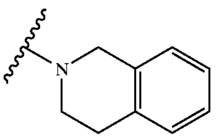 | 4 | 528 (M + H) |

Large Scale Preparation of Resin IIIc

Resin II (3.01 g, 2.74 mmol) was weighed into an oven-dried three-necked round bottomed flask fitted with an overhead stirring paddle, a temperature probe and an nitrogen inlet. 1-Methyl-2-pyrrolidinone (25 mL) was added followed by piperazine (2.36 g, 27.4 mmol) and cesium carbonate (8.93 g, 27.4 mmol). Additional 1-methyl-2-pyrrolidinone (10 mL) was added, and the reaction mixture was heated to 100 degrees Celsius and stirred 18 hours. The flask was cooled to room temperature, and the resin was collected in a sintered-disc funnel and washed with N,N-diethylformamide/water (1:1), water, 10% acetic acid/water, methanol, and methylene chloride (3x30 mL each solvent). The yield after drying in vacuo was 3.14 g of resin IIIb as pale yellow resin beads. The theoretical loading of the polymer was 0.86 mmol/g. TFA cleavage performed on 50 mg of resin IIIb as described in Step 3 yielded 21 mg of off-white solid spectroscopically indistinguishable from the compound of Example 209.

Step 6: Amide Bond Formation with Resin IIIc: Preparation of Resin VI

Into a fritted reaction vessel was placed the carboxylic acid (0.215 mmol) and 1-hydroxybenzotriazole (44 mg, 0.326 mmol). The vessel was capped under nitrogen, and 1-methyl-2-pyrrolidinone was added followed by diisopropylcarbodiimide (0.034 mL, 0.215 mmol). The solution was agitated on a tabletop shaker for 15 minutes, then resin IIIc (50 mg, 0.043 mmol) was added in one portion. The reaction mixture was shaken for 16 hours, then the resin was drained and washed with 1-methyl-2-pyrrolidinone, methanol and methylene chloride (3x1 mL each solvent). In the case of N-9-fluorenyl-methoxycarbonyl-protected amino acids, the resin was further treated with a piperidine/N,N-dimethylformamide solution (1:4, 1 mL) for 30 minutes. The resin was drained and washed with N,N-dimethylformamide, methanol and methylene chloride (3x1 mL each solvent).

The following hydroxamic acids were synthesized from resin IIIc using Step 6 with the indicated carboxylic acid, followed by release from the polymer using Step 3 reaction conditions.

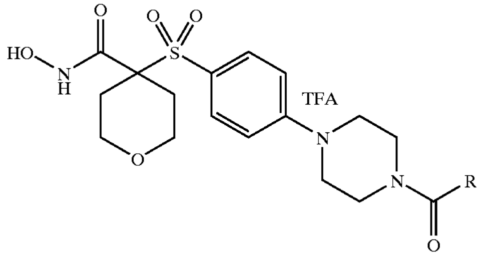

| Example Number | Carboxylic Acid | R | MS (ES) m/z |
|---|---|---|---|
| 200 | cyclo-hexanecarboxylic acid | 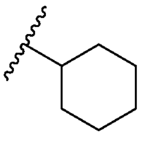 | 502 (M + Na) |
| 201 | 1,2,3,4-tetra-hydronaphthylene-2-carboxylic acid | 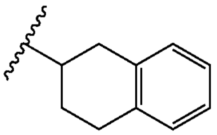 | 545 (M + $NH_4$) |
| 202 | cycloheptane-carboxylic acid | 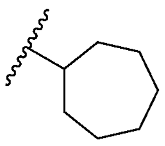 | 511 (M + $NH_4$) |

-continued

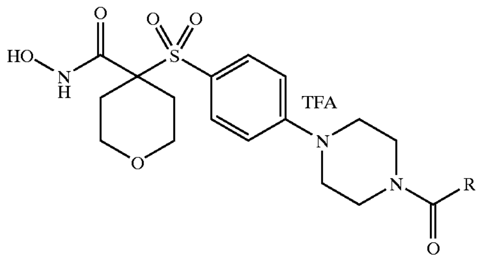

| Example Number | Carboxylic Acid | R | MS (ES) m/z |
|---|---|---|---|
| 203 | N-9-fluorenylmethoxy-carbonyl-L-proline | 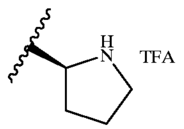 | 467 (M + H) |
| 204 | N-9-fluorenylmethoxy-carbonyl-L-valine | 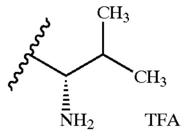 | 469 (M + H) |

Step 7: Preparation of Resin VII

Resin IIIc (1.0 g, 0.86 mmol) was weighed into an oven-dried 100 mL round-bottomed flask and a magnetic stirring bar and septum with a nitrogen needle were added. Methylene chloride (10 mL) was added, and the resin slurry was slowly stirred. p-Nitrophenylchloro-formate (0.867 g, 4.3 mmol) was added in one portion, followed by dropwise addition of diisopropylethylamine (0.75 mL, 4.3 mmol). A slight warming was noted with the addition. The reaction was stirred at room temperature for 18 hours, then the resin was collected in a sintered-disc glass funnel and washed with methylene chloride, methanol and methylene chloride (3x10 mL each solvent).

The polymer-bound product was dried in vacuo yielding 1.25 g of resin VII as brown resin beads. FTIR microscopy showed bands at 1798, 1733, 1696 and 1210 $cm^{-1}$. Theoretical loading of the polymer was 0.75 mmol/g.

Step 8: Reaction of Resin VII with Amines Preparation of Resin VIII

An 8 mL vial was charged with resin VII (50 mg, 0.038 mmol) and a small magnetic stirring bar, and a 0.5 M solution of the amine in 1-methyl-2-pyrrolidinone (1 mL) was added. The vial was capped and heated to 50 degrees Celsius. The resin slurry was gently stirred for 15 hours, then the vial was cooled to room temperature. The resin was collected in a fritted reaction vessel and washed with 1-methyl-2-pyrrolidinone, methanol and methylene chloride (3x10 mL each solvent).

The following hydroxamic acids were synthesized from resin VII using Step 8 reaction conditions with the indicated amine, followed by release from the polymer using Step 3 reaction conditions.

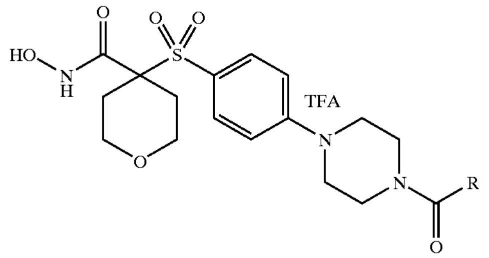

| Example Number | Carboxylic Acid | R | MS (ES) m/z |
|---|---|---|---|
| 205 | — | 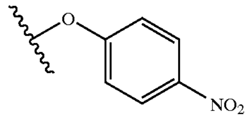 | 535 (M + H) |
| 206 | piperidine | 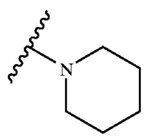 | 481 (M + H) |
| 207 | morpholine | 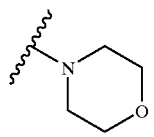 | 501 (M + Na) |
| 208 | dimethylamine | 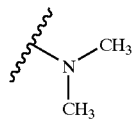 | 441 (M + H) |
| 209 | piperazine | 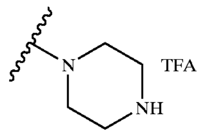 | 482 (M + H) |
| 210 | 1-methylpiperazine | 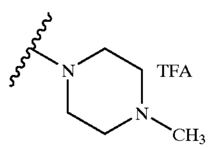 | 496 (M + H) |
| 211 | ethyl isonipecotate | 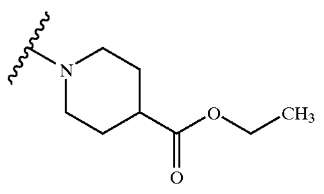 | 553 (M + H) |

-continued

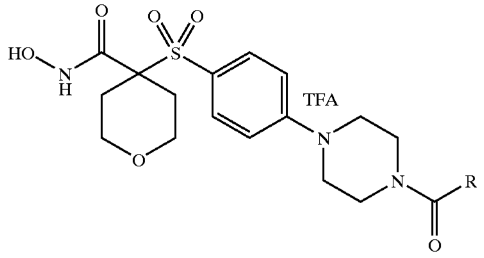

| Example Number | Carboxylic Acid | R | MS (ES) m/z |
|---|---|---|---|
| 212 | ethyl nipecotate | 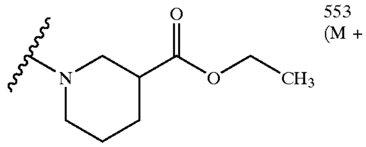 | 553 (M + H) |

EXAMPLE XXX

Preparation of 4-[(4-bromoophenyl)-sulfonyl] tetrahydro-2H-pyran-4-carboxylic Acid

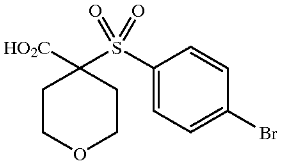

Part A: Preparatiion of

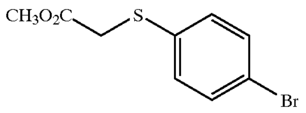

A 60% sodium hydride oil dispersion (4.0 g, 0.1 mole) was weighed into an oven-dried 3-necked 500 mL round-bottomed flask in a nitrogen glove bag, and the flask was fitted with an nitrogen inlet, a temperature probe, an overhead stirring paddle and rubber septa. Anhydrous tetrahydrofuran (200 mL) was added to the flask, which was then cooled in an ice bath. 4-Bromothiophenol (18.91 g, 0.1 mole) was added dropwise, maintaining a temperature less than 7 degrees Celsius. Vigorous gas evolution was noted throughout addition. After complete addition, the mixture was stirred for 10 minutes with cooling. Then, methyl bromoacetate (9.5 mL, 0.1 mole) was added dropwise, maintaining a temperature less than 7 degrees Celsius. The reaction was stirred for 10 minutes with cooling, then the ice bath was removed and the mixture stirred an additional 30 minutes. The reaction was quenched by the addition of 5 mL water, then solvent was removed on rotary evaporator. The residual oil was partitioned between ethyl acetate (200 mL) and water (200 mL). The organic layer was washed with 5% hydrogen choride/water (1×200 mL), saturated sodium bicarbonate (1×200 mL) and brine (1×200 mL). The organic phase was dried over magnesium sulfate and concentrated to give 24.53 g of the product as a yellow oil (94%). $^1$H NMR was consistent with the desired structure. The mass spectrum showed an m/z 260 (M+H).

Part B: Preparation of

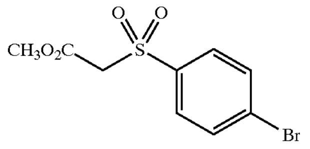

The compound of part A, above, (24.5 g, 0.094 mole) was weighed into a 1.0 L round-bottomed flask fitted with an overhead stirring paddle and temperature probe, then 550 mL of methanol were added, followed by 55 mL of water, causing the solution to become slightly turbid. The flask was immersed in an ice bath, and once the temperature fell below 5 degrees Celsius, Oxone® (144.5 g, 0.235 mole) was added portionwise over 5 minutes. A slight increase in temperature to 8 degrees Celsius was noted. The reaction was stirred with cooling for 10 minutes, then the ice bath was removed. After 4 hours, reversed-phase high pressure liquid chromatography showed a single component at 13.6 minutes. The reaction mixture was filtered, and the solid washed exhaustively with methanol. The combined filtrates were concentrated on a rotary evaporator, and the residual material partitioned between ethyl acetate (300 mL) and water (200 mL). The organic layer was washed with water (3x200 mL), saturated sodium bicarbonate (1x200 mL) and brine (1x200 mL), then the organic phase was dried over magnesium sulfate and concentrated to give 25 g of the product as a tan solid. Trituration with hexane provided 24.3 g of pure sulfone as an off-white solid (88%). $^1H$ NMR was consistent with the desired structure. The mass spectrum showed an m/z 293 (M+H).

Part C: Preparation of

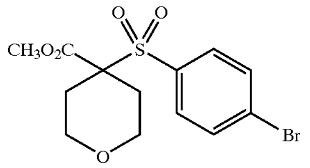

A 60% sodium hydride oil dispersion (5.76 g, 0.144 mole) was weighed into an oven-dried 3-necked 1.0 L round-bottomed flask in a nitrogen glove bag, and then the flask was fitted with an nitrogen inlet, a temperature probe, an overhead stirring paddle and rubber septa. Anhydrous N,N-dimethylformamide (250 mL) was added to the flask, mechanical stirring was initiated, and the mixture heated to 50 degrees Celsius. A solution of the compound of part B, above, (17.59 g, 0.06 mole) and dibromodiethyl ether (14.5 g, 0.06 mole) in 40 mL of N,N-dimethylformamide was added dropwise to the sodium hydride slurry, maintaining a temperature between 50–55 degrees Celsius and a steady evolution of hydrogen. After complete addition, the temperature of the reaction mixture was increased to 65 degrees Celsius, and the mixture was stirred for 2 hours. The flask was then cooled to room temperature, and the flask was immersed in an ice bath. When the temperature fell below 20 degrees Celsius, 0.5 L ice water was added.

The mixture was transferred to a 4.0 L separatory funnel, an additional 1.0 L of water was added, and the mixture was extracted with ethyl acetate (3x200 mL). The combined organic layers were washed with 5% hydrogen chloride/water (1x200 mL), saturated sodium carbonate (1x200 mL), and brine (1x200 mL), dried over magnesium sulfate, and concentrated in vacuo to give 18.2 g of crude product as a yellow semi-solid. Recrystallization from ethyl acetate/hexane gave 6.53 g of pure product as tan crystals (30%). $^1H$ NMR was consistent with the desired structure. The mass spectrum showed an m/z 363 (M+H).

Part D: Preparation of the Title compound

A solution of the compound of part C, above, (4.57 g, 12.6 mmol) in 50 mL of dry tetrahydrofuran in an oven-dried 100 mL round-bottomed flask was stirred at room temperature under nitrogen, and 4.84 g of potassium trimethylsilanolate (37.7 mmol) were added in one portion. The mixture was stirred for two hours, then 10 mL of water were added dropwise. The volatiles were removed in vacuo, and the residue partitioned between 100 mL ethyl ether and 100 mL water. The aqueous layer was acidified to a pH value of less than 2 using concentrated hydrogen chloride, causing a white precipitate. This mixture was extracted with ethyl acetate (3x75 mL), and the combined ethyl acetate layers were dried over magnesium sulfate and concentrated in vacuo to give 4.15 g of pure product as a white solid (94%). $^1H$ NMR ($CDCl_3/CD_3OD$) 2.10 (m, 4H), 3.28 (m, 2H), 3.90 (m, 2H), 7.60 (m, 4 H). The mass spectrum showed an m/z 349 (M+H).

Step 9: Attachment to Resin I: Preparation of Resin IX

Following the procedure outlined in Step 1 before, 3.13 g of the title compound of the above preparation was reacted with 3.73 g of resin I to give 5.19 g of polymer-bound hydroxymate as a tan polymeric solid. Theoretical loading on polymer was 0.86 mmol/g. FTIR microscopy showed bands at 1693 and 3332 $cm^{-1}$ indicative of the hydroxamate carbonyl and nitrogen-hydrogen stretches, respectively.

Step 10: Palladium Catalyzed Reaction of Resin IX with Boronic Acids: Preparation of Resin VII Into an 8 mL glass solid phase reaction vessel was weighed resin IX (50 mg, 0.043 mmol). The resin was washed with dry dimethoxyethane (2x3 mL). A 0.017 M solution of the palladium tetrakistriphenyl phosphine (0.6 mL, 0.01 mmol) was added to the vessel followed by a 0.6 M solution of the boronic acid in 1:1 dimethoxyethane/ethanol (0.6 mL, 0.36 mmol) and a 2M solution of potassium hydroxide in water (0.4 mL, 0.8 mmol). The vessel was maintained under a positive pressure of argon and heated at 90 degrees Celsius 16 hours. The vessel was cooled to room temperature, then the resin was drained and washed with 1-methyl-2-pyrrolidinone, 1-methyl-2-pyrrolidinone/water (1:1), water, acetic acid/water (1:9), methanol, and methylene chloride (3x3 mL each solvent).

The following hydroxamic acids were synthesized from resin IX using Step 10 reaction conditions with the indicated boronic acid, followed by cleavage from the polymer using Step 3 reaction conditions.

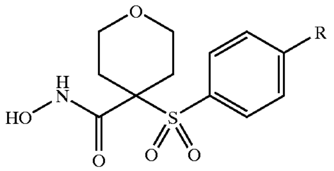
| Example Number | Boronic Acid | R | MS (ES) m/z |
|---|---|---|---|
| 213 | phenylboronic acid | 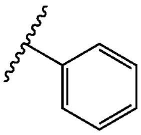 | 362 (M + H) |
| 214 | 3-nitrophenyl-boronic acid | 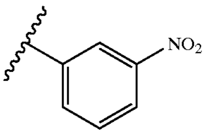 | 424 (M + $NH_4$) |
| 215 | thiophene-3-boronic acid | 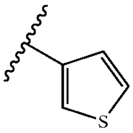 | 368 (M + H) |
| 216 | 4-chlorobenzene boronic acid | 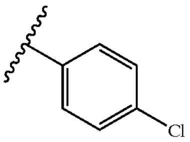 | 413 (M + $NH_4$) |
| 217 | 4-methyl-benzeneboronic acid | 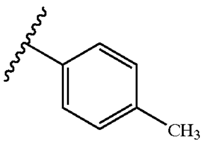 | 414 (M + K) |
| 218 | 4-(2-pyrrolidinyl-ethoxy)-benzeneboronic acid | 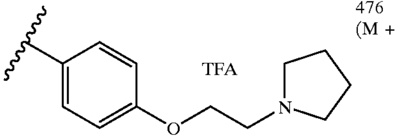 | 476 (M + $NH_4$) |
| 219 | 3-(tri-fluoromethyl)-benzeneboronic acid | 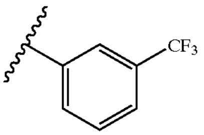 | 430 (M + H) |
| 220 | 4-fluoro-benzeneboronic acid | 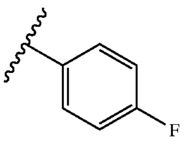 | 418 (M + K) |

-continued
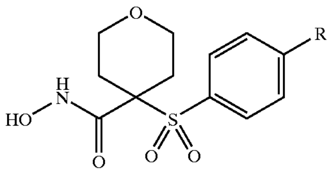
| Example Number | Boronic Acid | R | MS (ES) m/z |
|---|---|---|---|
| 221 | 4-(tri-fluoromethyl)-benzeneboronic acid | 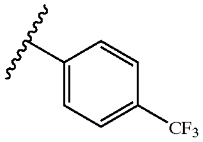 | 447 (M + $NH_4$) |
| 222 | 4-fluoro-3-methylbenzene-boronic acid | 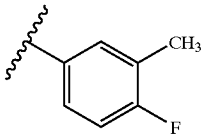 | 411 (M + $NH_4$) |
| 223 | 3,4-dimethyl-benzeneboronic acid | 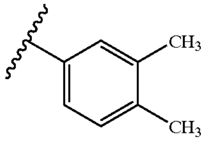 | 407 (M + $NH_4$) |
| 224 | 1-naphthylene-boronic acid | 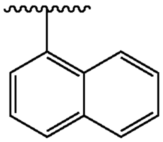 | 412 (M + H) |
| 225 | 2-methyl-benzeneboronic acid | 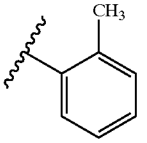 | 376 (M + H) |
| 226 | 4-t-butyl-benzeneboronic acid | 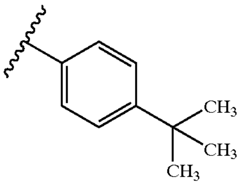 | 418 (M + H) |
| 227 | 2-naphthylene-boronic acid | 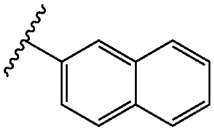 | 412 (M + H) |
| 228 | 3-formyl-benzeneboronic acid | 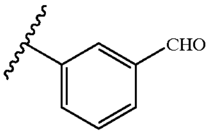 | 390 (M + H) |

-continued

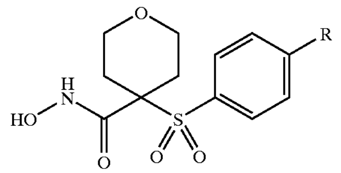

| Example Number | Boronic Acid | R | MS (ES) m/z |
|---|---|---|---|
| 229 | benzofuran-2-boronic acid | 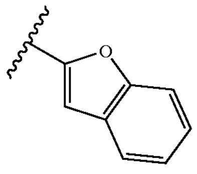 | 419 (M + $NH_4$) |
| 230 | 2-formyl-benzeneboronic acid | 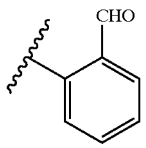 | 390 (M + H) |
| 231 | 4-formyl-benzeneboronic acid | 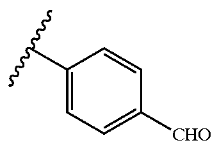 | 390 (M + H) |
| 232 | 3-amino-benzeneboronic acid | 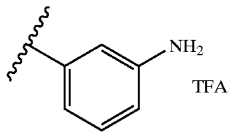 | 377 (M + H) |

EXAMPLE 233

Preparation of Monomethanesulfonate Salts: N-hydroxy-4-[[4-(phenylthio) phenyl]-sulfony]-1-(2-propynyl) -4-piperidine-carboxamide, Monomethanesulfonate

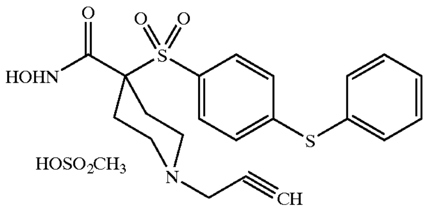

First Preparatiion

Part A: A solution of the compound of Example 9, Part J (2.1 g, 4.5 mmol) in warm $H_2O$ (200 mL) was admixed with $NaHCO_3$ at ambient temperature. After stirring for 20 minutes, the resulting white solid was isolated by filtration, washed with water and dried at 37 degree Celsius in a vacuum oven to afford the free base of the title compound as a white solid (1.7 g, 86%); Anal. calcd for $C_{21}H_{22}N_2O_4S_2$.0.3%$H_2O$: C, 57.86; H, 5.23; N, 6.43; S, 14.71. Found: C,57.84; H, 4.96; N, 6.39; S, 14.89.

Part B: Methanesulfonic acid (0.28 mL, 4.1 mmol) was added to a solution of the free base of part A (1.6 g, 3.7 mmol) in methanol (10 mL) at ambient temperature. After 3 hours, the resulting solid was isolated by filtration, washed with methanol, and dried at ambient temperature in a vacuum oven to afford the monomethanesulfonate titled compound as a white solid (1.6 g, 81%): Anal. calcd for $C_{21}H_{22}N_2O_4S_2$. $CH_4O_3$: C,48.51; H, 5.18; N, 5.14; S, 17.66. Found: C, 48.88; H, 5.15; N, 5.23; S, 17.81.

Second Preparation

Methanesulfonic acid (0.91 mL, 14 mmol) was added to a solution of the protected hydroxamate of Example 9, Part I (6.0 g, 12 mmol) in methanol (37 mL) under a nitrogen atmosphere. After 1 hour, the precipitate was isolated by filtration, washed with methanol, and dried at 40 degrees Celsius in a vacuum oven for 1 day to afford the monomethanesulfonate title compound as a white solid (5.5 g, 89%) identical to the material from Example 233, First Preparation.

Methanesulfonate salts of the other cyclic amine compounds disclosed herein can be similarly prepared using the methods of the above two preparations.

EXAMPLE 234–280

The compounds of Example 234–280 were prepared as described for the compounds of Example 129–199.

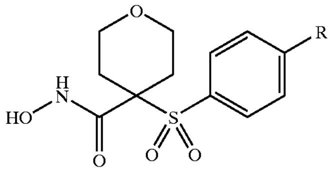
| Example Number | Resin | Amine | R | Position | MS (ES) m/z |
|---|---|---|---|---|---|
| 234 | IVb | N-methyl homopiperazine | 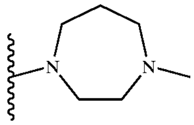 | 4 | 509 (M + H) |
| 235 | IVb | 6,7-dimethoxy-1,2,3,4-tetrahydro-isoquinoline HCl | 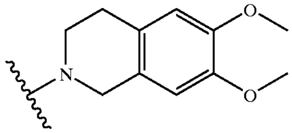 | 4 | 588 (M + H) |
| 236 | IVb | tetrahydro-pyridine | 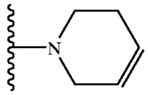 | 4 | 478 (M + H) |
| 237 | IVb | R-3-hydroxy-piperidine HCl | 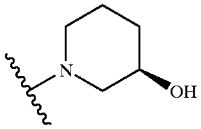 | 4 | 496 (M + H) |
| 238 | IVb | phenyl-piperazine | 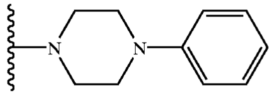 | 4 | 557 (M + H) |
| 239 | IVb | benzyl-piperazine | 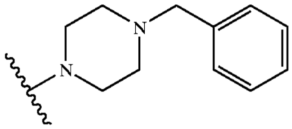 | 4 | 571 (M + H) |
| 240 | IVa | methyl homopiperazine | 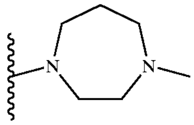 | 3 | 509 (M + H) |
| 241 | IVa | 6,7-dimethoxy-1,2,3,4-tetrahydro-isoquinoline HCl | 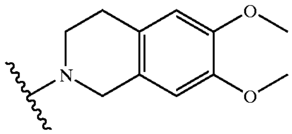 | 3 | 588 (M + H) |
| 242 | IVa | tetrahydro-pyridine | 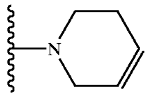 | 3 | 478 (M + H) |

-continued
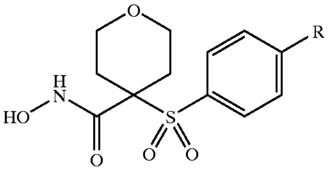
| Example Number | Resin | Amine | R | Position | MS (ES) m/z |
|---|---|---|---|---|---|
| 243 | IVa | R-3-hydroxy-piperidine HCl | 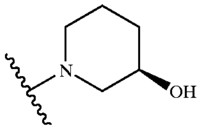 | 3 | 496 (M + H) |
| 244 | IVa | phenyl-piperazine | 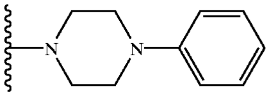 | 3 | 557 (M + H) |
| 245 | IVa | benzyl-piperazine | 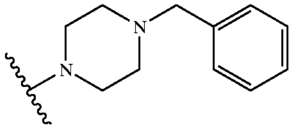 | 3 | 571 (M + H) |
| 246 | IVb | hydroxyethyl-piperazine | 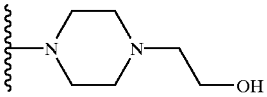 | 4 | 525 (M + H) |
| 247 | IVb | 1-(2,3-xylyl)-piperazine HCl | 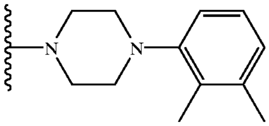 | 4 | 585 (M + H) |
| 247 | IVb | 1-(4-methoxy-phenyl)-piperazine 2HCl | 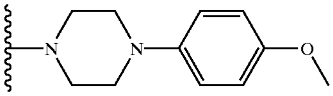 | 4 | 587 (M + H) |
| 249 | IVb | 1-(3-chlorophenyl)-piperazine HCl | 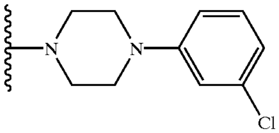 | 4 | 591 (M + H) |
| 250 | IVb | 1-(m-tolyl)-piperazine 2HCl | 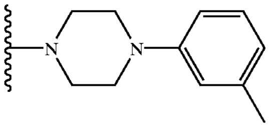 | 4 | 571 (M + H) |
| 251 | IVb | 1-(2,5-dimethyl-phenyl)piperazine | 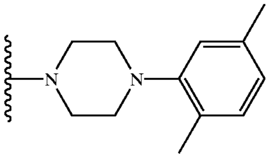 | 4 | 585 (M + H) |

-continued
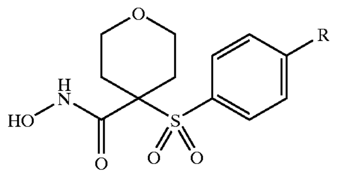
| Example Number | Resin | Amine | R | Position | MS (ES) m/z |
|---|---|---|---|---|---|
| 252 | IVb | 1-(p-toyl)-piperazine 2HCl | 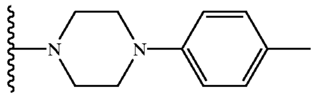 | 4 | 571 (M + H) |
| 253 | IVb | 1-(3-methoxy-phenyl)-piperazine 2HCl | 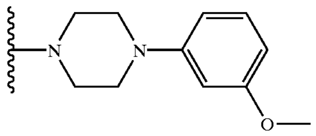 | 4 | 587 (M + H) |
| 254 | IVb | 1-(3,4-dichloro-phenyl)piperazine | 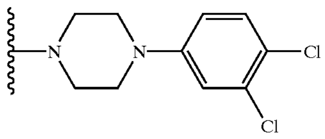 | 4 | 625 (M + H) |
| 255 | IVb | 1-(2-methoxy)-piperazine HCl | 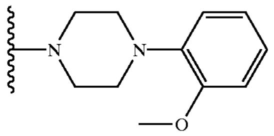 | 4 | 587 (M + H) |
| 256 | IVb | nipecotamide | 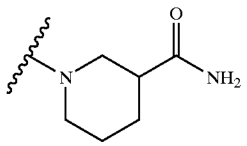 | 4 | 523 (M + H) |
| 257 | IVb | isonipecotamide | 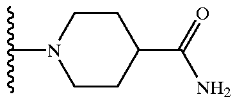 | 4 | 523 (M + H) |
| 258 | IVb | 1-(2-(2-hydroxy-ethoxyethyl)-piperazine | 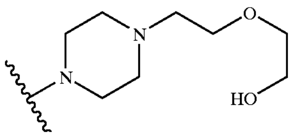 | 4 | 569 (M + H) |
| 259 | IVb | 1-ethyl-piperazine | 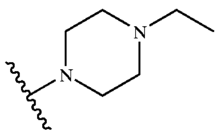 | 4 | 509 (M + H) |

-continued
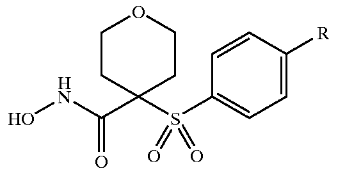
| Example Number | Resin | Amine | R | Position | MS (ES) m/z |
|---|---|---|---|---|---|
| 260 | IVb | 1-(2-chlorophenyl)-piperazine HCl | 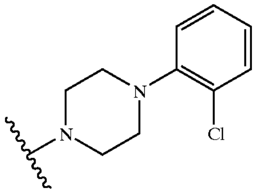 | 4 | 591 (M + H) |
| 261 | IVb | 1-(4-methoxy-phenyl)-2-methyl-piperazine | 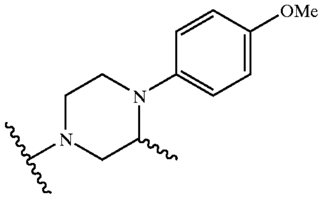 | 4 | 601 (M + H) |
| 262 | IVb | 2-methyl-piperidine | 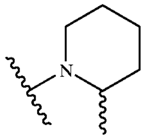 | 4 | 494 (M + H) |
| 263 | IVb | 3,5-dimethyl-piperidine | 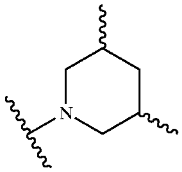 | 4 | 508 (M + H) |
| 264 | IVb | N-(2-piperidyl-methyl)-diethylamine | 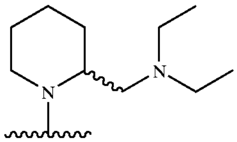 | 4 | 565 (M + H) |
| 265 | IVb | thiomorpholine HCl | 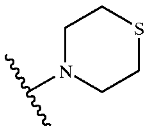 | 4 | 498 (M + H) |
| 266 | IVb | N-methyl-propargylamine | 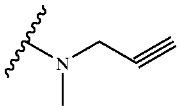 | 4 | 464 (M + H) |
| 267 | IVb | N-methyl-β-alaninenitrile | 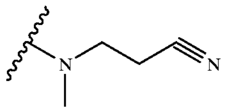 | 4 | 479 (M + H) |

-continued
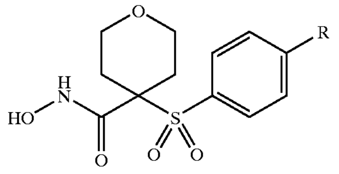
| Example Number | Resin | Amine | R | Position | MS (ES) m/z |
|---|---|---|---|---|---|
| 268 | IVb | 1-methyl-4-(methyl-amino)piperidine | 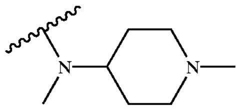 | 4 | 523 (M + H) |
| 269 | IVb | 2-ethyl-piperidine | 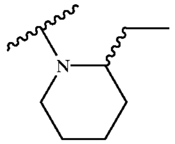 | 4 | 508 (M + H) |
| 270 | IVb | 1-piperazine-carboxaldehyde | 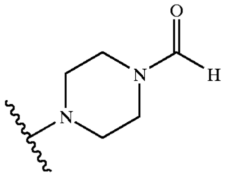 | 4 | 509 (M + H) |
| 271 | IVb | 2-piperidin-ethanol | 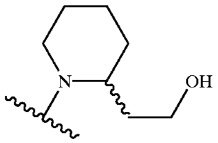 | 4 | 524 (M + H) |
| 272 | IVb | 2-(methylamino)-ethanol | 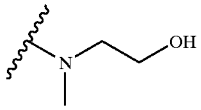 | 4 | 470 (M + H) |
| 273 | IVb | N-methylallyl-amine | 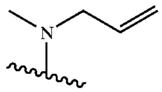 | 4 | 466 (M + H) |

-continued
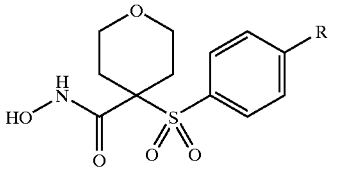
| Example Number | Resin | Amine | R | Position | MS (ES) m/z |
|---|---|---|---|---|---|
| 274 | IVb | 2-(piperidino-methyl)-piperidine | 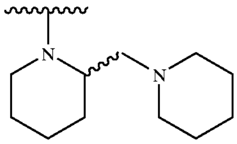 | 4 | 577 (M + H) |
| 275 | IVb | 1-(1-phenyl-ethyl)-piperazine | 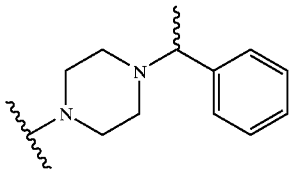 | 4 | 585 (M + H) |
| 276 | IVb | 1-(2-phenyl-ethyl)-piperazine | 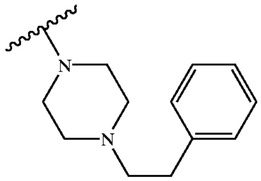 | 4 | 585 (M + H) |
| 277 | IVb | N,N-dimethyl-N'-ethylene-diamine | 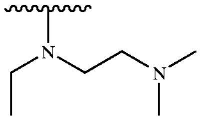 | 4 | 511 (M + H) |
| 278 | IVb | N,N-diethyl-N-methylene-ethylenediamine | 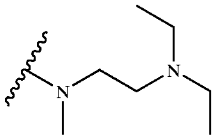 | 4 | 525 (M + H) |
| 279 | IVb | 1-cyclohexyl-piperazine | 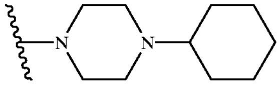 | 4 | 563 (M + H) |
| 280 | IVb | 2,6-dimethyl-piperidine | 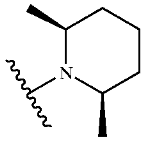 | 4 | 508 (M + H) |

EXAMPLE 281–288

The following hydroxamic acids were synthesized from Resin IX using Step 10 with the indicated boronic acid, followed by cleavage from the polymer using Step 3, as discussed previously for Example 213–232:

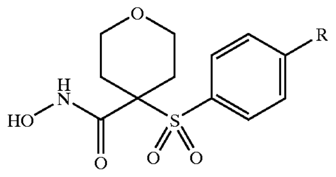

| Example Number | Boronic acid | R | MS (ES) m/z |
|---|---|---|---|
| 281 | 4-methoxy-benzeneboronic acid | 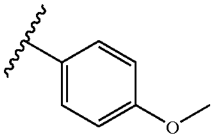 | 392 (M + H) |
| 282 | 3-methoxy-benzeneboronic acid | 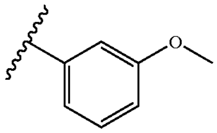 | 392 (M + H) |
| 283 | 4-methylthio-benzeneboronic acid | 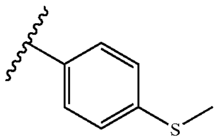 | 408 (M + H) |
| 284 | 4-MeNHSO$_2$-benzene boronic acid | 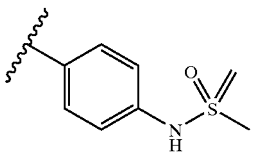 | 455 (M + H) |
| 285 | 4-carboxybenz-eneboronic acid | 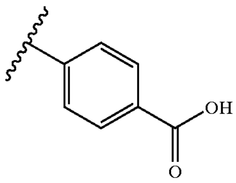 | 406 (M + H) |

-continued

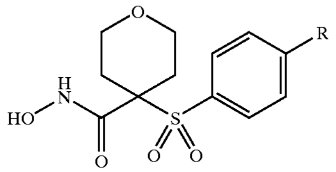

| Example Number | Boronic acid | R | MS (ES) m/z |
|---|---|---|---|
| 286 | 2-trifluoro-methylbenzene-boronic acid | 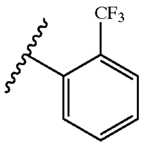 | 430 (M + H) |
| 287 | 3,5-bis-(tri-fluoromethyl)-benzeneboronic acid | 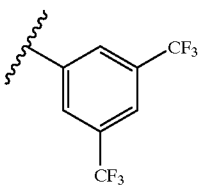 | 498 (M + H) |
| 288 | 2,3,4-trifluoro-benzeneboronic acid | 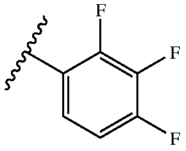 | 416 (M + H) |

EXAMPLE 289–294

Step 11: Preparation of Resin XI

Into a fritted reaction vessel was placed Resin IIIc (50 mg, 0.043 mmol). A 0.43 M solution of the isocyanate in 1-methyl-2-pyrrolidinone (1 ml, 0.43 mmol) was added followed by diisopropylethylamine (75 uL, 0.43 mmol). The vessel was capped under nitrogen, agitated on a tabletop shaker, and heated to 50 degrees Celsius for 48 hours. Then, the vessel was cooled to room temperature, and the resin was drained and washed with 1-methyl-2-pyrrolidinone, 1:1 1-methyl-2-pyrrolidinone/water, water, 1:9 acetic acid/ water, methanol and methylene chloride (3×1 mL each solvent).

The following hydroxamic acids were synthesized from Resin IIIc using Step 11 with the indicated isocyanate, followed by release from the polymer using the reaction conditions in Step 3.

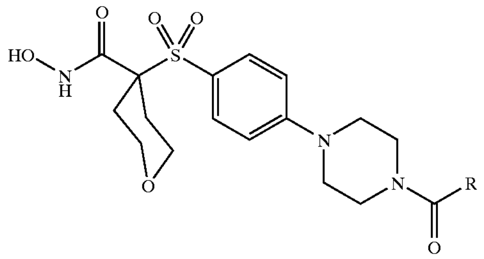

| Example Number | Isocyanate | R | MS (FAB) m/z |
|---|---|---|---|
| 289 | phenyl isocyanate | 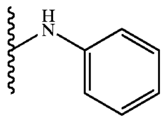 | 489.1 (M + H) |
| 290 | 4-fluorophenyl isocyanate | 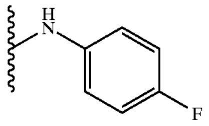 | 507.2 (M + H) |
| 291 | 4-phenoxyphenyl isocyanate | 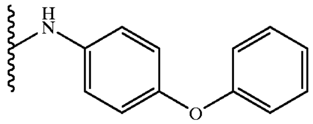 | 581.3 (M + H) |
| 292 | 4-butoxyphenyl isocyanate | 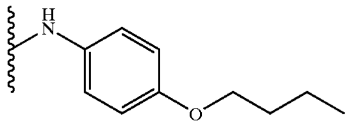 | 561.4 (M + H) |
| 293 | 4-phenylphenyl-isocyanate | 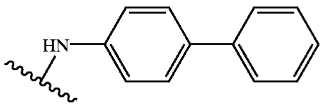 | 565.2 (M + H) |
| 294 | α,α,α-trifluoro m-tolyl isocyanate | 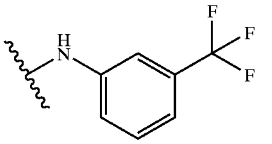 | 557.2 (M + H) |

EXAMPLE 295–300

Step 12: Synthesis of Resin XII

Into a fritted reaction vessel was placed resin VII (50 mg, 0.038 mmol) and cesium carbonate (122mg, 0.38 mmol). A 0.43 M solution of the phenol in 1-methyl-2-pyrrolidinone (1 mL, 0.43 mmol) was added, then the vessel was capped under nitrogen. The reaction mixture was agitated on a tabletop shaker and heated to 50 degrees Celsius for 48 hours. Then, the vessel was cooled to room temperature, and the resin was drained and washed with 1-methyl-2-pyrrolidinone, 1:1 1-methyl-2-pyrrolidinone/water, water, 1:9 acetic acid/water, methanol and methylene chloride (3×1 mL each solvent).

The following hydroxamic acids were synthesized from Resin IIIc using Step 11 with the indicated isocyanate, followed by release from the polymer using the reaction conditions in Step 3.

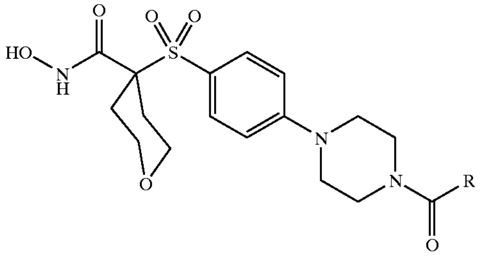

| Example Number | Phenol | R | MS (FAB) m/z |
|---|---|---|---|
| 295 | phenol | 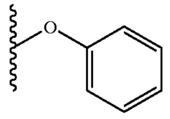 | 490 (M + H) |
| 296 | 3-methoxyphenol | 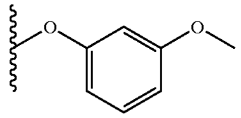 | 520 (M + H) |
| 297 | 4-chlorophenol | 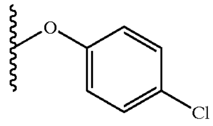 | 524.1 (M + H) |
| 298 | p-cresol | 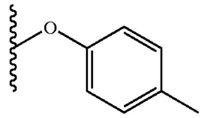 | 504.3 (M + H) |
| 299 | 4-phenylphenol | 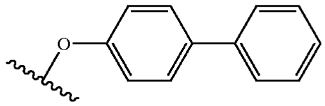 | 566.3 (M + H) |
| 300 | 4-hydroxy-diphenyl-methane | 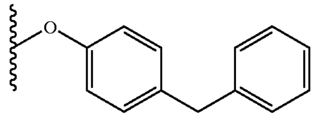 | 580.2 (M + H) |

EXAMPLE 301–323

Large Scale Preparation of Resin Xa

A fritted reaction vessel was charged with Resin IX (1 g, 0.86 mmnol) and a 0.008 M solution of tetrakis-(triphenylphosphine)palladium(0) in ethylene glycol dimethyl ether (5 mL, 0.04 mmol). A 1 M of 2-formylbenzeneboronic acid in a 1:1 mixture of ethanol and ethylene glycol dimethyl ether (6 mL, 6 mmol) was added followed by 1 M cesium carbonate in water (2 mL, 2 mmol). The vessel was sealed under argon and heated to 90 degrees Celsius for 16 hours. After this, the vessel was cooled to room temperature, and the resin drained and washed with the following sequence of solvents dimethylformamide, 1:1 dimethylformamide/water, dimethylformamide, water, methanol, methylene chloride (3x5 mL each solvent). The resin was dried in vacuo to yield 1.025 g of product as a tan polymeric solid. The theoretical loading of the polymer was 0.84 mmol/g. TFA cleavage performed on 35 mg of Resin Xa as described in Step 3 yielded 11.2 mg of a tan solid

Large Scale Preparation of Resin Xb

Preparation of Resin Xb followed the identical procedure described for preparation of resin Xa, except 3-formylbenzeneboronic acid was substituted for 2-formylbenzeneboronic acid. The yield after drying in vacuo was 1.052 g of Resin Xb as tan resin beads. The theoretical loading of the polymer was 0.84 mmol/g. TFA cleavage performed on 20 mg of Resin Xb as described in Step 3 yielded 6.5 mg of a tan solid.

Large Scale Preparation of Resin Xc

Preparation of Resin Xc followed the identical procedure described for preparation of resin Xa, except 4-formylbenzeneboronic acid was substituted for 2-formylbenzeneboronic acid. The yield after drying in vacuo was 1.03 g of Resin Xc as tan resin beads. The theoretical loading of the polymer was 0.84 mmol/g. TFA cleavage performed on 28 mg of Resin Xb as described in Step 3 yielded 9.4 mg of a tan solid.

Step 13: Synthesis of Resin XIII

Into a fritted reaction vessel was placed resin Xa, Xb or Xc (50 mg, 0.042 mmol). A 0.2 M solution of the amine in trimethylorthoformate (1 mL, 0.2 mmol) was added, and the vessel was capped under nitrogen. The reaction mixture was agitated on a tabletop shaker for 3 hours. Then, a 0.5 M solution of sodium triacetoxyborohydride in 1-methyl-2-pyrrolidinone (0.8 mL, 0.4 mmol) was added to the vessel, and the mixture was agitated an additional 40 hours. After this, the resin was drained and washed (3×1 mL each solvent) with the following sequence of solvents: 1-methyl-2-pyrrolidinone, methanol, water, methanol and methylene chloride.

The following hydroxamic acids were synthesized using the indicated resin-bound aldehyde and the indicated amine following the procedure outlined in Step 13 followed by release from the polymer using the procedure in Step 3:

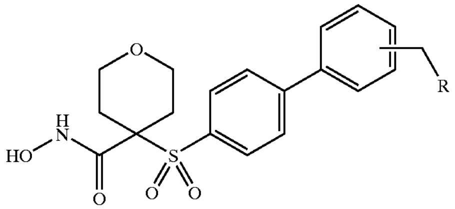

| Example Number | Resin | Amine | R | position | MS (ES) m/z |
|---|---|---|---|---|---|
| 301 | Xb | 1,2,3,4-tetrahydro-isoquinoline | TFA • 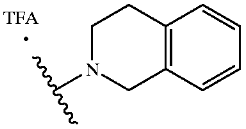 | 3 | 507 (M + H) |
| 302 | Xb | 1-methyl-piperazine | TFA 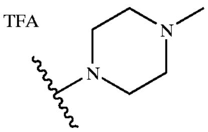 TFA | 3 | 474 (M + H) |
| 303 | Xb | piperazine | TFA 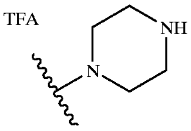 TFA | 3 | 460 (M + H) |
| 304 | Xb | benzylamine | TFA 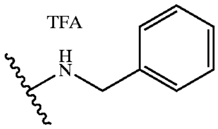 | 3 | 481 (M + H) |
| 305 | Xb | propylamine | TFA 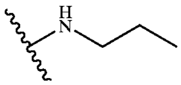 | 3 | 433 (M + H) |
| 306 | Xb | ethyl iso-nipecotate | TFA 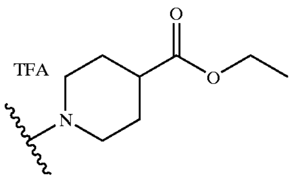 | 3 | 531 (M + H) |
| 307 | Xa | benzylamine | TFA 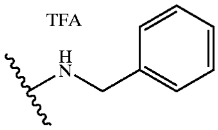 | 2 | 481 (M + H) |

-continued
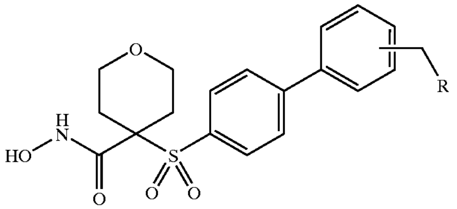
| Example Number | Resin | Amine | R | position | MS (ES) m/z |
|---|---|---|---|---|---|
| 308 | Xa | isopropyl-amine | TFA 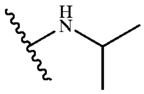 | 2 | 433 (M + H) |
| 309 | Xa | 1,2,3,4-tetrahydro-isoquinoline | TFA 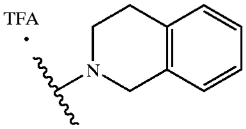 | 2 | 507 (M + H) |
| 310 | Xa | 1-methyl-piperazine | TFA 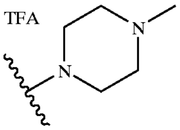 TFA | 2 | 474 (M + H) |
| 311 | Xc | piperidine | TFA 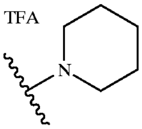 | 4 | 459 (M + H) |
| 312 | Xc | morpholine | TFA 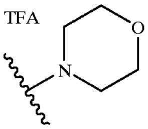 | 4 | 461 (M + H) |
| 313 | Xc | 1-methyl-piperazine | TFA 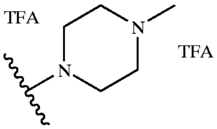 TFA | 4 | 474 (M + H) |
| 314 | Xc | 1-phenyl-piperazine | TFA TFA 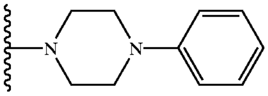 | 4 | 536 (M + H) |
| 315 | Xc | 1-benzyl-piperazine | TFA TFA 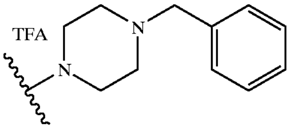 | 4 | 550 (M + H) |
| 316 | Xc | 1-(4-fluoro-phenyl)-piperazine | TFA TFA 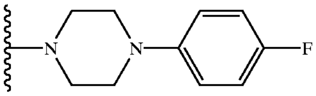 | 4 | 554 (M + H) |

-continued

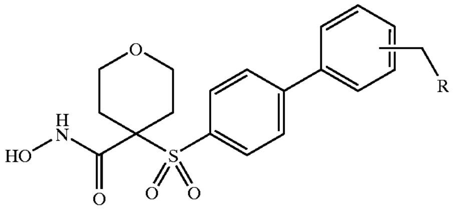

| Example Number | Resin | Amine | R | position | MS (ES) m/z |
|---|---|---|---|---|---|
| 317 | Xc | N,N,N'-trimethyl-ethylenediamine | TFA TFA 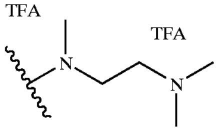 | 4 | 476 (M + H) |
| 318 | Xc | hexamethyl-eneimine | TFA 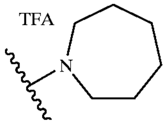 | 4 | 473 (M + H) |
| 319 | Xc | 1-methyl-homopiperazine | TFA TFA 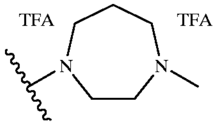 | 4 | 488 (M + H) |
| 320 | Xc | diethylamine | TFA 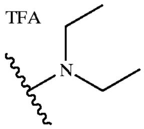 | 4 | 447 (M + H) |
| 321 | Xc | pyrrolidine | TFA 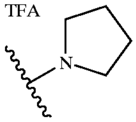 | 4 | 445 (M + H) |
| 322 | Xb | dimethylamine | TFA 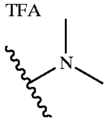 | 3 | 419 (M + H) |
| 323 | Xc | 1-t-butoxy-carbonyl-piperazine | TFA TFA 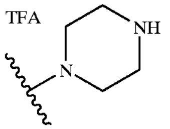 | 4 | 460 (M + H) |

Large Scale Preparation of Resin Xd

Preparation of Resin Xd followed the identical procedure described for preparation of resin Xa, except 4-carboxybenzeneboronic acid was substituted for 2-formylbenzeneboronic acid. The yield after drying in vacuo was 1.07 g of Resin Xd as a tan polymeric solid. The theoretical loading of the polymer was 0.83 mmol/g. TFA cleavage performed on 23.5 mg of Resin Xd as described in Step 3 yielded 4.9 mg of a tan solid.

Step 14: Synthesis of Resin XIV

Into a fritted reaction vessel was placed resin Xd (50 mg, 0.042 mmol). The resin was washed with 1-methyl-2-pyrrolidinone (2×3 mL), then a 1.0 M solution of benzotriazole-1-yl-oxy-tris-pyrrolidino-phosphonium hexafluorophosphate in 1-methyl-2-pyrrolidinone (0.2 mL, 0.2 mmol) was added followed by a 0.7 M solution of the amine in 1-methyl-2-pyrrolidinone (0.3 mL, 0.21 mmol) and a 1.0 M solution of the diisopropylethylamine in 1-methyl-2-pyrrolidinone (0.4 mL, 0.4 mmol). The vessel was capped under nitrogen, and the reaction mixture was agitated on a tabletop shaker for 24 hours. Then, the resin was drained and washed with 1-methyl-2-pyrrolidinone (3×1 mL). The reaction with the amine was repeated by addition of a 1.0 M solution of benzotriazole-1-yl-oxy-tris-pyrrolidinophosphonium hexafluorophosphate in 1-methyl-2-pyrrolidinone (0.2 mL, 0.2 mmol), a 0.7 M solution of the amine in 1-methyl-2-pyrrolidinone (0.3 mL, 0.21 mmol) and a 1.0 M solution of the diisopropylethylamine in 1-methyl-2-pyrrolidinone (0.4 mL, 0.4 mmol). The vessel was capped under nitrogen, and the reaction mixture was agitated an additional 8 hours. Then, the resin was drained and washed with the following sequence of solvents: 1-methyl-2-pyrrolidinone, 1:1 1-methyl-2-pyrrolidinone/water, water, 1:9 acetic acid/water, methanol, methylene chloride (3×1 mL each solvent).

The following hydroxamic acids were synthesized using Resin Xd and the indicated amine following the procedure outlined in Step 14 followed by release from the polymer using the procedure in Step 3:

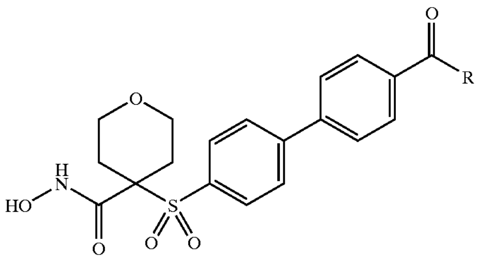

| Example | amine | R | MS (ES) m/z |
|---|---|---|---|
| 324 | propylamine | 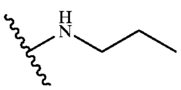 | 447 (M + H) |
| 325 | piperidine | 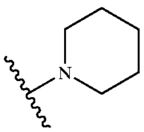 | 473 (M + H) |
| 326 | morpholine | 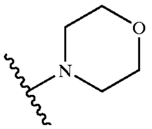 | 475 (M + H) |
| 327 | 1-methyl-piperazine | 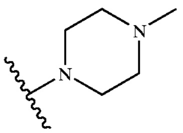 TFA | 488 (M + H) |
| 328 | diethylamine | 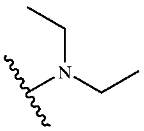 | 461 (M + H) |
| 329 | pyrrolidine | 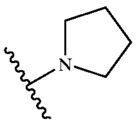 | 459 (M + H) |
| 330 | ethyl isonipecotate | 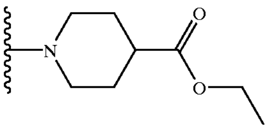 | 545 (M + H) |

-continued

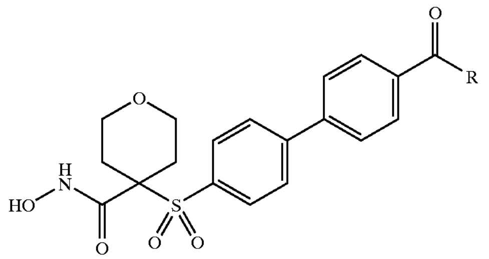

| Example | amine | R | MS (ES) m/z |
|---|---|---|---|
| 331 | 1-phenyl-piperazine | 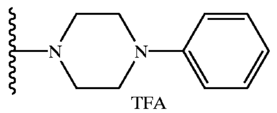 TFA | 550 (M + H) |
| 332 | ethyl nipecotate | 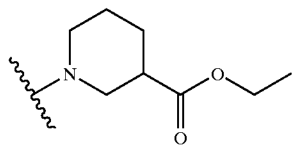 | 545 (M + H) |
| 333 | 1-benzyl-piperazine | TFA 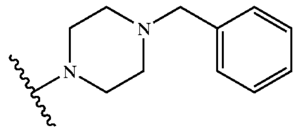 | 564 (M + H) |
| 334 | 3,5-dimethyl-piperidine | 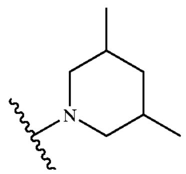 | 501 (M + H) |
| 335 | thiomorpholine hydrochloride | 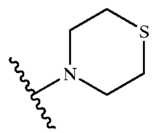 | 491 (M + H) |

EXAMPLE 336

Preparation of 4-[[4-[4- [[(9H-fluoren-9-ylmethoxy) carbonyl]amino]-1-piperidinyl]-phenyl]sulfonyl] tetrahydro-2H-pyran-4-carboxylic Acid Part A: To a solution of the product of Example 11, Part B (10.0 g, 34.7 mmol) in 1-methyl-2-pyrrolidinone (70 mL) was added 4-(N-t-butoxycarbonylamino)piperidine (10.43 g, 52.1 mmol), followed by diisopropylethylamine (6.0 mL, 34.7 mmol). The resulting mixture was heated at 80 degrees Celsius for 24 hours and then cooled to room temperature. The crude mixture was poured into 700 mL water, and the cloudy aqueous layer was extracted with ethyl acetate (3×150 mL). The combined organic layers were washed with 5% potassium hydrogen sulfate (2×150 mL) and brine (2×150 mL), dried over magnesium sulfate, and concentrated in vacuo to give the crude ester as a white foamy solid (13.04 g, 78%).

Part B: To a solution of the ester of part A (5.74 g, 11.9 mmol) in a mixture of ethanol (80 mL) and tetrahydrofuran (40 mL) was added 2 N sodium hydroxide (60 mL; 120 mmole). The resulting solution was heated to 60 degrees Celsius for 1 hour and then cooled to room temperature. The solution was concentrated in vacuo, and the residue was partitioned between water (300 mL) and ethyl acetate (200 mL). The aqueous layer was separated and acidified with concentrated hydrogen chloride to pH 2. A white precipitate formed, which was collected by vacuum filtration and dried in vacuo to give the carboxylic acid as a white solid (4.88 g, 88%).

Part C: To a suspension of the carboxylic acid from part B (4.88 g, 10.4 mmol) in methylene chloride (35 mL) was added trifluoroacetic acid (35 mL), resulting in dissolution of the solid. After fifteen minutes at ambient temperature, the solution was concentrated in vacuo. The product was triturated with diethyl ether to give the amino acid as an off-white solid (4.92 g, 98%).

Part D: A suspension of the amino acid from part C (4.92 g, 10.21 mmol) in a mixture of 10% sodium carbonate/water (35 mL), water (100 mL) and dioxane (100 mL) was cooled in an ice bath. To the cooled suspension is added a solution of 9-fluorenylmethylsuccinimidyl carbonate (3.79 g, 11.23 mmol) in dioxane (50 mL) dropwise. After complete addition, the ice bath was removed, and the mixture warmed to room temperature. After one hour, the solution was concentrated in vacuo, and the residue was partitioned between water (300 mL) and ethyl acetate (200 mL). The aqueous layer was separated and acidified with concentrated hydrogen chloride to pH 2. The white precipitate formed, which was collected by vacuum filtration, washed with hexanes and dried in vacuo to give the title compound as a white solid (5.46 g, 91%).

Step 15: Preparation of Resin XVI

Part A: Following the procedure outlined in Step 1 above, the product of Example 336 (2.4 g, 4.06 mmol) was reacted with Resin I (1.7 g, 2.03 mmol) to give Resin XV as a tan polymeric solid (2.82 g). Theoretical loading on polymer was 0.71 mmol/g.

Part B: Resin XV from part A above (2.76 g, 1.96 mmol) was suspended in a 1:4 piperidine/dimethylformamide solution (20 mL) in a fritted reaction vessel and agitated on a tabletop shaker for 5 minutes. The resin was drained, and an additional volume of a 1:4 mixture of piperidine/dimethylformamide (20 mL) was added to the vessel. The slurry was agitated at room temperature for 30 minutes. After this, the resin was drained and washed with dimethylformamide, methanol, and methylene chloride (3x20 mL each solvent). After drying in vacuo, the title resin was obtained as a tan polymeric solid (2.30 g).

Step 16: Acylation/Sulfonylation of Resin XVI

In a fritted reaction vessel, Resin XVI (50 mg, 0.043 mmol) was washed with 1-methyl-2-pyrrolidinone (2x1 mL). Then, a 0.22 M solution of the acylating or sulfonylating reagent in 1-methyl-2-pyrrolidinone (1 mL, 0.22 mmol) was added to the resin followed by diisopropylethylamine (40 uL, 0.22 mmol). The vessel was capped under nitrogen and agitated on a tabletop shaker at room temperature for 16 hours. Then, the resin was drained and washed with 1-methyl-2-pyrrolidinone, water, 1:9 acetic acid/water, methanol and methylene chloride (3x1 mL each solvent).

The following hydroxamic acids were synthesized from Resin XVI using Step 16 with the indicated acylating or sulfonylating reagent, followed by release from the polymer using the reaction conditions in Step 3.

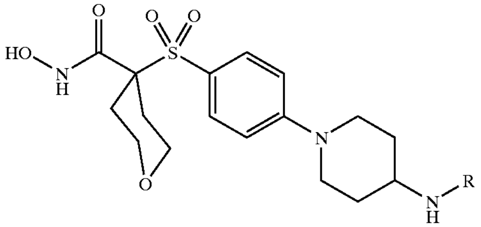

| Example | Acylating or Sulfonylating Reagent | R | MS (ES) m/z |
|---|---|---|---|
| 337 | benzoyl chloride | 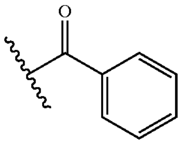 | 488.2 (M + H) |
| 338 | nicotinyl chloride-HCl | 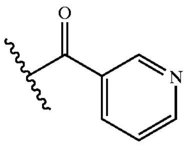 TFA | 489.2 (M + H) |
| 339 | benzenesulfonyl chloride | 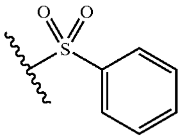 | 462 (M + H) |
| 340 | 1-methyl-imidazole-4-sulfonyl chloride | 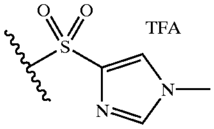 TFA | 528.2 (M + H) |

-continued
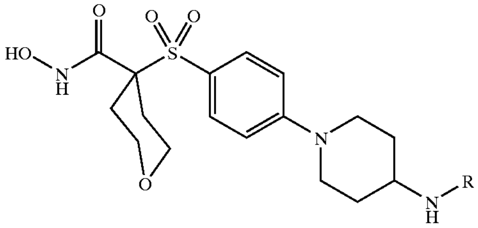
| Example | Acylating or Sulfonylating Reagent | R | MS (ES) m/z |
|---|---|---|---|
| 341 | acteyl chloride | 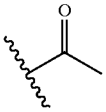 | 426.2 (M + H) |
| 342 | methanesulfonyl chloride | 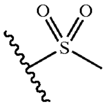 | 462.1 (M + H) |
| 343 | cyclohexyl isocyanate | 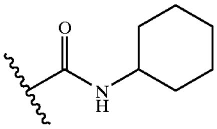 | 509 (M + H) |
| 344 | 2-methoxyphenyl isocyanate | 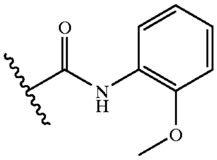 | 533 (M + H) |
| 345 | phenyl isocyanate | 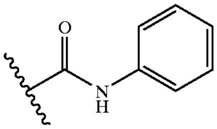 | 503 (M + H) |
| 346 | beta-phenylethyl isocyanate | 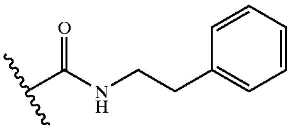 | 531 (M + H) |
| 347 | isopropyl isocyanate | 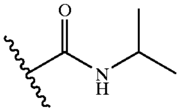 | 469 (M + H) |
| 348 | 4-fluorophenyl isocyanate | 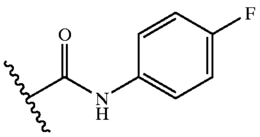 | 521 (M + H) |
| 349 | 4-(methylthio)-phenyl isocyanate | 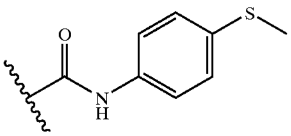 | 549 (M + H) |

-continued
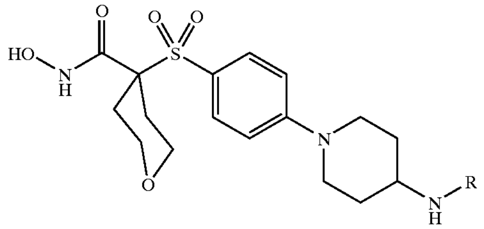
| Example | Acylating or Sulfonylating Reagent | R | MS (ES) m/z |
|---|---|---|---|
| 350 | 4-phenoxyphenyl isocyanate | 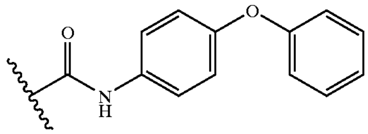 | 595 (M + H) |
| 351 | 4-phenylphenyl isocyanate | 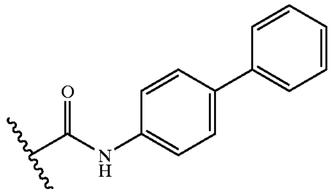 | 579 (M + H) |
| 352 | benzyl isocyanate | 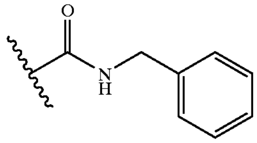 | 517 (M + H) |
| 353 | ethyl isocyanate | 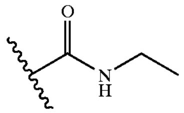 | 455 (M + H) |
| 354 | alpha,alpha,alpha-trifluoro-m-tolyl isocyanate | 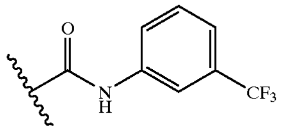 | 571 (M + H) |
| 355 | ethyl 3-isocyanato-propionate | 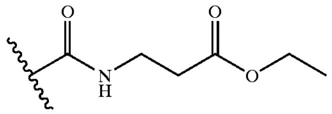 | 527 (M + H) |
| 356 | methyl oxalyl chloride | 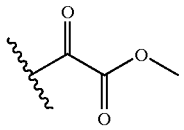 | 470 (M + H) |
| 357 | diethylcarbamyl chloride | 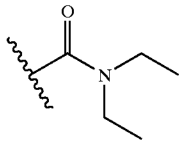 | 483 (M + H) |

-continued

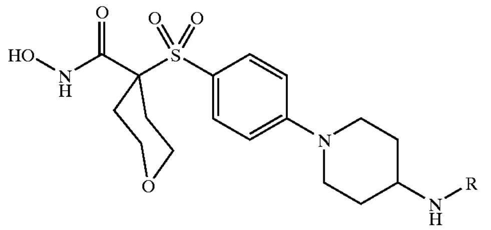

| Example | Acylating or Sulfonylating Reagent | R | MS (ES) m/z |
|---|---|---|---|
| 358 | dimethylcarbamyl chloride | 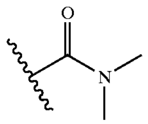 | 455 (M + H) |
| 359 | diisopropyl carbamyl chloride | 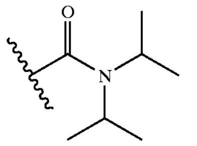 | 511 (M + H) |
| 360 | hydrocinnamoyl chloride | 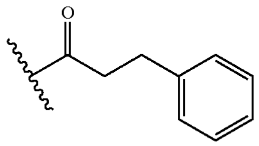 | 516 (M + H) |
| 361 | cinnamoyl chloride | 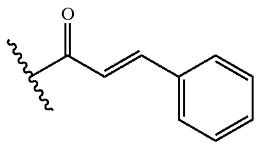 | 514 (M + H) |
| 362 | isobutyl-chloroformate | 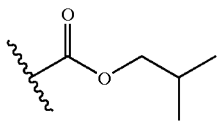 | 484 (M + H) |
| 363 | benzylchloro-formate | 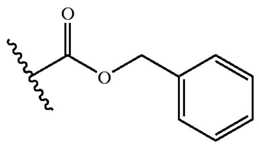 | 518 (M + H) |
| 364 | trichloroethyl-chloroformate | 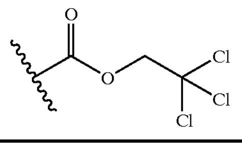 | 558 (M + H) |

EXAMPLE 365–371

Step 17: Reductive Alkylation of Resin XVI

In a fritted reaction vessel, Resin XVI (50 mg, 0.043 mmol) was washed methylene chloride (2×1 mL). Then, a 1 M solution of the aldehyde or ketone in methylene chloride (1 mL, 1 mmol) was added to the resin. The vessel was capped under nitrogen and agitated on a tabletop shaker at room temperature for 3 hours. The resin was drained and washed with methylene chloride (3×1 mL). Then, the resin was retreated with the 1 M solution of the aldehyde or ketone in methylene chloride (1 mL, 1 mmol). The resin was drained and washed with methylene chloride (3×1 mL each solvent). Then, a 1 M solution of sodium triacetoxyborohydride in 1-methyl-2-pyrrolidinone (1 L, 1 mmol) was added to the resin, and the reaction was stirred overnight. After this, the resin was drained and washed with 1-methyl-2-pyrrolidinone, methanol, water, 1:9 acetic acid/water, methanol and methylene chloride (3×1 mL each solvent).

The following hydroxamic acids were synthesized from Resin XVI using Step 17 with the indicated aldehyde or ketone, followed by release from the polymer using the conditions in Step 3.

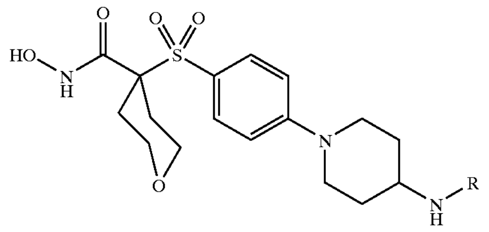

| Example Number | Aldehyde or Ketone | R | MS (ES) m/z |
|---|---|---|---|
| 365 | butyraldehyde | 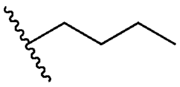 | 440 (M + H) |
| 366 | acetone | 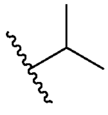 | 426 (M + H) |
| 367 | N-propyl-4-pyridone | 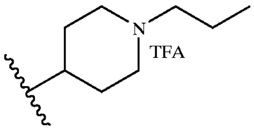 | 509 (M + H) |
| 368 | 4-t-butylcyclo-hexanone | 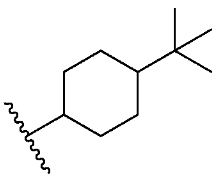 | 522 (M + H) |
| 369 | 2-pyridine-carboxaldehyde | 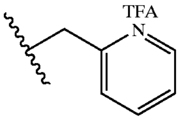 | 475 (M + H) |
| 370 | 4'-(trifluoro-methoxy)-acetophenone | 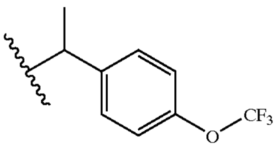 | 572 (M + H) |
| 371 | 2-furaldehyde | 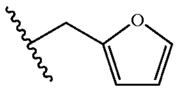 | 464 (M + H) |

EXAMPLE 372

Preparation of 4-[[4-(4-butoxyphenoxy)-phenyl] sulfonyl]tetrahydro-N-hydroxy-2H-pyran-4-carboxamide

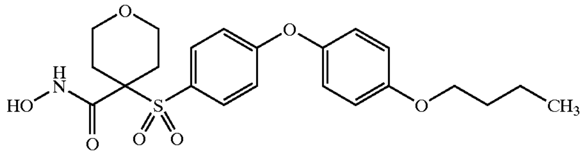

Part A:To a solution of the product of Example 55 (3.1 g, 8 mmol) in dimethylacetamide (20 mL) was added cesium carbonate (7.28 g, 24 mmol) and 4-butoxyphenol (2.66 g, 16 mmol). The slurry was stirred at ninety five degrees Celsius for nineteen hours. The reaction was concentrated in vacuo. The residue was taken up in ethyl acetate, washed with brine, dried over $Na_2SO_4$, filtered, and concentrated in vacuo. Chromatography (on silica, ethyl acetate/hexanes) provided the substituted THP hydroxamate as an off-white foam (3.96 g, 93%). HRMS (ES+) $M+NH_4^+$ calculated for $C_{27}H_{35}N_1O_8$ $S_1F$: 551.24, found 551.24.

Part B: To a solution of the THP hydroxamate from part A (3.9 g, 7.3 mmol) in 1,4-dioxane (20 mL) was added 4N HCl dioxane solution (20 mL) and methanol (20 mL). After fifteen minutes at ambient temperature the reaction was diluted with ethyl acetate and washed with water, dried over $Na_2SO_4$, filtered, and concentrated in vacuo. The product was recrystallized (acetone/hexanes) to give the title compound as a white solid (2.75 g, 84%). HRMS (ES+) $M+H^+$ calculated for $C_{22}H_{27}N_1O_7S_1$: 450.16, found 450.16.

EXAMPLE 373

Preparation of tetrahydro-N-hydroxy-4-[[4-[3-(trifluoromethyl)phenoxy]phenyl]-sulfonyl]-2H-pyran-4-carboxamide

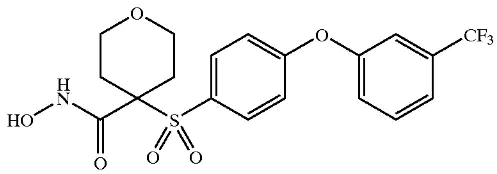

Part A: To a solution of the product of Example 55 (3.1 g, 8 mmol) in dimethylacetamide (20 mL) was added cesium carbonate (7.28 g, 24 mmol) and m-(trifluoromethyl)phenol (1.95 mL, 16 mmol). The slurry was stirred at ninety five degrees Celsius for nineteen hours. The reaction was concentrated in vacuo. The residue was taken up in ethyl acetate, washed with brine, dried over $Na_2SO_4$, filtered, and concentrated in vacuo. Chromatography (on silica, ethyl acetate/hexanes) provided the substituted THP hydroxamate as a white foam (4.1 g, 97%). HRMS (ES+) $M+H^+$ calculated for $C_{24}H_{26}N_1O_7$ $S_1F_3$: 530.15, found 530.14.

Part B: To a solution of the THP hydroxamate from part A (3.9 g, 7.4 mmol) in 1,4-dioxane (20 mL) was added 4N HCl dioxane solution (20 mL) and methanol (20 mL). After fifteen minutes at ambient temperature, the reaction was diluted with ethyl acetate and washed with water, dried over $Na_2SO_4$, filtered, and concentrated in vacuo. The product was recrystallized (acetone/hexanes) to give the title compound as a white solid (1.9 g, 58%). HRMS (ES+) M+H$^+$ calculated for $C_{19}H_{18}N_1O_6S_1F_3$: 446.09, found 446.09.

EXAMPLE 374

Preparation of tetrahydro-N-hydroxy-4-[[4-[4-(methylthio)phenoxy]phenyl]sulfonyl]-2H-pyran-4-carboxamide

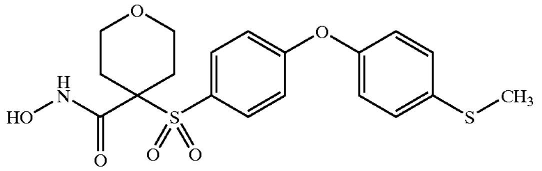

Part A: To a solution of the product of Example 55 (3.1 g, 8 mmol) in dimethylacetamide (20 mL) was added cesium carbonate (7.28 g, 24 mmol) and 4-(methylthio)phenol (2.24 g, 16 mmol). The slurry was stirred at ninety five degrees Celsius for twenty four hours. The reaction was concentrated in vacuo. The residue was taken up in ethyl acetate, washed with brine, dried over $Na_2SO_4$, filtered, and concentrated in vacuo. Chromatography (on silica, ethyl acetate/hexanes) provided the substituted THP hydroxamate as a white foam (4.1 g, 100%). HRMS (ES+) M+H$^+$ calculated for $C_{24}H_{29}N_1O_7$ $S_2$: 508.15, found 508.15.

Part B: To a solution of the THP hydroxamate from part A (4.0 g, 7.9 mmol) in 1,4-dioxane (20 mL) was added 4N HCl dioxane solution (20 mL) and methanol (20 mL). After fifteen minutes at ambient temperature, the reaction was diluted with ethyl acetate and washed with water, dried over $Na_2SO_4$, filtered, and concentrated in vacuo. The product was recrystallized (acetone/hexanes) to give the title compound as a white solid (1.9 g, 57%). HRMS (ES+) M+H$^+$ calculated for $C_{19}H_{21}N_1O_6S_2$: 424.09, found 424.09.

EXAMPLE 375

Preparation of tetrahydro-N-hydroxy-4-[[4-[4-(phenylmethyl)phenoxy]phenyl]-sulfonyl]-2H-pyran-4-carboxamide

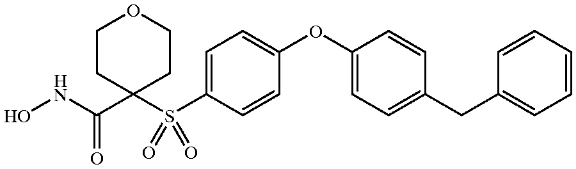

Part A: To a solution of the product of Example 55 (2.7 g, 7 mmol) in dimethylacetamide (15 mL) was added cesium carbonate (6.84 g, 21 mmol) and 4-hydroxydiphenylmethane (2.8 g, 14 mmol). The slurry was stirred at ninety degrees Celsius for nineteen hours. The reaction was concentrated in vacuo. The residue was taken up in ethyl acetate, washed with brine, dried over $Na_2SO_4$, filtered, and concentrated in vacuo. Chromatography (on silica, ethyl acetate/hexanes) provided the substituted THP hydroxamate as a light yellow foam (3.7 g, 96%). HRMS (ES+) M+H$^+$ calculated for $C_{30}H_{33}N_1O_7$ $S_1$: 552.21, found 552.21.

Part B: To a solution of the THP hydroxamate from part A (3.5 g, 6.4 mmol) in 1,4-dioxane (16 mL) was added 4N HCl dioxane solution (16 mL) and methanol (16 mL). After fifteen minutes at ambient temperature the reaction was diluted with ethyl acetate and washed with water, dried over $Na_2SO_4$, filtered, and concentrated in vacuo. The product was recrystallized (acetone/hexanes) to give the title compound as a white solid (1.95 g, 67%). HRMS (ES+) M+H$^+$ calculated for $C_{25}H_{25}N_1O_6S_1$: 468.15, found 468.15.

EXAMPLE 376

Preparation of tetrahydro-N-hydroxy-4-[[4-(4-hydroxyphenoxy)phenyl]sulfonyl]-2H-pyran-4-carboxamide

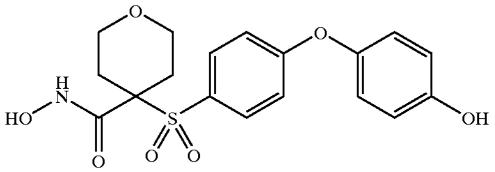

Part A:To a solution of the product of Example 55) (2.7 g, 7 mmol) in dimethylacetamide (20 mL) was added cesium carbonate (6.84 g, 21 mmol) and 4-(benzyloxy)phenol (2.8 g, 14 mmol). The slurry was stirred at ninety five degrees Celsius for six hours. The reaction was concentrated in vacuo. The residue was taken up in ethyl acetate, washed with brine, dried over $Na_2SO_4$, filtered, and concentrated in vacuo. Chromatography (on silica, ethyl acetate/hexanes) provided the substituted THP hydroxamate as a white foam (3.94 g, 99%). HRMS (ES+) M+NH$_4^+$ calculated for $C_{30}H_{33}N_1O_8$ $S_1$: 585.23, found 585.23.

Part B: To a solution of the THP hydroxamate from part A (1.5 g, 2.64 mmol) in glacial acetic acid (5 mL) was added concentrated HCl (5 mL) and the reaction was heated to sixty degrees Celsius for twenty minutes. The reaction was cooled, diluted with water (100 mL) and extracted with ethyl acetate. The ethyl acetate extract was washed with water three times, brine, dried over $Na_2SO_4$, filtered, and concentrated in vacuo. The product was recrystallized (acetone/hexanes) to give the title compound as a white solid (810 mg, 78%). HRMS (ES+) M+NH$_4^+$ calculated for $C_{18}H_{19}N_1O_7S_1$: 468.15, found 468.15.

EXAMPLE 377

Preparation of tetrahydro-N-hydroxy-4-[[4-[4-[(1-methylethyl)thio]phenoxy]-phenyl]-sulfonyl]-2H-pyran-4-carboxamide

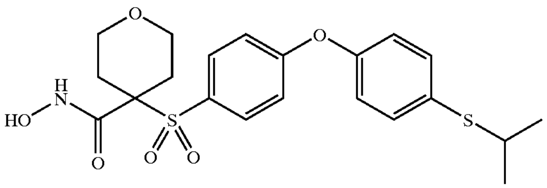

Part A: To a suspension of 4-hydroxythiophenol (5.0 g, 40 mmol) and potassium carbonate (8.0 g, 58 mmol) in dimethylformamide (70 mL) was added 2-iodopropane (7.0 g, 41 mmol). The slurry was stirred at ambient temperature for one hour. The reaction was concentrated in vacuo. The residue was taken up in ethyl acetate, washed two times with water, 10% HCl solution, brine, dried over $Na_2SO_4$, filtered, and concentrated in vacuo. Chromatography (on silica, ethyl acetate/hexanes) provided the substituted phenol as a clear colorless oil (5.1 g, 76%).

Part B: To a solution of the product of Example 55 (3.1 g, 8 mmol) in dimethylacetamide (20 mL) was added cesium carbonate (7.28 g, 24 mmol) and the phenol from part A (2.7 g, 16 mmol). The slurry was stirred at ninety five degrees Celsius for fifteen hours. The reaction was concentrated in vacuo. The residue was taken up in ethyl acetate, washed with brine, dried over $Na_2SO_4$, filtered, and concentrated in vacuo. Chromatography (on silica, ethyl acetate/hexanes) provided the substituted THP hydroxamate as a white foam (4.15 g, 97%). HRMS (ES+) M+H$^+$ calculated for $C_{26}H_{33}N_1O_7$ $S_2$: 536.18, found 538.17.

Part C: To a solution of the THP hydroxamate from part A (3.9 g, 7.3 mmol) in 1,4-dioxane (18 mL) was added 4N HCl dioxane solution (18 mL) and methanol (18 mL). After fifteen minutes at ambient temperature, the reaction was diluted with ethyl acetate and washed with water, dried over $Na_2SO_4$, filtered, and concentrated in vacuo. The product was recrystallized (acetone/hexanes) to give the title compound as an off white solid (2.32 g, 71%). HRMS (ES+) M+H$^+$ calculated for $C_{21}H_{25}N_1O_6S_2$: 452.12, found 452.12.

EXAMPLE 378

Preparation of tetrahydro-N-hydroxy-4-[[4-[4-(1-methylethoxy)phenoxy)phenyl]-sulfonyl]-2H-pyran-4-carboxamide

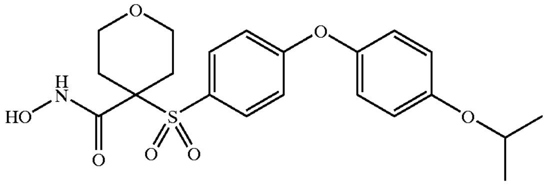

Part A: To a solution of benzoic acid, 4-hydroxyphenylester (8.57 g, 40 mmol) in dimethylacetamide (65 mL) was added potassium carbonate (8.3 g, 60 mmol) and 2-iodopropane (5 mL, 50 mmol). The slurry was stirred at sixty five degrees Celsius for one hour. The reaction was concentrated in vacuo. The residue was taken up in ethyl acetate, washed with water three times, brine, dried over $Na_2SO_4$, filtered, and concentrated in vacuo to yield the isopropoxy compound as a light gray solid (9.7 g, 95%).

Part B: To a slurry of the isopropoxy compound from part A (9.7 g, 38 mmol) in 1,4-dioxane (20 mL) and water (20 mL) was added 2.5N sodium hydroxide solution (26 mL, 65 mmol). The slurry was stirred at sixty degrees Celsius for four hours. The reaction was cooled and 6N hydrochloric acid solution was added until the pH=5. The reaction was extracted with methylene chloride. The organic layer was washed with 5% ammonium hydroxide solution four times, water, brine, dried over $Na_2SO_4$, filtered, and concentrated in vacuo to yield the phenol as an amber oil (5.4 g, 94%).

Part C: To a solution of the product of Example 55 (3.1 g, 8 mmol) in dimethylacetamide (20 mL) was added cesium carbonate (7.28 g, 24 mmol) and the phenol from part B (2.4 g, 16 mmol). The slurry was stirred at ninety five degrees Celsius for twenty one hours. The reaction was concentrated in vacuo. The residue was taken up in ethyl acetate, washed with water three times, brine, dried over $Na_2SO_4$, filtered, and concentrated in vacuo. Chromatography (on silica, ethyl acetate/hexanes) provided the substituted THP hydroxamate as an off white foam (3.65 g, 88%). HRMS (ES+) M+H$^+$ calculated for $C_{26}H_{33}N_1O_8$ $S_1$: 520.20, found 520.20.

Part D: To a solution of the THP hydroxamate from part C (3.5 g, 6.7 mmol) in 1,4-dioxane (17 mL) was added 4N HCl dioxane solution (17 mL) and methanol (17 mL). After fifteen minutes at ambient temperature, the reaction was diluted with ethyl acetate and washed with water, dried over $Na_2SO_4$, filtered, and concentrated in vacuo. The product was recrystallized (acetone/hexanes) to give the title compound as an off white solid (2.2 g, 80%). HRMS (ES+) M+H$^+$ calculated for $C_{21}H_{25}N_1O_7S_1$: 436.14, found 436.14.

EXAMPLE 379

Preparation of tetrahydro-N-hydroxy-4-[[4-[4-[(trifluoromethyl]phenoxy]-phenyl]-sulfonyl]-2H-pyran-4-carboxamide

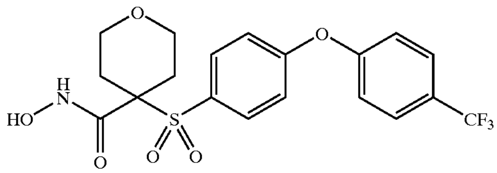

Part A: In dry equipment under nitrogen, sodium hydride (60% oil dispersion) (11. g, 0.275 mol) was added to a solution of 4-[4-(trifluoromethyl)phenoxy]-phenol (50.0 g, 0.197 mol) in dry dimethylformamide (150 mL) at zero degrees Celsius. After fifteen minutes, a solution of dimethylthiocarbamoyl chloride (32.0 g, 0.259 mol) in dry dimethylformamide (100 mL) was added. The reaction was stirred at ambient temperature for sixteen hours. The reaction was poured onto 10% hydrochloric acid solution (1 L). Vacuum filtration of the resulting precipitate provided the thiono compound as a white solid (67.0 g, 100%).

Part B: The thiono compound from part A (70 g, 0.2 mol) was heated to three hundred seventeen degrees Celsius for thirty minutes behind a safety shield. The reaction exothermed to three hundred thirty degrees Celsius. The heat was removed and the reaction came to ambient temperature to yield the thiocarbamate as a brown solid (70 g, 100%).

Part C: To a solution of the thiocarbamate from part B (65.0 g, 0.19 mol) in methanol (510 mL) with a subsurface nitrogen stream was added 2.5N sodium hydroxide solution (160 mL, 0.4 mol). The slurry was stirred at seventy four degrees Celsius for two hours. The reaction was cooled and the methanol removed in vacuo. The residue was diluted with water (100 mL) and extracted with diethyl ether four times. A subsurface stream of nitrogen was added to the aqueous solution and sodium chloroacetate (22.2 g, 0.19 mol) was added. The reaction was stirred an ambient temperature and after thirty minutes the nitrogen stream was removed. After twelve hours, the solution was cooled and 6N hydrochloric acid was added until the pH=1. The slurry was extracted with ethyl acetate four times. The combined ethyl acetate extracts were washed with 0.1N hydrochloric acid, water, brine, dried over $Na_2SO_4$, filtered and dried in vacuo to give the thioacetic acid as a tan solid (61.0 g, 98%).

Part D: To a solution of the thioacetic acid from part C (54.45 g, 0.166 mol) in tetrahydrofuran (370 mL) was added water (45 mL) and Oxone® (306 g, 0.498 mol) at twenty degrees Celsius. An exotherm to forty two degrees Celsius was noted. After two hours, the reaction was filtered and the cake was washed well with tetrahydrofuran and then water (250 mL) was added to the filtrate. The filtrate was concentrated in vacuo. The slurry was extracted with ethyl acetate four times. The combined extracts were washed with water three times, brine, dried over $MgSO_4$, filtered, and concentrated in vacuo to give the sulfone as a beige solid (60.0 g, 100%).

Part E: A solution of the sulfone from part D (119.52 g, 0.332 mol) in methanol (660 mL) and 4N hydrochloric acid in dioxane solution (20 mL) was stirred at ambient temperature for twelve hours. The reaction was heated to a boil and cooled slowly to ambient temperature. The resulting crystals were filtered, washed well with cold methanol, and dried to give the methyl ester as a white solid (89.4 g, 72%).

Part F: To a solution of the methyl ester from part E (64.5 g, 0.180 mol) in dimethylacetamide (360 mL) was added potassium carbonate (66.8 g, 0.48 mol), bis-(2-bromoethyl) ether (40 mL, 0.305 mol), 4-dimethylaminopyridine (1.1 g, 9 mmol), and tetrabutylammonium bromide (2.9 g, 9 mmol). The reaction was stirred overnight at ambient temperature. The reaction was slowly poured into 1N HCl (500 mL). The resulting precipitate was filtered, washed with water, then hexanes. The solid was recrystallized from methanol to give the pyran compound as a white solid (62.8 g, 79%). MS (ES+) $M+NH_4^+$ calculated for $C_{20}H_{19}0_{56}S_1F_3$: 462.12, found 462.12.

Part G: In dry equipment under nitrogen, the pyran compound from part F (64.0 g, 0.144 mol) was dissolved in dry tetrahydrofuran (250 mL) and a solution of potassium trimethylsilonate (55.9 g, 0.432 mol) in dry tetrahydrofuran (40 mL) was added at ambient temperature. After two hours, water (200 mL) was added and the solution concentrated in vacuo. The slurry was extracted with ethyl acetate to remove unreacted starting material. The aqueous solution was treated with 6N HCl until pH=1. The slurry was extracted with ethyl acetate and the combined extracts washed with water, brine, dried over $Na_2SO_4$, filtered, and concentrated in vacuo. The residue was heated in diethyl ether, the resulting solid filtered and dried to give the carboxylic acid as a white solid (56.3 g, 91%). HRMS (ES+) $M+NH_4^+$ calculated for $C_{19}H_{17}0_6$ $S_1F_3$: 448.10, found 448.10.

Part H: In dry equipment under nitrogen, the carboxylic acid from part G (49.0 g, 0.114 mol) was dissolved in dry dimethylformamide (280 mL) and the remaining reagents were added to the solution in the following order: N-hydroxybenzotriazole hydrate (18.5 g, 0.137 mol), N-methylmorpholine (37.5 mL, 0.342 mol), O-(tetrahydro-2H-pyran-2-yl)hydroxylamine (41.3 g, 0.353 mol), and 1-(3-dimethylaminopropyl)-3-ethylcarbodiimide hydrochloride 30.6 g, 0.160 mol). After four hours at ambient temperature, the reaction was concentrated in vacuo. The residue was taken up in ethyl acetate, washed with water, 5% $KHSO_4$, saturated $NaHCO_3$, brine, dried over $Na_2SO_4$, filtered, and concentrated in vacuo to give the THP hydroxamate as a white foam (62.6 g, 100%). HRMS (ES+) $M+NH_4^+$ calculated for $C_{24}H_{26}NO_7S_1F_3$: 547.17, found 547.17.

Part I: To a solution of the THP hydroxamate from part H (58.5 g, 0.11 mol) in 1,4-dioxane (280 mL) was added 4N HCl dioxane solution (280 mL) and methanol (280 mL). After fifteen minutes at ambient temperature, the reaction was diluted with ethyl acetate and washed with water, dried over $Na_2SO_4$, filtered, and concentrated in vacuo. The product was recrystallized (acetone/hexanes) to give the title compound as a white solid (42.79 g, 87%) HRMS (ES+) $M+NH_4^+$ calculated for $C_{19}H_{18}NO_6S_1F_3$: 463, found 463.

EXAMPLE 380

Preparation of 4-[[4-([1,1'-biphenyl]-4-yloxy]phenyl)sulfony]tetrahydro-N-hydroxy-2H-pyran-4-carboxamide

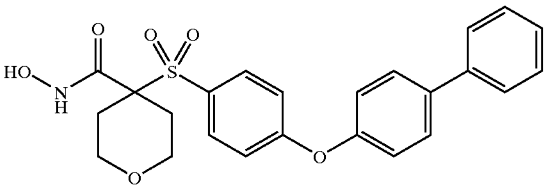

Part A: To a solution of the product of Example 55 (2.0 g, 5.2 mmol )in dimethylacetamide (8 mL) was added 4-phenylphenol (Aldrich, 1.3 g, 7.8 mmol) followed by cesium carbonate (6.8 g, 20.8 mmol). The reaction was heated at ninety-five degrees Celsius for five hours. Stripping the dimethylacetamide in vacuo afforded a brown solid (5.3 g, quantitative). Chromatography (reverse phase, C-18, acetonitrile/water) gave the THP-protected biphenyl product in solution.

Part B: To the collected THP-protected diphenyl product from A in acetonitrile/ water (50 mL) was slowly added 10% $HCl_{aq}$ (100 mL). After stirring overnight (about eighteen hours), the acetonitrile was stripped. The resultant precipitate was collected, giving the title compound as a white solid (2.0 g, 83%). MS (FAB) $M^+H$ calculated for $C_{24}H_{23}NO_6S$: 454, found 454.

EXAMPLE 381

Preparation of tetrahydro-N-hydroxy-4-[[4-[[4-(trifluoromethyl)phenyl]thio]phenyl]-sulfonyl]-2H-pyran-4-carboxamide

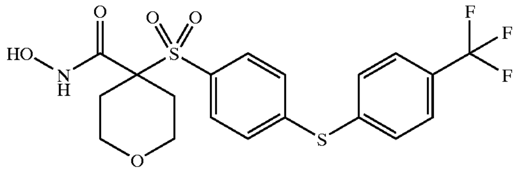

Part A: To a solution of the product of Example 55 (2.0 g, 5.2 mmol ) in dimethylacetamide (6 mL) was added 4-trifluoromethylthiophenol (Maybridge, 2.0 g, 11.2 mmol), followed by potassium carbonate (2.9 g, 20.8 mmol). The reaction was heated at sixty-five degrees Celsius for twelve hours. Stripping the dimethylacetamide in vacuo afforded a brown solid (6.5 g, quantitative). Chromatography (reverse phase, C-18, acetonitrile/water) gave the THP-protected trifluoromethyl product in solution.

Part B: To the solution of the crude THP-protected trifluoromethyl product from in acetonitrile/water (40 mL) was slowly added 10% $HCl_{aq}$ (100 mL). After stirring overnight (about eighteen hours), the acetonitrile was stripped. The resultant precipitate was collected, giving the title compound as a tan solid (0.75 g, 31%). MS (FAB) $M^+H$ calculated for $C_{19}H_{18}F_3NO_5S_2$: 462, found 462.

EXAMPLE 382

Preparation of Tetrahydro-N-hydroxy-4-[[4-[4-[(trifluoromethyl)thio]phenoxy]phenyl]-sulfonyl]-2H-pyran-4-carboxamide

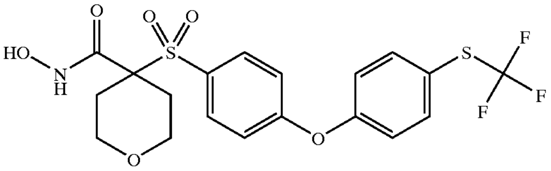

Part A: To a solution of the product of Example 55 (2.0 g, 5.2 mmol ) in dimethylacetamide (6 mL) was added 4-(trifluoromethylthio)thiophenol (Aldrich, 1.5 g, 7.8 mmol) followed by cesium carbonate (6.8 g, 20.8 mmol). After adding a catalytic amount of potassium fluoride, the reaction was heated at ninety-five degrees Celsius for twelve hours. Stripping the dimethylacetamide in vacuo afforded a brown solid (7.2 g, quantitative). Chromatography (reverse phase, C-18, acetonitrile/water) gave the THP-protected trifluoromethylthio product in solution.

Part B: To the solution of the crude THP-protected trifluoromethylthio product from A in acetonitrile/water (40 mL) was slowly added 10% $HCl_{aq}$ (100 mL). After stirring overnight (about eighteen hours), the acetonitrile was stripped. The resultant precipitate was collected, giving the title compound as a tan solid (0.60 g, 24 %). MS (FAB) $M^{-}H$ calculated for $C_{19}H_{18}F_3NO_6S_2$: 476, found 476.

EXAMPLE 380

Preparation of 4-[[4-[4-chloro-3-(trifluoro-methyl) phenoxy]phenyl]sulfonyl]-tetrahydro-N-hydroxy-2H-pyran-4-carboxamide

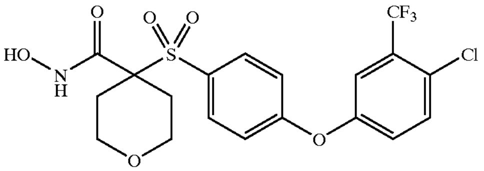

Part A: To a solution of the product of Example 55 (2.0 g, 5.2 mmol in dimethylacetamide (6 mL) was added 4-chloro-3-trifluoromethylphenol (Avocado, 1.5 g, 7.8 mmol) followed by cesium carbonate (6.8 g, 20.8 mmol). The reaction was heated at ninety-five degrees Celsius for twelve hours. Stripping the dimethylacetamide in vacuo afforded a brown solid (7.6 g, quantitative). Chromatography (reverse phase, C-18, acetonitrile/water) gave the THP-protected product in solution.

Part B: To the solution of the crude THP-protected product from in acetonitrile/water (40 mL) was slowly added 10% $HCl_{aq}$ (100 mL). After stirring overnight (about eighteen hours), the acetonitrile was stripped. The resultant precipitate was collected, giving the title compound as a white solid (0.92 g, 37%). MS (FAB) $M^{+}H$ calculated for $C_{19}H_{17}ClF_3NO_6S$: 480, found 480.

EXAMPLE 384

Preparation of 4-[[4-[4-(1,1-dimethylethyl)-phenoxy]phenyl]sulfonyl]tetrahydro-N-hydroxy-2H-pyran-4-carboxamide

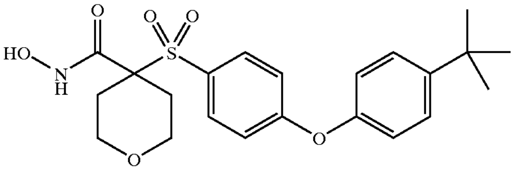

Part A: To a solution of the product of Example 55 (5.0 g, 12.9 mmol ) in dimethylacetamide (25 mL) was added 4-t-butylphenol (Avocado, 2.9 g, 19.4 mmol) followed by cesium carbonate (20.4 g, 20.862.5 mmol). The reaction was heated at ninety-five degrees Celsius for twelve hours. Stripping the dimethylacetamide in vacuo afforded a brown solid (9.4 g, quantitative). Chromatography (reverse phase, C-18, acetonitrile/water) gave the THP-protected product in solution.

Part B: To the solution of the crude THP-protected product from in acetonitrile/water (60 mL) was slowly added 10% $HCl_{aq}$ (100 mL). After stirring overnight (about eighteen hours), the acetonitrile was stripped. The resultant precipitate was collected, giving the title compound as a white solid (0.28 g, 5%). MS (FAB) $M^{+}H$ calculated for $C_{22}H_{27}NO_6S$: 434, found 434.

EXAMPLE 385

Preparation of 4-[[4-[3,5-bis(trifluoromethyl) phenoxy]phenyl]sulfonyl]tetrahydro-N-hydroxy-2H-pyran-4-carboxamide

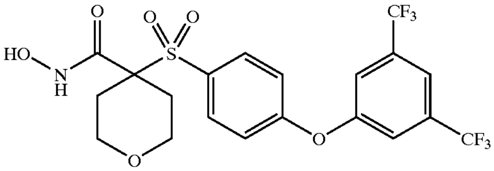

Part A: To a solution of the product of Example 55 (3.0 g, 7.7 mmol )in dimethylacetamide (15 mL) was added 3,5-ditrifluoromethylphenol (2.9 g, 19.4 mmol) followed by cesium carbonate (20.4 g, 20.862.5 mmol). The reaction was heated at ninety-five degrees Celsius for twelve hours. Stripping the dimethylacetamide in vacuo afforded a brown solid (14.7 g, quantitative). Chromatography (reverse phase, C-18, acetonitrile/water) gave the THP-protected product in solution.

Part B: To the solution of the crude THP-protected product from in acetonitrile water (60 mL) was slowly added 10% $HCl_{aq}$ (100 ML). After stirring overnight (about eighteen hours), the acetonitrile was stripped. The resultant precipitate was collected, giving the title compound as a white solid (1.2 g, 31%). MS (FAB) $M^{+}H$ calculated for $C_{20}H_{17}$ $F_6NO_6S$: 514, found 514.

EXAMPLE 386

Preparation of tetrahydro-N-hydroxy-4-[[4-[3-methyl-4-(1-methylethyl) phenoxy]phenyl]-sulfonyl]-2H-pyran-4-carboxamide

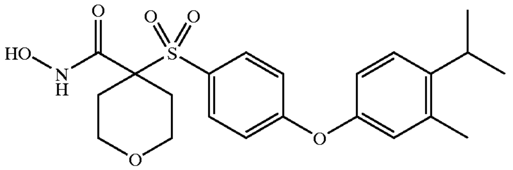

Part A: To a solution of the product of Example 55 (4.0 g, 10.3 mmol ) in dimethylacetamide (20 mL) was added 4-isopropyl-3-methylphenol (Aldrich, 2.3 g,15.5 mmol) followed by cesium carbonate (16.8 g, 51.5 mmol). The reaction was heated at ninety-five degrees Celsius for twelve hours. Stripping the dimethylacetamide in vacuo afforded a brown solid (18.3 g, quantitative). Chromatography (reverse phase, C.18, acetonitrile/water) gave the THP-protected product in solution.

Part B: To the solution of the crude THP-protected product from A in acetonitrile/water (40 mL) was slowly added 10% $HCl_{aq}$ (100 mL). After stirring overnight (about eighteen hours), the acetonitrile was stripped. The resultant precipitate was collected, giving the title compound as a tan solid (1.8 g, 40 %). MS (FAB) $M^-H$ calculated for $C_{22}H_{27}F_3NO_6S$: 432, found 432.

EXAMPLE 387

Preparation of Tetrahydro-N-hydroxy-4-[[4-[(2,2,3,3-tetrafluoro-2,3-dihydro-1,4-benzodioxin-6-yl]oxy] phenyl]sulfonyl]-2H-pyran-4-carboxamide

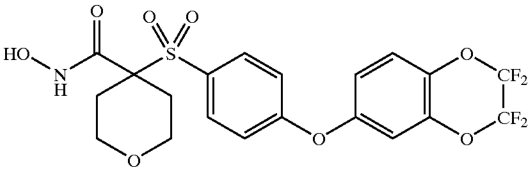

Part A: To a solution of the product of Example 55 (5.0 g, 12.9 mmol ) in dimethylacetamide (25 mL) was added 2,2,3,3-tetrafluoro-6-hydroxybenzodioxene (Oakwood, 4.3 g, 19.4 mmol) followed by cesium carbonate (21.0 g, 64.5 mmol). The reaction was heated at ninety-five degrees Celsius for five hours. Stripping the dimethylacetamide in vacuo afforded a brown solid (11.3 g, quantitative) Chromatography (reverse phase, C-18, acetonitrile/water) gave the THP-protected product in solution.

Part B: To the collected THP-protected product from A in acetonitrile/water (50 mL) was slowly added 10% $HCl_{aq}$ (100 mL). After stirring overnight (about eighteen hours), the acetonitrile was stripped. The resultant precipitate was collected, giving the title compound as a white solid (3.5 g, 54%). MS (FAB) $M^-H$ calculated for $C_{20}H_{17}F_4NO_8S$: 506, found 506.

EXAMPLE 388

Preparation of N-hydroxy-1-[2-(4-morpholinyl)-ethyl]-4-[[4-[4-(trifluoromethyl)phenoxy)-phenyl] sulfonyl]-4-piperidinecarboxamide, Dihydrochloride

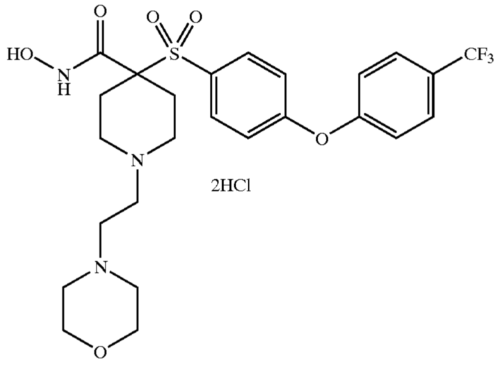

Part A: To a suspension of 4-bromopiperidine hydrobromide (107.0 g, 0.436 mol) in tetrahydrofuran (1 L) was slowly added triethylamine (122 mL, 0.872 mol) followed by di-tert-butyl dicarbonate (100 g, 0.458 mol), which was added in several portions. The resulting mixture was stirred at ambient temperature for 22 hours then filtered and concentrated in vacuo. The solids were washed with hexanes and then collected by filtration to give the Boc-piperidine compound as an amber oil (124 g, >100%).

Part B: To a solution of 4-fluorophenol (50.0 g, 0.390 mol) in acetone (400 mL), degassed with $N_2$, was added $Cs_2CO_3$ (159 g, 0.488 mol). After degassing the resulting mixture with $N_2$ for 5 minutes, the Boc-piperidine compound of part A (85.9 g, 0.325 mol) was added. The resulting mixture was stirred at ambient temperature for 18 hours and then filtered through a pad of Celite®, washing with acetone. The filtrate was concentrated in vacuo to provide the sulfide as a tan residue (98.5 g, 97%).

Part C: To a solution of the sulfide of part B (8.00 g, 25.7 mmol) in dichloromethane (90 mL) and methanol (15 mL) was added monoperoxyphthalic acid magnesium salt hexahydrate (19.1 g, 38.6 mmol) in two portions. The resulting mixture was stirred at ambient temperature for 1.5 hours and then filtered. The filtrate was washed with saturated $NaHCO_3$ and then with saturated NaCl. The combined aqueous layers were extracted with dichloromethane (100 mL). The combined organic layers were dried over $Na_2SO_4$ and then concentrated in vacuc. The resulting solids were washed with hexanes then dissolved in dichloromethane and filtered through a pad of Celite®, washing with dichloromethane. The filtrate was concentrated in vacuo and recrystallization from ethyl acetate provided the sulfone as a white crystalline solid (4.45 g, 50%).

Part D: To a solution of sulfone of part C (7.00 9, 20.4 mmol) in N,N-dimethylformamide (40 mL) was added $Cs_2CO_3$ (19.9 g, 61.2 mmol) and α,α,α-trifluoro-p-cresol (3.97 9, 24.5 mmol). The resulting mixture was heated at eighty degrees Celsius for 16 hours. After cooling to ambient temperature the reaction mixture was concentrated in vacuo. The resulting residue was treated with $H_2O$ and the solids were collected by filtration. The solids were then washed with hexanes then methanol to provide the biaryl ether as a tan solid (8.60 g, 87%).

Part E: To a solution of the biaryl ether of part D (8.59 g, 17.7 mmol) in tetrahydrofuran (100 mL), cooled to zero degrees Celsius, was slowly added lithium bis (trimethylsilyl)amide (22.0 mL, 1.0M in tetrahydrofuran, 22.0 mmol), at such a rate that the temperature of the reaction never exceeded one degree Celsius. The resulting mixture was stirred at zero degrees Celsius for 1 hour then a solution of methyl chloroformate (2.05 mL, 26.6 mmol) in tetrahydrofuran (5.0 mL) was slowly added, at such a rate that the temperature of the reaction mixture never exceeded four degrees Celsius. After the addition was complete, the mixture was slowly permitted to warm to ambient temperature. Saturated $NH_4Cl$ (50 mL) was added and the tetrahydrofuran was removed in vacuo. Water (50 mL) was added to the residue which was then extracted with ethyl acetate. The combined organic layers were washed with saturated NaCl and dried over $Na_2SO_4$. Recrystallization from methanol provided the methyl ester as a pale yellow crystalline solid (7.66 g, 80%).

Part F: To a solution of the methyl ester of part E (7.66 g, 14.1 mmol) in dioxane (30 mL) and methanol (10 mL) was added a solution of 4N HCl in dioxane (10 mL, 40 mmol). After stirring at ambient temperature for 2 hours additional 4N HCl in dioxane (10 mL, 40 mmol) was added. After stirring at ambient temperature for 2.5 hours, the reaction mixture was concentrated in vacuo to provide the amine as an off-white solid (6.80 g, >100%).

Part G: To a suspension of the amine of part F (3.00 g, 6.25 mmol) in acetonitrile (20 mL) was added $K_2CO_3$ (3.46 g, 25.0 mmol), 4-(2-chloroethyl)morpholine hydrochloride (1.22 g, 6.56 mmol) and a catalytic amount of NaI. The resulting mixture was heated at reflux for 22 hours. After cooling to ambient temperature, the reaction mixture was filtered through a pad of Celite, washing with ethyl acetate. The filtrate was concentrated in vacuo to provide the morpholinyl ethyl amine as a tan solid (3.45 g, >100%).

Part H: To a solution of the morpholinyl ethyl amine of part G (3.45 g, 6.25 mmol) in tetrahydrofuran (60 mL) was added potassium trimethylsilanolate (1.60 g, 12.50 mmol). After stirring at ambient temperature for 25 hours, $H_2O$ was added. The reaction mixture was then neutralized (pH 7) with 1N HCl. The tetrahydrofuran was removed in vacuo and the resulting precipitate was collected by filtration and washed with diethyl ether to provide the amino acid as an off-white solid (2.87 g, 85%).

Part I: To a suspension of the amino acid of part H (2.87 g, 5.29 mmol) in dichloromethane (25 mL) was added N-methylmorpholine (1.74 mL, 15.9 mmol), O-(tetrahydropuranyl) hydroxylamine (0.682 g, 5.82 mmol) and PyBroP® (2.96 g, 6.35 mmol). After stirring at ambient temperature for 19 hours additional N-methylmorpholine (0.872 mL, 7.94 mmol), O-(tetrahydropuranyl) hydroxylamine (0.310 g, 2.65 mmol) and PyBroP® (1.48 g, 3.17 mmol) were added. The resulting mixture was stirred at ambient temperature for 3 hours and then concentrated in vacuo. The residue was partitioned between ethyl acetate and $H_2O$. The organic layers were washed with saturated NaCl and dried over $Na_2SO_4$. Chromatography (on silica, methanol/chloroform) provided the protected hydroxamate as an off-white solid (2.62 g, 77%).

Part J: To a solution of the protected hydroxamate of part I (2.62 g, 4.08 mmol) in dioxane (9 mL) and methanol (3 mL) was added a solution of 4N HCl in dioxane (10 mL, 40.0 mmol). The resulting mixture was stirred at ambient temperature for 2 hours and then diethyl ether (20 mL) was added. The resulting solids were collected by filtration to give the title compound as an off-white solid (2.31 g, 90%). MS $MH^+$ calculated for $C_{25}H_{31}O_6N_3SF_3$: 558, found 558.

EXAMPLE 389

Preparation of N-hydroxy-1-(4-pyridinylmethyl)-4-[[4-[4-(trifluoromethyl)phenoxy]phenyl]-sulfonyl]-4-piperidinecarboxamide, Dihydrochloride

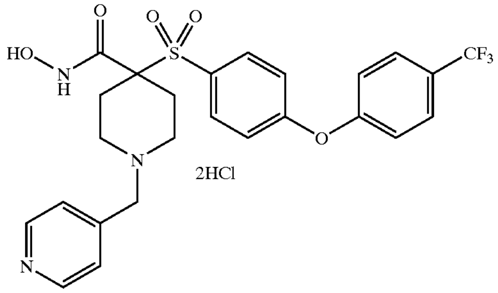

Part A: To a suspension of the amine of part F, Example 388 (1.50 g, 3.13 mmol) in acetonitrile (10 mL) were added $K_2CO_3$ (1.73 g, 12.5 mmol) and 4-picolyl chloride hydrochloride (0.565 g, 3.44 mmol). After stirring at reflux for 21.5 hours, the reaction mixture was filtered through a pad of Celite®, washing with ethyl acetate. The filtrate was concentrated in vacuo. Chromatography (on silica, ethyl acetate/hexanes) provided the picolyl amine as a clear gum (1.44 g, 86%).

Part B: To a solution of the picolyl amine of part A (1.44 g, 2.69 mmol) in tetrahydrofuran (20 mL) was added potassium trimethylsilanolate (0.690 g, 5.38 mmol). The resulting mixture was stirred at ambient temperature for 20 hours and then the tetrahydrofuran was removed by blowing $N_2$ over the reaction mixture. Water (8 mL) was added and the reaction mixture was neutralized (pH 7) with 2N HCl. The resulting precipitate was collected by filtration to provide the amino acid as a white solid (1.31 g, 94%).

Part C: To a suspension of the amino acid of part B (1.31 g, 2.52 mmol) in N,N-dimethylformamide (10 mL) was added 1-hydroxybenzotriazole (0.408 g, 3.02 mmol), N-methylmorpholine (0.831 mL, 7.56 mmol), O-(tetrahydropuranyl) hydroxylamine (0.443 g, 3.78 mmol) and 1-3-[(dimethylamino)propyl]-3-ethylcarbodiimide hydrochloride (0.676 g, 3.53 mmol). The resulting mixture was stirred at ambient temperature for 3 days then concentrated in vacuo. The residue was partitioned between $H_2O$ and ethyl acetate. The combined organic layers were washed with saturated $NaHCO_3$, saturated NaCl and dried over $Na_2SO_4$. Chromatography (on silica, ethyl acetae/hexanes) provided the protected hydroxamate as a white foam (1.24 g, 79%).

Part D: To a solution of the protected hydroxamate of part C (1.24 g, 2.00 mmol) in dioxane (6 mL) and methanol (2 mL) was added a solution of 4N HCl in dioxane (5.00 mL, 20.0 mmol). After stirring at ambient temperature for 2.5 hours the reaction mixture was concentrated in vacuo. The resulting foam was then treated again with a solution of 4N HCl in dioxane (3 mL) for 15 minutes then diethyl ether was added and the resulting precipitate was collected by filtration to provide the title compound as an off-white solid (1.04 g, 85%). MS $MH^+$ calculated for $C_{25}H_{25}O_5N_3SF_3$: 536, found 536.

EXAMPLE 390

Preparation of N-hydroxy-1-(3-pyridinylmethyl)-4-[[4-[4-trifluoromethyl)phenoxy]phenyl]-sulfonyl]-4-piperidinecarboxamide, Dihydrochloride

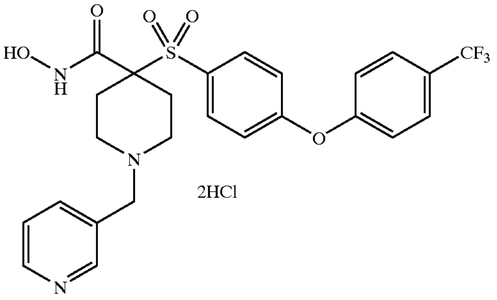

Part A: To a suspension of the amine of part F, Example 388 (1.00 g, 2.08 mmol) in acetonitrile (10 mL) was added $K_2CO_3$ (1.15 g, 8.33 mmol) and 3-picolyl chloride hydrochloride (0.375 g, 2.29 mmol). After stirring at reflux for 12 hours, the reaction mixture was filtered through a pad of Celite®, washing with ethyl acetate. The filtrate was concentrated in vacuo. Chromatography (on silica, ethyl acetate/hexanes) provided the picolyl amine as a pale yellow foam (0.740 g, 67%).

Part B: To a solution of the picolyl amine of part A (0.740 g, 1.38 mmol) in tetrahydrofuran (10 mL) was added potassium trimethylsilanolate (0.355 g, 2.77 mmol). The resulting mixture was stirred at ambient temperature for 17 hours, then additional potassium trimethylsilanolate (0.044 g, 0.343 mmol) was added and the resulting mixture was stirred at ambient temperature for 2 hours. The tetrahydrofuran was removed by blowing $N_2$ over the reaction mixture. Water (5 mL) was added and the reaction mixture was neutralized (pH 7) with 2N HCl. The resulting precipitate was collected by filtration and dried by concentration in vacuo with acetone to provide the amino acid as an off-white solid (0.700 g, 97%).

Part C: To a suspension of the amino acid of part 9 (0.700 g, 1.34 mmol) in N,N-dimethylformamide (10 mL) was added 1-hydroxybenzotriazole (0.218 g, 1.61 mmol), N-methylmorpholine (0.442 mL, 4.02 mmol), O-(tetrahydropuranyl) hydroxylamine (0.235 g, 2.01 mmol) and 1-3-[(dimethylamino)propyl]-3-ethylcarbodiimide hydrochloride (0.360 g, 1.88 mmol). The resulting mixture was stirred at ambient temperature for 23 hours, then concentrated in vacuo. The residue was partitioned between $H_2O$ and ethyl acetate. The combined organic layers were washed with $H_2O$, saturated $NaHCO_3$, saturated NaCl and dried over $Na_2SO_4$. Chromatography (on silica, ethyl acetae/hexanes) provided the protected hydroxamate as an off-white foam (0.500 g, 60%).

Part D: To a solution of the protected hydroxamate of part C (0.500 g, 0.807 mmol) in dioxane (1.5 mL) and methanol (0.5 mL) was added a solution of 4N HCl in dioxane (3.0 mL, 12.00 mmol). After stirring at ambient temperature for 2 hours, diethyl ether was added and the resulting precipitate was collected by filtration to provide the title compound as a yellow solid (0.363 g, 74%). MS $MH^+$ calculated for $C_{25}H_{25}O_5N_3SF_3$: 536, found 536.

EXAMPLE 391

Preparation of N-hydroxy-1-(2-pyridinylmethyl)-4-[[4-[4-(trifluoromethyl)phenoxy]phenyl]-sulfonyl]-4-piperidinecarboxamide, Dihydrochloride

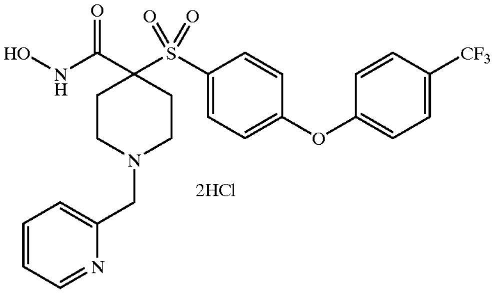

Part A: To a suspension of the amine of part F, Example 388 (1.26 g, 2.63 mmol) in acetonitrile (10 mL) was added $K_2CO_3$ (1.45 g, 10.5 mmol) and 2-picolyl chloride hydrochloride (0.475 g, 2.89 mmol). After stirring at reflux for 12 hours, the reaction mixture was filtered through a pad of Celite®, washing with ethyl acetate. The filtrate was concentrated in vacuo. Chromatography (on silica, ethyl acetate/hexanes) provided the picolyl amine as an amber oil (1.40 g, 99%).

Part B: To a solution of the picolyl amine of part A (1.40 g, 2.62 mmol) in tetrahydrofuran (20 mL) was added potassium trimethylsilanolate (0.672 g, 5.24 mmol). The resulting mixture was stirred at ambient temperature for 15 hours. The tetrahydrofuran was removed by blowing $N_2$ over the reaction mixture. $H_2O$ (5 mL) was added and the reaction mixture was neutralized (pH 7) with 2N HCl. The resulting precipitate was collected by filtration and dried by concentration in vacuo with acetonitrile to provide the amino acid as an off-white solid (1.07 g, 79%).

Part C: To a suspension of the amino acid of part B (1.07 g, 2.06 mmol) in N,N-dimethylformamide (10 mL) was added 1-hydroxybenzotriazole (0.333 g, 2.47 mmol), N-methylmorpholine (0.679 mL, 6.18 mmol), O-(tetrahydropuranyl) hydroxylamine (0.362 g, 3.09 mmol) and 1-3-[(dimethylamino)propyl]-3-ethylcarbodiimide hydrochloride (0.553 g, 2.88 mmol). The resulting mixture was stirred at ambient temperature for 19 hours, then concentrated in vacuo. The residue was partitioned between $H_2O$ and ethyl acetate. The combined organic layers were washed with $H_2O$, saturated $NaHCO_3$, saturated NaCl and dried over $Na_2SO_4$. Chromatography (on silica, methanol/dichloromethane) provided the protected hydroxamate as a white solid (1.03 g, 81%).

Part D: To a solution of the protected hydroxamate of part C (1.03 g, 1.66 mmol) in dioxane (3.0 mL) and methanol (1.0 mL) was added a solution of 4N HCl in dioxane (3.0 mL, 12.00 mmol). After stirring at ambient temperature for 1.5 hours, diethyl ether was added and the resulting precipitate was collected by filtration to provide the title compound as a pale pink solid (0.970 g, 96%). MS $MH^+$ calculated for $C_{25}H_{25}O_5N_3SF_3$: 536, found 536.

EXAMPLE 392

Preparation of N-hydroxy-4-[[4-[(4-methoxyphenyl) amino]phenyl]sulfonyl]-4-piperidinecarboxamide, Monohydrochloride

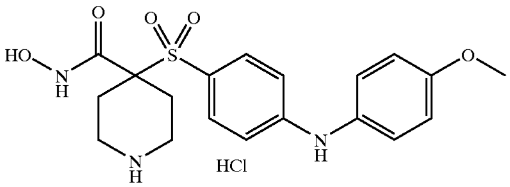

Part A: To the ester of part C, Example 91 (1.00 g, 2.17 mmol) was added $Cs_2CO_3$ (0.990 g, 3.04 mmol), BINAP (0.061 g, 0.098 mmol), tris(dibenzyldeneacetone) dipallidium (0) (0.060 g, 0.07 mmol), p-anisidine (0.320 g, 2.60 mmol) and toluene (4 mL). The resulting mixture was heated to one hundred degrees Celsius for 22 hours. After cooling to ambient temperature, diethyl ether was added and the mixture was filtered through a pad of Celite®, washing with ethyl acetate. The filtrate was concentrated in vacuo. Chromatography (on silica, ethyl acetate/hexane) provided the aniline as an orange foam (0.810 g, 74%).

Part B: To a solution of the aniline of part A (0.780 g, 1.55 mmol) in tetrahydrofuran (4.0 mL) was added potassium trimethylsilanolate (0.238 g, 1.86 mmol). The resulting mixture was stirred at ambient temperature for 17 hours, and then additional potassium trimethylsilanolate (0.020 g, 0.1955 mmol) was added. After stirring at ambient temperature for 24 hours additional potassium trimethylsilanolate (0.040 g, 0.310 mmol) was added. After stirring at ambient temperature for 26 hours, the solvent was removed by blowing $N_2$ over the mixture. To a suspension of the residue in dichloromethane (10 mL) was added added N-methylmorpholine (0.511 mL, 4.65 mmol), O-(tetrahydropuranyl) hydroxylamine (0.218 g, 1.86 mmol), followed by PyBroP® (1.08 g, 2.33 mmol). The resulting mixture was stirred at ambient temperature for 2 days and then concentrated in vacuo. The residue was partitioned between $H_2O$ and ethyl acetate. The combined organic layers were washed with saturated NaCl and dried over $Na_2SO_4$. Chromatography (on silica, ethyl acetate/hexane) provided the protected hydroxamate as an off-white solid (0.600 g, 66%).

Part C: To a solution of the protected hydroxamate of part B (0.580 g, 0.984 mmol) in dioxane (3 mL) and methanol (1 mL) was added a solution of 4N HCl in dioxane (2.5 mL, 10.0 mmol). The resulting mixture was stirred at ambient temperature for 1 hour, then diethyl ether (10 mL) was added. The solids were collected by filtration to give the title compound as a white solid (0.437 g, 100%). MS $MH^+$ calculated for $C_{19}H_{24}O_5N_3S$: 406, found 406.

EXAMPLE 393

Preparation of N-hydroxy-4-[[4-[[4-(trifluoromethoxy)phenyl)amino]phenyl]-sulfonyl)-4-piperidinecarboxamide, Monohydrochloride

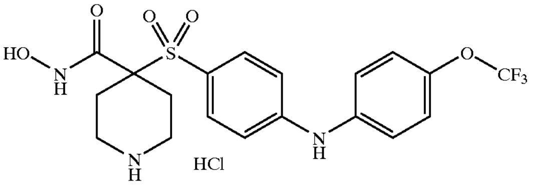

Part A: To a solution of the ester of part C, Example 91 (3.27 g, 7.09 mmol) was added $Cs_2CO_3$ (3.23 g, 9.92 mmol), BINAP (0.066 g, 0.107 mmol), tris(dibenzyldeneacetone)-dipallidium (0) (0.065 g, 0.071 mmol), 4-trifluoro-methoxyaniline (1.15 mL, 8.51 mmol) and toluene (14 mL). The resulting mixture was heated to one hundred degrees Celsius for 22 hours. After cooling to ambient temperature, the mixture was filtered through a pad of Celite®, washing with ethyl acetate, and the filtrate was concentrated in vacuo. Chromatography (on silica, ethyl acetate/hexane) provided the aniline as a tan solid (3.59 g, 91%).

Part B: To a solution of the aniline of part A (1.03 g, 1.84 mmol) in tetrahydrofuran (10 mL) was added potassium trimethylsilanolate (0.331 g, 2.58 mmol). The resulting mixture was stirred at ambient temperature for 24 hours, and then additional potassium trimethylsilanolate (0.118 g, 0.092 mmol) was added. After stirring at ambient temperature for 24 hours, the solvent was removed by blowing $N_2$ over the mixture. $H_2O$ was added and the reaction mixture was acidified (pH 3) with 1N HCl. The aqueous reaction mixture was extracted with ethyl acetate and the combined organic layers were washed with saturated NaCl and dried over $Na_2SO_4$. Concentration in vacuo provided the acid as a tan solid (1.01 g, 100%).

Part C: To a suspension of the acid of part B (1.00 g, 1.84 mmol) in N,N-dimethylformamide (10 mL) was added 1-hydroxybenzotriazole (0.298 g, 2.21 mmol), N-methylmorpholine (0.607 mL, 5.52 mmol), O-(tetrahydropuranyl) hydroxylamine (0.323 g, 2.76 mmol) and 1-3-[(dimethylamino)propyl]-3-ethylcarbodiimide hydrochloride (0.494 g, 2.58 mmol). The resulting mixture was stirred at ambient temperature for 17 hours then concentrated in vacuo. The residue was partitioned between $H_2O$ and ethyl acetate. The combined organic layers were washed with $H_2O$, saturated $NaHCO_3$, saturated NaCl and dried over $Na_2SO_4$. Chromatography (on silica, ethyl acetate/hexanes) provided the protected hydroxamate as a white solid (0.960 g, 81%).

Part D: To a solution of the protected hydroxamate of part C (0.960 g, 1.49 mmol) in dioxane (3 mL) and methanol (1 mL) was added a solution of 4N HCl in dioxane (4.0 mL, 16.0 mmol). The resulting mixture was stirred at ambient temperature for 2.5 hours. The solvent was then removed by blowing $N_2$ over the reaction mixture. Diethyl ether (20 mL) was added and the precipitate was collected by filtration to give the title compound as a pale pink solid (0.716 g, 100%). MS $MH^+$ calculated for $C_{19}H_{21}O_5N_3SF_3$: 460, found 460.

EXAMPLE 394

Preparation of N-hydroxy-1-(2-methoxyethyl)-4-[[4-[[4-(trifluoromethoxy)phenyl]amino]phenyl]sulfonyl]-4-piperidinecarboxamide, Monohydrochloride

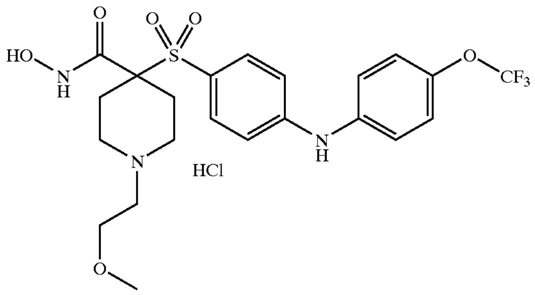

Part A: To a solution of the aniline of part A, Example 392(2.55 g, 4.57 mmol) in dioxane (9.0 mL) and methanol (3.0 mL) was added a solution of 4N HCl in dioxane (10 mL, 40 mmol). After stirring at ambient temperature for 2 hours, the reaction mixture was concentrated in vacuo to provide the amine as a tan solid (2.36 g, >100%).

Part B: To a suspension of the amine of part A (1.50 g, 3.03 mmol) in acetonitrile (12 mL) was added $K_2CO_3$ (1.26 g, 9.09 mmol) and 2-bromoethyl methyl ether (0.313 mL, 3.33 mmol). After stirring at reflux for 23 hours, $Cs_2CO_3$ (2.96 g, 9.09 mmol) was added. After 6 hours at reflux, the reaction mixture was filtered through a pad of Celite®, washing with dichloromethane. The filtrate was concentrated in vacuo. Chromatography (on silica, methanol/dichloromethane) provided the methoxy ethyl amine as a tan solid (1.13 g, 72%).

Part C: To a solution of the methoxy ethyl amine of part B (1.13 g, 2.19 mmol) in tetrahydrofuran (20 mL) was added potassium trimethylsilanolate (0.561 g, 4.38 mmol). The resulting mixture was stirred at ambient temperature for 18 hours, and then additional potassium trimethylsilanolate (0.140 g, 1.09 mmol) was added. After stirring at ambient temperature for 5 hours, the solvent was removed by blowing $N_2$ over the mixture. Water (8 mL) was added and the reaction mixture was neutralized (pH 7) with iN HCl. The solids were collected by filtration and dried by concentration in vacuo with acetonitrile to provide the amino acid as an off-white solid (0.900 g, 82%).

Part D: To a suspension of the amino acid of part C (0.900 g, 1.79 mmol) in N,N-dimethylformamide (8.0 mL) was added 1-hydroxybenzotriazole (0.290 g, 2.15 mmol), N-methylmorpholine (0.590 mL, 5.37 mmol), O-(tetrahydropuranyl) hydroxylamine (0.315 g, 2.69 mmol) and 1-3-[(dimethylamino)propyl]-3-ethylcarbodiimide hydrochloride (0.480 g, 2.51 mmol). The resulting mixture was stirred at ambient temperature for 16 hours then concentrated in vacuo. The residue was partitioned between $H_2O$ and ethyl acetate. The combined organic layers were washed with $H_2O$, saturated $NaHCO_3$, saturated NaCl and dried over $Na_2SO_4$. Chromatography (on silica, methanol/dichloromethane) provided the protected hydroxamate as an off-white solid (0.870 g, 81%).

Part E: To a solution of the protected hydroxamate of part D (0.870 g, 1.45 mmol) in dioxane (3 mL) and methanol (1 mL) was added a solution of 4N HCl in dioxane (10 mL, 40.0 mmol). The resulting mixture was stirred at ambient temperature for 2.0 hours. The reaction mixture was concentrated in vacuo and then treated again with 4N HCl (3 mL) for 30 minutes. The solvent was then removed by blowing $N_2$ over the reaction mixture. Diethyl ether (30 mL) was added, and the precipitate was collected by filtration to give the title compound as a pale pink solid (0.771 g, 96%). MS $MH^+$ calculated for $C_{22}H_{27}O_6N_3SF_3$: 518, found 518.

EXAMPLE 395

Preparation of N-hydroxy-4-[[4-[[4-(trifluoromethyl)phenyl]amino]phenyl]-sulfonyl]-4-piperidinecarboxamide, Monohydrochloride

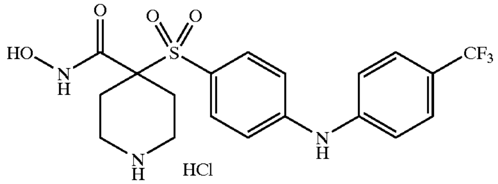

Part A: To a solution of the ester of part C, Example 91 (3.16 g, 6.85 mmol) was added $Cs_2CO_3$ (3.13 g, 9.59 mmol), BINAP (0.064 g, 0.103 mmol), tris(dibenzyldeneacetone)-dipallidium (0) (0.063 g, 0.069 mmol), α,α,α-trifluoromethylaniline (1.03 mL, 8.22 mmol) and toluene (14 mL). The resulting mixture was heated to one hundred degrees Celsius for 17 hours. After cooling to ambient temperature, the mixture was filtered through a pad of Celite®, washing with dichloromethane, and the filtrate was concentrated in vacuo. Chromatography (on silica, ethyl acetate/hexane) provided the aniline as a pale orange foam (3.08 g, 83%).

Part B: To a solution of the aniline of part A (1.00 g, 1.84 mmol) in tetrahydrofuran (10 mL) was added potassium trimethylsilanolate (0.473 g, 3.69 mmol). The resulting mixture was stirred at ambient temperature for 25 hours then the solvent was removed by blowing $N_2$ over the mixture. Water was added, and the reaction mixture was acidified (pH 3) with 1N HCl. The aqueous layer was extracted with ethyl acetate and the combined organic layers were washed with saturated NaCl and dried over $Na_2SO_4$. Concentration in vacuo provided the acid as an orange foam (1.00 g, >100%).

Part C: To a suspension of the acid of part B (0.972 g, 1.84 mmol) in N,N-dimethylformamide (10 mL) was added 1-hydroxybenzotriazole (0.298 g, 2.21 mmol), N-methylmorpholine (0.607 mL, 5.52 mmol), O-(tetrahydropuranyl) hydroxylamine (0.323 g, 2.76 mmol) and 1-3-[(dimethylamino)propyl]-3-ethylcarbodiimide hydrochloride (0.494 g, 2.58 mmol). The resulting mixture was stirred at ambient temperature for 18 hours, then concentrated in vacuo. The residue was partitioned between $H_2O$ and ethyl acetate. The combined organic layers were washed with $H_2O$, saturated $NaHCO_3$, saturated NaCl and dried over $Na_2SO_4$. Chromatography (on silica, ethyl acetate/hexanes) provided the protected hydroxamate as a white solid (0.970 g, 84%).

Part D: To a solution of the protected hydroxamate of part C (0.950 g, 1.51 mmol) in dioxane (3 mL) and methanol (1 mL) was added a solution of 4N HCl in dioxane (4.0 mL, 16.0 mmol). The resulting mixture was stirred at ambient temperature for 1.5 hours. Diethyl ether (20 mL) was added and the precipitate was collected by filtration to give the title compound as a white solid (0.630 g, 87%). MS $MH^+$ calculated for $C_{19}H_{21}O_4N_3SF_3$: 444, found 444.

EXAMPLE 396

Preparation of N-hydroxy-1-(2-methoxyethyl)-4-[[4-[[4-(trifluoromethyl)phenyl]amino]phenyl]sulfonyl]-4-piperidinecarboxamide, Monohydrochloride

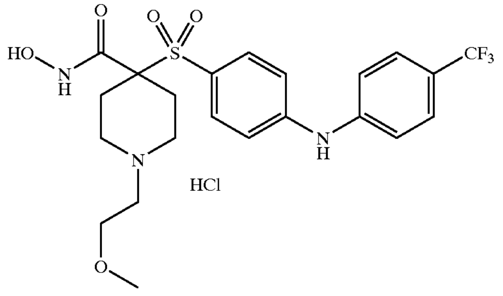

Part A: To a solution of the aniline of part A, Example 395 (2.07 g, 3.82 mmol) in dioxane (9.0 mL) and methanol (3.0 mL) was added a solution of 4N HCl in dioxane (10 mL, 40 mmol). After stirring at ambient temperature for 2 hours, the reaction mixture was concentrated in vacuo to provide the amine as a yellow solid (1.89 g, >100%).

Part B: To a suspension of the amine of part A (1.83 g, 3.82 mmol) in acetonitrile (20 mL) was added $K_2CO_3$ (1.58 g, 11.46 mmol) and 2-bromoethyl methyl ether (0.395 mL, 4.20 mmol). After stirring at reflux for 18 hours, the reaction mixture was filtered through a pad of Celite®, washing with dichloromethane and the filtrate was concentrated in vacuo. Chromatography (on silica, methanol/dichloromethane) provided the methoxy ethyl amine as an off-white solid (1.58 g, 83%).

Part C: To a solution of the methoxy ethyl amine of part B (1.58 g, 3.15 mmol) in tetrahydrofuran (30 mL) was added potassium trimethylsilanolate (0.810 g, 6.31 mmol). The resulting mixture was stirred at ambient temperature for 3 days, and then the solvent was removed by blowing $N_2$ over the mixture. Water (10 mL) was added and the reaction mixture was neutralized (pH 7) with 1N HCl. The solids were collected by filtration and dried by concentration in vacuo with acetonitrile to provide the amino acid as a pink solid (1.32 g, 86%).

Part D: To a suspension of the amino acid of part C (1.32 g, 2.71 mmol) in N,N-dimethylformamide (12 mL) was added 1-hydroxybenzotriazole (0.439 g, 3.25 mmol), N-methylmorpholine (0.894 mL, 8.13 mmol), O-(tetrahydropuranyl) hydroxylamine (0.476 g, 4.07 mmol) and 1-3-[(dimethylamino)propyl]-3-ethylcarbodiimide hydrochloride (0.727 g, 3.79 mmol). The resulting mixture was stirred at ambient temperature for 20 hours, then concentrated in vacuo. The residue was partitioned between $H_2O$ and ethyl acetate. The combined organic layers were washed with $H_2O$, saturated $NaHCC_3$, saturated NaCl and dried over $Na_2SO_4$. Chromatography (on silica, methanol/ethyl acetate) provided the protected hydroxamate as an off-white solid (1.39 g, 88%).

Part E: To a solution of the protected hydroxamate of part D (1.40 g, 2.39 mmol) in dioxane (3 mL) and methanol (1 mL) was added a solution of 4N HCl in dioxane (5.98 mL, 23.9 mmol). The resulting mixture was stirred at ambient temperature for 2.5 hours. The reaction mixture was concentrated almost to dryness, by blowing $N_2$ over the reaction mixture. Diethyl ether (25 mL) was added and the precipitate was collected by filtration. The resulting solid was dissolved in methanol (1 mL) and treated with 4N HCl in dioxane (1.5 mL). After stirring at ambient temperature for 1.5 hours, the reaction mixture was slowly added to diethyl ether (50 mL). The resulting precipitate was collected by filtration to give the title compound as an off-white solid (1.08 g, 84%). MS $MH^+$ calculated for $C_{22}H_{27}O_5N_3SF_3$: 502, found 502.

EXAMPLE 397

Preparation of ethyl 1-(2-methoxyethyl)-3-phenylpropoxy)phenyl]sulfonyl)-4-piperidinecarboxylate

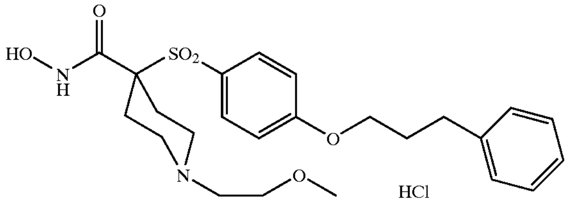

Part A: A mixture of the methoxyethyl amine, ethyl-4-[(4-fluorophenylsulfonyl)]-1-(2-methoxyethyl)-4-piperidinecarboxylate (1.5 g, 4.0 mmol), 3-phenyl-1-propanol (2.2 mL, 16 mmol), and $K_2CO_3$ (2.2 g, 16 mmol) in DMAC (6 mL) was heated at 125 degrees Celsius for 1 day and at 135 degrees Celsius for 3 days. After the mixture was concentrated in vacuo, diluted with water, and extracted with ethyl acetate. The organic layer was washed with water and brine, dried over magnesium sulfate, and concentrated in vacuo to give a crude oil. The oil was purified by flash chromatography (20:80 hexane/ethyl acetate) to afford the ether as a brown oil (1.35 g, 67%).

Part B: A mixture of the ether of part A (1.3 g, 2.7 mmol) and a 50% NaOH aqueous solution (2.1 g, 27 mmol) in THF (23 mL), EtOH (23 mL), and $H_2O$ (12 mL) was heated at 60 degrees Celsius under a nitrogen atmosphere for 24 hours. The material was concentrated in vacuo and triturated with diethyl ether to give a solid. The solid was dissolved in water, cooled with an ice bath, acidified with concentrated hydrochloric acid. The precipitate was isolated by filtration, washed with cold water, and dried at ambient temperature in a vacuum oven for 3 days to afford the crude acid.

A mixture of the above crude acid (1.1 g), N-hydroxybenzotriazole (0.36 g, 2.7 mmol), 4-methylmorpholine (0.74 mL, 6.7 mmol), O-tetrahydro-2H-pyran-2-yl-hydroxylamine (0.39 g, 3.3 mmol), 1-(3-dimethylaminopropyl)-3-ethylcarbodiimide hydrochloride (0.60 g, 3.1 mmol) in DMF (11 mL) was stirred at ambient temperature under a nitrogen atmosphere for 18 hours. The mixture was concentrated in vacuo, and dissolved into a solution of saturated $NaHCO_3$ (90 mL), ethyl acetate (25 mL), and a few drops of 2N NaOH. The aqueous layer was extracted with additional ethyl acetate. The combined ethyl acetate layers were washed with saturated $NaHCO_3$ solution, water, and brine. After drying over magnesium sulfate, the filtrate was concentrated in vacuo to give a dark yellow oil. The oil was purified by flash chromatography (40:60 acetonitrile/toluene) to afford the protected hydroxamate as a yellow oil (0.32 g, 25%): MS $MH^+$ calcd. for $C_{29}H_{40}N_2O_7S$ 561, found 561.

Part C: To a solution of the protected hydroxamate of part 2B (0.28 g, 0.50 mmol) in methanol (4.0 mL) was added acetyl chloride (0.11 mL, 1.5 mmol) and the solution was stirred at ambient temperature under a nitrogen atmosphere for 2.5 hours. The solution was diluted with diethyl ether and concentrated. The solid was triturated with diethyl ether and dried at 40 degrees Celsius in a vacuum oven to give the title compound as an off white solid (0.15 g, 20%): MS $MH^+$ calcd. for $C_{24}H_{32}N_2O_6S$ 477, found 477.

EXAMPLE 398

Preparation of 1-cyclopropyl-N-hydroxy-4-[[4-(2-phenoxyethoxy)phenyl]sulfonyl]-4-piperidinecarboxamide, Monohydrochloride

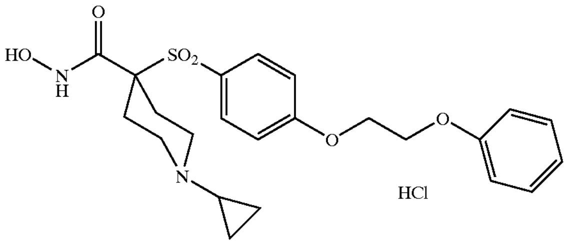

Part A: To a solution of the product of Example 9, part E (14.36 g, 40 mmol) in methanol (50 mL) was added acetic acid (24.5 g, 400 mmol), a portion (about 2 g) of 4-Angstrom molecular sieves, (1-ethoxycyclopropyl)-oxytrimethyl silane (25.8 mL, 148 mmol) and sodium cyanoborohydride (7.05 g, 112 mmol). The solution was heated at reflux for 8 hours. The precipitated solids were removed by filtration and the filtrate was concentrated in vacuo. The residue was diluted with $H_2O$ (400 mL) and extracted with ethyl acetate. The organic layer was washed with saturated NaCl and dried over $MgSO_4$, filtered and concentrated in vacuo. The solid was filtered, washed with $H_2O$/diethyl ether to give the desired cyclopropyl amine {ethyl-4-[(4-fluorophenyl-sulfonyl)]-1-cyclopropyl-4-piperidinecarboxylate} as a white solid (11.83 g, 81.5%). MS $MH^+$ calculated for $C_{17}H_{22}NO_4SF$: 356, found 356.

Part B: A solution of the cyclopropyl amine of Part A (2.0 g, 5.6 mmol), ethylene glycol phenyl ether (2.8 mL, 23 mmol), and cesium carbonate (7.3 g, 23 mmol) in DMAC (10 mL) was heat at 125–135 degrees Celsius for 18 hours under an atmosphere of nitrogen. The mixture was concentrated in vacuo, diluted with water, and extracted with ethyl acetate. The combined ethyl acetate layers were washed with water and brine, dried over magnesium sulfate, concentrated in vacuo, dissolved in diethyl ether, precipitated as the hydrochloride salt, and dried at 40 degrees Celsius in a vacuum oven. The solid was dissolved into a mixture of water, acetonitrile, and ethanol and then the pH was adjusted to 12 with 1N NaOH solution. The mixture was concentrated in vacuo to remove ethanol and acetonitrile. The solid was isolated by filtration, washed with water, and dried at 50 degrees Celsius in a vacuum oven to afford the ether as a white solid (1.8 g, 68%): MS+ calcd. for $C_{25}H_{31}NO_6S$ 474, found 474. Anal. calcd. for $C_{25}H_{31}NO_6S$: C, 63.40; H, 6.60; N, 2.96; S, 6.77. Found: C, 63.35; H, 6.59; N, 2.99; S, 6.61.

Part C: A mixture of the ether of part B (1.8 g, 3.7 mmol) and a 50% NaOH aqueous solution (3.0 g, 37 mmol) in THF (32 mL), EtOH (32 mL), and $H_2O$ (16 mL) was heated at 60 degrees Celsius under a nitrogen atmosphere for 24 hours. The material was concentrated in vacuo and triturated with diethyl ether to give a solid. The tan solid was dissolved into a mixture of water, ethanol, and THF, precipitated by adjusting the pH to 3 with concentrated hydrochloric acid, concentrated in vacuo, triturated with water, and dried at 50 degrees Celsius in a vacuum oven to give a crude white solid acid (2.3 g).

A mixture of the crude white solid acid (2.3 g), N-hydroxybenzotriazole (1.9 g, 14 mmol), 4-methylmorpholine (1.6 mL, 14 mmol), O-tetrahydro-2H-pyran-2-yl-hydroxylamine (1.1 g, 9.4 mmol), and 1-(3-dimethylaminopropyl)-3-ethylcarbodiimide hydrochloride (2.7 g, 14 mmol) in DMF (90 mL) was stirred at ambient temperature under a nitrogen atmosphere for 2 days. The mixture was concentrated in vacuo, diluted with water, and extracted with ethyl acetate. The organic layer was washed with 1N NaOH solution, water, and brine, dried over magnesium sulfate, concentrated in vacuo, and purification by flash chromatography (20:80 to 40:60 ethyl acetate/toluene) to afford the protected hydroxamate as a white solid: (0.43 g, 21%): MS MH+ calcd. for $C_{28}H_{36}N_2O_7S$ 545, found 545. Anal. calcd. for $C_{28}H_{36}N_2O_7S$: C, 61.74; H, 6.66; N, 5.14; S, 5.89. Found: C, 61.72; H, 6.75; N, 5.06; S, 5.91.

Additional compound was isolated by acidifying the aqueous layer to pH of 3, collecting the solid by filtration, and drying to give a white solid (0.80 g).

Part D: To an ambient temperature solution of acetyl chloride (0.31 mL, 4.4 mmol) in methanol (11 mL) under a nitrogen atmosphere was added the protected hydroxamate of part C (0.80 g, 1.5 mmol). After stirring for 2.5 hours, the precipitate was collected by filtration, washed with diethyl ether, and dried at 45 degrees Celsius in a vacuum oven to afford the title compound as a white solid (0.58 g, 15 79%): MS MH+ calcd. for $C_{23}H_{28}N_2O_6S$ 461, found 461. Anal. calcd. for $C_{23}H_{28}N_2O_6S.1.5HCl$: C, 53.62; H, 5.77; N, 5.44; S, 6.22. Found: C, 53.47; H, 5.79; N, 5.41; S, 6.16.

EXAMPLE 399

Preparation of hydroxy-1-(3-pyridinylmethyl)-4-[[4-[4-(trifluoromethoxy)phenoxy]phenyl]-sulfonyl]-4-piperidinecarboxamide, Dihydrochloride

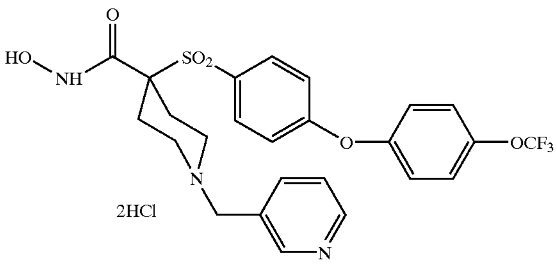

Part A: A solution of the amine hydrochloride salt of the product of Example 410(2.4 g, 4.6 mmol), 3-picolyl chloride (1.5 g, 8.8 mmol), and potassium carbonate (4.3 g, 31 mmol) in DMF (12) was heated at 50 degrees Celsius for 1 day under an atmosphere of nitrogen. The mixture was concentrated in vacuo, dissolved into water, and extracted with ethyl acetate. The organic layers were washed with water and brine, dried over magnesium sulfate, concentrated in vacuo. The residue was purified by flash chromatography (50:50 ethyl acetate/hexane) to afford the 3-picolyl amine as an amber oil (1.6 g, 60%): MS MH+ calcd. for $C_{27}H_{27}N_2O_6SF_3$ 565, found 565. Anal. calcd. for $C_{27}H_{27}N_2O_6SF_3$: C, 57.44; H, 4.82; N, 4.96; S, 5.68. Found: C, 57.49; H, 5.10; N, 4.69; S, 5.67

Part B: A mixture of the 3-picolyl amine of part 4A (1.5 g, 2.6 mmol) and a 50% NaOH aqueous solution (2.1 g, 26 mmol) in THF (22 mL), EtOH (22 mL), and $H_2O$ (11 mL) was heated at 65 degrees Celsius under a nitrogen atmosphere for 24 hours. The material was concentrated in vacuo and triturated with diethyl ether to give a solid. The tan solid was dissolved into water and the pH was adjusted to 1 with concentrated hydrochloric acid. The mixture was concentrated in vacuo, and dried in a 45 degrees Celsius vacuum oven to afford the crude white solid acid (2.5 g): MS MH+ calcd. for $C_{25}H_{23}N_2O_6SF_3$ 537, found 537.

Part C: A mixture of the crude white acid of part B (2.5 g), N-hydroxybenzotriazole (1.0 g, 7.7 mmol), 4-methylmorpholine (0.64 mL, 7.7 mmol), O-tetrahydro-2H-pyran-2-yl-hydroxylamine (0.60 g, 5.1 mmol), and 1-(3-dimethyl-aminopropyl)-3-ethylcarbodiimide hydrochloride (1.5 g, 7.7 mmol) in DMF (40 mL) was stirred at ambient temperature under a nitrogen atmosphere for 5 days. The mixture was concentrated in vacuo, diluted with ethyl acetate, and washed with water and brine. The organic layer was dried over magnesium sulfate, concentrated in vacuo, and purified by flash chromatography (5:95 methanol/chloroform) to afford the protected hydroxamate as a white foam (1.1 g, 66%): MS MH+ calcd. for $C_{30}H_{32}N_3O_7SF_3$ 636, found 636.

Part D: An ambient temperature solution of the protected hydroxamate of part C (1.0 g, 1.6 mmol) and acetyl chloride (0.34 mL, 4.7 mmol) in methanol (11 mL) under a nitrogen atmosphere was stirring for 2.5 hours, and then poured into diethyl ether. The solid was isolated by filtration and dried at 46 degrees Celsius in a vacuum oven to afford the title compound as a white solid (0.85 g, 87%): Anal. calcd. for $C_{25}H_{24}N_3O_6SF_3.2.2HCl$: C, 47.53; H, 4.18; N, 6.65; S, 5.08. Found: C, 47.27; H, 4.34; N, 6.60; S, 5.29. MS MH+ calcd. for $C_{25}H_{24}N_3O_6SF_3$ 552, found 552.

EXAMPLE 400

Preparation of N-Hydroxy-4-[4-(4-methoxyphenoxy)phenyl]sulfonyl]-1-(2-pyridinylmethyl)-4-piperidine-carboxamide, Dihydrochloride

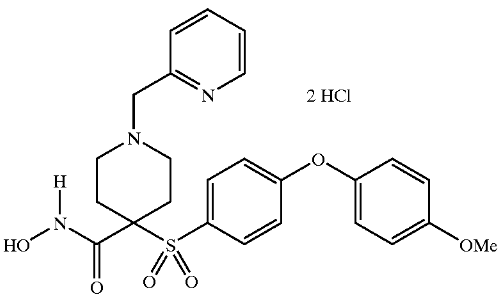

Part A: Ethyl-4-[(4-fluorophenylsulfonyl)]-4-piperidinecarboxylate hydrochloride (2.02 g, 5.76 mmol) was combined with powdered potassium carbonate (2.48 g, 18 mmol) and N,N-dimethylformamide (12 mL). 2-Picolyl hydrochloride (1.0 g, 6.1 mmol) was added, and the mixture was stirred for twenty-four hours at forty degrees Celsius. The reaction mixture was diluted with water (80 mL) and extracted with ethyl acetate (3×50 mL). The combined organic layers were dried over magnesium sulfate, concentrated, and subjected to chromatography (ethyl acetate) affording the desired pyridine ester as an oil (2.30 g, quantitative).

Part B: The pyridine ethyl ester from Part A (2.30 g, 5.76 mmol) was combined with powdered potassium carbonate (1.29 g, 9 mmol), 4-methoxyphenol (1.12 g, 9.0 mmol), and N,N-dimethylformamide (3 mL), and the mixture was heated at seventy five to eighty degrees C for twenty-four hours. Additional 4-methoxyphenol (300 mg) and potassium carbonate (350 mg) were added, and the mixture was stirred an additional three hours at ninety degrees Celsius. The mixture was diluted with water (50 mL) and extracted with ethyl acetate (3×50 mL). The combined organic layers were dried using magnesium sulfate, concentrated, and chromatographed, affording the desired ester as an oil (2.85 g, quantitative).

Part C: The ester of part B (2.85 g) was combined with ethanol (18 mL), water (6 mL), and potassium hydroxide (2.24 g, 40 mmol). The mixture was brought to reflux and heated for four and one-half hours. It was cooled to zero degrees Celsius and acidified using concentrated aqueous hydrogen chloride. The solvent was removed, and the resulting solids were dried by azeotroping with acetonitrile. Vacuum was applied until constant weight was achieved.

The crude acid hydrochloride was stirred with N-methylmorpholine (1 mL), 1-hydroxybenzotriazole (0.945 g, 7 mmol), O-tetrahydropyranyl hydroxylamine (0.82 g, 7 mmol), and N,N-dimethyformamide (21 mL). After ten minutes, 1-(3-dimethylaminopropyl)-3-ethylcarbodiimide hydrochloride (1.34 g, 7 mmol) was added, and the mixture was stirred overnight. The reaction was then diluted with half-saturated aqueous sodium bicarbonate (100 mL), and extracted with ethyl acetate (200 mL, then 50 mL). The combined organic layers were dried over magnesium sulfate, concentrated, and chromatographed (9:1 ethyl acetate:hexane) to afford the desired O-tetrahydropyranyl-protected hydroxamate as a yellow oil (2.82 g, 88%).

Part D: The O-tetrahydropyranyl-protected hydroxamate of part C (2.82 g, 5 mmol) was diluted with methanol (20 mL). Acetyl chloride (2.1 mL, 30 mmol) was added over two minutes. The reaction was stirred for 4 hours at ambient temperature, then concentrated to afford 2.59 g of crude dihydrochloridesalt, which was recrystallized from ethanol/water, affording 525 mg (18%) of the title hydroxamate in the first crop. MS (EI) $MH^+$ calculated for $C_{25}H_{27}N_3O_6S$: 498, found 498.

EXAMPLE 401

Preparation of N-Hydroxy-4-[4-(4-cyclohexylthio)phenyl]sulfonyl]-1-(2-methoxyethyl)-4-piperidine-carboxamide, Hydrochloride

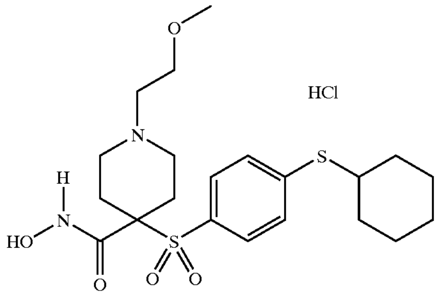

Part A: Ethyl-4-[(4-fluorophenylsulfonyl)]-1-(2-methoxyethyl)-4-piperidinecarboxylate (5.5 g, 14 mmol) was combined with powdered potassium carbonate (2.76 g, 20 mmol), N,N-dimethylformamide (7 mL), and cyclohexyl mercaptan (2.4 mL, 20 mmol) and was stirred at ambient temperature for two days. The temperature was raised to forty-five to fifty degrees Celsius and stirring was continued another 24 hours. Additional quantities of potassium carbonate (1.0 g) and cyclohexyl mercaptan (1.0 mL) were introduced and the reaction was heated sixteen additional hours. The mixture was diluted with water (50 mL), and extracted with ethyl acetate (100 mL, then 25 mL). The combined organic layers were dried, concentrated, and chromatographed (ethyl acetate) affording the desired sulfide as a yellow oil (3.59 mL, 53%).

Part B: The sulfide from Part A (3.59 gm, 7.4 mmol) was converted to tetrahydropyranyl-protected hydroxamate by saponification followed by 1-(3-dimethylaminopropyl)-3-ethylcarbodiimide hydrochloride coupling by the method of Example 401, part C, affording 2.16 g (54%) of the desired tetrahydropyranyl-protected hydroxamate as an oil.

Part C: The tetrahydropyranyl-protected hydroxamate from part B (2.16 g, 4 mmol) was diluted with methanol (16 mL). Acetyl chloride (1.1 mL, 16 mmol) was added over one minute. The reaction was stirred for four hours, then concentrated and azeotroped with acetonitrile to afford 1.11 g of crude product, which was recrystallized from absolute ethanol to afford in the first crop 804 mg of the title compound (41%). MS (EI) MH+ calculated for $C_{21}H_{32}N_2O_5S_2$: 457, found 457.

EXAMPLE 402

Preparation of N-Hydroxyl-1-(2-methoxyethyl)-4-[[(phenylmethoxy)phenyl]-sulfonyl]-4-piperidinecarboxamide

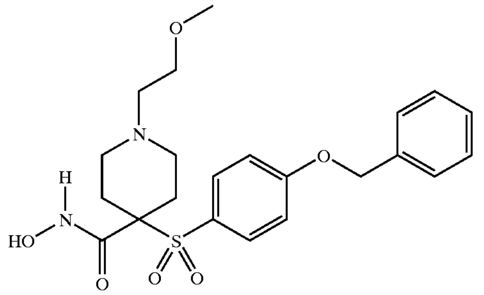

Part A: Ethyl-4-[(4-fluorophenylsulfonyl)]-1-(2-methoxyethyl)-4-piperidinecarboxylate (1.58 g, 4.5 mmol) was combined with powdered potassium carbonate (2.42 g , 18 mmol), N,N-dimethylacetamide (5 mL), and benzyl alcohol (1.94 mL, 18 mmol) and was stirred at one hundred forty degrees Celsius for sixteen hours. The mixture was diluted with water (50 mL), and extracted with ethyl acetate (125 mL, then 25 mL). The combined organic layers were dried, concentrated, and chromatographed (ethyl acetate) affording the desired ethyl ester as an oil (1.16 mL, 56%).

Part B: The ethyl ester from part A (1.16 gm, 2.5 mmol) was converted to the tetrahydropyranyl-protected hydroxamate by saponification followed by 1-(3-dimethylaminopropyl)-3-ethylcarbodiimide hydrochloride coupling by the method of Example 401, part C, affording 880 mg (80%) of the tetrahydropyranyl-protected hydroxamate as an oil.

Part C: The tetrahydropyranyl-protected hydroxamate from Part B (880 mg, 2.0 mmol) was diluted with methanol (8 mL). Acetyl chloride (0.68 mL, 10 wmol) was added over one minute. The reaction was stirred for three hours, then concentrated and azeotroped with acetonitrile to afford the crude product, which was converted to free base by adding enough saturated aqueous sodium bicarbonate (25 mL) to neutralize the hydrogen chloride, then extracting with ethyl acetate (100 mL, then 50 mL). The organic phase was dried with magnesium sulfate, concentrated, and chromatographed (9:1 dichloromethane:methanol, 1% ammonium hydroxide), affording the title hydroxamate as a glass, (327 mg, 36%). MS (EI) MH+ calculated for $C_{22}H_{28}N_2O_6S$: 447, found 447.

EXAMPLE 403

Preparation of N-hydroxyl-1-(1-methylethyl)-4-[[4-(2-phenylethoxy)-phenyl]sulfonyl3-4-piperidine Carboxamide

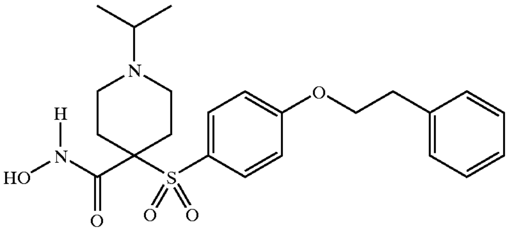

Part A: Ethyl-4-[(4-fluorophenylsulfonyl)]-1-(1-methylethyl)-4-piperidinecarboxylate (2.75 g, 7.7 mmol) was combined with powdered potassium carbonate (2.62 g, 19 mmol), N,N-dimethylformamide (10 mL), and 2-phenylethanol (2. mL, 19 mmol) and was stirred at eighty-five degrees Celsius for twenty four hours. Additional potassium carbonate (1.3 g) and 2-phenylethanol were added, and the temperature was raised to one hundred-ten degrees Celsius for forty-eight hours, then one hundred thirty-five degrees Celsius for four hours. The mixture was diluted with water (100 mL), and extracted with ethyl acetate (200 mL, then 25 mL). The combined organic layers were dried, concentrated, and chromatographed (ethyl acetate) affording the desired ethyl ester as an oil (3.19 mL, 90%).

Part B: The ethyl ester from Part A (3.19 gm, 6.9 mmol) was converted to tetrahydropyranyl-protected hydroxamate by saponification followed by 1-(3-dimethylaminopropyl)-3-ethylcarbodiimide hydrochloride coupling by the method of Example 401, part C, affording 2.27 g (64%) of the title compound as an oil.

Part C: The tetrahydropyranyl-protected hydroxamate from Part B (2.27 mg, 4.4 mmol) was diluted with methanol (16 mL). Acetyl chloride (0.68 mL,10 mmol) was added over one minute. The reaction was stirred for three hours, then concentrated and azeotroped with acetonitrile to afford the crude product, which was converted to free base by adding enough saturated sodium bicarbonate (25 mL) to neutralize the hydrogen chloride, then extracting with ethyl acetate (100, then 50 mL). The organic phase was dried with magnesium sulfate, concentrated, and chromatographed (9:1 dichloromethane:methanol, 1% ammonium hydroxide), affording the desired hydroxamate as a glass, (819 mg, 42%). MS (EI) MH+ calculated for $C_{23}H_{30}N_2O_5S$: 449, found 449.

EXAMPLE 404

Preparation of N-hydroxy-4-[(4-phenylthiophenyl) sulfonyl]-1-(2-propynyl)-4-piperidinecarboxamide, phosphoric acid salt

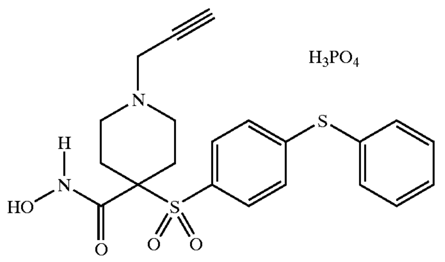

N-Hydroxy-4-[(4-phenylthiophenyl)sulfonyl]-1-(2-propynyl)-4-piperidinecarboxamide (430 mg, 1.0 mmol) was dissolved in methanol (15 mL). Concentrated phosphoric acid (67 μL) was added, and the solution was then concentrated in vacuc. The residue was recrystallized from methanol, isolated by filtration, and then recrystallized a second time from methanol/methyl t-butyl ether affording the title phosphate as a solid (215 mg, 41%). Analytical calculation for $C_{21}H_{22}N_2O_4.H_3PO_4$: C, 47.72; H, 4.77; N, 5.30, found: C, 47.63; H, 5.04; N, 4.82.

EXAMPLE 405

Preparation of N-hydroxy-4-[(4-phenylthiophenyl) sulfonyl]-1-(2-propynyl)-4-piperidinecarboxamide, p-toluenesulfonic Acid Salt

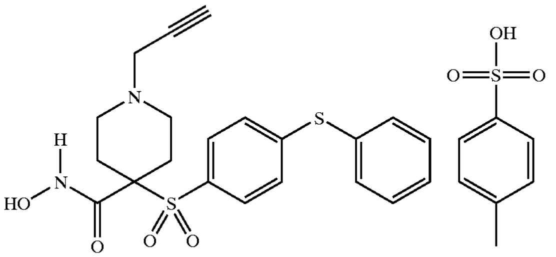

N-Hydroxy-4-[(4-phenylthiophenyl)sulfonyl]-1-(2-propynyl)-4-piperidinecarboxamide (516 mg, 1.0 mmol) was combined with p-toluenesulfonic acid, monohydrate (200 mg, 1.05 mmol), and the mixture was dissolved in methanol (3 mL). After four hours, the resulting white precipitate was collected by filtration affording 488 mg (81%) of the title tosylate salt, which was characterized spectroscopically.

EXAMPLE 406

Preparation of 4-[[4-[(2,3-dihydro-1H-inden-2-yl) amino]phenyl]sulfonyl]-N-hydroxy-4-piperidinecarboxamide, Monohydrochloride

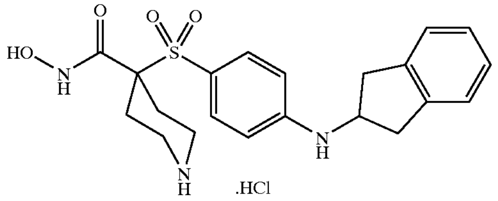

Part A: A solution of the product of Example 9, Part D (0.979 g, 2.36 mmol), 2-aminoindan hydrochloride (1.00 g, 5.89 mmol), and cesium carbonate (1.92 g, 5.89 mmol) in N,N-dimethylformamide (8 mL) was heated to 95 degrees Celsius for 22 hours. The reaction was then cooled, diluted with ethyl acetate (50 mL), and washed with three times with water and once with brine, then dried over sodium sulfate. Concentration gave a residue that was chromatographed on silica gel. Elution with ethyl acetate/hexane (30/70) afforded the desired 4-aminosulfone derivative (450 mg, 36%). MS (EI) $MH^+$ calculated for $C_{28}H_{36}N_2O_6S$: 529, found 529. HRMS M+ calculated for $C_{28}H_{36}N_2O_6S$: 528.2294, found 528.2306.

Part B: To a solution of the ethyl ester of part A (450 mg, 0.85 mmol) in ethanol (3 mL), water (2 mL) and tetrahydrofuran (3 mL) was added sodium hydroxide (340 mg, 8.5 mmol), and the solution was heated to 60 degrees Celsius for 26 hours. The solution was cooled and then diluted with water (10 mL) followed by 10% aqueous hydrochloric acid (3 mL) to bring the pH to 2. The resulting solution was extracted with ethyl acetate. The organic extracts were combined and washed with water and brine and dried over sodium sulfate to afford the desired carboxylic acid as a pale brown foam (376 mg, 88%). Analytical calculation for $C_{26}H_{32}N_2O_6S$: C, 62.38; H, 6.44; N, 5.60; S, 6.40. Found: C, 62.48; H, 6.69; N, 5.42; S, 6.27.

Part C: To a solution of the carboxylic acid of part B (305 mg, 0.609 mmol) in N,N-dimethylformamide (2 mL) was added 4-methylmorpholine (247 mg, 2.44 mmol), N-hydroxybenzotriazole (99 mg, 0.73 mmol), and 1-[3-(dimethylamino)propyl]-3-ethylcarbodiimide hydrochloride (152 mg, 0.79 mmol) followed by O-(tetrahydro-2H-pyran-2-yl) hydroxylamine (97 mg, 0.82 mmol). After stirring for 2 days at ambient temperature, the solution was concentrated to an oil. Water was added and the mixture was extracted with ethyl acetate. The organic extracts were washed with water and brine and dried over sodium sulfate. Concentration gave a brown foam that was chromatographed on silica gel. Elution with ethyl acetate/hexane (40/60) afforded the protected hydroxamate derivative as a colorless glass (0.38 g, 100%). MS $MH^+$ calculated for $C_{31}H_{41}N_3O_7S$: 600, found 600.

Part D: To a solution of the protected hydroxamate of part C (350 mg, 0.584 mmol) in methanol (3 mL) and 1,4-dioxane (1.5 mL) was added 4 N HCl/1,4-dioxane (1.5 mL, 6 mmol), and the solution was stirred at ambient temperature for 3 hours. Concentration gave a residue that was triturated with diethyl ether to afford the title compound as a solid, which was filtered and dried for 40 hours at 51 degrees Celsius (249 mg, 94%). HRMS (ESI) $MH^+$ calculated for $C_{21}H_{25}N_3O_4S$: 416.1644, found 416.1647.

EXAMPLE 407

Preparation of 4-[[4-(dimethylamino)-phenyl] sulfonyl]-N-hydroxy-4-piperidine-carboxamide, Monohydrochloride

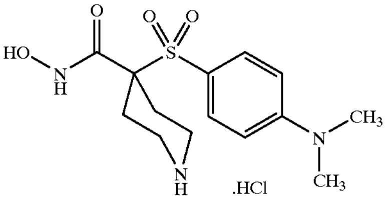

Part A: A solution of the product of Example 9, Part D (0.979 g, 2.36 mmol), 2-aminoindan hydrochloride (1.00 g, 5.89 mmol), and cesium carbonate (1.92 g, 5.89 mmol) in N,N-dimethylformamide (8 mL) was heated to 95 degrees Celsius for 22 hours. The reaction was then cooled, diluted with ethyl acetate (50 mL), and washed with three times with water and once with brine, then dried over sodium sulfate. Concentration gave a residue that was chromatographed on silica gel. Elution with ethyl acetate/hexane (30/70) afforded the 4-N,N-dimethylaminosulfone derivative (590 mg, 57%) alongside the product of example 406. MS (EI) $MH^+$ calculated for $C_{21}H_{32}N_2O_6S$: 441, found 441. HRMS calculated for $C_{21}H_{32}N_2O_6S$: 440.1981, found 440.1978.

Part B: To a solution of the ethyl ester of part A (580 mg, 1.3 mmol) in ethanol (4 mL), water (3 mL) and tetrahydrofuran (4 mL) was added sodium hydroxide (520 mg, 13 mmol), and the solution was heated to 62 degrees Celsius for 5 hours. The solution was cooled and then diluted with water (5 mL) followed by 10% aqueous hydrochloric acid (5 mL) to acidify to pH=2. The resulting solution was extracted with ethyl acetate. The organic extracts were combined and washed with water and brine and dried over sodium sulfate to afford the desired carboxylic acid as a pale brown foam (520 mg, 97%). MS $MH^+$ calculated for $C_{19}H_{28}N_2O_6S$: 413, found 413.

Part C: To a solution of the carboxylic acid of part B (500 mg, 1.21 mmol) in N,N-dimethylformamide (4 mL) was added 4-methylmorpholine (490 mg, 4.8 mmol), N-hydroxybenzotriazole (197 mg, 1.45 mmol), and 1-[3-(dimethylamino)propyl]-3-ethylcarbodiimide hydrochloride (302 mg, 1.57 mmol) followed by O-(tetrahydro-2H-pyran-2-yl) hydroxylamine (192 mg, 1.63 mmol). After stirring for 2 days at ambient temperature, the solution was concentrated to an oil. Water (25 mL) was added and the mixture was extracted with ethyl acetate. The organic extracts were washed with water and brine and dried over sodium sulfate. Concentration gave a brown oil, which crystallized from a mixture of ethyl acetate, hexane and methylene chloride (1:1:2) to afford the protected hydroxamate derivative as a colorless solid (506 mg, 82%). MS $MH^+$ calculated for $C_{24}H_{37}N_3O_7S$: 512, found 512.

Part D: To a solution of the protected hydroxamate of part C (477 mg, 0.932 mmol) in methanol (3 mL) and 1,4-dioxane (3 mL) was added 4 N HCl/1,4-dioxane (2.3 mL, 9.3 mmol), and the solution was stirred at ambient temperature for 3 hours. Concentration gave a residue that was triturated with diethyl ether to afford the title compound as a solid, which was filtered and dried for 40 hours at 51 degrees Celsius (372 mg, 100%). HRMS (ESI) $MH^+$ calculated for $C_{14}H_{21}N_3O_4S$: 328.1331, found 328.1343.

EXAMPLE 408

Preparation of 1-cyclopropyl-4-[[4-[(2,3-dihydro-1, 4-benzodioxin-6-yl)oxy]phenyl]-sulfonyl]-N-hydroxy-4-piperidine-carboxamide, Monohydrochloride

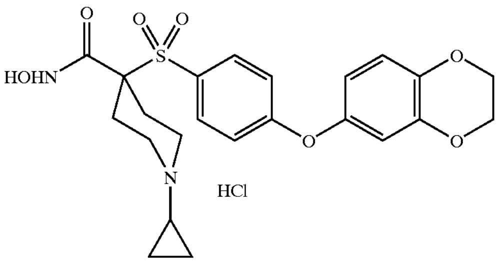

Part A: To a solution of the product of Example 398, Part A (1.36 g, 3.47 mol) in N,N-dimethylformamide (8 mL) was added 6-hydroxybenzo-1,4-dioxane (792 mg, 5.21 mmol) followed by cesium carbonate (2.83 g, 8.69 mmol) and the solution was heated at one hundred degrees Celsius for 20 hours. The solution was partitioned between ethyl acetate and $H_2O$. The aqueous layer was extracted with ethyl acetate and the combined organic layers were washed with $H_2O$ and saturated NaCl and dried over $Na_2SO_4$. Filtration through a silica pad (ethyl acetate/hexane) provided the phenoxyphenyl compound as an orange oil (1.81 g, quantitative yield). MS(CI) $MH^+$ calculated for $C_{25}H_{29}NO_7S$: 488, found 488.

Part B: To a solution of the phenoxyphenol compound of part A (1.81 g, <3.47 mmol) in tetrahydrofuran (10 mL) and ethanol (10 mL) was added sodium hydroxide (1.39 g, 34.7 mmol) in $H_2O$ (5 mL). The solution was heated to sixty degrees Celsius for 20 hours. The solution was concentrated in vacuo and the aqueous residue was acidified to pH=2 with 10% HCl. The resulting solid was collected by vacuum filtration to provide the acid as a yellow solid (1.23 g, 72%). MS(CI) $MH^+$ calculated for $C_{23}H_{25}NO_7S$: 460, found 460. HRMS calculated for $C_{23}H_{25}NO_7S$: 460.1430, found 460.1445.

Part C: To a suspension of the acid of part B (1.21 g, 2.46 mmol) in N,N-dimethylformamide (20 mL) was added N-hydroxybenzotriazole (399 mg, 2.95 mmol), 4-methylmorpholine (0.81 mL, 7.38 mmol) and O-(tetrahydro-2H-pyran-2-yl)hydroxylamine (432 mg, 3.69 mmol). After stirring for one hour 1-[3-(dimethylamino) propyl]-3-ethylcarbodiimide hydrochloride (660 mg, 3.44 mmol) was added and the solution was stirred for 20 hours at ambient temperature. The solution was partitioned between ethyl acetate and $H_2O$ and the aqueous layer was extracted with ethyl acetate. The organic layer was washed with saturated NaCl and dried over $Na_2SO_4$. Chromatography (on silica, ethyl acetate/hexane) provided the protected hydroxamate as a yellow oil (940 mg, 70%). MS (CI) $MH^+$ calculated for $C_{28}H_{34}N_2O_2S$: 559, found 559.

Part D: To a solution of the protected hydroxamate of part C (920 mg, 1.68 mmol) in 1,4-dioxane (15 mL) was added 4N HCl in 1,4-dioxane (10 mL). After stirring at ambient temperature for 2 hours the resulting precipitate was collected by vacuum filtration and washed with ethyl ether to provided the title compound as a white solid (510 mg, 60%). MS (CI) $MH^+$ calculated for $C_{23}H_{26}N_2O_7S$: 475, found 475. HRMS calculated for $C_{23}H_{26}NO_7S$: 475.1539, found 475.1553. Analytical calculation for $C_{23}H_{26}N_2O_7S.1.15HCl.0.5H_2O$: C, 52.57; H, 5.40; N, 5.33; Cl, 7.76. Found: C, 52.62; H, 5.42; N, 5.79; Cl, 7.71.

EXAMPLE 409

Preparation of N-hydroxy-4-[[4-[4-(trifluoromethyl) phenoxy]phenyl]sulfonyl]-4-piperidinecarboxamide, Monohydrochloride

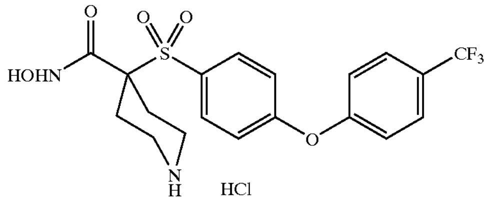

Part A: To a solution of the product of Example 9, Part D (1.5 g, 3.61 mmol) in N,N-dimethylformamide (10 mL) was added cesium carbonate (2.94 g, 9.03 mmol) and α,α,α-trifluoro-p-cresol (877 mg, 5.41 mmol). The solution was heated to ninety degrees Celsius for 20 hours. The solution was partitioned between ethyl acetate and $H_2O$ and the organic layer was washed with saturated NaCl and dried over $Na_2SO_4$. Filtration through a silica pad (ethyl acetate) provided the diaryl ether as a yellow oil (2.30 g, quantitative yield). MS(CI) $MH^+$ calculated for $C_{26}H_{30}NO_7SF_3$: 558, found 558.

Part B: To a solution of the diaryl ether of part A (2.30 g, <3.61 mmoL) in tetrahydrofuran (10 mL) and ethanol (10 mL) was added sodium hydroxide (1.44 g, 36.1 mmol) in $H_2O$ (5 mL) and the solution was heated to sixty degrees Celsius for 18 hours. The solution was concentrated and the aqueous residue was acidified to pH=2 with 10% HCl and extracted with ethyl acetate. The organic layer was washed with saturated NaCl and dried over $Na_2SO_4$. Concentration in vacuo provided the acid as a solid (2.11 g, quantitative yield). MS(CI) $MH^+$ calculated for $C_{24}H_{26}NO_7SF_3$: 530, found 530.

Part C: To a solution of the acid of part B (2.11 g, <3.61 mmol) in N,N-dimethylformamide (10 mL) was added N-hydroxybenzotriazole (586 mg, 4.33 mmol), 4-methylmorpholine (1.19 mL, 10.83 mmol) and O-(tetrahydro-2H-pyran-2-yl)hydroxylamine (634 mg, 5.41 mmol). After stirring for one hour, 1-[3-(dimethylamino) propyl]-3-ethylcarbodiimide hydrochloride (969 mg, 5.05 mmol) was added and the solution was stirred for 18 hours. The solution was partitioned between ethyl acetate and $H_2O$. The aqueous layer was extracted with ethyl acetate and the combined organic layers were washed with $H_2O$ and saturated NaCl and dried over $MgSO_4$. Chromatography (on silica, ethyl acetate/hexane) provided the protected hydroxamate as a clear, colorless oil (1.40 g, 62%). MS(CI) $MH^+$ calculated for $C_{29}H_{35}N_2O_8SF_3$: 629, found 629.

Part D: To a solution of the protected hydroxamate of part C (1.40 g, 2.23 mmol) in 1,4-dioxane (10 mL) was added 4N HCl in 1,4-dioxane (15 mL) and the solution was stirred for 2 hours. The solution was diluted with ethyl ether and the resulting precipitate was collected by vacuum filtration to provide the title compound as a white solid (747 mg, 70%). HPLC purity: 97.5%. MS(CI) $MH^+$ calculated for $C_{19}H_{19}N_2O_5SF_3$: 445, found 445. HRMS calculated for $C_{19}H_{19}N_2O_5SF_3$: 445.1045, found 445.1052. Analytical calculation for $C_{19}H_{19}N_2O_5SF_3$.0.5$H_2O$.1.0OHCl: C, 46.58; H, 4.32; N, 5.72; S, 6.55; Cl, 7.24. Found: C, 46.58; H, 3.82; N, 5.61; S, 6.96; Cl, 7.37.

EXAMPLE 410

Preparation of N-hydroxy-4-[[4-[(trifluoromethoxy) phenoxy]phenyl]sulfonyl]-4-piperidinecarboxamide, Monohydrochloride

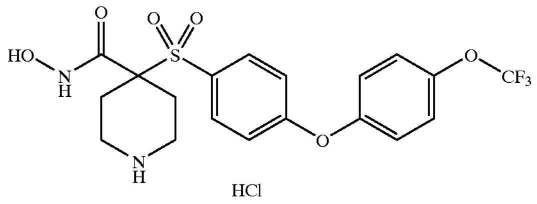

Part A: To a solution of the product of Example 9, Part D (1.5 g, 3.61 mmol) in N,N-dimethylformamide (10 mL) was added cesium carbonate (2.94 g, 9.03 mmol) and 4-(trifluoromethoxy)phenol (0.70 mL, 5.41 mmol). The solution was heated to ninety degrees Celsius for 20 hours. The solution was partitioned between ethyl acetate and $H_2O$ and the organic layer was washed with saturated NaCl and dried over $Na_2SO_4$. Filtration through a silica pad (ethyl acetate) provided the phenoxyphenol as a yellow oil (2.11 g, quantitative yield). MS(CI) $MNa^+$ calculated for $C_{26}H_{30}NO_8SF_3$: 596, found 596.

Part B: To a solution of the phenoxyphenol of part A (2.11 g, <3.61 mmoL) in tetrahydrofuran (10 mL) and ethanol (10 mL) was added sodium hydroxide (1.44 g, 36.1 mmol) in $H_2O$ (5 mL), and the solution was heated to sixty degrees Celsius for 18 hours. The solution was concentrated and the aqueous residue was acidified to pH=2 with 10% HCl and extracted with ethyl acetate. The organic layer was washed with saturated NaCl and dried over $Na_2SO_4$. Concentration in vacuo provided the acid as a solid (2.2 g, quantitative yield). MS(CI) $MH^+$ calculated for $C_{24}H_{26}NO_8SF_3$: 546, found 546.

Part C: To a solution of the acid of part B (2.2 g) in N,N-dimethylformamide (10 mL) was added N-hydroxybenzotriazole (586 mg, 4.33 mmol), 4-methylmorpholine (1.19 mL, 10.83 mmol) and O-(tetrahydro-2H-pyran-2-yl)hydroxylamine (634 mg, 5.41 mmol). After stirring for thirty minutes, 1-[3-(dimethylamino)propyl]-3-ethylcarbodiimide hydrochloride (969 mg, 5.05 mmol) was added and the solution was stirred for 96 hours. The solution was partitioned between ethyl acetate and $H_2O$. The aqueous layer was extracted with ethyl acetate and the combined organic layers were washed with $H_2O$ and saturated NaCl and dried over $MgSO_4$. Chromatography (on silica, ethyl acetate/hexane) provided the protected hydroxamate as a clear, colorless oil (1.26 g, 53%)

Part D: To a solution of the protected hydroxamate of part C (1.26 g, 1.96 mmol) in 1,4-dioxane (10 mL) was added 4N HCl in 1,4-dioxane (10 mL) and the solution was stirred for 2 hours. The solution was diluted with ethyl ether and the resulting precipitate was collected by vacuum filtration to provide the title compound as a white solid (455 mg, 47%). HPLC purity: 98%. MS(CI) $MH^+$ calculated for $C_{19}H_{19}N_2O_6SF_3$: 461, found 461. HRMS calculated for $C_{19}H_{19}N_2O_6SF_3$: 461.0994, found 461.0997. Analytical calculation for $C_{19}H_{19}N_2O_6SF_3$.1.0HCl: C, 45.93; H, 4.06; N, 5.64; S, 6.45; Cl, 6.45. Found: C, 46.23; H, 4.07; N, 5.66; S, 6.59; Cl, 7.03.

EXAMPLE 411

Preparation of 1-cyclopropyl-4-[[4-[(2,3-dihydro-1,4-benzodioxin-6-yl)amino]-phenyl]sulfonyl]-N-hydroxy-4-piperidine-carboxamide, Monohydrochloride

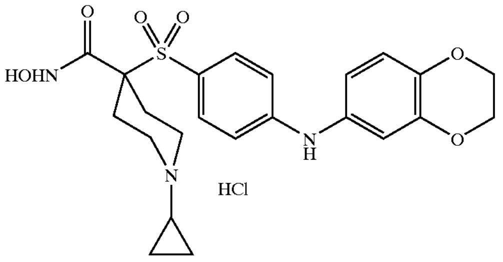

Part A: To a solution of ester of part C, Example 91 (1.57 g, 3.40 mmol) in 1,4-dioxane (5 mL) was added 4M HCl in 1,4-dioxane (10 mL). After stirring for one hour the resulting precipitate was collected by vacuum filtration to provide the amine hydrochloride salt as a white solid (1.16 g, 86%).

Part B: To a slurry of the amine hydrochloride salt of part A (1.16 g, 2.91 mmol) in methanol (10 mL) was added acetic acid (1.68 mL, 29.1 mmol) followed by (1-ethyoxycyclopropyl)-oxytrimethylsilane (3.51 mL, 17.5 mmol) and sodium cyanoborohydride (823 mg, 13.1 mmol). The solution was heated to reflux for six hours. The solution was filtered and the filtrate was concentrated in vacuo. The residue was dissolved into ethyl acetate and washed with $H_2O$, aqueous sodium hydroxide and saturated NaCl and dried over $MgSO_4$. Concentration in vacuo provided the N-cyclopropyl compound as a white solid (1.03 g, 88%).

Part C: To a solution of the N-cyclopropyl compound of part B (1.0 g, 2.49 mmol) in toluene (6 mL) was added cesium carbonate (1.14 g, 3.49 mmol), tris (dibenzylideneacetone)dipalladium(0) (69 mg, 0.075 mmol) R-(+)-2,2'-bis(diphenylphosphino)-1,1'-binaphthyl (69 mg, 0.112 mmol) and 1,4-benzodioxane-6-amine (451 mg, 2.99 mmol) and the solution was heated to one hundred degrees Celsius for 19 hours. The solution was diluted with ethyl ether and filtered through Super Cel®. The filtrate was concentrated and chromatography (on silica, ethyl acetate/hexane) provided the aniline compound as an orange oil (561 mg, 48%). MS(CI) $MH^+$ calculated for $C_{24}H_{28}N_2O_6S$: 473, found 473.

Part D: To a solution of the aniline compound of part C (550 mg, 1.16 mmol) in tetrahydrofuran (10 mL) was added potassium trimethylsilanolate (297 mg, 3.48 mmol) and the solution was stirred for 18 hours at ambient temperature. The solution was concentrated and the resulting residue was suspended in $H_2O$. The solid was collected by vacuum filtration to provide the crude acid (282 mg).

Part E: To a solution of the crude acid of part D (282 mg, 0.62 mmol) in N,N-dimethylformamide (10 mL) was added N-hydroxybenzotriazole (100 mg, 0.74 mmol), 4-methylmorpholine (0.20 mL, 1.86 mmol), and O-(tetrahydro-2H-pyran-2-yl) hydroxylamine (108 mg, 0.93 mmol). After stirring for 30 minutes, 1-[3-(dimethylamino) propyl]-3-ethylcarbodiimide hydrochloride (166 mg, 0.87 mmol) was added and the solution was stirred for 72 hours. The solution was partitioned between ethyl acetate and $H_2O$ and the aqueous layer was extracted with ethyl acetate. The combined organic layers were washed with $H_2O$ and saturated MaCl and dried over $Na_2SO_4$. Chromatography (on silica, ethyl acetate/hexane) provided the protected hydroxamate as a white solid (150 mg, 43%). MS (CI) $MH^+$ calculated for $C_{28}H_{35}N_3O_7S$: 558, found 558.

Part F: To a solution of protected hydroxamate of part E (133 mg, 0.24 mmol) in 1,4-dioxane (5 mL) was added 4N HCl in 1,4-dioxane (10 mL) and the solution was stirred for 1.5 hours. The solution was diluted with ethyl ether and the resulting precipitate was collected by vacuum filtration to provide the title hydroxamate as a white solid (80 mg, 66%). MS(CI) $MH^+$ calculated for $C_{23}H_{27}N_3O_6S$: 474, found 474. HRMS calculated for $C_{23}H_{27}N_3O_6S$: 474.1699, found 474.1715. Analytical calculation for $C_{23}H_{27}N_3O_6S.1.5HCl.1.5H_2O$: C, 49.75; H, 5.72; N, 7.57; S, 5.77; Cl, 9.58. Found: C, 49.78; H, 5.52; N, 8.05; S, 9.16; Cl, 5.76.

EXAMPLE 412

Preparation of 1-cyclopropyl-4-[[4-[4-[[4-(2,3-dimethylphenyl)-1-piperazinyl]-carbonyl]-1-piperidinyl]phenyl]sulfonyl]-N-hydroxy-4-piperidine-carboxamide, Trihydrochloride

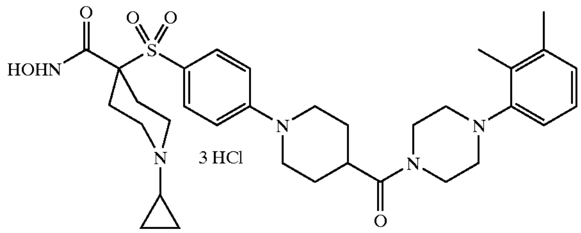

Part A: To a solution of the isonipecotic acid (10.5 g, 81.3 mmol) in $H_2O$ (325 mL) was added sodium carbonate (8.37 g, 81.3 mmol) and the solution was stirred until homogeneous. To this solution was added di-tert-butyl dicarbonate (18.22 g, 83.5 mmol) in 1,4-dioxane (77 mL) dropwise, and the resulting solution was stirred for 72 hours at ambient temperature. The solution was concentrated in vacuo and the resulting aqueous solution was washed with ethyl ether. The aqueous solution was acidified to pH=2 with concentrated HCl. The solution was extracted with ethyl ether and concentrated in vacuo provided a white solid. Recrystallization (ethyl acetate) provided N-Boc-isonipecotic acid as a white solid (10 g, 54%).

Part B: To a solution of the N-Boc-isonipecotic acid of part A (2.14 g, 9.33 mmol) in dichloromethane (19 mL) were added 1-[3-(dimethylamino)propyl]-3-ethylcarbodiimide hydrochloride (1.82 g, 9.49 mmol), N-hydroxybenzotriazole (1.32 g, 9.77 mmol) and 1-(2,3-xylyl)piperazine monohydrochloride (2.47 g, 10.89 mmol). After 30 minutes diisopropylethylamine (0.74 mL, 20.7 mmol) was added, and the solution was stirred for 18 hours. The solution was concentrated in vacuo and the residue was dissolved into ethyl acetate and washed with 1M HCl, saturated $NaHCO_3$ and saturated NaCl. The solution was dried over $MgSO_4$. Recrystallization (ethyl acetate/hexane) provided the amide as an off-white solid (2.65 g, 71%).

Part C: To a solution of the amide of part B (1.0 g, 3.75 mmol) in dichloromethane (5 mL) was added trifluoroacetic acid (5 mL) and the solution was stirred for 15 minutes. The solution was concentrated in vacuo and the resulting oil was dissolved into N,N-dimethylacetamide (10 mL). To this solution was added the product of Example 398, Part A (979 mg, 2.50 mmol) and cesium carbonate (3.67 g, 11.25 mmol)

and the solution was heated at one hundred and ten degrees Celsius for 17 hours. The solution was partitioned between ethyl acetate and $H_2O$. The organic layer was washed with $H_2O$ and saturated NaCl and dried over $Na_2SO_4$. Concentration in vacuo provided the piperidine compound as a white solid (1.89 g, quantitative yield). MS(CI) $MH^+$ calculated for $C_{35}H_{48}N_4O_5S$: 637, found 637.

Part D: To a solution of the piperidine compound of part C (1.89 g) in ethanol (8 mL) and tetrahydrofuran (8 mL) was added sodium hydroxide (1.0 g, 25 mmol) in $H_2O$ (5 mL). The solution was heated to fifty degrees Celsius for 8 hours and at sixty-two degrees Celsius for 8 hours. The solution was concentrated in vacuo and the residue was diluted with $H_2O$ and acidified to pH=3 with 3M HCl. The resulting precipitate was collected by vacuum filtration to provide the acid as a white solid (1.16 g, 65%). MS(CI) $MH^+$ calculated for $C_{33}H_{44}N_4O_5S$: 609, found 609.

Part E: To a solution of the acid of part D (1.16 g, 1.62 mmol) in N,N-dimethylformamide (10 mL) were added N-hydroxybenzotriazole (262 mg, 1.94 mmol), 4-methylmorpholine (0.90 mL, 8.2 mmol) and O-(tetrahydro-2H-pyran-2-y)1 hydroxylamine (284 mg, 2.4 mmol). After stirring for 45 minutes, 1-[3-(dimethylamino) propyl]-3-ethylcarbodiimide hydrochloride (334 mg, 2.2 mmol) was added and the solution was stirred for 18 hours at ambient temperature. The solution was partitioned between ethyl acetate and $H_2O$ and the organic layer was washed with $H_2O$ and saturated NaCl and dried over $Na_2SO_4$. Trituration (dichloromethane) provided the protected hydroxamate as a white solid (850 mg, 75%). MS(CI) $MH^+$ calculated for $C_{38}H_{53}N_5O_6S$: 708, found 708.

Analytical calculation for $C_{38}H_{53}N_5O_6S.0.5H_2O$: C, 63.66; H, 7.59; N, 9.77; S, 4.47. Found: C, 63.68; H, 7.54; N, 9.66; S, 4.67.

Part F: To a solution of the protected hydroxamate of part E (746 mg, 1.07 mmol) in methanol (10 mL) was added 4M HCl in 1,4-dioxane (10 mL) and the solution was stirred for one hour. The resulting solid was collected by vacuum filtration and washed with ethyl ether to provide the title compound as a white solid (650 mg, 83%). MS(CI) $MH^+$ calculated for $C_{33}H_{45}N_5O_5S$: 624, found 624. HRMS calculated for $C_{33}H_{49}N_5O_5S$: 624.3220, found 624.3253. Analytical calculation for $C_{33}H_{45}N_5O_5S.3.5HCl.H_2O$: C, 51.82; H, 6.59; N, 9.16. Found: C, 52.04; H, 6.30; N, 8.96.

EXAMPLE 413

Preparation of 4-[[4-[4-[[4-(2,3-dimethylphenyl)-1-piperazinyl]carbonyl]-1-piperidinyl]phenyl]sulfonyl]-N-hydroxy-1-(2-methoxyethyl)-4-piperidine-carboxamide, Trihydrochloride

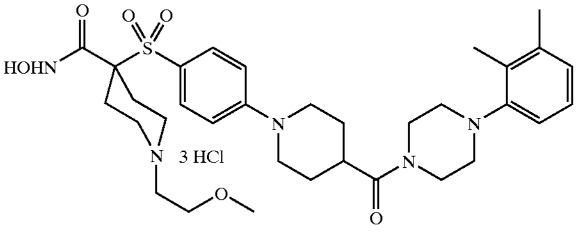

Part A: To a solution of the isonipecotic acid (10.5 g, 81.3 mmol) in $H_2O$ (325 mL) was added sodium carbonate (8.37 g, 81.3 mmol) and the solution was stirred until homogeneous. To this solution was added di-tert-butyl dicarbonate (18.22 g, 83.5 mmol) in 1,4-dioxane (77 mL) dropwise and the resulting solution was stirred for 72 hours at ambient temperature. The solution was concentrated in vacuo and the resulting aqueous solution was washed with ethyl ether. The aqueous solution was acidified to pH=2 with concentrated HCl. The solution was extracted with ethyl ether and concentration in vacuo provided a white solid. Recrystallization (ethyl acetate) provided N-Boc-isonipecotic acid as a white solid (10 g, 54%).

Part B: To a solution of the N-Boc-isonipecotic acid of part A (2.14 g, 9.33 mmol) in dichloromethane (19 mL) were added 1-[3-(dimethylamino)propyl]-3-ethylcarbodiimide hydrochloride (1.82 g, 9.49 mmol), N-hydroxybenzotriazole (1.32 g, 9.77 mmol) and 1-(2,3-xylyl)piperazine monohydrochloride (2.47 g, 10.89 mmol). After 30 minutes, diisopropylethylamine (0.74 mL, 20.7 mmol) was added and the solution was stirred for 18 hours. The solution was concentrated in vacuo and the residue was dissolved into ethyl acetate and washed with 1M HCl, saturated $NaHCO_3$ and saturated NaCl. The solution was dried over $MgSO_4$. Recrystallization (ethyl acetate/hexane) provided the amide as an off-white solid (2.65 g, 71%).

Part C: To a solution of the amide of part B (965 mg, 2.41 mmol) in dichloromethane (5 mL) was added trifluoroacetic acid (5 mL) and the solution was stirred for 15 minutes. The solution was concentrated in vacuo and the resulting oil was dissolved into N,N-dimethylacetamide (10 mL). To this solution were added ethyl-4-[(4-fluorophenylsulfonyl)]-1-(2-methoxyethyl)-4-piperidinecarboxylate (600 mg, 1.61 mmol) and cesium carbonate (2.75 g, 8.43 mmol), and the solution was heated at one hundred and ten degrees Celsius for 20 hours. The solution was partitioned between ethyl acetate and $H_2O$. The organic layer was washed with $H_2O$ and saturated NaCl and dried over $Na_2SO_4$. Concentration in vacuo provided the piperidine compound as a white solid (1.26 g, quantitative yield). MS(CI) $MH^+$ calculated for $C_{35}H_{50}N_4O_6S$: 655, found 655.

Part D: To a solution of the piperidine compound of part C (1.26 g) in ethanol (5 mL) and tetrahydrofuran (5 mL) was added sodium hydroxide (644 mg, 16 mmol) in $H_2O$ (5 mL). The solution was heated to sixty degrees Celsius for 8 hours and at sixty-two degrees Celsius for 8 hours. The solution was concentrated in vacuo and the residue was diluted with $H_2O$ and acidified to pH=3 with 3M HCl. The resulting precipitate was collected by vacuum filtration to provide the acid as a white solid (650 mg, 65%). MS (CI) $MH^+$ calculated for $C_{33}H_{46}N_4O_6S$: 627, found 627.

Part E: To a solution of the acid of part D (620 g, 0.94 mmol) in N,N-dimethylformamide (10 mL) were added N-hydroxybenzotriazole (152 mg, 1.13 mmol), 4-methylmorpholine (0.52 mL, 4.7 mmol) and O-(tetrahydro-2H-pyran-2-yl) hydroxylamine (165 mg, 1.4 mmol). After stirring for 45 minutes, 1-[3-(dimethylamino) propyl-3-ethylcarbodiimide hydrochloride (252 mg, 1.32 mmol) was added and the solution was stirred for 18 hours at ambient temperature. The solution was partitioned between ethyl acetate and $H_2O$, and the organic layer was washed with $H_2O$ and saturated NaCl, and dried over $Na_2SO_4$. Concentration in vacuo provided the protected hydroxamate as a white solid (641 mg, 94%). MS(CI) $MH^+$ calculated for $C_{38}H_{55}N_5O_7S$: 726, found 726.

Part F: To a solution of the protected hydroxamate of part E (630 mg, 0.87 mmol) in methanol (8 mL) was added 4M HCl in 1,4-dioxane (10 mL) and the solution was stirred for one hour. The resulting solid was collected by vacuum filtration and washed with ethyl ether to provide the title compound as a white solid (624 mg, 83%). MS (CI) $MH^+$ calculated for $C_{33}H_{47}N_5O_6S$: 642, found 642.

EXAMPLE 414

Preparation of N-hydroxy-4-[[4-[4-(1-methylethyl) phenoxy]phenyl]sulfonyl]-1-(2-propynyl)-4-piperidinecarboxamide, Monohdyrochloride

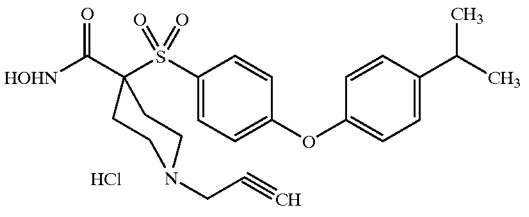

Part A: To a solution of the product of Example 9, Part E (6.0 g, 15.4 mmol) and powdered $K_2CO_3$ (8.0 g, 38.5 mmol) in N,N-dimethylformamide (70 mL) was added 4-isopropyl phenol (5.24 g, 38.5 mmol) at ambient temperature, and the solution was heated to ninety degrees Celsius for 32 hours. The solution was concentrated under high vacuum and the residue was dissolved in ethyl acetate. The organic layer was washed with 1N NaOH, $H_2O$ and dried over $MgSO_4$. Chromatography on silica eluting with ethyl acetate/hexane provided the diaryl ether as light yellow gel (6.89 g, 87%).

Part B: To a solution of diaryl ether of part A (6.89 g, 14.7 mmol) in ethanol (14 mL) and tetrahydrofuran (14 mL) was added NaOH (5.88 g, 147 mmol) in $H_2O$ (28 mL) from an addition funnel at ambient temperature. The solution was then heated to sixty degrees Celsius for 17 hours and ambient temperature for 24 hours. The solution was concentrated in vacuo and diluted with water. The aqueous layer was extracted with ether and acidified to pH=2. Vacuum filtration of white precipitation provided the acid as a white solid (6.56 g, quantitative yield).

Part C: To the solution of acid of part B (6.56 g, 14.86 mmol), N-methyl morpholine (6.5 mL, 59.4 mmol), 1-hydroxybenzotriazole (6.0 g, 44.6 mmol) and O-tetrahydropyranyl hydroxyl amine (3.5 g, 29.7 mmol) in N,N-dimethylformamide (50 mL) was added 1-[3-(dimethylamino)propyl]-3-ethylcarbodiimide hydrochloride (8.5 g, 44.6 mmol), and the solution was stirred at ambient temperature for 20 hours. The solution was concentrated under high vacuum and the residue was dissolved in ethyl acetate. The organic layer was washed with saturated aqueous $NaHCO_3$, $H_2O$ and dried over $MgSO_4$. Concentration in vacuo and chromatography on silica eluting with ethyl acetate/hexane provided the tetrahydropyranyl-protected hydroxamate as a white foam (8.03 g, quantitative yield).

Part D: To a solution of 4N HCl in dioxane (37 mL, 149 mmol) was added a solution of the tetrahydropyranyl-protected hydroxamate of part C (8.03 g, 14.9 mmol) in methanol (5 mL) and dioxane (15 mL) and the solution was stirred at ambient temperature for 3 hours. Concentration in vacuo and trituration with diethyl ether provided the title compound as a white solid (5.0 g, 71.1%). Analytical calculation for $C_{24}H_{28}N_2O_5S.HCl.0.9H_2O$: C, 56.61; H, 6.10; N, 5.50; S, 6.30. Found: C, 56.97; H, 6.05; N, 5.41; S, 5.98. HRMS $MH^+$ calculated for $C_{24}H_{28}N_2O_5S$: 457.1797, found 457.1816.

EXAMPLE 415

Preparation of 4-[[4-(1,3-benzodioxol-5-yloxy) phenyl)sulfonyl]-N-hydroxy-1-(2-methoxyethyl)-4-piperidinecarboxamide, Monohydrochloride

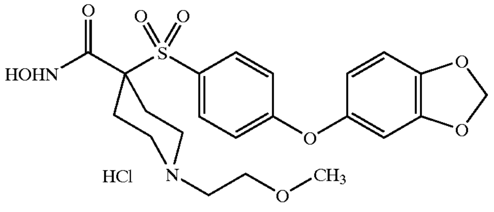

Part A: To a solution of the product of Example 9, Part D (25 g, 67.3 mmol) and powdered $K_2CO_3$ (23.3 g, 169 mmol) in N,N-dimethylformamide (150 mL) was added sesamol (23.2 g, 168 mmol) at ambient temperature and solution was heated to ninety degrees Celsius for 25 hours. The solution was concentrated under high vacuum and the residue was dissolved in ethyl acetate. The organic layer was washed with 1N NaOH, $H_2O$ and dried over $MgSO_4$. Chromatography on silica eluting with ethyl acetate/hexane provided the desired diaryl ether as light yellow gel (33.6 g, 93.6%).

Part B: To a solution of diaryl ether of part A (4.0 g, 7.4 mmol) in dichloromethane (7 mL) cooled to zero degrees Celsius was added trifluroacetic acid (7 mL) and the solution was stirred at ambient temperature for 2 hours. Concentration in vacuo provided the amine trifluoroacetate salt as a light yellow gel. To the solution of the trifluoroacetate salt and $K_2CO_3$ (3.6 g, 26 mmol) in N,N-dimethylformamide (50 mL) was added 2-bromoethyl methyl ether (1.8 mL, 18.7 mmol) and the solution was stirred at ambient temperature for 36 hours. The N,N-dimethylformamide was evaporated under high vacuum and residue was diluted with ethyl acetate.

The organic layer was washed with water and dried over $Mg_2SO_4$. Concentration in vacuo provided the methoxyethyl amine as a light yellow gel (3.7 g, quantitative yield).

Part C: To a solution of methoxyethyl amine of part B (3.7 g, 7.5 mmol) in ethanol (7 mL) and tetrahydrofuran (7 mL) was added NaOH (3.0 g, 75 mmol) in $H_2O$ (15 mL) from an addition funnel at ambient temperature. The solution was then heated to sixty degrees Celsius for 19 hours and ambient temperature for 12 hours. The solution was concentrated in vacuo and diluted with water. The aqueous layer was extracted with ether and acidified to pH=2. Vacuum filtration of the white precipitate provided the acid as a white solid (4.0 g, quantitative yield).

Part D: To a solution of the acid of part C (4.0 g, 7.5 mmol), N-methyl morpholine (3.3 mL, 30 mmol), 1-hydroxybenzotriazole (3.0 g, 22.5 mmol) and O-tetrahydropyranyl hydroxyl amine (1.8 g, 15 mmol) in N,N-dimethylformamide (100 mL) was added 1-[3-(dimethylamino)propyl]-3-ethylcarbodiimide hydrochloride (4.3 g, 22.5 mmol), and the solution was stirred at ambient temperature for 4 days. The solution was concentrated under high vacuum and the residue was dissolved in ethyl acetate. The organic layer was washed with saturated aqueous $NaHCO_3$, $H_2O$ and dried over $Mg_2SO_4$. Concentration in vacuo and chromatography on silica eluting with ethyl acetate/hexane provided the tetrahydropyranyl-protected hydroxamate as a white foam (2.40 g, 57.1%).

Part E: To a solution of 4N HCl in dioxane (11 mL, 43 mmol) was added a solution of the tetrahydropyranyl-protected hydroxamate of part D (2.4 g, 4.3 mmol) in methanol (2 mL) and dioxane (6 mL) and the solution was stirred at ambient temperature for 3 hours. Concentration in vacuo and trituration with ether provided hydroxamate hydrochloride salt as a white solid (1.88 g, 85.8%). Analytical calculation for $C_{22}H_{26}N_2O_8S.HCl.H_2O$: C, 49.58; H, 5.48; N, 5.26; S, 6.02. Found: C, 49.59; H, 5.53; N, 5.06; S, 5.71. HRMS $MH^+$ calculated for $C_{22}H_{26}N_2O_8S$: 479.1488, found 479.1497.

EXAMPLE 416

Preparation of N-hydroxy-1-(2-methoxyethyl)-4-[[4-[4-(trifluoro-methoxy)phenoxy]phenyl]sulfonyl}-4-piperidinecarboxamide, Monohydrochloride

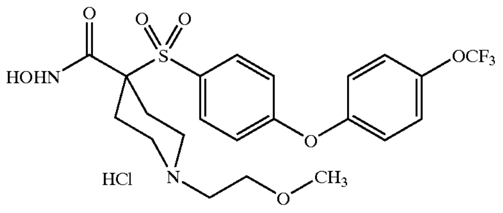

Part A: To a solution of the product of Example 9, Part D (30 g, 161 mmol) in dichloromethane (50 mL) cooled to zero degrees Celsius was added trifluroacetic acid (25 mL) and the solution was stirred at ambient temperature for 1 hour. Concentration in vacuo provided the amine trifluoroacetate salt as a light yellow gel. To the solution of the trifluoroacetate salt and $K_2CO_3$ (3.6 g, 26 mmol) in N,N-dimethylformamide (50 mL) cooled to zero degrees Celsius was added 2-bromoethyl methyl ether (19 mL, 201 mmol), and solution was stirred at ambient temperature for 36 hours. Then, N,N-dimethylformamide was evaporated under high vacuum and the residue was diluted with ethyl acetate. The organic layer was washed with water and dried over $MgSO_4$. Concentration in vacuo provided the methoxyethyl amine as a light yellow gel (26.03 g, 86.8%).

Part B: To a solution of methoxyethyl amine (6.0 g, 16.0 mmol) of part A and powdered $K_2CO_3$ (4.44 g, 32 mmol) in N,N-dimethylformamide (30 mL) was added 4-(trifluoromethoxy)phenol (5.72 g, 32 mmol) at ambient temperature and the solution was heated to ninety degrees Celsius for 25 hours. The solution was concentrated under high vacuum and the residue was dissolved in ethyl acetate. The organic layer was washed with 1N NaOH, $H_2O$ and dried over $MgSO_4$. Chromatography on silica eluting with ethyl acetate/hexane provided trifluoromethoxy phenoxyphenyl sulfone as a light yellow gel (7.81 g, 91.5%).

Part C: To a solution of trifluoromethoxy phenoxyphenyl sulfone of part B (7.81 g, 14.7 mmol) in ethanol (14 mL) and tetrahydrofuran (14 mL) was added NaOH (5.88 g, 147 mmol) in $H_2O$ (28 mL) from an addition funnel at ambient temperature. The solution was then heated to sixty degrees Celsius for 18 hours. The solution was concentrated in vacuo and diluted with water. The aqueous layer was extracted with ether and acidified to pH=2. Vacuum filtration of white precipitation provided the acid as a white solid (5.64 g, 73.3%).

Part D: To a solution of the acid of part C (5.64 g, 10.8 mmol), N-methyl morpholine (4.8 mL, 43.1 mmol), 1-hydroxybenzotriazole (4.38 g, 32.4 mmol) and O-tetrahydropyranyl hydroxyl amine (2.5 g, 21.6 mmol) in N,N-dimethylformamide (50 mL) was added 1-[3-(dimethylamino)propyl]-3-ethylcarbodiimide hydrochloride (6.2 g, 32.4 mmol), and the solution was stirred at ambient temperature for 24 hours. The solution was concentrated under high vacuum and the residue was dissolved in ethyl acetate. The organic layer was washed with saturated aqueous $NaHCO_3$, $H_2O$ and dried over $MgSO_4$. Concentration in vacuo and chromatography on silica eluting with ethyl acetate/hexane provided the tetrahydropyranyl-protected hydroxamate as a white foam (6.65 g, quantitative yield).

Part E: To a solution of 4N HCl in dioxane (28 mL, 110 mmol) was added a solution of the tetrahydropyranyl-protected hydroxamate of part D (6.65 g, 11.03 mmol) in methanol (3 mL) and dioxane (9 mL) and was stirred at ambient temperature for 3 hours. Concentration in vacuo and trituration with diethyl ether provided the title compound as a white solid (4.79 g, 78.2%). Analytical calculation for $C_{22}H_{25}N_2O_7SF_3.HCl.0.5H_2O$: C, 46.85; H, 4.83; N, 4.97; S, 5.69. Found: C, 46.73; H, 4.57; N, 4.82; S, 5.77.

EXAMPLE 417

Preparation of N-hydroxy-1-(2-methoxyethyl)-4-[[4-[4-(1-methylethyl)-phenoxy]phenyl]sulfonyl]-4-piperidinecarboxamide, Monohydrochloride

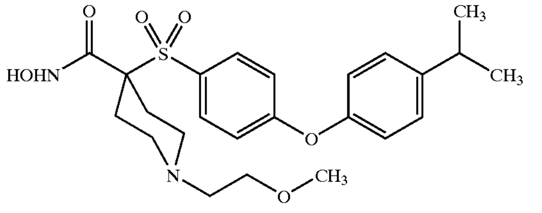

Part A: To a solution of ethyl-4-[(4-fluorophenylsulfonyl)]-1-(2-methoxyethyl)-4-piperidinecarboxylate (1.47 g, 3.9 mmol) and powdered $K_2CO_3$ (1.6 g, 11.7 mmol) in N,N-dimethylformamide (15 mL) was added 4-isopropylphenol (1.07 g, 7.8 mmol) at ambient temperature and the solution was heated to ninety degrees Celsius for 24 hours. The solution was concentrated under high vacuum and the residue was dissolved in ethyl acetate. The organic layer was washed with 1N NaOH, $H_2O$ and dried over $MgSO_4$. Chromatography on silica eluting with ethyl acetate/hexane provided the diaryl ether as a light yellow gel (1.77 g, 92.2%).

Part B: To a solution of diaryl ether of part A (1.77 g, 3.6 mmol) in ethanol (3.5 mL) and tetrahydrofuran (3.5 mL) was added NaOH (1.46 g, 36 mmol) in $H_2O$ (7 mL) at ambient temperature. The solution was then heated to sixty degrees Celsius for 18 hours. The solution was concentrated in vacuo and diluted with water. The aqueous layer was extracted with diethyl ether and acidified to pH=2. Vacuum filtration of the white precipitate provided the acid as a white solid (1.39 g, 83.7%).

Part C: To the solution of the acid of part B (1.39 g, 3.0 mmol), N-methyl morpholine (1 mL, 9 mmol), 1-hydroxybenzotriazole (1.22 g, 9 mmol) and O-tetrahydropyranyl hydroxyl amine (0.72 g, 6.0 mmol) in N,N-dimethylformamide (90 mL) was added 1-[3-(dimethylamino)propyl]-3-ethylcarbodiimide hydrochloride (1.72 g, 9.0 mmol), and solution was stirred at ambient temperature for 48 hours. The solution was concentrated under high vacuum and the residue was dissolved in ethyl acetate. The organic layer was washed with saturated aqueous $NaHCO_3$, $H_2O$ and dried over $MgSO_4$. Concentration in vacuo and chromatography on silica eluting with ethyl acetate/hexane provided the tetrahydropyranyl-protected hydroxamate as a white foam (1.65 g, 98.2%).

Part D: To a solution of 4N HCl in dioxane (7.35 mL, 29.4 mmol) was added a solution of the tetrahydropyranyl-protected hydroxamate of part C (1.65 g, 2.94 mmol) in methanol (1 mL) and dioxane (3 mL), and the solution was stirred at ambient temperature for 3 hours. Concentration in vacuo and trituration with diethyl ether provided the title compound as a white solid (1.2 g, 79.5%). Analytical calculation for $C_{24}H_{32}N_2O_6S.HCl.0.5H_2O$: C, 55.22; H, 6.56; N, 5.37; S, 6.14. Found: C, 55.21; H, 6.41; N, 5.32; S, 6.18.

EXAMPLE 418

Preparation of N-hydroxy-1-(2-methoxyethyl)-4-[[4-[4-(trifluoromethyl)-phenoxy]phenyl]sulfonyl}-4-4-piperidinecarboxamide, Monohydrochloride

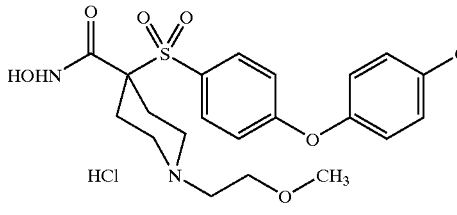

Part A: To a solution of ethyl-4-((4-fluorophenylsulfonyl)]-1-(2-methoxyethyl)-4-piperidinecarboxylate (6 g, 16.0 mmol) and powdered $K_2CO_3$ (4.44 g, 32 mmol) in N,N-dimethylformamide (50 mL) was added 4-trifluoromethylphenol (5.72 g, 32 mmol) at ambient temperature, and the solution was heated to ninety degrees Celsius for 48 hours. The solution was concentrated under high vacuum and the residue was dissolved in ethyl acetate. The organic layer was washed with 1N NaOH, $H_2O$ and dried over $MgSO_4$. Chromatography on silica eluting with ethyl acetate/hexane provided the desired diaryl ether as a light yellow gel (2.66 g, 32.1%).

Part B: To a solution of the diaryl ether of part A (1.5 g, 2.9 mmol) in ethanol (3 mL) and tetrahydrofuran (3 mL) was added NaOH (1.22 g, 29 mmol) in $H_2O$ (6 mL) at ambient temperature. The solution was then heated to sixty degrees Celsius for 18 hours. The solution was concentrated in vacuo and diluted with water. The aqueous layer was extracted with diethyl ether and acidified to pH=2. Vacuum filtration of the white precipitate provided the desired acid as a white solid (1.0 g, 70.9%).

Part C: To the solution of the acid of part B (1.0 g, 2.05 mmol), N-methyl morpholine (0.68 mL, 6.1 mmol), 1-hydroxybenzotriazole (0.84 g, 6.15 mmol) and O-tetrahydropyranyl hydroxyl amine (0.5 g, 4.1 mmol) in N,N-dimethylformamide (20 mL) was added 1-[3-(dimethylamino)propyl]-3-ethylcarbodiimide hydrochloride (1.18 g, 6 mmol), and solution was stirred at ambient temperature for 24 hours. The solution was concentrated under high vacuum and the residue was dissolved in ethyl acetate. The organic layer was washed with saturated $NaHCO_3$, $H_2O$ and dried over $MgSO_4$. Concentration in vacuo and chromatography on silica eluting with ethyl acetate/hexane provided the tetrahydropyranyl-protected hydroxamate as a white foam (1.16 g, 96.7%).

Part D: To a solution of 4N HCl in dioxane (5 mL, 20 mmol)) was added a solution of the tetrahydropyranyl-protected hydroxamate of part C (1.16 g, 2 mmol) in methanol (1 mL) and dioxane (3 mL) and was stirred at ambient temperature for 3 hours. Concentration in vacuo and trituration with diethyl ether provided the title compound as a white solid (0.79 g, 74.5%). Analytical calculation for $C_{22}H_{25}N_2O_6SF_3.HCl$: C, 49.03; H, 4.86; N, 5.20; S, 5.95. Found: C, 48.85; H, 4.60; N, 5.22; S, 6.13.

EXAMPLE 419

Preparation of N-hydroxy-1-(2-methoxyethyl)-4-[[4-[4-[(trifluoro-methyl)thio]phenoxy]phenyl]sulfonyl]-4-piperidinecarboxamide, Monohydrochloride

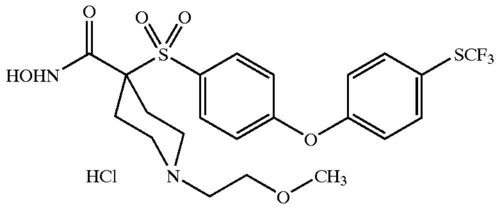

Part A: To a solution of ethyl-4-[(4-fluorophenylsulfonyl)]-1-(2-methoxyethyl)-4-piperidinecarboxylate (5 g, 13.4 mmol) and powdered $K_2CO_3$ (3.7 g, 27 mmol) in N,N-dimethylformamide (20 mL) was added 4-(trifluoromethylthio)phenol (3.9 g, 20 mmol) at ambient temperature, and solution was heated to ninety degrees Celsius for 24 hours. The solution was concentrated under high vacuum, and the residue was dissolved in ethyl acetate. The organic layer was washed with 1N NaOH, $H_2O$ and dried over $MgSO_4$. Chromatography on silica eluting with ethyl acetate/hexane provided the desired diaryl ether as a light yellow gel (5.94 g, 81.04%).

Part B: To a solution of the diaryl ether of part A (5.94 g, 210 mmol) in ethanol (10 mL) and tetrahydrofuran (10 mL) was added NaOH (4.34 g, 108 mmol) in $H_2O$ (20 mL) dropwise at ambient temperature. The solution was then heated to sixty degrees Celsius for 24 hours and ambient temperature for anther 24 hours. The solution was concentrated in vacuo and diluted with water. The aqueous layer was extracted with diethyl ether and acidified to pH=2. Vacuum filtration of the white precipitate provided the acid as a white solid (5.5 g, quantitative yield).

Part C: To the solution of the acid of part B (5.5 g, 10.8 mmol), N-methyl morpholine (3.6 mL, 32.4 mmol), 1-hydroxybenzotriazole (4.4 g, 32.4 mmol) and O-tetrahydropyranyl hydroxyl amine (2.6 g, 21.8 mmol) in N,N-dimethylformamide (200 mL) was added 1-[3-(dimethylamino)propyl]-3-ethylcarbodiimide hydrochloride (6.2 g, 32.4 mmol), and the solution was stirred at ambient temperature for 24 hours. The solution was concentrated under high vacuum and the residue was dissolved in ethyl acetate. The organic layer was washed with saturated aqueous $NaHCO_3$, $H_2O$ and dried over $MgSO_4$. Concentration in vacuo and chromatography on silica eluting with ethyl acetate/hexane provided the tetrahydropyranyl-protected hydroxamate as a white foam (4.66 g, 69.8%).

Part D: To a solution of 4N HCl in dioxane (20 mL, 79 mmol)) was added a solution of the tetrahydropyranyl-protected hydroxamate of part C (4.65 g, 7.9 mmol) in methanol (2.5 mL) and dioxane (8 mL) and was stirred at ambient temperature for 3 hours. Concentration in vacuo and trituration with diethyl ether provided the title compound as a white solid (3.95 g, 92.1%). Analytical calculation for $C_{22}H_{25}N_2O_6S_2F_3$.HCl: C, 46.27; H, 4.59; N, 4.91; S, 11.23. Found: C, 46.02; H, 4.68; N, 4.57; S, 11.11.

EXAMPLE 420

Preparation of N-hydroxy-1-(1-methylethyl)-4-[[4-[4-(1-methylethyl)-phenoxy]phenyl]sulfonyl]-4-piperidinecarboxamide, Monohydrochloride

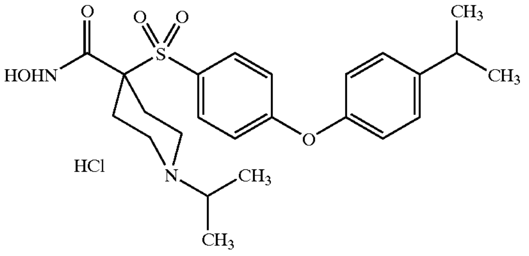

Part A: To a solution of the product of Example 9, Part D (30 g, 161 mmol) in dichloromethane (40 mL) cooled to zero degrees Celsius was added trifluroacetic acid (30 m), and the solution was stirred at ambient temperature for 1 hour. Concentration in vacuo provided the trifluoroacetate salt as a light yellow gel. To the solution of the trifluoroacetate salt and triethylamine (28 mL, 201 mmol) in dichloromethane (250 mL) cooled to zero degrees Celsius, were added acetone (24 mL, 320 mmol) and sodium triacetoxyborohydride (68 g, 201 mmol) in small portions followed by addition of acetic acid (18.5 mL, 320 mmol), and solution was stirred at ambient temperature for 48 hours. Then, the dichloromethane was evaporated under high vacuum and the residue was diluted with diethyl ether. The organic layer was washed with 1N NaOH, water and dried over $MgSO_4$. Concentration in vacuo provided the isopropyl amine as a light yellow gel (21.03 g, 72.8%).

Part B: To a solution of isopropyl amine (4 g, 11.2 mmol) of part A and powdered $K_2CO_3$ (3.09 g, 22.4 mmol) in N,N-dimethylformamide (30 mL) was added 4-isopropylphenol (3.05 g, 22 mmol) at ambient temperature and the solution was heated to ninety degrees Celsius for 25 hours. The solution was concentrated under high vacuum and the residue was dissolved in ethyl acetate. The organic layer was washed with 1N NaOH, $H_2O$ and dried over $MgSO_4$. Chromatography on silica eluting with ethyl acetate/hexane provided the desired diaryl ether as a light yellow gel (5.10 g, 96.2%).

Part C: To a solution of the diaryl ether of part B (5.10 g, 10.77 mmol) in ethanol (10 mL) and tetrahydrofuran (10 mL) was added NaOH (4.3 g, 108 mmol) in $H_2O$ (20 mL) from an addition funnel at ambient temperature. The solution was then heated to sixty degrees Celsius for 24 hours and at ambient temperature for anther 24 hours. The solution was concentrated in vacuo and diluted with water. The aqueous layer was extracted with diethyl ether and acidified to pH=2. Vacuum filtration of the white precipitate provided the desired acid as a white solid (4.80 g, quantitative yield).

Part D: To the solution of the acid of part C (4.80 g, 10.8 mmol), N-methyl morpholine (3.6 mL, 32.4 mmol), 1-hydroxybenzotriazole (4.4 g, 32.4 mmol) and O-tetrahydropyranyl hydroxyl amine (2.6 g, 21.6 mmol) in N,N-dimethylformamide (100 mL) was added 1-[3-(dimethylamino)propyl]-3-ethylcarbodiimide hydrochloride (6.17 g, 32.4 mmol), and the solution was stirred at ambient temperature for 7 days. The solution was filtered to eliminate the unreacted starting material and the filtrate was concentrated under high vacuum. The residue was dissolved in ethyl acetate and the organic layer was washed with saturated aqueous $NaHCO_3$, $H_2O$ and dried over $MgSO_4$. Concentration in vacuo and chromatography on silica eluting with ethyl acetate/hexane provided the tetrahydropyranyl-protected hydroxamate as a white foam (2.45 g, 41.7%).

Part E: To a solution of 4N HCl in dioxane (11.2 mL, 45 mmol) was added a solution of the tetrahydropyranyl-protected hydroxamate of part D (2.45 g, 11.03 mmol) in methanol (4 mL) and dioxane (8 mL) and was stirred at ambient temperature for 3 hours. Concentration in vacuo and trituration with diethyl ether provided the title compound as a white solid (2.01 g, 89.7%). Analytical calculation for $C_{24}H_{32}N_2O_5S$.HCl.0.5$H_2O$: C, 56.96; H, 6.77; N, 5.54; S, 6.34. Found: C, 56.58; H, 6.71; N, 5.44; S, 6.25.

EXAMPLE 421

Preparation of 4-[[4-(1,3-benzodioxol-5-yloxy)phenyl]sulfonyl]-1-cyclopropyl-N-hydroxy-4-piperidinecarboxamide, Monohydrochloride

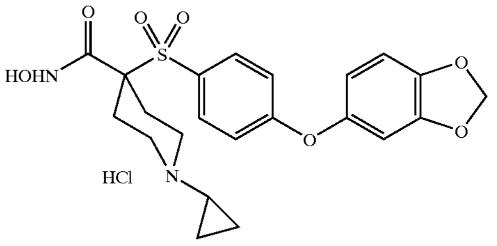

Part A To a solution of the product of Example 9, Part D (9.0 g, 22.0 mmol) in DMF (30 mL) was added $K_2CO_3$ (4.55 g, 33 mmol), and sesamol (4.55 g, 33 mmol). The solution was stirred at ninety degrees Celsius for 24 hours. The solution was diluted with $H_2O$ (400 mL) and extracted with ethyl acetate. The organic layer was washed with saturated NaCl and dried over $MgSO_4$, filtered and concentrated in vacuo. Chromatography on silica gel eluting with 10% ethyl acetate/hexane provided the desired ester as an oil (9.3 g, 79%). HRMS $MH^+$ calculated for $C_{26}H_{31}NSO_9$: 534.1798, found 534.1796.

Part B: To a solution of the ester of part A (9.3 g, 17 mmol) in ethyl acetate (100 mL) cooled to zero degrees C. was bubbled gaseous HCl for 10 minutes. The reaction was stirred at this temperature for 0.5 hours. The solution was concentrated in vacuo to give the hydrochloride salt (7.34 g, 92%). MS $MH^+$ calculated for $C_{21}H_{23}NSO_7$: 434.1273, found 434.1285.

Part C: To a solution of the hydrochloride salt of part B (7.34 g, 15.6 mmol) in methanol (60 mL) was added acetic acid (8.94 mL, 156 mmol), a portion (about 2 g) of 4-Å molecular sieves, (1-ethoxycyclopropyl)-oxytrimethyl silane (18.82 mL, 93.6 mmol) and sodium cyanoborohydride (4.41 g, 70.2 mmol). The solution was refluxed for 8 hours. The precipitate was removed by filtration and the filtrate concentrated in vacuo. The residue was diluted with $H_2O$ (400 mL) and extracted with ethyl acetate. The organic layer was washed with saturated NaCl and dried over $MgSO_4$, filtered and concentrated in vacuo. Chromatography on silica gel eluting with 100% ethyl acetate) provided the desired cyclopropyl amine as a solid (7.9 gm, 100%). MS $MH^+$ calculated for $C_{24}H_{27}NSO_7$: 474.1586, found 474.1599.

Part D: To a solution of cyclopropyl amine from part C (7.9 g, 16.7 mmol) in ethanol (50 mL) and tetrahydrofuran (50 mL) was added a solution of NaOH (6.68 g, 166.8 mmol) in water (30 mL) and the solution was heated at sixty degrees Celsius for 18 hours. The solution was concentrated in vacuo and the aqueous residue was acidified to pH=3. The resulting precipitate was filtered to give desired carboxylic acid (6.14 g, 76%). MS $MH^+$ calculated for $C_{22}H_{25}NSO_7$: 446.1273. Found 446.1331.

Part E: To a solution of the carboxylic acid of part D (6.14 g, 12.7 mmol) in DMF (60 mL) was added 1-hydroxybenzotriazole (2.06 g, 15.2 mmol), N-methyl morpholine (4.2 mL, 38.0 mmol) and O-tetrahydropyranyl hydroxyl amine (2.23 g, 19.0 mmol) followed by 1,3-(dimethylamino)propyl]-3-ethylcarbodiimide hydrochloride (3.41 g, 17.8 mmol). The solution was stirred at ambient temperature for 18 hours. The solution was diluted with $H_2O$ (400 mL) and extracted with ethyl acetate. The organic layer was washed with saturated NaCl and dried over $MgSO_4$, filtered and concentrated in vacuo. Chromatography on silica gel eluting with 40% ethyl acetate/hexane provided the desired tetrahydropyranyl-protected hydroxamate as a solid (6.67 g, 96%).

Part F: To a solution of tetrahydropyranyl-protected hydroxamate of part E (6.67 g, 12.0 mmol) in dioxane (70 mL) was added 4 N HCl/dioxane (6.6 mL). After stirring at ambient temperature for 3 hours, the solution was concentrated in vacuo. Chromatography on a C18 reverse phase column, eluting with acetonitrile/(HCl)water, provided a white solid (4.21 gm, 69%). MS $MH^+$ calculated for $C_{22}H_{24}N_2SO_7$: 461.1382. Found 461.1386.

EXAMPLE 422

Preparation of 1-cyclopropyl-4-[[4-(4-ethoxyphenoxy)phenyl]sulfonyl]-N-hydroxy-4-piperidinecarboxamide, Monohydrochloride

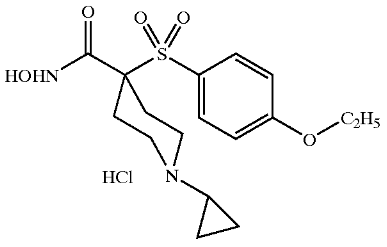

Part A: To a solution of the product of Example 9, Part D (8.0 g, 19.2 mmol) in DMF (30 mL) was added $K_2CO_3$ (4.00 g, 28.8 mmol) and 4-ethoxyphenol (3.99 g, 28.8 mmol). The solution was stirred at ninety degrees Celsius for 24 hours. The solution was diluted with $H_2O$ (400 mL) and extracted with ethyl acetate. The organic layer was washed with saturated NaCl and dried over $MgSO_4$, filtered and concentrated in vacuo. Chromatography on silica gel eluting with 10% ethyl acetate/hexane provided the desired ester as an oil (9.62 g, 94%). MS $MH^+$ calculated for $C_{27}H_{35}NSO_8$: 534.2162. Found 534.2175.

Part P: To a solution of ester of part A (9.62 g, 18 mmo) in ethyl acetate (100 mL) cooled to zero degrees Celcius was bubbled gaseous HCl for 5 minutes. The reaction was stirred at this temperature for 0.5 hours. The solution was then concentrated in vacuo to give a the hydrochloride salt (8.1 g, 96%). MS $MH^+$ calculated for $C_{22}H_{27}NSO_6$: 434.1637. Found 434.1637.

Part C: To a solution of the hydrochloride salt of part B (8.1 g, 17.2 mmol) in methanol (70 mL) was added acetic acid (9.86 mL, 172 mmol), a portion of 4-Å molecular sieves (ca. 2 g), (1-ethoxycyclopropyl)-oxytrimethyl silane (20.7 mL, 103 mmol) and sodium cyanoborohydride (4.86 g, 77.4 mmol). The solution was refluxed for 8 hours. The precipitate was removed by filtration and the filtrate was concentrated in vacuo. The residue was diluted with $H_2O$ (400 mL) and extracted with ethyl acetate. The organic layer was washed with 1 N NaOH, saturated NaCl and dried over $MgSO_4$, filtered and concentrated in vacuo. Trituration with diethyl ether provided the desired cyclopropyl amine as a white solid (6.84 g, 84%).

Part D: To a solution of cyclopropyl amine from part C (6.84 gm, 14.0 mmol) in ethanol (50 mL) and tetrahydrofuran (50 mL) was added a solution of NaOH (5.60 g, 140 mmol) in water (30 mL) and the solution was heated at sixty degrees Celsius for 18 hours. The solution was concentrated in vacuo and the aqueous residue was acidified to pH=3. Filtration gave the desired acid (6.07 g, 88%). MS $MH^+$ calculated for $C_{22}H_{27}NSO_6$: 446. Found 446.

Part E: To a solution of the acid of part D (6.07 g, 12.6 mmol) in DMF (60 mL) was added 1-hydroxybenzotriazole (2.04 g, 15.1 mmol), N-methyl morpholine (4.15 mL, 37.8 mmol) and O-tetrahydropyranyl hydroxyl amine (2.21 g, 18.9 mmol) followed by 1,3-(dimethylamino)propyl]-3-ethylcarbodiimide hydrochloride (3.38 g, 17.6 mmol). The solution was stirred at ambient temperature for 18 hours. The solution was diluted with $H_2O$ (400 mL) and extracted with ethyl acetate. The organic layer was washed with saturated NaCl and dried over $MgSO_4$, filtered and concentrated in vacuo. Chromatography on silica gel eluting with 60% ethyl acetate/hexane provided the desired tetrahydropyranyl-protected hydroxamate as a white foam (6.29 g, 92%). MS $MH^+$ calculated for $C_{28}H_{36}N_2SO_7$: 545.2321. Found 545.2316.

Part F: To a solution of the tetrahydropyranyl-protected hydroxamate of part E (2.84 g, 5.0 mmol) in dioxane (40 mL) was added 4 N HCl/dioxane (30 mL). After stirring at ambient temperature for 2.5 hours, the solution was concentrated in vacuo. Trituration of the resulting solid with diethyl ether and filtration gave the desired hydroxamate as a white solid (2.33 g, 90%). MS $M^+$ calculated for $C_{23}H_{28}N_2SO_6$: 460.1677. Found 460.1678.

EXAMPLE 423

Preparation of 4-[[4-(cyclohexylthio)-phenyl]sulfonyl]-N-hydroxy-1-(methylsulfonyl)-4-piperidinecarboxamide

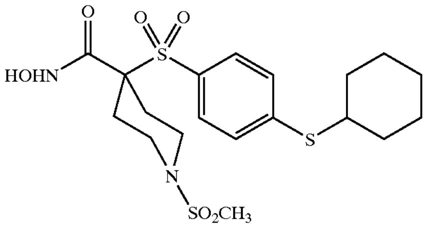

Part A: To a solution of the product of Example 9, Part D (10.0 g, 24.0 mmol) in DMF (20 mL) was added $K_2CO_3$ (4.99 g, 36.0 mmol), cyclohexyl mercaptan (4.40 g, 36.0 mmol). The solution was stirred at ninety degrees Celsius for 48 hrs. The solution was diluted with $H_2O$ (400 mL) and extracted with ethyl acetate. The organic layer was washed with saturated NaCl and dried over $MgSO_4$, filtered and concentrated in vacuo. Trituration with ethanol provided the desired sulfide as a white solid (7.16 g, 58%).

Part B: To a solution of sulfide from part B (9.46 g, 18.5 mmol) in ethanol (30 mL) and tetrahydrofuran (30 mL) was added a solution of NaOH (7.39 g, 185 mmol) in water (15 mL) and the solution was heated at sixty-five degrees Celsius for 18 hours. The solution was concentrated in vacuo and the aqueous residue was acidified to pH=3.5. The resulting white solid was collected by filtration washed with $H_2O$ and ethyl ether to give desired carboxylic acid (8.57 g, 95%).

Part C: To a solution of carboxylic acid of part B (8.3 g, 17.0 mmol) in ethyl acetate (200 mL) cooled to zero degrees Celsius was bubbled gaseous HCl for 15 min. The reaction was then stirred at this temperature for 0.5 hour. The solution was concentrated in vacuo to afford a residue which was triturated with diethyl ether to afford the desired hydrochloride salt as a white solid (7.03 g, 98%). MS MH+ calculated for $C_{18}H_{25}NS_2O_4$: 384.1303. Found 384.1318.

Part D: To a solution of the hydrochloride salt of part C (1.0 g, 2.4 mmol) was added N-methyl morpholine (654 mL, 5.9 mmol) followed by mesyl chloride (280 mL, 3.6 mmol) in methylene chloride (20 mL). The solution was stirred at ambient temperature for 18 hours. The solution was diluted with $H_2O$ (400 mL) and extracted with methylene chloride. The organic layer was washed with water, saturated NaCl and dried over $MgSO_4$, filtered and concentrated in vacuo to yield the desired methanesulfomanide as a foam (1.0 g, quantitative yield)

Part E: To a solution of the methanesulfonamide of part D (1.3 g, 2.9 mmol) in DMF (30 mL) was added 1-hydroxybenzotriazole (474 mg, 3.5 mmol), N-methyl morpholine (956 mL, 8.7 mmol), tetrahydropyranyl hydroxyl amine (509 mg, 4.3 mmol) followed by 1-3-(dimethylamino)propyl]-3-ethylcarbodiimide hydrochloride (778 mg, 4.06 mmol). The solution was stirred at ambient temperature for 18 hours. The solution was diluted with $H_2O$ (400 mL) and extracted with ethyl acetate. The organic layer was washed with saturated NaCl and dried over $MgSO_4$, filtered and concentrated in vacuo. Chromatography on silica gel eluting with 30% ethyl acetate/hexane provided the desired tetrahydropyranyl-protected hydroxamate as a white foam (1.05 g, 82%).

Part F: To a solution of the tetrahydropyranyl-protected hydroxamate of part E (1.05 g, 1.97 mmol) in dioxane (30 mL) was added 4 N HCl/dioxane (10 mL). After stirring at ambient temperature for 2.5 hours, the solution was concentrated in vacuo. Chromatography on C18 reverse phase column eluting with acetonitrile/(HCl) water provided a white solid (602 mg, 64%). MS $M^+$ for $C_{19}H_{28}N_2S_3O_6$: 477, found 477.

EXAMPLE 424

Preparation of N-hydroxy-1-(methylsulfonyl)-4-[[4-(phenylthio)-phenyl]sulfonyl]-4-piperidinecarboxamide

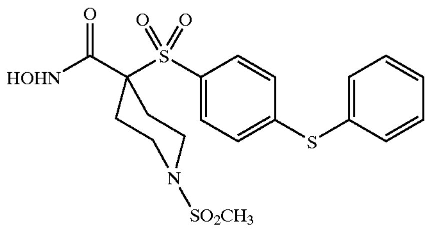

Part A: To a solution of the product of Example 9, Part D (40.0 g, 96.0 mmol) in DMF (200 mL) was added $K_2CO_3$ (20 g, 144 mmol) and thiophenol (22.2 g, 144 mmol). The solution was stirred at ambient temperature for 24 hrs. The solution was then diluted with $H_2O$ (1 L) and extracted with ethyl acetate. The organic layer was washed with water, saturated NaCl and dried over $MgSO_4$, filtered and concentrated in vacuo. Chromatography (on silica, eluting with 15% ethyl acetate/hexane) provided the desired sulfide as a white solid (44.4 g, 91%).

Part B: To a solution of sulfide of part A (31.2 g, 6.6 mmol) in ethyl acetate (500 mL) cooled to zero degrees Celsius was bubbled gaseous HCl for 30 minutes. The reaction was stirred at this temperature for 1.5 hours. The solution was concentrated in vacuo and resulting solid was triturated with diethyl ether to provide the hydrochloride salt as a white solid (26.95 g, 96%).

Part C: To a solution of the hydrochloride salt of part B (2.0 g, 4.7 mmol), were added N-methyl morpholine (1.29 mL, 11.7 mmol), followed by mesyl chloride (550 mL, 7.05 mmol) in methylene chloride (35 mL). The solution was stirred at ambient temperature for 48 hours. The solution was diluted with $H_2O$ (400 mL) and extracted with methylene chloride. The organic layer was washed with water, saturated NaCl and dried over $MgSO_4$, filtered and concentrated in vacuo to yield the desired methanesulfonamide as a white solid (2.17 gm, 96%).

Part D: To a solution of the methane sulfonamide from part C (2.1 g, 4.3 mmol) in ethanol (25 mL) and tetrahydrofuran (25 mL) was added a solution of NaOH (1.72 g, 43 mmol) in water (10 mL) and the solution was heated at sixty degrees Celsius for 18 hours. The solution was concentrated in vacuo and the aqueous residue was acidified to pH=3.5. The resulting precipitate was filtered to give the desired carboxylic acid as a white solid (2.1 g, quantitative yield).

Part E: To a solution of the carboxylic acid of part D (1.98 g, 4.3 mmol) in DMF (30 mL) were added 1-hydroxybenzotriazole (705 mg, 5.2 mmol), N-methyl morpholine (1.54 mL, 12.9 mmol) and O-tetrahydropyranyl hydroxyl amine hydrochloride (755 mg, 6.5 mmol) followed by 1-3-(dimethylamino)propyl]-3-ethyl carbodiimide hydrochloride (1.17 g, 6.1 mmol). The solution was stirred at ambient temperature for 5 days. The solution was diluted with $H_2O$ (400 mL) and extracted with ethyl acetate. The organic layer was washed with saturated NaCl and dried over $MgSO_4$, filtered and concentrated in vacuo. Chromatography on C18 reverse phase column, eluting with acetonitrile/(HCl) water provided the desired tetrahydropyranyl-protected hydroxamate as a white solid (1.86 g, 80%). HRMS $MH^+$ calculated for $C_{24}H_{30}N_2S_3O_7$: 555.1293, found 555.1276.

Part F: To a solution of tetrahydropyranyl-protected hydroxamate of part E (1.86 g, 3.5 mmol) in dioxane (30 mL) and methanol (10 mL) was added 4 N HCl/dioxane (20 mL). After stirring at ambient temperature for 2.5 hours, the solution was concentrated in vacuo. Chromatography on a C18 reverse phase column eluting with acetonitrile/(HCl) water provided the title compound as a white solid (1.48 gm, 91%). HRMS $MH^+$ calculated for $C_{19}H_{22}N_2S_3O_6$: 471.0718 Found 471.0728.

EXAMPLE 425

Preparation of 1-cyclopropyl-N-hydroxy-4-[[4-[4-(trifluoromethoxy)phenoxy]-phenyl]sulfonyl]-4-piperidine-carboxamide, Monohydrochloride

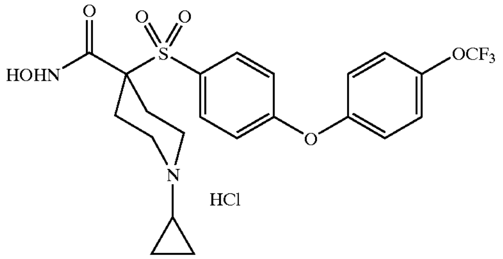

Part A: To a solution of the product of Example 398, Part A (6.97 g, 19.6 mmol) in DMF (500 mL) was added $K_2CO_3$ (3.42 g, 18.0 mmol) and 4-(triflouromethoxy)-phenol (3.7 g, 24.8 mmol). The solution was stirred at ninety degrees Celsius for 40 hours. The solution was diluted with $H_2O$ (600 mL) and extracted with ethyl acetate. The organic layer was washed with water, saturated NaCl and dried over $MgSO_4$, filtered and concentrated in vacuo to afford the desired diaryl ether as an oil (8.5 g, quantitative). HRMS $MH^+$ calculated for $C_{24}H_{26}NSO_6F_3$: 514.1511. Found 514.1524.

Part B: To a solution of diaryl ether from part A (8.4 g, 16.4 mmol) in ethanol (50 mL) and tetrahydrofuran (50 mL) was added a solution of NaOH (6.54 g, 164 mmol) in water (20 mL) and the solution was heated at sixty degrees Celsius for 18 hours. The solution was concentrated in vacuo to remove most of organic solvents and the aqueous residue was acidified to pH=4.0. The resulting precipitate was filtered to give the desired filtered to give the hydrochloride salt as a white solid (5.01 g, 63%). HRMS $MH^+$ calculated for $C_{22}H_{22}NSO_6F_3$: 486.1198, found 486.1200.

Part C: To a solution of the hydrochloride salt of part B (5.0 g, 10.3 mmol) in DMF (80 mL) were added 1-hydroxybenzotriazole (1.65 g, 12.3 mmol), N-methyl morpholine (3.4 mL, 30.9 mmol) and O-tetrahydropyranyl hydroxyl amine hydrochloride (1.8 g, 15.4 mmol) followed by 1-3-(dimethylamino)propyl]-3-ethylcarbodiimide hydrochloride (1.60 g, 12.3 mmol). The solution was stirred at ambient temperature for 42 hours. The solution was diluted with $H_2O$ (400 mL) and extracted with ethyl acetate. The organic layer was washed with saturated NaCl and dried over $MgSO_4$, filtered and concentrated in vacuo. Chromatography on silica gel, eluting with 30% ethyl acetate/hexane provided the desired tetrahydropyranyl-protected hydroxamate as a white solid (5.41 g, 89%).

Part D: To a solution of tetrahydropyranyl-protected hydroxamate of part C (5.4 g, 9.2 mmol) in dioxane (80 mL) and methanol (20 mL) was added 4 N HCl/dioxane (50 mL). The reaction was stirred at ambient temperature for 2.5 hours, the solution was concentrated in vacuo. Trituration with diethyl ether afforded the title compound as a white solid (4.02 g, 81%). HRMS $MH^+$ calculated for $C_{22}H_{23}N_2SO_6F_3$: 501.1307, found 501.1324.

EXAMPLE 426

Preparation of 1-cyclopropyl-4-[(4-ethoxyphenyl) sulfonyl]-N-hydroxy-4-piperidinecarboxamide, Monohydrochloride

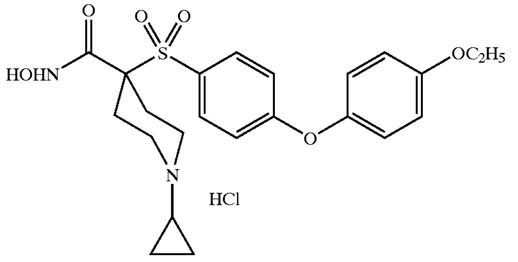

Part A: To a solution of the product of Example 398, Part A (5.87 g, 16.5 mmol) in DMF (50 mL) was added $K_2CO_3$ (3.42 g, 24.7 mmol) and α, α,α-(trifluoromethyl)-p-cresol (4.01 g, 24.7 mmol). The solution was stirred at ninety degrees Celsius for 48 hours. The solution was diluted with $H_2O$ (400 mL) and extracted with ethyl acetate. The organic layer was washed with water, saturated NaCl and dried over $MgSO_4$ filtered and concentrated in vacuo to give the crude product, containing a large percentage of starting material (8.39 g). To this material (8.39 g) in ethanol (50 mL) and tetrahydrofuran (50 mL) was added a solution of NaOH (6.75 g, 169 mmol) in water (20 mL) and the solution was heated at sixty degrees Celsius for 18 hours. The solution was concentrated in vacuo and the aqueous residue was acidified to pH=3.5. The resulting precipitate was filtered to give the desired hydrochloride salt as a waxy solid (5.04 g, 64%).

Part B: To a solution of the hydrochloride salt of part A (5.0 g, 10.3 mmol) in DMF (80 mL) were added 1-hydroxybenzotriazole (1.73 g, 12.8 mmol), N-methyl morpholine (3.5 mL, 31.8 mmol) and O-tetrahydropyranyl hydroxyl amine hydrochloride (1.86 g, 15.9 mmol) followed by 1-3-(dimethylamino)propyl]-3-ethylcarbodiimide hydrochloride (2.84 g, 14.8 mmol). The solution was stirred at ambient temperature for 18 hours. The solution was diluted with $H_2O$ (400 mL) and extracted with ethyl acetate. The organic layer was washed with saturated NaCl and dried over $MgSO_4$, filtered and concentrated in vacuo. Chromatography on silica gel eluting with 30% ethyl acetate/hexane provided the desired tetrahydropyranyl-protected hydroxamate as a white solid (1.5 g, 32%).

Part C: To a solution of tetrahydropyranyl-protected hydroxamate of part D (1.5 g, 3.3 mmol) in dioxane (30 mL) and methanol (15 mL) was added 4 N HCl/dioxane (50 mL). The reaction was stirred at ambient temperature for 2 hours, then the solution was concentrated in vacuo. Trituration of the residue with diethyl ether afforded the title compound as a white solid (1.09 g, 81%). MS $MH^+$ for $C_{17}H_{24}N_2SO_5$: 369 found 369.

EXAMPLE 427

Preparation of 1-cyclopropyl-N-hydroxy-4-[[4-[4-(trifluoromethyl) phenoxy]phenyl]sulfonyl]-4-piperidinecarboxamide, Monohydrochloride

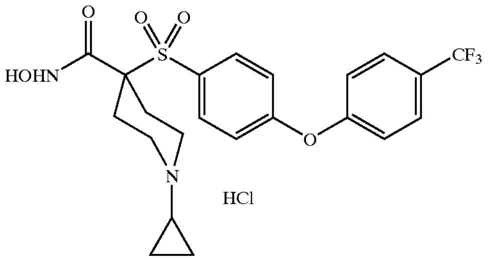

Part A: To a solution of the product of Example 398, Part A (5.96 g, 15.0 mmol) in DMF (100 mL) was added $K_2CO_3$ (12.34 g, 38.0 mmol) and α,α,α-trifluoromethyl phenol (3.65 g, 22.5 mmol). The solution was stirred ninety degree Celsius for 28 hours. The solution was diluted with $H_2O$ (400 mL) and extracted with ethyl acetate. The organic layer was washed with water, saturated NaCl and dried over $MgSO_4$, filtered and concentrated in vacuo to afford desired aryl ether as an oil (7.54 g, quantitative)

Part B: To a solution of aryl ether from part A (7.54 g, 15.0 mmol) in ethanol (40 mL) and tetrahydrofuran (40 mL) was added a solution of NaOH (6.06 g, 151.0 mmol) in water (20 mL) and the solution was heated at sixty degrees Celsius for 18 hours. The solution was concentrated in vacuo and the aqueous residue was acidified to pH=2.0. The resulting precipitate was filtered to give the desired hydrochloride salt as a white solid (7.98 g, quantitative). MS $MH^+$ calculated for $C_{22}H_{22}NSO_5$ $F_3$: 470, found 470.

Part C: To a solution of the hydrochloride salt of part B (7.60 g, 15.0 mmol) in DMF (100 mL) were added 1-hydroxybenzotriazole (2.44 g, 18.0 mmol), N-methyl morpholine (3.4 mL, 30.9 mmol ) and O-tetrahydropyranyl hydroxyl amine hydrochloride (2.63 g, 22.5 mmol) followed by 1-3-(dimethylamino)propyl]-3-ethylcarbodiimide hydrochloride (4.02 g, 21.0 mmol). The solution was-stirred at ambient temperature for 96 hours. The solution was diluted with $H_2O$ (400 mL) and extracted with ethyl acetate. The organic layer was washed with saturated NaCl and dried over $MgSo_4$, filtered and concentrated in vacuo. Chromatography on silica eluting with 30% ethyl acetate/hexane provided the desired tetrahydropyranyl-protected hydroxamate as a white solid (5.93 g, 69%).

Part D: To a solution of tetrahydropyranyl-protected hydroxamate of part C (3.8 g, 6.7 mmol) in dioxane (100 mL) was added 4 N HCl/dioxane (30 mL). The reaction was stirred at ambient temperature for 2 hours, then the solution was concentrated in vacuo. Trituration with diethyl ether afforded the title compound as a white solid (3.33 g, 96%). MS $MH^+$ calculated for $C_{22}H_{23}N_2SO_5F_3$: 485, found 485.

EXAMPLE 428

Preparation of N-hydroxy-1-(1-methylethyl) -4-[[4-[4-(trifluoromethyl)-phenoxy]phenyl]sulfonyl]-4-piperidinecarboxamide, Monohydrochloride

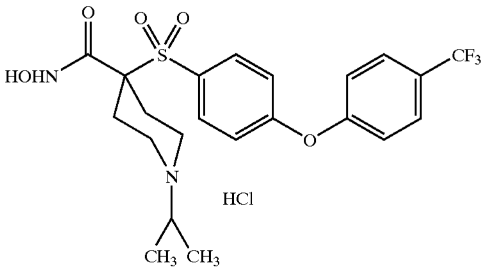

Part A: To a solution of the product of Example 9, Part D (30.0 g, 80.8 mmol) in methylene chloride (100 mL) was added trifluoroacetic acid (30 mL) in methylene chloride (40 mL). The solution was stirred at ambient temperature for two hours. The solution was concentrated in vacuo. To the residue dissolved in methylene chloride (150 mL) at zero degrees Celsius were added triethylamine (28.0 mL, 277 mmol), acetone (24.0 mL, 413 mmol), sodium cyanoborohydride (68 g, 323.1 mmol) and acetic acid (18.5 mL, 308 mmol) . The reaction mixture was stirred at ambient temperature for 18 hours. The solution was diluted with 1N NaOH and extracted with ethyl ether. The organic layer was washed with 1N NaOH, water, saturated NaCl and dried over $MgSO_4$, filtered and concentrated in vacuo to provided the desired isopropylamine (21.03 g, 72%).

Part B: To a solution of the isopropylamine of part A (4.04 g, 11.0 mmol) in DMF (50 mL) was added $CsCO_3$ (10.75g, 33.3 mmol) and α,α,α-trifluoro-p-cresol (2.67g, 16.5 mmol). The solution was stirred at ninety degrees Celsius for 40 hours. The solution was diluted with $H_2O$ (400 mL) and extracted with ethyl acetate. The organic layer was washed with water, saturated NaCl and dried over $MgSO_4$, filtered and concentrated in vacuo. Chromatography on silica gel, eluting with 30% ethyl acetate/hexane, provided the desired diaryl ether as an oil (5.35 g, 97%). HRMS $MH^+$ calculated for $C_{24}H_{28}NSO_5F_3$: 500.1640, found: 500.1678.

Part C: To a solution of the diaryl ether from part B (5.3 g, 10.6 mmol) in ethanol (50 mL) and tetrahydrofuran (50 mL) was added a solution of NaOH (4.2 g, 106.0 mmol) in water (25 mL) and the solution was heated at sixty degrees Celsius for 18 hours. The solution was concentrated in vacuo and the aqueous residue was acidified to pH=3.0. The resulting precipitate was filtered to give the desired hydrochloride salt as a white solid (5.38 g, quantitative). MS $MH^+$ calculated for $C_{22}H_{24}NSO_5F_3$: 472.1406, found 471.472.1407.

Part D: To a solution of the hydrochloride salt of part C (5.4 g, 10.6 mmol) in DMF (90 mL) were added 1-hydroxybenzotriazole (1.72 g, 12.3 mmol), N-methyl morpholine (3.5 mL, 32.0 mmol) and O-tetrahydropyranyl hydroxyl amine hydrochloride (1.87 g, 15.9 mmol) followed by 1-3-(dimethylamino)propyl]-3-ethylcarbodiimide hydrochloride (2.8 g, 15.0 mmol). The solution was stirred at ambient temperature for 144 hours. The solution was diluted with $H_2O$ (400 mL) and extracted with ethyl acetate. The organic layer was washed with saturated NaCl and dried over $MgSO_4$, filtered and concentrated in vacuo. Chromatography on silica gel, eluting with 2% methanol/ethyl acetate, provided the desired tetrahydropyranyl-protected hydroxamate as a white solid (2.74 g, 45%). HRMS $MH^+$ calculated for $C_{27}H_{33}N_2SO_5F_3$: 571.2090, found 571.2103

Part E: To a solution of tetrahydropyranyl-protected hydroxamate of part D (2.7 g, 4.7 mmol) in dioxane (50 mL) was added 4 N HCl/dioxane (20 mL). The reaction was stirred at ambient temperature for 2 hours. Filtration afforded the title compound as a white solid (2.08 g, 84%). MS $MH^+$ calculated for $C_{22}H_2SN_2SO_5F_3$: 487, found 487.

EXAMPLE 429

Preparation of 1-ethyl-N-hydroxy-4-[[4-[4-(trifluoromethyl)phenoxy]phenyl]-sulfonyl]-4-piperidinecarboxamide, Monohydrochloride

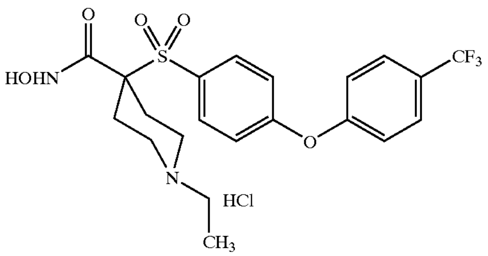

Part A: To a solution of the product of Example 9, Part D (48 g, 115.0 mmol) in ethyl acetate (750 mL) cooled to zero degrees Celsius was bubbled gaseous HCl for 45 minutes, and stirred at that temperature for 7 hours. The solution was concentrated in vacuo to afford a residue that was triturated with diethyl ether to afford the desired hydrochloride salt as a white solid (32.76 g, 81%).

Part B: To a solution of hydrochloride salt of part A (15.8 g, 45.0 mmol) in DMF (75 mL) was added $K_2CO_3$ (12.4 g, 90.0 mmol) and bromoethane (3.4 mL, 45.0 mmol). The solution was stirred at ambient temperature for 18 hours. The solution was diluted with $H_2O$ (200 mL) and extracted with ethyl acetate. The organic layer was washed with water, saturated NaCl and dried over MgSO4, filtered and concentrated in vacuo to provide the desired ethyl amine as an oil (15.4 g, quantitative).

Part C: To a solution of ethyl amine of part B (5.2 g, 15.0 mmol) in DMF (50 mL) was added $CsCO_3$ (12.21 g, 37.5 mmol) and α,α,α-trifluoro-p-cresol (3.65 g, 23.0 mmol). The solution was stirred ninety degrees Celsius for 25 hours. The solution was diluted with $H_2O$ (400 mL) and extracted with ethyl acetate. The organic layer was washed with water, saturated NaCl and dried over $MgSO_4$, filtered and concentrated in vacuo. Chromatography on silica gel, eluting with 20% ethyl acetate/hexane, provided the desired diaryl ether as an oil (7.3 g, quantitative yield).

Part D: To a solution of diaryl ether from part C (7.3 g, 15.0 mmol) in ethanol (40 mL) and tetrahydrofuran (40 mL) was added a solution of NaOH (6.0 g, 150 mmol) in water (30 mL), and the solution was heated at sixty degrees Celsius for 16 hours. The solution was concentrated in vacuo and the aqueous residue was acidified to pH=4.0. The resulting precipitate was filtered to give the desired hydrochloride salt as a white solid (5.96 g, 80%). HRMS $MH^+$ calculated for $C_{21}H_{22}NSO_5F_3$: 458.1249, found 458.1260

Part E: To a solution of the hydrochloride salt of part D (5.96 g, 12.0 mmol) in DMF (80 mL) were added 1-hydroxybenzotriazole (1.96 g, 14.0 mmol), N-methyl morpholine (3.9 mL, 36.0 mmol) and O-tetrahydropyranyl hydroxyl amine hydrochloride (2.11 g, 18.0 mmol) followed by 1-3-(dimethylamino)propyl]-3-ethylcarbodiimide hydrochloride (3.24 g, 17.0 mmol). The solution was stirred at ambient temperature for 168 hours. The insoluble material was removed by filtration and the filtrate was diluted with $H_2O$ (400 mL) and extracted with ethyl acetate. The organic layer was washed with saturated NaCl and dried over $MgSO_4$, filtered and concentrated in vacuo. Chromatography on silica gel eluting with 70% ethyl acetate/hexane provided the desired tetrahydropyranyl-protected hydroxamate as a white solid (2.80 g, 41%).

Part F: To a solution of tetrahydropyranyl-protected hydroxamate of part E (2.8 g, 5.0 mmol) in dioxane (80 mL) was added 4 N HCl/dioxane (20 mL). The reaction was stirred at ambient temperature for 5 hours, and the solution was concentrated in vacuo. Trituration with diethyl ether afforded the title compound as a white solid (2.08 g, 84%). MS $MH^+$ calculated for $C_{21}H_{23}N_2SO_5F_3$: 473, found 473.

EXAMPLE 430

Preparation of t-ethyl-N-hydroxy-4-[[4-[4-(1-methylethyl)phenoxy]phenyl]-sulfonyl]-4-piperidinecarboxamide, Monohydrochloride

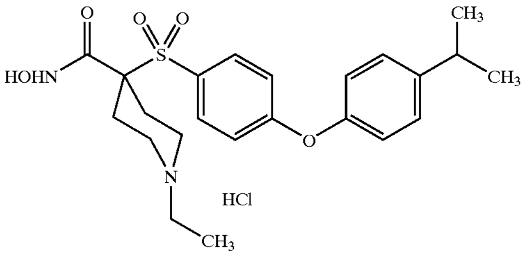

Part A: To a solution of the product of Example 9, Part D (48 g, 115.0 mmol) in ethyl acetate (750 mL) cooled to zero degrees Celsius was bubbled gaseous HCl for 45 minutes. The reaction was stirred at this temperature for 7 hours. The solution was concentrated in vacuo to afford a residue which was triturated with diethyl ether to afford the desired hydrochloride salt as a white solid (32.8 g, 81%).

Part B: T o a solution of the hydrochloride salt of part A (15.8 g, 45.0 mmol) in DMF (75 mL) was added $K_2CO_3$ (12.4 g, 90.0 mmol) and bromoethane (3.4 mL, 45.0 mmol). The solution was stirred at ambient temperature for 18 hours. The solution was diluted with $H_2O$ (200 mnL) and extracted with ethyl acetate. The organic layer was washed with water, saturated NaCl and dried over $MgSO_4$, filtered and concentrated in vacuo to afford the desired ethyl amine as an oil (15.4 g, quantitative).

Part C: To a solution of ethyl amine of part B (5.2 g, 15.0 mmol) in DMF (50 mL) was added $CsCO_3$ (12.2 g, 37.5 mmol) and 4-isopropylphenol (3.15 g, 23.0 mmol) . The solution was stirred at ninety degrees Celsius for 5 hours. The solution was diluted with $H_2O$ (400 mL) and extracted with ethyl acetate. The organic layer was washed with water, saturated NaCl and dried over $MgSO_4$, filtered and concentrated in vacuo. Chromatography on silica gel eluting with 20% ethyl acetate/hexane provided the desired diaryl ether as an oil (6.2 g, 95%). HRMS $MH^+$ calculated for $C_{25}H_{33}N_3SO_5$: 460.2158, found: 460.2160.

Part D: To a solution of diaryl ether from part C (6.2 g, 13.0 mmol) in ethanol (40 mL) and tetrahydrofuran (40 mL) was added a solution of NaOH (5.2 g, 130 mmol) in water (30 mL) and the solution was heated at sixty degrees Celsius for 16 hours. The solution was concentrated in vacuo and the aqueous residue was acidified to pH=4.0. The resulting precipitate was filtered and washed with $H_2O$ and diethyl ether to give desired hydrochloride salt (6.0 g, quantitative) . HRMS $MH^+$ calculated for $C_{23}H_{29}NSO_5$: 432.1845, found 432.1859.

Part E: To a solution of the hydrochloride salt of part D (6.08 g, 13.0 mmol) in DMF (80 mL) were added 1-hydroxybenzotriazole (2.11 g, 15.6 mmol), N-methyl morpholine (4.3 mL, 39.0 mmol) and O-tetrahydropyranyl hydroxyl amine hydrochloride (2.28 g, 19.5 mmol) followed by 1-3-(dimethylamino)propyl]-3-ethylcarbodiimide hydrochloride (3.49 g, 18.2 mmol). The solution was stirred at ambient temperature for 168 hours. Insoluble material was removed by filtration and the filtrate was diluted with $H_2O$ (400 mL) and extracted with ethyl acetate. The organic layer was washed with saturated NaCl and dried over $MgSO_4$, filtered and concentrated in vacuo. Chromatography on silica gel eluting with 50% ethyl acetate/hexane provided the desired tetrahydropyranyl-protected hydroxamate as a white solid (1.7 g, 25%). HRMS $MH^+$ calculated for $C_{28}H_{38}N_2SO_6$: 531.2529, found 531.2537.

Part F: To a solution of tetrahydropyranyl-protected hydroxamate of part E (1.7 g, 3.0 mmol) in dioxane (60 mL) was added 4 N HCl/dioxane (10 mL) The reaction was stirred at ambient temperature for 4 hours, and the solution was concentrated in vacuo. Chromatography on C18 reverse phase column eluting with acetonitrile/(HCl) water provided the title compound as a white solid (860 mg, 59%). HRMS $MH^+$ calculated for $C_{23}H_{30}N_2SO_5$: 447.1954, found 447.1972

EXAMPLE 431

Preparation of 1-cyclopropyl-N-hydroxy -4-[[4-[4-(1-methylethyl)phenoxy]phenyl]-sulfonyl]-4-piperidine-carboxamide, Monohydrochloride

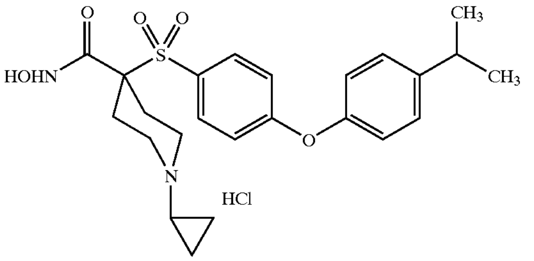

Part A: To a solution of the product of Example 398, Part A (4.0 g, 10.2 mmol) in DMF (40 mL) was added $K_2CO_3$ (12.46 g, 38.0 mmol) and 4-isopropylphenol (4.99g, 15.3 mmol). The solution was stirred at ninety degrees Celsius for 24 hours. The solution was diluted with $H_2O$ (400 mL) and extracted with ethyl acetate. The organic layer was washed with water, saturated NaCl and dried over $MgSO_4$, filtered and concentrated in vacuo. Chromatography on silica eluting with 30% ethyl acetate/hexane provided the desired diaryl ether as a white solid (3.89 g, 76%). HRMS $MH^+$ calculated for $C_{26}H_{33}NSO_5$: 472.2158, found: 472.2171.

Part B: To a solution of diaryl ether from part A (3.89 g, 8.20 mmol) in ethanol (40 mL) and tetrahydrofuran (40 mL) was added a solution of NaOH (3.30 g, 82.5 mmol) in water (25 mL) and the solution was heated at sixty degrees Celsius for 18 hours. The solution was concentrated in vacuo to remove most of the organic solvents and the aqueous residue was acidified to pH=3.0. The resulting precipitate was filtered and washed with $H_2O$ and ethyl ether to give desired hydrochloride salt (7.98 g, quantitative) as a white solid. MS $MH^+$ calculated for $C_{24}H_{29}NSO_5$: 444, found: 444.

Part C: To a solution of the hydrochloride salt of part B (3.6 g, 7.0 mmol) in DMF (70 mL) were added 1-hydroxybenzotriazole (1.22 g, 9.0 mmol), N-methyl morpholine (2.3 mL, 21.0 mmol) and O-tetrahydropyranyl hydroxyl amine hydrochloride (1.23 g, 10.5 mmol) followed by 1-3-(dimethylamino)propyl]-3-ethylcarbodiimide hydrochloride (2.01 g, 10.4 mmol). The solution was stirred at ambient temperature for 15 days. The solution was diluted with $H_2O$ (400 mL) and extracted with ethyl acetate. The organic layer was washed with saturated NaCl and dried over $MgSO_4$, filtered and concentrated in vacuo. Chromatography on silica gel, eluting with 15% ethyl acetate/hexane, provided the desired tetrahydropyranyl-protected hydroxamate as a white solid (3.51 g, 92%). HRMS $MH^+$ calculated for $C_{29}H_{38}N_2SO_6$: 543.2529, found 543.2539.

Part D: To a solution of tetrahydropyranyl-protected hydroxamate of part C (3.51 g, 6.0 mmol) in methanol (10 mL) and dioxane (200 mL) was added 4 N HCl/dioxane (30 mL). After stirring at ambient temperature for 2.5 hours, the solution was concentrated in vacuo. Trituration with diethyl ether afforded the title compound as a white solid (2.56 g, 86%). MS $MH^+$ calculated for $C_{24}H_{30}N_2SO_5$: 459.1875, found 459.1978.

EXAMPLE 432

Preparation of N-hydroxy-4-[[4-[4-(1-methylethoxy)phenoxy]phenyl]sulfonyl]-1-(1-methylethyl)-4-piperidinecarboxamide, Monohydrochloride

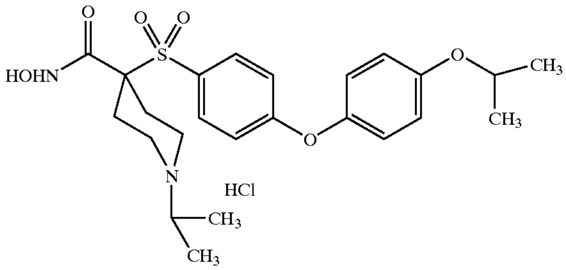

Part A: To a solution of ethyl-4-[(4-fluorophenylsulfonyl)]-1-(1-methylethyl)-4-piperidinecarboxylate (2.0 g, 5.4 mmol) in N,N-dimethylformamide (10 mL) was added 4-isopropyloxyphenol, which may be prepared according to the procedure of *J. Indian Chem. Soc.,* 73, 1996, 507–511, (1.63 g, 10.7 mmol) and cesium carbonate (7 g, 21.5 mmol) and the resulting suspension was heated at 60 degrees Celsius for 16 hours. The reaction mixture was then concentrated in vacuo. The residue was dissolved in ethyl acetate and washed with 1 N sodium hydroxide, water and brine and dried over magnesium sulfate. Concentration of the organic phase gave a residue which was purified by chromatography on silica gel eluting with ethyl acetate/hexane to afford the desired aryl ether (1.06 g, 39%).

Part B: To a solution of the aryl ether (1.06 g, 2.1 mmol) in ethanol (20 mL) and water (20 mL) was added sodium hydroxide (0.84 g, 21 mmol) and the mixture was heated to 65 degrees Celsius for 16 hours. The solvents were then removed in vacuo. Water (50 mL) was added and the mixture was again concentrated in vacuo and the resulting mixture was acidified with 2 N HCl to pH=4–5. The solid precipitate was collected by filtration and rinsed with diethyl ether to afford the desired carboxylic acid (3.13 g, 100%).

Part C: A solution of the carboxylic acid of part B (1.0 g, 2.0 mmol) in thionyl chloride (5 mL) was refluxed for 2 hours . The solvent was removed in vacuo. To the resulting residue in DMF (10 mL) was added N-methyl morpholine (0.66 mL, 6.0 mmol)) and O-tetrahydropyranyl hydroxyl amine hydrochloride (351 mg, 3.0 mmol). The solution was stirred at ambient temperature for 18 hours. The suspension was filtered and the filtrate was diluted with $H_2O$ (400 mL) and extracted with ethyl acetate. The organic layer was washed with saturated NaCl and dried over $MgSO_4$, filtered and concentrated in vacuo. Chromatography on silica gel eluting with 90% ethyl acetate/hexane provided the desired tetrahydropyran-protected hydroxamate as a white solid (280 mg, 23%). HRMS $MH^+$ calculated for $C_{29}H_{40}N_2SO_7$: 561.2634, found 561.2653.

Part D: To a solution of tetrahydropyranyl-protected hydroxamate of part C (275 mg, 0.48 mmol) in dioxane (15 mL) was added 4 N HCl/dioxane (5 mL). After stirring at ambient temperature for 2 hours, the solution was concentrated in vacuo. Trituration with diethyl ether and filtration of the resulting solid gave the title compound as a white solid (193 mg, 76%). MS $MH^+$ calculated for $C_{24}H_{32}N_2SO_6$: 477, found 477.

EXAMPLE 433

Preparation of 4-[[4-[(2-fluorophenyl)-thio]phenyl] sulfonyl]-N-hydroxy-4-piperidinecarboxamide, Monohydrochloride

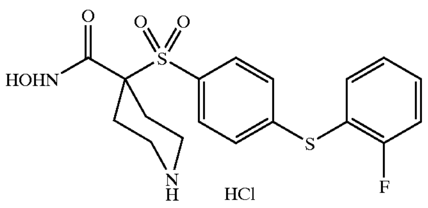

Part A: To a solution of the product of Example 9, Part D (6.0 g, 14.4 mmol) in N,N-dimethylformamide (30 mL) were added 2-fluorothiophenol (2.22 g, 17.3 mmol) and potassium carbonate (2.40 g, 17.3 mmol), and the resulting suspension was stirred at ambient temperature for 48 hours. The reaction mixture was then diluted with ethyl acetate (200 mL) and washed with 1 N sodium hydroxide (200 mL) and brine (3×). Concentration of the organic phase afforded a residue that was purified by chromatography on silica gel, eluting with ethyl acetate/hexane (1:4), to afford the desired aryl sulfide (8.0 grams, 100%) as a white solid.

Part B: To a solution of the ethyl ester of part A (8.0 g, 15 mmol) in ethanol (90 mL) and water (20 mL) was added sodium hydroxide (6.1 g, 152 mmol), and the mixture was heated to 65 degrees Celsius for 16 hours. Volatile organics were removed in vacuo and the resulting aqueous mixture was acidified with 2 N HCl to pH=3–4. Solid sodium chloride was added and the mixture was extracted with ethyl acetate. The combined organic extracts were washed with brine and dried with magnesium sulfate. Removal of the solvent afforded the desired carboxylic acid (4.92 g, 68%).

Part C: To a solution of the carboxylic acid of part B (4.92 g, 9.93 mmol) in N,N-dimethylformamide (100 mL) were added 4-methylmorpholine (1.52 g, 15.0 mmol), N-hydroxybenzotriazole (1.62 g, 12.0 mmol) and 1-[3-(dimethylamino)propyl]-3-ethylcarbodiimide hydrochloride (2.70 g, 14.1 mmol), followed by O-(tetrahydro-2H-pyran-2-yl)hydroxylamine (2.24 g, 15.0 mmol). After stirring for 16 hours at ambient temperature, the reaction mixture was concentrated to a residue that was dissolved in ethyl acetate (200 mL) and washed with water and brine. Concentration and purification by chromatography on silica gel afforded the protected hydroxamate derivative (4.9 mg, 83%).

Part D: Hydrogen chloride gas was bubbled for 10 minutes through an ice bath-cooled solution of the protected hydroxamate of part C (4.9 g, 8.24 mmol) in ethyl acetate (30 mL). The mixture was then allowed to stand at ambient temperature for 2 hours, after which time the solvent was removed in vacuo. Fresh ethyl acetate (30 mL) was added and then removed in vacuo, and this procedure was repeated. Ethyl acetate (50 mL) was then added and the solid was collected by filtration to afford a solid that was purified by reverse-phase chromatography,, eluting with acetonitrile/water (gradient of 20/80 up to 100% acetonitrile), to afford the title compound (1.9 g, 43%). Analytical calculation for $C_{18}H_{19}FN_2O_4S_2$.HCl: C, 48.37; H, 4.51; N, 6.27; Cl, 7.93. Found: C, 48.14; H, 4.33; N, 6.21; Cl, 8.64. HRMS (ESI) $MH^+$ calculated for $C_{18}H_{19}FN_2O_4S_2$: 411.0849, found 411.0844.

EXAMPLE 434

Preparation of 4-[[4-[(2-fluorophenyl)-thio]phenyl] sulfonyl]-N-hydroxy-1-(2-propynyl)-4-piperidinecarboxamide, Monohydrochloride

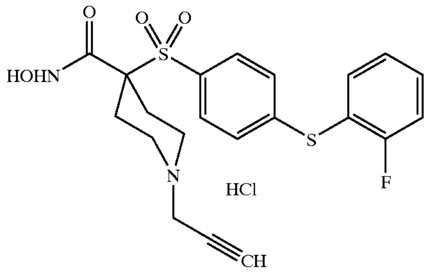

Part A: To a solution of the product of Example 9, Part F (4.46 g, 12.6 mmol) in N,N-dimethylformamide (30 mL) were added 2-fluorothiophenol (1.94 g, 15.1 mmol) and potassium carbonate (2.09 g, 15.1 mmol), and the resulting suspension was stirred at ambient temperature for 48 hours. The reaction mixture was then diluted with ethyl acetate (200 mL) and washed with 1 N sodium hydroxide (200 mL) and brine (3×). Concentration of the organic phase afforded the desired aryl sulfide (5.2 grams, 90%).

Part B: To a solution of the ethyl ester of part A (5.1 g, 11.4 mmol) in ethanol (90 mL) and water (30 mL) was added sodium hydroxide (5.0 g, 125 mmol), and the mixture was heated to 65 degrees Celsius for 16 hours. Organics were removed in vacuo and the resulting aqueous mixture was acidified with 2 N HCl to pH=3–4. Solid sodium chloride was added and the mixture was extracted with ethyl acetate.

The combined organic extracts were washed with brine and dried with magnesium sulfate. Removal of the solvent afforded the desired carboxylic acid (4.5 g, 94%).

Part C: To a solution of the carboxylic acid of part B (4.5 g, 11.0 mmol) in N,N-dimethylformamide (50 mL) were added 4-methylmorpholine (1.62 g, 16.0 mmol), N-hydroxybenzotriazole (1.73 g, 12.8 mmol), and 1-[3-(dimethylamino)propyl]-3-ethylcarbodiimide hydrochloride (2.87 g, 14.9 mmol) followed by O-(tetrahydro-2H-pyran-2-yl)hydroxylamine (2.39 g, 16.0 mmol). After stirring for 16 hours at ambient temperature, the reaction mixture was concentrated to a residue that was dissolved in ethyl acetate (200 mL) and washed with water and brine. Concentration and purification by chromatography on silica gel afforded the protected hydroxamate derivative that was used directly in the next step.

Part D: Hydrogen chloride gas was bubbled for 10 minutes through an ice bath-cooled solution of the protected hydroxamate of part C in ethyl acetate (30 mL). The mixture was then allowed to stand at ambient temperature for 2 hours after which time the solvent was removed in vacua. Fresh ethyl acetate (30 mL) was added and then removed in vacuo, and this procedure was repeated. Ethyl acetate (50 mL) was then added and the solid was collected by filtration to afford a solid which was purified by reverse-phase chromatography eluting with acetonitrile/water (gradient of 20/80 up to 100% acetonitrile) to afford the title compound (1.85 g, 35% for parts C and D). HRMS (ESI) $MH^+$ calculated for $C_{21}H_{21}FN_2O_4S_2$: 449.1005, found 449.1023.

EXAMPLE 435

Preparation of 4-[[4-(4-ethoxyphenoxy)-phenyl]sulfonyl]-N-hydroxy-1-(2-propynyl)-4-piperidinecarboxamide, Monohydrochloride

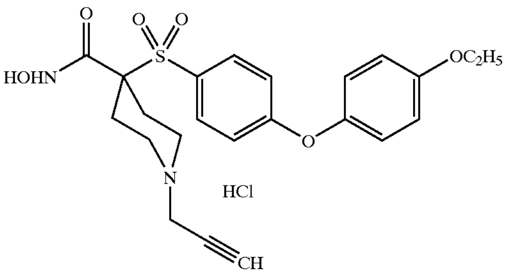

Part A: To a solution of the product of Example 9, Part F (8.00 g, 22.6 mmol) in N,N-dimethylformamide (50 mL) were added 4-ethoxyphenol (9.38 g, 70 mmol) and cesium carbonate (22.8 g, 70 mmol), and the resulting suspension was heated at 75 degrees Celsius for 20 hours. The reaction mixture was then diluted with ethyl acetate (1000 mL) and washed with 1 N sodium hydroxide, water and brine. Concentration of the organic phase gave a residue that was purified by chromatography on silica gel, eluting with ethyl acetate/hexane (1:2), to afford the desired diaryl ether (10.5 grams, 99%).

Part B: To a solution of the ethyl ester of part A (10.5 g, 22.3 mmol) in ethanol (70 mL) and water (60 mL) was added sodium hydroxide (8.9 g, 222 mmol), and the mixture was heated to 65 degrees Celsius for 16 hours. Volatile organics were removed in vacuo and the resulting aqueous mixture was acidified with 2 N HCl to pH=3–4. Solid sodium chloride was added and the mixture was extracted with ethyl acetate. The combined organic extracts were washed with brine and dried with magnesium sulfate. Removal of the solvent afforded the desired carboxylic acid (10 g, 100%).

Part C: To a solution of the carboxylic acid of part B (10 g, 22.5 mmol) in N,N-dimethylformamide (50 mL) were added 4-methylmorpholine (3.42 g, 33.8 mmol), N-hydroxybenzotriazole (3.66 g, 27.1 mmol), and 1-[3-(dimethylamino)propyl]-3-ethylcarbodiimide hydrochloride (6.05 g, 31.6 mmol) followed by O-(tetrahydro-2H-pyran-2-yl)hydroxylamine (5.05 g, 33.8 mmol). After stirring for 16 hours at ambient temperature, the reaction mixture was concentrated to a residue that was dissolved in ethyl acetate (200 mL) and washed with water and brine. Concentration and purification by chromatography on silica gel, eluting with ethyl acetate/hexane (1:1), afforded the protected hydroxamate derivative (6.5 g, 53%) which was used directly in the next step.

Part D: To a solution of the protected hydroxamate of part C in methanol/1,4-dioxane (1:3, 70 mL.) was added 4 N HCl/1,4-dioxane (30 mL) and the solution was stirred at ambient temperature for 4 hours. The solvent was then removed in vacuo. Methanol (40 mL) was added and then removed in vacuo. Diethyl ether (100 mL) was added and the resulting solid was collected by filtration to afford the title compound (4.3 g, 72%). Analytical calculation for $C_{23}H_{26}N_2O_6S.HCl.H_2O$: C, 53.85; H, 5.70; N, 5.46; Cl, 6.91; S, 6.25. Found: C, 53.65; H, 5.62; N, 5.41; Cl, 6.86; S, 6.48. MS (ESI) $MH^+$ calculated for $C_{23}H_{26}N_2O_6S$: 459, found 459.

EXAMPLE 436

Preparation of N-hydroxy-4-[[4-[4-(methylsulfonyl)phenoxy]phenyl]-sulfonyl]-1-(2-propynyl)-4-piperidinecarboxamide, Monohydrochloride

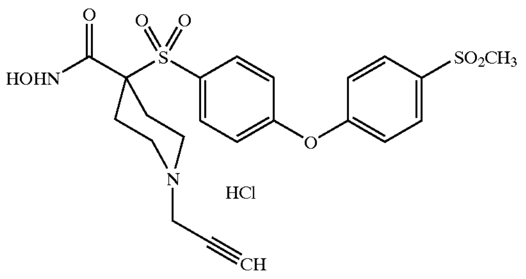

Part A: To a solution of the product of Example 9, Part F (2.5 g, 6.4 mmol) in N,N-dimethylformamide (15 mL) were added 4-methylsulphonylphenol (3.5 g, 20.3 mmol) and cesium carbonate (8.7 g, 27 mmol), and the resulting suspension was heated at 90 degrees Celsius for 16 hours. The reaction mixture was then concentrated in vacuo. The residue was dissolved in ethyl acetate (500 mL) and washed with 1 N sodium hydroxide, water and brine. Concentration of the organic phase gave a residue which was purified by chromatography on silica gel eluting with ethyl acetate/hexane (1:1) to afford the desired aryl ether (2.5 grams, 77%).

Part B: To a solution of the ethyl ester of part A (2.5 g, 4.9 mmol) in ethanol (50 mL) and water (30 mL) was added sodium hydroxide (2.0 g, 49 mmol) and the mixture was heated to 65 degrees Celsius for 8 hours. The solvents were removed in vacuo. Water (50 mL) was added, the mixture was again concentrated in vacuo and the resulting mixture was acidified with 2 N HCl to pH=4–5. The solid precipitate was collected by filtration to afford the desired carboxylic acid (1.57 g, 67%).

Part C: To a solution of the carboxylic acid of part B (1.57 g, 3.3 mmol) in N,N-dimethylformamide (15 mL) were added 4-methylmorpholine (0.5 g, 4.9 mmol), N-hydroxybenzotriazole (0.53 g, 3.9 mmol), and 1-[3-

(dimethylamino)propyl]-3-ethylcarbodiimide hydrochloride (0.88 g, 4.6 mmol) followed by O-(tetrahydro-2H-pyran-2-yl)hydroxylamine (0.74, 4.9 mmol). After stirring for 16 hours at ambient temperature, the reaction mixture was concentrated to a residue that was dissolved in ethyl acetate (200 mL) and washed with water and brine. Concentration and purification by chromatography on silica gel, eluting with ethyl acetate/hexane, afforded the protected hydroxamate derivative (1.5 g, 79%), which was used directly in the next step.

Part D: To a solution of the protected hydroxamate of part C (1.5 g, 2.60 mmol) in methanol/1,4-dioxane (1:3, 40 mL) was added 4 N HCl/1,4-dioxane (10 mL), and the solution was stirred at ambient temperature for 3 hours. The solvent was then removed in vacuo. Methanol (30 mL) was added and then removed in vacuo. Diethyl ether (100 mL) was added and the resulting solid was collected by filtration to afford the title compound (1.35 g, 98%). Analytical calculated for $C_{22}H_{24}N_2O_7S_2$.HCl: C, 49.95; H, 4.76; N, 5.30; Cl, 6.70; S, 12.12. Found: C, 49.78; H, 4.56; N, 5.25; Cl, 6.98; S, 11.98. HRMS (ESI) $MH_+$ calculated for $C_{22}H_{24}N_2O_7S_2$: 493.1103, found 493.1116.

EXAMPLE 437

Preparation of N-hydroxy-4-[[4-[(phenylmethyl) amino]phenyl]sulfonyl]-1-(2-propynyl-4-piperidinecarboxamide, Monohydrochloride

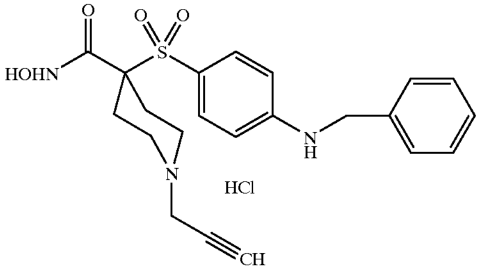

Part A: To a solution of the product of Example 9, Part F (2.5 g, 6.4 mmol) in N,N-dimethylformamide (30 mL) were added benzylamine (3.44 g, 32.1 mmol) and cesium carbonate (10.5 g, 32.3 mmol) and the resulting suspension was heated at 100 degrees Celsius for 16 hours. The reaction mixture was then concentrated in vacuo. The residue was dissolved in ethyl acetate (500 mL) and washed with water and brine and dried over magnesium sulfate. Concentration of the organic phase gave a residue that was purified by chromatography on silica gel, eluting with ethyl acetate/hexane (1:1), to afford the desired benzyl aniline derivative (2.5 grams, 88%).

Part B: To a solution of the ethyl ester of part A (2.5 g, 5.67 mmol) in ethanol (50 mL) and water (30 mL) was added sodium hydroxide (2.27 g, 56.7 mmol), and the mixture was heated to 65 degrees Celsius for 8 hours. The solvents were removed in vacuo. Water (50 mL) was added and the mixture was again concentrated in vacuo and the resulting mixture was acidified with 2 N HCl to pH=4–5. The solid precipitate was collected by filtration and rinsed with diethyl ether to afford the desired carboxylic acid (2.3 g, 98%).

Part C: To a solution of the carboxylic acid of part B (2.3 g, 5.57 mmol) in N,N-dimethylformamide (15 mL) were added 4-methylmorpholine (0.85 g, 8.36 mmol), N-hydroxybenzotriazole (0.9 g, 6.69 mmol), and 1-[3-(dimethylamino)propyl]-3-ethylcarbodiimide hydrochloride (1.5 g, 7.8 mmol) followed by O-(tetrahydro-2H-pyran-2-yl)hydroxylamine (1.25, 8.36 mmol). After stirring for 16 hours at ambient temperature, the reaction mixture was concentrated to a residue which was dissolved in ethyl acetate and washed with water and brine. Concentration and purification by chromatography on silica gel, eluting with ethyl acetate/hexane, afforded the protected hydroxamate derivative which was used directly in the next step.

Part D: Hydrogen chloride gas was bubbled for 10 minutes through an ice bath-cooled solution of the protected hydroxamate of part C in ethyl acetate (50 mL). The solvent was then removed in vacuo. Ethyl acetate (100 mL) was added and then removed in vacuo. Ethyl acetate (100 mL) was then added and the resulting solid was collected by filtration to afford the title compound (1.6 g, 62% for steps C and D). HRMS (ESI) $MH^+$ calculated for $C_{22}H_{25}N_3O_4S$: 428.1644, found 428.1652.

EXAMPLE 438

Preparation of 1-ethyl-N-hydroxy-4-[[4-[[4-[trifluoromethyl)phenyl]methoxy]-phenyl]sulfonyl]-4-piperidine-carboxamide, Monohydrochloride

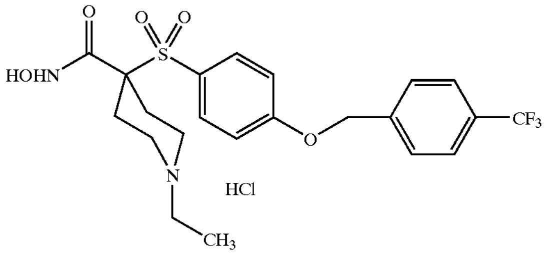

Part A: To a solution of the product of Example 429, Part B (1.0 g, 2.9 mmol) in N,N-dimethylacetamide (30 mL) were added 4-(trifluoromethyl)benzyl alcohol (1.53 g, 8.74 mmol) and cesium carbonate (2.85 g, 8.74 mmol), and the resulting suspension was heated at 95–100 degrees Celsius for 8 hours. The reaction mixture was then concentrated in vacuo. The residue was dissolved in ethyl acetate and washed with 1 N sodium hydroxide, water and brine. Concentration of the organic phase gave a residue that was purified by chromatography on silica gel eluting with ethyl acetate/hexane to afford the desired aryl ether (0.8 grams, 54%).

Part B: To a solution of the ethyl ester of part A (0.8 g, 1.5 mmol) in ethanol (50 mL) and water (50 mL) was added sodium hydroxide (1.0 g, 25 mmol) and the mixture was heated to 60 degrees Celsius for 16 hours. The solvents were removed in vacuo. Water (50 mL) was added and the mixture was acidified with 2 N HCl to pH=4. The solid precipitate was collected by filtration to afford the desired carboxylic acid (0.75 g, 99%).

Part C: To a solution of the carboxylic acid of part B (0.75 g, 1.54 mmol) in N,N-dimethylformamide (10 mL) were added 4-methylmorpholine (0.47 g, 4.6 mmol), N-hydroxybenzotriazole (0.25 g, 1.85 mmol), and 1-[3-(dimethylamino)propyl]-3-ethylcarbodiimide hydrochloride (0.41 g, 2.16 mmol) followed by O-(tetrahydro-2H-pyran-2-yl)hydroxylamine (0.35, 2.3 mmol). After stirring for 16 hours at ambient temperature, the reaction mixture was concentrated to a residue that was dissolved in ethyl acetate (200 mL) and washed with water and brine. Concentration and purification by chromatography on silica gel, eluting with ethyl acetate/hexane, afforded the protected hydroxamate derivative (250 mg, 57%).

Part D: To a solution of the protected hydroxamate of part C (250 mg, 0.43 mmol) in methanol/1,4-dioxane (1:3, 20 mL) was added 4 N HCl/1,4-dioxane (5 mL) and the solution was stirred at ambient temperature for 3 hours. The solvent was then removed in vacuo. An additional portion of ethyl acetate was added and then removed in vacuo. Diethyl ether (100 mL) was added and the resulting solid was collected by filtration to afford the title compound (190 mg, 82%). MS (CI) $MH^+$ calculated for $C_{22}H_{25}F_3N_2O_5S$: 487, found 487.

EXAMPLE 439

Preparation of t-cyclopropyl-N-hydroxy-4-[[4-[4-(1-methylethoxy)phenoxy]-phenyl]-sulfonyl]-4-piperidinecarboxamide, Monohydrochloride

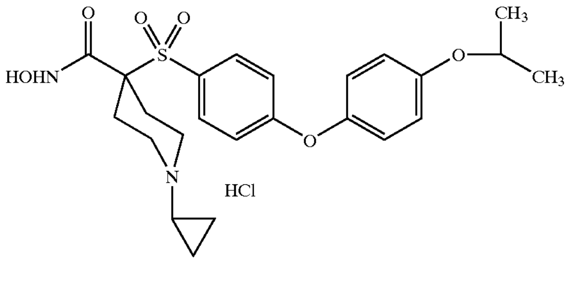

Part A: To a solution of the product of Example 398, Part A (2.49 g, 7.0 mmol) in N,N-dimethylacetamide (30 mL) were added 4-isopropoxyphenol, which may be prepared according to the procedure of *J. Indian Chem. Soc.* 73, 1996, 507–511,(1.28 g, 8.4 mmol) and cesium carbonate (5.48 g, 16.8 mmol), and the resulting suspension was heated at 60 degrees Celsius for 16 hours. The reaction mixture was then concentrated in vacuo. The residue was dissolved in ethyl acetate and washed with 1 N sodium hydroxide, water and brine. Concentration of the organic phase gave a residue which was purified by chromatography on silica gel, eluting with ethyl acetate/hexane, to afford the desired aryl ether (2.8 grams, 82%).

Part B: To a solution of the ethyl ester of part A (2.8 g, 5.7 mmol) in ethanol (50 mL) and water (50 mL) was added sodium hydroxide (2.3 g, 57 mmol) and the mixture was heated to 60 degrees Celsius for 16 hours. The solvents were removed in vacuo. Water (50 mL) was added and the mixture was acidified with 2 N HCl to pH=4. The solid precipitate was collected by filtration to afford the desired carboxylic acid (1.4 g, 53%).

Part C: To a solution of the carboxylic acid of part B (1.4 g, 3.1 mmol) in N,N-dimethylformamide (15 mL) were added 4-methylmorpholine (0.92 g, 9.1 mmol), N-hydroxybenzotriazole (0.49 g, 3.66 mmol), and 1-[3-(dimethylamino)propyl]-3-ethylcarbodiimide hydrochloride (0.82 g, 4.26 mmol) followed by O-(tetrahydro-2H-pyran-2-yl)hydroxylamine (0.68 g, 4.5 mmol). After stirring for 16 hours at ambient temperature, the reaction mixture was concentrated to a residue that was dissolved in ethyl acetate and washed with water and brine. Concentration and purification by chromatography on silica gel, eluting with ethyl acetate/hexane, afforded the protected hydroxamate derivative which was used directly in the next step.

Part D: To a solution of the protected hydroxamate from part C in methanol/1,4-dioxane (1:3, 20 mL) was added 4 N HCl/1,4-dioxane (10 mL) and the solution was stirred at ambient temperature for 3 hours. The solvent was then removed in vacuo. An additional portion of ethyl acetate was added and then removed in vacuo. Diethyl ether was added and the resulting solid was collected by filtration to afford the title compound (0.3 g, 19% for parts C and D together). Analytical calculation for $C_{24}H_{30}N_2O_6S.HCl$: C, 56.41; H, 6.11; N, 5.48. Found: C, 56.04; H, 5.82; N, 5.44. MS (CI) MH+ calculated for $C_{24}H_{30}N_2O_6S$: 475, found 475.

EXAMPLE 440

Preparation of 4-[[4-[[2-(4-chlorophenyl)-ethyl]amino]phenyl]-sulfonyl]-1-ethyl-N-hydroxy-4-piperidinecarboxamide, Monohydrochloride

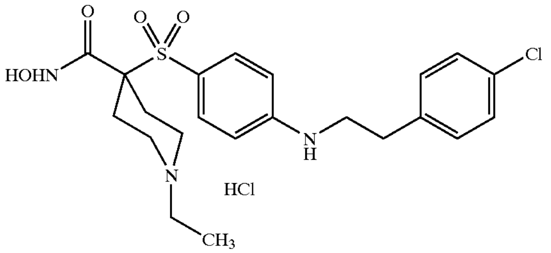

Part A: To a solution of the product of Example 429, Part B (1.0 g, 2.91 mmol) in N,N-dimethylacetamide (20 mL) were added 4-chlorophenethylamine (0.91 g, 5.8 mmol) and cesium carbonate (3.80 g, 11.6 mmol), and the resulting suspension was heated at 90 degrees Celsius for 24 hours. The reaction mixture was then concentrated in vacuo. The residue was dissolved in ethyl acetate and washed with 1 N sodium hydroxide, water and brine. Concentration of the organic phase gave a residue which was purified by chromatography on silica gel eluting with ethyl acetate/hexane to afford the desired aryl ether (0.8 grams, 58%).

Part B: To a solution of the ethyl ester of part A (0.8 g, 1.7 mmol) in ethanol (50 mL) and water (50 mL) was added sodium hydroxide (1.0 g, 25 mmol), and the mixture was heated to 60 degrees Celsius for 16 hours. The solvents were removed in vacuo. Water (50 mL) was added and the mixture was acidified with 2 N HCl to pH=4. The solid precipitate was collected by filtration to afford the desired carboxylic acid (0.75 g, 92%).

Part C: To a solution of the carboxylic acid of part B (0.75 g, 1.7 mmol) in N,N-dimethylformamide (20 mL) were added 4-methylmorpholine (0.51 g, 5.1 mmol), N-hydroxybenzotriazole (0.27 g, 2.0 mmol), and 1-[3-(dimethylamino)propyl]-3-ethylcarbodiimide hydrochloride (0.45 g, 2.3 mmol) followed by O-(tetrahydro-2H-pyran-2-yl)hydroxylamine (0.37 g, 2.5 mmol). After stirring for 16 hours at ambient temperature the reaction mixture was concentrated to a residue which was dissolved in ethyl acetate and washed with water and brine. Concentration and purification by chromatography on silica gel, eluting with ethyl acetate/hexane, afforded the protected hydroxamate derivative which was used directly in the next step.

Part D: To a solution of the protected hydroxamate from part C in methanol/1,4-dioxane was added 4 N HCl/1,4-dioxane (10 mL) and the solution was stirred at ambient temperature for 3 hours. The solvent was then removed in vacuo. An additional portion of ethyl acetate was added and then removed in vacuo. Diethyl ether was added and the resulting solid was collected by filtration to afford the title compound (30 mg, 4% for parts C and D together).

EXAMPLE 441

Preparation of N-hydroxy-1-(2-methoxyethyl)-4-[[4-[[[4-(trifluoro-methoxy)phenyl]methyl]amino]phenyl]-sulfonyl]-4-piperidinecarboxamide, Monohydrochloride

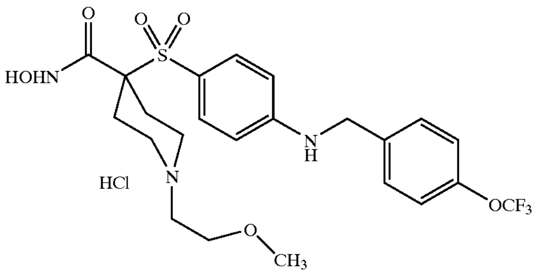

Part A: To a solution of ethyl-4-[(4-fluorophenylsulfonyl)]-1-(2-methoxyethyl)-4-piperidinecarboxylate (1.38 g, 3.7 mmol) in N,N-dimethylformamide (20 mL) were added 4-(trifluoro-methyloxy)benzylamine (1.0 g, 5.2 mmol) and cesium carbonate (1.7 g, 5.2 mmol), and the resulting suspension was heated at 90 degrees Celsius for 24 hours. The reaction mixture was then concentrated in vacuo. The residue was dissolved in ethyl acetate and washed with 1 N sodium hydroxide, water and brine. Concentration of the organic phase gave a residue that was purified by chromatography on silica gel, eluting with ethyl acetate/hexane, to afford the desired trifluoromethoxy compound (0.6 grams, 30%).

Part B: To a solution of the ethyl ester of part A (0.6 g, 1.1 mmol) in ethanol (30 mL), water (30 mL) and tetrahydrofuran (15 mL) was added sodium hydroxide (0.44 g, 11 mmol), and the mixture was heated to 60 degrees Celsius for 16 hours. The solvents were removed in vacuo. Water (50 mL) was added and the mixture was acidified with 2 N HCl to pH=4. The solid precipitate was collected by filtration to afford the desired carboxylic acid (0.5 g, 88%).

Part C: To a solution of the carboxylic acid of part B (0.50 g, 0.98 mmol) in N,N-dimethylformamide (10 mL) were added 4-methylmorpholine (0.15 g, 1.5 mmol), N-hydroxybenzotriazole (0.16 g, 1.2 mmol), and 1-[3-(dimethylamino)propyl]-3-ethylcarbodiimide hydrochloride (0.27 g, 1.4 mmol) followed by O-(tetrahydro-2H-pyran-2-yl)hydroxylamine (0.22 g, 1.5 mmol). After stirring for 16 hours at ambient temperature, the reaction mixture was concentrated to a residue that was dissolved in ethyl acetate and washed with water and brine. Concentration and purification by chromatography on silica gel, eluting with ethyl acetate/hexane, afforded the protected hydroxamate derivative (110 mg, 18%).

Part D: To a solution of the protected hydroxamate from part C (110 mg, 0.18 mmol) in methanol/1,4-dioxane (1:4, 20 mL) was added 4 N HCl/1,4-dioxane (7 mL) and the solution was stirred at ambient temperature for 3 hours. The solvent was then removed in vacuo. An additional portion of methanol (20 mL) was added and then removed in vacuo. Diethyl ether was added and the resulting solid was collected by filtration to afford the title compound (30 mg, 31%). MS (ESI) $MH^+$ calculated for $C_{23}H_{28}F_3N_3O_6S$: 532, found 532.

EXAMPLE 442

Preparation of N-hydroxy-4-[[4-[4-(1-methylethoxy)phenoxy]phenyl]sulfonyl]-1-(2-methoxyethyl)-4-piperidinecarboxamide, Monohydrochloride

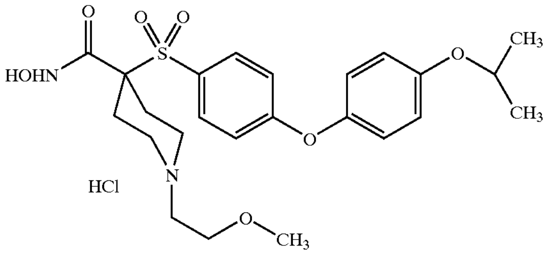

Part A: To a solution of ethyl-4-[(4-fluorophenylsulfonyl)]-1-(2-methoxyethyl)-4-piperidinecarboxylate (2.0 g, 5.4 mmol) in N,N-dimethylformamide (20 mL) were added 4-isopropoxyphenol, which can be prepared according to the procedure of *T. Indian Chem. Soc.* 73, 1996, 507–511, (1.63 g, 10.7 mmol) and cesium carbonate (7 g, 21.5 mmol), and the resulting suspension was heated at 60 degrees Celsius for 16 hours. The reaction mixture was then concentrated in vacuo. The residue was dissolved in ethyl acetate and washed with 1 N sodium hydroxide, water and brine and dried over magnesium sulfate. Concentration of the organic phase gave a residue that was purified by chromatography on silica gel, eluting with ethyl acetate/hexane, to afford the desired aryl ether (1.37 grams, 50%).

Part B: To a solution of the ethyl ester of part A (1.37 g, 2.7 mmol) in ethanol (30 mL) and water (30 mL) was added sodium hydroxide (1.08 g, 27 mmol), and the mixture was heated to 65 degrees Celsius for 16 hours. The solvents were then removed in vacuo. Water (50 mL) was added and the mixture was again concentrated in vacuo and the resulting mixture was acidified with 2 N HCl to pH=4–5. The solid precipitate was collected by filtration and rinsed with diethyl ether to afford the desired carboxylic acid (1.25 g, 100%).

Part C: To a suspension of the carboxylic acid of part B (1.25 g, 2.7 mmol) in N,N-dimethylformamide (15 mL) were added 4-methylmorpholine (0.82 g, 8.1 mmol), O-(tetrahydro-2H-pyran-2-yl)hydroxylamine (0.61, 4.1 mmol) followed by bromo-tris-pyrrolidino-phosphonium hexafluorophosphate (PyBroP, 1.51 g, 3.3 mmol). After stirring for 16 hours at ambient temperature, the reaction mixture was concentrated to a residue that was dissolved in ethyl acetate and washed with water and brine. Concentration and purification by chromatography on silica, gel eluting with ethyl acetate/hexane, afforded the protected hydroxamate derivative (1.0 g, 63%).

Part D: Hydrogen chloride gas was bubbled for 5 minutes through an ice bath-cooled solution of the protected hydroxamate of part C (1.0 g, 1.7 mmol) in ethyl acetate (20 mL). After stirring at ambient temperature for 5 hours, the solvent was removed in vacuo. Ethyl acetate (30 mL) was added and then removed in vacuo. Ethyl acetate (30 mL) was again added and the resulting solid was collected by filtration to afford the title compound (0.5 g, 56%). Analytical calculation for $C_{24}H_{32}N_2O_7S.HCl.1.5H_2O$: C, 51.84; H, 6.53; N, 5.04; Cl, 6.38; S, 5.77. Found: C, 51.87; H, 6.12; N, 4.92; Cl, 6.38; S, 5.84. MS $MH^+$ calculated for $C_{24}H_{32}N_2O_7S$: 493, found 493.

EXAMPLE 443

Preparation of N-Hydroxy-1-(2-5 pyridinylmethyl)-4-[4-(4-trifluoro-methoxyphenoxy)phenyl]sulfonyl]-4-piperidinecarboxamide, Dihydrochloride

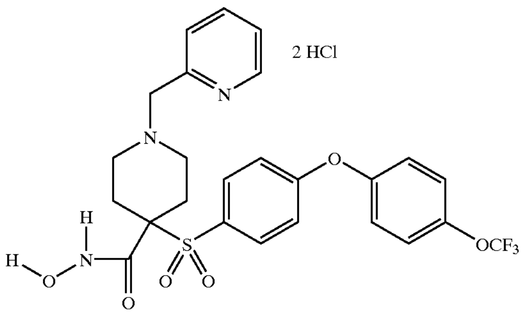

Part A: The aryl flouride from Example 9, Part D (6.22 g, 15 mmol) was combined with powdered potassium carbonate (3.04 g, 22 mmol), 4-(trifluoromethoxy)phenol (3.92 g, 322 mmol), and N,N-dimethylforamide (7 mL), and the mixture was stirred at ninety degrees Celcius for sixteen hours. Additional 4-(trifluoromethoxy)-phenol (1 g) and potassium carbonate (800 mg) were added and the reaction was continued at one hundred and fifteen degrees Celsius for twenty additional hours. The mixture was diluted with water (100 mL) and extracted with ethyl acetate (100 mL, then 2x25 mL). The combined organic layers were dried using magnesium sulfate, concentrated, and chromatographed, affording the desired aryl ether as an oil (9.6 g, about quantitative).

Part B: The aryl ether from part A (9.6 g, about 15 mmol) was dissolved in ethyl acetate (45 mL). A solution of HCl in dioxane (4N, 12 mL) was added, and the mixture was stirred at ambient temperature for three hours. Thin layer chromatography indicated incomplete deprotection. Concentrated aqueous HCl (4 mL) was added and the reaction was heated to reflux with a heat gun several times. The solution was concentrated and was then azeotroped with acetonitrile to afford the desired piperidine hydrochloride salt as a foam (9.6 g). Nuclear magnetic resonance spectroscopy indicated some contaminating 4-(trifluoromethoxy)phenol, which must have been carried through from part A.

The piperidine hydrochloride salt (6.0 g) was dissolved in ethyl acetate (125 mL) and washed with aqueous sodium hydroxide (2 g NaOH in 50 mL water). The organic layer was dried with magnesium sulfate and filtered through a pad of silica gel. The phenol contaminant was eluted. The desired piperidine was then freed from the filter cake by elution with methanol containing 1% aqueous ammonium hydroxide (circa 100 mL). The filtrate was concentrated and azeotroped with acetonitrile to yield 3.3 g (7.3 mmol).

Part C: The piperidine from Part B (1.24 g, 2.7 mmol) was combined with powdered potassium carbonate (828 mg, 6.0 mmol), 2-picolyl hydrochloride (492 mg, 3.0 mmol), and N,N-dimethylformamide (3 mL), and the mixture was stirred at ambient temperature for two hours, then heated at fifty degrees Celsius for two additional hours. The mixture was diluted with water (40 mL) and extracted with ethyl acetate (150 mL, then 50 mL). The combined organic layers were dried using magnesium sulfate, concentrated, and chromatographed, affording the desired ester as an oil (1.13 g, 74%).

Part D: The ester from part C (1.1 g, 2.0 mmol) was combined with ethanol (6 mL), water (2 mL), and potassium hydroxide (0.90 g, 16 mmol). The mixture was brought to reflux and heated for four and one-half hours. The solution was then cooled to zero degrees Celsius and acidified using concentrated aqueous hydrogen chloride. The solvent was removed, and the resulting solids were dried by azeotroping with acetonitrile. A vacuum was applied until constant weight was achieved.

The crude acid hydrochloride salt was stirred with N-methylmorpholine (about 0.5 mL), 1-hydroxybenzotriazole (0.405 g, 3 mmol), O-tetrahydropyranyl hydroxylamine (0.35 g, 3.0 mmol), and N,N-dimethyformamide (9 mL). After ten minutes, 1-(3-dimethylaminopropyl)-3-ethylcarbodiimide hydrochloride (0.57 g, 3.0 mmol) was added, and the mixture was stirred overnight. The reaction was then diluted with half-saturated aqueous sodium bicarbonate (50 mL), and extracted with ethyl acetate (100 mL, then 25 mL). The combined organic layers were dried over magnesium sulfate, concentrated, and chromatographed (9:1 ethyl acetate: methanol) to afford the desired tetrahydropyranyl-protected hydroxamate as a yellow oil (1.20 g, 95%).

Part E: The tetrahydropyranyl-protected hydroxamate (1.20 g, 1.90 mmol) was diluted with methanol (9 mL). Acetyl chloride (0.78 mL, 11 mmol) was added over two minutes. The reaction was stirred for 2 hours at ambient temperature, then concentrated to afford the desired dihydrochloride salt (1.20 g, quantitative yield) as a white crystalline solid. Anaytical calculation for $C_{25}H_{24}F_3N_3O_6S.2HCl.1/3\ H_2O$: C, 47.58; H, 4.07; N, 6.66. Found: C, 47.31; H, 4.14; N, 6.80.

EXAMPLE 444

In Vitro Metalloprotease Inhibition

The compounds prepared in the manner described in the Examples above were assayed for activity by an in vitro assay. Following the procedures of Knight et al., *FEBS Lett.* 296(3):263 (1992). Briefly, 4-aminophenylmercuric acetate (APMA) or trypsin-activated MMPs were incubated with various concentrations of the inhibitor compound at room temperature for 5 minutes.

More specifically, recombinant human MMP-13, MMP-1, MMP-2 and MMP-9 enzymes were prepared in laboratories of the assignee following usual laboratory procedures. MMP-13 from a full length cDNA clone was expressed as a proenzyme using a baculovirus as discussed in V. A. Luckow, Insect Cell Expression Technology, pages 183–218, in *Protein Engineering: Principles and Practice,* J. L. Cleland et al eds., Wiley-Liss, Inc., (1996). See, also, Luckow et al., *J. Virol.,* 67:4566–4579 (1993); O'Reilly et al., *Baculovirus Expression Vectors: A Laboratory Manual,* W. H. Freeman and Company, New York, (1992); and King et al., *The Baculovirus Expression System: A Laboratory Guide,* Chapman & Hall, London (1992) for further details on use of baculovirus expression systems. The expressed enzyme was purified first over a heparin agarose column and then over a chelating zinc chloride column. The proenzyme was activated by APMA for use in the assay.

MMP-1 expressed in transfected HT-1080 cells was provided by Dr. Harold Welgus of Washington University, St. Louis, Mo. The enzyme was also activated using APMA and was then purified over a hydroxamic acid column. Dr. Welgus also provided transfected HT-1080 cells that expressed MMP-9. Transfected cells that expressed MMP-2 were provided by Dr. Gregory Goldberg, also of Washington University. Studies carried out using MMP-2 in the presence of 0.02% 2-mercaptoethanol are shown in the table below with an asterisk. Further specifics for preparation and use of these enzymes can be found in the scientific literature describing these enzymes. See, for example, *Enzyme Nomenclature,* Academic Press, San Diego, Calif. (1992) and the citations therein, and Frije et al., *J. Biol. Chem.,* 26(24): 16766–16773 (1994). The enzyme substrate is a methoxycoumarin-containing polypeptide having the following sequence:

MCA-ProLeuGlyLeuDpaAlaArg$NH_2$, wherein MCA is methoxycoumarin and Dpa is 3-(2,4-dinitrophenyl)-L-2,3-diaminopropionyl alanine. This substrate is commercially available from Baychem as product M-1895.

The buffer used for assays contained 100 mM Tris-HCl, 100 mM NaCl, 10 mM $CaCl_2$ and 0.05 percent polyethyleneglycol (23) lauryl ether at a pH value of 7.5. Assays were carried out at room temperature, and dimethyl sulfoxide (DMSO) at a final concentration of 1 percent was used to dissolve inhibitor compound.

The assayed inhibitor compound in DMSO/buffer solution was compared to an equal amount of DMSO/buffer with no inhibitor as control using Microfluor™ White Plates (Dynatech). The inhibitor or control solution was maintained in the plate for 10 minutes and the substrate was added to provide a final concentration of 4 $\mu$M.

In the absence of inhibitor activity, a fluorogenic peptide was cleaved at the gly-leu peptide bond, separating the highly fluorogenic peptide from a 2,4-dinitrophenyl quencher, resulting in an increase of fluorescence intensity (excitation at 328 nm/emission at 415 nm). Inhibition was measured as a reduction in fluorescent intensity as a function of inhibitor concentration, using a Perkin Elmer L550 plate reader. The $IC_{50}$ values were calculated from those values. The results are set forth in the Inhibition Tables A and P below, reported in terms of $IC_{50}$ to three significant figures, where appropriate.

Inhibition TABLE A

| | (nM) | | | |
|---|---|---|---|---|
| Example Number | MMP-13 $IC_{50}$ (nM) | MMP-2 $IC_{50}$ (nM) | MMP-1 $IC_{50}$ (nM) | MMP-9 $IC_{50}$ (nM) |
| 1 | 5.1 | 2.6 | 6600 | 31.6 |
| 2 | 0.25 | 0.1 | 220 | 1.4 |
| 3 | 0.3 | 0.2 | 1140 | |
| 4 | 0.35 | 0.23 | 1090 | 5 |
| 5 | 4800 | 1800 | >10000 | |
| 6 | 0.25 | 0.15 | 327 | |
| 7 | 37.2 | 1.8 | >10000 | 235 |
| 8 | 24.1 | 4 | >10000 | 290 |
| 9 | 0.5 | 0.2 | 9000 | 1.5 |
| 10 | 0.4 | 0.2 | 1600 | 0.3 |
| 11 | 6 | 4.4 | >10000 | |
| 12 | <0.1 | <0.1 | 464 | |
| 13 | 0.6 | 0.4 | >10000 | 8 |
| 14 | 0.1 | <0.1 | 464 | |
| 15 | 0.4 | 0.2 | 3600 | 0.2 |
| 16 | 2.4 | 100 | >10000 | 2500 |
| 17 | 0.3 | 0.2 | 400 | 0.3 |
| 18 | 0.5 | 0.3 | 800 | |
| 19 | 9 | 13.9 | >10000 | |
| 20 | 1.7 | 23.5 | 10000 | |
| 21 | 0.6 | 1.3 | >10000 | |
| 22 | 1.2 | 0.9 | >10000 | |
| 23 | 0.2 | <0.1 | 2275 | |
| 24 | 0.4 | 1 | >10000 | 3.7 |
| 25 | 3 | 2.6 | >10000 | |
| 26 | 0.5 | 0.2 | 7700 | 7 |
| 27 | 0.45 | 0.4 | >10000 | 4 |
| 28 | <0.1 | <0.1 | 770 | |
| 29 | 0.3 | 0.15 | >10,000 | |

Inhibition TABLE B

| | (nM) | | | |
|---|---|---|---|---|
| Example Number | MMP-1 $IC_{50}$ (nM) | MMP-2 $IC_{50}$ (nM) | MMP-9 $IC_{50}$ (nM) | MMP-13 $IC_{50}$ (nM) |
| 30 | 350 | 0.1 | 0.3 | 0.1 |
| 31 | 370 | <0.1 | | 0.2 |
| 32 | >10000 | 0.1 | 2.5 | 0.2 |
| 33 | >10000 | 0.5 | 9.4 | 0.8 |
| 34 | >10000 | 1.1 | | 1.2 |
| 35 | >10000 | 0.3 | 3 | 0.5 |
| 36 | 7300 | 0.4 | 8 | 0.6 |
| 37 | 1000 | 0.2 | | 0.3 |
| 38 | >10000 | 20 | 135 | 22 |
| 39 | >10000 | 230 | | 24.5 |
| 40 | 4400 | 0.4 | 2.4 | 1.9 |
| 41 | 1200 | 0.15 | | 0.2 |
| 42 | 2200 | 0.2 | 1.3 | 0.4 |
| 43 | 7000 | 0.4 | | 0.8 |
| 44a | >10000 | <0.1 | | 0.2 |
| 44b | >10000 | 8000 | | >10000 |
| 45 | 8800 | 2.5 | | 1.7 |
| 46 | 710000 | — | — | 710000 |
| 47a | >10000 | 7 | | 14.6 |
| 47b | >10000 | 3000 | | 3100 |
| 48 | 210 | 0.2 | | 0.25 |
| 49 | >10000 | 76.9 | | 90.0 |
| 51 | 5500 | 0.7 | | 1.3 |
| 52 | >10000 | 2.7 | | 5.9 |
| 53 | >10000 | 0.3 | 92 | 1.5 |
| 54 | >10000 | 60 | | 120 |
| 55 | 1200 | 0.1 | | 0.3 |
| 56 | 1500 | <0.1 | | 0.15 |
| 57 | 1200 | <0.1 | | 0.2 |
| 58 | >10000 | 83 | | 30 |
| 59 | >10000 | 130 | | 180 |
| 60 | >10000 | 64 | | 147 |
| 61 | >10000 | 1500 | | 2000 |
| 62 | >10000 | >10000 | | >10000 |
| 63 | >10000 | 18.1 | 530 | 1.5 |
| 64 | 1470 | <0.1 | | 0.15 |
| 65 | 8000 | 0.6 | 4.4 | 0.7 |
| 66 | >10000 | 4590 | | 36000 |
| 67 | 1600 | 239 | | 268 |
| 68 | >10000 | 5.3 | 130 | 6 |
| 69 | 1140 | <0.1 | 0.2 | <0.1 |
| 70 | 1500 | 0.2 | 7.3 | 0.8 |
| 71 | 3600 | 0.35 | 5 | 0.8 |
| 72 | 2100 | <0.1 | | 0.3 |
| 73 | 1140 | <0.1 | 0.2 | <0.1 |
| 74 | >10000 | 130 | | 480 |
| 75 | >10000 | 60 | | 900 |
| 78 | >10000 | 6 | 50 | 10 |
| 79 | >10000 | 1 | | 1.7 |
| 80 | 3000 | 0.1 | 1.8 | 0.2 |
| 81 | 3300 | 0.1 | | 0.3 |
| 82 | 4000 | 0.1 | | 0.3 |
| 83 | 8000 | 1.2 | 5 | 1.5 |
| 84 | 8000 | 1.8 | | 2.5 |
| 85 | 500 | <0.1 | 0.4 | <0.1 |
| 86 | >10000 | 2.5 | | 3.5 |
| 87 | 7200 | 0.8 | 13.9 | 0.35 |
| 88 | 1100 | 0.2 | 0.5 | 0.2 |
| 89 | 1200 | 0.15 | 0.4 | 0.25 |
| 90 | 1200 | 0.1 | | 0.1 |
| 91 | 1800 | 1.5 | 40 | 2.1 |
| 92 | >10000 | 1800 | | 2430 |
| 93 | 8000 | 0.4 | 3.5 | 0.7 |
| 94 | 268 | <0.1 | 0.4 | <0.1 |
| 95 | >10000 | 1 | 3.6 | 0.5 |
| 96 | 5000 | 0.2 | 1.3 | 0.3 |
| 97 | 4000 | 8.2 | | 16.7 |
| 98 | >10000 | 37 | | 23.4 |
| 99 | >10000 | 0.4 | | 1 |
| 100 | 435 | <0.1 | 0.3 | 0.15 |
| 101 | 1800 | 0.3 | 2.9 | 0.45 |
| 102 | 2000 | <0.1 | | 0.2 |
| 103 | >10000 | 0.8 | 10 | 0.7 |
| 104 | >10000 | 1.5 | 42.8 | 0.65 |

Inhibition TABLE B-continued

| | (nM) | | | |
|---|---|---|---|---|
| Example Number | MMP-1 $IC_{50}$ (nM) | MMP-2 $IC_{50}$ (nM) | MMP-9 $IC_{50}$ (nM) | MMP-13 $IC_{50}$ (nM) |
| 105 | >10000 | 3500 | 114 | 0.85 |
| 106 | >10000 | 27.1 | | 12.1 |
| 107 | >10000 | 12.1 | | 6 |
| 108 | 2000 | 0.4 | | 0.4 |
| 109 | 500 | 0.1 | 0.7 | 0.3 |
| 110 | 2700 | 0.4 | 10 | 0.5 |
| 111 | 3700 | 0.5 | | 1.3 |
| 112 | 1000 | 7 | | 3.2 |
| 113 | >10000 | 0.9 | | 4 |
| 114 | 3000 | 0.65 | 31.6 | 0.4 |
| 115 | 4500 | 0.3 | 31.6 | 0.6 |
| 116 | 2350 | 2 | 15.3 | 5.5 |
| 117 | 3700 | 0.6 | 45.4 | 4.8 |
| 118 | 2850 | 0.3 | 50 | 0.8 |
| 119 | >10000 | 1.5 | 30 | 1.7 |
| 120 | 4000 | 0.4 | | 0.4 |
| 121 | 1200 | <0.1 | | 0.2 |
| 122 | 600 | 0.1 | | 0.15 |
| 123 | 3600 | 1.8 | 27.8 | 1.8 |
| 124 | 1000 | 0.5 | | 1.1 |
| 125 | >10000 | 0.4 | 7 | 0.5 |
| 126 | 8000 | 11.3 | | 10 |
| 127 | >10000 | 37 | | 40 |
| 128 | >10000 | 23.8 | | 20 |
| 129 | >10000 | >100 | | 1000 |
| 130 | >10000 | 57.7 | | 45.9 |
| 131 | >10000 | 650 | | 10 |
| 132 | >10000 | 420 | | |
| 133 | >10000 | 90 | | 27 |
| 134 | 9000 | 29 | | 4 |
| 135 | >10000 | 500 | | 65 |
| 136 | >10000 | 445 | | 40 |
| 137 | >10000 | 300 | | 34.7 |
| 138 | >10000 | >100 | | >100 |
| 139 | >10000 | 1000 | | 25.4 |
| 140 | >10000 | 1000 | | 60 |
| 141 | >10000 | >100 | | >100 |
| 142 | >10000 | 600 | | 70 |
| 143 | >10000 | 900 | | 23.9 |
| 144 | >10000 | 800 | | 30.7 |
| 145 | >10000 | >100 | | >100 |
| 146 | >10000 | 650 | | 32.6 |
| 147 | >10000 | 2700 | | 31 |
| 148 | >10000 | 2400 | | 31 |
| 149 | >10000 | 1600 | | 15.5 |
| 150 | >10000 | 1300 | | 14.5 |
| 151 | >10000 | 1500 | | 35 |
| 152 | >10000 | 2400 | | 16.5 |
| 153 | >10000 | 2700 | | 13.5 |
| 154 | >10000 | 1600 | | 27 |
| 155 | >10000 | >1000 | | >100 |
| 156 | >10000 | 3300 | | 27.8 |
| 157 | >10000 | 6000 | | 90 |
| 158 | >10000 | 5000 | | 80 |
| 159 | >10000 | 2500 | | 15.6 |
| 160 | >10000 | 4700 | | 33.7 |
| 161 | >10000 | >1000 | | >100 |
| 162 | >10000 | >1000 | | >100 |
| 163 | >10000 | 4000 | | 77.4 |
| 164 | >10000 | 1750 | | 20 |
| 165 | >10000 | 330 | | 13.6 |
| 166 | >10000 | >1000 | | >100 |
| 167 | >10000 | >1000 | | >100 |
| 168 | >10000 | >1000 | | >100 |
| 169 | 10000 | >1000 | | >100 |
| 170 | 10000 | >1000 | | >100 |
| 171 | >10000 | >1000 | | >100 |
| 172 | >10000 | >1000 | | >100 |
| 173 | >10000 | >1000 | | >100 |
| 174 | 8000 | 900 | | >100 |
| 175 | 10000 | >1000 | | >100 |
| 176 | >10000 | 400 | | 25 |
| 177 | >10000 | 400 | | 21 |
| 178 | >10000 | 540 | | >100 |
| 179 | >10000 | 440 | | 100 |
| 180 | 5000 | 128 | | 4 |
| 181 | 10000 | 121 | | 6.1 |
| 182 | >10000 | 240 | | 4 |
| 183 | >10000 | 288 | | 40 |
| 184 | >10000 | 94 | | 7 |
| 185 | >10000 | 210 | | 17.5 |
| 186 | >10000 | 120 | | 10 |
| 187 | >10000 | 290 | | 12.1 |
| 188 | >10000 | 350 | | 9.4 |
| 189 | 3700 | 94 | | 8 |
| 190 | >10000 | 220 | | 10.6 |
| 191 | >10000 | 350 | | 4 |
| 192 | >10000 | 330 | | 10 |
| 193 | >10000 | 390 | | 6 |
| 194 | 10000 | 165 | | 8 |
| 195 | 10000 | 100 | | 14.5 |
| 196 | >10000 | 240 | | 25 |
| 197 | 7000 | 145 | | 8 |
| 198 | >10000 | 270 | | 14.5 |
| 199 | >10000 | 155 | | 1.4 |
| 200 | >10000 | 24 | | 17.5 |
| 201 | >10000 | 22.4 | | 13.6 |
| 202 | >10000 | 54 | | 9.15 |
| 203 | 8500 | 31 | | 30 |
| 204 | >10000 | 25 | | 27.1 |
| 205 | 7300 | 12.7 | | 2 |
| 206 | >10000 | >10.0 | | 20 |
| 207 | >10000 | 30.6 | | 28 |
| 208 | >10000 | 27 | | 27 |
| 209 | >10000 | 19 | | 20 |
| 210 | >10000 | 27 | | 20 |
| 211 | >10000 | 33 | | 24 |
| 212 | >10000 | 33 | | 20 |
| 213 | 310 | <1.0 | | <1.0 |
| 214 | 1100 | <1.0 | | <1.0 |
| 215 | 250 | <1.0 | | <1.0 |
| 216 | 1000 | <1 | | <1.0 |
| 217 | 600 | <1.0 | | <1.0 |
| 218 | >10000 | <1.0 | | <1.0 |
| 219 | >10000 | <1.0 | | <1.0 |
| 220 | 145 | <1.0 | | <1.0 |
| 221 | 1600 | <1.0 | | <1.0 |
| 222 | 100 | <1.0 | | <1.0 |
| 223 | 1100 | <1.0 | | <1.0 |
| 224 | >10000 | 18.1 | | 16.7 |
| 225 | >10000 | 54 | | 70 |
| 226 | >10000 | 18.6 | | 6 |
| 227 | >10000 | <1 | | <1 |
| 228 | 600 | <1.0 | | <1.0 |
| 229 | >10000 | <1 | | <1 |
| 230 | >10000 | >100 | | >100 |
| 231 | 650 | <1.0 | | <1.0 |
| 232 | 100 | <1.0 | | <1.0 |

EXAMPLE 445

In Vivo Angiogenesis Assay

The study of angiogenesis depends on a reliable and reproducible model for the stimulation and inhibition of a neovascular response. The corneal micropocket assay provides such a model of angiogenesis in the cornea of a mouse. See, *A Model of Angiogenesis in the Mouse Cornea; Kenyon, B M, et al., Investigative Ophthalmology & Visual Science, July* 1996, Vol. 37, No. 8.

In this assay, uniformly sized Hydron™ pellets containing bFGF and sucralfate were prepared and surgically implanted into the stroma mouse cornea adjacent to the temporal limbus. The pellets were formed by making a suspension of 20 μL sterile saline containing 10 μg recombinant bFGF, 10 mg of sucralfate and 10 μL of 12 percent Hydron™ in ethanol. The slurry was then deposited on a 10×10 mm piece of sterile nylon mesh. After drying, the nylon fibers of the mesh were separated to release the pellets.

The corneal pocket is made by anesthetizing a 7 week old C57Bl/6 female mouse, then proptosing the eye with a jeweler's forceps. Using a dissecting microscope, a central, intrastromal linear keratotomy of approximately 0.6 mm in length is performed with a #15 surgical blade, parallel to the insertion of the lateral rectus muscle. Using a modified cataract knife, a lamellar micropocket is dissected toward the temporal limbus. The pocket is extended to within 1.0 mm of the temporal limbus. A single pellet was placed on the corneal surface at the base of the pocket with a jeweler's forceps. The pellet was then advanced to the temporal end of the pocket. Antibiotic ointment was then applied to the eye.

Mice were dosed on a daily basis for the duration of the assay. Dosing of the animals was based on bioavailability and overall potency of the compound. an exemplary dose was 10 or 50 mg/kg (mpk) bid, po. Neovascularization of the corneal stroma begins at about day three and was permitted to continue under the influence of the assayed compound until day five. At day five, the degree of angiogenic inhibition was scored by viewing the neovascular progression with a slit lamp microscope.

The mice were anesthetized and the studied eye was once again proptosed. The maximum vessel length of neovascularization, extending from the limbal vascular plexus toward the pellet was measured. In addition, the contiguous circumferential zone of neovascularization was measured as clock hours, where 30 degrees of arc equals one clock hour. The area of angiogenesis was calculated as follows.

$$\text{area} = \frac{(0.4 \times \text{clock hours} \times 3.14 \times \text{vessel length (in mm)})}{2}$$

Five to six mice were utilized for each compound in each study. The studied mice were thereafter compared to control mice and the difference in the area of neovascularization was recorded as an averaged value. Each group of mice so studied constitutes an "n" value of one, so that "n" values greater than one represent multiple studies whose averaged result is provided in the table. A contemplated compound typically exhibits about 25 to about 75 percent inhibition, whereas the vehicle control exhibits zero percent inhibition.

Data for four compounds of the above examples are provided below at dosages of 10 and 50 mpk.

Inhibition of Angiogenesis

| Example | Dosage 10 mpk | 50 mpk |
|---|---|---|
| Marimastat | — | 48 (n = 6) |
| 4 | 18 (n = 3) | 41 (n = 6) |
| 9 | 50 (n = 2) | 46 (n = 3) |
| 10 | 47 (n = 1) | 54 (n = 2) |
| 24 | 53 (n = 1) | 78 (n = 1) |

EXAMPLE 446

In Vivo PC-3 Tumor Reduction

PC-3 human pancreatic cancer cells (ATCC CRL 1435) were grown to 90% confluence in F12/MEM (Gibco) containing 7% FBS (Gibco). Cells were mechanically harvested using a rubber scraper, and then washed twice with cold medium. The resulting cells were resuspended in cold medium with 30% matrigel (Collaborative Research) and the cell-containing medium was maintained on ice until used.

Balb/c nu/nu mice at 7–9 weeks of age were anesthetized with avertin [2,2,2-tribromethanol/t-amyl alcohol (1 g/l mL) diluted 1:60 into phosphate-buffered sline] and 3–5×$10^6$ of the above cells in 0.2 mL of medium were injected into the left flank of each mouse. Cells were injected in the morning, whereas dosing with an inhibitor began at 6 PM. The animals were gavaged BID from day zero (cell injection day) to day 25–30, at which time the animals were euthanized and tumors weighed.

Compounds were dosed at 10 mg/mL in 0.5% methylcellulose/0.1% polysorbate 80 to provide a 50 mg/kg (mpk) dose twice each day, or diluted to provide a 10 mg/kg (mpk) dose twice each day. Tumor measurements began on day 7 and continued every third or fourth day until completion of the study. Groups of ten mice were used in each study and nine to ten survived. Each group of mice so studied constitutes an "n" value of one, so that "n" values greater than one represent multiple studies whose averaged result is provided in the table. The results of this study for several of the before discussed compounds are shown below as average reductions in tumor weight.

Average Percentage Reduction In Tumor Weight

| Example | Dosage 10 mpk | 50 mpk |
|---|---|---|
| Marimastat | <5 | 39 (n = 2) |
| 4 | 33 (n = 2) | 43 (n = 2) |
| 9 | 40 (n = 1) | 60 (n = 1) |
| 10 | nt | 59 (n = 1) |

EXAMPLE 447

Tumor Necrosis Factor Assays

Cell Culture.

The cells used in the assay are the human moncytic line U-937 (ATCC CRL-1593). The cells are grown in RPMI w/10% FCS and PSG supplement (R-10) and are not permitted to overgrow. The assay is carried out as follows:

1. Count, then harvest cells by centrifugation. Resuspend the pellet in R-10 supplement to a concentration of 1.540×$10^6$ cells/mL.
2. Add test compound in 65 uL R-10 to the appropriate wells of a 96-well flat bottom tissue culture plate. The initial dilution from a DMSO stock (100 mM compound) provides a 400 uM solution, from which five additional three-fold serial dilutions are made. Each dilution of 65 ul (in triplicate) yields final compound test concentrations of 100 $\mu$M, 33.3 $\mu$M, 11.1 $\mu$M, 3.7 $\mu$M, 1.2 $\mu$M and 0.4 $\mu$M.
3. The counted, washed and resuspended cells (200,000 cells/well) in 130 $\mu$L are added to the wells.
4. Incubation is for 45 minutes to one hour at 37° C. in 5% CO2 in a water saturated container.
5. R-10 (65 uL)containing 160 ng/mL PMA (Sigma) is added to each well.
6. The test system is incubated at 37° C. in 5% CO2 overnight (18–20 hours) under 100% humidity.

7. Supernatant, 150 $\mu$L, is carefully removed from each well for use in the ELISA assay.
8. For toxicity, a 50 $\mu$L aliquot of working solution containg 5 mL R-10, 5 mL MTS solution [CellTiter 96 AQueous One Solution Cell Proliferation Assay Cat.#G358/0,1 (Promega Biotech)] and 250 ul PMS solution are added to each well containing the remaining supernatant and cells and the cells incubated at 37° C. in 5% $CO_2$ until the color develops. The system is excited at 570 nm and read at 630 nm.

TNF Receptor II ELISA Assay

1. Plate 100 $\mu$L/well 2 ug/mL mouse anti-human TNFrII antibody (R&D Systems #MAB226) in 1× PBS (pH 7.1, Gibco) on NUNC-Immuno Maxisorb plate. Incubate the plate at 4° C. overnight (about 18–20 hours).
2. Wash the plate with PBS-Tween (1× PBS w/ 0.05% Tween).
3. Add 200 $\mu$L 5% BSA in PBS and block at 37° C. in a water saturated atmosphere for 2 hours.
4. Wash the plate with PBS-Tween.
5. Add sample and controls (100 ul of each) to each well. The standards are 0, 50, 100, 200, 300 and 500 pg recombinant human TNFrII (R&D Systems #226-B2) in 100 $\mu$L 0.5% BSA in PBS. The assay is linear to between 400–500 pg of standard.
6. Incubate at 37° C. in a saturated atmosphere for 1.5 hours.
7. Wash the plate with PBS-Tween.
8. Add 100 $\mu$L goat anti-human TNFrII polyclonal (1.5 $\mu$g/mL R&D Systems #AB226-PB in 0.5% BSA in PBS).
9. Incubate at 37° C. in a saturated atmosphere for 1 hour.
10. Wash the plate with PBS-Tween.
11. Add 100 pL anti-goat IgG-peroxidase (1:50,000 in 0.5% BSA in PBS, Sigma #A5420).
11. Incubate at 37° C. in a saturated atmosphere for 1 hour.
12. Wash the plate with PBS-Tween.
13. Add 10 $\mu$L KPL TMB developer, develop at room temperature (usually about 10 minutes), then terminate with phosphoric acid and excite at 450 nm and read at 570 nm.

TNFα ELISA Assay

Coat Immulon® 2 plates with 0.1 mL/well of lug/mL Genzyme mAb in 0.1 M NaHCO3 pH 8.0 buffer overnight (about 18–20 hours) at 4° C., wrapped tightly in Saran® wrap.

Flick out coating solution and block plates with 0.3 mL/well blocking buffer overnight at 4° C., wrapped in Saran® wrap.

Wash wells thoroughly 4× with wash buffer and completely remove all wash buffer. Add 0.1 mL/well of either samples or rhTNFα standards. Dilute samples if necessary in appropriate diluant (e.g. tissue culture medium). Dilute standard in same diluant. Standards and samples should be in triplicates.

Incubate at 37° C. for 1 hour in humified container.

Wash plates as above. Add 0.1 mL/well of 1:200 dilution of Genzyme rabbit anti-hTNF Repeat incubation.

Repeat wash. Add 0.1 mL/well of 1 $\mu$g/mL Jackson goat anti-rabbit IgG (H+L)-peroxidase.

Incubate at 37° C. for 30 minutes.

Repeat wash. Add 0.1 mL/well of peroxide-ABTS solution.

Incubate at room temperature for 5–20 minutes.

Read OD at 405 nm.

12 Reagents are:

Genzyme mouse anti-human TNF? monoclonal (Cat.# 80-3399-01)

Genzyme rabbit anti-human TNF? polyclonal (Cat.#IP-300)

Genzyme recombinant human TNF? (Cat.#TNF-H).

Jackson Immunoresearch peroxide-conjugated goat anti-rabbit IgG (H+L) (Cat.#111-035-144).

Kegaard/Perry peroxide ABTS solution (Cat#50-66-01).

Immulon 2 96-well microtiter plates.

Blocking solution is 1 mg/mL gelatin in PBS with 1× thimerasol.

Wash buffer is 0.5 mL Tween® 20 in 1 liter of PBS.

Results

| Example Number | MTS Toxicity $TD_{50}$ in micromolar | TNFRII Release $IC_{50}$ in micromolar | TNFα Release $IC_{50}$ in micromolar |
|---|---|---|---|
| DMSO | >100 | >100 | >100 |
| 4 | >100 | >100 | >50 |
| 6 | >100 | >100 | >50 |
| 9 | >100 | >100 | >50 |
| 10 | >100 | >100 | >50 |
| 13 | >100 | >100 | >50 |
| 27 | 100 | >100 | >80 |
| 35 | >100 | >100 | >80 |
| 69 | 100 | >100 | >80 |
| 95 | >100 | >100 | >50 |
| 379 | 80 | >100 | 80 |

EXAMPLE 448

Pharmacokinetic (PK)-evaluation of MMP Inhibitors in Rats

Under metofane anesthesia, the femoral artery (all 8 rats) and femoral vein (only 4 of 8 rats) are isolated and canulated with PESO tubing and secured with 3.0 silk suture. The following determinations require two catheters, with the venous line being used for infusion of compound (in the group of rats that receives compound via the intraveneous (IV)route.), and the arterial line being used for collection of blood samples. The rats are then placed in restraining cages that permit minimal movement and allowed to recover from anesthesia for approximately 30 minutes. At time 0 (prior to dosing), blood samples (400 $\mu$L) are collected from arterial cannula.

One group of rats (4 rats per group) receives compound via the oral route at a dosing volume of 2 mL/kg (10 mg/mL, dissolved in 0.5% methylcellulose, 0.1% Tween® 20), while the other group of rats receives compound via the intravenous cannula, at a dosing volume of 2 ml/kg (10 mg/mL, dissolved in 10% EtOH, 50% PEG 400, 40% saline). The blood samples are collected from the arterial cannula at 15, 30, 60, 120, 240, and 360 minutes from the oral group with an additional 3 minute sample being collected from IV group. After each sample, the cannulas are flushed with PBS containing 10 units/ml heparin. The animals are subjected to euthanasia with an excess of anesthesia.or carbon monoxide asphyxiation when the study is terminated at 6 hours. Blood samples from each time point are assayed for MMP-13 enzyme inhibitory activity and the circulating concentration of compound plus active metabolites is estimated based on the standard curve. Pharmacokinetic (PK) parameters are calculated by the VAX computer program CSTRIP. The parameters are defined in textbooks such as *Goodman and Gilman's The Pharmacological Basis of Therapeutics,* eighth ed., McGraw-Hill, Inc., New York (1993) and the references therein.

| | Rat Intraveneous 20 mpk | | | Rat Oral 20 mpk | | | |
|---|---|---|---|---|---|---|---|
| Example Number | t1/2 Hour | AUC (0–∞) hr * μg/mL | Blood Level @ 3 min μg/mL | Cmax μg/mL | AUC (0–6 hr) hr * μg/mL | BA % | Blood Level @ 6 hr μg/mL |
| 4 | 1.77 | 24.80 | 37.60 | 1.84 | 4.14 | 16.7 | 0.254 |
| 6 | 1.19 | 46.39 | 84.72 | 22.88 | 16.45 | 35.5 | 0.345 |
| 9 | 1.10 | 33.67 | 42.17 | 13.63 | 9.43 | 28.0 | 0.281 |
| 10 | 0.84 | 43.01 | 73.00 | 18.47 | 12.93 | 30.1 | 0.134 |
| 12 | 0.86 | 22.11 | 73.54 | 1.00 | 2.45 | 11.1 | 0.121 |
| 13 | 1.03 | 43.08 | 91.07 | 21.98 | 18.08 | 42.0 | 0.228 |
| 14 | 1.25 | 12.92 | 12.10 | 4.13 | 7.66 | 59.3 | 0.102 |
| 15 | 1.01 | 49.29 | 120.83 | 27.16 | 18.19 | 36.9 | 0.192 |
| 17 | 0.74 | 37.10 | 63.44 | 15.72 | 13.32 | 35.9 | 0.135 |
| 22 | 1.47 | 14.05 | 18.06 | 0.82 | 1.82 | 13.0 | 0.174 |
| 23 | 0.85 | 25.01 | 59.92 | 7.31 | 5.93 | 23.7 | 0.087 |
| 24 | 2.49 | 37.35 | 62.52 | 9.79 | 15.88 | 42.5 | 0.545 |
| 25 | — | — | — | 1.48 | | | 0.173 |
| 26 | 0.58 | 17.51 | 64.01 | 0.29 | 0.83 | 4.7 | 0.051 |
| 27 | 1.10 | 43.32 | 43.69 | 10.87 | 21.24 | 49.0 | 0.427 |
| 28 | — | — | — | 10.02 | 24.28 | | 0.537 |
| 32 | 1.03 | 38.94 | 51.48 | 7.65 | 13.48 | 34.6 | 0.529 |
| 33 | 1.91 | 29.96 | 24.13 | 3.33 | 8.25 | 27.5 | 0.543 |
| 34 | — | — | — | 2.13 | | | 0.495 |
| 35 | — | — | — | 12.59 | 26.97 | | 1.237 |
| 36 | 0.65 | 5.74 | 19.66 | 0.16 | 0.73 | 12.7 | 0.072 |
| 40 | — | — | — | 1.55 | | | 0.128 |
| 42 | — | — | — | 0.71 | | | 0.036 |
| 43 | 0.82 | 18.79 | 61.76 | 4.17 | 3.24 | 17.2 | 0.040 |
| 53 | 0.97 | 10.78 | 31.68 | 0.37 | 0.48 | 4.4 | BLD |
| 65 | — | — | — | 0.99 | | | 0.080 |
| 68 | — | — | — | 3.41 | | | 0.038 |
| 69 | 1.87 | 63.78 | 44.00 | 8.58 | 22.89 | 35.9 | 1.172 |
| 70 | — | — | — | 3.08 | | | 0.131 |
| 71 | — | — | — | 4.00 | | | 0.452 |
| 72 | — | — | — | 1.42 | 2.03 | | 0.062 |
| 73 | — | — | — | 1.89 | 6.87 | | 0.372 |
| 79 | 1.82 | 6.11 | 13.99 | 0.02 | 0.07 | 1.1 | 0.010 |
| 80 | — | — | 40.83 | 0.03 | | | 0.003 |
| 81 | 0.76 | 38.21 | 89.01 | 5.06 | 6.40 | 16.7 | 0.074 |
| 89 | — | — | — | 1.68 | | | 0.196 |
| 90 | — | — | — | 0.08 | | | 0.041 |
| 91 | — | — | — | 0.17 | | | 0.138 |
| 93 | 1.81 | 13.48 | 20.88 | 0.35 | 1.55 | 11.5 | 0.126 |
| 94 | 1.71 | 25.13 | 43.37 | 0.87 | 1.34 | 5.3 | 0.050 |
| 95 | 1.06 | 19.74 | 34.71 | 1.74 | 4.86 | 24.6 | 0.148 |
| 96 | | | | 0.43 | | | 0.076 |
| 99 | 0.68 | 35.68 | 99.49 | 14.25 | 8.05 | 22.6 | 0.071 |
| 100 | 1.50 | 24.60 | 26.06 | 3.12 | 11.30 | 45.9 | 0.506 |
| 103 | 1.10 | 19.66 | 31.11 | 2.55 | 0.09 | 19.9 | 0.092 |
| 104 | 0.66 | 9.86 | 29.82 | 9.89 | 4.88 | 49.4 | 0.008 |
| 108 | — | — | — | 2.96 | | | 0.108 |
| 109 | 1.12 | 7.13 | 13.91 | 0.93 | 0.85 | 11.9 | 0.027 |
| 110 | | | 2.67 | 0.02 | | | 0.015 |
| 111 | 0.65 | 8.49 | 33.56 | 0.45 | 1.11 | 13.1 | 0.054 |
| 115 | 1.36 | 7.81 | 12.95 | 1.17 | 2.00 | 25.6 | 0.058 |
| 117 | 0.78 | 8.69 | 40.50 | 0.18 | 0.28 | 3.3 | 0.016 |
| 118 | 1.85 | 10.97 | 17.18 | 0.75 | 3.32 | 30.3 | 0.268 |
| 121 | — | — | — | 0.31 | | | 0.055 |
| 123 | — | — | — | 1.43 | | | 0.017 |
| 125 | 0.73 | 15.73 | 25.36 | 1.11 | 2.50 | 15.9 | 0.119 |
| 233 | 0.85 | 23.12 | 31.90 | 3.33 | 6.22 | 26.9 | 0.584 |
| 379 | 1.74 | 51.41 | 37.54 | 4.30 | 16.80 | 32.7 | 1.154 |
| 382 | 1.71 | 73.68 | 48.81 | 7.27 | 36.12 | 49.0 | 3.113 |
| 387 | — | — | — | 0.65 | | | 0.558 |
| 388 | 0.94 | 26.10 | 34.62 | 0.15 | 0.68 | 2.6 | 0.073 |
| 390 | 1.50 | 127.63 | 120.60 | 23.21 | 44.20 | 34.6 | 1.780 |
| 391 | 1.45 | 120.92 | 82.87 | 24.02 | 73.24 | 60.6 | 2.680 |
| 400 | | | 104.34 | 8.55 | | | 0.160 |
| 408 | 3.30 | 25.18 | 57.40 | 9.46 | 4.17 | 16.6 | 0.015 |
| 410 | 1.78 | 29.83 | 40.08 | 0.63 | 2.08 | 6.7 | 0.223 |

-continued

| | Rat Intraveneous 20 mpk | | | Rat Oral 20 mpk | | | |
|---|---|---|---|---|---|---|---|
| Example Number | t1/2 Hour | AUC (0–∞) hr * μg/mL | Blood Level @ 3 min μg/mL | Cmax μg/mL | AUC (0–6 hr) hr * μg/mL | BA % | Blood Level @ 6 hr μg/mL |
| 414 | 0.73 | 26.15 | 61.89 | 5.31 | 6.22 | 23.8 | 0.021 |
| 416 | 2.94 | 230.70 | 111.17 | 29.63 | 156.71 | 67.9 | 20.52 |
| 418 | 2.42 | 209.92 | 78.55 | 20.65 | 77.52 | 36.9 | 7.347 |
| 421 | — | — | — | 13.08 | 19.21 | | 0.206 |
| 427 | 2.85 | 36.72 | 50.74 | 4.16 | 8.44 | 23.0 | 0.440 |
| 437 | — | — | — | 4.21 | 4.43 | | 0.128 |
| 438 | 2.14 | 9.05 | 7.46 | 0.39 | 1.86 | 20.6 | 0.316 |

From the foregoing, it will be observed that numerous modifications and variations can be effectuated without departing from the true spirit and scope of the novel concepts of the present invention. It is to be understood that no limitation with respect to the specific example presented is intended or should be inferred. The disclosure is intended to cover by the appended claims all such modifications as fall within the scope of the claims.

What is claimed:

1. A process for treating a host mammal having a condition associated with pathological matrix metalloprotease (MMP) activity, wherein:

the process comprises administering a metalloprotease inhibitor compound or a pharmaceutically acceptable salt thereof in an effective amount to a mammalian host having such a condition;

said compound or salt inhibits the activity of one or more of MMP-2, MMP-9, and MMP-13, while exhibiting substantially less inhibiting activity against MMP-1;

said compound corresponds in structure to formula (II) below:

II

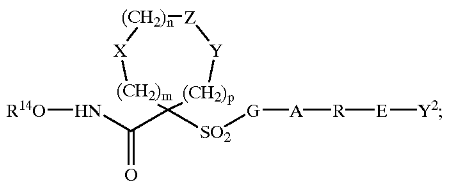

$R^{14}$is selected from the group consisting ofhydrogen and $C(W)R^{15}$;

W is selected from the group consisting of O and S;

$R^{15}$ is selected from the group consisting of $C_1$–$C_6$-alkyl, aryl, $C_1$–$C_6$-alkoxy, heteroaryl-$C_1$–$C_6$-alkyl, $C_3$–$C_8$-cycloalkyl-$C_1$–$C_6$-alkyl, aryloxy, aryl-$C_1$–$C_6$-alkoxy, aryl-$C_1$–$C_6$-alkyl, heteroaryl, and amino-$C_1$–$C_6$-alkyl, wherein:

the aminoalkyl nitrogen optionally is substituted with up to two substituents independently selected from the group consisting of $C_1$–$C_6$-alkyl, aryl, aryl-$C_1$–$C_6$-alkyl, $C_3$–$C_8$-cycloalkyl-$C_1$–$C_6$-alkyl, aryl-$C_1$–$C_6$-alkoxycarbonyl, $C_1$–$C_6$-alkoxycarbonyl, and $C_1$–$C_6$-alkanoyl, or the aminoalkyl nitrogen optionally is substituted with two substituents such that the aminoalkyl nitrogen and the two substituents together form a 5- to 8-membered heterocyclo or heteroaryl ring;

m is selected from the group consisting of zero, 1, and 2;

n is selected from the group consisting of zero, 1, and 2;

p is selected from the group consisting of zero, 1, and 2;

the sum of m+n+p is selected from the group consisting of 1, 2, 3, and 4;

as to X, Y, and Z:

(a) one of X, Y, and Z is selected from the group consisting of $NR^6$, O, S, S(O), $S(O)_2$, and $NS(O)_2R^7$, and the remaining two of X, Y, and Z are $CR^8R^9$ and $CR^{10}R^{11}$, or (b) X and Z or Z and Y together constitute a moiety that is selected from the group consisting of $NR^6C(O)$, $NR^6S(O)$, $NR^6S(O)_2$, $NR^6S$, $NR^6O$, SS, $NR^6NR^6$, and OC(O), with the remaining one of X and Y being $CR^8R^9$, or (c) n is zero and X, Y, and Z together constitute a moiety selected from the group consisting of:

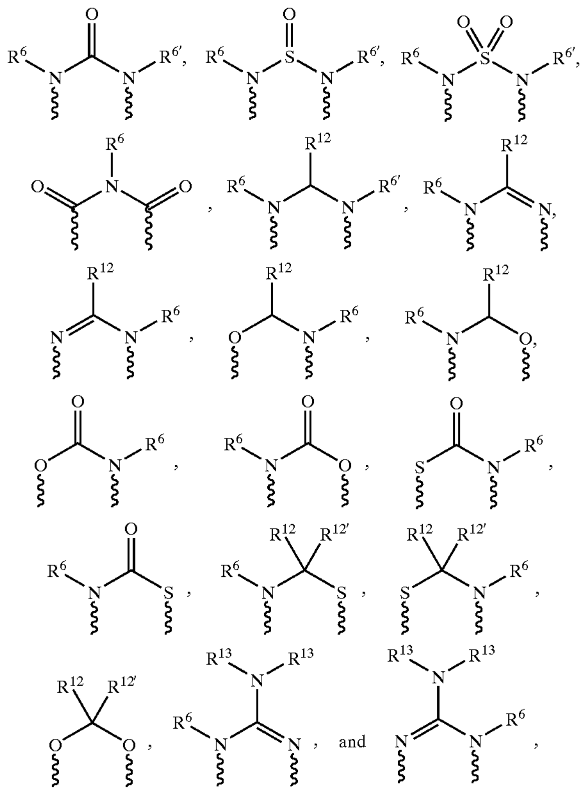

wherein the wavy lines are bonds to the atoms of the depicted ring;

each $R^6$ and $R^{6'}$ is independently selected from the group consisting of hydrogen, $C_1$–$C_6$-alkanoyl, $C_6$-aryl-$C_1$–$C_6$-alkyl, aroyl, bis($C_1$–$C_6$-alkoxy-$C_1$–$C_6$-alkyl)-$C_1$–$C_6$-alkyl, $C_1$–$C_6$-alkyl, $C_1$–$C_6$-haloalkyl, $C_1$–$C_6$-perfluoroalkyl, $C_1$–$C_6$-trifluoromethylalkyl, $C_1$–$C_6$-perfluoroalkoxy-$C_1$–$C_6$-alkyl, $C_1$–$C_6$-alkoxy-$C_1$–$C_6$-alkyl, $C_3$–$C_6$-cycloalkyl, $C_3$–$C_8$-heterocycloalkyl, $C_3$–$C_8$-heterocycloalkylcarbonyl, $C_6$-aryl, $C_5$–$C_6$-heterocyclo, $C_5$–$C_6$-heteroaryl, $C_3$–$C_8$-cycloalkyl-$C_1$–$C_6$-alkyl, $C_6$-aryloxy-$C_1$–$C_6$-alkyl, heteroaryloxy-$C_1$–$C_6$-alkyl, heteroaryl-$C_1$–$C_6$-alkoxy-$C_1$–$C_6$-alkyl, heteroarylthio-$C_1$–$C_6$-alkyl, $C_6$-arylsulfonyl, $C_1$–$C_6$-alkylsulfonyl, $C_5$–$C_6$-heteroarylsulfonyl, carboxy-$C_1$–$C_6$-alkyl, $C_1$–$C_4$-alkoxycarbonyl-$C_1$–$C_6$-alkyl, aminocarbonyl, $C_1$–$C_6$-alkyliminocarbonyl, $C_6$-aryliminocarbonyl, $C_5$–$C_6$-heterocycloiminocarbonyl, $C_6$-arylthio-$C_1$–$C_6$-alkyl, $C_1$–$C_6$-alkylthio-$C_1$–$C_6$-alkyl, $C_6$-arylthio-$C_3$–$C_6$-alkenyl, $C_1$–$C_4$-alkylthio-$C_3$–$C_6$-alkenyl, $C_5$–$C_6$-heteroaryl-$C_1$–$C_6$-alkyl, halo-$C_1$–$C_6$-alkanoyl, hydroxy-$C_1$–$C_6$-alkanoyl, thiol-$C_1$–$C_6$-alkanoyl, $C_3$–$C_6$-alkenyl, $C_3$–$C_6$-alkynyl, $C_1$–$C_4$-alkoxy-$C_1$–$C_4$-alkyl, $C_1$–$C_5$-alkoxycarbonyl, aryloxycarbonyl, $NR^8R^9$—$C_1$–$C_5$-alkylcarbonyl, hydroxy-$C_1$–$C_5$-alkyl, aminocarbonyl, hydroxyaminocarbonyl, aminosulfonyl, amino-$C_1$–$C_6$-alkylsulfonyl, and amino-$C_1$–$C_6$-alkyl, wherein:

the aminocarbonyl, aminosulfonyl, aminoalkylsulfonyl, or aminoalkyl nitrogen optionally is substituted with up to two substituents independently selected from the group consisting of $C_1$–$C_6$-alkyl, aryl-$C_1$–$C_6$-alkyl, $C_3$–$C_8$-cycloalkyl, and $C_1$–$C_6$-alkanoyl;

$R^7$ is selected from the group consisting of arylalkyl, aryl, heteroaryl, heterocyclo, $C_1$–$C_6$-alkyl, $C_3$–$C_6$-alkynyl, $C_3$–$C_6$-alkenyl, $C_1$–$C_6$-carboxyalkyl, and $C_1$–$C_6$-hydroxyalkyl;

as to $R^8$:

$R^8$ is selected from the group consisting of hydrogen, hydroxy, $C_1$–$C_6$-alkyl, aryl, aryl-$C_1$–$C_6$-alkyl, heteroaryl, heteroaryl-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, arylalkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylaryl-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, the sulfoxide of any said thio substituents, the sulfone of any said thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl, wherein:

the aminoalkyl nitrogen optionally is substituted with up to two radicals independently selected from the group consisting of $C_1$–$C_6$-alkyl, aryl-$C_1$–$C_6$-alkyl, cycloalkyl, and $C_1$–$C_6$-alkanoyl, $R^8$ and $R^9$, together with the carbon to which they are bonded, form a carbonyl group, or $R^8$ and $R^9$ or $R^8$ and $R^{10}$, together with the atom(s) to which they are bonded, form a 5- to 8-member carbocyclic ring or a 5- to 8-member heterocyclic ring containing one or two heteroatoms independently selected from the group consisting of nitrogen, oxygen, and sulfur;

as to $R^9$:

$R^9$ is selected from the group consisting of hydrogen, hydroxy, $C_1$–$C_6$-alkyl, aryl, aryl-$C_1$–$C_6$-alkyl, heteroaryl, heteroaryl-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, arylalkoxy-$C_1$–$C_6$—, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylaryl-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, the sulfoxide of any said thio substituents, the sulfone of any said thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl, wherein:

the aminoalkyl nitrogen optionally is substituted with up to two radicals independently selected from the group consisting of $C_1$–$C_6$-alkyl, aryl-$C_1$–$C_6$-alkyl, cycloalkyl, and $C_1$–$C_6$-alkanoyl, $R^8$ and $R^9$, together with the carbon to which they are bonded, form a carbonyl group, or $R^8$ and $R^9$, together with the carbon to which they are bonded, form a 5- to 8-member carbocyclic ring or a 5- to 8-member heterocyclic ring containing one or two heteroatoms independently selected from the group consisting of nitrogen, oxygen, and sulfur;

as to $R^{10}$:

$R^{10}$ is selected from the group consisting of hydrogen, hydroxy, $C_1$–$C_6$-alkyl, aryl, aryl-$C_1$–$C_6$-alkyl, heteroaryl, heteroaryl-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl cycloalkyl, cycloalkyl-$C_1$–$C_6$alkyl, heterocycloalkyl-$C_1$–$C_6$-alkyl, $C_1$–$C_6$-alkoxy-$C_1$–$C_6$-alkyl, arylalkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylaryl-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, the sulfoxide of any said thio substituents, the sulfone of any said thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl, wherein:

the aminoalkyl nitrogen optionally is substituted with up to two radicals independently selected from the group consisting of $C_1$–$C_6$-alkyl, aryl-$C_1$–$C_6$-alkyl, cycloalkyl, and $C_1$–$C_6$-alkanoyl, $R^{10}$ and $R^{11}$, together with the carbon to which they are bonded, form a carbonyl group, or $R^8$ and $R^{10}$ or $R^{10}$ and $R^{11}$, together with the atom(s) to which they are bonded, form a 5- to 8-member carbocyclic ring, or a 5- to 8-member heterocyclic ring containing one or two heteroatoms independently selected from the group consisting of nitrogen, oxygen, and sulfur;

as to $R^{11}$:

$R^{11}$ is selected from the group consisting of hydrogen, hydroxy, $C_1$–$C_6$-alkyl, aryl, aryl-$C_1$–$C_6$-alkyl, heteroaryl, heteroaryl-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio- $C_1$–$C_6$-alkyl cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, arylalkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylaryl-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, the sulfoxide of any said thio substituents, the sulfone of any said thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl, wherein:

the aminoalkyl nitrogen optionally is substituted with up to two radicals independently selected from the group consisting of $C_1$–$C_6$-alkyl, aryl-$C_1$–$C_6$-alkyl, cycloalkyl, and $C_1$–$C_6$-alkanoyl, $R^{10}$ and $R^{11}$, together with the carbon to which they are bonded, form a carbonyl group, or $R^{10}$ and $R^{11}$, together with the carbon to which they are bonded, form a 5- to 8-member carbocyclic ring or a 5- to 8-member heterocyclic ring containing one or two heteroatoms independently selected from the group consisting of nitrogen, oxygen, and sulfur;

only one of $R^8$ and $R^9$ or $R^{10}$ and $R^{11}$ is hydroxy;

$R^{12}$ and $R^{12'}$ are independently selected from the group consisting of hydrogen, $C_1$–$C_6$-alkyl, aryl, aryl-$C_1$–$C_6$-alkyl, heteroaryl, heteroarylalkyl, $C_2$–$C_6$-alkynyl, $C_2$–$C_6$-alkenyl, thiol-$C_1$–$C_6$-alkyl, cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aryloxy-$C_1$–$C_6$-alkyl, amino-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylaryl-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, $C_1$–$C_6$-alkylthio-$C_1$–$C_6$-alkyl, arylthio-$C_1$–$C_6$-alkyl, heteroarylthio-$C_1$–$C_6$-alkyl, the sulfoxide of any said thio substituents, the sulfone of any said thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl, wherein:

the aminoalkyl nitrogen optionally is substituted with up to two radicals independently selected from the group consisting of $C_1$–$C_6$-alkyl, aryl-$C_1$–$C_6$-alkyl, cycloalkyl, and $C_1$–$C_6$-alkanoyl;

$R^{13}$ is selected from the group consisting of hydrogen, benzyl, phenyl, $C_1$–$C_6$-alkyl, $C_2$–$C_6$-alkynyl, $C_2$–$C_6$-alkenyl, and $C_1$–$C_6$-hydroxyalkyl;

G—A—R—E—$Y^2$ is a substituent that has a length greater than that of a pentyl group but less than that of an icosyl group, wherein:

G is selected from the group consisting of aryl and heteroaryl;

A is selected from the group consisting of:

(1) —O—,
(2) —S—,
(3) —$NR^{17}$,
(4) —CO—N($R^{17}$),
(5) —N($R^{17}$)—CO—,
(6) —CO—O—,
(7) —O—CO—,
(8) —O—CO—O—,
(9) —HC═CH—,
(10) —NH—CO—NH—,
(11) —C≡C—,
(12) —NH—CO—O—,
(13) —O—CO—NH—,
(14) —N═N—,
(15) —NH—NH—,
(16) —CS—N($R^{18}$),
(17) —N($R^{18}$)—CS—, and
(18) a bond;

$R^{17}$ is selected from the group consisting of hydrogen, $C_1$–$C_4$-alkyl, and phenyl;

$R^{18}$ is selected from the group consisting of hydrogen, $C_1$–$C_4$-alkyl, and phenyl;

R is selected from the group consisting of alkyl, alkoxyalkyl, aryl, heteroaryl, cycloalkyl, heterocycloalkyl, arylalkyl, heteroarylalkyl, heterocycloalkylalkyl, cycloalkylalkyl, cycloalkoxyalkyl, heterocycloalkoxyalkyl, aryloxyalkyl, heteroaryloxyalkyl, arylthioalkyl, heteroarylthioalkyl, cycloalkylthioalkyl, and heterocycloalkylthioalkyl, wherein:

the aryl, heteroaryl, cycloalkyl, or heterocycloalkyl optionally is substituted with up to two radicals independently selected from the group consisting of halo, alkyl, perfluoroalkyl, perfluoroalkoxy, perfluoroalkylthio, trifluoromethylalkyl, amino, alkoxycarbonylalkyl, alkoxy, $C_1$–$C_2$-alkylene-dioxy, hydroxycarbonylalkyl, hydroxycarbonylalkylamino, nitro, hydroxy, hydroxyalkyl, alkanoylamino, and alkoxycarbonyl, and R is other than alkyl or alkoxyalkyl when A is —O—or —S—;

E is selected from the group consisting of:

(1) —CO($R^{19}$)—,
(2) —($R^{19}$)CO—,
(4) —HNCO—,
(5) —CO—,
(6) —$SO_2$—$R^{19}$—,
(7) —$R^{19}$—$SO_2$—,
(8) —$SO_2$—,
(9) —NH—$SO_2$—,
(10) —$SO_2$—NH—, and
(11) a bond;

$R^{19}$ is selected from the group consisting of heterocycloalkyl and cycloalkyl; and $Y^2$ is selected from the group consisting of hydrogen, alkyl, alkoxy, haloalkyl, aryl, arylalkyl, cycloalkyl, heteroaryl, hydroxy, aryloxy, arylalkoxy, heteroaryloxy, heteroarylalkyl, perfluoroalkoxy, perfluoroalkylthio, trifluoromethylalkyl, alkenyl, heterocycloalkyl, cycloalkyl, trifluoromethyl, alkoxycarbonyl, and aminoalkyl, wherein:

the aryl, heteroaryl, or heterocycloalkyl optionally is substituted with up to two radicals independently selected from the group consisting of alkanoyl, halo, nitro, arylalkyl, aryl, alkoxy, and amino, wherein:

the amino nitrogen optionally is substituted with up to two groups independently selected from the group consisting of hydrogen, alkyl, and arylalkyl.

2. The process according to claim 1, wherein said —G—A—R—E—Y substituent contains two to four carbocyclic or heterocyclic rings.

3. The process according to claim 2, wherein each of the two to four rings has 6 ring members.

4. The process according to claim 1, wherein said —G—A—R—E—$Y^2$ substituent has a length that is greater than that of hexyl group but less than that of a stearyl group.

5. The process according to claim 1, wherein A is selected from the group consisting of —O—and —S—.

6. The process according to claim 1, wherein R is selected from the group consisting of aryl, heteroaryl, cycloalkyl, and heterocycloalkyl.

7. The process according to claim 1, wherein E is a bond.

8. The process according to claim 1, wherein $Y^2$ is selected from the group consisting of hydrogen, alkyl, alkoxy, perfluoroalkoxy, and perfluoroalkylthio.

9. A compound or a pharmaceutically acceptable salt thereof, wherein:

the compound corresponds in structure to Formula II:

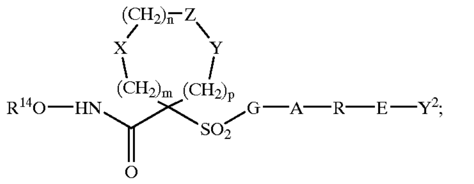

II $R^{14}$ is selected from the group consisting of hydrogen and $C(W)R^{15}$;

W is selected from the group consisting of O and S;

$R^{15}$ is selected from the group consisting of $C_1$–$C_6$-alkyl, aryl, $C_1$–$C_6$-alkoxy, heteroaryl-$C_1$–$C_6$-alkyl, $C_3$–$C_8$-cycloalkyl-$C_1$–$C_6$-alkyl, aryloxy, aryl-$C_{1-C6}$-alkoxy, aryl-$C_1$–$C_6$-alkyl, heteroaryl, and amino-$C_1$–$C_6$-alkyl, wherein:

the aminoalkyl nitrogen optionally is substituted with up to two substituents independently selected from the group consisting of $C_1$–$C_6$-alkyl, aryl, aryl-$C_1$–$C_6$-alkyl, $C_3$–$C_8$-cycloalkyl-$C_1$–$C_6$-alkyl, aryl-$C_1$–$C_6$-alkoxycarbonyl, $C_1$–$C_6$-alkoxycarbonyl, and $C_1$–$C_6$-alkanoyl, or the aminoalkyl nitrogen optionally is substituted with two substituents such that the aminoalkyl nitrogen and the two substituents together form a 5- to 8-membered heterocyclo or heteroaryl ring;

m is selected from the group consisting of zero, 1, and 2;

n is selected from the group consisting of zero, 1, and 2;

p is selected from the group consisting of zero, 1, and 2;

the sum of m+n+p is selected from the group consisting of 1, 2, 3, and 4;

as to X, Y, and Z:

(a) one of X, Y, and Z is selected from the group consisting of $NR^6$, O, S, S(O), $S(O)_2$, and $NS(O)_2R^7$, and the remaining two of X, Y, and Z are $CR^8R^9$ and $CR^{10}R^{11}$, or (b) X and Z or Z and Y together constitute a moiety that is selected from the group consisting of $NR^6C(O)$, $NR^6S(O)$, $NR^6S(O)_2$, $NR^6S$, $NR^6O$, SS, $NR^6NR^{6'}$, and OC(O), with the remaining one of X and Y being $CR^8R^9$, or (c) n is zero and X, Y, and Z together constitute a moiety selected from the group consisting of:

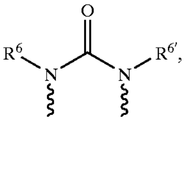, 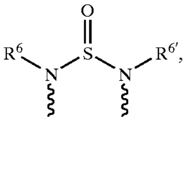, 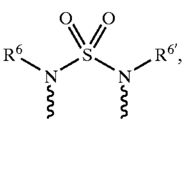,

-continued

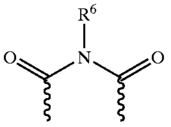, 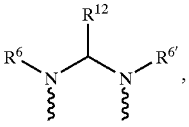, 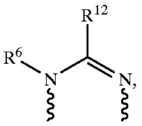,

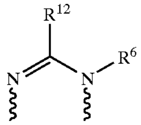, 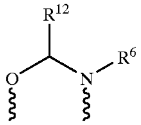, 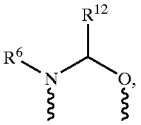,

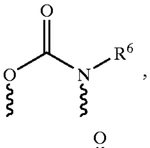, 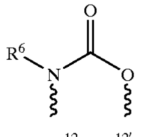, 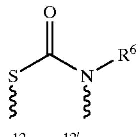,

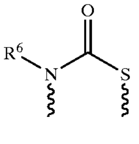, 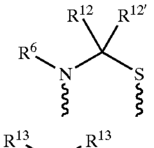, 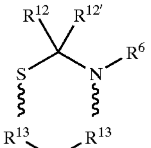,

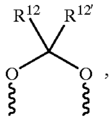, 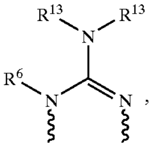, and 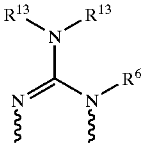, wherein the wavy lines are bonds to the atoms of the depicted ring;

each $R^6$ and $R^{6'}$ is independently selected from the group consisting of hydrogen, $C_1$–$C_6$-alkanoyl, $C_6$-aryl-$C_1$–$C_6$-alkyl, aroyl, bis($C_1$–$C_6$-alkoxy-$C_1$–$C_6$-alkyl)-$C_1$–$C_6$-alkyl, $C_1$–$C_6$-alkyl, $C_1$–$C_6$-haloalkyl, $C_1$–$C_6$-perfluoroalkyl, $C_1$–$C_6$-trifluoromethylalkyl, $C_1$–$C_6$-perfluoroalkoxy-$C_1$–$C_6$-alkyl, $C_1$–$C_6$-alkoxy-$C_1$–$C_6$-alkyl, $C_3$–$C_6$-cycloalkyl, $C_3$–$C_8$-heterocycloalkyl, $C_3$–$C_8$-heterocycloalkylcarbonyl, $C_6$-aryl, $C_5$–$C_6$-heterocyclo, $C_5$–$C_6$-heteroaryl, $C_3$–$C_8$-cycloalkyl-$C_{1-6}$-alkyl, $C_6$-aryloxy-$C_1$–$C_6$-alkyl, heteroaryloxy-$C_1$–$C_6$-alkyl, heteroaryl-$C_{1-6}$-alkoxy-$C_1$–$C_6$-alkyl, heteroarylthio-$C_1$–$C_6$-alkyl, $C_6$-arylsulfonyl, $C_1$–$C_6$-alkylsulfonyl, $C_5$–$C_6$-heteroarylsulfonyl, carboxy-$C_1$–$C_6$-alkyl, $C_1$–$C_4$-alkoxycarbonyl-$C_1$–$C_6$-alkyl, aminocarbonyl, $C_1$–$C_6$-alkyliminocarbonyl, $C_6$-aryliminocarbonyl, $C_5$–$C_6$-heterocycloiminocarbonyl, $C_6$-arylthio-$C_1$–$C_6$-alkyl, $C_1$–$C_6$-alkylthio-$C_1$–$C_6$-alkyl, $C_6$-arylthio-$C_3$–$C_6$-alkenyl, $C_1$–$C_4$-alkylthio-$C_3$–$C_6$-alkenyl, $C_5$–$C_6$-heteroaryl-$C_1$–$C_6$-alkyl, halo-$C_1$–$C_6$-alkanoyl, hydroxy-$C_1$–$C_6$-alkanoyl, thiol-$C_1$–$C_6$-alkanoyl, $C_3$–$C_6$-alkenyl, $C_3$–$C_6$-alkynyl, $C_1$–$C_4$-alkoxy-$C_1$–$C_4$-alkyl, $C_1$–$C_5$-alkoxycarbonyl, aryloxycarbonyl, $NR^8R^9$—$C_1$–$C_5$-alkylcarbonyl, hydroxy-$C_1$–$C_5$-alkyl, aminocarbonyl, hydroxyaminocarbonyl, aminosulfonyl, amino–$C_1$–$C_6$-alkylsulfonyl, and amino–$C_1$–$C_6$-alkyl, wherein:

the aminocarbonyl, aminosulfonyl, aminoalkylsulfonyl, or aminoalkyl nitrogen optionally is substituted with up to two substituents independently selected from the group consisting of $C_1$–$C_6$-alkyl, aryl-$C_1$–$C_6$-alkyl, $C_3$–$C_8$-cycloalkyl, and $C_1$–$C_6$-alkanoyl;

$R^7$ is selected from the group consisting of arylalkyl, aryl, heteroaryl, heterocyclo, $C_1$–$C_6$-alkyl, $C_3$–$C_6$-alkynyl, $C_3$–$C_6$-alkenyl, $C_1$–$C_6$-carboxyalkyl, and $C_1$–$C_6$-hydroxyalkyl;

as to $R^8$:

$R^8$ is selected from the group consisting of hydrogen, hydroxy, $C_1$–$C_6$-alkyl, aryl, aryl-$C_1$–$C_6$-alkyl, heteroaryl, heteroaryl-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, arylalkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylaryl-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, the sulfoxide of any said thio substituents, the sulfone of any said thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl, wherein:

the aminoalkyl nitrogen optionally is substituted with up to two radicals independently selected from the group consisting of $C_1$–$C_6$-alkyl, aryl-$C_1$–$C_6$-alkyl, cycloalkyl, and $C_1$–$C_6$-alkanoyl, $R^8$ and $R^9$, together with the carbon to which they are bonded, form a carbonyl group, or $R^8$ and $R^9$ or $R^8$ and $R^{10}$, together with the atom(s) to which they are bonded, form a 5- to 8-member carbocyclic ring or a 5- to 8-member heterocyclic ring containing one or two heteroatoms independently selected from the group consisting of nitrogen, oxygen, and sulfur;

as to $R^9$:

$R^9$ is selected from the group consisting of hydrogen, hydroxy, $C_1$–$C_6$-alkyl, aryl, aryl-$C_1$–$C_6$-alkyl, heteroaryl, heteroaryl-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, arylalkoxy-$C_1$–$C_6$—, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylaryl-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, the sulfoxide of any said thio substituents, the sulfone of any said thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl, wherein:

the aminoalkyl nitrogen optionally is substituted with up to two radicals independently selected from the group consisting of $C_1$–$C_6$-alkyl, aryl-$C_1$–$C_6$-alkyl, cycloalkyl, and $C_1$–$C_6$-alkanoyl, $R^8$ and $R^9$, together with the carbon to which they are bonded, form a carbonyl group, or $R^8$ and $R^9$, together with the carbon to which they are bonded, form a 5- to 8-member carbocyclic ring or a 5- to 8-member heterocyclic ring containing one or two beteroatoms independently selected from the group consisting of nitrogen, oxygen, and sulfur;

as to $R^{10}$:

$R^{10}$ is selected from the group consisting of hydrogen, hydroxy, $C_1$–$C_6$-alkyl, aryl, aryl-$C_1$–$C_6$-alkyl, heteroaryl, heteroaryl-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, arylalkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylaryl-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, the sulfoxide of any said thio substituents, the sulfone of any said thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl, wherein:

the aminoalkyl nitrogen optionally is substituted with up to two radicals independently selected from the group consisting of $C_1$–$C_6$-alkyl, aryl-$C_1$–$C_6$-alkyl, cycloalkyl, and $C_1$–$C_6$-alkanoyl, $R^{10}$ and $R^{11}$, together with the carbon to which they are bonded, form a carbonyl group, or $R^8$ and $R^{10}$ or $R^{10}$ and $R^{11}$, together with the atom(s) to which they are bonded, form a 5- to 8-member carbocyclic ring, or a 5- to 8-member heterocyclic ring containing one or two heteroatoms independently selected from the group consisting of nitrogen, oxygen, and sulfur;

as to $R^{11}$:

$R^{11}$ is selected from the group consisting of hydrogen, hydroxy, $C_1$–$C_6$-alkyl, aryl, aryl-$C_1$–$C_6$-alkyl, heteroaryl, heteroaryl-$C_1$–$C_6$-alkyl, $C_2$–$C_6$-alkynyl, $C_2$–$C_6$-alkenyl, thiol-$C_1$–$C_6$-alkyl, $C_1$–$C_6$-alkylthio-$C_1$–$C_6$-alkyl cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, arylalkoxy-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylaryl-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, arylthio-$C_1$–$C_6$-alkyl, heteroarylthio-$C_1$–$C_6$-alkyl, the sulfoxide of any said thio substituents, the sulfone of any said thio substituents, perfluoro-$C_1$–$C_6$-alkyl, tri fluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl, wherein:

the aminoalkyl nitrogen optionally is substituted with up to two radicals independently selected from the group consisting of $C_1$–$C_6$-alkyl, aryl-$C_1$–$C_6$-alkyl, cycloalkyl, and $C_1$–$C_6$-alkanoyl, $R^{10}$ and $R^{11}$ , together with the carbon to which they are bonded, form a carbonyl group, or $R^{10}$ and $R^{11}$, together with the carbon to which they are bonded, form a 5- to 8-member carbocyclic ring or a 5- to 8-member heterocyclic ring containing one or two heteroatoms independently selected from the group consisting of nitrogen, oxygen, and sulfur;

only one of $R^8$ and $R^9$ or $R^{10}$ and $R^{11}$ is hydroxy;

$R^{12}$ and $R^{12'}$ are independently selected from the group consisting of hydrogen, $C_1$–$C_6$-alkyl, aryl, aryl-$C_1$–$C_6$-alkyl, heteroaryl, heteroarylalkyl, $C_2$–$C_6$-alkynyl, $C_2$–$C_6$-alkenyl, thiol-$C_1$–$C_6$-alkyl, cycloalkyl, cycloalkyl-$C_1$–$C_6$-alkyl, heterocycloalkyl-$C_1$–$C_6$-alkyl, $C_1$–$C_6$-alkoxy-$C_1$–$C_6$-alkyl, aryloxy-$C_1$–$C_6$-alkyl, amino-$C_1$–$C_6$-alkyl, $C_1$–$C_6$-alkoxy-$C_1$–$C_6$-alkoxy-$C_1$–$C_6$-alkyl, hydroxy-$C_1$–$C_6$-alkyl, hydroxycarbonyl-$C_1$–$C_6$-alkyl, hydroxycarbonylaryl-$C_1$–$C_6$-alkyl, aminocarbonyl-$C_1$–$C_6$-alkyl, aryloxy-$C_1$–$C_6$-alkyl, heteroaryloxy-$C_1$–$C_6$-alkyl, $C_1$–$C_6$-alkylthio-$C_1$–$C_6$-alkyl, arylthio-$C_1$–$C_6$-alkyl, heteroarylthio-$C_1$–$C_6$-alkyl, the sulfoxide of any said thio substituents, the sulfone of any said thio substituents, perfluoro-$C_1$–$C_6$-alkyl, trifluoromethyl-$C_1$–$C_6$-alkyl, halo-$C_1$–$C_6$-alkyl, alkoxycarbonylamino-$C_1$–$C_6$-alkyl, and amino-$C_1$–$C_6$-alkyl, wherein:

the aminoalkyl nitrogen optionally is substituted with up to two radicals independently selected from the group consisting of $C_1$–$C_6$-alkyl, aryl-$C_1$–$C_6$-alkyl, cycloalkyl, and $C_1$–$C_6$-alkanoyl;

$R^{13}$ is selected from the group consisting of hydrogen, benzyl, phenyl, $C_1$–$C_6$-alkyl, $C_2$–$C_6$-alkynyl, $C_2$–$C_6$-alkenyl, and $C_1$–$C_6$-hydroxyalkyl;

G—A—R—E—$Y^2$ is a substituent that has a length greater than that of a pentyl group but less than that of an icosyl group, wherein:

G is selected from the group consisting of aryl and heteroaryl;

A is selected from the group consisting of:

(1) —O—,
(2) —S—,
(3) —$NR^{17}$—,
(4) —CO—N($R^{17}$)
(5) —N($R^{17}$)—CO—,
(6) —CO—O—,
(7) —O—CO—,
(8) —O—CO—O—,
(9) —HC=CH—,
(10) —NH—CO—NH—,
(11) —C≡C—,
(12) —NH—CO—O—,
(13) —O—CO—NH—,
(14) —N=N—,
(15) —NH—NH—,
(16) —CS—N($R^{18}$)—,
(17) —N($R^{18}$)—CS—, and
(18) a bond;

$R^{17}$ is selected from the group consisting of hydrogen, $C_1$–$C_4$-alkyl, and phenyl;

$R^{18}$ is selected from the group consisting of hydrogen, $C_1$–$C_4$-alkyl, and phenyl;

R is selected from the group consisting of alkyl, alkoxyalkyl, aryl, heteroaryl, cycloalkyl, heterocycloalkyl, arylalkyl, heteroarylalkyl, heterocycloalkylalkyl, cycloalkylalkyl, cycloalkoxyalkyl, heterocycloalkoxyalkyl, aryloxyalkyl, heteroaryloxyalkyl, arylthioalkyl, heteroarylthioalkyl, cycloalkylthioalkyl, and heterocycloalkylthioalkyl, wherein:

the aryl, heteroaryl, cycloalkyl, or heterocycloalkyl optionally is substituted with up to two radicals independently selected from the group consisting of halo, alkyl, perfluoroalkyl, perfluoroalkoxy, perfluoroalkylthio, trifluoromethylalkyl, amino, alkoxycarbonylalkyl, alkoxy, $C_1$–$C_2$-alkylene-dioxy, hydroxycarbonylalkyl, hydroxycarbonylalkylamino, nitro, hydroxy, hydroxyalkyl, alkanoylamino, and alkoxycarbonyl, and R is other than alkyl or alkoxyalkyl when A is —O— or —S—;

E is selected from the group consisting of:

(1) —CO($R^{19}$)—,
(2) —($R^{19}$)CO—,
(3) —CONH—,
(4) —HNCO—,
(5) —CO—,
(6) —$SO_2$—$R^{19}$—,
(7) —$R^{19}$—$SO_2$—,
(8) —$SO_2$—,
(9) —NH—$SO_2$—,
(10) —$SO_2$—NH—, and
(11) a bond;

$R^{19}$ is selected from the group consisting of heterocycloalkyl and cycloalkyl; and $Y^2$ is selected from the group consisting of hydrogen, alkyl, alkoxy, haloalkyl, aryl, arylalkyl, cycloalkyl, heteroaryl, hydroxy, aryloxy, arylalkoxy, heteroaryloxy, heteroarylalkyl, perfluoroalkoxy, perfluoroalkylthio, trifluoromethylalkyl, alkenyl, heterocycloalkyl, cycloalkyl, trifluoromethyl, alkoxycarbonyl, and aminoalkyl, wherein:

the aryl, heteroaryl, or heterocycloalkyl optionally is substituted with up to two radicals independently selected from the group consisting of alkanoyl, halo, nitro, arylalkyl, aryl, alkoxy, and amino, wherein:

the amino nitrogen optionally is substituted with up to two groups independently selected from the group consisting of hydrogen, alkyl, and arylalkyl.

10. The compound or salt according to claimr 9, wherein said —G—A—R—E—$Y^2$ substituent contains two to four carbocyclic or heterocyclic rings.

11. The compound or salt according to claim 9, wherein each of the two to four rings has 6 ring members.

12. The compound or salt according to claim 9, wherein said —G—A—R—E—$Y^2$ substituent has a length that is greater than that of a hexyl group and less than that of a stearyl group.

13. The compound or salt according to claim 9, wherein A is selected from the group consisting of —O— and —S—.

14. The compound or salt according to claim 9, wherein R is selected from the group consisting of aryl, heteroaryl, cycloalkyl, and heterocycloalkyl.

15. The compound or salt according to claim 9, wherein E is a bond.

16. The compound or salt according to claim 9, wherein $Y^2$ is selected from the group consisting of hydrogen, alkyl, alkoxy, perfluoroalkoxy, and perfluoroalkylthio.

17. The compound or salt according to claim 9, wherein $R^{14}$ is hydrogen.

18. The compound or salt according to claim 9, wherein:

W is O; and $R^{15}$ is selected from the group consisting of $C_1$–$C_6$-alkyl, aryl, $C_1$–$C_6$-alkoxy, heteroaryl-$C_1$–$C_6$-alkyl, $C_3$–$C_8$-cycloalkyl-$C_1$–$C_6$-alkyl, and aryloxy.

19. A pharmaceutical composition that comprises a compound or salt according to claim 9, dissolved or dispersed in a pharmaceutically acceptable carrier.

* * * * *

UNITED STATES PATENT AND TRADEMARK OFFICE

CERTIFICATE OF CORRECTION

PATENT NO. : 6,541,489 B1
DATED : April 1, 2003
INVENTOR(S) : Thomas E. Barta et al.

It is certified that error appears in the above-identified patent and that said Letters Patent is hereby corrected as shown below:

Column 728,
Line 59, replace "-G-A-R-E-Y" with -- -G-A-R-E-$Y^2$ --.

Column 732,
Line 40, replace "tri fluoromethyl-$C_1$-$C_6$" with -- trifluoromethyl-$C_1$-$C_6$- --.

Signed and Sealed this

Eleventh Day of November, 2003

JAMES E. ROGAN
*Director of the United States Patent and Trademark Office*

UNITED STATES PATENT AND TRADEMARK OFFICE

CERTIFICATE OF CORRECTION

PATENT NO. : 6,541,489 B1 Page 1 of 1
DATED : April 1, 2003
INVENTOR(S) : Thomas E. Barta et al.

It is certified that error appears in the above-identified patent and that said Letters Patent is hereby corrected as shown below:

Title page,
Item [75], Inventors, should read as follows: -- Thomas E. Barta, Evanston, IL; Daniel P. Becker, Glenview, IL; Louis J. Bedell. Prospect Heights, IL; Teri L. Boehm, Ballwin, MO; Jeffery N, Carroll, St. Louis, MO; Gary A. DeCrescenzo, St. Charles, MO; Theresa R. Fletcher, Kirkwood, MO; John N. Freskos, Clayton, MO; Daniel P. Getman, Chesterfield, MO; Susan L. Hockerman, Kirkwood, MO; Carol P. Howard, Fenton, MO; Clara I. Villamil, Glenview, IL; Stephen A. Kolodziej, Ballwin, MO; Madeleine H. Li, Plainsboro, NJ; Joseph J. McDonald, Ballwin, MO; Deborah A. Mischke, Defiance, MO; Patrick B. Mullins, St. Louis, MO; Joseph G. Rico, O'Fallon, MO; Nathan W. Stehle, Grafton, WI --

Signed and Sealed this

Nineteenth Day of April, 2005

JON W. DUDAS
*Director of the United States Patent and Trademark Office*

UNITED STATES PATENT AND TRADEMARK OFFICE
Certificate

Patent No. 6,541,489 B1 Patented: April 1, 2003

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Thomas E. Barta, Evanston, IL; Daniel P. Becker, Glenview, IL; Louis J. Bedell, Prospect Heights, IL; Terry L. Boehm, Ballwin, MO; Jeffery N. Carroll, St. Louis, MO; Gary A. DeCrescenzo, St. Charles, MO; Theresa R. Fletcher, Kirkwood, MO; John N. Freskos, Clayton, MO; Daniel P. Getman, Chesterfield, MO; Susan L. Hockerman, Kirkwood, MO; Carol P. Howard, Fenton, MO; Clara I. Villamil, Glenview, IL; Stephen A. Kolodziej, Ballwin, MO; Madeleine H. Li, Plainsboro, NJ; Joseph J. McDonald, Ballwin, MO; Deborah A. Mischke, Defiance, MO; Patrick B. Mullins, St. Louis, MO; Joseph G. Rico, O'Fallon, MO; Nathan W. Stehle, Grafton, WI; and Gunnar J. Hanson, Skokie, IL.

Signed and Sealed this Tenth Day of January 2006.

CECILIA TSANG
*Supervisory Patent Examiner*
Art Unit 1625